(12) United States Patent
Arnold et al.

(10) Patent No.: US 7,468,371 B2
(45) Date of Patent: Dec. 23, 2008

(54) TRICYCLIC PYRAZOLE KINASE INHIBITORS

(75) Inventors: Lee D. Arnold, Niantic, CT (US);
Jürgen Dinges, Grayslake, IL (US);
Richard W. Dixon, Jefferson, MA (US);
Stevan W. Djuric, Libertyville, IL (US);
Anna M. Ericsson, Schrewsbury, MA (US); Kimba Fischer, Longmont, CO (US); Alan F. Gasiecki, Vernon Hills, IL (US); Vijaya J. Gracias, Lindenhurst, IL (US); James H. Holms, Gurnee, IL (US); Makoto Takeshita, Fukui (JP); Michael R. Michaelides, Libertyville, IL (US); Melanie A. Muckey, Trevor, WI (US); Paul Rafferty, Westborough, MA (US); Douglas H. Steinman, Morton Grove, IL (US); Carol K. Wada, Gurnee, IL (US); Zhiren Xia, Gurnee, IL (US); Irini Akritopoulou-Zanze, Lake Bluff, IL (US); Henry Q. Zhang, Grayslake, IL (US)

(73) Assignee: Abbott Laboratories Inc., Abbott Park, IL (US)

( * ) Notice: Subject to any disclaimer, the term of this patent is extended or adjusted under 35 U.S.C. 154(b) by 370 days.

(21) Appl. No.: 11/089,473

(22) Filed: Mar. 24, 2005

(65) Prior Publication Data

US 2006/0014816 A1 Jan. 19, 2006

Related U.S. Application Data

(60) Provisional application No. 60/556,005, filed on Mar. 24, 2004.

(51) Int. Cl.
*A61K 31/496* (2006.01)
*A61K 31/415* (2006.01)
*C07D 231/54* (2006.01)
*C07D 409/14* (2006.01)

(52) U.S. Cl. .......... 514/254.05; 544/358; 544/359; 544/366; 544/371; 548/356.1; 548/358.1; 548/359.1; 514/252.12; 514/254.01; 514/403; 514/406

(58) Field of Classification Search .......... 544/358, 544/359, 366, 371; 548/356.1, 358.1, 359.1; 514/252.12, 252.13, 254.01, 254.05, 254.06, 514/403, 406
See application file for complete search history.

(56) References Cited

U.S. PATENT DOCUMENTS

| | | | |
|---|---|---|---|
| 6,291,504 B1 | 9/2001 | Nugiel et al. | 514/403 |
| 6,297,238 B1 | 10/2001 | Doyle et al. | 514/232.8 |
| 6,407,103 B2 | 6/2002 | Doyle et al. | 514/232.8 |
| 6,462,036 B1 | 10/2002 | Doyle et al. | 514/218 |
| 2001/0027195 A1 | 10/2001 | Nugiel et al. | 514/232.8 |

FOREIGN PATENT DOCUMENTS

| | | |
|---|---|---|
| WO | 99/54308 | 10/1999 |
| WO | 00/27822 | 5/2000 |
| WO | 00/59901 | 10/2000 |
| WO | 01/87846 | 11/2001 |
| WO | 02/44174 | 6/2002 |
| WO | 02/46182 | 6/2002 |
| WO | 02/070494 | 9/2002 |
| WO | 03/004491 | 1/2003 |
| WO | 03/007883 | 1/2003 |
| WO | 03/033499 | 4/2003 |
| WO | 03/070236 | 8/2003 |

OTHER PUBLICATIONS

Nugiel et al., "Indenopyrazoles as Novel Cyclin Dependent Kinase (CDK) Inhibitors," J. Med. Chem. 44:1334-1336 (2001).
Nugiel et al., "Synthesis and Evaluation of Indenopyrazoles as Cyclin-Dependent Kinase Inhibitors. 2. Probing the Indeno Ring Substitutent Pattern," J. Med. Chem. 46:5224-5232 (2002).
Yue et al., "Synthesis and Evaluation of Indenopyrazoles as Cyclin-Dependent Kinase Inhibitors. 3. Structure Activity Relationships as C3[1,2]," J. Med. Chem. 45:5233-5248 (2002).

*Primary Examiner*—Golam M. M. Shameem
(74) *Attorney, Agent, or Firm*—B. Gregory Donner

(57) ABSTRACT

Compounds of the present invention are useful for inhibiting protein tyrosine kinases. Also disclosed are methods of making the compounds, compositions containing the compounds, and methods of treatment using the compounds.

20 Claims, No Drawings

TRICYCLIC PYRAZOLE KINASE INHIBITORS

This application claims priority from U.S. Provisional Patent Application Ser. No. 60/556,005, filed Mar. 24, 2004, incorporated herein by reference.

TECHNICAL FIELD

The present invention relates to compounds which are useful for inhibiting protein tyrosine kinases, methods of making the compounds, compositions containing the compounds, and methods of treatment using the compounds.

BACKGROUND OF THE INVENTION

Protein tyrosine kinases (PTKs) are enzymes which catalyse the phosphorylation of specific tyrosine residues in cellular proteins. This post-translational modification of these substrate proteins, often enzymes themselves, acts as a molecular switch regulating cell proliferation, activation, or differentiation. Aberrant or excessive PTK activity has been observed in many disease states including benign and malignant proliferative disorders as well as diseases resulting from inappropriate activation of the immune system (e.g., autoimmune disorders), allograft rejection, and graft vs. host disease.

Endothelial-cell specific receptor PTKs such as KDR and Tie-2 mediate the angiogenic process, and are thus involved in supporting the progression of cancers and other diseases involving inappropriate vascularization (e.g., diabetic retinopathy, choroidal neovascularization due to age-related macular degeneration, psoriasis, arthritis, retinopathy of prematurity, and infantile hemangiomas).

The non-receptor tyrosine kinases represent a collection of cellular enzymes which lack extracellular and transmembrane sequences. At present, over twenty-four individual non-receptor tyrosine kinases, comprising eleven subfamilies (Src, Frk, Btk, Csk, Abl, Zap70, Fes/Fps, Fak, Jak, Ack and LIMK) have been identified. At present, the Src subfamily of non-receptor tyrosine kinases is comprised of the largest number of PTKs and includes Src, Yes, Fyn, Lyn, Lck, Blk, Hck, Fgr and Yrk. The Src subfamily of enzymes has been linked to oncogenesis and immune responses.

The identification of effective small compounds which specifically inhibit signal transduction and cellular proliferation by modulating the activity of tyrosine kinases to regulate and modulate abnormal or inappropriate cell proliferation, differentiation, or metabolism is therefore desirable. In particular, the identification of methods and compounds that specifically inhibit the function of a tyrosine kinase which is essential for angiogenic processes or the formation of vascular hyperpermeability leading to edema, ascites, effusions, exudates, and macromolecular extravasation and matrix deposition as well as associated disorders would be beneficial.

SUMMARY OF THE INVENTION

In its principle embodiment, the present invention provides compounds of formula (I)

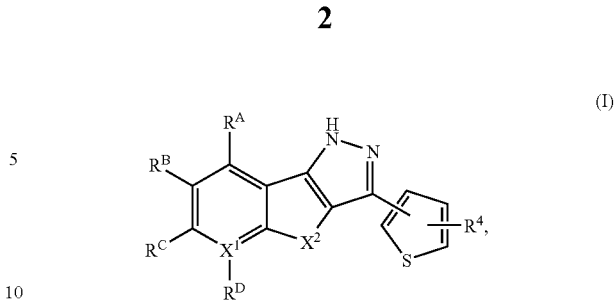

or a therapeutically acceptable salt thereof, wherein $X^1$ is selected from the group consisting of C and N;

$X^2$ is selected from the group consisting of $CH_2$, C=O, and O;

$R^A$, $R^B$, and $R^C$ are independently selected from the group consisting of hydrogen, alkoxyalkoxy, alkoxyalkoxyalkyl, alkoxyalkyl, alkoxycarbonyl, carboxy, halogen, heteroaryl, heteroarylalkoxy, heteroarylalkyl, heteroarylcarbonyl, heteroaryloxy, heterocycle, heterocyclealkoxy, heterocyclealkyl, heterocyclecarbonyl, heterocycleoxy, $R^aR^bN$—, $(R^aR^bN)$alkoxy, $(R^aR^bN)$alkyl, $(R^aR^bN)$carbonyl, and $(NR^aR^bN)$carbonylalkoxy, and $(R^aR^bN)$carbonylalkyl;

$R^D$ is absent or selected from the group consisting of hydrogen, alkoxyalkoxy, alkoxyalkoxyalkyl, alkoxyalkyl, alkoxycarbonyl, carboxy, halogen, heteroaryl, heteroarylalkoxy, heteroarylalkyl, heteroarylcarbonyl, heteroaryloxy, heterocycle, heterocyclealkoxy, heterocyclealkyl, heterocyclecarbonyl, heterocycleoxy, $R^aR^bN$—, $(R^aR^bN)$alkoxy, $(R^aR^bN)$alkyl, $(R^aR^bN)$carbonyl, and $(NR^aR^bN)$carbonylalkoxy, and $(R^aR^bN)$carbonylalkyl;

$R^a$ and $R^b$ are independently selected from the group consisting of hydrogen, alkoxyalkyl, alkyl, alkylcarbonyl, formyl, heteroarylalkyl, heterocyclealkyl, and $(Z^1Z^2N)$alkyl;

$Z^1$ and $Z^2$ are independently selected from the group consisting of hydrogen, alkyl, formyl, and alkylcarbonyl;

$R^4$ is selected from the group consisting of heteroaryl, C≡$CR^5$, $(CH_2)_nNR^6C(O)NR^7R^8$, $(CH_2)_nNR^6C(O)OR^8$, $(CH_2)_nNR^6C(NCN)NR^7R^8$, $(CH_2)_nOC(O)NR^7R^8$, CH=$NNR^6C(O)NR^7R^8$, CH=$NOR^8$, and CH=$NOCH_2C(O)NR^7R^8$;

n is 1, 2, 3, 4, or 5;

$R^5$ is selected from the group consisting of alkoxyalkoxyalkyl, alkoxyalkyl, alkoxycarbonylalkoxyalkyl, alkyl, aryl, aryloxyalkyl, arylthioalkyl, arylsulfinylalkyl, arylsulfonylalkyl, cycloalkyl, cycloalkylalkoxyalkyl, cycloalkylalkyl, cycloalkyloxyalkyl, haloalkoxyalkyl, haloalkoxyalkoxyalkyl, heteroaryl, heteroarylalkoxyalkyl, heteroarylalkyl, heteroaryloxyalkyl, heterocycle, heterocyclealkoxyalkyl, heterocyclealkyl, heterocyclecarbonylalkyl, heterocyclecarbonyloxyalkyl, heterocycleoxyalkyl, $(NR^aR^b)$carbonylalkoxyalkyl, $(NR^cR^d)$alkyl, $(CH_2)_nNR^6C(O)NR^7R^8$, $(CH_2)_nNR^6C(O)OR^8$, $(CH_2)_nNR^6C(NCN)NR^7R^8$, $(CH_2)_nOC(O)NR^7R^8$, and CH=$NNR^6C(O)NR^7R^8$;

$R^c$ is selected from the group consisting of hydrogen and alkyl;

$R^d$ is selected from the group consisting of alkylsulfonyl, arylsulfonyl, heteroarylcarbonyl, and heteroarylcarbonyl;

$R^6$ and $R^7$ are each independently selected from the group consisting of hydrogen, alkoxy, alkoxyalkyl, alkyl, aryl, arylalkyl, cycloalkyl, and cycloalkylalkyl; and $R^8$ is selected from the group consisting of hydrogen, alkoxyalkoxyalkyl, alkoxyalkyl, alkoxycarbonylalkoxyalkyl, alkoxycarbonylalkyl, alkyl, aryl, arylalkoxyalkyl, arylalkyl, aryloxyalkyl, arylthioalkyl, arylsulfinylalkyl, arylsulfonylalkyl, cyanoalkyl, cycloalkyl, cycloalkylalkyl, haloalkoxyalkoxyalkyl, haloalkoxyalkyl, haloalkyl, heteroaryl, heteroarylalkoxyalkyl, heteroarylalkyl, heteroaryloxyalkyl, heterocycle, heterocyclealkoxyalkyl, heterocyclecarbonylalkyl, heterocyclecarbonyloxyalkyl, heterocycleoxyalkyl, heterocyclealkyl, hydroxyalkyl, $(R^aR^b\text{-}N)$alkyl, $(R^aR^bN)$carbonylalkoxyalkyl, and $(R^aR^bN)$carbonylalkyl; or $R^7$ and $R^8$, together with the nitrogen atom to which they are attached, form a heterocycle ring selected from the group consisting of piperazine, piperidine, and morpholine.

DETAILED DESCRIPTION OF THE INVENTION

Typically, one of $R^B$ and $R^C$ is heteroaryl, heteroarylalkyl, heterocycle, or heterocyclealkyl, and the other of $R^B$ and $R^C$ is hydrogen or fluorine. Examples of specific substituents for $R^B$ and $R^C$ include, but are not limited to, 4-acetylpiperazin-1-ylmethyl, 4-cyclopropylpiperazin-1-yl, 4-cyclopropylpiperazin-1-ylmethyl, 4-formylpiperazin-1-ylmethyl, 4-methanesulfonylpiperazin-1-yl, 4-methanesulfonylpiperazin-1-ylmethyl, 4-methylpiperazin-1-yl, 4-methylpiperazin-1-ylmethyl, 2-(4-methylpiperazin-1-yl)ethyl, 4-methyl-2-oxopiperazin-1-ylmethyl, 5-methyl-2,5-diazabicyclo[2.2.1]hept-2-ylmethyl, morpholin-4-yl, hexahydropyrrolo[1,2-a]pyrazin-2-yl, 4-hydroxy-4-methylpiperidin-1-yl, piperidin-1-yl, 1H-1,2,3-triazol-1-ylmethyl, 2H-1,2,3-triazol-2-ylmethyl, 1H-1,2,4-triazol-1-ylmethyl, and 1H-imidazol-1-ylmethyl. $R^A$ is hydrogen and $R^D$, when present, is typically hydrogen or fluorine. $X^1$ is typically C and $X^2$ is typically $CH_2$.

In another embodiment, the present invention relates to a compound of formula (I) wherein $R^4$ is heteroaryl and $R^A$, $R^B$, $R^C$, $R^D$, $X^1$, and $X^2$ are as defined in formula (I).

In another embodiment, the present invention relates to a compound of formula (I) wherein $R^4$ is heteroaryl wherein the heteroaryl is pyridinyl; one of $R^B$ and $R^C$ is heteroaryl, heteroarylalkyl, heterocycle, or heterocyclealkyl and the other of $R^B$ and $R^C$ is independently hydrogen or fluorine; $R^A$ is hydrogen; $R^D$ is hydrogen or fluorine; $X^1$ is C; and $X^2$ is $CH_2$.

In another embodiment, the present invention relates to a compound of formula (I) wherein $R^4$ is heteroaryl wherein the heteroaryl is pyridinyl; one of $R^B$ and $R^C$ is heteroaryl, heteroarylalkyl, heterocycle, or heterocyclealkyl and the other of $R^B$ and $R^C$ is hydrogen or fluorine; $R^A$ is hydrogen; $R^D$ is absent; $X^1$ is N; and $X^2$ is $CH_2$.

In another embodiment, the present invention relates to a compound of formula (I) wherein $R^4$ is heteroaryl wherein the heteroaryl is pyridinyl; one of $R^B$ and $R^C$ is heteroaryl, heteroarylalkyl, heterocycle, or heterocyclealkyl and the other of $R^B$ and $R^C$ is hydrogen or fluorine; $R^A$ is hydrogen; $R^D$ is hydrogen or fluorine; $X^1$ is C; and $X^2$ is O.

In another embodiment, the present invention relates to a compound of formula (I) wherein $R^4$ is $(CH_2)_nNR^6C(O)NR^7R^8$ and n, $R^A$, $R^B$, $R^C$, $R^D$, $X^1$, $X^2$, $R^6$, $R^7$ and $R^8$ are as defined in formula (I).

In another embodiment, the present invention relates to a compound of formula (I) wherein $R^4$ is $(CH_2)_nNR^6C(O)NR^7R^8$; n is 1; $R^6$ is hydrogen, alkoxy, alkoxyalkyl, alkyl, or cycloalkyl; $R^7$ is hydrogen; $R^8$ is alkyl, cycloalkyl, or aryl wherein the aryl is an optionally substituted phenyl; one of $R^B$ and $R^C$ is heteroaryl, heteroarylalkyl, heterocycle, or heterocyclealkyl and the other of $R^B$ and $R^C$ is hydrogen or fluorine; $R^A$ is hydrogen; $R^D$ is hydrogen or fluorine; $X^1$ is C; and $X^2$ is $CH_2$.

In another embodiment, the present invention relates to a compound of formula (I) wherein $R^4$ is $(CH_2)_nNR^6C(O)NR^7R^8$; n is 1; $R^6$ is hydrogen, alkoxy, alkoxyalkyl, alkyl, or cycloalkyl; $R^7$ is hydrogen; $R^8$ is alkyl, cycloalkyl, or aryl wherein the aryl is an optionally substituted phenyl; one of $R^B$ and $R^C$ is heteroaryl, heteroarylalkyl, heterocycle, or heterocyclealkyl and the other of $R^B$ and $R^C$ is hydrogen or fluorine; $R^A$ is hydrogen; $R^D$ is absent; $X^1$ is N; and $X^2$ is $CH_2$.

In another embodiment, the present invention relates to a compound of formula (I) wherein $R^4$ is $(CH_2)_nNR^6C(O)NR^7R^8$; n is 1; $R^6$ is hydrogen, alkoxy, alkoxyalkyl, alkyl, or cycloalkyl; $R^7$ is hydrogen; $R^8$ is alkyl, cycloalkyl, or aryl wherein the aryl is an optionally substituted phenyl; one of $R^B$ and $R^C$ is heteroaryl, heteroarylalkyl, heterocycle, or heterocyclealkyl and the other of $R^B$ and $R^C$ is hydrogen or fluorine; $R^A$ is hydrogen; $R^D$ is hydrogen or fluorine; $X^1$ is C; and $X^2$ is O.

In another embodiment, the present invention relates to a compound of formula (I) wherein $R^4$ is $(CH_2)_nNR^6C(O)OR^8$; and n, $R^A$, $R^B$, $R^C$, $R^D$, $X^1$, $X^2$, $R^6$, and $R^8$ are as defined formula (I).

In another embodiment, the present invention relates to a compound of formula (I) wherein $R^4$ is $(CH_2)_nNR^6C(O)OR^8$; n is 1; $R^6$ is hydrogen or alkyl; $R^8$ is alkyl, cycloalkyl, or aryl wherein the aryl is an optionally substituted phenyl; one of $R^B$ and $R^C$ is heteroaryl, heteroarylalkyl, heterocycle, or heterocyclealkyl and the other of $R^B$ and $R^C$ is hydrogen or fluorine; $R^A$ is hydrogen; $R^D$ is hydrogen or fluorine; $X^1$ is C; and $X^2$ is $CH_2$.

In another embodiment, the present invention relates to a compound of formula (I) wherein $R^4$ is $(CH_2)_nNR^6C(O)OR^8$; n is 1; $R^6$ is hydrogen or alkyl; $R^8$ is alkyl, cycloalkyl, or aryl wherein the aryl is an optionally substituted phenyl; one of $R^B$ and $R^C$ is heteroaryl, heteroarylalkyl, heterocycle, or heterocyclealkyl and the other of $R^B$ and $R^C$ is hydrogen or fluorine; $R^A$ is hydrogen; $R^D$ is absent; $X^1$ is N; and $X^2$ is $CH_2$.

In another embodiment, the present invention relates to a compound of formula (I) wherein $R^4$ is $(CH_2)_nNR^6C(O)OR^8$; n is 1; $R^6$ is hydrogen or alkyl; $R^8$ is alkyl, cycloalkyl, or aryl wherein the aryl is an optionally substituted phenyl; one of $R^B$ and $R^C$ is heteroaryl, heteroarylalkyl, heterocycle, or heterocyclealkyl and the other of $R^B$ and $R^C$ is hydrogen or fluorine; $R^A$ is hydrogen; $R^D$ is hydrogen or fluorine; $X^1$ is C; and $X^2$ is O.

In another embodiment, the present invention relates to a compound of formula (I) wherein $(CH_2)_nNR^6C(NCN)NR^7R^8$; and n, $R^A$, $R^B$, $R^C$, $R^D$, $X^1$, $X^2$, $R^6$, $R^7$, and $R^8$ are as defined in formula (I).

In another embodiment, the present invention relates to a compound of formula (I) wherein $R^4$ is $(CH_2)_nNR^6C(NCN)NR^7R^8$; n is 1; $R^6$ is hydrogen or alkyl; $R^7$ is hydrogen or alkyl; $R^8$ is alkyl, cycloalkyl, or aryl wherein the aryl is an optionally substituted phenyl; one of $R^B$ and $R^C$ is heteroaryl, heteroarylalkyl, heterocycle, or heterocyclealkyl and the other of $R^B$ and $R^C$ is hydrogen or fluorine; $R^A$ is hydrogen; $R^D$ is hydrogen or fluorine; $X^1$ is C; and $X^2$ is $CH_2$.

In another embodiment, the present invention relates to a compound of formula (I) wherein $R^4$ is $(CH_2)_nNR^6C(NCN)NR^7R^8$; n is 1; $R^6$ is hydrogen or alkyl; $R^7$ is hydrogen or alkyl; $R^8$ is alkyl, cycloalkyl, or aryl wherein the aryl is an optionally substituted phenyl; one of $R^B$ and $R^C$ is heteroaryl, heteroarylalkyl, heterocycle, or heterocyclealkyl and the other of $R^B$ and $R^C$ is hydrogen or fluorine; $R^A$ is hydrogen; $R^D$ is absent; $X^1$ is N; and $X^2$ is $CH_2$.

In another embodiment, the present invention relates to a compound of formula (I) wherein $R^4$ is $(CH_2)_nNR^6C(NCN)NR^7R^8$; n is 1; $R^6$ is hydrogen or alkyl; $R^7$ is hydrogen or alkyl; $R^8$ is alkyl, cycloalkyl, or aryl wherein the aryl is an optionally substituted phenyl; one of $R^B$ and $R^C$ is heteroaryl, heteroarylalkyl, heterocycle, or heterocyclealkyl and the other of $R^B$ and $R^C$ is hydrogen or fluorine; $R^A$ is hydrogen; $R^D$ is hydrogen or fluorine; $X^1$ is C; and $X^2$ is O.

In another embodiment, the present invention relates to a compound of formula (I) wherein $(CH_2)_nOC(O)NR^7R^8$; and n, $R^A$, $R^B$, $R^C$, $R^D$, $X^1$, $X^2$, $R^7$, and $R^8$ are as defined in formula (I).

In another embodiment, the present invention relates to a compound of formula (I) wherein $R^4$ is $(CH_2)_nOC(O)NR^7R^8$; n is 1; $R^7$ is hydrogen or alkyl; $R^8$ is alkyl, cycloalkyl, or aryl wherein the aryl is an optionally substituted phenyl; one of $R^B$ and $R^C$ is heteroaryl, heteroarylalkyl, heterocycle, or heterocyclealkyl and the other of $R^B$ and $R^C$ is hydrogen or fluorine; $R^A$ is hydrogen; $R^D$ is hydrogen or fluorine; $X^1$ is C; and $X^2$ is $CH_2$.

In another embodiment, the present invention relates to a compound of formula (I) wherein $R^4$ is $(CH_2)_nOC(O)NR^7R^8$; n is 1; $R^7$ is hydrogen or alkyl; $R^8$ is alkyl, cycloalkyl, or aryl wherein the aryl is an optionally substituted phenyl; one of $R^B$ and $R^C$ is heteroaryl, heteroarylalkyl, heterocycle, or heterocyclealkyl and the other of $R^B$ and $R^C$ is hydrogen or halogen; $R^A$ is hydrogen; $R^D$ is absent; $X^1$ is N; and $X^2$ is $CH_2$.

In another embodiment, the present invention relates to a compound of formula (I) wherein $R^4$ is $(CH_2)_nOC(O)NR^7R^8$; n is 1; $R^7$ is hydrogen or alkyl; $R^8$ is alkyl, cycloalkyl, or aryl wherein the aryl is an optionally substituted phenyl; one of $R^B$ and $R^C$ is heteroaryl, heteroarylalkyl, heterocycle, or heterocyclealkyl and the other of $R^B$ and $R^C$ is hydrogen or fluorine; $R^A$ is hydrogen; $R^D$ is hydrogen or fluorine; $X^1$ is C; and $X^2$ is O.

In another embodiment, the present invention relates to a compound of formula (I) wherein $CH=NNR^6C(O)NR^7R^8$; and $R^A$, $R^B$, $R^C$, $R^D$, $X^1$, $X^2$, $R^6$, $R^7$, and $R^8$ are as defined in formula (I).

In another embodiment, the present invention relates to a compound of formula (I) wherein $R^4$ is $CH=NNR^6C(O)NR^7R^8$; $R^6$ is hydrogen or alkyl; $R^7$ is hydrogen or alkyl; $R^8$ is alkyl, cycloalkyl, or aryl wherein the aryl is an optionally substituted phenyl; one of $R^B$ and $R^C$ is heteroaryl, heteroarylalkyl, heterocycle, or heterocyclealkyl and the other of $R^B$ and $R^C$ is hydrogen or fluorine; $R^A$ is hydrogen; $R^D$ is hydrogen or fluorine; $X^1$ is C; and $X^2$ is $CH_2$.

In another embodiment, the present invention relates to a compound of formula (I) wherein $R^4$ is $CH=NNR^6C(O)NR^7R^8$; $R^6$ is hydrogen or alkyl; $R^7$ is hydrogen or alkyl; $R^8$ is alkyl, cycloalkyl, or aryl wherein the aryl is an optionally substituted phenyl; one of $R^B$ and $R^C$ is heteroaryl, heteroarylalkyl, heterocycle, or heterocyclealkyl and the other of $R^B$ and $R^C$ is hydrogen or fluorine; $R^A$ is hydrogen; $R^D$ is absent; $X^1$ is N; and $X^2$ is $CH_2$.

In another embodiment, the present invention relates to a compound of formula (I) wherein $R^4$ is $CH=NNR^6C(O)NR^7R^8$; $R^6$ is hydrogen or alkyl; $R^7$ is hydrogen or alkyl; $R^8$ is alkyl, cycloalkyl, or aryl wherein the aryl is an optionally substituted phenyl; one of $R^B$ and $R^C$ is heteroaryl, heteroarylalkyl, heterocycle, or heterocyclealkyl and the other of $R^B$ and $R^C$ is hydrogen or fluorine; $R^A$ is hydrogen; $R^D$ is hydrogen or fluorine; $X^1$ is C; and $X^2$ is O.

In another embodiment, the present invention relates to a compound of formula (I) wherein $CH=NOR^8$; and $R^A$, $R^B$, $R^C$, $R^D$, $X^1$, $X^2$, and $R^8$ are as defined in formula (I).

In another embodiment, the present invention relates to a compound of formula (I) wherein $R^4$ is $CH=NOR^8$; $R^8$ is hydrogen, alkyl, cycloalkyl, or aryl wherein the aryl is an optionally substituted phenyl; one of $R^B$ and $R^C$ is heteroaryl, heteroarylalkyl, heterocycle, or heterocyclealkyl and the other of $R^B$ and $R^C$ is hydrogen or fluorine; $R^A$ is hydrogen; $R^D$ is hydrogen or fluorine; $X^1$ is C; and $X^2$ is $CH_2$.

In another embodiment, the present invention relates to a compound of formula (I) wherein $R^4$ is $CH=NOR^8$; $R^8$ is hydrogen, alkyl, cycloalkyl, or aryl wherein the aryl is an optionally substituted phenyl; one of $R^B$ and $R^C$ is heteroaryl, heteroarylalkyl, heterocycle, or heterocyclealkyl and the other of $R^B$ and $R^C$ is hydrogen or fluorine; $R^A$ is hydrogen; $R^D$ is absent; $X^1$ is N; and $X^2$ is $CH_2$.

In another embodiment, the present invention relates to a compound of formula (I) wherein $R^4$ is $CH=NOR^8$; $R^8$ is hydrogen, alkyl, cycloalkyl, or aryl wherein the aryl is an optionally substituted phenyl; one of $R^B$ and $R^C$ is heteroaryl, heteroarylalkyl, heterocycle, or heterocyclealkyl and the other of $R^B$ and $R^C$ is hydrogen or fluorine; $R^A$ is hydrogen; $R^D$ is hydrogen or fluorine; $X^1$ is C; and $X^2$ is O.

In another embodiment, the present invention relates to a compound of formula (I) wherein $CH=NOCH_2C(O)NR^7R^8$; and $R^A$, $R^B$, $R^C$, $R^D$, $X^1$, $X^2$, $R^7$, and $R^8$ are as defined in formula (I).

In another embodiment, the present invention relates to a compound of formula (I) wherein $R^4$ is $CH=NOCH_2C(O)NR^7R^8$; $R^7$ is hydrogen or alkyl; $R^8$ is alkyl, cycloalkyl, or aryl wherein the aryl is an optionally substituted phenyl; one of $R^B$ and $R^C$ is heteroaryl, heteroarylalkyl, heterocycle, or heterocyclealkyl and the other of $R^B$ and $R^C$ is hydrogen or fluorine; and $R^A$ is hydrogen; $R^D$ is hydrogen or fluorine; $X^1$ is C; and $X^2$ is $CH_2$.

In another embodiment, the present invention relates to a compound of formula (I) wherein $R^4$ is $CH=NOCH_2C(O)NR^7R^8$; $R^7$ is hydrogen or alkyl; $R^8$ is alkyl, cycloalkyl, or aryl wherein the aryl is an optionally substituted phenyl; one of $R^B$ and $R^C$ is heteroaryl, heteroarylalkyl, heterocycle, or heterocyclealkyl and the other of $R^B$ and $R^C$ is hydrogen or fluorine; $R^A$ is hydrogen; $R^D$ absent; $X^1$ is N; and $X^2$ is $CH_2$.

In another embodiment, the present invention relates to a compound of formula (I) wherein $R^4$ is $CH=NOCH_2C(O)NR^7R^8$; $R^7$ is hydrogen or alkyl; $R^8$ is alkyl, cycloalkyl, or aryl wherein the aryl is an optionally substituted phenyl; one of $R^B$ and $R^C$ is heteroaryl, heteroarylalkyl, heterocycle, or heterocyclealkyl and the other of $R^B$ and $R^C$ is hydrogen or fluorine; $R^A$ is hydrogen; $R^D$ is hydrogen or fluorine; $X^1$ is C; and $X^2$ is O.

In another embodiment, the present invention relates to a compound of formula (I) wherein $C=CR^5$; and $R^A$, $R^B$, $R^C$, $R^D$, $X^1$, $X^2$, and $R^5$ are as defined in formula (I).

In another embodiment, the present invention relates to a compound of formula (I) wherein $R^4$ is $C=CR^5$; $R^5$ is of alkoxyalkoxyalkyl, alkoxyalkyl, alkoxycarbonylalkoxyalkyl, aryl, aryloxyalkyl, arylthioalkyl, arylsulfinylalkyl, arylsulfonylalkyl, cycloalkyl, cycloalkylalkoxyalkyl, cycloalkylalkyl, cycloalkyloxyalkyl, haloalkoxyalkoxyalkyl, haloalkoxyalkyl, heteroaryl, heteroarylalkoxyalkyl, heteroarylalkyl, heteroaryloxyalkyl, heterocyclealkoxyalkyl, heterocyclealkyl, heterocycleoxyalkyl, $(NR^aR^b)$carbonylalkoxyalkyl, $(NR^cR^d)$alkyl, $(CH_2)_nNR^6C(O)NR^7R^8$, $(CH_2)_nNR^6C(O)OR^8$, $(CH_2)_nNR^6C(NCN)NR^7R^8$, $(CH_2)_nOC(O)NR^7R^8$, and $CH=NNR^6C(O)NR^7R^8$; and n, $R^a$, $R^b$, $R^c$, $R^d$, $R^A$, $R^B$, $R^C$, $R^D$, $X^1$, $X^2$, $R^6$, $R^7$, and $R^8$ are as defined in formula (I).

In another embodiment, the present invention relates to a compound of formula (I) wherein $R^4$ is $C=CR^5$; $R^5$ is alkoxyalkyl, alkoxyalkoxyalkyl, aryloxyalkyl, cycloalkylalkoxyalkyl, cycloalkyloxyalkyl, haloalkoxyalkyl, or haloalkoxyalkoxyalkyl; and $R^A$, $R^B$, $R^C$, $R^D$, $X^1$, $X^2$, $R^6$, $R^7$, and $R^8$ are as defined in formula (I).

In another embodiment, the present invention relates to a compound of formula (I) wherein $R^4$ is $C=CR^5$; $R^5$ is alkoxyalkyl, alkoxyalkoxyalkyl, aryloxyalkyl, cycloalkylalkoxyalkyl, cycloalkyloxyalkyl, haloalkoxyalkyl, or haloalkoxyalkoxyalkyl; one of $R^B$ and $R^C$ is heteroaryl, heteroarylalkyl, heterocycle, or heterocyclealkyl and the other of $R^B$ and $R^C$ is hydrogen or fluorine; $R^A$ is hydrogen; $R^D$ is hydrogen or fluorine; $X^1$ is C; and $X^2$ is $CH_2$.

In another embodiment, the present invention relates to a compound of formula (I) wherein $R^4$ is C≡$CR^5$; $R^5$ is alkoxyalkyl, alkoxyalkoxyalkyl, aryloxyalkyl, cycloalkylalkoxyalkyl, cycloalkyloxyalkyl, haloalkoxyalkyl, or haloalkoxyalkoxyalkyl; one of $R^B$ and $R^C$ is heteroaryl, heteroarylalkyl, heterocycle, or heterocyclealkyl and the other of $R^B$ and $R^C$ is hydrogen or fluorine; $R^A$ is hydrogen; $R^D$ is absent; $X^1$ is N; and $X^2$ is $CH_2$.

In another embodiment, the present invention relates to a compound of formula (I) wherein $R^4$ is C≡$CR^5$; $R^5$ is alkoxyalkyl, alkoxyalkoxyalkyl, aryloxyalkyl, cycloalkylalkoxyalkyl, cycloalkyloxyalkyl, haloalkoxyalkyl, or haloalkoxyalkoxyalkyl; one of $R^B$ and $R^C$ is heteroaryl, heteroarylalkyl, heterocycle, or heterocyclealkyl and the other of $R^B$ and $R^C$ is hydrogen or fluorine; $R^A$ is hydrogen; $R^D$ is hydrogen or fluorine; $X^1$ is C; and $X^2$ is O.

In another embodiment, the present invention relates to a compound of formula (I) wherein $R^4$ is C≡$CR^5$; $R^5$ is alkoxyalkoxyalkyl wherein the alkoxyalkoxyalkyl is (2-methoxyethoxy)methyl, (2-ethoxyethoxy)methyl, (2-isopropoxyethoxy)methyl, (2-isobutoxyethoxy)methy, or (2-methoxy-1-methylethoxy)methyl; one of $R^B$ and $R^C$ is heteroaryl, heteroarylalkyl, heterocycle, or heterocyclealkyl and the other of $R^B$ and $R^C$ is hydrogen or fluorine; $R^A$ is hydrogen; $R^D$ is hydrogen or fluorine; $X^1$ is C; and $X^2$ is $CH_2$.

In another embodiment, the present invention relates to a compound of formula (I) wherein $R^4$ is C≡$CR^5$; $R^5$ is alkoxyalkoxyalkyl wherein the alkoxyalkoxyalkyl is (2-methoxyethoxy)methyl, (2-ethoxyethoxy)methyl, (2-isopropoxyethoxy)methyl, (2-isobutoxyethoxy)methy, or (2-methoxy-1-methylethoxy)methyl; one of $R^B$ and $R^C$ is heteroaryl, heteroarylalkyl, heterocycle, or heterocyclealkyl and the other of $R^B$ and $R^C$ is hydrogen or fluorine; $R^A$ is hydrogen; $R^D$ is absent; $X^1$ is N; and $X^2$ is $CH_2$.

In another embodiment, the present invention relates to a compound of formula (I) wherein $R^4$ is C≡$CR^5$; $R^5$ is alkoxyalkoxyalkyl wherein the alkoxyalkoxyalkyl is (2-methoxyethoxy)methyl, (2-ethoxyethoxy)methyl, (2-isopropoxyethoxy)methyl, (2-isobutoxyethoxy)methy, or (2-methoxy-1-methylethoxy)methyl; one of $R^B$ and $R^C$ is heteroaryl, heteroarylalkyl, heterocycle, or heterocyclealkyl and the other of $R^B$ and $R^C$ is hydrogen or fluorine; $R^A$ is hydrogen; $R^D$ is hydrogen or fluorine; $X^1$ is C; and $X^2$ is O.

In another embodiment, the present invention relates to a compound of formula (I) wherein $R^4$ is C≡$CR^5$; $R^5$ is alkoxyalkoxyalkyl wherein the alkoxyalkoxyalkyl is (2-methoxyethoxy)methyl, (2-ethoxyethoxy)methyl, (2-isopropoxyethoxy)methyl, (2-isobutoxyethoxy)methy, (2-methoxy-1-methylethoxy)methyl; one of $R^B$ and $R^C$ is 4-acetylpiperazin-1-ylmethyl, 4-cyclopropylpiperazin-1-yl, 4-cyclopropylpiperazin-1-ylmethyl, 4-formylpiperazin-1-ylmethyl, 4-methanesulfonylpiperazin-1-yl, 4-methanesulfonylpiperazin-1-ylmethyl, 4-methylpiperazin-1-yl, 4-methylpiperazin-1-ylmethyl, 2-(4-methylpiperazin-1-yl)ethyl, 4-methyl-2-oxopiperazin-1-ylmethyl, 5-methyl-2,5-diazabicyclo[2.2.1]hept-2-ylmethyl, morpholin-4-yl, hexahydropyrrolo[1,2-a]pyrazin-2-yl, 4-hydroxy-4-methylpiperidin-1-yl, piperidin-1-yl, 1H-1,2,3-triazol-1-ylmethyl, 2H-1,2,3-triazol-2-ylmethyl, 1H-1,2,4-triazol-1-ylmethyl, or 1H-imidazol-1-ylmethyl and the other of $R^B$ and $R^C$ is hydrogen or fluorine; $R^A$ is hydrogen; $R^D$ is hydrogen or fluorine; $X^1$ is C; and $X^2$ is $CH_2$.

In another embodiment, the present invention relates to a compound of formula (I) wherein $R^4$ is C≡$CR^5$; $R^5$ is alkoxyalkoxyalkyl wherein the alkoxyalkoxyalkyl is to (2-methoxyethoxy)methyl, (2-ethoxyethoxy)methyl, (2-isopropoxyethoxy)methyl, (2-isobutoxyethoxy)methy, (2-methoxy-1-methylethoxy)methyl; one of $R^B$ and $R^C$ is 4-acetylpiperazin-1-ylmethyl, 4-cyclopropylpiperazin-1-yl, 4-cyclopropylpiperazin-1-ylmethyl, 4-formylpiperazin-1-ylmethyl, 4-methanesulfonylpiperazin-1-yl, 4-methanesulfonylpiperazin-1-ylmethyl, 4-methylpiperazin-1-yl, 4-methylpiperazin-1-ylmethyl, 2-(4-methylpiperazin-1-yl)ethyl, 4-methyl-2-oxopiperazin-1-ylmethyl, 5-methyl-2,5-diazabicyclo[2.2.1]hept-2-ylmethyl, morpholin-4-yl, hexahydropyrrolo[1,2-a]pyrazin-2-yl, 4-hydroxy-4-methylpiperidin-1-yl, piperidin-1-yl, 1H-1,2,3-triazol-1-ylmethyl, 2H-1,2,3-triazol-2-ylmethyl, 1H-1,2,4-triazol-1-ylmethyl, or 1H-imidazol-1-ylmethyl and the other of $R^B$ and $R^C$ is hydrogen or fluorine; $R^A$ is hydrogen; $R^D$ is absent; $X^1$ is N; and $X^2$ is $CH_2$.

In another embodiment, the present invention relates to a compound of formula (I) wherein $R^4$ is C≡$CR^5$; $R^5$ is alkoxyalkoxyalkyl wherein the alkoxyalkoxyalkyl is (2-methoxyethoxy)methyl, (2-ethoxyethoxy)methyl, (2-isopropoxyethoxy)methyl, (2-isobutoxyethoxy)methy, (2-methoxy-1-methylethoxy)methyl; one of $R^B$ and $R^C$ is 4-acetylpiperazin-1-ylmethyl, 4-cyclopropylpiperazin-1-yl, 4-cyclopropylpiperazin-1-ylmethyl, 4-formylpiperazin-1-ylmethyl, 4-methanesulfonylpiperazin-1-yl, 4-methanesulfonylpiperazin-1-ylmethyl, 4-methylpiperazin-1-yl, 4-methylpiperazin-1-ylmethyl, 2-(4-methylpiperazin-1-yl)ethyl, 4-methyl-2-oxopiperazin-1-ylmethyl, 5-methyl-2,5-diazabicyclo[2.2.1]hept-2-ylmethyl, morpholin-4-yl, hexahydropyrrolo[1,2-a]pyrazin-2-yl, 4-hydroxy-4-methylpiperidin-1-yl, piperidin-1-yl, 1H-1,2,3-triazol-1-ylmethyl, 2H-1,2,3-triazol-2-ylmethyl, 1H-1,2,4-triazol-1-ylmethyl, or 1H-imidazol-1-ylmethyl and the other of $R^B$ and $R^C$ is hydrogen or fluorine; $R^A$ is hydrogen; $R^D$ is hydrogen or fluorine; $X^1$ is C; and $X^2$ is O.

In another embodiment, the present invention relates to a compound of formula (I) wherein $R^4$ is C≡$CR^5$; $R^5$ is haloalkoxyalkoxyalkyl wherein the haloalkoxyalkoxyalkyl is (2-difluoromethoxyethoxy)methyl or (2-trifluoromethoxyethoxy)methyl; one of $R^B$ and $R^C$ is heteroaryl, heteroarylalkyl, heterocycle, or heterocyclealkyl and the other of $R^B$ and $R^C$ is hydrogen or fluorine; $R^A$ is hydrogen; $R^D$ is hydrogen or fluorine; $X^1$ is C; and $X^2$ is $CH_2$.

In another embodiment, the present invention relates to a compound of formula (I) wherein $R^4$ is C≡$CR^5$; $R^5$ is haloalkoxyalkoxyalkyl wherein the haloalkoxyalkoxyalkyl is (2-difluoromethoxyethoxy)methyl or (2-trifluoromethoxyethoxy)methyl; one of $R^B$ and $R^C$ is heteroaryl, heteroarylalkyl, heterocycle, or heterocyclealkyl and the other of $R^B$ and $R^C$ is hydrogen or fluorine; $R^A$ is hydrogen; $R^D$ is absent; $X^1$ is N; and $X^2$ is $CH_2$.

In another embodiment, the present invention relates to a compound of formula (I) wherein $R^4$ is C≡$CR^5$; $R^5$ is haloalkoxyalkoxyalkyl wherein the haloalkoxyalkoxyalkyl is (2-difluoromethoxyethoxy)methyl or (2-trifluoromethoxyethoxy)methyl; one of $R^B$ and $R^C$ is heteroaryl, heteroarylalkyl, heterocycle, or heterocyclealkyl and the other of $R^B$ and $R^C$ is hydrogen or fluorine; $R^A$ is hydrogen; $R^D$ is hydrogen or fluorine; $X^1$ is C; and $X^2$ is O.

In another embodiment, the present invention relates to a compound of formula (I) wherein $R^4$ is C≡$CR^5$; $R^5$ is haloalkoxyalkoxyalkyl wherein the haloalkoxyalkoxyalkyl is (2-difluoromethoxyethoxy)methyl or (2-trifluoromethoxyethoxy)methyl; one of $R^B$ and $R^C$ is 4-acetylpiperazin-1-ylmethyl, 4-cyclopropylpiperazin-1-yl, 4-cyclopropylpiperazin-1-ylmethyl, 4-formylpiperazin-1-ylmethyl, 4-methanesulfonylpiperazin-1-yl, 4-methanesulfonylpiperazin-1-ylmethyl, 4-methylpiperazin-1-yl, 4-methylpiperazin-1-ylmethyl, 2-(4-methylpiperazin-1-yl)ethyl, 4-methyl-2-oxopiperazin-1-ylmethyl, 5-methyl-2,5-diazabicyclo[2.2.1]hept-2-ylmethyl, morpholin-4-yl, hexahydropyrrolo[1,2-a]pyrazin-2-yl, 4-hydroxy-4-methylpiperidin-1-yl, piperidin-1-yl, 1H-1,2,3-triazol-1-ylmethyl, 2H-1,2,3-triazol-2-ylmethyl, 1H-1,2,4-triazol-1-ylmethyl, or 1H-imidazol-1-ylmethyl and the other of $R^B$ and $R^C$ is hydrogen or fluorine; $R^A$ is hydrogen; $R^D$ is hydrogen or fluorine; $X^1$ is C; and $X^2$ is $CH_2$.

In another embodiment, the present invention relates to a compound of formula (I) wherein $R^4$ is C≡$CR^5$; $R^5$ is haloalkoxyalkoxyalkyl wherein the haloalkoxyalkoxyalkyl is (2-difluoromethoxyethoxy)methyl or (2-trifluoromethoxyethoxy)methyl; one of $R^B$ and $R^C$ is 4-acetylpiperazin-1-ylmethyl, 4-cyclopropylpiperazin-1-ylmethyl, 4-cyclopropylpiperazin-1-ylmethyl, 4-formylpiperazin-1-ylmethyl, 4-methanesulfonylpiperazin-1-ylmethyl, 4-methanesulfonylpiperazin-1-ylmethyl, 4-methylpiperazin-1-ylmethyl, 4-methylpiperazin-1-ylmethyl, 2-(4-methylpiperazin-1-yl)ethyl, 4-methyl-2-oxopiperazin-1-ylmethyl, 5-methyl-2,5-diazabicyclo[2.2.1]hept-2-ylmethyl, morpholin-4-yl, hexahydropyrrolo[1,2-a]pyrazin-2-yl, 4-hydroxy-4-methylpiperidin-1-yl, piperidin-1-yl, 1H-1,2,3-triazol-1-ylmethyl, 2H-1,2,3-triazol-2-ylmethyl, 1H-1,2,4-triazol-1-ylmethyl, or 1H-imidazol-1-ylmethyl and the other of $R^B$ and $R^C$ is hydrogen or fluorine; $R^A$ is hydrogen; $R^D$ is absent; $X^1$ is N; and $X^2$ is $CH_2$.

In another embodiment, the present invention relates to a compound of formula (I) wherein $R^4$ is C≡$CR^5$; $R^5$ is haloalkoxyalkoxyalkyl wherein the haloalkoxyalkoxyalkyl is (2-difluoromethoxyethoxy)methyl or (2-trifluoromethoxyethoxy)methyl; one of $R^B$ and $R^C$ is 4-acetylpiperazin-1-ylmethyl, 4-cyclopropylpiperazin-1-ylmethyl, 4-cyclopropylpiperazin-1-ylmethyl, 4-formylpiperazin-1-ylmethyl, 4-methanesulfonylpiperazin-1-ylmethyl, 4-methanesulfonylpiperazin-1-ylmethyl, 4-methylpiperazin-1-ylmethyl, 4-methylpiperazin-1-ylmethyl, 2-(4-methylpiperazin-1-yl)ethyl, 4-methyl-2-oxopiperazin-1-ylmethyl, 5-methyl-2,5-diazabicyclo[2.2.1]hept-2-ylmethyl, morpholin-4-yl, hexahydropyrrolo[1,2-a]pyrazin-2-yl, 4-hydroxy-4-methylpiperidin-1-yl, piperidin-1-yl, 1H-1,2,3-triazol-1-ylmethyl, 2H-1,2,3-triazol-2-ylmethyl, 1H-1,2,4-triazol-1-ylmethyl, or 1H-imidazol-1-ylmethyl and the other of $R^B$ and $R^C$ is hydrogen or fluorine; $R^A$ is hydrogen; $R^D$ is hydrogen or fluorine; $X^1$ is C; and $X^2$ is O.

In another embodiment, the present invention relates to a compound of formula (I) wherein $R^4$ is C≡$CR^5$; $R^5$ is cycloalkylalkoxyalkyl or cycloalkyloxyalkyl; one of $R^B$ and $R^C$ is heteroaryl, heteroarylalkyl, heterocycle, or heterocyclealkyl and the other of $R^B$ and $R^C$ is hydrogen or fluorine; $R^A$ is hydrogen; $R^D$ is hydrogen or fluorine; $X^1$ is C; and $X^2$ is $CH_2$.

In another embodiment, the present invention relates to a compound of formula (I) wherein $R^4$ is C≡$CR^5$; $R^5$ is cycloalkylalkoxyalkyl or cycloalkyloxyalkyl; one of $R^B$ and $R^C$ is heteroaryl, heteroarylalkyl, heterocycle, or heterocyclealkyl and the other of $R^B$ and $R^C$ is hydrogen or fluorine; $R^A$ is hydrogen; $R^D$ is absent; $X^1$ is N; and $X^2$ is $CH_2$.

In another embodiment, the present invention relates to a compound of formula (I) wherein $R^4$ is C≡$CR^5$; $R^5$ is cycloalkylalkoxyalkyl or cycloalkyloxyalkyl; one of $R^B$ and $R^C$ is heteroaryl, heteroarylalkyl, heterocycle, or heterocyclealkyl and the other of $R^B$ and $R^C$ is hydrogen or fluorine; $R^A$ is hydrogen; $R^D$ is hydrogen or fluorine; $X^1$ is C and $X^2$ is O.

In another embodiment, the present invention relates to a compound of formula (I) wherein $R^4$ is C≡$CR^5$; $R^5$ is cyclobutyloxymethyl, cyclohexyloxymethyl, cyclopentyloxymethyl, or cyclopropylmethoxymethyl; one of $R^B$ and $R^C$ is 4-acetylpiperazin-1-ylmethyl, 4-cyclopropylpiperazin-1-yl, 4-cyclopropylpiperazin-1-ylmethyl, 4-formylpiperazin-1-ylmethyl, 4-methanesulfonylpiperazin-1-ylmethyl, 4-methanesulfonylpiperazin-1-ylmethyl, 4-methylpiperazin-1-yl, 4-methylpiperazin-1-ylmethyl, 2-(4-methylpiperazin-1-yl)ethyl, 4-methyl-2-oxopiperazin-1-ylmethyl, 5-methyl-2,5-diazabicyclo[2.2.1]hept-2-ylmethyl, morpholin-4-yl, hexahydropyrrolo[1,2-a]pyrazin-2-yl, 4-hydroxy-4-methylpiperidin-1-yl, piperidin-1-yl, 1H-1,2,3-triazol-1-ylmethyl, 2H-1,2,3-triazol-2-ylmethyl, 1H-1,2,4-triazol-1-ylmethyl, or 1H-imidazol-1-ylmethyl and the other of $R^B$ and $R^C$ is hydrogen or fluorine; $R^A$ is hydrogen; $R^D$ is hydrogen or fluorine; $X^1$ is C; and $X^2$ is $CH_2$.

In another embodiment, the present invention relates to a compound of formula (I) wherein $R^4$ is C≡$CR^5$; $R^5$ is cyclobutyloxymethyl, cyclohexyloxymethyl, cyclopentyloxymethyl, or cyclopropylmethoxymethyl; one of $R^B$ and $R^C$ is 4-acetylpiperazin-1-ylmethyl, 4-cyclopropylpiperazin-1-yl, 4-cyclopropylpiperazin-1-ylmethyl, 4-formylpiperazin-1-ylmethyl, 4-methanesulfonylpiperazin-1-ylmethyl, 4-methanesulfonylpiperazin-1-ylmethyl, 4-methylpiperazin-1-yl, 4-methylpiperazin-1-ylmethyl, 2-(4-methylpiperazin-1-yl)ethyl, 4-methyl-2-oxopiperazin-1-ylmethyl, 5-methyl-2,5-diazabicyclo[2.2.1]hept-2-ylmethyl, morpholin-4-yl, hexahydropyrrolo[1,2-a]pyrazin-2-yl, 4-hydroxy-4-methylpiperidin-1-yl, piperidin-1-yl, 1H-1,2,3-triazol-1-ylmethyl, 2H-1,2,3-triazol-2-ylmethyl, 1H-1,2,4-triazol-1-ylmethyl, or 1H-imidazol-1-ylmethyl and the other of $R^B$ and $R^C$ is hydrogen or fluorine; $R^A$ is hydrogen; $R^D$ is absent; $X^1$ is N; and $X^2$ is $CH_2$.

In another embodiment, the present invention relates to a compound of formula (I) wherein $R^4$ is C≡$CR^5$; $R^5$ is cyclobutyloxymethyl, cyclohexyloxymethyl, cyclopentyloxymethyl, or cyclopropylmethoxymethyl; one of $R^B$ and $R^C$ is 4-acetylpiperazin-1-ylmethyl, 4-cyclopropylpiperazin-1-yl, 4-cyclopropylpiperazin-1-ylmethyl, 4-formylpiperazin-1-ylmethyl, 4-methanesulfonylpiperazin-1-ylmethyl, 4-methanesulfonylpiperazin-1-ylmethyl, 4-methylpiperazin-1-yl, 4-methylpiperazin-1-ylmethyl, 2-(4-methylpiperazin-1-yl)ethyl, 4-methyl-2-oxopiperazin-1-ylmethyl, 5-methyl-2,5-diazabicyclo[2.2.1]hept-2-ylmethyl, morpholin-4-yl, hexahydropyrrolo[1,2-a]pyrazin-2-yl, 4-hydroxy-4-methylpiperidin-1-yl, piperidin-1-yl, 1H-1,2,3-triazol-1-ylmethyl, 2H-1,2,3-triazol-2-ylmethyl, 1H-1,2,4-triazol-1-ylmethyl, or 1H-imidazol-1-ylmethyl and the other of $R^B$ and $R^C$ is hydrogen or fluorine; $R^A$ is hydrogen; $R^D$ is hydrogen or fluorine; $X^1$ is C; and $X^2$ is O.

In another embodiment, the present invention relates to a compound of formula (I) wherein $R^4$ is C≡$CR^5$; $R^5$ is ($NR^cR^d$)alkyl; $R^c$ is hydrogen; $R^d$ is arylsulfonyl; one of $R^B$ and $R^C$ is heteroaryl, heteroarylalkyl, heterocycle, or heterocyclealkyl and the other of $R^B$ and $R^C$ is hydrogen or fluorine; $R^A$ is hydrogen; $R^D$ is hydrogen or fluorine; $X^1$ is C; and $X^2$ is $CH_2$.

In another embodiment, the present invention relates to a compound of formula (I) wherein $R^4$ is C≡$CR^5$; $R^5$ is ($NR^cR^d$)alkyl; $R^c$ is hydrogen; $R^d$ is arylsulfonyl; one of $R^B$ and $R^C$ is heteroaryl, heteroarylalkyl, heterocycle, or heterocyclealkyl and the other of $R^B$ and $R^C$ is hydrogen or fluorine; $R^A$ is hydrogen; $R^D$ is absent; $X^1$ is N; and $X^2$ is $CH_2$.

In another embodiment, the present invention relates to a compound of formula (I) wherein $R^4$ is C≡$CR^5$; $R^5$ is ($NR^cR^d$)alkyl; $R^c$ is hydrogen; $R^d$ is arylsulfonyl; one of $R^B$ and $R^C$ is heteroaryl, heteroarylalkyl, heterocycle, or heterocyclealkyl and the other of $R^B$ and $R^C$ is hydrogen or fluorine; $R^A$ is hydrogen; $R^D$ is hydrogen or fluorine; $X^1$ is C; and $X^2$ is O.

In another embodiment, the present invention relates to a compound of formula (I) wherein $R^4$ is C═$CR^5$; $R^5$ is $(NR^cR^d)$alkyl; $R^c$ is hydrogen; $R^d$ is arylsulfonyl; one of $R^B$ and $R^C$ is 4-acetylpiperazin-1-ylmethyl, 4-cyclopropylpiperazin-1-yl, 4-cyclopropylpiperazin-1-ylmethyl, 4-formylpiperazin-1-ylmethyl, 4-methanesulfonylpiperazin-1-yl, 4-methanesulfonylpiperazin-1-ylmethyl, 4-methylpiperazin-1-yl, 4-methylpiperazin-1-ylmethyl, 2-(4-methylpiperazin-1-yl)ethyl, 4-methyl-2-oxopiperazin-1-ylmethyl, 5-methyl-2,5-diazabicyclo[2.2.1]hept-2-ylmethyl, morpholin-4-yl, hexahydropyrrolo[1,2-a]pyrazin-2-yl, 4-hydroxy-4-methylpiperidin-1-yl, piperidin-1-yl, 1H-1,2,3-triazol-1-ylmethyl, 2H-1,2,3-triazol-2-ylmethyl, 1H-1,2,4-triazol-1-ylmethyl, or 1H-imidazol-1-ylmethyl and the other of $R^B$ and $R^C$ is hydrogen or fluorine; $R^A$ is hydrogen; $R^D$ is hydrogen or fluorine; $X^1$ is C; and $X^2$ is $CH_2$.

In another embodiment, the present invention relates to a compound of formula (I) wherein $R^4$ is C═$CR^5$; $R^5$ is $(NR^cR^d)$alkyl; $R^c$ is hydrogen; $R^d$ is arylsulfonyl; one of $R^B$ and $R^C$ is 4-acetylpiperazin-1-ylmethyl, 4-cyclopropylpiperazin-1-yl, 4-cyclopropylpiperazin-1-ylmethyl, 4-formylpiperazin-1-ylmethyl, 4-methanesulfonylpiperazin-1-yl, 4-methanesulfonylpiperazin-1-ylmethyl, 4-methylpiperazin-1-yl, 4-methylpiperazin-1-ylmethyl, 2-(4-methylpiperazin-1-yl)ethyl, 4-methyl-2-oxopiperazin-1-ylmethyl, 5-methyl-2,5-diazabicyclo[2.2.1]hept-2-ylmethyl, morpholin-4-yl, hexahydropyrrolo[1,2-a]pyrazin-2-yl, 4-hydroxy-4-methylpiperidin-1-yl, piperidin-1-yl, 1H-1,2,3-triazol-1-ylmethyl, 2H-1,2,3-triazol-2-ylmethyl, 1H-1,2,4-triazol-1-ylmethyl, or 1H-imidazol-1-ylmethyl and the other of $R^B$ and $R^C$ is hydrogen or fluorine; $R^A$ is hydrogen; $R^D$ is absent; $X^1$ is N; and $X^2$ is $CH_2$.

In another embodiment, the present invention relates to a compound of formula (I) wherein $R^4$ is C═$CR^5$; $R^5$ is $(NR^cR^d)$alkyl; $R^c$ is hydrogen; $R^d$ is arylsulfonyl; one of $R^B$ and $R^C$ is 4-acetylpiperazin-1-ylmethyl, 4-cyclopropylpiperazin-1-yl, 4-cyclopropylpiperazin-1-ylmethyl, 4-formylpiperazin-1-ylmethyl, 4-methanesulfonylpiperazin-1-yl, 4-methanesulfonylpiperazin-1-ylmethyl, 4-methylpiperazin-1-yl, 4-methylpiperazin-1-ylmethyl, 2-(4-methylpiperazin-1-yl)ethyl, 4-methyl-2-oxopiperazin-1-ylmethyl, 5-methyl-2,5-diazabicyclo[2.2.1]hept-2-ylmethyl, morpholin-4-yl, hexahydropyrrolo[1,2-a]pyrazin-2-yl, 4-hydroxy-4-methylpiperidin-1-yl, piperidin-1-yl, 1H-1,2,3-triazol-1-ylmethyl, 2H-1,2,3-triazol-2-ylmethyl, 1H-1,2,4-triazol-1-ylmethyl, or 1H-imidazol-1-ylmethyl and the other of $R^B$ and $R^C$ is hydrogen or fluorine; $R^A$ is hydrogen; $R^D$ is hydrogen or fluorine; $X^1$ is C; and $X^2$ is O.

In another embodiment, the present invention relates to a compound of formula (I) wherein $R^4$ is C═$CR^5$; $R^5$ is haloalkoxyalkyl; one of $R^B$ and $R^C$ is 4-cyclopropylpiperazin-1-yl and the other of $R^B$ and $R^C$ is hydrogen or fluorine; $R^A$ is hydrogen; $R^D$ is hydrogen or fluorine; $X^1$ is C; and $X^2$ is $CH_2$.

In another embodiment, the present invention relates to a compound of formula (I) wherein $R^4$ is C═$CR^5$; $R^5$ is haloalkoxyalkyl; one of $R^B$ and $R^C$ is 4-cyclopropylpiperazin-1-yl and the other of $R^B$ and $R^C$ is hydrogen or fluorine; $R^A$ is hydrogen; $R^D$ is absent; $X^1$ is N; and $X^2$ is $CH_2$.

In another embodiment, the present invention relates to a compound of formula (I) wherein $R^4$ is C═$CR^5$; $R^5$ is haloalkoxyalkyl; one of $R^B$ and $R^C$ is 4-cyclopropylpiperazin-1-yl and the other of $R^B$ and $R^C$ is hydrogen or fluorine; $R^A$ is hydrogen; $R^D$ is hydrogen or fluorine; $X^1$ is C; and $X^2$ is O.

In another embodiment, the present invention relates to a compound of formula (I) wherein $R^4$ is C═$CR^5$; $R^5$ is alkoxyalkyl; one of $R^B$ and $R^C$ is 4-cyclopropylpiperazin-1-yl and the other of $R^B$ and $R^C$ is hydrogen or fluorine; $R^A$ is hydrogen; $R^D$ is hydrogen or fluorine; $X^1$ is C; and $X^2$ is $CH_2$.

In another embodiment, the present invention relates to a compound of formula (I) wherein $R^4$ is C═$CR^5$; $R^5$ is alkoxyalkyl; one of $R^B$ and $R^C$ is 4-cyclopropylpiperazin-1-yl and the other of $R^B$ and $R^C$ is hydrogen or fluorine; $R^A$ is hydrogen; $R^D$ is absent; $X^1$ is N; and $X^2$ is $CH_2$.

In another embodiment, the present invention relates to a compound of formula (I) wherein $R^4$ is C═$CR^5$; $R^5$ is alkoxyalkyl; one of $R^B$ and $R^C$ is 4-cyclopropylpiperazin-1-yl and the other of $R^B$ and $R^C$ is hydrogen or fluorine; $R^A$ is hydrogen; $R^D$ is hydrogen or fluorine; $X^1$ is C; and $X^2$ is O.

In another embodiment, the present invention relates to a compound of formula (I) wherein $X^1$ is selected from the group consisting of C and N; $X^2$ is selected from the group consisting of $CH_2$ and O; $R^A$ is hydrogen; $R^B$ is selected from the group consisting of heteroaryl, heteroarylalkoxy, heteroarylalkyl, heteroarylcarbonyl, heteroaryloxy, heterocycle, heterocyclealkoxy, heterocyclealkyl, heterocyclecarbonyl, heterocycleoxy, $R^aR^bN$—, $(R^aR^bN)$alkoxy, $(R^aR^bN)$alkyl, $(R^aR^bN)$carbonyl, $(NR^aR^bN)$carbonylalkoxy, and $(R^aR^bN)$carbonylalkyl; $R^C$ is selected from the group consisting of hydrogen, alkoxyalkoxy, alkoxyalkoxyalkyl, alkoxyalkyl, alkoxycarbonyl, carboxy, and halogen; $R^D$ is absent or selected from the group consisting of hydrogen and halogen; $R^a$ and $R^b$ are independently selected from the group consisting of hydrogen, alkoxyalkyl, alkyl, alkylcarbonyl, formyl, heteroarylalkyl, heterocyclealkyl, and $(Z^1Z^2N)$alkyl; $Z^1$ and $Z^2$ are independently selected from the group consisting of hydrogen, alkyl, formyl, and alkylcarbonyl; $R^4$ is C═$CR^5$; $R^5$ is selected from the group consisting of alkoxyalkoxyalkyl, alkoxycarbonylalkoxyalkyl, arylthioalkyl, arylsulfinylalkyl, arylsulfonylalkyl, cycloalkyl, cycloalkylalkoxyalkyl, cycloalkylalkyl, cycloalkyloxyalkyl, haloalkoxyalkoxyalkyl, heteroaryl, heteroaryloxyalkyl, heterocycle, heterocyclecarbonylalkyl, heterocyclecarbonyloxyalkyl, heterocycleoxyalkyl, $(NR^aR^b)$carbonylalkoxyalkyl, $(NR^cR^d)$alkyl; $R^c$ is selected from the group consisting of hydrogen and alkyl; and $R^d$ is selected from the group consisting of alkylsulfonyl, arylsulfonyl, heteroarylcarbonyl, and heteroarylcarbonyl.

In another embodiment, the present invention relates to a compound of formula (I) wherein $X^1$ is selected from the group consisting of C and N; $X^2$ is selected from the group consisting of $CH_2$ and O; $R^A$ is hydrogen; $R^B$ is selected from the group consisting of hydrogen, alkoxyalkoxy, alkoxyalkoxyalkyl, alkoxyalkyl, alkoxycarbonyl, carboxy, and halogen; $R^C$ is selected from the group consisting of heteroaryl, heteroarylalkoxy, heteroarylalkyl, heteroarylcarbonyl, heteroaryloxy, heterocycle, heterocyclealkoxy, heterocyclealkyl, heterocyclecarbonyl, heterocycleoxy, $R^aR^bN$—, $(R^aR^bN)$alkoxy, $(R^aR^bN)$alkyl, $(R^aR^bN)$carbonyl, $(NR^aR^bN)$carbonylalkoxy, and $(R^aR^bN)$carbonylalkyl; $R^D$ is absent or selected from the group consisting of hydrogen and halogen; $R^a$ and $R^b$ are independently selected from the group consisting of hydrogen, alkoxyalkyl, alkyl, alkylcarbonyl, formyl, heteroarylalkyl, heterocyclealkyl, and $(Z^1Z^2N)$alkyl; $Z^1$ and $Z^2$ are independently selected from the group consisting of hydrogen, alkyl, formyl, and alkylcarbonyl; $R^4$ is C═$CR^5$; $R^5$ is selected from the group consisting of alkoxyalkoxyalkyl, alkoxycarbonylalkoxyalkyl, arylthioalkyl, arylsulfinylalkyl, arylsulfonylalkyl, cycloalkyl, cycloalkylalkoxyalkyl, cycloalkylalkyl, cycloalkyloxyalkyl, haloalkoxyalkoxyalkyl, heteroaryl, heteroaryloxyalkyl, heterocycle, heterocyclecarbonylalkyl, heterocyclecarbonyloxyalkyl, heterocycleoxyalkyl, $(NR^aR^b)$carbonylalkoxyalkyl, $(NR^cR^d)$alkyl; $R^c$ is selected from the group consisting of hydrogen and alkyl; and $R^d$ is selected from the group consisting of alkylsulfonyl, arylsulfonyl, heteroarylcarbonyl, and heteroarylcarbonyl.

In another embodiment, the present invention relates to a pharmaceutical composition comprising a compound of formula (I) or a therapeutically acceptable salt thereof, in combination with a therapeutically acceptable carrier.

In another embodiment, the present invention relates to a method for inhibiting a protein kinase in a patient in recognized need of such treatment comprising administering to the patient a therapeutically acceptable amount of a compound of formula (I), or a therapeutically acceptable salt thereof.

In another embodiment, the present invention relates to a method for treating cancer in a patient in recognized need of such treatment comprising administering to the patient a therapeutically acceptable amount of a compound of formula (I), or a therapeutically acceptable salt thereof.

As used in the present specification the following terms have the meanings indicated:

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein, means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkoxyalkyl" as used herein, means an alkoxyalkoxy group, as defined herein, appended to the parent molecular moiety through an alkyl group, as defined herein. Representative examples of alkoxyalkoxyalkyl include, but are not limited to, tert-butoxymethoxymethyl, ethoxymethoxymethyl, (2-methoxyethoxy)methyl, and 2-(2-methoxyethoxy)ethyl.

The term "alkoxyalkyl" as used herein, means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkoxy" as used herein, means an alkoxycarbonyl group, as defined herein, appended to the parent molecular moiety through an alkoxy group, as defined herein. Representative examples of alkoxycarbonylalkoxy include, but are not limited to, 3-(methoxycarbonyl)propoxy, 4-(ethoxycarbonyl)butoxy, and 2-(tert-butoxycarbonyl)ethoxy.

The term "alkoxycarbonylalkoxyalkyl" as used herein, means an alkoxycarbonylalkoxy group, as defined herein, appended to the parent molecular moiety through an alkyl group, as defined herein. Representative examples of alkoxycarbonylalkoxyalkyl include, but are not limited to, 2-(3-(methoxycarbonyl)propoxy)ethyl, 2-(4-(ethoxycarbonyl)butoxy)ethyl, and 2-(2-(tert-butoxycarbonyl)ethoxy)ethyl.

The term "alkoxycarbonylalkyl" as used herein, means an alkoxycarbonyl group, as defined herein, appended to the parent molecular moiety through an alkyl group, as defined herein. Representative examples of alkoxycarbonylalkyl include, but are not limited to, 3-methoxycarbonylpropyl, 4-ethoxycarbonylbutyl, and 2-tert-butoxycarbonylethyl.

The term "alkoxysulfonyl" as used herein, means an alkoxy group, as defined herein, appended appended to the parent molecular moiety through a sulfonyl group, as defined herein. Representative examples of alkoxysulfonyl include, but are not limited to, methoxysulfonyl, ethoxysulfonyl and propoxysulfonyl.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonylalkyl" as used herein, means an alkylcarbonyl group, as defined herein, appended to the parent molecular moiety through an alkyl group, as defined herein. Representative examples of alkylcarbonylalkyl include, but are not limited to, 2-oxopropyl, 3,3-dimethyl-2-oxopropyl, 3-oxobutyl, and 3-oxopentyl.

The term "alkylcarbonyloxy" as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylene" means a divalent group derived from a straight or branched chain hydrocarbon of from 1 to 8 carbon atoms. Representative examples of alkylene include, but are not limited to, —$CH_2$—, —$CH(CH_3)$—, —$C(CH_3)_2$—, —$CH_2CH_2$—, —$CH_2CH_2CH_2CH_2$—, —$CH_2C(CH_3)_2CH_2$—, —$CH_2CH_2CH_2CH_2$—, and —$CH_2CH(CH_3)CH_2$—.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio.

The term "alkylthioalkyl" as used herein, means an alkylthio group, as defined herein, appended to the parent molecular moiety through an alkyl group, as defined herein. Representative examples of alkylthioalkyl include, but are not limited, methylthiomethyl and 2-(ethylthio)ethyl.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "aryl" as used herein, means a phenyl group, or a bicyclic or a tricyclic fused ring system wherein one or more of the fused rings is a phenyl group. Bicyclic fused ring systems are exemplified by a phenyl group fused to a cycloalkyl group, as defined herein, or another phenyl group. Tricyclic fused ring systems are exemplified by a bicyclic fused ring system fused to a cycloalkyl group, as defined herein, or another phenyl group. Representative examples of aryl include, but are not limited to, anthracenyl, azulenyl, fluorenyl, indanyl, indenyl, naphthyl, phenyl and tetrahydronaphthyl.

The aryl groups of this invention can be substituted with 0, 1, 2, 3, 4, or 5 substituents independently selected from alkenyl, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylthio, alkylthioalkyl, alkynyl, carboxy, carboxyalkyl, cyano, cyanoalkyl, ethylenedioxy, formyl, haloalkoxy, haloalkyl, halogen, hydroxy, hydroxyalkyl, mercapto, methylenedioxy, nitro, $R^aR^bN$—, and $(R^aR^bN)$carbonyl.

The term "arylalkoxy" as used herein, means an aryl group, as defined herein, appended to the parent molecular moiety through an alkoxy group, as defined herein. Representative examples of arylalkoxy include, but are not limited to, 2-phenylethoxy, 3-naphth-2-ylpropoxy, and 5-phenylpentyloxy.

The term "arylalkoxyalkyl" as used herein, means an arylalkoxy group, as defined herein, appended to the parent molecular moiety through an alkyl group, as defined herein. Representative examples of arylalkoxyalkyl include, but are not limited to, 2-phenylethoxymethyl, 3-naphth-2-ylpropoxymethyl, and 5-phenylpentyloxymethyl.

The term "arylalkyl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "aryloxy" as used herein, means an aryl group, as defined herein, appended to the parent molecular moiety through an oxygen atom. Representative examples of aryloxy include, but are not limited to, phenoxy, naphthyloxy, 3-bromophenoxy, 4-chlorophenoxy, 4-methylphenoxy, and 3,5-dimethoxyphenoxy.

The term "aryloxyalkyl" as used herein, means an aryloxy group, as defined herein, appended to the parent molecular moiety through an alkyl group, as defined herein. Representative examples of aryloxyalkyl include, but are not limited to, phenoxymethyl, 2-phenoxyethyl, 3-naphth-2-yloxypropyl and 3-bromophenoxymethyl.

The term "arylsulfinyl" as used herein, means an aryl group, as defined herein, appended to the parent molecular moiety through a sulfinyl group. Representative examples of arylsulfinyl include, but are not limited to, phenylsulfinyl and 2-naphthylsulfinyl.

The term "arylsulfinylalkyl" as used herein, means an arylsulfinyl group, as defined herein, appended to the parent molecular moiety through an alkyl group. Representative examples of arylsulfinylalkyl include, but are not limited to, 2-(phenylsulfinyl)ethyl and 2-(2-naphthylsulfinyl)ethyl.

The term "arylsulfonyl" as used herein, means an aryl group, as defined herein, appended to the parent molecular moiety through a sulfonyl group. Representative examples of arylsulfonyl include, but are not limited to, phenylsulfonyl and 2-naphthylsulfonyl.

The term "arylsulfonylalkyl" as used herein, means an arylsulfonyl group, as defined herein, appended to the parent molecular moiety through an alkyl group. Representative examples of arylsulfonylalkyl include, but are not limited to, 2-(phenylsulfonyl)ethyl and 2-(2-naphthylsulfonyl)ethyl.

The term "arylthio" as used herein, means an aryl group, as defined herein, appended to the parent molecular moiety through a sulfur atom. Representative examples of arylthio include, but are not limited to, phenylthio and 2-naphthylthio.

The term "arylthioalkyl" as used herein, means an arylthio group, as defined herein, appended to the parent molecular moiety through an alkyl group, as defined herein. Representative examples of arylthioalkyl include, but are not limited to, phenylthiomethyl, 2-naphth-2-ylthioethyl, and 5-phenylhexylthiomethyl.

The term "carbonyl" as used herein, means a —C(O)— group.

The term "carboxy" as used herein, means a —CO$_2$H group.

The term "carboxyalkyl" as used herein, means a carboxy group, as defined herein, appended to the parent molecular moiety through an alkyl group, as defined herein. Representative examples of carboxyalkyl include, but are not limited to, carboxymethyl, 2-carboxyethyl, and 3-carboxypropyl.

The term "cyano" as used herein, means a —CN group.

The term "cyanoalkyl" as used herein, means a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "cycloalkyl" as used herein, means a saturated cyclic hydrocarbon group containing from 3 to 8 carbons, examples of cycloalkyl include cyclopropyl, cyclobutyl, cyclopentyl, cyclohexyl, cycloheptyl, and cyclooctyl.

The cycoalkyl groups of the present invention are optionally substituted with 1, 2, 3, or 4 substituents selected from alkenyl, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylthio, alkylthioalkyl, alkynyl, carboxy, carboxyalkyl, cyano, cyanoalkyl, ethylenedioxy, formyl, haloalkoxy, haloalkyl, halogen, hydroxy, hydroxyalkyl, mercapto, methylenedioxy, nitro, oxo, $R^aR^bN$— and $(R^aR^bN)$carbonyl.

The term "cycloalkylalkoxy" as used herein, means a cycloalkyl group, as defined herein, appended to the parent molecular moiety through an alkoxy group, as defined herein.

The term "cycloalkylalkoxyalkyl" as used herein, means a cycloalkylalkoxy group, as defined herein, appended to the parent molecular moiety through an alkyl group, as defined herein.

The term "cycloalkylalkyl" as used herein, means a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, and 4-cycloheptylbutyl.

The term "cycloalkyloxy" as used herein, means a cycloalkyl group, as defined herein, appended to the parent molecular moiety through an oxygen atom.

The term "cycloalkyloxyalkyl" as used herein, means a cycloalkyloxy group, as defined herein, appended to the parent molecular moiety through an alkyl group.

The term "ethylenedioxy" as used herein, means a —O(CH$_2$)$_2$O— group wherein the oxygen atoms of the ethylenedioxy group are attached to the parent molecular moiety through one carbon atom forming a 5 membered ring or the oxygen atoms of the ethylenedioxy group are attached to the parent molecular moiety through two adjacent carbon atoms forming a six membered ring.

The term "formyl" as used herein, means a —C(O)H group.

The term "halo" or "halogen" as used herein, means —Cl, —Br, —I or —F.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, difluoromethoxy, trifluoromethoxy, and pentafluoroethoxy.

The term "haloalkoxyalkoxy" as used herein, means a haloalkoxy group, as defined herein, appended to the parent molecular moiety through an alkoxy group, as defined herein. Representative examples of haloalkoxyalkoxy include, but are not limited to, 2-(chloromethoxy)ethoxy, 2-(2-fluoroethoxy)ethoxy, 2-(trifluoromethoxy)ethoxy, and 2-(pentafluoroethoxy)ethoxy.

The term "haloalkoxyalkoxyalkyl" as used herein, means a haloalkoxyalkoxy group, as defined herein, appended to the parent molecular moiety through an alkyl group, as defined herein. Representative examples of haloalkoxyalkoxyalkyl include, but are not limited to, (2-(chloromethoxy)ethoxy)methyl, (2-(2-fluoroethoxy)ethoxy)methyl, (2-(trifluoromethoxy)ethoxy)methyl, (2-(pentafluoroethoxy)ethoxy)methyl, (2-(difluoromethoxy)ethoxy)methyl, 2-(2-(chloromethoxy)ethoxy)ethyl, 2-(2-(2-fluoroethoxy)ethoxy)ethyl, 2-(2-(trifluoromethoxy)ethoxy) ethyl, 2-(2-(difluoromethoxy)ethoxy)ethyl, and 2-(2-(pentafluoroethoxy)ethoxy)ethyl.

The term "haloalkoxyalkyl" as used herein, means a haloalkoxy group, as defined herein, appended to the parent molecular moiety through an alkyl group, as defined herein. Representative examples of haloalkoxyalkyl include, but are not limited to, (2-(chloromethoxy)ethoxy)methyl, (2-(2-fluoroethoxy)ethoxy)methyl, (2-(trifluoromethoxy)ethoxy)methyl, and (2-(pentafluoroethoxy)ethoxy)methyl.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, means an aromatic monocyclic ring or an aromatic bicyclic ring. The aromatic monocyclic rings are five or six membered rings containing at least one heteroatom independently selected from the group consisting of N, O, and S. The five membered aromatic monocyclic rings have two double bonds and the six membered aromatic monocyclic rings have three double bonds. The aromatic bicyclic rings consist of an aromatic monocyclic ring fused to a phenyl group or fused to an additional aromatic monocyclic ring. Nitrogen heteroatoms contained within the heteroaryl can be optionally oxidized to the N-oxide or optionally protected with a nitrogen protecting group known to those in the art. The heteroaryl rings are connected to the parent molecular moiety through a carbon or nitrogen atom. Representative examples of heteroaryl include, but are not limited to, benzothienyl, benzoxadiazolyl, cinnolinyl, furopyridinyl, furyl, imidazolyl, indazolyl, indolyl, isoxazolyl, isoquinolinyl, isothiazolyl, naphthyridinyl, oxadiazolyl, oxazolyl, pyridinyl, pyridazinyl, pyrimidinyl, pyrazinyl, pyrazolyl, pyrrolyl, pyridinium N-oxide, quinolinyl, tetrazolyl, thiadiazolyl, thiazolyl, thieno[2,3-b]thiophene, thienopyridinyl, thienyl, triazolyl, and triazinyl.

The heteroaryl groups of the present invention are substituted with 0, 1, 2, 3, or 4 substituents independently selected from alkenyl, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylthio, alkylthioalkyl, alkynyl, carboxy, carboxyalkyl, cyano, cyanoalkyl, ethylenedioxy, formyl, haloalkoxy, haloalkyl, halogen, hydroxy, hydroxyalkyl, mercapto, methylenedioxy, nitro, R$^a$R$^b$N— and (R$^a$R$^b$N)carbonyl.

The term "heteroarylalkoxy" as used herein, means a heteroaryl group, as defined herein, appended to the parent molecular moiety through an alkoxy group, as defined herein.

The term "heteroarylalkoxyalkyl" as used herein, means a heteroarylalkoxy group, as defined herein, appended to the parent molecular moiety through an alkyl group, as defined herein.

The term "heteroarylalkyl" as used herein, means a heteroaryl, as defined herein, appended to the parent molecular moiety through an alkyl group, as defined herein. Representative examples of heteroarylalkyl include, but are not limited to, fur-3-ylmethyl, 1H-imidazol-2-ylmethyl, 1H-imidazol-4-ylmethyl, 1-(pyridin-4-yl)ethyl, pyridin-3-ylmethyl, 6-chloropyridin-3-ylmethyl, pyridin-4-ylmethyl, (6-(trifluoromethyl)pyridin-3-yl)methyl, (6-(cyano)pyridin-3-yl)methyl, (2-(cyano)pyridin-4-yl)methyl, (5-(cyano)pyridin-2-yl)methyl, (2-(chloro)pyridin-4-yl)methyl, pyrimidin-5-ylmethyl, 2-(pyrimidin-2-yl)propyl, thien-2-ylmethyl, thien-3-ylmethyl, [1,2,3]triazolylmethyl, and [1,2,4]triazolylmethyl.

The term "heteroarylcarbonyl" as used herein, means a heteroaryl group, as defined herein, appended to the parent molecular moiety through a carbonyl group, as defined herein. Representative examples of heteroarylcarbonyl include, but are not limited to, fur-3-ylcarbonyl, 1H-imidazol-2-ylcarbonyl, 1H-imidazol-4-ylcarbonyl, pyridin-3-ylcarbonyl, 6-chloropyridin-3-ylcarbonyl, pyridin-4-ylcarbonyl, (6-(trifluoromethyl)pyridin-3-yl)carbonyl, (6-(cyano)pyridin-3-yl)carbonyl, (2-(cyano)pyridin-4-yl)carbonyl, (5-(cyano)pyridin-2-yl)carbonyl, (2-(chloro)pyridin-4-yl)carbonyl, pyrimidin-5-ylcarbonyl, pyrimidin-2-ylcarbonyl, thien-2-ylcarbonyl, and thien-3-ylcarbonyl.

The term "heteroaryloxy" as used herein, means a heteroaryl group, as defined herein, appended to the parent molecular moiety through an oxygen atom. Representative examples of heteroaryloxy include, but are not limited to, fur-3-yloxy, 1H-imidazol-2-yloxy, 1H-imidazol-4-yloxy, pyridin-3-yloxy, 6-chloropyridin-3-yloxy, pyridin-4-yloxy, (6-(trifluoromethyl)pyridin-3-yl) oxy, (6-(cyano)pyridin-3-yl) oxy, (2-(cyano)pyridin-4-yl)oxy, (5-(cyano)pyridin-2-yl)oxy, (2-(chloro)pyridin-4-yl)oxy, pyrimidin-5-yloxy, pyrimidin-2-yloxy, thien-2-yloxy, and thien-3-yloxy.

The term "heteroaryloxyalkyl" as used herein, means a heteroaryloxy group, as defined herein, appended to the parent molecular moiety through an alkyl group, as defined herein. Representative examples of heteroaryloxyalkyl include, but are not limited to, pyridin-3-yloxymethyl and 2-quinolin-3-yloxyethyl.

The term "heterocycle," as used herein, means a cyclic, non-aromatic, saturated or partially unsaturated three-, four-, five-, six-, or seven-membered ring where at least one atom is selected from the group consisting of oxygen, nitrogen, and sulfur. The term "heterocycle" also includes bicyclic systems where a heterocycle ring is fused to a phenyl group, a cycloalkenyl group, a cycloalkyl group, or an additional heterocycle. Bicyclic systems also include a heterocyclic ring in which two non-adjacent atoms (wherein the non-adjacent atoms are both carbon atoms or are one carbon atom and one nitrogen atom or are both nitrogen atoms) are linked by an alkylene of between one and eight carbon atoms. The heterocycles of the present invention are attached to the parent molecular group through any substitutable carbon or nitrogen atom in the group. Representative examples of heterocycle include, but are not limited to, azetidinyl, azepanyl, aziridinyl, 2,5-diazabicyclo[2.2.1]heptyl, diazepinyl, 1,3-dioxolanyl, 1,4-dioxanyl, dithianyl, imidazolinyl, imidazolidinyl, morpholinyl, oxazolidinyl, piperazinyl, piperidinyl, pyranyl, hexahydropyrrolo[1,2-a]pyrazinyl, pyrrolinyl, pyrrolidinyl, tetrahydrofuranyl, tetrahydrothienyl, thienyl, thiomorpholinyl, 1,1-dioxidothiomorpholinyl (thiomorpholine sulfone), and thiopyranyl.

The heterocycles of the present invention can be optionally substituted with one, two, three, four, or five substituents independently selected from the group consisting of alkenyl, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylsulfonyl, alkylthio, alkylthioalkyl, alkynyl, carboxy, carboxyalkyl, cyano, cyanoalkyl, cycloalkyl, ethylenedioxy, formyl, haloalkoxy, haloalkyl, halogen, hydroxy, hydroxyalkyl, mercapto, methylenedioxy, nitro, oxo, $R^aR^bN$—, and $(R^aR^bN)$carbonyl.

The term "heterocyclealkoxy" as used herein, means a heterocycle group, as defined herein, appended to the parent molecular moiety through an alkoxy group, as defined herein. Representative examples of heterocyclealkoxy include, but are not limited to, 2-pyridin-3-ylethoxy, 3-quinolin-3-ylpropoxy, and 5-pyridin-4-ylpentyloxy.

The term "heterocyclealkoxyalkyl" as used herein, means a heterocyclealkoxy group, as defined herein, appended to the parent molecular moiety through an alkyl group, as defined herein. Representative examples of heterocyclealkoxyalkyl include, but are not limited to, 2-(2-pyridin-3-ylethoxy)ethyl, 2-(3-quinolin-3-ylpropoxy)ethyl, and 2-(5-pyridin-4-ylpentyloxy)ethyl.

The term "heterocyclealkyl" as used herein, means a heterocycle, as defined herein, appended to the parent molecular moiety through an alkyl group, as defined herein. Representative examples of heterocyclealkyl include, but are not limited to, pyridin-3-ylmethyl and 2-pyrimidin-2-ylpropyl.

The term "heterocyclecarbonyl" as used herein, means a heterocycle, as defined herein, appended to the parent molecular moiety through a carbonyl group, as defined herein. Representative examples of heterocyclecarbonyl include, but are not limited to, pyridin-3-ylcarbonyl and quinolin-3-ylcarbonyl.

The term "heterocyclecarbonylalkyl" as used herein, means a heterocyclecarbonyl, as defined herein, appended to the parent molecular moiety through an alkyl group, as defined herein. Representative examples of heterocyclecarbonylalkyl include, but are not limited to, pyridin-3-ylcarbonylmethyl and quinolin-3-ylcarbonylmethyl.

The term "heterocyclecarbonyloxy" as used herein, means a heterocyclecarbonyl group, as defined herein, appended to the parent molecular moiety through an oxygen atom. Representative examples of heterocyclecarbonyloxy include, but are not limited to, pyridin-3-ylcarbonyloxy and quinolin-3-ylcarbonyloxy.

The term "heterocyclecarbonyloxyalkyl" as used herein, means a heterocyclecarbonyloxy group, as defined herein, appended to the parent molecular moiety through an alkyl group, as defined herein. Representative examples of heterocyclecarbonyloxyalkyl include, but are not limited to, 2-(pyridin-3-ylcarbonyloxy)ethyl and 2-(quinolin-3-ylcarbonyloxy)ethyl.

The term "heterocyclecarbonylalkyl" as used herein, means a heterocyclecarbonyl group, as defined herein, appended to the parent molecular moiety through an alkyl group, as defined herein. Representative examples of heterocyclecarbonylalkyl include, but are not limited to, 2-(pyridin-3-ylcarbonyl)ethyl and 2-(quinolin-3-ylcarbonyl)ethyl.

The term "heterocycleoxy" as used herein, means a heterocycle group, as defined herein, appended to the parent molecular moiety through an oxygen atom. Representative examples of heterocycleoxy include, but are not limited to, pyridin-3-yloxy and quinolin-3-yloxy.

The term "heterocycleoxyalkyl" as used herein, means a heterocycleoxy group, as defined herein, appended to the parent molecular moiety through an alkyl group, as defined herein. Representative examples of heterocycleoxyalkyl include, but are not limited to, pyridin-3-yloxymethyl and 2-quinolin-3-yloxyethyl.

The term "hydroxy" as used herein, means an —OH group.

The term "hydroxyalkyl" as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "mercapto" as used herein, means a —SH group.

The term "methylenedioxy" as used herein, means a —OCH$_2$O— group wherein the oxygen atoms of the methylenedioxy are attached to the parent molecular moiety through two adjacent carbon atoms.

The term "nitrogen protecting group" as used herein, means those groups intended to protect an amino group against undesirable reactions during synthetic procedures. Preferred nitrogen protecting groups are acetyl, benzoyl, benzyl, benzyloxycarbonyl (Cbz), formyl, phenylsulfonyl, tert-butoxycarbonyl (Boc), tert-butylacetyl, trifluoroacetyl, and triphenylmethyl (trityl).

The term "nitro" as used herein, means a —NO$_2$ group.

The term "$R^aR^bN$—" as used herein, means two groups, $R^a$ and $R^b$, which are appended to the parent molecular moiety through a nitrogen atom. $R^a$ and $R^b$ are each independently hydrogen, alkyl, alkylcarbonyl, or formyl. Representative examples of $R^aR^bN$— include, but are not limited to, amino, methylamino, acetylamino, and acetylmethylamino.

The term "$(R^aR^bN)$alkoxy" as used herein, means a $R^aR^bN$— group, as defined herein, appended to the parent molecular moiety through an alkoxy group, as defined herein. Representative examples of $(R^aR^bN)$alkoxy include, but are not limited to, 2-aminoethoxy, 2-(dimethylamino)ethoxy, 3-(dimethylamino)propoxy, and 2-(ethylmethylamino)ethoxy.

The term "$(R^aR^bN)$alkyl" as used herein, means a $R^aR^bN$— group, as defined herein, appended to the parent molecular moiety through an alkyl group, as defined herein. Representative examples of $(R^aR^bN)$alkyl include, but are not limited to, 2-aminoethyl, 2-(dimethylamino)ethyl, 3-(dimethylamino)propyl, and 2-(ethylmethylamino)ethyl.

The term "$(R^aR^bN)$carbonyl" as used herein, means a $R^aR^bN$— group, as defined herein, appended to the parent molecular moiety through a carbonyl group, as defined herein. Representative examples of $(R^aR^bN)$carbonyl include, but are not limited to, aminocarbonyl, (methylamino)carbonyl, (dimethylamino)carbonyl, and (ethylmethylamino)carbonyl.

The term "($R^aR^bN$)carbonylalkoxy" as used herein, means a ($R^aR^bN$)carbonyl group, as defined herein, appended to the parent molecular moiety through an alkoxy group, as defined herein. Representative examples of ($R^aR^bN$)carbonylalkoxy include, but are not limited to, 2-(aminocarbonyl)ethoxy, 2-(methylaminocarbonyl)ethoxy, 2-(dimethylaminocarbonyl)ethoxy, and 2-(ethylmethylaminocarbonyl)ethoxy.

The term "($R^aR^bN$)carbonylalkoxyalkyl" as used herein, means a ($R^aR^bN$)carbonylalkoxy group, as defined herein, appended to the parent molecular moiety through an alkyl group, as defined herein. Representative examples of ($R^aR^bN$)carbonylalkoxyalkyl include, but are not limited to, 2-(2-(aminocarbonyl)ethoxy)ethoxy, 2-2-(methylaminocarbonyl)ethoxy)ethyl, 2-(2-(dimethylaminocarbonyl)ethoxy)ethyl, and 2-(2-(ethylmethylaminocarbonyl)ethoxy)ethyl.

The term "($R^aR^bN$)carbonylalkyl" as used herein, means a ($R^aR^bN$)carbonyl group, as defined herein, appended to the parent molecular moiety through an alkyl group, as defined herein. Representative examples of ($R^aR^bN$)carbonylalkyl include, but are not limited to, 2-(aminocarbonyl)ethyl, 2-(methylaminocarbonyl)ethyl, 2-(dimethylaminocarbonyl)ethyl, and 2-(ethylmethylaminocarbonyl)ethyl.

The term "$R^cR^dN$—" as used herein, means two groups, $R^c$ and $R^d$, which are appended to the parent molecular moiety through a nitrogen atom. $R^c$ is selected from the group consisting of hydrogen and alkyl. $R^d$ is selected from the group consisting of alkylsulfonyl, arylsulfonyl, and heteroarylcarbonyl. Representative examples of $R^cR^dN$— include, but are not limited to, methylsulfonylamino, phenylsulfonylamino, and fur-2-ylcarbonylamino.

The term "($R^cR^dN$)alkyl" as used herein, means a $R^cR^dN$— group, as defined herein, appended to the parent molecular moiety through an alkyl group, as defined herein. Representative examples of ($R^cR^dN$)alkyl include, but are not limited to, (methylsulfonylamino)methyl, phenylsulfonylaminomethyl, and fur-2-ylcarbonylaminomethyl.

The term "oxo" as used herein, means a =O moiety.

The term "sulfinyl" as used herein, means a —S(O)— group.

The term "sulfonyl" as used herein, means a —SO$_2$— group.

The compounds of the present invention can exist as therapeutically acceptable salts. The term "therapeutically acceptable salt," as used herein, represents salts or zwitterionic forms of the compounds of the present invention which are water or oil-soluble or dispersible, which are suitable for treatment of diseases without undue toxicity, irritation, and allergic response; which are commensurate with a reasonable benefit/risk ratio, and which are effective for their intended use. The salts can be prepared during the final isolation and purification of the compounds or separately by reacting an $R^aR^bN$— or an $R^cR^dN$— group with a suitable acid. Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, 2-hydroxyethansulfonate, lactate, maleate, mesitylenesulfonate, methanesulfonate, naphthylenesulfonate, nicotinate, 2-naphthalenesulfonate, oxalate, pamoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Also, $R^aR^bN$— or $R^cR^dN$— groups in the compounds of the present invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric.

The present compounds can also exist as therapeutically acceptable prodrugs. The term "therapeutically acceptable prodrug," refers to those prodrugs or zwitterions which are suitable for use in contact with the tissues of patients without undue toxicity, irritation, and allergic response, are commensurate with a reasonable benefit/risk ratio, and are effective for their intended use. The term "prodrug," refers to compounds which are rapidly transformed in vivo to parent compounds of formula (I) for example, by hydrolysis in blood.

When it is possible that, for use in therapy, therapeutically effective amounts of a compound of formula (I), as well as therapeutically acceptable salts thereof, may be administered as the raw chemical, it is possible to present the active ingredient as a pharmaceutical composition. Accordingly, the invention further provides pharmaceutical compositions, which include therapeutically effective amounts of compounds of formula (I), or therapeutically acceptable salts thereof, and one or more pharmaceutically acceptable carriers, diluents, or excipients. The compounds of formula (I) and therapeutically acceptable salts thereof are as described above. The carrier(s), diluent(s), or excipient(s) must be acceptable in the sense of being compatible with the other ingredients of the formulation and not deleterious to the recepient thereof. In accordance with another aspect of the invention there is also provided a process for the preparation of a pharmaceutical formulation including admixing a compound of formula (I), or a therapeutically acceptable salt thereof, with one or more pharmaceutically acceptable carriers, diluents, or excipients.

Pharmaceutical formulations may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of formula (I), depending on the condition being treated, the severity of the condition, the time of administration, the route of administration, the rate of excretion of the compound employed, the duration of treatment, and the age, gender, weight, and condition of the patient, or pharmaceutical formulations may be presented in unit dose forms containing a predetermined amount of an active ingredient per dose. Preferred unit dosage formulations are those containing a daily dose or sub-dose, as herein above recited, or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intramuscular, intravenous, or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by cumminuting the compound to a suitable fine size and mixing with a similarly comminuted pharmaceutical cerrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, wasces, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an altenative to granulating, the powder mixture can be run through the tablet machine and the result is imperfectly formed slugs broken into granules. The granules can be lubricated to prevent sticking to the tablet forming dies by means of the addition of stearic acid, a stearate salt, is talc, or mineral oil. The lubricated mixture is then compressed into tablets. The compounds of the present invention can also be combined ith a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added ot these coatings to distinguis different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxy ethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or susain the release as for example by coating or embedding particulate material in polymers, wax, or the like.

The compounds of formula (I), and therapeutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The compounds of formula (I), and therapeutically acceptable salts thereof, may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder having a particle size for example in the range 20 to 500 microns which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of a compound of formula (I) for the treatment of neoplastic growth, for example colon or breast carcinoma, will generally be in the range of 0.1 to 100 mg/kg body weight of recipient (mammal) per day and more usually in the range of 1 to 10 mg/kg body weight per day.

The compounds of the present invention and therapeutically acceptable salts thereof, may be employed alone or in combination with other therapeutic agents for the treatment of the above-mentioned conditions. In particular, in anti-cancer therapy, combination with other chemotherapeutic, hormonal, or antibody agents is envisaged as well as combination with surgical therapy and radiotherapy. Combination therapies according to the present invention thus comprise the administration of at least one compound of formula (I), or a therapeutically acceptable salt thereof, and the use of at least one other cancer treatment method. Preferably, combination therapies according to the present invention comprise the administration of at least one other pharmaceutically active agent, preferably an anti-neoplastic agent. The compound(s) of formula (I) and the other pharmaceutically active agent(s) may be administered together or separately and when administered separately this may occur simultaneously or sequentially in any order. The amounts of the compound(s) of formula (I) and the other pharmaceutically active agent(s) and the relative timings of administration will be selected in order to achieve the desired combined therapeutic effect.

The compounds of formula (I), or therapeutically acceptable salts thereof, and at least one additional cancer treatment therapy may be employed in combination concomitantly or sequentially in any therapeutically appropriate combination with such other anti-cancer therapies. In one embodiment, the other anti-cancer therapy is at least one additional chemotherapeutic therapy including administration of at least one anti-neoplastic agent. The administration in combination of a compound of formula (I), or therapeutically acceptable salts thereof, with other anti-neoplastic agents may be in combination in accordance with the invention by administration concomitantly in (1) a unitary pharmaceutical composition including both compounds or (2) separate pharmaceutical compositions each including one of the compounds. Alternatively, the combination may be administered separately in a sequential manner wherein one anti-neoplastic agent is administered first and the other second or vice versa. Such sequential administration may be close in time or remote in time.

Anti-neoplastic agents may incdue anti-neoplastic effects in a cell-cycle specific manner, i.e., are phase specific and act at a specific phase of the cell cycle, or bind DNA and act in a non cell-cycle specific manner, i.e., are non-cell cycle specific and operate by other mechanisms.

Anti-neoplastic agents useful in combination with the compounds and salts of formula (I) include the following:

(1) cell cycle specific anti-neoplastic agents including, but not limited to, diterpenoids such as paclitaxel and its analog docetaxel; vinca alkaloids such as vinblastine, vincristine, vindesine, and vinorelbine; epipodophyllotoxins such as etoposide and teniposide; fluoropyrimidines such as 5-fluorouracil and fluorodeoxyuridine; antimetabolites such as allopurinol, fludurabine, methotrexate, cladrabine, cytarabine, mercaptopurine, and thioguanine; and camptothecins such as 9-amino camptothecin, irinotecan, topotecan, CPT-11, and the various optial forms of 7-(-4-methylpiperazino-methylene)-10,11-ethylenedioxy-20-camptothecin;

(2) cytotoxic chemotherapeutic agents including, but not limited to, alkylating agents such as melphalan, chlorambucil, cyclophosphamide, mechlorethamine, hexamethylmelamine, busulfan, carmustine, lomustine, and dacarbazine; anti-tumor antibiotics such as doxorubicin, daunomycin, epirubicin, idarubicin, mitomycin-C, dacttainomycin, and mithramycin; and platinum coordination complexes such as cisplatin, carboplatin, and oxaliplatin; and (3) other chemotherapeutic agents including, but not limited to, anti-estrogens such as tomixefen, toremifene, raloxifene, droloxifene, and iodoxyfene; progesterogens such as megastrol acetate; aromatase inhibitors such as anastrozole, letrazole, vorazole, and exemestane; antiandrogens such as flutamide, nilutamide, bicalutamide, and cyproterone acetate; LHRH agonists and antagonists such as goserelin acetate and luprolide, testosterone 5α-dihydroreductase inhibitors such as finasteride; metallopreteinase inhibitors such as marimastat; antiprogestogens; urokinase plasminogen activator receptor function inhibitors; growth factor function inhibitors such as inhibitors of the functions of hepatocyte growth factor; erb-B2, erb-B4, epidermal growth factor receptor (EGFR), platelet derived growth factor receptor (PDGFR), vascular endothelial growth factor receptor (VEGFR and TIE-2 (other than those VEGFR and TIE-2 inhibitors described in the present invention)); and other tyrosine kinase inhibitors such as inhibitors of CDK2 and CDK4 inhibitors.

Determination of Biological Activity

The in vitro potency of compounds of the present invention at inhibiting protein kinases was determined by the procedures detailed below.

The potency of compounds can be determined by the amount of inhibition of the phosphorylation of an exogenous substrate, such as a synthetic peptide, relative to control (Z. Songyang et al., Nature. 373:536-539).

KDR Tyrosine Kinase Production Using Baculovirus System:

The coding sequence for the human KDR intra-cellular domain (aa789-1354) was generated through PCR using cDNAs isolated from HUVEC cells. A poly-His6 sequence was introduced at the N-terminus of this protein as well. This fragment was cloned into transfection vector pVL1393 at the Xba 1 and Not 1 site. Recombinant baculovirus (BV) was generated through co-transfection using the BaculoGold Transfection reagent (PharMingen). Recombinant BV was plaque purified and verified through Western analysis. For protein production, SF-9 cells were grown in SF-900-II medium at 2×106/ml, and were infected at 0.5 plaque forming units per cell (MOI). Cells were harvested at 48 hours post infection.

Purification of KDR

SF-9 cells expressing (His)$_6$ KDR(aa789-1354) were lysed by adding 50 ml of Triton X-100 lysis buffer (20 mM Tris, pH 8.0, 137 mM NaCl, 10% glycerol, 1% Triton X-100, 1 mM PMSF, 10 μg/ml aprotinin, 1 μg/ml leupeptin) to the cell pellet from 1 L of cell culture. The lysate was centrifuged at 19,000 rpm in a Sorval SS-34 rotor for 30 min at 4° C. The cell lysate was applied to a 5 ml NiCl$_2$ chelating sepharose column, equilibrated with 50 mM HEPES, pH7.5, 0.3 M NaCl. KDR was eluted using the same buffer containing 0.25 M imidazole. Column fractions were analyzed using SDS-PAGE and an ELISA assay (below) which measures kinase activity. The purified KDR was exchanged into 25 mM HEPES, pH7.5, 25 mM NaCl, 5 mM DTT buffer and stored at −80° C.

Human Tie-2 Kinase Production and Purification

The coding sequence for the human Tie-2 intra-cellular domain (aa775-1124) was generated through PCR using cDNAs isolated from human placenta as a template. A poly-His$_6$ sequence was introduced at the N-terminus and this construct was cloned into transfection vector pVL 1939 at the Xba 1and Not 1 site. Recombinant BV was generated through co-transfection using the BaculoGold Transfection reagent (PharMingen). Recombinant BV was plaque purified and verified through Western analysis. For protein production, SF-9 insect cells were grown in SF-900-II medium at 2×106/ml, and were infected at MOI of 0.5. Purification of the His-tagged kinase used in screening was analogous to that described for KDR.

Human Flt-1 Tyrosine Kinase Production and Purification

The baculoviral expression vector pVL1393 (Phar Mingen, Los Angeles, Calif.) was used. A nucleotide sequence encoding poly-His6 was placed 5' to the nucleotide region encoding the entire intracellular kinase domain of human Flt-1 (amino acids 786-1338). The nucleotide sequence encoding the kinase domain was generated through PCR using cDNA libraries isolated from HUVEC cells. The histidine residues enabled affinity purification of the protein as a manner analogous to that for KDR and ZAP70. SF-9 insect cells were infected at a 0.5 multiplicity and harvested 48 hours post infection.

EGFR Tyrosine Kinase Source

EGFR was purchased from Sigma (500 units/50 μL) and the EGF ligand was acquired from Oncogene Research Products/Calbiochem.

Protein Kinase Source

Lck, Fyn, Src, Blk, Csk, and Lyn, and truncated forms thereof may be commercially obtained (e.g., from Upstate Biotechnology Inc. and Santa Cruz Biotechnology Inc.) or purified from known natural or recombinant sources using conventional methods.

Homogenous Time-Resolved Fluorescence (HTRF) In Vitro Kinase Assay (Mathis, G., HTRF(R) Technology. J Biomol Screen, 1999. 4(6): p. 309-314; Alfred J. Kolb, Paul V. Kaplita, David J. Hayes, Young-Whan Park, Christine Pernell, John S. Major and Gérard Mathis, Drug Discovery Today, 1998, 3, 333-342.):

For example, purified enzyme was mixed with 4 μM N-biotinylated substrate (e.g., poly(Glu$_4$Tyr)) and various concentrations of inhibitor in reaction buffer (50 mM HEPES, pH 7.1, 10 mM MgCl$_2$, 2 mM MnCl$_2$, 0.1% BSA and 1 mM DTT, 40 μL final volume). The kinase reaction was initiated by addition of ATP (1 mM final conc.) in a black 96-well plate (Packard). After 30-60 minutes incubation at room temperature, the reaction was quenched by addition of a buffered EDTA solution (final approximate concentrations: 30 mM EDTA, 0.1% BSA, 0.1% Triton X-100 and 0.24M KF) and a solution of revelation agents (to give 0.084 ng/well streptavidin-XL-665 (Cis-Bio) and 6.5 ng/well antiphsophotyrosine mAb PT66-K Europium kryptate) was added to the reaction mixture. The quenched reaction was allowed to stand at room temperature for 3 hour and then read in a time-resolved fluorescence detector (Discovery, Packard) at 620 nm and 665 nm simultaneously. A 337 nm nitrogen laser was used for excitation. The ratio between the signal of 620 nm and 665 nm was used to determine IC$_{50s}$ for compounds of the present invention. Compounds of the present invention inhibited KDR at IC$_{50's}$ between about 50,000 nm to about 1 nM. Preferred compounds of the present invention inhibited KDR at IC$_{50's}$ between about 200 nM to about 1 nM.

More specific details for the various enzymes are included below in Table 1.

TABLE 1

| | | | | | | | | | |
|---|---|---|---|---|---|---|---|---|---|
| | | | | HTRF ASSAYS | | | | | |
| Enzyme | Construct | MW (kD) | Enz. Reaction Conc. (ng/well) | Assay Buffer | Substrate | Peptide Substrate Conc. (μM) | ATP Conc. (mM) | DMSO Conc. (%) | Reaction Time (min) |
| Lck (Truncated) | 62-509 | 52 | 2.1 | MOPSO | bio-LCK peptide | 4 | 1 | 5 | 60 |
| Src (UBI) | NA | 60 | 0.15 U/well | MOPSO | bio-LCK peptide | 4 | 1 | 5 | 60 |
| Lyn | His6-Tag | 52 | 0.5 | MOPSO | bio-LCK peptide | 4 | 1 | 5 | 60 |
| Fyn (Catalytic Domain) | His6-Tag (257-534) | 34 | 0.15 | MOPSO | bio-LCK peptide | 4 | 1 | 5 | 60 |
| Csk | His6-Tag | 50 | 0.33 | MOPSO | bio-PGT | 4 | 1 | 5 | 10 |

TABLE 1-continued

| | | | HTRF ASSAYS | | | | | | |
|---|---|---|---|---|---|---|---|---|---|
| Enzyme | Construct | MW (kD) | Enz. Reaction Conc. (ng/well) | Assay Buffer | Substrate | Peptide Substrate Conc. (µM) | ATP Conc. (mM) | DMSO Conc. (%) | Reaction Time (min) |
| Lck (Catalytic Domain) | His6-Tag | 35 | 1 | MOPSO | bio-LCK peptide | 4 | 1 | 5 | 60 |
| Blk (Catalytic Domain) | His6-Tag | 60 | 0.15 | MOPSO | bio-LCK peptide | 4 | 1 | 5 | 60 |
| KDR | His6-KDR 789-1354 | 63 | 7 | HEPES | bio-FGFR peptide | 4 | 1 | 5 | 60 |
| Tie2 | His6-Tag | 40 | 12.6 | HEPES | bio-PGT | 10 ng/well | 1 | 5 | 10 |
| cKIT | GST-Fusion | 70 | 4* | HEPES | bio-FGFR peptide | 0.5* | 1 | 5 | 60 |
| Flt1 | His6-Tag | 65 | | HEPES | bio-FGFR peptide | 4 | 1 | 5 | 60 |
| CSF-1r | M-His(6)-CSF-1R Q547-C972 | 50 | 10 | HEPES | bio-Lck peptide | 4 | 1 | 5 | 60 |

Substrates

Bio-FGFR peptide means biotin-(6-aminohexanoic acid)-FGFR peptide wherein the FGFR peptide is as described in Z. Songyang et. al., Nature, 373:536-539 (1995) except that alanine amide was added to the carboxy end.

Bio-LCK peptide means biotin-(6-aminohexanoic acid)-Lck peptide wherein the Lck peptide is as described in Z. Songyang et. al., Nature, 373:536-539 (1995) except that glycine-alanine was added to the amino end, valine was substituted for alanine at the +2 position, and alanine was truncated.

One well contains a total of 40 µL reagents.

Compounds of the present invention have therapeutic utility in the treatment of diseases involving both identified, including those not mentioned herein, and as yet unidentified protein tyrosine kinases which are inhibited by compounds of the present invention.

Cellular Receptor PTK Assays

The following cellular assay was used to determine the level of activity and effect of the different compounds of the present invention on KDR/VEGFR2. Similar receptor PTK assays employing a specific ligand stimulus can be designed along the same lines for other tyrosine kinases using techniques well known in the art.

KDR Cellular Assay

The ability of compounds to inhibit KDR phosphorylation in cells was measured by ELISA following the protocol outlined below.

Day 1 Protocol

KDR transfected 3T3 (embryonic mouse) cells added to 96-well tissue culture plates at 20,000 cells/well. Plates were covered and placed in a 37° C. humidified incubator with 5% CO$_2$ overnight, to allow cells to adhere. Coating solution was prepared: 500 µl/vial PBS was added to 2 vials of anti-KDR antibody, then 1 ml solubilized anti-KDR antibody into 29.0 ml bicarbonate buffer. Coating solution was added to all wells at 150 µl/well (final amount anti-KDR=1 µg/well) and placed at 4° C. overnight.

Day 2 Protocol

Blocking solution (2.1 g dry milk+42 ml PBS=5% milk in PBS) was placed on a stir plate for 30 min. Assay plates were washed twice with PBST, and 200 µl/well blocking solution was added to all wells. Assay plates were covered with plate sealers and placed in a 37° C. microplate chamber until just before cell lysate transfer. Compound stocks were thawed or prepared in DMSO as 5 mM stocks. Dilution medium (DM, 1% DMSO in DMEM) and compounds were diluted by half-log increments for concentration response analysis. Conditioned media was dumped from the tissue culture plates, and plates were blotted dry. Standard solution in DM, compound dilutions in DM, or DM (for high control, negative control, and reference wells) were added to the tissue culture plates, 25 µl/well. Each pair of tissue culture plates was prepared with the same compounds, solutions, and layout; and will be combined later; Tissue culture plates were covered and placed in the 37° C. microplate chamber for 20 min.

VEGF solution was prepared: 110 µl VEGF stock+10.89 ml DM=100 ng/ml VEGF. VEGF solution or DM (for reference wells) was added to the tissue culture plates, 25 µl/well. Tissue culture plates were covered and placed in the 37° C. microplate chamber for 10 min. RIPA buffer was prepared (240 µl NaVO3 stock+240 µl PIC stock+24 µl NaF stock+23.496 ml RIPA base) and added to the tissue culture plates, 50 µl/well. Tissue culture plates were covered and placed on a Labline plate shaker for 10 min (speed about 5). Assay plates were washed twice with PBST. Cell lysates from matching wells of each pair of tissue culture plates were combined to=200 µl/well, and were pipetted up and down to mix.

Cell lysates were transferred to the assay plates using the same layouts, 170 µl/well. Assay plates were covered with plate sealers and placed on a Labline plate shaker for 2 hr (speed about 5). Assay plates were washed 5 times with PBST. Biotin antibody solution was prepared (16 µl biotin antibody stock+32 ml PBST=2000× dilution) and added to the assay plates, 150 µl/well. Assay plates were covered with plate sealers and placed on a Labline plate shaker for 90 min Assay plates were washed 5 times with PBST. Streptavidin-HRP solution was prepared (16 µl streptavidin-HRP stock+32 ml PBST=2000× dilution) and added to the assay plates, 150 µl/well. Assay plates were covered with plate sealers and placed on a Labline plate shaker for 60 min. Assay plates were washed 5 times with PBST. Substrate was added to the assay plates, 100 µl/well. As assay plates developed, the plates were each monitored on a Molecular Devices Spectramax set to 650 nm, until the signal in the high control wells was around 0.6 OD and the signal in the negative control wells was around 0.1-0.15 OD. Stop solution was added to the assay plates, 100 µl/well. The plates were read on a Molecular Devices Spectramax set to 450 nm.

Data was calculated by Assay Explorer, using same-plate high control wells as 0% and reference standard wells as 100% inhibition of KDR phosphorylation. The $IC_{50}$ values were calculated by non-linear regression analysis of the concentration response data Reagents & Materials All reagents are reagent grade or better and are available commercially unless otherwise indicated.

96-well tissue culture plate: flat bottom tissue culture-treated, Costar 3599.

PBS: 1× phosphate-buffered saline, pH 7.4, without calcium chloride, without magnesium chloride; Invitrogen/Gibco 10010 lot 1187052+1201198.

Anti-KDR antibody: anti-human VEGF R2 (KDR) antibody, R&D Systems AF357 lot CUE02405A, 5 mg per vial at 2.630 mg/ml; divided into 38 µl aliquots; stored at −30° C.

Bicarbonate buffer: 1 packet BupH carbonate-bicarbonate buffer pack (Pierce 28382 lot DH58189B)+500 ml nH2O, stored at room temperature.

96-well assay plate: EIA/RIA Easywash plate, high binding; Costar 3369.

Dry milk: purchased from Biorad.

PBST: 1 ml tween+1 L PBS=1% tween in PBS, stored at room temperature.

Tween: Tween 20, Sigma P-1379 lot 033K0711.

DMEM 11965: Dulbecco's modified Eagle medium, high glucose, with L-glutamine, with pyroxidine hydrochloride, without sodium pyruvate; Invitrogen/Gibco 11965 lot 1212380.

VEGF stock: 1 ml PBS/BSA (PBS+0.1% BSA, prepared by Keith Glaser and stored at room temperature, catalog and lot numbers unknown) added to 1 vial VEGF (recombinant human VEGF, R&D Systems 293-VE lot 1116311, 10 µg per vial)=10 µg/ml; divided into 55 µl aliquots; stored at −80° C.

$NaVO_3$ stock: 12.19 mg/ml sodium metavanadate (Sigma S-6383 lot 092K0853, FW 121.9) in nH2O=100 mM, heated at 37° C. to solubilize, then divided into 120 µl aliquots; stored at −20° C.; final concenartion 1 mM in RIPA buffer PIC stock: protease inhibitor cocktail (Sigma P-8340 lot 044K4106); divided into 120 µl aliquots; stored at −20° C.; final dilution 100× in RIPA buffer NaF stock: 41.99 mg/ml sodium fluoride (Sigma S-7920 lot 070K0120, FW 41.99) in $nH_2O$=1 M, divided into 12 µl aliquots; stored at −20° C.; final concentration 1 mM in RIPA buffer.

RIPA base: prepared in $nH_2O$ to 500 ml final volume with components below, pH'd to 7.4; stored at 4° C.

3.94 g Trizma hydrochloride (Sigma T-3253 lot 108H5406, FW 157.6)=50 mM.

5.0 ml Igepal CA-630 (Sigma I-3021 lot 122K0040)=1%.

1.25 g deoxycholic acid, sodium salt (Sigma D-6750 lot 44F-0504, FW 414.5)=0.25%.

4.383 g NaCl (Fisher S271-3 lot 005493, FW 58.44)=150 mM.

226.1 mg EDTA (Sigma E-5391 lot 33H0478, FW 452.2)=1 mM.

Biotin antibody stock: anti-phosphotyrosine, biotin-conjugate, mouse monoclonal IgG2bκ, clone 4G10; Upstate Biotechnology 16-103 lot 23957.

Streptavidin-HRP stock: streptavidin, horseradish peroxidase conjugate; Upstate Biotechnology 18-152 lot 26275, bottle opened Jul. 1, 2004

Substrate: Enhanced K-blue substrate (TMB), Neogen 308177 lot 040405

Stop solution: 14.5 ml phosphoric acid (Sigma P-5811 lot 051K3451, FW 98.00, 17.245 M)+235.5 ml $nH_2O$=1 M; stored at room temperature.

In vivo Uterine Edema Model

This assay measures the capacity of compounds to inhibit the acute increase in uterine weight in mice which occurs in the first few hours following estrogen stimulation. This early onset of uterine weight increase is known to be due to edema caused by increased permeability of uterine vasculature. Cullinan-Bove and Koss (Endocrinology (1993), 133:829-837) demonstrated a close temporal relationship of estrogen-stimulated uterine edema with increased expression of VEGF mRNA in the uterus. These results have been confirmed by the use of neutralizing monoclonal antibody to VEGF which significantly reduced the acute increase in uterine weight following estrogen stimulation (WO 97/42187). Hence, this system can serve as a model for in vivo inhibition of VEGF signalling and the associated hyperpermeability and edema.

Materials: All hormones can be purchased from Sigma (St. Louis, Mo.) or Cal Biochem (La Jolla, Calif.) as lyophilized powders and prepared according to supplier instructions. Vehicle components (DMSO, Cremaphor EL) can be purchased from Sigma (St. Louis, Mo.). Mice (Balb/c, 8-12 weeks old) can be purchased from Taconic (Germantown, N.Y.) and housed in a pathogen-free animal facility in accordance with institutional Animal Care and Use Committee Guidelines.

Method

Day 1: Balb/c mice are given an intraperitoneal (i.p.) injection of 12.5 units of pregnant mare's serum gonadotropin (PMSG).

Day 3: Mice receive 15 units of human chorionic gonadotropin (hCG) i.p.

Day 4: Mice are randomized and divided into groups of 5-10. Test compounds are administered by i.p., i.v. or p.o. routes depending on solubility and vehicle at doses ranging from 1-100 mg/kg. Vehicle control group receive vehicle only and two groups are left untreated.

Thirty minutes later, experimental, vehicle and 1 of the untreated groups are given an i.p. injection of 17-estradiol (500 mg/kg). After 2-3 hours, the animals are sacrificed by $CO_2$ inhalation. Following a midline incision, each uterus was isolated and removed by cutting just below the cervix and at the junctions of the uterus and oviducts. Fat and connective tissue were removed with care not to disturb the integrity of the uterus prior to weighing (wet weight). Uteri are blotted to remove fluid by pressing between two sheets of filter paper with a one liter glass bottle filled with water. Uteri are weighed following blotting (blotted weight). The difference between wet and blotted weights is taken as the fluid content of the uterus. Mean fluid content of treated groups is compared to untreated or vehicle treated groups. Significance is determined by Student's test. Non-stimulated control group is used to monitor estradiol response.

Certain compounds of this invention which are inhibitors of angiogenic receptor tyrosine kinases can also be shown active in a Matrigel implant model of neovascularization. The Matrigel neovascularization model involves the formation of new blood vessels within a clear marble of extracellular matrix implanted subcutaneously which is induced by the presence of proangiogenic factor producing tumor cells (for examples see: Passaniti, A., et al, Lab. Investig. (1992), 67(4), 519-528; Anat. Rec. (1997), 249(1), 63-73; Int. J. Cancer (1995), 63(5), 694-701; Vasc. Biol. (1995), 15(11), 1857-6). The model preferably runs over 3-4 days and endpoints include macroscopic visual/image scoring of neovascularization, microscopic microvessel density determinations, and hemoglobin quantitation (Drabkin method) following removal of the implant versus controls from animals untreated with inhibitors. The model may alternatively employ bFGF or HGF as the stimulus.

The compounds of the present invention may be used in the treatment of protein kinase-mediated conditions, such as benign and neoplastic proliferative diseases and disorders of the immune system. Such diseases include autoimmune diseases, such as rheumatoid arthritis, thyroiditis, type 1 diabetes, multiple sclerosis, sarcoidosis, inflammatory bowel disease, Crohn's disease, myasthenia gravis and systemic lupus erythematosus; psoriasis, organ transplant rejection (e.g.,. kidney rejection, graft versus host disease), benign and neoplastic proliferative diseases, human cancers such as lung, breast, stomach, bladder, colon, pancreatic, ovarian, prostate and rectal cancer and hematopoietic malignancies (leukemia and lymphoma), glioblastoma, infantile hemangioma, and diseases involving inappropriate vascularization (for example diabetic retinopathy, retinopathy of prematurity, choroidal neovascularization due to age-related macular degeneration, and infantile hemangiomas in human beings). Such inhibitors may be useful in the treatment of disorders involving VEGF mediated edema, ascites, effusions, and exudates, including for example macular edema, cerebral edema, acute lung injury and adult respiratory distress syndrome (ARDS). In addition, the compounds of the invention may be useful in the treatment of pulmonary hypertension, particularly in patients with thromboembolic disease (J. Thorac. Cardiovasc. Surg. 2001, 122 (1), 65-73).

Synthetic Methods

Abbreviations which have been used in the descriptions of the schemes and the examples that follow are: Ts for toluenesulfonyl; THF for tetrahydrofuran; DMF for N,N-dimethylformamide; Ms for methanesulfonyl; DPPA for diphenylphosphoryl azide; DBU for 1,8-diazabicyclo[5.4.0]undec-7-ene; PPh$_3$ for triphenylphosphine; and dba for dibenzylideneacetone.

The compounds and processes of the present invention will be better understood in connection with the following synthetic schemes which illustrate the methods by which the compounds of the invention may be prepared. Starting materials can be obtained from commercial sources or prepared by well-established literature methods known to those of ordinary skill in the art.

The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (Protective Groups In Organic Synthesis, Wiley and Sons, 1999).

This invention is intended to encompass compounds having formula (I) when prepared by synthetic processes or by metabolic processes. Preparation of the compounds of the invention by metabolic processes include those occurring in the human or animal body (in vivo) or processes occurring in vitro.

The compounds and processes of the present invention will be better understood in connection with the following synthetic schemes, which illustrate the methods by which the compounds of the invention may be prepared. Starting materials can be obtained from commercial sources or prepared by well-established literature methods known to those of ordinary skill in the art. The groups $R^a$, $R^b$, $R^A$, $R^B$, $R^C$, $R^D$, $R^4$, $R^5$, and $R^8$ are as defined above unless otherwise noted below.

This invention is intended to encompass compounds having formula (I) when prepared by synthetic processes or by metabolic processes. Preparation of the compounds of the invention by metabolic processes include those occurring in the human or animal body (in vivo) or processes occurring in vitro.

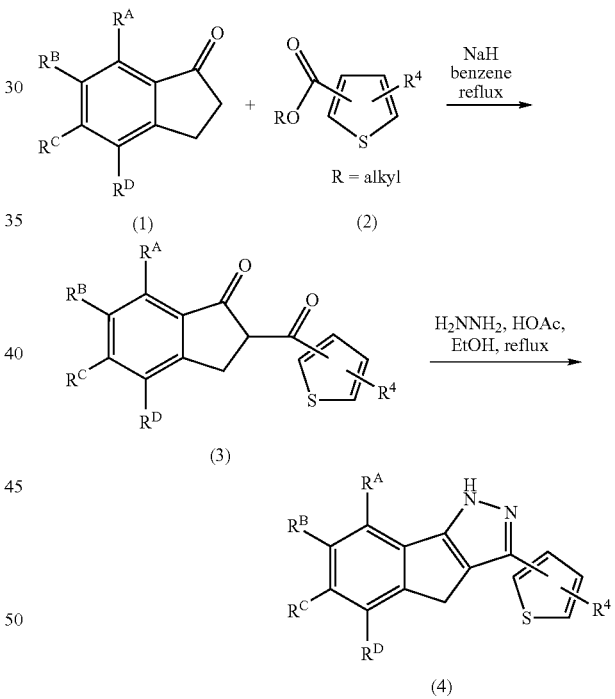

Tricyclic pyrazoles of formula (4) can be prepared as described in Scheme 1. Compounds of formula (1), purchased or prepared using chemistry known to those of the art, are treated with a base, such as sodium hydride, and a thiophene of formula (2), purchased or prepared using chemistry known to those in the art, to provide compounds of formula (3). Typically, the reaction is conducted in benzene at temperatures of about 80° C. for about 2.5 hours. Compounds of formula (3) can be treated with hydrazine, typically in the form of its monohydrate, and an acid such as acetic acid to provide compounds of formula (4). Typically, the reaction is conducted in ethanol at temperatures of about 78° C. for about 4 hours.

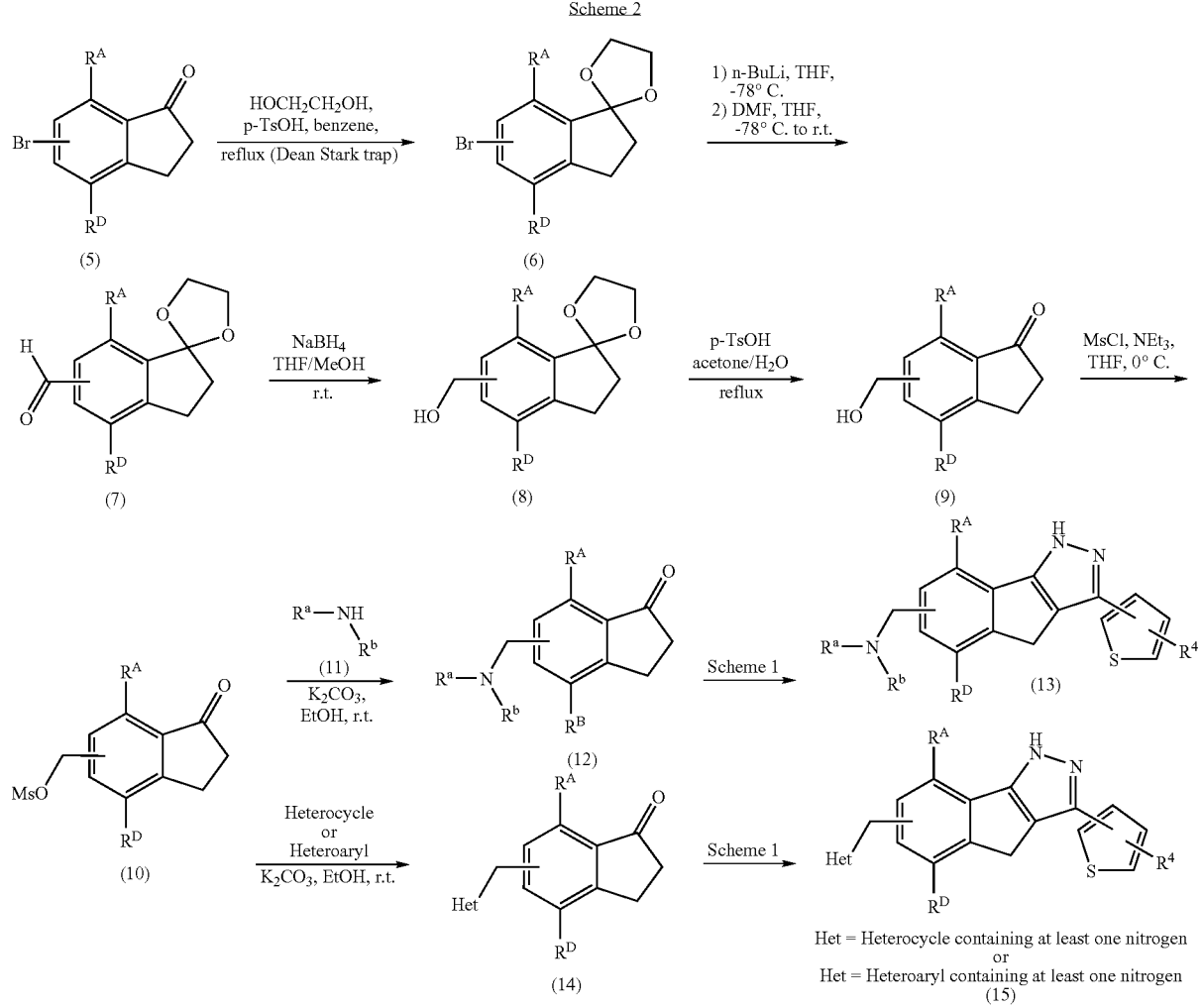

Scheme 2

Het = Heterocycle containing at least one nitrogen
or
Het = Heteroaryl containing at least one nitrogen
(15)

Tricyclic pyrazoles of formula (14) and (15), wherein $R^B$ or $R^C$ is $(R^aR^bN)$alkyl, heterocyclealkyl, or heteroarylalkyl, are prepared as described in Scheme 1. Compounds of formula (5), purchased or prepared using chemistry known in the art, are treated with ethylene glycol in the presence of an acidic catalyst such as p-toluenesulfonic acid monohydrate to provide ketals of formula (6). Typically, the reaction is conducted in benzene under azeotropic conditions at temperatures of about 70° C. to about 80° C. for about 24 hours. Compounds of formula (6) are treated with an alkyllithium, such as n-butyllithium, and N,N-dimethylformamide to provide compounds of formula (7). Typically, the reaction is conducted in tetrahydrofuran at about −78° C. with warming to about 25° C. with total reaction times about 1 to about 4 hours. Compounds of formula (7) are treated with a reducing agent such as sodium borohydride to provide alcohols of formula (8). Typically, the reductions are conducted in a mixture of tetrahydrofuran and methanol at temperatures of about 25° C. in about 2 hours. Alcohols of formula (8) can be treated with p-toluenesulfonic acid monohydroate to provide compounds of formula (9). Typically, the reaction is carried out in a mixture of acetone and water at temperatures of about 56° C. to about 100° C. with reaction time of about 1 hour. Compounds of formula (9) are treated with methanesulfonyl chloride (or p-toluenesulfonyl chloride) in the presence of a base such as triethylamine to provide mesylates of formula (10) (or tosylates). Typically, the reaction is conducted in tetrahydrofuran at temperature of about 0° C. for about 30 minutes to about 1 hour. Compounds of formula (10) are treated with amines $(R^aR^bNH)$ of formula (11) to provide compounds of formula (12). Compounds of formula (12) are treated to conditions as described in Scheme 1 to provide compounds of formula (13) substituted in the $R^B$ or $R^C$ position with an $(R^aR^bN)$alkyl group. Additionally, compounds of formula (10) are treated with a heterocycle containing at least one nitrogen or treated with a heteroaryl group containing at least one nitrogen to provide compounds of formula (14). Compounds of formula (14) are treated to the conditions described in Scheme 1 to provide compounds of formula (15) substituted in the $R^B$ or $R^C$ position with at least one nitrogen containing heterocycle including, but not limited to, piperidines, piperazines, morpholines, pyrrolidines, azepines, diazepines, azetidines, or aziridines) or at least one nitrogen containing heteroaryl group including, but not limited to triazoles, pyrroles, or imidazoles. Typically, the reactions are conducted in ethanol in the presence of a base such as potassium carbonate at about 25° C. for are about 3 hours to about 16 hours.

Scheme 3
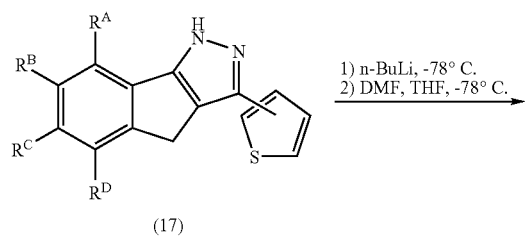
(17)
→ 1) n-BuLi, -78° C.
2) DMF, THF, -78° C.
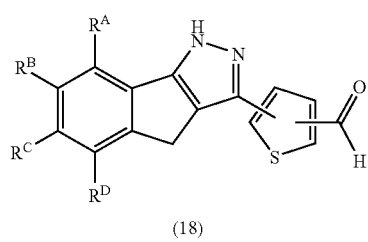
(18)
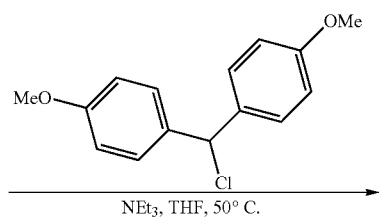
NEt₃, THF, 50° C.
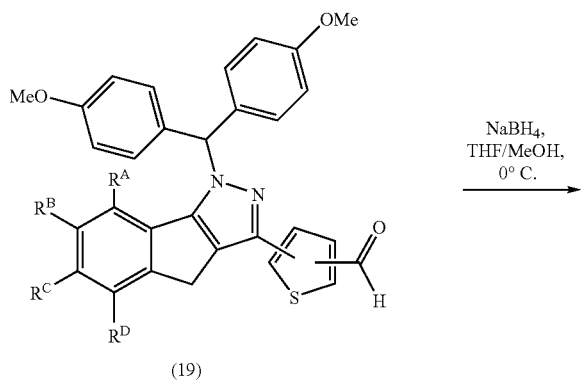
(19)
NaBH₄,
THF/MeOH,
0° C.
→
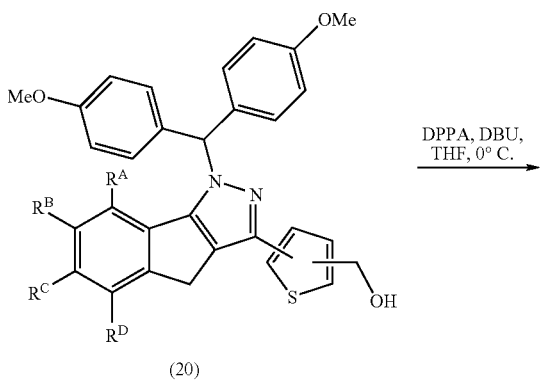
(20)
DPPA, DBU,
THF, 0° C.
→
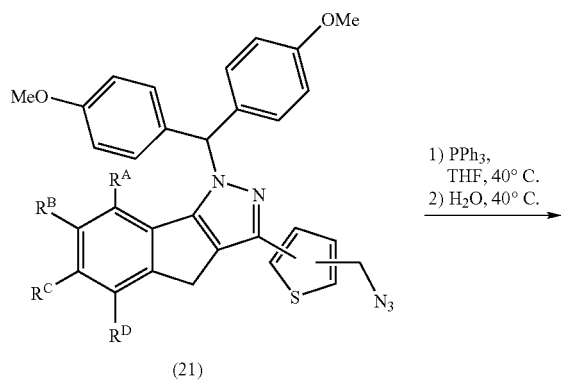
(21)
1) PPh₃,
THF, 40° C.
2) H₂O, 40° C.
→
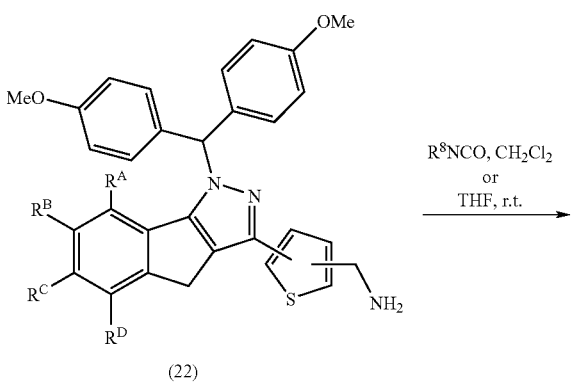
(22)
R⁸NCO, CH₂Cl₂
or
THF, r.t.
→

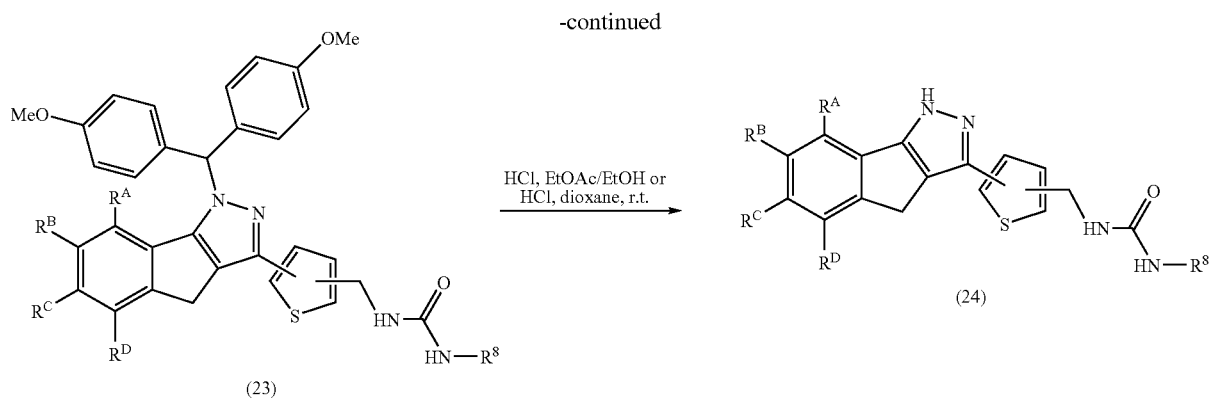

Compounds of formula (24) can be prepared as described in Scheme 3.

Compounds of formula (17) are treated with an alkyllithium, such as n-butyllithium, and N,N-dimethylformamide to provide compounds of formula (18). Typically, the reaction is conducted in tetrahydrofuran at temperatures of about −78° C. for about 1 hour. Compounds of formula (18) are treated with 4,4'-dimethoxybenzhydryl chloride in the presence of a base, typically triethylamine to provide compounds of formula (19). Typically, the reaction is conducted in tetrahydrofuran at temperatures of about 50° C. for about 2.5 hours. Compounds of formula (19) are treated with a reducing agent such as sodium borohydride to provide compounds of formula (20). Typically the reaction is conducted in a mixture of tetrahydrofuran and methanol at temperatures from about 0° C. to about 25° C. for about 3 hours. Compounds of formula (20) are treated with diphenylphosphoryl azide in the presence of a base such as 1,8-diazabicyclo[5.4.0]undec-7ene to provide compounds of formula (21). Typically the reaction is carried out in tetrahedrofuran in the dark. The reaction temperature typically is about 0° C. to about 25° C. and the reaction time is about 2 hours. Compounds of formula (21) are treated with triphenylphosphine in tetrahydrofuran at temperatures of about 40° C. for about 12 hours, water is added to the reaction mixture, and the mixture is heated to about 40° C. for about 6 hours to provide amines of formula (22). Compounds of formula (22) are treated with substituted isocyanates in a solvent such as tetrahydrofuran or dichloromethane to provide compounds of formula (23). Typically, the reaction is conducted at about 25° C. for about 4 to about 12 hours. Compounds of formula (23) are treated with an acid, typically hydrochloric acid, in a solvent such as 1,4-dioxane or a mixture of ethanol and ethyl acetate at about 25° C. for about 12 hours to provide tricyclic pyrazoles of formula (24).

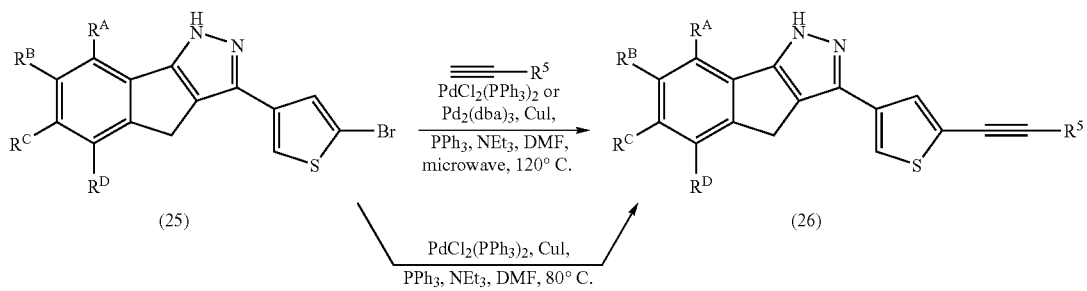

Tricyclic pyrazoles of formula (26) are prepared as described in Scheme 4. Bromo compounds of formula (25) are treated with a substituted alkyne to provide compounds of formula (26). Typically, the reaction is conducted in the presence of a metal catalyst such as dichlorobis(triphenylphosphine)palladium(II) or tris(dibenzylideneacetone)dipalladium(0), a co-catalyst such as copper iodide, a base such as triethylamine or diethylamine, and triphenylphosphine. The reaction is typically conducted in N,N-dimethylformamide either at temperatures of about 80° C. for about 2 hours or in a microwave oven at temperatures of about 120° C. for about 25 minutes.

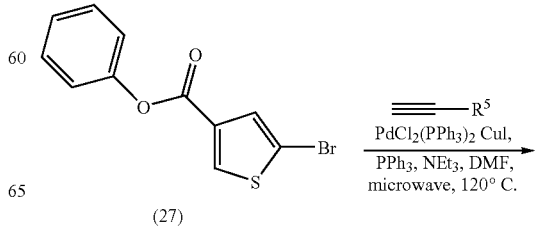

-continued

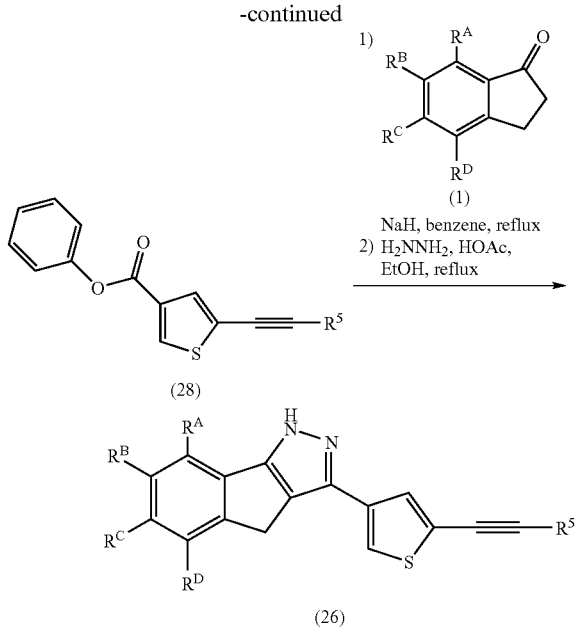

An alternative synthesis of compounds of formula (26) is shown in Scheme 5. Compounds of formula (27) are reacted with a substituted alkyne to form compounds of formula (28). Typically, the reaction is conducted in the presence of a metal catalyst such as dichlorobis(triphenylphosphine)palladium (II) a co-catalyst such as copper iodide, a base such as triethylamine or diethylamine, and triphenylphosphine. The reaction is typically conducted in N,N-dimethylformamide either at temperatures of about 80° C. for about 2 hours or in a microwave oven at temperatures of about 120° C. for about 25 minutes. Compounds of formula (28) are treated with compounds of formula (1) as described in Scheme 1 to provide compounds of formula (26).

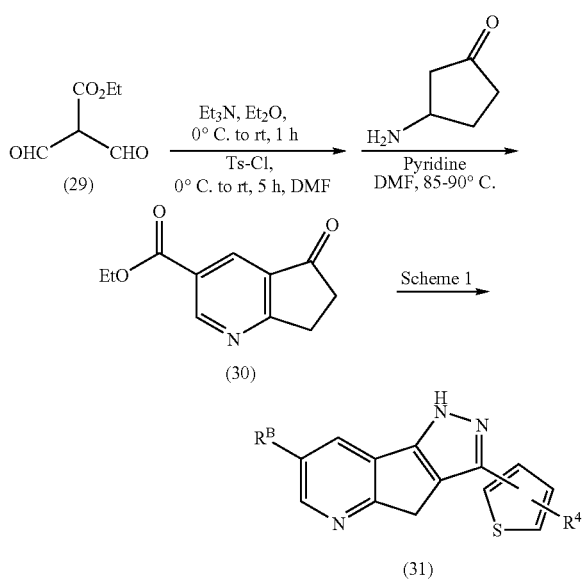

Compounds of formula (31), wherein $R^B$ and $R^4$ are as defined in Formula (I), can be prepared as described in Scheme 6. Ethyl 2-formyl-3-oxopropanoate can be treated with a base such as triethylamine, para-toluenesulfonyl chloride, and 3-aminocyclopent-2-en-1-one to provide dihydrocyclopenta[b]pyridin-5-ones of formula (30). Dihydrocyclopenta[b]pyridin-5-ones of formula (30) can be treated as described in Scheme 1 to provide compounds of formula (31).

The present invention will now be described in connection with certain preferred embodiments which are not intended to limit its scope. On the contrary, the present invention covers all alternatives, modifications, and equivalents as can be included within the scope of the claims. Thus, the following examples, which include preferred embodiments, will illustrate the preferred practice of the present invention, it being understood that the examples are for the purposes of illustration of certain preferred embodiments and are presented to provide what is believed to be the most useful and readily understood description of its procedures and conceptual aspects.

Compounds of the invention were named by ACD/ChemSketch version 5.0 (developed by Advanced Chemistry Development, Inc., Toronto, ON, Canada) or were given names consistent with ACD nomenclature.

EXAMPLE 1

3-(4-bromophenyl)propanoic acid

A mixture of a 60% suspension of sodium hydride in mineral oil (4.8 g, 120 mmol) in N,N-dimethylformamide (50 mL) at about 5° C. was treated with diethyl malonate (36.4 mL, 240 mmol). The mixture was stirred for about 5 minutes, slowly treated with a solution of 4-bromobenzyl bromide (20.0 g, 80 mmol) in N,N-dimethylformamide (20 mL), stirred at room temperature overnight, diluted with water, and extracted with ethyl acetate. The combined organic extracts were dried (MgSO$_4$), filtered, and concentrated under high vacuum. The residue was dissolved in a mixture of acetic acid (46 mL), water (30 mL), and concentrated sulfuric acid (13 mL) and was heated to reflux for 18 hours. The reaction mixture was cooled, concentrated under high vacuum, and diluted with water. The formed crystalline solid was collected by filtration, washed with water and diethyl ether, and was dried under high vacuum to provide the desired product. MS (DCI-NH$_3$): m/z 246, 248 (M+NH$_4$)$^+$.

EXAMPLE 2

5-bromo-2-(2-carboxyethyl)benzoic acid

A solution of 2-(2-carboxyethyl)benzoic acid (5 g, 25.8 mmol) in 71% nitric acid (20 mL) in an amber vial was treated with bromine (1.3 mL, 25.8 mmol). The vial was capped and heated to about 90° C. for about 20 hours. The reaction was cooled, poured into water and 1M hydrochloric acid, and extracted with ethyl acetate. The organic layer was washed with water, dried (Na$_2$SO$_4$), filtered, and concentrated under vacuum. The residue was purified by flash chromatography on silica gel using dichloromethane/methanol (20:1) as eluent to provide the desired product. MS (ESI): m/z 271, 273 (M−H)$^−$.

EXAMPLE 3

6-bromo-1-indanone

A suspension of Example 1 (23.5 g, 91 mmol) in toluene (10 mL) was treated thionyl chloride (10 mL, 137 mmol) and the mixture was stirred at about 60° C. for about 1 hour. The mixture was concentrated under reduced pressure and was slowly added to a mixture of aluminum chloride (13.4 g, 100 mmol) in 1,2-dichloroethane (90 mL) at about 5° C. The reaction mixture was stirred at room temperature for about 1 hour, poured into ice water and was extracted with dichloromethane. The combined organic extracts were washed successively with water, 5% aqueous sodium bicarbonate and brine, dried (MgSO$_4$), filtered and concentrated under vacuum. The residue was purified by flash chromatography on silica gel using hexane/ethyl acetate (2:1) as eluent to present the desired product. MS (DCI-NH$_3$): m/z 228, 230 (M+NH$_4$)$^+$.

EXAMPLE 4

6-bromo-4-nitro-1-indanone

Fuming nitric acid (20 mL, 476 mmol) was cooled to about 0° C. and treated slowly with Example 3 (4 g, 18.95 mmol) over a period of about 30 minutes. The reaction mixture was allowed to warm to about 10° C. over about 30 minutes and then the mixture was poured into ice water (100 mL). The white precipitate was collected by filtration and was washed with water. The solid was dissolved in dichloromethane and the solution was washed with 5% aqueous sodium hydroxide and water. The organic layer was dried (Na$_2$SO$_4$), filtered and concentrated. The residue was purified by flash column chromatography on silica gel using hexane/ethyl acetate (2:1) as the mobile phase to provide the desired product. MS (ESI): m/z 254, 256 (M−H)$^−$.

EXAMPLE 5

1-oxo-4-indanecarboxylic acid

A mixture of 2-(2-carboxyethyl)benzoic acid (1.0 g, 5.15 mmol), sodium chloride (320 mg, 5.41 mmol) and aluminum chloride (3.43 g, 25.75 mmol) was heated to about 160° C. for about 2 hours. The mixture was cooled with an acetone/dry ice bath and a mixture of ice and water was slowly added, followed by concentrated hydrochloric acid (AMOUNT). The mixture was filtered and the obtained solid was purified by flash chromatography on silica gel using dichloromethane/methanol (50:1) as eluent. The product was further recrystallized from methanol to provide the desired product. MS (ESI): m/z 175 (M−H)$^−$.

EXAMPLE 6

6-bromo-1-oxo-4-indanecarboxylic acid

The desired product was prepared by substituting 5-bromo-2-(2-carboxyethyl)benzoic acid for 2-(2-carboxyethyl)benzoic acid in Example 5. MS (ESI): m/z 253, 255 (M−H)$^−$.

EXAMPLE 7

4-nitro-1-indanone

A suspension of chromium(VI) oxide (36.7 g, 367.7 mmol) in acetic acid (400 mL) was added slowly to a solution of 4-nitroindane (20 g, 122.6 mmol) in glacial acetic acid (500 mL). Extra acetic acid (200 mL) was used to transfer all the chromium(VI)oxide. The reaction was stirred vigorously at room temperature for about 5 hours and was then quenched with water (200 mL). Most of the acetic acid was removed under high vacuum and the crude product was extracted with ethyl acetate. The organic layer was washed with saturated aqueous sodium bicarbonate, dried (Na$_2$SO$_4$), filtered and concentrated. The residue was purified by flash chromatography on silica gel using first hexane/ethyl acetate (20:1) as eluent to remove unreacted starting material and then hexane/ethyl acetate (10:1) to provide the desired product. MS (ESI): m/z 176 (M−H)$^−$.

EXAMPLE 8

1-(ethoxymethyl)-4-methylpiperazine

To a suspension of paraformaldehyde and potassium carbonate in ethanol at about 0° C. was added 1-methylpiperazine dropwise. The mixture was stirred vigorously at room temperature for about 67 hours and filtered. The filter cake was washed with diethyl ether and the combined filtrates were concentrated under vacuum. The residue was distilled under reduced pressure (30° C. at 2.5 Torr) to provide the desired product. $^1$H NMR (500 MHz, DMSO-d$_6$): δ 1.09 (t, J=6.8 Hz, 3H), 2.14 (s, 3H), 2.28 (m, 4H), 2.56 (m, 4H), 3.40 (q, J=6.8 Hz, 2H), 3.96 (s, 2H).

EXAMPLE 9

4-hydroxy-5-[(4-methyl-1-piperazinyl)methyl]-1-indanone

A solution of 4-hydroxy-1-indanone (1.0 g, 6.75 mmol) and Example 8 (1.17 g, 7.42 mmol) in acetonitrile (15 mL) was heated to reflux for about 16 hours. The mixture was cooled, concentrated under vacuum and the residue was purified by flash column chromatography on silica gel using dichloromethane/methanol (15:1) as the mobile phase to provide the desired product. MS (DCI-NH$_3$): m/z 261 (M+H)$^+$.

EXAMPLE 10

5-[(4-methyl-1-piperazinyl)methyl]-1-oxo-2,3-dihydro-1H-inden-4-yl methoxyacetate To a solution of Example 9 (100 mg, 0.38 mmol) in pyridine (1 mL) was added methoxyacetyl chloride (40 mg, 0.38 mmol) under vigorous stirring. The mixture was shaken for about 1 hour and then the solvent was removed under vacuum. The residue was purified by flash column chromatography on silica gel using hexane/ethyl acetate (1:1) as the mobile phase to provide the desired product. MS (APCI): m/z 333 (M+H)$^+$.

EXAMPLE 11

4-propoxy-1-indanone

To a suspension of 4-hydroxy-1-indanone (1.0 g, 6.75 mmol) in acetone (30 mL) was added potassium carbonate (2.8 g, 20.24 mmol) and propyl iodide (0.72 mL, 7.42 mmol) and the reaction mixture was heated to reflux for about 7 hours. The reaction was cooled, concentrated under vacuum and partitioned between water and dichloromethane. The layers were separated and the aqueous layer was extracted with dichloromethane. The combined organic extracts were dried (Na$_2$SO$_4$), filtered and concentrated under vacuum and the residue was purified by flash column chromatography on silica gel using dichloromethane as the mobile phase to provide the desired product. MS (APCI): m/z 191 (M+H)$^+$.

EXAMPLE 12

5-{[(1-oxo-2,3-dihydro-1H-inden-4-yl)oxy]methyl}-1,3-oxazolidin-2-one

A mixture of 4-hydroxy-1-indanone (500 mg, 3.37 mmol), cesium carbonate (2.0 g, 6.14 mmol) and 5-chloromethyl-2-oxazolidinone (503 mg, 3.71 mmol) in N,N-dimethylformamide (5 mL) was stirred under nitrogen in a heavy walled process vial in a microwave synthesizer at about 200° C. for about 5 minutes. The reaction mixture was cooled, concentrated under vacuum and the residue was purified by flash column chromatography on silica gel using dichloromethane/methanol (50:1) as the mobile phase to provide the desired product. MS (ESI): m/z 248 (M+H)$^+$.

| Example Number | R | MS (APCI): | Reference Procedure |
|---|---|---|---|
| 13 | (butyl chain) | m/z 205 (M + H)$^+$ | Example 11 |
| 14 | (methoxyethyl chain) | m/z 207 (M + H)$^+$ | Example 11 |
| 15 | (ethyl ester chain) | m/z 235 (M + H)$^+$ | Example 11 |
| 16 | (methoxycarbonyl furan chain) | m/z 287 (M + H)$^+$ | Example 12 |
| 17 | (tetrahydrofuran methyl) | m/z 233 (M + H)$^+$ | Example 12 |
| 18 | (tetrahydropyran methyl) | m/z 247 (M + H)$^+$ | Example 12 |
| 19 | (cyanomethyl) | m/z 188 (M + H)$^+$ | Example 12 |

EXAMPLE 20

6'-bromo-2',3'-dihydrospiro[1,3-dioxolane-2,1'-indene]

A mixture of Example 3 (13.0 g, 61.8 mmol), p-toluenesulfonic acid (23 mg, 0.12 mmol) and ethylene glycol (27.6 mL, 494.6 mmol) in benzene (140 mL) was heated to reflux for about 24 hours, using a Dean-Stark trap to separate the forming water. The mixture was cooled, poured into excess 5% aqueous sodium bicarbonate and was extracted with toluene. The combined organic extracts were washed with brine, dried (MgSO$_4$), filtered and concentrated under vacuum. The residue was purified by flash column chromatography on silica gel using dichloromethane as the mobile phase to provide the desired product. MS (DCI-NH$_3$): m/z 254, 256 (M)$^+$.

| Example Number | R$_1$ | R$_2$ | R$_3$ | $^1$H NMR (500 MHz, CD$_3$OD) | MS (ESI) | Reference Procedure |
|---|---|---|---|---|---|---|
| 21 | H | Br | H | | m/z 254, 256 (M)$^+$ | Example 20 |
| 22 | H | H | NO$_2$ | | m/z 222 (M + H)$^+$ | Example 20 |
| 23 | Br | H | NO$_2$ | δ 2.26(m, 2H) 2.94(dt, J=6.8, 1.0 Hz, 2H)4.00 (m, 4H) 7.37(dt, J=8.1, 1.0 Hz, 1H) 7.70(d, J= 8.1 Hz, 1H). | | Example 20 |

EXAMPLE 24

1-methyl-4-[(4'-nitro-2',3'-dihydrospiro[1,3-dioxolane-2,1'-inden]-6'-yl)carbonyl]piperazine Example 23 (1.1 g, 0.81 mmol) was treated with triethylamine (20 mL, 143.5 mmol), 1-methylpiperazine (0.73 mL, 6.6 mmol) and [1,1'bis(diphenylphosphino) ferrocene] dichloropalladium(II) complex with dichloromethane (1:1) (150 mg, 0.18 mmol). The mixture was carbonylated at 130 psi and about 110° C. for about 20 hours. The mixture was filtered through diatomaceous earth (Celite®), concentrated under vacuum and the residue was purified by flash column chromatography on silica gel using dichloromethane/methanol (20:1) as the mobile phase to provide the desired product. MS (ESI) m/z 348 (M+H)$^+$.

EXAMPLE 25

2',3'-dihydrospiro[1,3-dioxolane-2,1'-inden]-4'-amine

A solution of Example 22 (10.1 g, 45.6 mmol) in ethyl acetate (120 mL) and ethanol (120 mL) was treated with 10 wt. % palladium on activated carbon (1.0 g) and the mixture was hydrogenated at 60 psi and ambient temperature for about 1 hour. The reaction mixture was filtered through diatomaceous earth (Celite®) and was concentrated under vacuum to provide the desired product. MS (ESI): m/z 192 (M+H)$^+$.

EXAMPLE 26

3-oxo-5-indanecarboxylic acid

To a solution of Example 20 (1.0 g, 3.92 mmol) in tetrahydrofuran (10 mL) at −78° C. was added dropwise 2.5M solution of n-butyllithium in hexanes (2.35 mL, 5.88 mmol). Carbon dioxide gas was bubbled through the reaction mixture for about 5 minutes and the reaction mixture was warmed to 0° C. Cold water was added and the pH was adjusted to about 2 using 1N hydrochloric acid. The tetrahydrofuran was removed by rotary evaporation, the precipitate was collected by vacuum filtration and was washed with cold water to provide the desired product. MS (DCI-NH$_3$): m/z 194 (M+NH$_4$)$^+$.

EXAMPLE 27

6'-[(4-methyl-1-piperazinyl)carbonyl]-2',3'-dihydrospiro[1,3-dioxolane-2,1'-inden]-4'-ammine To a solution of Example 24 (300 mg, 0.86 mmol) in ethanol (10 mL) was added Raney® Nickel (300 mg) and the mixture was hydrogenated at 60 psi at room temperature for about 2 hours. The mixture was filtered through diatomaceous earth (Celite®) and the filtrate was concentrated under vacuum to provide Example 27. MS (ESI): m/z 318 (M+H)$^+$.

EXAMPLE 28

2',3'-dihydrospiro[1,3-dioxolane-2,1'-inden]-6'-yl-methanol

To a solution of Example 20 (13 g, 50.9 mmol) in tetrahydrofuran (150 mL) was added a 2.5M solution of n-butyllithium in hexanes (30.5 mL, 76.4 mmol) dropwise at about −78° C. The mixture was treated dropwise with a solution of N,N-dimethylformamide (39.4 mL, 509.0 mmol) in tetrahydrofuran (40 mL), warmed to ambient temperature, poured into water, and extracted with ethyl acetate. The combined organic extracts were washed with brine, dried (MgSO$_4$), filtered and concentrated under vacuum. The residue was dissolved in a mixture of tetrahydrofuran (15 mL) and methanol (150 mL), cooled to 0° C., treated portionwise with sodium borohydride (2.6 g, 68.7 mmol), stirred at room temperature for about 2 hours, concentrated under vacuum, diluted with water, and extracted with ethyl acetate. The combined organic extracts were washed with brine, dried (MgSO$_4$), filtered and evaporated under reduced pressure. The residue was purified by flash column chromatography on silica gel using hexane/ethyl acetate (2:1) as the mobile phase to provide the desired product. MS (DCI-NH$_3$): m/z 207 (M+H)$^+$.

EXAMPLE 29

2',3'-dihydrospiro[1,3-dioxolane-2,1'-inden]-5'-yl-methanol

The desired product was prepared by substituting Example 21 for Example 20 in Example 28. MS (DCI-NH$_3$): m/z 207 (M+H)$^+$.

EXAMPLE 30

N,N-dimethyl-2',3'-dihydrospiro[1,3-dioxolane-2,1'-inden]-4'-amine

To a solution of Example 25 (100 mg, 0.52 mmol) in N,N-dimethylformamide (1 mL) was added acetic acid (0.1 mL) and a 37% aqueous solution of formaldehyde (0.5 mL, 5.23 mmol) and the mixture was stirred at room temperature for about 1 hour. Then sodium cyanoborohydride (330 mg, 5.23 mmol) was added and stirring at room temperature was continued overnight. The reaction was quenched by addition of saturated aqueous sodium bicarbonate and the mixture was extracted with dichloromethane. The combined organic extracts were dried (MgSO$_4$), filtered, and concentrated under vacuum to provide the desired product. MS (ESI): m/z 220 (M+H)$^+$.

EXAMPLE 31

N-(1-oxo-2,3-dihydro-1H-inden-4-yl)acetamide

To a vigorously stirred solution of Example 25 (3.9 g, 20.6 mmol) in pyridine (40 mL) was slowly added acetyl chloride (1.6 mL, 22.6 mmol). The reaction was stirred at room temperature for about 15 minutes and then the solvent was removed under vacuum. The residue was dissolved in acetone (38 mL) and water (12 mL) and p-toluenesulfonic acid (3.9 g, 20.6 mmol) was added. The mixture was heated to reflux for about 1 hour, cooled, and concentrated under vacuum. The aqueous layer was extracted with ethyl acetate and the combined organic layers were washed with saturated aqueous sodium bicarbonate, dried (Na$_2$SO$_4$), filtered, and concentrated under vacuum. The residue was purified by flash column chromatography on silica gel using hexane/ethyl acetate (1:1) as the mobile phase to provide the desired product. MS (ESI): m/z 188 (M−H)$^−$.

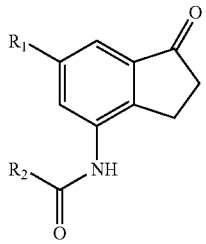

| Example Number | R₁ | R₂ | MS (ESI): | Reference Procedure |
|---|---|---|---|---|
| 32 | H | (propyl group) | m/z 204 (M + H)⁺ | Example 31 |
| 33 | H | (butyl group) | m/z 218 (M + H)⁺ | Example 31 |
| 34 | H | (methoxymethyl group) | m/z 220 (M + H)⁺ | Example 31 |
| 35 | (4-methylpiperazinyl carbonyl group) | (methoxymethyl group) | m/z 346 (M + H) | Example 31 |

EXAMPLE 36 ethyl 1-oxo-2,3-dihydro-1H-inden-4-ylcarbamate

To a vigorously stirred solution of Example 25 (500 mg, 2.61 mmol) in pyridine (15 mL) was slowly added ethyl chloroformate (0.27 mL, 2.87 mmol). The reaction was stirred at room temperature for about 3 hours and then the solvent was removed under vacuum. The residue was dissolved in acetone (4 mL) and water (1 mL) and p-toluenesulfonic acid (494 mg, 2.61 mmol) was added. The mixture was heated to reflux for about 1 hour, cooled, and concentrated under vacuum. The aqueous layer was extracted with ethyl acetate and the combined organic extracts were washed with saturated aqueous sodium bicarbonate, dried ($Na_2SO_4$), filtered, and concentrated under vacuum. The residue was purified by preparative HPLC on a Waters Symmetry C8 column (25 mm×100 mm, 7 µm particle size) using a gradient of 10% to 100% acetonitrile:0.1% aqueous TFA over 8 minutes (10 minutes run time) at a flow rate of 40 mL/minute to provide the desired product. MS (APCI) m/z 220 (M+H)⁺.

EXAMPLE 37

N-(1-oxo-2,3-dihydro-1H-inden-4-yl)ethanesulfonamide

To a vigorously stirred solution of Example 25 (500 mg, 2.61 mmol) in pyridine (15 mL) was slowly added ethyl sulfonyl chloride (0.27 mL, 2.87 mmol). The reaction was stirred at room temperature for about 3 hours and then the solvent was removed under vacuum. The residue was dissolved in acetone (4 mL) and water (1 mL) and p-toluenesulfonic acid (494 mg, 2.61 mmol) was added. The mixture was heated to reflux for about 1 hour, cooled, and concentrated under vacuum. The aqueous layer was extracted with ethyl acetate and the combined organic extracts were washed with saturated aqueous sodium bicarbonate, dried ($Na_2SO_4$), filtered and concentrated under vacuum. The residue was purified by preparative HPLC on a Waters Symmetry C8 column (25 mm×100 mm, 7 µm particle size) using a gradient of 10% to 100% acetonitrile:0.1% aqueous TFA over about 8 minutes (10 minutes run time) at a flow rate of 40 mL/minute to provide the desired product. MS (APCI) m/z 240 (M+H)⁺.

EXAMPLE 38 tert-butyl N-(2-tert-butoxy-2-oxoethyl)-N-[(1-oxo-2,3-dihydro-1H-inden-4-yl)carbonyl]glycinate To a solution of Example 5 (500 mg, 2.84 mmol) in dichloromethane (10 mL) was added 1,3-diisopropylcarbodiimide (0.44 mL, 2.84 mmol), 1-hydroxybenzotriazole hydrate (115 mg, 0.85 mmol), and di-t-butyl iminodiacetate (1.04 g, 4.26 mmol). The mixture was stirred at room temperature for about 24 hours, quenched with water, and extracted with diethyl ether. The combined organic extracts were washed with brine and saturated aqueous sodium bicarbonate, dried ($Na_2SO_4$), filtered and concentrated under vacuum. The residue was purified by flash column chromatography on silica gel using hexane/ethyl acetate (1:1) as the mobile phase to provide the desired product. MS (ESI): m/z 402 (M−H)⁻.

EXAMPLE 39 tert-butyl N-[(1-oxo-2,3-dihydro-1H-inden-4-yl)carbonyl]glycinate

To a solution of Example 5 (250 mg, 1.42 mmol) in N,N-dimethylformamide (4 mL) was added 1,3-diisopropylcarbodiimide (0.268 mL, 1.70 mmol), 1-hydroxybenzotriazole hydrate (58 mg, 0.4 mmol), and t-butyl glycinate (223 mg, 1.7 mmol). The mixture was stirred at room temperature overnight, quenched with saturated aqueous sodium bicarbonate, and extracted with ethyl acetate. The combined organic extracts were washed with brine, dried ($Na_2SO_4$), filtered, and concentrated under vacuum. The residue was purified by flash column chromatography on silica gel using hexane/ethyl acetate (50:1) as the mobile phase to provide the desired product. MS (APCI): m/z 290 $(M+H)^+$.

EXAMPLE 40

N,N-dimethyl-1-oxo-4-indanecarboxamide

To a solution of Example 5 (300 mg, 1.70 mmol) in N,N-dimethylformamide (3 mL) was added dimethyl amine hydrochloride (139 mg, 1.70 mmol), 1-hydroxybenzotriazole hydrate (253 mg, 1.87 mmol), triethylamine (0.48 mL, 3.4 mmol) and 1-(3-dimethylaminopropyl)-3-ethylcarbodiimide hydrochloride (358 mg, 1.87 mmol). The reaction mixture was stirred at room temperature overnight, quenched by addition of saturated aqueous sodium bicarbonate, and extracted with ethyl acetate. The combined organic extracts were dried ($Na_2SO_4$), filtered, and concentrated under vacuum. The residue was purified by flash column chromatography on silica gel using dichloromethane/methanol (20:1) as the mobile phase to provide the desired product. MS (APCI): m/z 204 $(M+H)^+$.

EXAMPLE 41 tert-butyl N-[(6-bromo-1-oxo-2,3-dihydro-1H-inden-4-yl)carbonyl]glycinate

To a solution of Example 6 (250 mg, 0.98 mmol) in N,N-dimethylformamide (5 mL) was added N-cyclohexylcarbodiimide-N'-methyl polystyrene (761 mg, 1.5 mmol) and 1-hydroxybenzotriazole hydrate (255 mg, 1.7 mmol). The mixture was agitated at room temperature for about 5 minutes, treated with t-butyl glycinate (150 mg, 1.2 mmol), shaken for about 15 hours, and filtered. The filtrate was concentrated under vacuum and the residue was purified by flash column chromatography on silica gel using hexane/ethyl acetate (1:1) as the moblie phase to provide the desired product. MS (APCI): m/z 311, 313 $(M+H-tBu)^+$.

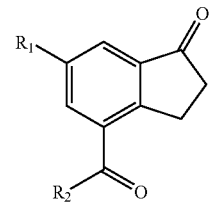

| Example Number | $R_1$ | $R_2$ | MS (APCI): | Reference Procedure |
|---|---|---|---|---|
| 42 | H | (N-methylpiperazinyl) | m/z 259 $(M + H)^+$ | Example 41 |
| 43 | Br | (tert-butoxycarbonylmethyl-N-methyl) | m/z 382, 384 $(M + H)^+$ | Example 41 |
| 44 | H | (tert-butyl ester, NH, stereocenter) | m/z 247 $(M + H - tBu)^+$ | Example 39 |
| 45 | H | (tert-butyl ester, NH, stereocenter) | m/z 247 $(M + H - tBu)^+$ | Example 39 |

-continued

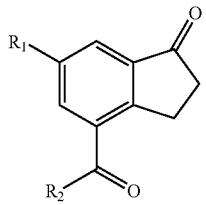

| Example Number | R₁ | R₂ | MS (APCI): | Reference Procedure |
|---|---|---|---|---|
| 46 | H | ethyl piperidine-3-carboxylate (N-linked) | m/z 316 (M + H)⁺ | Example 39 |
| 47 | H | ethyl piperidine-4-carboxylate (N-linked) | m/z 316 (M + H)⁺ | Example 39 |
| 48 | H | tert-butyl 3-aminopropanoate (NH-linked) | m/z 247 (M + H − tBu)⁺ | Example 39 |
| 49 | H | ethyl piperidine-3-carboxylate (N-linked) | m/z 316 (M + H)⁺ | Example 39 |

EXAMPLE 50

N-[2-(diethylamino)ethyl]-3-oxo-5-indanecarboxamide

To a solution of Example 26 (100 mg, 0.57 mmol) in N,N-dimethylformamide (2.8 mL) was added 1-hydroxybenzotriazole hydrate (115 mg, 0.85 mmol). The reaction mixture was cooled to 0° C. and N-methyl morpholine (187 µL, 1.7 mmol) and 1-(3-dimethylaminopropyl)-3-ethylcarbodiimide hydrochloride (163 mg, 0.85 mmol) were added. The reaction mixture was stirred at about 0° C. for about 15 minutes and then at about 23° C. for about 1 hour before N,N-diethylethylenediamine (88 µL, 0.62 mmol) was added. The reaction mixture was stirred overnight at about 23° C. and was then concentrated under vacuum. The residue was purified by flash chromatography on silica gel using dichloromethane/methanol (20:1) and 0.5% ammonium hydroxide as eluent to provide the desired product. MS (DCI-NH₃): m/z 275 (M+H)⁺.

EXAMPLE 51

6-(hydroxymethyl)-1-indanone

A solution of Example 28 (8.0 g, 38.7 mmol) and p-toluenesulfonic acid (7.4 g, 38.7 mmol) in a mixture of water (20 mL) and acetone (85 mL) was heated to reflux for about 1 hour. The mixture was concentrated under vacuum, diluted with water, and neutralized by careful addition of potassium carbonate (2.7 g, 19.4 mmol). The precipitate was collected by filtration, washed with minimal water and diethyl ether, and dried under vacuum to provide the desired product. MS (DCI-NH₃): m/z 180 (M+NH₄)⁺.

EXAMPLE 52

5-(hydroxymethyl)-1-indanone

The desired product was prepared by substituting Example 29 for Example 28 in Example 51. MS (DCI-NH₃): m/z 180 (M+NH₄)⁺.

EXAMPLE 53

4-(dimethylamino)-1-indanone

The desired product was prepared by substituting Example 30 for Example 28 in Example 51. The crude product was purified by flash chromatography on silica gel using dichloromethane/methanol (50:1) as eluent to provide the desired product. MS (ESI): m/z 176 (M+H)⁺.

EXAMPLE 54

(3-oxo-2,3-dihydro-1H-inden-5-yl)methyl methanesulfonate

To a mixture of Example 51 (3.8 g, 23.6 mmol) and triethylamine (4.3 mL, 30.7 mmol) in tetrahydrofuran (50 mL) was added methanesulfonyl chloride (2.2 mL, 28.3 mmol) dropwise at about 0° C. After about 30 minutes stirring at about 0° C., the reaction mixture was diluted with water and was extracted with ethyl acetate. The combined organic extracts were washed with brine, dried ($MgSO_4$), filtered, and evaporated under reduced pressure to provide the desired product. MS ($DCI-NH_3$): m/z 258 $(M+NH_4)^+$.

EXAMPLE 55

(1-oxo-2,3-dihydro-1H-inden-5-yl)methyl methanesulfonate

The desired product was prepared by substituting Example 52 for Example 51 in Example 54. MS ($DCI-NH_3$): m/z 258 $(M+NH_4)^+$.

EXAMPLE 56

6-[(4-methyl-1-piperazinyl)methyl]-1-indanone

To a suspension of Example 54 (5.6 g, 23.3 mmol) and potassium carbonate (6.4 g, 46.6 mmol) in ethanol (200 mL) was added 1-methylpiperazine (5.2 mL, 46.6 mmol) dropwise at about 0° C. The mixture was stirred at room temperature for about 3 hours, concentrated under vacuum, diluted with water, and was extracted with ethyl acetate. The combined organic extracts were dried ($MgSO_4$), filtered, and evaporated under reduced pressure. The residue was purified by flash column chromatography on silica gel using dichloromethane/methanol (5:1) as the mobile phase to provide the desired product. MS ($DCI-NH_3$): m/z 245 $(M+H)^+$.

EXAMPLE 57

6-(1H-imidazol-1-ylmethyl)-1-indanone

To a solution of Example 54 (3.2 g, 13.3 mmol) in N,N-dimethylformamide (60 mL) was added imidazole (4.5 g, 65.95 mmol) and the solution was stirred at room temperature overnight. The reaction mixture was poured into water and was extracted with ethyl acetate. The combined organic extracts were washed with brine, dried ($MgSO_4$), filtered and evaporated under reduced pressure. The residue was purified by flash column chromatography on silica gel using dichloromethane/methanol (15:1) as the mobile phase to provide the desired product. MS ($DCI-NH_3$): m/z 213 $(M+H)^+$.

EXAMPLE 58

5-[(2-furylmethyl)(methyl)amino]-1-indanone

A solution of 5-fluoro-1-indanone (1.0 g, 6.66 mmol) and N-methylfurfurylamine (2.0 g, 18.0 mmol) in ethanol (10 mL) was heated to about 80° C. for about 2 days. The reaction mixture was concentrated under vacuum and the residue was purified by flash column chromatography on silica gel using hexane/ethyl acetate (2:1) as the mobile phase to provide the desired product. MS (ESI): m/z 242 $(M+H)^+$.

EXAMPLE 59 ethyl 1-methyl-4-piperidinecarboxylate

To ethyl isonipecotate (10 g, 64 mmol) was slowly added a 37% aqueous solution of formaldehyde (10 mL, 128 mmol) followed by formic acid (10 mL, 233 mmol) and the mixture was heated to reflux for about 3 days. The mixture was allowed to cool to room temperature, the pH was adjusted to 2 by addition of concentrated hydrochloric acid and the mixture was extracted with ethyl acetate. The pH of the aqueous layer was then adjusted to 11 by addition of 2N aqueous sodium hydroxide, and the aqueous layer was extracted with ethyl acetate. The combined organic extracts of the second extraction were dried ($MgSO_4$), filtered, and concentrated under vacuum to provide the desired product. $^1H$ NMR (500 MHz, $CDCl_3$-d): δ 1.25 (t, J=6 Hz, 3H), 1.40 (m, 1H), 1.59 (m, 1H), 1.62 (m, 1H), 1.95 (m, 2H), 2.06 (m, 1H), 2.26 (s, 3H), 2.71 (m, 1H), 2.94 (m, 1H), 4.13 (dd, J=6 Hz, 2H).

EXAMPLE 60

(1-methyl-4-piperidinyl)methanol

To a suspension of lithium aluminum hydride (0.88 g, 23 mmol) in tetrahydrofuran (50 mL) was added dropwise a solution of Example 59 (1.03 g, 6 mmol) in tetrahydrofuran (10 mL) and the mixture was heated to reflux for about 2 hours. The mixture was cooled to about 0° C. and saturated aqueous sodium hydroxide (3.5 mL) was added dropwise. After stirring for about 10 minutes at room temperature, the mixture was filtered, the filter cake was washed with tetrahydrofuran and the combined filtrates were dried ($Na_2SO_4$), filtered and concentrated under vacuum to provide the desired product. $^1H$ NMR (500 MHz, $CDCl_3$): δ 1.10 (m, 1H), 1.60-2.00 (m, 4H), 2.10 (m, 2H), 2.28 (s, 3H), 2.65 (m, 1H), 2.82 (m, 1H), 3.57 (dd, J=8, 14 Hz, 1H), 3.63 (dd, J=8, 14 Hz, 1H), 3.70 (m, 1H).

EXAMPLE 61

4-(chloromethyl)-1-methylpiperidine

To Example 60 (0.78 g, 6 mmol) was added thionyl chloride (10 mL) and the mixture was heated to reflux for about 2 hours. The mixture was cooled and concentrated to dryness. The residue was washed with acetone, suspended in saturated aqueous sodium carbonate and extracted with dichloromethane. The combined organic extracts were dried ($Na_2SO_4$), filtered and concentrated under vacuum to provide the desired product. MS (ESI): m/z 148 $(M+H)^+$.

EXAMPLE 62

5-[2-(4-morpholinyl)ethoxy]-1-indanone

To a solution of 5-hydroxy-1-indanone (610 mg, 4.1 mmol) in acetonitrile (30 mL) was added 4-(2-chloroethyl)morpholine hydrochloride (3.8 g, 20.5 mmol) and potassium carbonate (680 mg 4.9 mmol) and the mixture was heated to reflux for about 3 days. The solvent was removed under vacuum and the residue was purified by flash column chromatography on silica gel using ethyl acetate as the mobile phase to provide the desired product. MS (ESI): m/z 262 $(M+H)^+$.

EXAMPLE 63

5,6-dihydroxy-1-indanone

A solution of 5,6-dimethoxy-indan-1-one (6.1 g, 31.7 mmol) in dichloromethane (150 mL) was cooled to about −78° C. and boron tribromide (7.1 mL, 75.1 mmol) was added dropwise. After the addition, the reaction was stirred for about 1 hour while being allowed to warm to room temperature. The mixture was poured into ice water under vigorous stirring. The pink precipitate was collected by filtration, washed with water, and dried under high vacuum to provide the desired product. MS (APCI): m/z 165 (M+H)$^+$.

EXAMPLE 64

6-hydroxy-5-methoxy-1-indanone

A mixture of Example 63 (2.0 g, 12 mmol), iodomethane (1.9 mL, 30 mmol), and lithium carbonate (2.2 g, 30 mmol) in N,N-dimethylformamide (40 mL) was heated to 55° C. for 24 hours. The solution was concentrated under vacuum and was diluted with a 2% solution of hydrochloric acid in water. The precipitate was collected by filtration and was dried under high vacuum to provide the desired product. $^1$H NMR (500 MHz, CD$_3$OD): δ 2.63 (t, J=6 Hz, 6H), 3.05 (t, J=6 Hz, 6H), 3.98 (s, 3H), 7.05 (s, 2H).

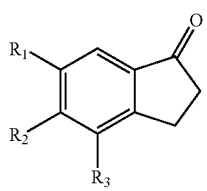

| Example Number | R$_1$ | R$_2$ | R$_3$ | MS | Reference Procedure |
|---|---|---|---|---|---|
| 65 | H | *N-methylpiperazinyl* | H | (DCI-NH$_3$): m/z 231 (M + H)$^+$ | Example 58 |
| 66 | H | *morpholinyl* | H | (DCI-NH$_3$): m/z 218 (M + H)$^+$ | Example 58 |
| 67 | *4-formylpiperazin-1-ylmethyl* | H | H | (DCI-NH$_3$): m/z 259 (M + H)$^+$ | Example 56 |
| 68 | *3-(dimethylamino)pyrrolidin-1-ylmethyl* | H | H | (DCI-NH$_3$): m/z 259 (M + H)$^+$ | Example 56 |
| 69 | *pyrrolidin-1-ylmethyl* | H | H | (DCI-NH$_3$): m/z 216 (M + H)$^+$ | Example 56 |
| 70 | *4-methylpiperidin-1-ylmethyl* | H | H | (DCI-NH$_3$): m/z 244 (M + H)$^+$ | Example 56 |
| 71 | *4-ethylpiperazin-1-ylmethyl* | H | H | (DCI-NH$_3$): m/z 259 (M + H)$^+$ | Example 56 |

-continued

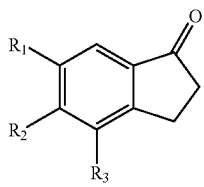

| Example Number | R₁ | R₂ | R₃ | MS | Reference Procedure |
|---|---|---|---|---|---|
| 72 | 2,6-dimethylmorpholinylmethyl | H | H | (DCI-NH$_3$): m/z 260 (M + H)$^+$ | Example 56 |
| 73 | 1,2,4-triazol-1-ylmethyl | H | H | (DCI-NH$_3$): m/z 214 (M + H)$^+$ | Example 56 |
| 74 | 2-methylimidazol-1-ylmethyl | H | H | (DCI-NH$_3$): m/z 227 (M + H)$^+$ | Example 56 |
| 75 | 1,2,3-triazol-1-ylmethyl | H | H | (DCI-NH$_3$): m/z 214 (M + H)$^+$ | Example 56 |
| 76 | (4-isopropylpiperazin-1-yl)methyl | H | H | (DCI-NH$_3$): m/z 273 (M + H)$^+$ | Example 56 |
| 77 | (4-methylpiperazin-1-yl)carbonyl | H | H | (DCI-NH$_3$): m/z 259 (M + H)$^+$ | Example 24 |
| 78 | H | (4-methylpiperazin-1-yl)carbonyl | H | (DCI-NH$_3$): m/z 259 (M + H)$^+$ | Example 24 |
| 79 | H | morpholin-4-ylcarbonyl | H | (DCI-NH$_3$): m/z 246 (M + H)$^+$ | Example 24 |
| 80 | H | (4-methylpiperazin-1-yl)methyl | H | (DCI-NH$_3$): m/z 245 (M + H)$^+$ | Example 56 |

-continued

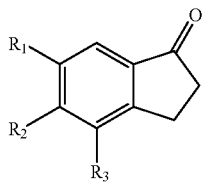

| Example Number | R₁ | R₂ | R₃ | MS | Reference Procedure |
|---|---|---|---|---|---|
| 81 | H | (1,2,3-triazol-1-ylmethyl) | H | (DCI-NH₃): m/z 214 (M + H)⁺ | Example 56 |
| 82 | H | (4-ethoxycarbonyl-piperazin-1-ylmethyl) | H | | Example 56 |
| 83 | H | (2,6-dimethylmorpholin-4-ylmethyl) | H | (DCI-NH₃): m/z 260 (M + H)⁺ | Example 56 |
| 84 | H | (4-methylpiperidin-1-ylmethyl) | H | | Example 56 |
| 85 | H | (1,2,4-triazol-1-ylmethyl) | H | | Example 56 |
| 86 | (4-methylpiperazin-1-yl)carbonyl | H | (tert-butoxycarbonylmethyl-aminocarbonyl) | (ESI): m/z 414 (M − H)⁻ | Example 24 |
| 87 | H | (imidazol-1-ylmethyl) | H | (APCI): m/z 199 (M + H)⁺ | Example 58 |
| 88 | H | (4-ethylpiperazin-1-ylmethyl) | H | (APCI): m/z 259 (M + H)⁺ | Example 56 |
| 89 | H | (4-isopropylpiperazin-1-ylmethyl) | H | (APCI): m/z 273 (M + H)⁺ | Example 56 |

-continued

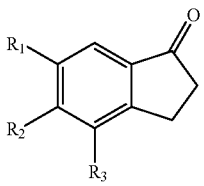

| Example Number | $R_1$ | $R_2$ | $R_3$ | MS | Reference Procedure |
|---|---|---|---|---|---|
| 90 | H | (1-methylpiperidin-4-yl)methoxy | H | (ESI): m/z 260 (M + H)$^+$ | Example 62 |
| 91 | H | 2-(dimethylamino)ethoxy | H | (APCI): m/z 220 (M + H)$^+$ | Example 62 |
| 92 | H | 2-(diethylamino)ethoxy | H | (APCI): m/z 248 (M + H)$^+$ | Example 62 |
| 93 | H | 3-(dimethylamino)propoxy | H | (APCI): m/z 234 (M + H)$^+$ | Example 62 |
| 94 | H | (dimethylcarbamoyl)methoxy | H | (APCI): m/z 234 (M + H)$^+$ | Example 62 |
| 95 | 2-(morpholin-4-yl)ethoxy | OCH$_3$ | H | (APCI): m/z 292 (M + H) | Example 62 |

EXAMPLE 96

5-(1H-imidazol-1-ylmethyl)-1-indanone

A mixture of Example 80 (1.0 g, 4.09 mmol) and methyl iodide (1.0 mL, 16.3 mmol) in N,N-dimethylformamide (10 mL) was stirred at room temperature for about 17 hours. The reaction mixture was concentrated under vacuum, a solution of imidazole (0.83 g, 8.18 mmol) and triethylamine (1.14 mL, 8.18 mmol) in N,N-dimethylformamide (10 mL) was added and the mixture heated to about 80° C. for about 5 hours. The reaction was quenched by addition of saturated aqueous ammonium chloride, the layers were separated and the aqueous layer was extracted with dichloromethane. The combined organic extracts were dried (MgSO$_4$), filtered, and concentrated under vacuum to provide the desired product. MS (ESI): m/z 213 (M+H)$^+$.

EXAMPLE 97

5-(2-pyrimidinyloxy)-1-indanone

A mixture of 2-chloropyrimidine (220 mg, 1.9 mmol), 5-hydroxyindan-1-one (209 mg, 1.4 mmol) and potassium carbonate (250 mg, 1.8 mmol) in N,N-dimethyl formamide (5 mL) was heated to about 100° C. overnight. The reaction was cooled to room temperature and the solvent was evaporated under high vacuum. The residue was purified by flash column chromatography on silica gel using ethyl acetate/methanol (99:1) as the mobile phase to provide the desired product. $^1$H NMR (500 MHz, CDCl$_3$): δ 2.75 (t, J=7 Hz, 2H), 3.18 (t, J=7 Hz, 2H), 7.09 (m, 1H), 7.25 (d, J=7 Hz, 1H), 7.32 (s, 1H), 7.82 (d, J=7 Hz, 1H), 8.62 (d, J=7 Hz, 1H).

EXAMPLE 98

3-[(E)-2-nitrovinyl]thiophene

To a solution of 3-thiophenecarboxaldehyde (57.0 g, 502 mmol) and nitromethane (29.9 mL, 552 mmol) in methanol (100 mL) was added a solution of sodium hydroxide (22.1 g, 552 mmol) in water (45 mL) at a rate that kept the temperature at less than 5° C. The mixture was allowed to stand at about 0° C. for about 30 minutes. The precipitate was collected by filtration, dissolved in a minimum amount of ice-cold water and, poured into an ice-cold mixture of concentrated hydrochloric acid (96.7 mL, 1178 mmol) and water (152 mL). The precipitate was collected by filtration and was recrystallized from aqueous ethanol to provide the desired product. MS (DCI-NH$_3$): m/z 173 (M+NH$_4$)$^+$.

EXAMPLE 99

2-(3-thienyl)ethanamine

To a suspension of lithium aluminum hydride (25.9 g, 681.2 mmol) in diethyl ether (900 mL) was added a solution of Example 98 (39.1 g, 252.3 mmol) in diethyl ether (600 mL) and tetrahydrofuran (100 mL) at such a rate that the mixture was kept at a gentle reflux. The mixture was stirred at ambient temperature for about an hour and then excess lithium aluminum hydride was destroyed by slow addition of the minimum required amount of water. The mixture was filtered through diatomaceous earth (Celite®) and the filter cake was washed with diethyl ether. The combined filtrates were dried (MgSO$_4$), filtered, and concentrated under vacuum. The residue was purified by flash column chromatography on silica gel using dichloromethane/methanol (10:1)+1% ammonium hydroxide as the mobile phase to provide the desired product. MS (DCI-NH$_3$): m/z 128 (M+H)$^+$.

EXAMPLE 100

N-methylene-N-[2-(3-thienyl)ethyl]amine

A 37% aqueous solution of formaldehyde (11.8 mL, 157.9 mmol) was carefully added with stirring to Example 99 (20.1 g, 157.9 mmol). The reaction mixture was then stirred at about 100° C. for about 3 hours and at room temperature for about 1 hour. The mixture was diluted with dichloromethane and was washed with water. The organic layer was dried (MgSO$_4$), filtered and concentrated under vacuum to provide the desired product. MS (DCI-NH$_3$): m/z 140 (M+H)$^+$.

EXAMPLE 101

4,5,6,7-tetrahydrothieno[2,3-c]pyridine

To Example 100 (24.0 g, 157.9 mmol) was added dropwise a solution of concentrated hydrochloric acid (17.4 mL) in water (21 mL) and the mixture was stirred at room temperature for about 2 hours. The solution was evaporated to dryness, the residue was dissolved in methanol (300 mL), cooled with an ice bath, and was neutralized by addition of triethylamine (22.0 mL, 157.9 mmol). After stirring for about 30 minutes, the solvents were concentrated under vacuum, the residue was dissolved in water and was extracted with ethyl acetate. The combined organic extracts were dried (MgSO$_4$), filtered, and concentrated under vacuum. The residue was purified by flash chromatography on silica gel using dichloromethane/methanol (15:1) as eluent to provide the desired product. MS (DCI-NH$_3$): m/z 140 (M+H)$^+$.

EXAMPLE 102 tert-butyl 4,7-dihydrothieno[2,3-c]pyridine-6(5H)-carboxylate

To a solution of Example 101 (1.0 g, 7.2 mmol) in tetrahydrofuran (10 mL) was added triethylamine (1.1 mL, 7.9 mmol) and di-tert-butyl dicarbonate (2.0 mL, 8.62 mmol) and the mixture was stirred at ambient temperature overnight. The mixture was poured into water and was extracted with ethyl acetate. The combined organic extracts were dried (MgSO$_4$), filtered, and concentrated under vacuum. The residue was purified by flash chromatography on silica gel using hexane/ethyl acetate (2:1) as eluent to provide the desired product. MS (DCI-NH$_3$): m/z 240 (M+H)$^+$.

EXAMPLE 103 tert-butyl 2-formyl-4,7-dihydrothieno[2,3-c]pyridine-6(5H)-carboxylate

To a solution of Example 102 (250 mg, 1.04 mmol) in tetrahydrofuran (8.0 mL) was added a 1.6M solution of n-butyllithium in hexanes (3.3 mL, 5.22 mmol) dropwise at about −78° C. The mixture was stirred at about −78° C. for about 1 hour and then a solution of N,N-dimethylformamide (0.4 mL, 5.22 mmol) in tetrahydrofuran (2.0 mL) was added dropwise. The mixture was stirred at about −78° C. for about 1 hour and then the reaction was quenched by addition of aqueous ammonium chloride. After warming to room temperature, water was added and the mixture was acidified by addition of citric acid. The mixture was extracted with ethyl acetate, the combined organic extracts were dried (MgSO$_4$), filtered and concentrated under vacuum. The residue was purified by flash chromatography on silica gel using hexane/ethyl acetate (2:1) as eluent to provide the desired product. MS (DCI-NH$_3$): m/z 268 (M+H)$^+$.

EXAMPLE 104

6-(tert-butoxycarbonyl)-4,5,6,7-tetrahydrothieno[2,3-c]pyridine-2-carboxylic acid A solution of Example 103 (190 mg, 0.71 mmol) in ethanol (3.0 mL) was sequentially treated with a solution of silver nitrate (241 mg, 1.42 mmol) in water (0.5 mL) and a solution of potassium hydroxide (159 mg, 2.84 mmol) in water (3.0 mL). The suspension was stirred at room temperature for about 1 hour and filtered. The filter cake was washed with water and diethyl ether and the combined filtrates were acidified by addition of citric acid. The layers were separated and the aqueous layer was extracted with diethyl ether. The combined organic extracts were dried (MgSO$_4$), filtered and concentrated under vacuum. The residue was purified by flash chromatography on silica gel using dichloromethane/methanol (5:1) as eluent to provide the desired product. MS (DCI-NH$_3$): m/z 283 (M)$^+$.

EXAMPLE 105

4-methyl-2-thiophenecarboxylic acid

To an aqueous solution of sodium hypochlorite (available chlorine 5%) (92.6 mL, 143.0 mmol) at about 0° C. was added sodium hydroxide (1.14 g, 28.6 mmol) and the mixture was stirred at about 0° C. until all of the sodium hydroxide had dissolved. To this solution was added 2-acetyl-4-methylthiophene (2.0 g, 14.3 mmol) at about 0° C. After the addition was complete, the mixture was heated to about 70° C. for about 3 hours, then the solution was cooled and was carefully quenched by addition of a solution of sodium bisulfite (23 g) in water (150 mL). After stirring for about 20 minutes, the solution was acidified by addition of concentrated hydrochloric acid and the precipitate was collected by filtration and dried under high vacuum to provide the desired product. MS (DCI-NH$_3$): m/z 160 (M+NH$_4$)$^+$.

EXAMPLE 106

5-bromo-3-thiophenecarboxylic acid

Thiophene-3-carboxylic acid (5.0 g, 39.0 mmol) was dissolved in glacial acetic acid (40 mL) and a solution of bromine (1.9 mL, 37.9 mmol) in glacial acetic acid (25 mL) was added dropwise. After about 2 hours, the reaction mixture was poured into ice water (200 mL) and the formed precipitate was collected by filtration. The filter cake was washed with a minimal amount of ice water and was recrystallized from water to provide the desired product. MS (DCI-NH$_3$): m/z 206, 208 (M)$^+$.

EXAMPLE 107

4-bromo-2-thiophenecarboxylic acid

To a solution of chromium(VI)oxide (1.57 g, 15.70 mmol) in water (3 mL) was added dropwise concentrated sulfuric acid (1.3 mL, 23.55 mmol). The formed precipitate was re-dissolved by slow addition of the minimum required amount of water and the solution was cooled with an ice bath. This solution was then added dropwise to a solution of 4-bromo-2-thiophenecarboxaldehyde (2.0 g, 10.47 mmol) in acetone (20 mL) at about 5° C. The reaction mixture was stirred at about 5° C. for about 30 minutes and then at room temperature for about 2 hours. Methanol (30 mL) was added to the reaction mixture to destroy excess oxidant and the formed solids were collected by filtration. The filtrate was concentrated under vacuum and the residue was partitioned between diethyl ether and water. The organic extract was washed with water and brine, dried (MgSO$_4$), filtered and concentrated under vacuum to provide the desired product. MS (DCI-NH$_3$): m/z 206, 208 (M)$^+$.

EXAMPLE 108 phenyl 3-bromobenzoate

To a solution of phenol (2.3 g, 24.4 mmol) and triethylamine (3.2 g, 32 mmol) in diethyl ether (150 mL) was slowly added 3-bromobenzoyl chloride (5 g, 22.8 mmol) and the mixture was heated to reflux for about 1 hour. The mixture was cooled, filtered, and the filtrate was successively washed with water, 0.2N hydrochloric acid, and saturated aqueous sodium carbonate. The organic layer was dried (MgSO$_4$), filtered, and concentrated under vacuum. The residue was triturated with hexane and dried under vacuum to provide the desired product. $^1$H NMR (500 MHz, CDCl$_3$) δ 7.22 (m, 3H), 7.42 (m, 3H), 7.79 (d, J=8 Hz, 1H), 8.15 (d, J=8 Hz, 1H), 8.37 (br s, 1H).

EXAMPLE 109 phenyl 4-iodobenzoate

The desired product was prepared by substituting 4-iodobenzoyl chloride for 3-bromobenzoyl chloride in Example 108. MS (ESI): m/z 325 (M+H)$^+$.

EXAMPLE 110 phenyl 2-thiophenecarboxylate

Phenol (5.0 g, 39.0 mmol), a 1M solution of 1,3-dicyclohexylcarbodiimide in dichloromethane (39.0 mL, 39.0 mmol) and 4-dimethylaminopyridine (0.5 g, 3.9 mmol) were added to a solution of thiophene-2-carboxylic acid (5.0 g, 39.0 mmol) in diethyl ether (400 mL) at about 0° C. The reaction mixture was stirred overnight while being allowed to warm to room temperature. The precipitate was collected by filtration and was washed with diethyl ether. The combined filtrates were washed successively with water, 5% aqueous acetic acid, water and brine, dried (MgSO$_4$), filtered and concentrated under vacuum. The residue was purified by flash column chromatography on silica gel using hexane/ethyl acetate (5:1) as the mobile phase to provide phenyl thiophene-2-carboxylate. MS (DCI-NH$_3$): m/z 222 (M+NH$_4$)$^+$.

| Example Number | R | MS (DCI-NH$_3$): | Synthesis Protocol |
|---|---|---|---|
| 111 | 3-thienyl | m/z 222 (M + NH$_4$)$^+$ | Example 110 |
| 112 | 5-bromo-2-thienyl | m/z 300, 302 (M + NH$_4$)$^+$ | Example 110 |
| 113 | 5-bromo-3-thienyl | m/z 300, 302 (M + NH$_4$)$^+$ | Example 110 |

-continued

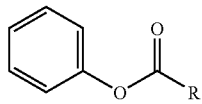

| Example Number | R | MS (DCI-NH$_3$): | Synthesis Protocol |
|---|---|---|---|
| 114 | 3-methylthiophen-2-yl | m/z 236 (M + NH$_4$)$^+$ | Example 110 |
| 115 | 3-chlorothiophen-2-yl | m/z 256 (M + NH$_4$)$^+$ | Example 110 |
| 116 | 5-methylthiophen-2-yl | m/z 236 (M + NH$_4$)$^+$ | Example 110 |
| 117 | 5-chlorothiophen-2-yl | m/z 256 (M + NH$_4$)$^+$ | Example 110 |
| 118 | benzo[b]thiophen-2-yl | m/z 272 (M + NH$_4$)$^+$ | Example 110 |
| 119 | 4-bromophenyl | m/z 294, 296 (M + NH$_4$)$^+$ | Example 110 |
| 120 | 4-bromo-2-fluorophenyl | m/z 312, 314 (M + NH$_4$)$^+$ | Example 110 |
| 121 | thiazol-4-yl | m/z 223 (M + NH$_4$)$^+$ | Example 110 |
| 122 | 3,5-dimethylisoxazol-4-yl | m/z 235 (M + NH$_4$)$^+$ | Example 110 |

-continued

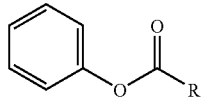

| Example Number | R | MS (DCI-NH$_3$): | Synthesis Protocol |
|---|---|---|---|
| 123 | 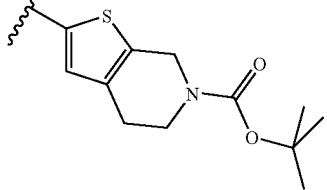 | m/z 377 (M + NH$_4$)$^+$ | Example 110 |
| 124 | 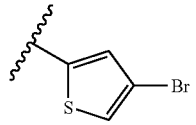 | m/z 282 (M + H)$^+$ | Example 110 |
| 125 |  | m/z 300, 302 (M + NH$_4$)$^+$ | Example 110 |

EXAMPLE 126 phenyl 5-(3-phenoxy-1-propynyl)-3-thiophenecarboxylate

A mixture of phenyl 5-bromothiophene-3-carboxylate, Example 113 (100 mg, 0.35 mmol), (prop-2-ynyloxy)benzene (93 mg, 0.71 mmol), triphenylphosphine (19 mg, 0.071 mmol), dichlorobis(triphenylphosphine)palladium(II) (12 mg, 0.018 mmol), copper iodide (1 mg, 0.006 mmol) and triethylamine (0.74 mL, 5.30 mmol) in N,N-dimethylformamide (1 mL) was stirred under nitrogen in a heavy walled process vial in a microwave synthesizer at about 120° C. for about 25 minutes. The reaction mixture was concentrated under vacuum and the residue was purified by flash column chromatography on silica gel using hexane/ethyl acetate (2:1) as the mobile phase to provide the desired product. MS (DCI-NH$_3$): m/z 352 (M+NH$_4$)$^+$.

EXAMPLE 127

3-(2-methoxyethoxy)-1-propyne

To a 60% suspension of sodium hydride in mineral oil (3.55 g, 89.2 mmol) was added tetrahydrofuran (100 mL) and the mixture was cooled to about 5° C. To this suspension was added dropwise a solution of propargyl alcohol (5.0 g, 89.2 mmol) in tetrahydrofuran (20 mL) and the mixture was stirred for about 30 minutes. Then 2-bromoethyl methyl ether was added and the mixture was stirred overnight while being allowed to warm to room temperature. The reaction was quenched by addition of water and the layers were separated. The aqueous layer was extracted with diethyl ether and the combined organic extracts were dried (MgSO$_4$) and filtered. The organic solvents were carefully distilled off at atmospheric pressure and the residue was purified by flash chromatography on silica gel using diethyl ether/n-pentane (1:3) as eluent to provide the desired product. $^1$H NMR (500 MHz, DMSO-d$_6$): δ 2.44 (m, 1H), 3.39 (s, 3H), 3.57 (m, 2H), 3.70 (m, 2H), 4.21 (d, J=3.0 Hz, 2H).

EXAMPLE 128 phenyl 5-[3-(2-methoxyethoxy)-1-propynyl]-3-thiophenecarboxylate

The desired product was prepared by substituting Example 127 for phenyl propargyl ether in Example 126. $^1$H NMR (500 MHz, CDCl$_3$): δ 3.42 (s, 3H), 3.60 (t, J=5 Hz, 2H), 3.78 (d, J=5 Hz, 2H), 4.45 (s, 2H), 7.19 (d, J=7 Hz, 2H), 7.28 (m, 1H), 7.42 (t, J=7 Hz, 2H), 7.82 (s, 1H), 8.19 (s, 1H).

EXAMPLE 129 phenyl 3-(3-phenoxy-1-propynyl)benzoate

The desired product was prepared by substituting Example 108 for Example 113 in Example 126. $^1$H NMR (500 MHz, CDCl$_3$) δ 4.97 (s, 2H), 7.01 (t, J=8 Hz, 1H), 7.05 (d, J=8 Hz, 2H), 7.20 (d, J=8 Hz, 2H), 7.30 (t, J=8 Hz, 2H), 7.34 (t, J=8 Hz, 1H), 7.42 (t, J=8 Hz, 2H), 7.44 (t, J=8 Hz, 1H), 7.69 (d, J=8 Hz, 1H), 8.15 (d, J=8 Hz, 1H), 8.28 (s, 1H).

EXAMPLE 130 phenyl 4-(3-phenoxy-1-propynyl)benzoate

The desired product was prepared by substituting Example 109 for Example 113 in Example 126. MS (ESI): m/z 329 (M+H)$^+$.

EXAMPLE 131

2-chloro-N-(3-methylphenyl)acetamide

To a suspension of potassium carbonate (773 mg, 5.59 mmol) in dichloromethane (25 mL) was added m-toluidine (0.5 mL, 4.66 mmol) followed by dropwise addition of chloroacetyl chloride (0.44 mL, 5.59 mmol) and the mixture was stirred at ambient temperature overnight. The reaction was quenched by addition of water, the layers were separated and the aqueous layer was extracted with ethyl acetate. The combined organic extracts were dried (MgSO$_4$), filtered and concentrated under vacuum to provide 2-chloro-N-m-tolyl-acetamide. MS (DCI-NH$_3$): m/z 201 (M+NH$_4$)$^+$.

EXAMPLE 132

(2S)-2-bromo-N-(3-methylphenyl)propanamide

To a solution of (S)-(−)-2-bromopropionic acid (0.25 mL, 2.77 mmol), m-toluidine (0.30 mL, 2.77 mmol) and 1-hydroxybenzotriazole hydrate (560 mg, 4.16 mmol) in tetrahydrofuran (25 mL) was added a 1M solution of 1,3-dicyclohexylcarbodiimide in dichloromethane (5.54 mL, 5.54 mmol). The mixture was stirred at about 0° C. for about 2 hours, then it was warmed to room temperature and filtered. The filtrate was concentrated and the residue was purified by flash chromatography on silica gel using hexane/ethyl acetate (2:1) as eluent to provide the desired product. MS (DCI-NH$_3$): m/z 259, 261 (M+NH$_4$)$^+$.

EXAMPLE 133 phenyl 4-{2-[(3-methylphenyl)amino]-2-oxoethoxy}benzoate

To a solution of 2-chloro-N-m-tolyl-acetamide (580 mg, 3.16 mmol) and phenyl 4-hydroxybenzoate (677 mg, 3.16 mmol) in acetone (20 mL) was added potassium carbonate (502 mg, 3.63 mmol) and potassium iodide (26 mg, 0.16 mmol) and the mixture was heated to reflux overnight. The mixture was concentrated under vacuum, water was added, and the mixture was extracted with ethyl acetate. The combined organic extracts were dried (MgSO$_4$), filtered, and concentrated under vacuum. The residue was purified by flash chromatography on silica gel using hexane/ethyl acetate (2:1) as eluent to provide the desired product. MS (DCI-NH$_3$): m/z 379 (M+NH$_4$)$^+$.

EXAMPLE 134 phenyl 4-({(1R)-1-methyl-2-[(3-methylphenyl)amino]-2-oxoethyl}oxy)benzoate

The desired product was prepared by substituting Example 132 for 2-chloro-N-m-tolyl-acetamide in Example 133. MS (DCI-NH$_3$): m/z 393 (M+NH$_4$)$^+$.

EXAMPLE 135 phenyl 4-[2-(2-methoxyethoxy)ethoxy]benzoate

To a solution of phenyl 4-hydroxybenzoate (2.1 g, 9.8 mmol) in tetrahydrofuran (40 mL) was added a 60% suspension of sodium hydride in mineral oil (408 mg, 10.2 mmol) and the mixture was stirred at room temperature for about 30 minutes. Then 1-bromo-2-(2-methoxyethoxy)ethane (2.5 g, 13.7 mmol) was added and stirring was continued for about 5 days. The mixture was poured into saturated aqueous sodium carbonate and was extracted with ethyl acetate, the combined organic extracts were washed with saturated aqueous sodium carbonate, dried (Na$_2$SO$_4$), filtered, and concentrated under vacuum. The residue was purified by flash chromatography on silica gel using hexane/ethyl acetate (10:1) as eluent to provide the desired product. $^1$H NMR (500 MHz, CDCl$_3$) δ 3.40 (s, 3H), 3.60 (m, 2H), 3.76 (m, 2H), 3.92 (t, J=8 Hz, 2H), 4.22 (t, J=8 Hz, 2H), 7.00 (d, J=8 Hz, 2H), 7.22 (m, 3H), 7.42 (d, J=8 Hz, 2H), 8.17 (d, J=8 Hz, 2H).

EXAMPLE 136 phenyl 4-(2-phenoxyethoxy)benzoate

A mixture of phenyl 4-hydroxybenzoate (2.14 g, 10 mmol), 2-phenoxyethyl bromide (12.1 g, 60 mmol) and potassium carbonate (4.1 g, 30 mmol) in 1,4-dioxane (60 mL) was heated to reflux for about 2 days. The mixture was cooled, filtered and concentrated under vacuum. The residue was purified by flash chromatography on silica gel using hexane/ethyl acetate (3:1) as eluent to provide the desired product. $^1$H NMR (500 MHz, CDCl$_3$) δ 4.39 (m, 2H), 4.42 (m, 2H), 6.97 (d, J=8 Hz, 2H), 6.99 (t, J=8 Hz, 1H), 7.03 (d, J=8 Hz, 2H), 7.21 (d, J=8 Hz, 2H), 7.25 (m, 1H), 7.35 (t, J=8 Hz, 2H), 7.42 (t, J=8 Hz, 2H), 8.17 (d, J=8 Hz, 2H).

EXAMPLE 137 phenyl 4-(2-ethoxyethoxy)benzoate

The desired product was prepared by substituting 2-bromoethyl ethyl ether for 2-phenoxyethyl bromide in Example 136. $^1$H NMR (500 MHz, CDCl$_3$) δ 1.28 (t, J=8 Hz, 3H), 3.60 (q, J=8 Hz, 2H), 3.82 (t, J=8 Hz, 2H), 4.22 (t, J=8 Hz, 2H), 7.00 (d, J=8 Hz, 2H), 7.21 (d, J=8 Hz, 2H), 7.25 (m, 1H), 7.42 (t, J=8 Hz, 2H), 8.17 (d, J=8 Hz, 2H).

EXAMPLE 138

7-[(4-methyl-1-piperazinyl)methyl]-3-(2-thienyl)-1,4-dihydroindeno[1,2-c]pyrazole A mixture of Example 56 (250 mg, 1.02 mmol), Example 110 (208 mg, 1.02 mmol) and a 60% suspension of sodium hydride in mineral oil (102 mg, 2.56 mmol) in benzene (5 mL) was heated to reflux for about 2.5 hours. The reaction was cooled and quenched by dropwise addition of 50% aqueous acetic acid. The solvents were evaporated and the residue was dried under high vacuum for about 1 hour. The residue was dissolved in ethanol (5 mL), hydrazine monohydrate (74 µL, 1.53 mmol) and acetic acid (176 µL, 3.07 mmol) were added and the mixture was heated to reflux for about 4 hours. The mixture was cooled, concentrated under vacuum and the residue was purified by flash chromatography on silica gel using dichloromethane/methanol (10:1)+1% ammonium hydroxide as eluent to provide 284 mg (79%) of the desired product. $^1$H NMR (300 MHz, DMSO-$d_6$): δ 2.15 (s, 3H), 2.28-2.46 (m, 8H), 3.53 (s, 2H), 3.73 (s, 2H), 7.17 (dd, J=5.1, 3.4 Hz, 1H), 7.21 (dd, J=7.8, 1.4 Hz, 1H), 7.45 (dd, J=3.4, 1.0 Hz, 1H), 7.50 (d, J=7.8 Hz, 1H), 7.57 (m, 2H). MS (ESI): m/z 351 (M+H)$^+$.

EXAMPLE 139

3-(5-bromo-2-thienyl)-6-methoxy-1,4-dihydroindeno[1,2-c]pyrazole

The procedure for Example 138 was used, substituting 5-methoxy-1-indanone for Example 56 and Example 112 for Example 110. The crude product was triturated with 1N hydrochloric acid, the precipitate was collected by filtration and was dried under high vacuum to provide 1.15 g (85%) of the desired product as the hydrochloric acid salt. $^1$H NMR (300 MHz, DMSO-$d_6$) δ 3.71 (s, 2H), 3.81 (s, 3H), 6.95 (dd, J=2.4, 8.5 Hz, 1H), 7.18 (d, J=2.4 Hz, 1H), 7.24 (d, J=4.1 Hz, 1H), 7.28 (d, J=4.1 Hz, 1H), 7.52 (d, J=8.5 Hz, 1H). MS (ESI): m/z 346,348 (M+H)$^+$.

EXAMPLE 140

3-(3-chloro-2-thienyl)-7-[(4-methyl-1-piperazinyl)methyl]-1,4-dihydroindeno[1,2-c]pyrazole The procedure for Example 138 was used, substituting Example 115 for Example 110. The crude product was purified by preparative HPLC on a Waters Symmetry C8 column (25 mm×100 mm, 7 µm particle size) using a gradient of 10% to 100% acetonitrile:0.1% aqueous TFA over about 8 minutes (10 minutes run time) at a flow rate of 40 mL/minute to provide 125 mg (13%) of the desired product as the trifluoroacetic acid salt. $^1$H NMR (500 MHz, DMSO-$d_6$) δ 2.80 (s, 3H), 3.00-3.50 (m, 8H), 3.84 (s, 2H), 3.91 (br s, 2H), 7.16 (d, J=5.5 Hz, 1H), 7.31 (d, J=7.8 Hz, 1H), 7.58 (d, J=7.8 Hz, 1H), 7.66 (s, 1H), 7.71 (d, J=5.5 Hz, 1H). MS (ESI): m/z 385 (M+H)$^+$.

EXAMPLE 141

6-[(4-methyl-1-piperazinyl)methyl]-3-(1,3-thiazol-2-yl)-1,4-dihydroindeno[1,2-c]pyrazole A mixture of Example 80 (170 mg, 0.70 mmol), thiazole-2-carboxylic acid ethyl ester (166 mg, 1.05 mmol), and a 60% suspension of sodium hydride in mineral oil (127 mg, 3.17 mmol) in benzene (3 mL) was heated to reflux for about 2.5 hours. The reaction was cooled and quenched by dropwise addition of 50% aqueous acetic acid. The solvents were evaporated and the residue was dried under high vacuum for about 1 hour. The residue was dissolved in ethanol (3 mL), hydrazine monohydrate (60 µL, 1.23 mmol) and acetic acid (75 µL, 1.31 mmol) were added and the mixture was heated to reflux for about 4 hours. The mixture was cooled, concentrated under vacuum and the residue was purified by flash chromatography on silica gel using dichloromethane/methanol (10:1)+1% ammonium hydroxide as eluent to provide 7 mg (3%) of the desired product. $^1$H NMR (500 MHz, CDCl$_3$): δ 2.3-2.7 (m, 11H), 3.60 (s, 2H), 3.83 (s, 2H), 7.34 (d, J=7.8 Hz, 1H), 7.43 (d, J=3.1 Hz, 1H), 7.53 (s, 1H), 7.73 (d, J=7.5 Hz, 1H), 7.90 (d, J=3.1 Hz, 1H). MS (ESI): m/z 352 (M+H)$^+$.

EXAMPLE 142

3-(3,4-dimethylthieno[2,3-b]thien-2-yl)-6-[(4-methyl-1-piperazinyl)methyl]-1,4-dihydroindeno[1,2-c]pyrazole The procedure for Example 141 was used, substituting butyl 3,4-dimethylthieno[2,3-b]thiophene-2-carboxylate for thiazole-2-carboxylic acid ethyl ester. The crude product was purified by preparative HPLC on a Waters Symmetry C8 column (25 mm×100 mm, 7 µm particle size) using a gradient of 10% to 100% acetonitrile:0.1% aqueous TFA over 8 minutes (10 minutes run time) at a flow rate of 40 mL/minute to provide 33 mg (10%) of the desired product as the trifluoroacetic acid salt. $^1$H NMR (500 MHz, DMSO-$d_6$): δ 2.51 (s, 3H), 2.60 (s, 3H), 2.80 (s, 3H), 3.00-3.50 (m, 8H), 3.74 (s, 2H), 3.88 (br s, 2H), 7.21 (s, 1H), 7.39 (d, J=7.6 Hz, 1H), 7.58 (s, 1H), 7.66 (d, J=7.6 Hz, 1H). MS (ESI): m/z 435 (M+H)$^+$.

EXAMPLE 143

6-[(4-methyl-1-piperazinyl)methyl]-3-(4-methyl-2-thienyl)-1,4-dihydroindeno[1,2-c]pyrazole To a solution of 4-methyl-thiophene-2-carboxylic acid (44 mg, 0.31 mmol) in benzene (1 mL) was added 1,1'-carbonyldiimidazole (50 mg, 0.31 mmol) and the mixture was agitated at about 80° C. for about 1 hour. To a separate solution of Example 80 (50 mg, 0.21 mmol) in benzene (1 mL) was added a 60% suspension of sodium hydride in mineral oil (16 mg, 0.68 mmol) and the mixture was agitated at about 80° C. for about 1 hour. Both solutions were combined and agitated at about 80° C. for about 1 hour before ethanol (50 µL) was added. The reaction mixture was kept at about 80° C. for about an additional 30 minutes, then 5 drops of acetic acid were added and the mixture was concentrated to dryness in high vacuum. The residue was dissolved in ethanol (3 mL), acetic acid (41 µL, 0.72 mmol) was added, followed by hydrazine monohydrate (30 µL, 0.62 mmol), and the mixture was heated to about 80° C. overnight. The mixture was concentrated under vacuum and the residue was purified by preparative HPLC on a Waters Symmetry C8 column (25 mm×100 mm, 7 µm particle size) using a gradient of 10% to 100% acetonitrile:0.1% aqueous TFA over 8 minutes (10 minutes run time) at a flow rate of 40 mL/minute to provide 75 mg (44%) of the desired product as the trifluoroacetic acid salt. $^1$H NMR (300 MHz, DMSO-$d_6$): δ 2.27 (s, 3H), 2.77 (s, 3H), 3.00-3.50 (m, 8H), 3.74 (s, 2H), 3.88 (br s, 2H), 7.16 (s, 1H), 7.28 (s, 1H), 7.35 (d, J=7.8 Hz, 1H), 7.55 (s, 1H), 7.62 (d, J=7.8 Hz, 1H). MS (ESI): m/z 365 (M+H)$^+$.

| | R₁ | R₂ | R₃ | R₄ | MS (ESI): | Example Number (Reference Procedure) |
|---|---|---|---|---|---|---|
| | H | H | H | 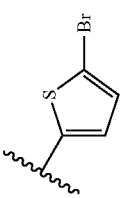 | m/z 317, 319 (M + H)⁺ | Example 144 (Example 138) |
| | Br | H | H | 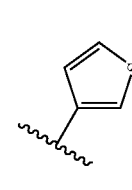 | m/z 317, 319 (M + H)⁺ | Example 145 (Example 138) |
| | H | 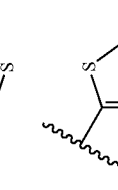 | H | 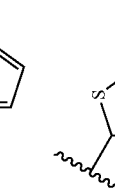 | m/z 351 (M + H)⁺ | Example 146 (Example 138) |
| | H | 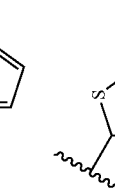 | H | 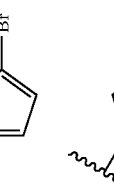 | m/z 429, 431 (M + H)⁺ | Example 147 (Example 138) |
| | H | 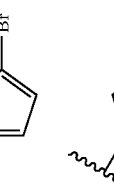 | H | | m/z 429, 431 (M + H)⁺ | Example 148 (Example 138) |

-continued

| R₁ | R₂ | R₃ | R₄ | MS (ESI): | Example Number (Reference Procedure) |
|---|---|---|---|---|---|
| N-methylpiperazinyl-CH₂- | H | H | 5-bromothiophen-3-yl | m/z 429, 431 (M + H)⁺ | Example 149 (Example 138) |
| H | N-methylpiperazinyl-CH₂- | H | 3-methylthiophen-2-yl | m/z 365 (M + H)⁺ | Example 150 (Example 138) |
| N-methylpiperazinyl-CH₂- | H | H | 3-methylthiophen-2-yl | m/z 365 (M + H)⁺ | Example 151 (Example 138) |
| H | N-methylpiperazinyl-CH₂- | H | 3-chlorothiophen-2-yl | m/z 385 (M + H)⁺ | Example 152 (Example 138) |
| H | N-methylpiperazinyl-CH₂- | H | 5-methylthiophen-2-yl | m/z 365 (M + H)⁺ | Example 153 (Example 138) |

| R₁ | R₂ | R₃ | R₄ | MS (ESI): | Example Number (Reference Procedure) |
|---|---|---|---|---|---|
| N-methylpiperazinyl-CH₂- | H | H | 5-methyl-thien-2-yl | m/z 365 (M + H)⁺ | Example 154 (Example 138) |
| H | N-methylpiperazinyl-CH₂- | H | 5-chloro-thien-2-yl | m/z 385 (M + H)⁺ | Example 155 (Example 138) |
| N-methylpiperazinyl-CH₂- | H | H | 5-chloro-thien-2-yl | m/z 385 (M + H)⁺ | Example 156 (Example 138) |
| H | N-methylpiperazinyl-CH₂- | H | benzothien-2-yl | m/z 401 (M + H)⁺ | Example 157 (Example 138) |
| N-methylpiperazinyl-CH₂- | H | H | benzothien-2-yl | m/z 401 (M + H)⁺ | Example 158 (Example 138) |

-continued
| R₁ | R₂ | R₃ | R₄ | MS (ESI): | Example Number (Reference Procedure) |
|---|---|---|---|---|---|
| H | 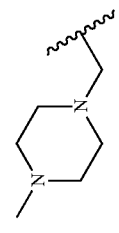 | H | 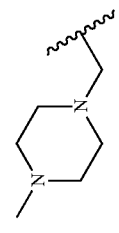 | m/z 423, 425 (M + H)⁺ | Example 159 (Example 138) |
| H | 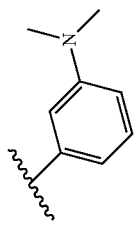 | H | 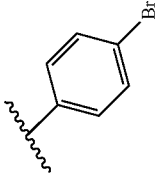 | m/z 441, 443 (M + H)⁺ | Example 160 (Example 138) |
| H | 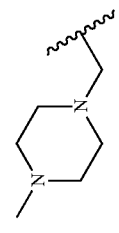 | H | 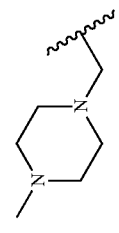 | m/z 388 (M + H)⁺ | Example 161 (Example 143) |
| H | 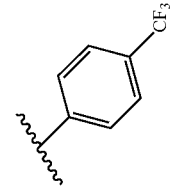 | H | 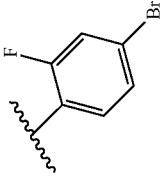 | m/z 413 (M + H)⁺ | Example 162 (Example 143) |

-continued
| R₁ | R₂ | R₃ | R₄ | MS (ESI): | Example Number (Reference Procedure) |
|---|---|---|---|---|---|
| H | 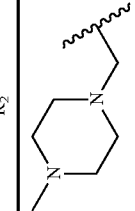 | H | 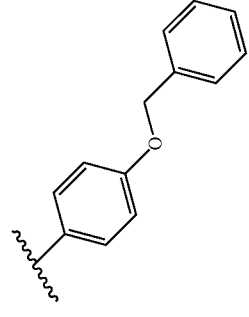 | m/z 451 (M + H)⁺ | Example 163 (Example 143) |
| H | 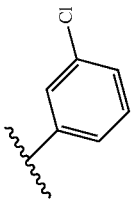 | H | 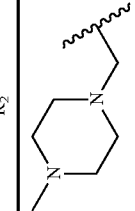 | m/z 379 (M + H)⁺ | Example 164 (Example 143) |
| H | 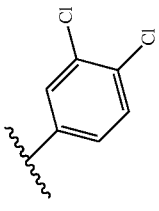 | H | 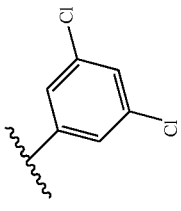 | m/z 414 (M + H)⁺ | Example 165 (Example 143) |
| H | 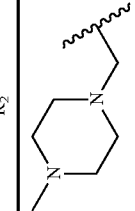 | H | 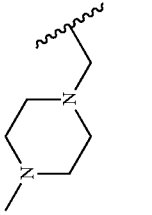 | m/z 414 (M + H)⁺ | Example 166 (Example 143) |

-continued

| R₁ | R₂ | R₃ | R₄ | MS (ESI): | Example Number (Reference Procedure) |
|---|---|---|---|---|---|
| H | [1-methylpiperazin-4-yl-methyl] | H | [thiazol-4-yl] | m/z 352 (M + H)⁺ | Example 167 (Example 138) |
| H | [1-methylpiperazin-4-yl-methyl] | H | [2-methylthiazol-4-yl] | m/z 366 (M + H)⁺ | Example 168 (Example 141) |
| H | [1-methylpiperazin-4-yl-methyl] | H | [thiazol-5-yl] | m/z 352 (M + H)⁺ | Example 169 (Example 138) |
| [1-methylpiperazin-4-yl-methyl] | H | H | [thiazol-2-yl] | m/z 352 (M + H)⁺ | Example 170 (Example 141) |
| H | [1-methylpiperazin-4-yl-methyl] | H | [5-methylisoxazol-3-yl] | m/z 350 (M + H)⁺ | Example 171 (Example 141) |

-continued
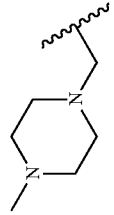
| R₁ | R₂ | R₃ | R₄ | MS (ESI): | Example Number (Reference Procedure) |
|---|---|---|---|---|---|
| H |  | H | 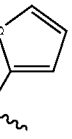 | m/z 364 (M + H)⁺ | Example 172 (Example 140) |
| H | H | OMe | 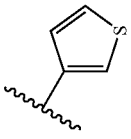 | m/z 269 (M + H)⁺ | Example 173 (Example 140) |
| H | H | OMe | 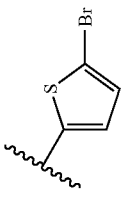 | m/z 269 (M + H)⁺ | Example 174 (Example 140) |
| H | H | OMe |  | m/z 347, 349 (M + H)⁺ | Example 175 (Example 140) |

-continued

| R₁ | R₂ | R₃ | R₄ | MS (ESI): | Example Number (Reference Procedure) |
|---|---|---|---|---|---|
| H | [1-methylpiperazin-4-yl-methyl] | H | [4,5,6,7-tetrahydrothieno[3,2-c]pyridine-5-carboxylic acid tert-butyl ester-2-yl] | m/z 506 (M + H)⁺ | Example 176 (Example 138) |
| H | [1-methylpiperazin-4-yl-methyl] | H | [5-(pyridin-2-yl)thiophen-2-yl] | m/z 428 (M + H)⁺ | Example 177 (Example 140) |
| [1-methylpiperazin-4-yl-methyl] | H | H | [5-(pyridin-2-yl)thiophen-2-yl] | m/z 428 (M + H)⁺ | Example 178 (Example 140) |
| H | [imidazol-1-yl-methyl] | H | [4-(3-phenoxyprop-1-ynyl)thiophen-2-yl] | m/z 449 (M + H)⁺ | Example 179 (Example 138) |

-continued

| R₁ | R₂ | R₃ | R₄ | MS (ESI): | Example Number (Reference Procedure) |
|---|---|---|---|---|---|
| H | 2-(morpholin-4-yl)ethoxy | H | 4-(5-bromothiophen-2-yl) | m/z 446, 448 (M + H)⁺ | Example 180 (Example 138) |
| H | 2-(morpholin-4-yl)ethoxy | H | 2-(5-bromothiophen-2-yl) | m/z 446, 448 (M + H)⁺ | Example 181 (Example 138) |
| H | 2-(morpholin-4-yl)ethoxy | H | thiophen-3-yl | m/z 368 (M + H)⁺ | Example 182 (Example 138) |
| H | N-methyl-N-(furan-2-ylmethyl)amino | H | thiophen-3-yl | m/z 348 (M + H)⁺ | Example 183 (Example 140) |
| H | 4-methylpiperazin-1-yl | H | thiophen-2-yl | m/z 337 (M + H)⁺ | Example 184 (Example 140) |

-continued
| R₁ | R₂ | R₃ | R₄ | MS (ESI): | Example Number (Reference Procedure) |
|---|---|---|---|---|---|
| H | 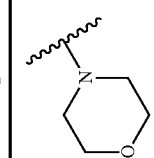 | H |  | m/z 402, 404 (M + H)⁺ | Example 185 (Example 138) |
| 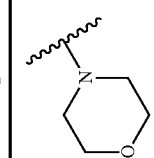 | H | H | 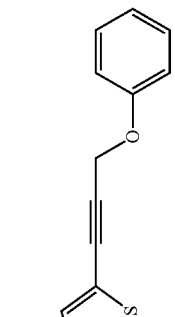 | m/z 495 (M + H)⁺ | Example 186 (Example 140) |
| 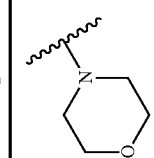 | H | H | 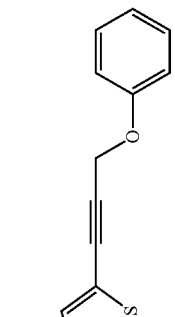 | m/z 467 (M + H)⁺ | Example 187 (Example 140) |
| 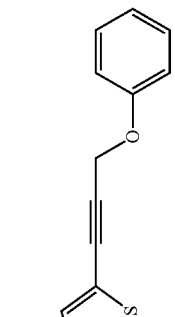 | H | H | 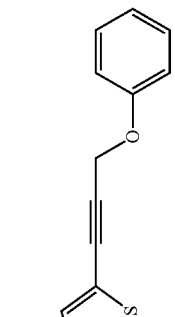 | m/z 495 (M + H)⁺ | Example 188 (Example 140) |

-continued

| R₁ | R₂ | R₃ | R₄ | MS (ESI): | Example Number (Reference Procedure) |
|---|---|---|---|---|---|
| pyrrolidin-1-ylmethyl | H | H | 2-(3-phenoxyprop-1-ynyl)thiophen-4-yl | m/z 452 (M + H)⁺ | Example 189 (Example 140) |
| (4-methylpiperidin-1-yl)methyl | H | H | 2-(3-phenoxyprop-1-ynyl)thiophen-4-yl | m/z 480 (M + H)⁺ | Example 190 (Example 140) |
| (4-ethylpiperazin-1-yl)methyl | H | H | 2-(3-phenoxyprop-1-ynyl)thiophen-4-yl | m/z 495 (M + H)⁺ | Example 191 (Example 140) |
| (2,6-dimethylmorpholin-4-yl)methyl | H | H | 2-(3-phenoxyprop-1-ynyl)thiophen-4-yl | m/z 494 (M − H)⁻ | Example 192 (Example 140) |

-continued

| R₁ | R₂ | R₃ | R₄ | MS (ESI): | Example Number (Reference Procedure) |
|---|---|---|---|---|---|
| (1H-pyrazol-1-ylmethyl) | H | H | (phenoxymethyl-ethynyl-thiophene) | m/z 448 (M − H)⁻ | Example 193 (Example 140) |
| (2-methyl-1H-imidazol-1-ylmethyl) | H | H | (phenoxymethyl-ethynyl-thiophene) | m/z 463 (M + H)⁺ | Example 194 (Example 140) |
| (1H-1,2,3-triazol-1-ylmethyl) | H | H | (phenoxymethyl-ethynyl-thiophene) | m/z 450 (M + H)⁺ | Example 195 (Example 140) |
| (4-isopropylpiperazin-1-ylmethyl) | H | H | (phenoxymethyl-ethynyl-thiophene) | m/z 509 (M + H)⁺ | Example 196 (Example 140) |

-continued

[Structure: pyrazole fused indene core with R1, R2, R3, R4 substituents]

| R_1 | R_2 | R_3 | R_4 | MS (ESI): | Example Number (Reference Procedure) |
|---|---|---|---|---|---|
| H | H | H | (thiophene linked to C≡C-CH2-O-phenyl) | m/z 369 (M + H)+ | Example 197 (Example 138) |
| H | H | Br | (2-thienyl) | m/z 318 (M + H)+ | Example 198 (Example 140) |
| H | H | NHC(O)CH3 | (3-thienyl) | m/z 296 (M + H)+ | Example 199 (Example 140) |
| H | H | NHC(O)CH3 | (2-bromo-4-thienyl) | m/z 374, 376 (M + H)+ | Example 200 (Example 138) |

-continued

| R₁ | R₂ | R₃ | R₄ | MS (ESI): | Example Number (Reference Procedure) |
|---|---|---|---|---|---|
| H | H | NHC(O)CH₃ | thiophene-alkyne-CH₂-O-phenyl | m/z 424 (M − H)⁻ | Example 201 (Example 138) |
| H | H | N(CH₃)₂ | 3-thienyl | m/z 282 (M + H)⁺ | Example 202 (Example 140) |
| H | H | NHC(O)CH₂CH₃ | 3-thienyl | m/z 310 (M + H)⁺ | Example 203 (Example 140) |
| H | H | NHC(O)CH₂CH₂CH₃ | 3-thienyl | m/z 324 (M + H)⁺ | Example 204 (Example 140) |
| H | H | NHC(O)CH₂OCH₃ | 3-thienyl | m/z 326 (M + H)⁺ | Example 205 (Example 138) |

-continued
| Example Number (Reference Procedure) | R₁ | R₂ | R₃ | R₄ | MS (ESI): |
|---|---|---|---|---|---|
| Example 206 (Example 140) | H | H | 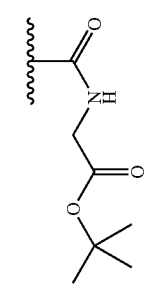 | 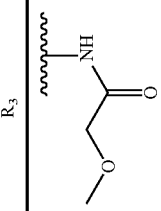 | m/z 404, 406 (M + H)⁺ |
| Example 207 (Example 140) | 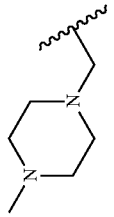 | H | 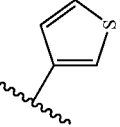 | 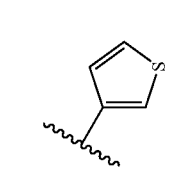 | m/z 522 (M + H)⁺ |
| Example 208 (Example 140) | H | 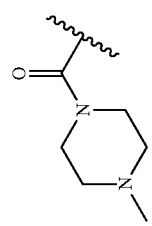 | H | 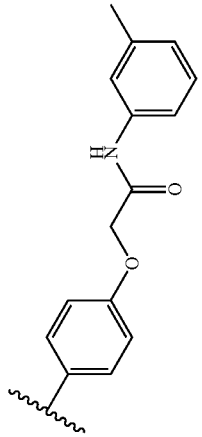 | m/z 508 (M + H)⁺ |

-continued
| R₁ | R₂ | R₃ | R₄ | MS (ESI): | Example Number (Reference Procedure) |
|---|---|---|---|---|---|
| H | 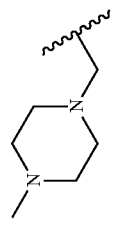 | H | 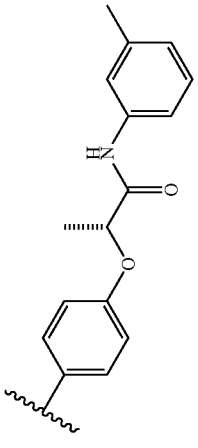 | m/z 522 (M + H)⁺ | Example 209 (Example 140) |
| H | 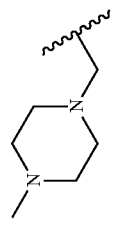 | OH | 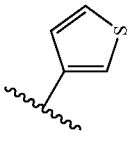 | m/z 367 (M + H)⁺ | Example 210 (Example 140) |
| 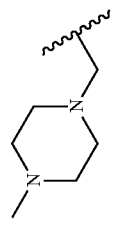 | H | H | 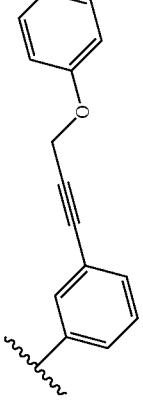 | m/z 443 (M + H)⁺ | Example 211 (Example 138) |
| 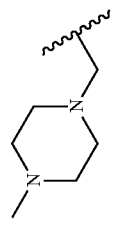 | H | H | 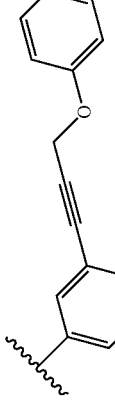 | m/z 475 (M + H)⁺ | Example 212 (Example 140) |

-continued

| R₁ | R₂ | R₃ | R₄ | MS (ESI): | Example Number (Reference Procedure) |
|---|---|---|---|---|---|
| *N-methylpiperazinylmethyl* | H | H | *4-(3-phenoxyprop-1-ynyl)phenyl* | m/z 475 (M + H)⁺ | Example 213 (Example 138) |
| *imidazolylmethyl* | H | H | *4-(3-phenoxyprop-1-ynyl)phenyl* | m/z 443 (M + H)⁺ | Example 214 (Example 138) |

| R₁ | R₂ | R₃ | R₄ | MS (ESI): | Example Number (Reference Procedure) |
|---|---|---|---|---|---|
| H |  | H | 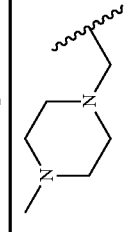 | m/z 475 (M + H)⁺ | Example 215 (Example 140) |
| H |  | H |  | m/z 443 (M + H)⁺ | Example 216 (Example 140) |
| H |  | H |  | m/z 475 (M + H)⁺ | Example 217 (Example 140) |

-continued
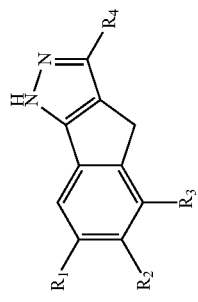
| R1 | R2 | R3 | R4 | MS (ESI): | Example Number (Reference Procedure) |
|---|---|---|---|---|---|
| H | 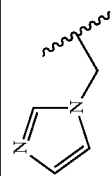 | H | 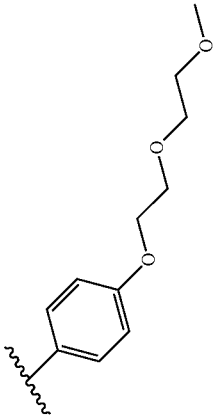 | m/z 443 (M + H)+ | Example 218 (Example 140) |
| H | 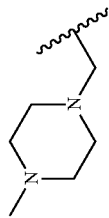 | H | (see structure) | m/z 463 (M + H)+ | Example 219 (Example 140) |

-continued
| R₁ | R₂ | R₃ | R₄ | MS (ESI): | Example Number (Reference Procedure) |
|---|---|---|---|---|---|
| H | 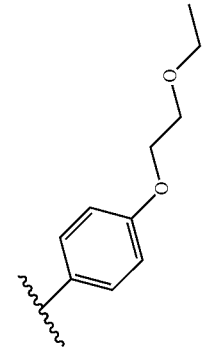 | H | 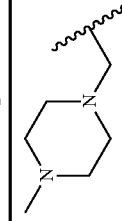 | m/z 481 (M + H)⁺ | Example 220 (Example 138) |
| H | 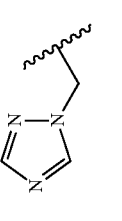 | H | 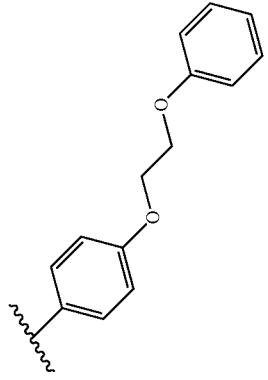 | m/z 433 (M + H)⁺ | Example 221 (Example 140) |
| H | 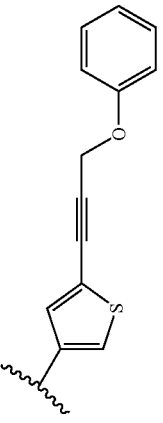 | H | 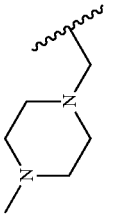 | m/z 450 (M + H)⁺ | Example 222 (Example 140) |

-continued
| R₁ | R₂ | R₃ | R₄ | MS (ESI): | Example Number (Reference Procedure) |
|---|---|---|---|---|---|
| H | H | 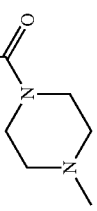 | 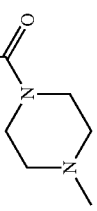 | m/z 365 (M + H)⁺ | Example 223 (Example 140) |
| Br | H | 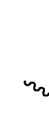 | 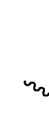 | m/z 474, 472 (M − H)⁻ | Example 224 (Example 140) |
| Br | H | 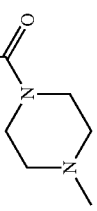 | 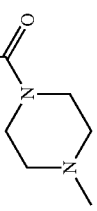 | m/z 488, 490 (M + H)⁺ | Example 225 (Example 140) |
| H | H | 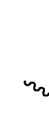 | 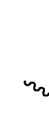 | m/z 510 (M + H)⁺ | Example 226 (Example 140) |

-continued

| R₁ | R₂ | R₃ | R₄ | MS (ESI): | Example Number (Reference Procedure) |
|---|---|---|---|---|---|
| H | H | *N,N-dimethylamide* | 3-thienyl | m/z 310 (M + H)⁺ | Example 227 (Example 140) |
| H | H | *tert-butyl ester of α-methyl amino acid (S)* | 3-thienyl | m/z 410 (M + H)⁺ | Example 228 (Example 140) |
| H | H | *tert-butyl ester of α-methyl amino acid (R)* | 3-thienyl | m/z 410 (M + H)⁺ | Example 229 (Example 140) |
| H | H | *ethyl piperidine-3-carboxylate amide* | 3-thienyl | m/z 422 (M + H)⁺ | Example 230 (Example 140) |

-continued
| R₁ | R₂ | R₃ | R₄ | MS (ESI): | Example Number (Reference Procedure) |
|---|---|---|---|---|---|
| H | H | 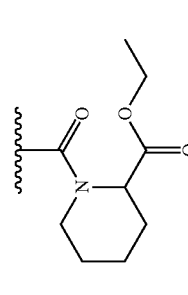 | 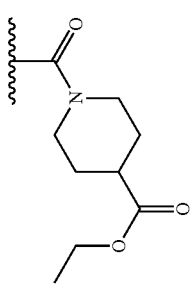 | m/z 422 (M + H)⁺ | Example 231 (Example 140) |
| H | H | 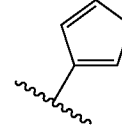 | 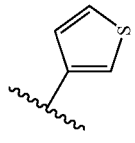 | m/z 422 (M + H)⁺ | Example 232 (Example 140) |
| H | H | 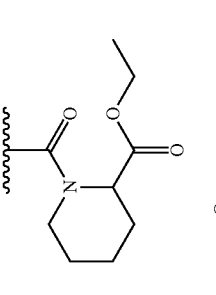 | 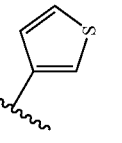 | m/z 410 (M + H)⁺ | Example 233 (Example 140) |
| H | H | 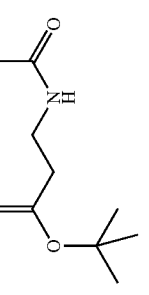 | 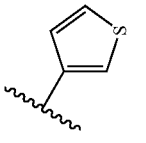 | m/z 396 (M + H)⁺ | Example 234 (Example 140) |
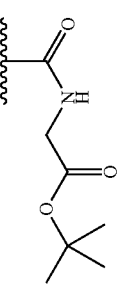
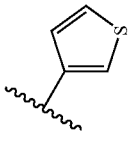

-continued
| R₁ | R₂ | R₃ | R₄ | MS (ESI): | Example Number (Reference Procedure) |
|---|---|---|---|---|---|
| H | 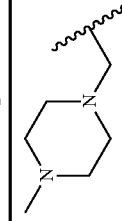 | 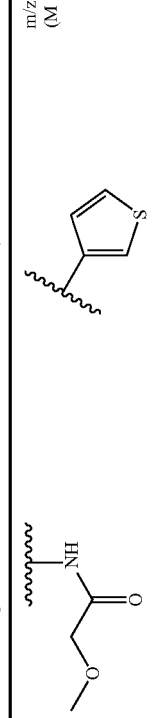 | 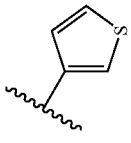 | m/z 439 (M + H)⁺ | Example 235 (Example 140) |
| H | H | 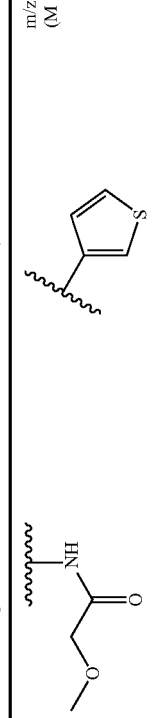 | 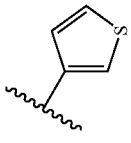 | m/z 297 (M + H)⁺ | Example 236 (Example 140) |
| H | H | 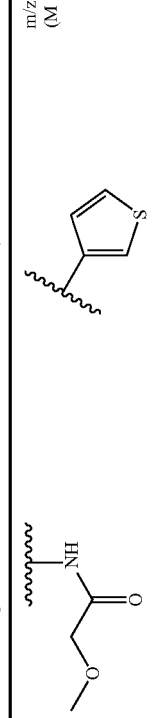 | 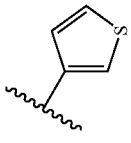 | m/z 311 (M + H)⁺ | Example 237 (Example 140) |
| H | H | 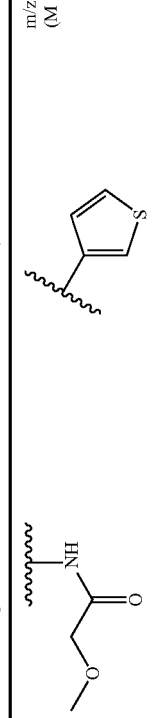 | 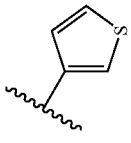 | m/z 313 (M + H)⁺ | Example 238 (Example 140) |
| H | H | 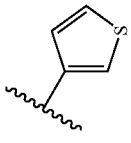 | 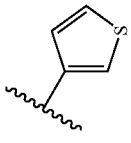 | m/z 341 (M + H)⁺ | Example 239 (Example 140) |

-continued
| R₁ | R₂ | R₃ | R₄ | MS (ESI): | Example Number (Reference Procedure) |
|---|---|---|---|---|---|
| H | H | 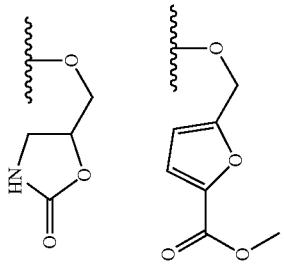 | 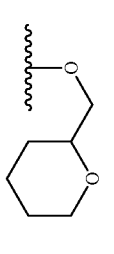 | m/z 354 (M + H)⁺ | Example 240 (Example 140) |
| H | H | 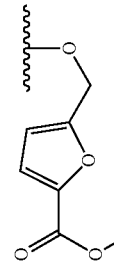 | 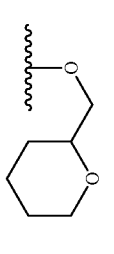 | m/z 393 (M + H)⁺ | Example 241 (Example 140) |
| H | H | 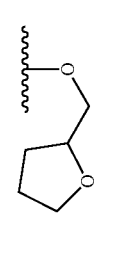 | 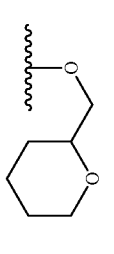 | m/z 339 (M + H)⁺ | Example 242 (Example 140) |
| H | H | 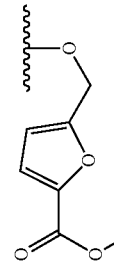 | 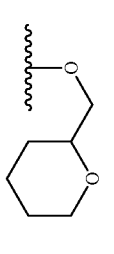 | m/z 353 (M + H)⁺ | Example 243 (Example 140) |
| H | H | 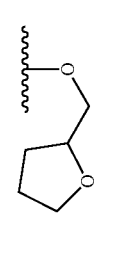 | 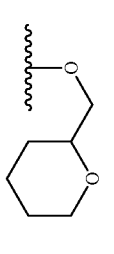 | m/z 294 (M + H)⁺ | Example 244 (Example 140) |

-continued
| Example Number (Reference Procedure) | R₁ | R₂ | R₃ | R₄ | MS (ESI): |
|---|---|---|---|---|---|
| Example 245 (Example 140) | H | 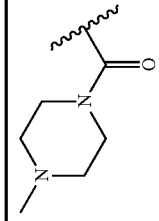 | H | 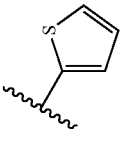 | m/z 365 (M + H)⁺ |
| Example 246 (Example 140) | H | 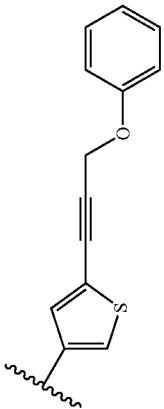 | H | 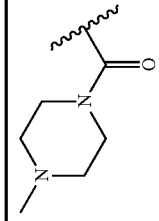 | m/z 352 (M + H)⁺ |
| Example 247 (Example 140) | H | H | H | 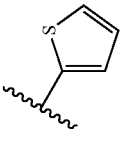 | m/z 495 (M + H)⁺ |
| Example 248 (Example 138) | 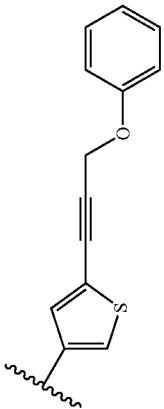 | H | 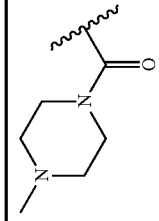 | 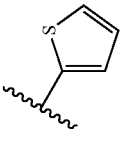 | m/z 326 (M + H)⁺ |
| Example 249 (Example 140) | H | H | 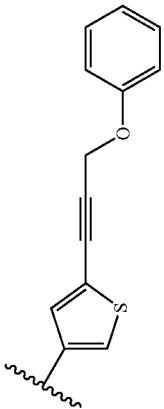 | 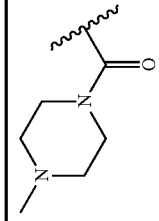 | m/z 346 (M + H)⁺ |

-continued

| R₁ | R₂ | R₃ | R₄ | MS (ESI): | Example Number (Reference Procedure) |
|---|---|---|---|---|---|
| H | (N-methylpiperidin-4-yl)methoxy | H | 3-phenoxyprop-1-ynyl-thiophen-2-yl | m/z 496 (M + H)⁺ | Example 250 (Example 140) |
| H | 2-(1H-pyrazol-1-yl)ethyl | H | 3-phenoxyprop-1-ynyl-thiophen-2-yl | m/z 450 (M + H)⁺ | Example 251 (Example 140) |
| H | ethyl 4-piperazinecarboxylate-ethyl | H | 3-phenoxyprop-1-ynyl-thiophen-2-yl | m/z 539 (M + H)⁺ | Example 252 (Example 140) |
| H | 2-(2,6-dimethylmorpholin-4-yl)ethyl | H | 3-phenoxyprop-1-ynyl-thiophen-2-yl | m/z 496 (M + H)⁺ | Example 253 (Example 140) |

-continued

| Example Number (Reference Procedure) | R₁ | R₂ | R₃ | R₄ | MS (ESI): |
|---|---|---|---|---|---|
| Example 254 (Example 140) | H | 4-methylpiperidin-1-yl-ethyl | H | 4-(3-phenoxyprop-1-ynyl)thiophen-3-yl | m/z 480 (M + H)⁺ |
| Example 255 (Example 140) | 4-methylpiperazin-1-yl-carbonyl | H | H | thiophen-3-yl | m/z 365 (M + H)⁺ |
| Example 256 (Example 140) | 4-methylpiperazin-1-yl-carbonyl | H | methoxyacetamido | thiophen-3-yl | m/z 452 (M + H)⁺ |
| Example 257 (Example 138) | imidazol-1-yl-ethyl | H | H | 5-bromothiophen-3-yl | m/z 397, 399 (M + H)⁺ |

-continued

| R₁ | R₂ | R₃ | R₄ | MS (ESI): | Example Number (Reference Procedure) |
|---|---|---|---|---|---|
| ethyl-CH₂CH₂-NH-C(O)- (N,N-diethylaminoethylamide) | H | H | 2-bromothiophen-4-yl | m/z 459, 461 (M+H)⁺ | Example 258 (Example 138) |
| imidazol-1-yl-CH₂CH₂- | H | H | 2-bromothiophen-4-yl | m/z 398, 400 (M+H)⁺ | Example 259 (Example 138) |
| H | imidazol-1-yl-CH₂CH₂- | H | 2-bromothiophen-4-yl | m/z 398, 400 (M+H)⁺ | Example 260 (Example 138) |
| H | (4-methylpiperazin-1-yl)-CH₂CH₂- | H | 4-bromothiophen-2-yl | m/z 429, 431 (M+H)⁺ | Example 261 (Example 138) |
| (4-methylpiperazin-1-yl)-C(O)- | H | H | 2-bromothiophen-4-yl | m/z 443, 445 (M+H)⁺ | Example 262 (Example 138) |

-continued

| R1 | R2 | R3 | R4 | MS (ESI): | Example Number (Reference Procedure) |
|---|---|---|---|---|---|
| H | pyrimidin-2-yloxy | H | 4-(3-methoxyethoxy-prop-1-ynyl)thiophen-4-yl (see structure) | m/z 445 (M + H)+ | Example 263 (Example 138) |
| H | 2-morpholinoethoxy | H | 5-bromothiophen-3-yl | m/z 446, 448 (M + H)+ | Example 264 (Example 138) |
| H | 2-(dimethylamino)-2-oxoethoxy | H | 5-bromothiophen-3-yl | m/z 418, 420 (M + H)+ | Example 265 (Example 138) |

| Example Number | $^1$H NMR |
|---|---|
| 144 | (500 MHz, DMSO-$d_6$)δ 3.75(s, 2H), 7.25(br s, 1H), 7.30(m, 2H), 7.38(dd, J=7.5, 7.5Hz, 1H), 7.58(d, J=7.8Hz, 1H), 7.62(br s, 1H). |
| 145 | (300 MHz, DMSO-$d_6$)δ 3.80(s, 2H), 7.46(dd, J=1.7, 8.1Hz, 1H), 7.53(d, J=13.9Hz, 1H), 7.56(dd, J=1.4, 5.1Hz, 1H), 7.72(m, 1H), 7.80(m, 1H), 7.86(m, 1H). |
| 146 | (300 MHz, CDCl$_3$)δ 2.36(s, 3H), 3.59(s, 2H), 3.75(s, 2H), 7.13(dd, J=3.7, 4.8Hz, 1H), 7.30(d, J=7.8Hz, 1H), 7.35(m, 2H), 7.49(s, 1H), 7.63(d, J=7.8Hz, 1H). |
| 147 | (500 MHz, CDCl$_3$)δ 2.32(s, 3H), 2.4-2.65(m, 8H), 3.58(s, 2H), 3.70(s, 2H), 7.06(m, 2H), 7.31(d, J=7.5Hz, 1H), 7.50(s, 1H), 7.59(d, J=7.8Hz, 1H). |
| 148 | (500 MHz, CDCl$_3$)δ 2.32(s, 3H), 2.40-2.65(m, 8H), 3.58(s, 2H), 3.70(s, 2H), 7.29(d, J=7.8Hz, 1H), 7.37(d, J=1.4Hz, 1H), 7.40(d, J=1.4Hz, 1H), 7.49(s, 1H), 7.61(d, J=7.8Hz, 1H). |
| 149 | (300 MHz, DMSO-$d_6$)δ 2.15(s, 3H), 2.28-2.45(m, 8H), 3.52(s, 2H), 3.78(s, 2H), 7.20(d, J=7.5Hz, 1H), 7.48(d, J=7.5Hz, 1H), 7.58(s, 1H), 7.64(s, 1H), 7.84(s, 1H). |
| 150 | (500 MHz, DMSO-$d_6$)δ 2.15(s, 6H), 2.25-2.50(m, 8H), 3.50(s, 2H), 3.70(s, 2H), 7.01(m, 1H), 7.28(d, J=7.6Hz, 1H), 7.47(s, 1H), 7.58(m, 2H). |
| 151 | (500 MHz, DMSO-$d_6$)δ 2.15(s, 6H), 2.25-2.50(m, 8H), 3.53(s, 2H), 3.69(s, 2H), 7.00(m, 1H), 7.20(d, J=7.6Hz, 1H), 7.48(d, J=7.6Hz, 1H), 7.58(m, 2H). |
| 152 | (500 MHz, DMSO-$d_6$)δ 2.15(s, 3H), 2.23-2.48(m, 8H), 3.50(s, 2H), 3.81(s, 2H), 7.14(d, J=5.3Hz, 1H), 7.29(d, J=7.7Hz, 1H), 7.48(s, 1H), 7.56(d, J=7.7Hz, 1H), 7.68(d, J=5.3Hz, 1H). |
| 153 | (500 MHz, DMSO-$d_6$)δ 2.15(s, 3H), 2.25-2.45(m, 8H), 2.49(s, 3H), 3.50(s, 2H), 3.70(s, 2H), 6.85(s, 1H), 7.23(s, 1H), 7.27(d, J=7.4Hz, 1H), 7.48(s, 1H), 7.55(d, J=7.4Hz, 1H). |
| 154 | (500 MHz, DMSO-$d_6$)δ 2.15(s, 3H), 2.25-2.45(m, 8H), 2.49(s, 3H), 3.52(s, 2H), 3.69(s, 2H), 6.85(s, 1H), 7.19(d, J=7.7Hz, 1H), 7.23(br s, 1H), 7.49(d, J=7.7Hz, 1H), 7.57(s, 1H). |
| 155 | (500 MHz, DMSO-$d_6$)δ 2.15(s, 3H), 2.25-2.45(m, 8H), 3.50(s, 2H), 3.74(s, 2H), 7.18(d, J=3.7Hz, 1H), 7.26(br s, 1H), 7.29(d, J=7.3Hz, 1H), 7.49(s, 1H), 7.55(d, J=7.3Hz, 1H). |
| 156 | (500 MHz, DMSO-$d_6$)δ 2.15(s, 3H), 2.25-2.45(m, 8H), 3.52(s, 2H), 3.72(s, 2H), 7.17(d, J=2.8Hz, 1H), 7.21(d, J=7.8Hz, 1H), 7.26(br s, 1H), 7.50(d, J=7.8Hz, 1H), 7.57(s, 1H). |
| 157 | (500 MHz, DMSO-$d_6$)δ 2.15(s, 3H), 2.25-2.45(m, 8H), 3.52(s, 2H), 3.84(s, 2H), 7.31(d, J=7.8Hz, 1H), 7.39(m, 2H), 7.52(s, 1H), 7.58(d, J=7.8Hz, 1H), 7.73(s, 1H), 7.89(d, J=7.5Hz, 1H), 7.99(d, J=7.8Hz, 1H). |
| 158 | (500 MHz, DMSO-$d_6$)δ 2.16(s, 3H), 2.25-2.45(m, 8H), 3.54(s, 2H), 3.83(s, 2H), 7.23(d, J=7.8Hz, 1H), 7.38(m, 2H), 7.53(d, 7.8Hz, 1H), 7.60(s, 1H), 7.73(s, 1H), 7.88(d, J=7.5Hz, 1H), 7.99(d, J=7.8Hz, 1H). |
| 159 | (500 MHz, CDCl$_3$)δ 2.30(s, 3H), 2.25-2.45(m, 8H), 3.57(s, 2H), 3.75(s, 2H), 7.28(m, J=8.4Hz, 1H), 7.49(s, 1H), 7.55(m, 2H), 7.59(m, 2H), 7.63(d, J=7.5Hz, 1H). |
| 160 | (500 MHz, CDCl$_3$)δ 2.32(s, 3H), 2.25-2.45(s, 8H), 3.59(s, 2H), 3.82(s, 2H), 7.34(d, J=7.8Hz, 1H), 7.43(m, 2H), 7.51(s, 1H), 7.61(t, J=8.3Hz, 1H), 7.74(d, J=7.8Hz, 1H). |
| 161 | (500 MHz, DMSO-$d_6$)δ 2.76(s, 3H), 2.94(s, 6H), 3.00-3.50(m, 8H), 3.82(s, 2H), 3.92(br s, 2H), 6.71(d, J=8.4Hz, 1H), 7.06(d, J=7.5Hz, 1H), 7.15(s, 1H), 7.26(t, J=7.8Hz, 1H), 7.35(d, J=7.8Hz, 1H), 7.55(s, 1H), 7.64(d, J=7.8Hz, 1H). |
| 162 | (500 MHz, DMSO-$d_6$)δ 2.78(s, 3H), 3.00-3.50(m, 8H), 3.87(s, 2H), 3.92(m, 2H), 7.39(d, J=8.1Hz, 1H), 7.59(s, 1H), 7.67(d, J=7.8Hz, 1H), 7.86(m, 2H), 8.03(m, 2H). |
| 163 | (500 MHz, DMSO-$d_6$)δ 2.80(s, 3H), 3.00-3.50(m, 8H), 3.85(s, 2H), 3.94(s, 2H), 5.18(s, 2H), 7.15(m, 2H), 7.33-7.42(m, 4H), 7.48(m, 2H), 7.58(s, 1H), 7.67(d, J=7.8Hz, 1H), 7.75(m, 2H). |
| 164 | (500 MHz, DMSO-$d_6$)δ 2.79(s, 3H), 3.00-3.50(m, 8H), 3.91(m, 4H), 7.39(d, J=7.8Hz, 1H), 7.43(d, J=8.1Hz, 1H), 7.54(t, J=7.9Hz, 1H), 7.59(s, 1H), 7.67(d, J=7.5Hz, 1H), 7.78(d, J=7.8Hz, 1H), 7.87(s, 1H). |
| 165 | (500 MHz, DMSO-$d_6$)δ 2.79(s, 3H), 3.00-3.50(m, 8H), 3.91(m, 4H), 7.39(d, J=7.8Hz, 1H), 7.59(s, 1H), 7.67(d, J=7.5Hz, 1H), 7.78(m, 1H), 8.04(s, 1H). |
| 166 | (500 MHz, DMSO-$d_6$)δ 2.79(s, 3H), 3.00-3.50(m, 8H), 3.87(br s, 2H), 3.93(s, 2H), 7.39(d, J=7.5Hz, 1H), 7.58(s, 1H), 7.60(t, J=1.6Hz, 1H), 7.67(d, J=7.5Hz, 1H), 7.82(m, 2H). |
| 167 | (500 MHz, CDCl$_3$)δ 2.31(s, 3H), 2.25-2.45(m, 8H), 3.58(s, 2H), 3.81(s, 2H), 7.33(d, J=7.8Hz, 1H), 7.52(s, 2H), 7.77(d, J=7.8Hz, 1H), 8.94(d, J=1.9Hz, 1H). |
| 168 | (300 MHz, CDCl$_3$)δ 2.34(s, 3H), 2.25-2.45(m, 8H), 2.79(s, 3H), 3.59(s, 2H), 3.77(s, 2H), 7.28(s, 1H), 7.33(d, J=8.8Hz, 1H), 7.51(s, 1H), 7.76(d, J=7.8Hz, 1H). |
| 169 | (500 MHz, CDCl$_3$)δ 2.29(s, 3H), 2.25-2.45(m, 8H), 3.53(s, 2H), 3.69(s, 2H), 7.26(d, J=7.8Hz, 1H), 7.47(s, 1H), 7.53(d, J=8.1Hz, 1H), 8.09(s, 1H), 8.74(s, 1H). |
| 170 | (500 MHz, CDCl$_3$)δ 2.44(s, 3H), 2.65-2.85(m, 8H), 3.65(s, 2H), 3.82(s, 2H), 7.26(d, J=7.8Hz, 1H), 7.43(d, J=3.3Hz, 1H), 7.48(d, J=7.8Hz, 1H), 7.77(s, 1H), 7.92(d, J=3.3Hz, 1H). |
| 171 | (400 MHz, CDCl$_3$)δ 2.38(s, 3H), 2.52(s, 3H), 2.55-2.75(m, 8H), 3.60(s, 2H), 3.78(s, 2H), 6.35(s, 1H), 7.32(d, J=8.0Hz, 1H), 7.49(s, 1H), 7.68(d, J=7.7Hz, 1H). |
| 172 | (500 MHz, CDCl$_3$)δ 2.39(s, 3H), 2.54(s, 3H), 2.89(s, 3H), 3.55-3.65(m, 8H), 3.74(s, 2H), 4.23(s, 2H), 7.46(d, J=7.8Hz, 1H), 7.67(s, 1H), 7.82(d, J=7.8Hz, 1H). |
| 173 | (500 MHz, CDCl$_3$)δ 3.68(s, 2H), 3.94(s, 3H), 6.86(t, J=4.5Hz, 1H), 7.10(dd, J=5.1, 3.6Hz, 1H), 7.34(m, 4H). |
| 174 | (500 MHz, DMSO-$d_6$)δ 3.69(s, 2H), 3.89(s, 3H), 6.96(d, J=8.1Hz, 1H), 7.27(d, J=7.5Hz, 1H), 7.36(t, J=7.8Hz, 1H), 7.58(dd, J=5.0, 1.2Hz, 1H), 7.69(dd, J=5.0, 2.8Hz, 1H), 7.86(d, J=1.9Hz, 1H). |
| 175 | (400 MHz, DMSO-$d_6$)δ 3.63(s, 2H), 3.89(s, 3H), 6.98(d, J=7.7Hz, 1H), 7.26(m, 3H), 7.38(t, J=7.8Hz, 1H). |
| 176 | (500 MHz, DMSO-$d_6$)δ 1.44(s, 9H), 2.15(s, 3H), 2.25-2.45(m, 8H), 2.68(m, 2H), 3.50(s, 2H), 3.62(m, 2H), 3.70(s, 2H), 4.58(br s, 2H), 7.11(s, 1H), 7.28(d, J=7.8Hz, 1H), 7.48(s, 1H), 7.55(d, J=7.8Hz, 1H). |
| 177 | (500 MHz, DMSO-$d_6$)δ 2.81(s, 3H), 3.00-3.50(m, 8H), 3.84(s, 2H), 4.00(br s, 2H), 7.30(ddd, J=7.5, 4.7, 1.3Hz, 1H), 7.42(d, J=7.8Hz, 1H), 7.51(d, J=3.7Hz, 1H), 7.63(s, 1H), 7.68(d, J=7.8Hz, 1H), 7.86(m, 2H), 7.97(ddd, J=8.1, 1.0, 1.0Hz, 1H), 8.55(ddd, J=5.0, 1.9, 1.0Hz, 1H). |
| 178 | (500 MHz, DMSO-$d_6$)δ 2.82(s, 3H), 3.00-3.50(m, 8H), 3.84(s, 2H), 4.06(br s, 2H), 7.30(ddd, J=7.5, 4.7, 1.2Hz, 1H), 7.35(d, J=7.5Hz, 1H), 7.50(d, J=3.7Hz, 1H), 7.63(d, J=7.8Hz, 1H), 7.73(s, 1H), 7.86(m, 2H), 7.97(ddd, J=8.1, 1.0, 1.0Hz, 1H), 8.55(ddd, J=5.0, 1.9, 1.0Hz, 1H). |
| 179 | (500 MHz, DMSO-$d_6$)δ 3.83(s, 2H), 5.11(s, 2H), 5.48(s, 2H), 7.00(m, 1H), 7.05(m, 2H), 7.35(m, 2H), 7.42(d, J=8.4Hz, 1H), 7.63(s, 1H), 7.69(m, 2H), 7.73(s, 1H), 7.81(s, 1H), 7.89(s, 1H), 9.23(s, 1H). |
| 180 | (300 MHz, DMSO-$d_6$)δ 2.72(t, J=7Hz, 2H), 3.30(m, 4H), 3.59(t, J=5Hz, 4H), 3.76(s, 2H), 4.14(t, J=7Hz, 2H), 6.94(d, J=7Hz, 1H), 7.17(d, J=7Hz, 1H), 7.54(d, J=7Hz, 1H), 7.61(s, 1H), 7.81(s, 1H). |
| 181 | (500 MHz, DMSO-$d_6$)δ 3.20-3.55(m, 8H), 3.60(t, J=4.7Hz, 2H), 3.72(s, 2H), 4.40(t, J=4.7Hz, 2H), 7.02(dd, J=2.5, 8.4Hz, 1H), 7.23(d, J=3.8Hz, 1H), 7.25(d, J=2.5Hz, 1H), 7.27(d, J=3.8Hz, 1H), 7.55(d, J=8.4Hz, 1H). |
| 182 | (500 MHz, DMSO-$d_6$)δ 3.15-3.55(m, 8H), 3.61(t, J=3Hz, 2H), 3.80(s, 2H), 4.41(t, J=5Hz, 2H), 7.02(d, J=7Hz, 1H), 7.26(s, 1H), 7.55(d, J=5Hz, 1H), 7.60(d, J=7Hz, 1H), 7.70(d, J=3, 5Hz, 1H), 7.82(d, J=3Hz, 1H). |

| Example Number | ¹H NMR |
|---|---|
| 183 | (300 MHz, DMSO-d₆) δ 3.00(s, 3H), 3.71(s, 2H), 4.56(s, 2H), 6.27(d, J=3Hz, 1H), 6.37(dd, J=2, 3Hz, 1H), 6.82(d, J=2.8Hz, 1H), 7.04(s, 1H), 7.43(d, J=8Hz, 1H), 7.53(d, J=7Hz, 1H), 7.56(s, 1H), 7.68(m, 1H), 7.79(m, 1H). |
| 184 | (500 MHz, DMSO-d₆) δ 2.88(s, 3H), 3.02(t, J=8Hz, 2H), 3.19(m, 2H), 3.54(d, J=8Hz, 2H), 3.71(s, 2H), 3.89(d, J=8Hz, 2H), 7.02(d, J=7Hz, 1H), 7.17(t, J=5Hz, 1H), 7.28(s, 1H), 7.44(m, 1H), 7.51(d, J=7Hz, 1H), 7.56(m, 1H). |
| 185 | (400 MHz, DMSO-d₆) δ 3.22(m, 4H), 3.30(s, 2H), 3.74(m, 4H), 6.90(d, 1H), 7.07(d, J=8.9Hz, 1H), 7.32(d, J=4.3Hz, 1H), 7.65(d, J=8.9Hz, 1H), 7.82(d, J=4.3Hz, 1H). |
| 186 | (500 MHz, DMSO-d₆) δ 3.00-3.50(m, 8H), 3.88(s, 2H), 4.45(s, 2H), 5.11(s, 2H), 7.01(m, 1H), 7.06(m, 2H), 7.35(m, 2H), 7.40(d, J=7.8Hz, 1H), 7.67(d, J=7.8Hz, 1H), 7.75(s, 1H), 7.83(s, 1H), 7.90(s, 1H), 8.06(s, 1H). |
| 187 | (500 MHz, DMSO-d₆) δ 3.05-3.35(m, 8H), 3.85(s, 2H), 4.18(br s, 2H), 5.11(s, 2H), 7.01(m, 1H), 7.05(m, 2H), 7.35(m, 3H), 7.62(d, J=8Hz, 1H), 7.74(s, 1H), 7.77(br s, 1H), 7.90(s, 1H), 8.90(br s, 2H). |
| 188 | (500 MHz, DMSO-d₆) δ 2.30(m, 2H), 2.83(s, 6H), 3.35-3.70(m, 5H), 3.88(br s, 2H), 4.47(m, 2H), 5.12(s, 2H), 7.01(m, 1H), 7.06(m, 2H), 7.37(m, 2H), 7.42(d, J=8Hz, 1H), 7.65(d, J=8Hz, 1H), 7.74(s, 1H), 7.83(br s, 1H), 7.90(s, 1H). |
| 189 | (500 MHz, DMSO-d₆) δ 1.86(m, 2H), 2.05(m, 2H), 3.14(m, 2H), 3.39(m, 2H), 3.87(s, 2H), 4.45(s, 2H), 5.12(s, 2H), 7.01(m, 1H), 7.05(m, 2H), 7.35(m, 2H), 7.42(d, J=8Hz, 1H), 7.65(d, J=8Hz, 1H), 7.75(s, 1H), 7.85(br s, 1H), 7.90(s, 1H). |
| 190 | (500 MHz, DMSO-d₆) δ 0.90(d, J=8Hz, 3H), 1.35(m, 2H), 1.62(m, 1H), 1.80(m, 2H), 2.95(m, 2H), 3.38(m, 2H), 3.87(s, 2H), 4.37(d, J=5Hz, 2H), 5.11(s, 2H), 7.01(m, 1H), 7.06(m, 2H), 7.35(m, 2H), 7.39(d, J=8Hz, 1H), 7.65(d, J=8Hz, 1H), 7.74(s, 1H), 7.82(br s, 1H), 7.90(s, 1H). |
| 191 | (500 MHz, DMSO-d₆) δ 1.20(t, J=8Hz, 3H), 2.90-3.70(m, 10H), 3.82(s, 2H), 3.89(br s, 2H), 5.10(s, 2H), 7.00(m, 1H), 7.06(m, 2H), 7.29(d, J=8Hz, 1H), 7.35(m, 2H), 7.37(d, J=8Hz, 1H), 7.70(br s, 1H), 7.74(s, 1H), 7.89(s, 1H). |
| 192 | (500 MHz, DMSO-d₆) δ 1.13(d, J=8Hz, 6H), 2.72(m, 2H), 3.32(m, 2H), 3.80(m, 2H), 3.87(s, 2H), 4.40(br s, 2H), 5.10(s, 2H), 7.00(m, 1H), 7.05(m, 2H), 7.35(m, 2H), 7.41(d, J=8Hz, 1H), 7.66(d, J=8Hz, 1H), 7.74(s, 1H), 7.82(br s, 1H), 7.90(s, 1H). |
| 193 | (500 MHz, DMSO-d₆) δ 3.80(br s, 2H), 5.10(br s, 2H), 5.50(s, 2H), 7.00(m, 1H), 7.05(m, 2H), 7.24(d, J=8Hz, 1H), 7.34(m, 2H), 7.54(m, 2H), 7.72(s, 1H), 7.87(s, 1H), 8.00(s, 1H), 8.72(s, 1H). |
| 194 | (500 MHz, DMSO-d₆) δ 2.62(s, 3H), 3.82(s, 2H), 5.11(s, 2H), 5.46(s, 2H), 7.00(m, 1H), 7.05(m, 2H), 7.29(d, J=8Hz, 1H), 7.35(m, 2H), 7.60(m, 2H), 7.65(br s, 1H), 7.72(m, 2H), 7.89(br s, 1H). |
| 195 | (400 MHz, DMSO-d₆) δ 3.80(s, 2H), 5.08(s, 2H), 5.72(s, 2H), 7.00(m, 1H), 7.05(m, 2H), 7.25(d, J=8Hz, 1H), 7.35(m, 2H), 7.56(m, 2H), 7.72(s, 1H), 7.76(s, 1H), 7.87(s, 1H), 8.2(s, 1H). |
| 196 | (400 MHz, DMSO-d₆) δ 1.22(d, J=8Hz, 6H), 3.05-3.60(m, 9H), 3.84(s, 2H), 4.06(br s, 2H), 5.11(s, 2H), 7.00(m, 1H), 7.05(m, 2H), 7.35(m, 3H), 7.59(d, J=8Hz, 1H), 7.74(s, 2H), 7.89(s, 1H). |
| 197 | (500 MHz, DMSO-d₆) δ 3.82(s, 2H), 5.11(s, 2H), 7.00(m, 1H), 7.06(m, 2H), 7.29(m, 1H), 7.35(m, 3H), 7.56(d, J=7.8Hz, 2H), 7.66(m, 1H), 7.74(s, 1H), 7.89(s, 1H). |
| 198 | (300 MHz, DMSO-d₆) δ 3.74(s, 2H), 7.20(d, J=3.7, 5.0Hz, 1H), 7.36(d, J=7.8Hz, 1H), 7.53(m, 2H), 7.69(m, 2H). |
| 199 | (500 MHz, CD₃OD) δ 2.23(s, 3H) 3.79(s, 2H) 7.38(t, J=7.8Hz, 1H) 7.50(d, J=7.8Hz, 1H) 7.54(d, J=4.1Hz, 1H) 7.57(m, 2H) 7.75(m, 1H). |
| 202 | (400 MHz, CD₃OD) δ 3.41(s, 6H), 4.09(s, 2H), 7.57(dd, J=5.0, 1.4Hz, 1H), 7.63(m, 3H), 7.81(dd, J=2.9, 1.4Hz, 1H), 7.86(dd, J=7.1, 1.5Hz, 1H). |
| 203 | (500 MHz, CD₃OD) δ 1.28(t, J=7.6Hz, 3H), 2.52(q, J=7.7Hz, 2H), 3.79(s, 2H), 7.38(t, J=7.8Hz, 1H), 7.50(d, J=8.1Hz, 1H), 7.54(dd, J=5.1, 1.4Hz, 1H), 7.58(m, 2H), 7.76(dd, J=2.8, 1.2Hz, 1H). |
| 204 | (500 MHz, CD₃OD) δ 1.08(t, J=7.5Hz, 3H), 1.80(m, 2H), 2.47(t, J=7.3Hz, 2H), 3.78(s, 2H), 7.38(t, J=7.8Hz, 1H), 7.48(m, 1H), 7.54(m, 1H), 7.57(m, 2H), 7.74(m, 1H). |
| 205 | (500 MHz, CD₃OD) δ 3.57(s, 3H), 3.80(s, 2H), 4.14(s, 2H), 7.41(t, J=7.6Hz, 1H), 7.56(m, 3H), 7.61(d, J=7.8Hz, 1H), 7.76(m, 1H). |
| 206 | (500 MHz, CD₃OD) δ 3.56(s, 3H), 3.78(s, 2H), 4.14(s, 2H), 7.40(t, J=7.8Hz, 1H), 7.54(m, 3H), 7.70(m, 1H). |
| 207 | (500 MHz, CD₃OD) δ 1.53(s, 9H), 2.93(s, 3H), 3.10-3.50(m, 8H), 4.09(s, 2H), 4.15(s, 2H), 7.55(m, 1H), 7.60(m, 1H), 7.70(d, J=1.6Hz, 1H), 7.79(s, 1H), 7.95(s, 1H). |
| 208 | (500 MHz, DMSO-d₆) δ 2.29(s, 3H), 2.81(s, 3H), 3.00-3.50(m, 8H), 3.86(s, 2H), 4.02(br s, 2H), 4.76(s, 2H), 6.91(d, J=7.8Hz, 1H), 7.14(m, 1H), 7.21(t, J=7.8Hz, 1H), 7.40(d, J=7.8Hz, 1H), 7.43(d, J=7.8Hz, 1H), 7.49(s, 1H), 7.60(s, 1H), 7.68(d, J=7.8Hz, 1H), 7.77(m, 2H), 10.03(s, 1H). |
| 209 | (500 MHz, DMSO-d₆) δ 1.58(d, J=6.4Hz, 3H), 2.27(s, 3H), 2.80(s, 3H), 3.00-3.50(m, 8H), 3.84(s, 2H), 3.99(br s, 2H), 4.95(q, J=6.4Hz, 1H), 6.89(d, J=7.6Hz, 1H), 7.09(m, 2H), 7.19(t, J=7.6Hz, 1H), 7.39(d, J=7.9Hz, 1H), 7.42(d, J=7.9Hz, 1H), 7.48(s, 1H), 7.58(s, 1H), 7.67(d, J=7.6Hz, 1H), 7.74(m, 2H), 10.10(s, 1H). |
| 210 | (300 MHz, DMSO-d₆) δ 2.81(s, 3H), 3.00-3.50(m, 8H), 3.72(s, 2H), 4.04(br s, 2H), 5.75(s, 1H), 7.19(d, J=7.8Hz, 1H), 7.27(d, J=7.8Hz, 1H), 7.54(dd, J=5.1, 1.4Hz, 1H), 7.73(dd, J=5.1, 3.1Hz, 1H), 7.82(dd, J=3.1, 1.4Hz, 1H). |
| 211 | (300 MHz, DMSO-d₆) δ 3.86(s, 2H), 5.08(br s, 2H), 5.29(s, 2H), 6.92(s, 1H), 7.00(m, 1H), 7.07(m, 2H), 7.22(m, 2H), 7.36(m, 2H), 7.42(m, 1H), 7.54(m, 3H), 7.82(m, 3H), 13.35(br s, 1H). |
| 212 | (300 MHz, DMSO-d₆) δ 2.80(s, 3H), 3.10-3.50(m, 8H), 3.84(s, 2H), 3.92(br s, 2H), 5.08(s, 2H), 7.00(m, 1H), 7.08(m, 3H), 7.42(d, J=8Hz, 1H), 7.55(m, 1H), 7.59(d, J=8Hz, 1H), 7.65(s, 1H), 7.82(d, J=8Hz, 1H), 8.90(s, 1H). |
| 213 | (300 MHz, DMSO-d₆) δ 2.15(s, 3H), 2.20-2.45(m, 8H), 3.53(s, 2H), 3.85(s, 2H), 5.08(s, 2H), 7.00(m, 1H), 7.05(m, 2H), 7.22(m, 2H), 7.35(m, 2H), 7.50(d, J=8Hz, 1H), 7.58(m, 3H), 7.83(d, J=8Hz, 2H). |
| 214 | (300 MHz, DMSO-d₆) δ 3.86(br s, 2H), 5.06(s, 2H), 5.28(s, 2H), 6.92(s, 1H), 7.00(m, 1H), 7.06(m, 2H), 7.22(m, 2H), 7.34(m, 2H), 7.56(m, 4H), 7.80(m, 3H), 13.35(s, 1H). |
| 215 | (500 MHz, DMSO-d₆) δ 2.78(s, 3H), 3.00-3.50(m, 8H), 3.86(br s, 2H), 3.89(s, 2H), 5.09(s, 2H), 7.00(m, 1H), 7.08(m, 2H), 7.36(m, 3H), 7.43(d, J=8Hz, 1H), 7.53(t, J=8Hz, 1H), 7.58(s, 1H), 7.66(d, J=8Hz, 1H), 7.84(d, J=8Hz, 1H), 7.89(s, 1H). |
| 216 | (500 MHz, DMSO-d₆) δ 3.90(s, 2H), 5.09(s, 2H), 5.50(s, 2H), 7.01(m, 1H), 7.08(m, 2H), 7.35(m, 2H), 7.43(d, J=8Hz, 2H), 7.53(t, J=8Hz, 1H), 7.64(s, 1H), 7.70(m, 2H), 7.83(m, 2H), 7.88(s, 1H), 9.25(s, 1H). |
| 217 | (500 MHz, DMSO-d₆) δ 2.78(s, 3H), 3.08(s, 2H), 3.00-3.50(m, 8H), 3.88(br s, 4H), 5.05(s, 2H), 6.98(m, 1H), 7.03(m, 2H), 7.34(m, 3H), 7.56(m, 3H), 7.65(d, J=8Hz, 1H), 7.82(d, J=8Hz, 2H). |
| 218 | (500 MHz, DMSO-d₆) δ 3.89(s, 2H), 5.05(s, 2H), 5.48(s, 2H), 6.99(m1H), 7.05(m, 2H), 7.33(m, 2H), 7.42(d, J=8Hz, 1H), 7.56(d, J=8Hz, 1H), 7.63(s, 1H), 7.69(m, 2H), 7.81(m, 3H), 9.22(s, 1H). |
| 219 | (500 MHz, DMSO-d₆) δ 2.80(br s, 3H), 3.10-3.55(m, 8H), 3.25(s, 3H), 3.47(m, 2H), 3.60(m, 2H), 3.76(m, 2H), 3.85(s, 2H), 4.15(m, 2H), 7.07(m, 2H), 7.36(d, J=8Hz, 1H), 7.56(s, 1H), 7.66(d, J=8Hz, 1H), 7.74(m, 2H). |

| Example Number | ¹H NMR |
|---|---|
| 220 | (500 MHz, DMSO-d₆)δ 2.15(s, 3H), 2.20-2.45(m, 8H), 3.50(s, 2H), 3.82(s, 2H), 4.34(m, 2H), 4.38(m, 2H), 6.96(m, 1H), 7.00(m, 2H), 7.12(m, 2H), 7.30(m, 3H), 7.48(s, 1H), 7.60(br s, 1H), 7.77(m, 2H). |
| 221 | (500 MHz, DMSO-d₆)δ 1.14(t, J=8Hz, 3H), 2.81(s, 3H), 3.10-3.40(m, 8H), 3.52(q, J=8Hz, 2H), 3.72(m, 2H), 3.86(s, 2H), 4.00(br s, 2H), 4.15(m, 2H), 7.09(m, 2H), 7.40(d, J=8Hz, 1H), 7.60(s, 1H), 7.68(d, J=8Hz, 1H), 7.74(m, 2H). |
| 222 | (500 MHz, DMSO-d₆)δ 3.80(s, 2H), 5.11(s, 2H), 5.48(s, 2H), 7.00(m, 1H), 7.05(m, 2H), 7.29(d, J=8Hz, 1H), 7.35(m, 2H), 7.48(s, 1H), 7.63(d, J=8Hz, 1H), 7.72(s, 1H), 7.87(s, 1H), 8.00(s, 1H), 8.70(s, 1H). |
| 223 | (500 MHz, DMSO-d₆)δ 2.84(s, 3H), 3.00-3.50(m, 8H), 3.79(s, 2H), 7.28(dd, J=7.8, 1.2Hz, 1H), 7.48(t, J=7.6Hz, 1H), 7.57(dd, J=5.0, 1.2Hz, 1H), 7.71(dd, J=5.0, 2.8Hz, 1H), 7.75(d, J=7.8Hz, 1H), 7.86(dd, J=1.2, 2.8 1H). |
| 224 | (500 MHz, CD₃OD)δ 1.52(s, 9H), 4.04(s, 2H), 4.05(s, 2H), 7.53(dd, J=5.0, 1.2Hz, 1H), 7.58(dd, J=3.1, 5.0Hz, 1H), 7.76(d, J=2.8, 1.2Hz, 1H), 7.78(d, J=1.9Hz, 1H), 7.99(d, J=1.9Hz, 1H). |
| 225 | (500 MHz, CD₃OD)δ 1.52(s, 9H), 4.04(s, 2H), 4.05(s, 2H), 7.53(dd, J=5.0, 1.2Hz, 1H), 7.58(dd, J=2.8, 4.8Hz, 1H), 7.76(d, J=2.8, 1.2Hz, 1H), 7.78(d, J=1.6Hz, 1H), 7.99(d, J=1.6Hz, 1H). |
| 226 | (500 MHz, CD₃OD)δ 1.32(s, 9H), 1.56(s, 9H), 3.85(s, 2H), 4.01(s, 2H), 4.28(s, 2H), 7.25(d, J=7.6, 1.1Hz, 1H), 7.47(t, J=7.6Hz, 1H), 7.52(dd, J=5.0, 1.2Hz, 1H), 7.58(dd, J=5.0, 3.1Hz, 1H), 7.74(d, J=2.8, 1.2Hz, 1H), 7.82(dd, J=7.5, 1.0Hz, 1H). |
| 227 | (400 MHz, CD₃OD)δ 2.99(s, 3H), 3.18(s, 3H), 3.80(s, 2H), 7.27(dd, J=7.7, 1.2Hz, 1H), 7.48(t, J=7.7Hz, 1H), 7.55(m, 2H), 7.78(m, 2H). |
| 228 | (500 MHz, CD₃OD)δ 1.50(d, J=7.5Hz, 3H), 1.52(s, 9H), 4.05(m, 2H), 4.54(q, J=7.5Hz, 2H), 7.49(t, J=7.6Hz, 1H), 7.54(m, 1H), 7.57(m, 1H), 7.61(d, J=7.8Hz, 1H), 7.75(m, 1H), 7.86(m, 1H). |
| 229 | (500 MHz, CD₃OD)δ 1.50(d, J=7.2Hz, 3H), 1.52(s, 9H), 4.05(m, 2H), 4.54(q, J=7.5Hz, 2H), 7.49(t, J=7.6Hz, 1H), 7.54(d, J=4.1Hz, 1H), 7.57(m, 1H), 7.61(m, 1H), 7.75(m, 1H), 7.86(d, J=7.2Hz, 1H). |
| 230 | (500 MHz, CD₃OD)δ 1.17(t, J=7.2Hz, 3H), 1.51(m, 1H), 1.72(m, 1H), 1.88(m, 1H), 2.09(m, 1H), 2.65(m, 1H), 3.48(m, 2H), 3.60(q, J=7.2Hz, 2H), 3.67(m, 1H), 3.82(br s, 2H), 4.50(m, 1H), 7.26(m, 1H), 7.48(t, J=7.5Hz, 1H), 7.54(dd, J=5.0, 1.2Hz, 1H), 7.57(dd, J=5.0, 2.8Hz, 1H), 7.78(dd, J=2.8, 1.2Hz, 1H), 7.80(d, J=7.8Hz, 1H). |
| 231 | (500 MHz, CD₃OD)δ 1.25(t, J=7.0Hz, 3H), 1.63(m, 1H), 1.77(m, 1H), 1.87(m, 1H), 2.08(m, 1H), 2.68(m, 1H), 3.18(m, 1H), 3.62(m, 1H), 3.80(s, 2H), 4.14(q, J=7.0Hz, 2H), 4.56(m, 1H), 7.26(d, J=6.5Hz, 1H), 7.49(t, J=7.5Hz, 1H), 7.54(dd, J=1.2, 5.0Hz, 1H), 7.57(dd, J=2.8, 5.0Hz, 1H), 7.77(dd, J=1.2, 2.8Hz, 1H), 7.80(d, J=7.5Hz, 1H). |
| 233 | (500 MHz, CD₃OD)δ 1.48(s, 9H), 2.63(t, J=6.7Hz, 2H), 3.66(t, J=6.7Hz, 2H), 4.05(s, 2H), 7.47(t, J=7.6Hz, 1H), 7.55(m, 3H), 7.76(m, 1H), 7.85(m, 1H). |
| 235 | (500 MHz, CD₃OD)δ 2.35-2.75(m, 8H), 2.45(s, 3H), 3.39(s, 3H), 3.56(s, 2H), 3.63(s, 2H), 4.56(s, 2H), 7.40(d, J=7.8Hz, 1H), 7.58(d, J=7.5Hz, 1H), 7.63(dd, J=5.0, 2.8Hz, 1H), 7.74(dd, J=5.0, 1.2Hz, 1H), 8.60(dd, J=3.1, 1.2Hz, 1H). |
| 236 | (500 MHz, CD₃OD)δ 1.10(t, J=7.5Hz, 3H), 1.87(m, 2H), 3.70(s, 2H), 4.07(t, J=6.4Hz, 2H), 6.91(dd, J=6.5, 2.5Hz, 1H), 7.31(m, 2H), 7.54(m, 2H), 7.74(dd, J=2.8, 1.25Hz, 1H). |
| 237 | (500 MHz, CD₃OD)δ 1.02(t, J=7.3Hz, 3H), 1.57(m, 2H), 1.83(m, 2H), 3.71(s, 2H), 4.12(t, J=6.4Hz, 2H), 6.93(m, 1H), 7.34(t, J=7.0Hz, 2H), 7.57(m, 2H), 7.78(m, 1H). |
| 238 | (300 MHz, CD₃OD)δ 3.47(s, 3H), 3.77(s, 2H), 3.83(m, 2H), 4.27(m, 2H), 6.97(m, 1H), 7.35(m, 2H), 7.57(m, 2H), 7.79(dd, J=2.7, 1.4Hz, 1H). |
| 239 | (500 MHz, CD₃OD)δ 1.29(t, J=7.0Hz, 3H), 3.80(s, 2H), 4.27(q, J=7.2Hz, 2H), 4.84(s, 2H), 6.85(d, J=7.5Hz, 1H), 7.35(m, 2H), 7.56(m, 2H), 7.77(dd, J=2.8, 1.2Hz, 1H). |
| 240 | (500 MHz, CD₃OD)δ 3.66(dd, J=9.0, 5.9Hz, 1H), 3.76(s, 2H), 3.82(t, J=9.0Hz, 1H), 4.29(dd, J=10.6, 4.4Hz, 1H), 4.36(dd, J=10.6, 3.1Hz, 1H), 5.07(m, 1H), 7.01(m, 1H), 7.38(m, 2H), 7.55(dd, J=5.1, 1.4Hz, 1H), 7.58(dd, J=5.0, 2.8Hz, 1H), 7.81(dd, J=2.8, 1.2Hz, 1H). |
| 241 | (500 MHz, CD₃OD)δ 3.73(s, 2H), 3.87(s, 3H), 5.25(s, 2H), 6.69(d, J=3.4Hz, 1H), 7.07(dd, J=6.9, 2.2Hz, 1H), 7.23(d, J=3.4Hz, 1H), 7.37(m, 2H), 7.54(m, 2H), 7.75(m, 1H). |
| 242 | (500 MHz, CD₃OD)δ 1.88(m, 1H), 1.98(m, 1H), 2.05(m, 1H), 2.15(m, 1H), 3.75(d, J=6.9Hz, 2H), 3.86(m, 1H), 3.96(m, 1H), 4.08(m, 1H), 4.13(m, 1H), 4.34(m, 1H), 6.96(dd, J=6.9, 2.2Hz, 1H), 7.34(m, 2H), 7.54(dd, J=1.2, 5.0Hz, 1H), 7.58(dd, J=3.1, 5.0Hz,, 1H), 7.79(dd, J=2.8, 1.2Hz, 1H). |
| 243 | (500 MHz, CD₃OD)δ 1.48-1.67(m, 4H), 1.78(m, 1H), 1.94(m, 1H), 3.56(m, 1H), 3.75(s, 2H), 3.80(m, 1H), 4.06(m, 3H), 6.93(m, 1H), 7.34(m, 2H), 7.56(m, 2H), 7.77(dd, J=2.8, 1.6Hz, 1H). |
| 244 | (500 MHz, CD₃OD)δ 3.78(s, 2H), 5.11(s, 2H), 7.07(d, J=8.1Hz, 1H), 7.44(m, 2H), 7.56(m, 2H), 7.77(dd, J=2.8, 1.2Hz, 1H). |
| 245 | (500 MHz, CD₃OD)δ 2.96(s, 3H), 3.10-3.60(m, 8H), 3.89(s, 2H), 7.51(d, J=7.8Hz, 1H), 7.54(dd, J=5.1, 1.1Hz, 1H), 7.58(dd, J=5.1, 3.1Hz, 1H), 7.70(s, 1H), 7.77(dd, J=3.0, 1.1Hz, 1H), 7.81(d, J=7.8Hz, 1H). |
| 246 | (500 MHz, CD₃OD)δ 3.45-3.80(m, 8H), 3.85(s, 2H), 7.16(dd, J=5.0, 3.4Hz, 1H), 7.47(m, 3H), 7.65(s, 1H), 7.77(d, J=7.8Hz, 1H). |
| 247 | (400 MHz, DMSO-d₆)δ 2.84(s, 3H), 3.45-3.65(m, 8H), 3.89(s, 2H), 5.11(s, 2H), 7.00(m, 1H), 7.05(m, 2H), 7.36(m, 3H), 7.66(d, J=8Hz, 1H), 7.73(s, 1H), 7.75(d, J=1Hz, 1H), 7.91(d, J=1Hz, 1H). |
| 248 | (500 MHz, CD₃OD)δ 1.35(t, J=7.2Hz, 3H), 3.78(s, 2H), 4.24(q, J=7.0Hz, 2H), 7.36(t, J=7.8Hz, 1H), 7.51(d, J=7.5Hz, 1H), 7.56(m, 3H), 7.76(dd, J=2.8, 1.2Hz, 1H). |
| 249 | (500 MHz, CD₃OD)δ 1.39(t, J=7.3Hz, 3H), 3.20(q, J=7.4Hz, 2H), 3.89(s, 2H), 7.39(m, 2H), 7.57(m, 3H), 7.77(dd, J=3.0, 1.4Hz, 1H). |
| 250 | (500 MHz, DMSO-d₆)δ 1.06(m, 1H), 1.51(m, 1H), 1.63(m, 1H), 1.70(m, 1H), 1.80(m, 1H), 1.90(m, 1H), 2.01(m, 1H), 2.16(s, 3H), 2.63(m, 1H), 2.81(m, 1H), 3.76(s, 2H), 3.89(m, 2H), 5.10(s, 2H), 6.92(m, 1H), 7.05(m, 3H), 7.14(s, 1H), 7.35(m, 2H), 7.53(m, 1H), 7.71(m, 1H), 7.86(m, 1H). |
| 251 | (500 MHz, DMSO-d₆)δ 3.81(s, 2H), 5.10(s, 2H), 5.68(s, 2H), 7.00(m, 1H), 7.05(m, 2H), 7.34(m, 3H), 7.50(s, 1H), 7.64(m, 1H), 7.72(s, 1H), 7.75(s, 1H), 7.87(m, 1H), 8.21(s, 1H). |
| 252 | (500 MHz, DMSO-d₆)δ 1.20(t, J=7Hz, 3H), 3.05-3.25(m, 8H), 3.87(s, 2H), 4.08(q, J=7Hz, 2H), 4.40(br s, 2H), 5.11(s, 2H), 7.01(m, 1H), 7.05(m, 2H), 7.35(m, 2H), 7.48(d, J=8Hz, 1H), 7.68(s, 1H), 7.75(m, 2H), 7.92(s, 1H). |
| 253 | (500 MHz, DMSO-d₆)δ 1.13(d, J=5Hz, 6H), 2.72(m, 2H), 3.33(m, 3H), 3.88(s, 2H), 4.38(s, 2H), 5.11(s, 2H), 7.01(m, 1H), 7.05(m, 2H), 7.35(m, 2H), 7.51(m, 1H), 7.69(s, 1H), 7.75(m, 2H), 7.92(s, 1H). |
| 254 | (500 MHz, DMSO-d₆)δ 0.91(d, J=7Hz, 3H), 1.32(m, 2H), 1.59(m, 2H), 1.81(m, 3H), 2.95(m, 2H), 3.87(s, 2H), 4.33(s, 2H), 5.11(s, 2H), 7.01(m, 1H), 7.05(m, 2H), 7.35(m, 2H), 7.48(d, J=8Hz, 1H), 7.68(s, 1H), 7.75(m, 2H), 7.91(s, 1H). |
| 255 | (500 MHz, CD₃OD)δ 2.98(s, 3H), 3.15-3.60(m, 8H), 3.90(s, 2H), 7.45(dd, J=7.8, 1.6Hz, 1H), 7.55(dd, J=5.0, 1.2Hz, 1H), 7.59(dd, J=5.3, 3.1Hz, 1H), 7.71(d, J=7.8Hz, 1H), 7.78(dd, J=2.8, 1.2Hz, 1H), 7.82(s, 1H). |

| Example Number | 1H NMR |
|---|---|
| 256 | (500 MHz, CD$_3$OD) δ 2.98(s, 3H), 3.10-3.55(m, 8H), 3.59(s, 3H), 3.92(s, 2H), 4.17(br s, 2H), 7.32(m, 1H), 7.54(m, 2H), 7.59(dd, J=5.0, 2.8Hz, 1H), 7.77(dd, J=2.8, 1.2Hz, 1H). |
| 263 | (500 MHz, DMSO-d$_6$) δ 3.28(s, 3H), 3.55(t, J=5Hz, 2H), 3.65(t, J=5Hz, 2H), 3.88(s, 2H), 4.48(s, 2H), 7.10(d, J=7Hz, 1H), 7.29(d, J=7Hz, 1H), 7.41(s, 1H), 7.60(m, 2H), 7.76(s, 1H), 7.86(s, 1H), 8.68(d, J=6Hz, 2H). |

EXAMPLE 266

3-(3-thienyl)-1,4-dihydroindeno[1,2-c]pyrazol-5-amine

A suspension of Example 199 (1 g, 3.4 mmol) and concentrated hydrochloric acid (10 mL) in methanol (30 mL) was heated to reflux for about 5 hours. The solvents were concentrated under vacuum and to the residue was added 5% aqueous sodium hydroxide. The mixture was extracted with dichloromethane, the combined organic extracts were dried (Na$_2$SO$_4$), filtered, and concentrated under vacuum. The residue was purified by preparative HPLC on a Waters Symmetry C8 column (25 mm×100 mm, 7 μm particle size) using a gradient of 10% to 100% acetonitrile:0.1% aqueous TFA over 8 minutes (10 minutes run time) at a flow rate of 40 mL/minute to provide 700 mg (82%) of the desired product as the trifluoroacetic acid salt. $^1$H NMR (500 MHz, CD$_3$OD) δ 3.86 (s, 2H), 7.20 (d, J=8.7 Hz, 1H), 7.47 (t, J=7.8 Hz, 1H), 7.56 (dd, J=5.0, 1.2 Hz, 1H), 7.61 (dd, J=7.8, 5.0 Hz, 1H), 7.66 (d, J=7.2 Hz, 1H), 7.79 (dd, J=2.8, 1.2 Hz, 1H). MS (ESI): m/z 254 (M+H)$^+$.

EXAMPLE 267

N-[3-(3-thienyl)-1,4-dihydroindeno[1,2-c]pyrazol-5-yl]-4-morpholinecarboxamide

To a solution of Example 266 (31 mg, 0.12 mmol) in pyridine (1 mL) was added 4-morpholinecarbonyl chloride (20 mg, 0.13 mmol) and the mixture was stirred at room temperature for about 10 minutes. The solvent was removed under vacuum and the residue was purified by preparative HPLC on a Waters Symmetry C8 column (25 mm×100 mm, 7 μm particle size) using a gradient of 10% to 100% acetonitrile: 0.1% aqueous TFA over 8 minutes (10 minutes run time) at a flow rate of 40 mL/minute to provide 2 mg (2%) of the desired product as the trifluoroacetic acid salt. $^1$H NMR (500 MHz, CD$_3$OD) δ 3.58 (m, 4H), 3.77 (m, 6H), 7.25 (dd, J=7.8, 1.0 Hz, 1H), 7.36 (t, J=7.8 Hz, 1H), 7.55 (m, 3H), 7.75 (dd, J=2.5, 1.2 Hz, 1H). MS (ESI): m/z 367 (M+H)$^+$.

EXAMPLE 268

3-[5-(3-phenoxy-1-propynyl)-3-thienyl]-1,4-dihydroindeno[1,2-c]pyrazol-5-amine

The procedure for Example 266 was used, substituting Example 201 for Example 199. The crude product was purified by flash chromatography on silica gel using dichloromethane/methanol (10:1) as eluent to provide the desired product. MS (APCI): m/z 384 (M+H)$^+$.

EXAMPLE 269 methyl 4-oxo-4-{[3-(3-thienyl)-1,4-dihydroindeno[1,2-c]pyrazol-5-yl]amino}butanoate To a solution of Example 266 (30 mg, 0.12 mmol) in pyridine (1 mL) was added 3-(carbomethoxy)propionyl chloride (15 μL, 0.12 mmol) and the mixture was stirred at room temperature for about 30 minutes. The solvent was removed under vacuum and the residue was purified by preparative HPLC on a Waters Symmetry C8 column (25 mm×100 mm, 7 μm particle size) using a gradient of 10% to 100% acetonitrile:0.1% aqueous TFA over 8 minutes (10 minutes run time) at a flow rate of 40 mL/minute to provide 12 mg (20%) of the desired product as the trifluoroacetic acid salt. $^1$H NMR (500 MHz, CD$_3$OD) δ 2.76 (m, 2H), 2.81 (m, 2H), 3.72 (s, 3H), 3.78 (s, 2H), 7.38 (t, J=7.8 Hz, 1H), 7.48 (d, J=7.8 Hz, 1H), 7.54 (dd, J=5.0, 1.2 Hz, 1H), 7.57 (m, 2H), 7.75 (dd, J=2.8, 1.2 Hz, 1H). MS (ESI): m/z 368 (M+H)$^+$.

EXAMPLE 270

2-chloro-N-[3-(3-thienyl)-1,4-dihydroindeno[1,2-c]pyrazol-5-yl]acetamide

To a solution of Example 266 (70 mg, 0.15 mmol) in acetone (1 mL) was added a saturated aqueous solution of sodium bicarbonate (0.5 mL) and chloroacetyl chloride (0.012 mL, 0.15 mmol) and the mixture was heated at about 50° C. for about 1.5 hours. The solvents were concentrated under vacuum and the residue was purified by preparative HPLC on a Waters Symmetry C8 column (25 mm×100 mm, 7 μm particle size) using a gradient of 10% to 100% acetonitrile:0.1% aqueous TFA over 8 minutes (10 minutes run time) at a flow rate of 40 mL/minute to provide the desired product as the trifluoroacetate salt. MS (APCI): m/z 329 (M)$^+$.

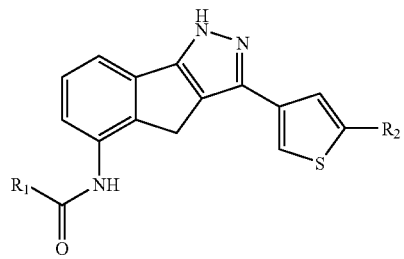

| Example Number | R₁ | R₂ | ¹H NMR | MS (ESI): | Reference Procedure |
|---|---|---|---|---|---|
| 271 | furan-2-yl | H | (500 MHz, CD₃OD)δ 3.86(s, 2H), 6.68(dd, J=3.4, 1.9Hz, 1H), 7.31 (d, J=2.8Hz, 1H), 7.44 (t, J=7.5Hz, 1H), 7.48 (m, 1H), 7.54(m, 2H), 7.65(m, 1H), 7.75(m, 1H), 7.79(dd, J=1.7, 0.8Hz, 1H). | m/z 348 (M + H)⁺ | Example 269 |
| 272 | methoxycarbonylmethyl | H | (500 MHz, CD₃OD)δ 3.85(s, 2H), 3.99(s, 3H), 7.45(t, J=7.8Hz, 1H), 7.55(m, 2H), 7.58 (dd, J=2.8, 5.0Hz, 1H), 7.66(d, J=7.2Hz, 1H), 7.79(dd, J =2.8, 1.2Hz, 1H). | m/z 340 (M + H)⁺ | Example 269 |
| 273 | acetoxyethyl | H | (500 MHz, CD₃OD)δ 2.21(s, 3H), 3.79(s, 2H), 4.81(s, 2H), 7.41 (t, J=7.6Hz, 1H), 7.48 (d, J=7.5Hz, 1H), 7.54 (dd, J=5.0, 1.2Hz, 1H), 7.58(dd, J=5.3, 3.1Hz, 1H), 7.61(d, J=7.2Hz, 1H), 7.76(dd, J=2.8, 1.2Hz, 1H). | m/z 354 (M + H)⁺ | Example 269 |
| 274 | phenyl | H | (500 MHz, CD₃OD)δ 3.88(s, 2H), 7.47(m, 2H), 7.54(m, 4H), 7.62 (d, J=7.2Hz, 1H), 7.66 (dd, J=6.4, 2.0Hz, 1H), 7.75(dd, J=2.6, 1.4Hz, 1H), 8.04(d, J=7.2Hz, 2H). | m/z 358 (M + H)⁺ | Example 269 |
| 275 | 5-methylisoxazol-3-yl | H | (500 MHz, CD₃OD)δ 2.54(s, 3H), 3.86(s, 2H), 6.60(s, 1H), 7.45 (t, J=7.6Hz, 1H), 7.57 (m, 3H), 7.67(m, 1H), 7.76(m, 1H), 8.55(s, 1H). | m/z 363 (M + H)⁺ | Example 269 |
| 276 | 2-methoxyethoxymethyl | H | (500 MHz, CD₃OD)δ 3.43(s, 3H), 3.69(m, 2H), 3.82(s, 2H), 3.84 (m, 2H), 4.23(s, 2H), 7.42(t, J=7.8Hz, 1H), 7.54(dd, J=5.0, 1.2Hz, 1H), 7.60(m, 3H), 7.79 (dd, J=3.1, 1.2Hz, 1H). | m/z 370 (M + H)⁺ | Example 269 |
| 277 | thiophen-2-ylmethyl | H | (500 MHz, CD₃OD)δ 3.73(s, 2H), 4.02(s, 2H), 7.03(dd, J=5.0, 3.4Hz, 1H), 7.10(d, J= 2.8Hz, 1H), 7.34(d, J= 5.3Hz, 1H), 7.40(t, J= 7.6Hz, 1H), 7.51(d, J= | m/z 378 (M + H)⁺ | Example 269 |

-continued

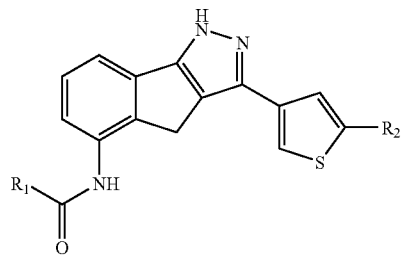

| Example Number | R₁ | R₂ | ¹H NMR | MS (ESI): | Reference Procedure |
|---|---|---|---|---|---|
| | | | 5.0Hz, 2H), 7.59(m, 2H), 7.74(d, J=1.9Hz, 1H). | | |
| 278 | methyl butanoate group | H | (500 MHz, CD₃OD)δ 2.06(m, 2H), 2.50(t, J=7.3Hz, 2H), 2.56(t, J=7.5Hz, 2H), 3.70(s, 3H), 3.79(s, 2H), 7.39 (t, J=7.6Hz, 1H), 7.49 (d, J=7.5Hz, 1H), 7.55 (dd, J=5.1, 1.4Hz, 1H), 7.58(m, 2H), 7.76(dd, J=3.1, 1.2Hz, 1H). | m/z 382 (M + H)⁺ | Example 269 |
| 279 | phenoxyethyl | H | (500 MHz, CD₃OD)δ 3.60(s, 2H), 7.06(t, J=7.2Hz, 1H), 7.13(d, J=8.1Hz, 2H), 7.40(m, 3H), 7.49(m, 2H), 7.60 (m, 2H), 7.69(dd, J=2.5, 0.9Hz, 1H). | m/z 388 (M + H)⁺ | Example 269 |
| 280 | 4-methyl-1,2,3-thiadiazolyl | H | (500 MHz, CD₃OD)δ 2.96(s, 3H), 3.86(s, 2H), 7.46(t, J=7.8Hz, 1H), 7.54(m, 3H), 7.68 (m, J=5.9, 2.2Hz, 1H), 7.75(d, J=1.6Hz, 1H). | m/z 380 (M + H)⁺ | Example 269 |
| 281 | 4-pyridyl | H | (500 MHz, CD₃OD)δ 3.88(s, 2H), 7.47(m, 2H), 7.54(m, 2H), 7.69 (dd, J=7.0, 1.4Hz, 1H), 7.75(m, 1H), 8.08(d, J=5.3Hz, 2H), 8.84(d, J=5.6Hz, 2H). | m/z 359 (M + H)⁺ | Example 269 |
| 282 | 2-pyridyl | H | (500 MHz, CD₃OD)δ 3.92(s, 2H), 7.46(t, J=7.8Hz, 1H), 7.57(d, J=1.9Hz, 2H), 7.64(m, 2H), 7.79(t, J=2.0Hz, 1H), 7.95(d, J=8.1Hz, 1H), 8.06(m, 1H), 8.27 (d, J=7.8Hz, 1H), 8.78 (d, J=4.4Hz, 1H). | m/z 359 (M + H)⁺ | Example 269 |
| 283 | 3-pyridyl | H | (500 MHz, CD₃OD)δ 3.88(s, 2H), 7.47(m, 2H), 7.54(m, 2H), 7.65 (dd, J=8.4, 4.7Hz, 1H), 7.68(dd, J=6.9, 1.2Hz, 1H), 7.75(dd, J=2.6, 1.4Hz, 1H), 8.46(d, J=8.4Hz, 1H), 8.78(dd, J=4.8, 1.4Hz, 1H), 9.19 (d, J=1.2Hz, 1H). | m/z 359 (M + H)⁺ | Example 269 |

-continued

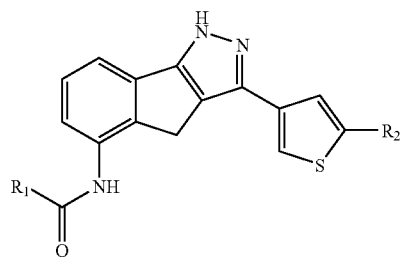

| Example Number | R₁ | R₂ | ¹H NMR | MS (ESI): | Reference Procedure |
|---|---|---|---|---|---|
| 284 | 1-methyl-5-chloro-pyrazol-4-yl | H | (500 MHz, CD₃OD)δ 3.85(s, 2H), 3.93(s, 3H), 7.43(t, J=7.6Hz, 1H), 7.50(d, J=7.2Hz, 1H), 7.53(dd, J=5.0, 1.2Hz, 1H), 7.56(dd, J= 5.0, 2.8Hz, 1H), 7.64 (d, J=7.5Hz, 1H), 7.76 (dd, J=2.8, 1.2Hz, 1H), 8.12(s, 1H). | m/z 396 (M + H)⁺ | Example 269 |
| 285 | 4-(dimethylamino)phenyl | H | (500 MHz, DMSO-d₆)δ 3.02(s, 6H), 3.84(s, 2H), 6.79(m, 2H), 7.38 (t, J=7.8Hz, 1H), 7.49 (m, 2H), 7.56(d, J=5.0 Hz, 1H), 7.68(m, 1H), 7.83(m, 1H), 7.92(m, 2H). | m/z 401 (M + H)⁺ | Example 269 |
| 286 | 1-acetylpiperidin-4-yl | H | (500 MHz, CD₃OD)δ 1.74(m, 1H), 1.84(m, 1H), 2.00(m, 2H), 2.14 (s, 3H), 2.80(m, 2H), 3.25(m, 1H), 3.78(s, 2H), 4.05(m, 1H), 4.60 (m, 1H), 7.39(t, J=7.8 Hz, 1H), 7.47(d, J=7.2 Hz, 1H), 7.54(dd, J= 5.0, 1.2Hz, 1H), 7.58 (m, 2H), 7.76(dd, J= 3.1, 1.2Hz, 1H). | m/z 407 (M + H)⁺ | Example 269 |
| 287 | methoxycarbonylmethyl | 3-phenoxyprop-1-ynyl | (500 MHz, CD₃OD)δ 3.82(s, 2H), 3.98(m, 3H), 5.00(s, 2H), 6.99 (m, 1H), 7.04(m, 2H), 7.31(m, 2H), 7.43(t, J= 7.8Hz, 1H), 7.53(d, J= 7.2Hz, 1H), 7.66(m, 2H), 7.72(s, 1H). | m/z 470 (M + H)⁺ | Example 269 |
| 288 | 2-methoxyethoxymethyl | 3-phenoxyprop-1-ynyl | (500 MHz, CD₃OD)δ 3.42(s, 3H), 3.68(m, 2H), 3.79(s, 2H), 3.84 (m, 2H), 4.23(s, 2H), 5.00(s, 2H), 6.99(m, 1H), 7.04(m, 2H), 7.32 (m, 2H), 7.41(t, J=7.8 Hz, 1H), 7.62(m, 3H), 7.72(s, 1H). | m/z 516 (M + H)⁺ | Example 269 |
| 289 | ethoxycarbonylmethyl | 3-phenoxyprop-1-ynyl | (500 MHz, CD₃OD)δ 1.32(t, J=7.0Hz, 3H), 3.78(s, 2H), 4.25(q, J= 7.0Hz, 2H), 4.57(s, 2H), 5.00(s, 2H), 6.99 (m, 1H), 7.04(m, 2H), 7.31(m, 2H), 7.39(t, J= 7.6Hz, 1H), 7.55(m, 2H), 7.62(s, 1H), 7.71 (s, 1H). | m/z 498 (M + H)⁺ | Example 269 |

-continued

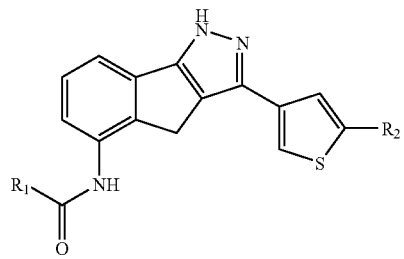

| Example Number | R₁ | R₂ | ¹H NMR | MS (ESI): | Reference Procedure |
|---|---|---|---|---|---|
| 290 | Cl-CH₂- | -C≡C-CH₂-O-C₆H₅ | | m/z 460 (M + H)⁺ | Example 270 |

EXAMPLE 291

1-{[3-(3-thienyl)-1,4-dihydroindeno[1,2-c]pyrazol-5-yl]carbonyl}-3-piperidinecarboxylic acid A solution of Example 230 (106 mg, 0.25 mmol) in tetrahydrofuran (0.5 mL) was treated with a 1:1 mixture of 1M aqueous lithium hydroxide and methanol (1 mL) at ambient temperature for about 2.5 hours. The solvents were evaporated and the residue was purified by preparative HPLC on a Waters Symmetry C8 column (25 mm×100 mm, 7 μm particle size) using a gradient of 10% to 100% acetonitrile:0.1% aqueous TFA over 8 minutes (10 minutes run time) at a flow rate of 40 mL/minute to provide 30 mg (29%) of the desired product as the trifluoroacetate salt. ¹H NMR (500 MHz, CD₃OD) δ 1.51 (m, 1H), 1.72 (m, 1H), 1.88 (m, 1H), 2.09 (m, 1H), 2.65 (m, 1H), 3.48 (m, 2H), 3.67 (m, 1H), 3.82 (br s, 2H), 4.50 (m, 1H), 7.27 (m, 1H), 7.48 (t, J=7.5 Hz, 1H), 7.54 (d, J=4.1 Hz, 1H), 7.57 (dd, J=2.8, 5.0 Hz, 1H), 7.78 (s, 1H), 7.80 (d, J=6.9 Hz, 1H). MS (ESI): m/z 394 (M+H)⁺.

EXAMPLE 292

N-{[7-[(4-methyl-1-piperazinyl)carbonyl]-3-(3-thienyl)-1,4-dihydroindeno[1,2-c]pyrazol-5-yl]carbonyl}glycine A solution of Example 207 (9 mg, 0.01 mmol) in dichloromethane (0.5 mL) was treated with trifluoroacetic acid (0.5 mL) and the mixture was agitated at room temperature for about 2 hours. The solvent was concentrated under vacuum to provide 4 mg (58%) of the desired product as the trifluoroacetate salt. ¹H NMR (500 MHz, CD₃OD) □ 2.98 (s, 3H), 3.10-3.60 (m, 8H), 4.15 (s, 2H), 4.17 (s, 2H), 7.55 (d, J=5.0 Hz, 1H), 7.60 (dd, J=5.1, 3.0 Hz, 1H), 7.71 (d, J=1.2 Hz, 1H), 7.79 (dd, J=2.8, 1.2 Hz, 1H), 7.96 (d, J=1.2 Hz, 1H). MS (ESI): m/z 466 (M+H)⁺.

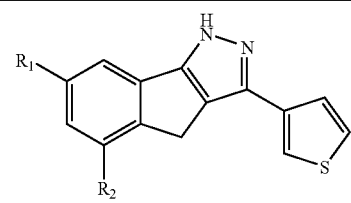

| R₁ | R₂ | ¹H NMR(500 MHz, CD₃OD) | MS (ESI): | Example Number (Reference Procedure) |
|---|---|---|---|---|
| Br | HOOC-CH₂-NH-C(O)- | δ4.05(s, 2H), 4.14(s, 2H), 7.53(dd, J=5.3, 1.2Hz, 1H), 7.58(dd, J=5.3, 3.1Hz, 1H), 7.78(dd, J=2.8, 1.2Hz, 1H), 7.80(d, J=1.9Hz, 1H), 8.00(d, J=1.9Hz, 1H). | m/z 416, 418 (M − H)⁻ | Example 293 (Example 292) |
| Br | HOOC-CH₂-N(CH₃)-C(O)- | δ3.18(s, 3H), 3.80(s, 2H), 4.15(s, 2H), 7.48(d, J=1.9Hz, 1H), 7.53(m, 2H), 7.74(dd, J=2.5, 1.6Hz, 1H), 7.87(d, J=1.6Hz, 1H). | m/z 430, 432 (M − H)⁻ | Example 294 (Example 292) |

-continued

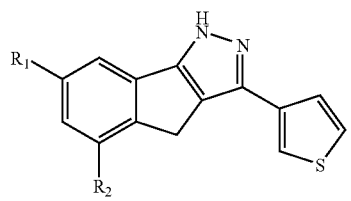

| R₁ | R₂ | ¹H NMR(500 MHz, CD₃OD) | MS (ESI): | Example Number (Reference Procedure) |
|---|---|---|---|---|
| H | -C(=O)-) | δ3.88(s, 2H), 4.11(s, 2H), 4.38(s, 2H), 7.30(d, J=7.5Hz, 1H), 7.49(t, J=7.6Hz, 1H), 7.53(dd, J=5.0, 1.2Hz, 1H), 7.58(dd, J=5.0, 2.8Hz, 1H), 7.78(dd, J=2.8, 1.2Hz, 1H), 7.83(d, J=7.8Hz, 1H). | m/z 398 (M + H)⁺ | Example 295 (Example 292) |
| H | -) | δ4.09(s, 2H), 4.15(s, 2H), 7.50(t, J=7.6Hz, 1H), 7.55(dd, J=5.0, 1.2Hz, 1H), 7.58(dd, J=5.0, 2.8Hz, 1H), 7.65(d, J=7.8Hz, 1H), 7.77(dd, J=2.8, 1.6Hz, 1H), 7.87(d, J=7.8Hz, 1H). | m/z 340 (M + H) | Example 296 (Example 292) |
| H | -) | δ1.55(d, J=7.5Hz, 3H), 4.07(m, 2H), 4.66(q, J=7.2Hz, 1H), 7.50(t, J=7.6Hz, 1H), 7.55(dd, J=5.0, 1.2Hz, 1H), 7.58(dd, J=5.0, 2.8Hz, 1H), 7.63(dd, J=7.6, 1.1Hz, 1H), 7.78(dd, J=2.8, 1.2Hz, 1H), 7.86(dd, J=7.8, 0.9Hz, 1H). | m/z 354 (M + H)⁺ | Example 297 (Example 292) |
| H | -) | δ1.55(d, J=7.5Hz, 3H), 4.06(m, 2H), 4.66(q, J=7.2Hz, 1H), 7.49(t, J=7.6Hz, 1H), 7.54(dd, J=5.0, 1.2Hz, 1H), 7.57(dd, J=5.0, 2.8Hz, 1H), 7.62(dd, J=7.6, 1.1Hz, 1H), 7.76(dd, J=2.8, 1.2Hz, 1H), 7.86(dd, J=7.8, 0.9Hz, 1H). | m/z 354 (M + H)⁺ | Example 298 (Example 292) |
| H | -) | δ1.62(m, 1H), 1.78(m, 1H), 1.88(m, 1H), 2.10(m, 1H), 2.66(m, 1H), 3.19(m, 2H), 3.64(m, 1H), 3.81(s, 2H), 4.56(m, 1H), 7.27(d, J=6.9Hz, 1H), 7.49(t, J=7.6Hz, 1H), 7.54(dd, J=5.0, 1.2Hz, 1H), 7.57(dd, J=5.0, 2.8Hz, 1H), 7.78(dd, J=3.0, 1.4Hz, 1H), 7.80(d, J=6.9Hz, 1H). | m/z 394 (M + H)⁺ | Example 299 (Example 291) |
| H | -) | δ2.70(t, J=6.9Hz, 2H), 3.69(t, J=6.7Hz, 2H), 4.04(s, 2H), 7.47(t, J=7.6Hz, 1H), 7.56(m, 3H), 7.77(dd, J=2.8, 1.2Hz, 1H), 7.84(d, J=7.2Hz, 1H). | m/z 354 (M + H)⁺ | Example 300 (Example 292) |
| H | | δ3.81(s, 2H), 4.78(s, 2H), 6.86(d, J=7.8Hz, 1H), 7.35(m, 2H), 7.56(m, 2H), 7.76(m, 1H). | m/z 313 (M + H)⁺ | Example 301 (Example 291) |

EXAMPLE 302

2-({[7-[(4-methyl-1-piperazinyl)methyl]-3-(3-thienyl)-1,4-dihydroindeno[1,2-c]pyrazol-5-yl]methyl}amino)ethanol To a solution of Example 207 (20 mg, 0.04 mmol) in tetrahydrofuran (2 mL) was added a 1M solution of lithium aluminum hydride in tetrahydrofuran (0.23 mL, 0.23 mmol) and the mixture was heated to reflux for about 30 minutes. The mixture was cooled to room temperature, the reaction was quenched with water and the mixture was extracted with ethyl acetate. The combined organic extracts were washed with saturated aqueous potassium carbonate, dried ($Na_2SO_4$), filtered and evaporated to dryness. The residue was purified by preparative HPLC on a Waters Symmetry C8 column (25 mm×100 mm, 7 μm particle size) using a gradient of 10% to 100% acetonitrile:0.1% aqueous TFA over 8 minutes (10 minutes run time) at a flow rate of 40 mL/minute to provide 4 mg (11%) of the desired product as the trifluoroacetate salt. $^1$H NMR (500 MHz, $CD_3OD$) δ 2.90 (s, 3H), 3.00-5.50 (m, 10H), 3.82 (s, 2H), 3.89 (m, 2H), 3.97(s, 2H), 4.44 (s, 2H), 7.47 (s, 1H), 7.57 (dd, J=5.0, 1.2 Hz, 1H), 7.61 (dd, J=5.0, 2.8 Hz, 1H), 7.79(dd, J=2.8, 1.2 Hz, 1H), 7.84 (s, 1H). MS (ESI): m/z 424 (M+H)$^+$.

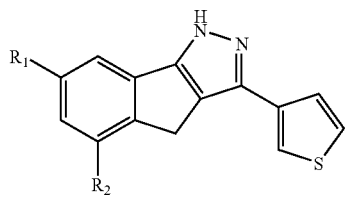

| $R_1$ | $R_2$ | $^1$H NMR | MS (ESI): | Example Number (Reference Procedure) |
|---|---|---|---|---|
| H | ![HO-propyl-NH-] | (500 MHz, $CD_3OD$)δ 1.97(m, 2H), 3.33(m, 2H), 3.74(t, J=5.6Hz, 2H), 3.97(s, 2H), 4.42(s, 2H), 7.44(d, J=7.0Hz, 1H), 7.53(t, J=7.6Hz, 1H), 7.57(dd, J=5.0, 1.2Hz, 1H), 7.61(dd, J=5.0, 2.8Hz, 1H), 7.79(dd, J=2.8, 1.2Hz, 1H), 7.82(d, J=7.0Hz, 1H). | m/z 326 (M + H)$^+$ | Example 303 (Example 302) |
| H | ![3-hydroxymethylpiperidine] | (500 MHz, $CD_3OD$)δ 1.33(m, 1H), 1.80(m, 2H), 1.98(m, 2H), 2.92(t, J=12.2Hz, 1H), 3.08(m, 1H), 3.41(dd, J=11.1, 6.9Hz, 1H), 3.55(dd, J=11.1, 4.7Hz, 1H), 3.64(m, 2H), 3.99(s, 2H), 4.51(s, 2H), 7.49(d, J=7.0Hz, 1H), 7.55(t, J=7.5Hz, 1H), 7.59(dd, J=5.0, 1.2Hz, 1H), 7.61(dd, J=5.0, 2.8Hz, 1H), 7.81(dd, J=2.7, 1.2Hz, 1H), 7.85(d, J=7.6Hz, 1H). | m/z 366 (M + H)$^+$ | Example 304 (Example 302) |
| H | ![4-hydroxymethylpiperidine] | (500 MHz, $CD_3OD$)δ 1.51(m, 2H), 1.80(m, 1H), 2.00(m, 2H), 3.19(m, 2H), 3.45(d, J=6.1Hz, 2H), 3.65(m, 2H), 3.99(s, 2H), 4.49(s, 2H), 7.48(d, J=7.6Hz, 1H), 7.55(t, J=7.6Hz, 1H), 7.58(dd, J=5.0, 1.2Hz, 1H), 7.61(dd, J=5.0, 2.8Hz, 1H), 7.80(dd, J=2.8, 1.5Hz, 1H), 7.85(d, J=7.3Hz, 1H). | m/z 366 (M + H)$^+$ | Example 305 (Example 302) |

-continued

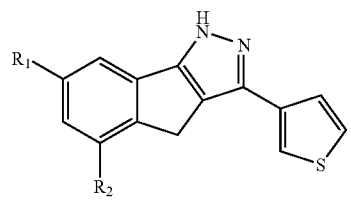

| R₁ | R₂ | ¹H NMR | MS (ESI): | Example Number (Reference Procedure) |
|---|---|---|---|---|
| H | ![piperidinyl-CH2OH] | (500 MHz, CD₃OD)δ 1.67(m, 2H), 1.86(m, 2H), 1.95(m, 1H), 2.04(m, 1H), 3.09(m, 1H), 3.40(m, 2H), 3.76(m, 1H), 3.94(m, 1H), 4.15(m, 2H), 4.39(m, 1H), 5.07(m, 1H), 7.48(d, J=7.6Hz, 1H), 7.53(t, J=7.6Hz, 1H), 7.59(m, 2H), 7.79(dd, J=2.7, 1.5Hz, 1H), 7.84(d, J=7.6Hz, 1H). | m/z 366 (M + H)⁺ | Example 306 (Example 302) |
| H | HO-CH₂CH₂-N(CH₂CH₂OH)-CH₂- | (500 MHz, CD₃OD)δ 3.43(m, 2H), 3.58(m, 2H), 3.98(t, J=5.1Hz, 4H), 4.02(s, 2H), 4.73(s, 2H), 7.53(m, 2H), 7.57(dd, J=5.0, 1.2Hz, 1H), 7.60(dd, J=5.0, 2.8Hz, 1H), 7.79(dd, J=2.8, 1.2Hz, 1H), 7.86(dd, J=6.9, 1.6Hz, 1H). | m/z 356 (M + H)⁺ | Example 307 (Example 302) |
| H | N-methylpiperazinyl-CH₂- | (500 MHz, CD₃OD)δ 2.80-3.05(m, 7H), 3.34(m, 4H), 3.91(s, 2H), 3.93(s, 2H), 7.34(d, J=7.5Hz, 1H), 7.41(t, J=7.5Hz, 1H), 7.56(dd, J=5.0, 1.2Hz, 1H), 7.59(dd, J=5.0, 2.8Hz, 1H), 7.71(d, J=7.5Hz, 1H), 7.80(dd, J=2.8, 1.2Hz, 1H). | m/z 351 (M + H)⁺ | Example 308 (Example 302) |
| H | (CH₃)₂N-CH₂- | (400 MHz, CD₃OD)δ 2.98(s, 6H), 3.98(s, 2H), 4.51(s, 2H), 7.45(d, J=7.7Hz, 1H), 7.58(m, 3H), 7.80(dd, J=2.8, 1.2Hz, 1H), 7.86(d, J=7.4Hz, 1H). | m/z 296 (M + H)⁺ | Example 309 (Example 302) |
| H | HO-CH₂CH₂-NH-C(=O)- | (500 MHz, CD₃OD)δ 3.56(t, J=5.8Hz, 2H), 3.77(t, J=5.8Hz, 2H), 4.07(s, 2H), 7.48(t, J=7.6Hz, 1H), 7.55(dd, J=5.2, 1.2Hz, 1H), 7.59(dd, J=5.0, 2.8Hz, 1H), 7.60(d, J=7.6Hz, 1H), 7.77(dd, J=2.9, 1.4Hz, 1H), 7.85(d, J=7.6Hz, 1H). | m/z 326 (M + H)⁺ | Example 310 (Example 302) |
| N-methylpiperazinyl-CH₂- | CH₃O-CH₂CH₂-NH-CH₂- | (500 MHz, CD₃OD)δ 2.28(s, 3H), 2.30-2.70(m, 8H), 3.39(s, 2H), 3.51(br s, 2H), 3.61(s, 2H), 3.76(s, 3H), 3.78(s, 2H), 7.03(m, 2H), 7.54(m, 2H), 7.72(dd, J=2.9, 1.2Hz, 1H). | m/z 424 (M + H)⁺ | Example 311 (Example 302) |

EXAMPLE 312

2-(4-methyl-1-piperazinyl)-N-[3-(3-thienyl)-1,4-dihydroindeno[1,2-c]pyrazol-5-yl]acetamide To a solution of Example 270 (8 mg, 0.017 mmol) in ethanol (1 mL) was added 1-methylpiperazine (1 mL) and the mixture was stirred at ambient temperature for about 2 hours. The solvents were concentrated under vacuum and the residue was recrystallized from methanol to provide 4 mg (51%) of the desired product. $^1$H NMR (500 MHz, CD$_3$OD) δ 2.41 (s, 3H), 2.60-2.85 (m, 8H), 3.30 (s, 2H), 3.80 (s, 2H), 7.40 (t, J=7.6 Hz, 1H), 7.56 (m, 3H), 7.71 (d, J=8.4 Hz, 1H), 7.75 (m, 1H). MS (ESI): m/z 394 (M+H)$^+$.

775263.0 EXAMPLE 313

2-(4-methyl-1-piperazinyl)-N-{3-[5-(3-phenoxy-1-propynyl)-3-thienyl]-1,4-dihydroindeno[1,2-c]pyrazol-5-yl}acetamide The procedure for Example 312 was used, substituting Example 290 for Example 270 to provide 26 mg (99%) of the desired product. $^1$H NMR (500 MHz, CD$_3$OD) δ 2.38 (s, 3H), 2.60-2.80 (m, 8H), 3.78 (s, 2H), 4.46 (s, 2H), 4.98 (s, 2H), 6.99 (m, 1H), 7.03 (m, 2H), 7.32 (m, 2H), 7.40 (t, J=7.6 Hz, 1H), 7.61 (m, 2H), 7.70 (s, 1H), 7.77 (d, J=7.6 Hz, 1H). MS (ESI): m/z 524 (M+H)$^+$.

EXAMPLE 314

6-bromo-1,4-dihydroindeno[1,2-c]pyrazole

To a mixture of a 60% suspension of sodium hydride in mineral oil (6.83 g, 284.8 mmol) and ethylformate (24.2 mL, 284.8 mmol) in benzene (100 mL) at about 0° C. was added a solution of 5-bromo-1-indanone (30.0 g, 142.4 mmol) in benzene (100 mL) over about 90 minutes. The reaction was then stirred for about 17 hours while being allowed to warm to room temperature. The formed precipitate was collected by filtration and was dissolved in ethanol (600 mL). To this solution was added hydrazine monohydrate (17 mL, 350.5 mmol) and acetic acid (19.2 mL, 335.4 mmol) and the reaction mixture was heated under reflux for about 3 hours. The mixture was cooled, concentrated under vacuum and the precipitate was collected by filtration and was dried under high vacuum to provide the desired product. MS (DCI-NH$_3$): m/z 235, 237 (M+H)$^+$.

EXAMPLE 315

7-bromo-1,4-dihydroindeno[1,2-c]pyrazole

The procedure for Example 314 was used, substituting Example 3 for 5-bromo-1-indanone to provide the desired product. MS (DCI-NH$_3$): m/z 235, 237 (M+H)$^+$.

EXAMPLE 316

1,4-dihydroindeno[1,2-c]pyrazole-6-carbaldehyde

To a solution of Example 314 (9.0 g, 38.3 mmol) in tetrahydrofuran (200 mL) at about −78° C. was slowly added a 1.9M solution of phenyllithium in cyclohexane/diethyl ether (50.4 mL, 95.7 mmol), followed by a 1.4M solution of sec-butyllithium in cyclohexane (68.4 mL, 95.7 mmol). The reaction was stirred at about −78° C. for about 30 minutes before N,N-dimethylformamide (23.7 mL, 30.6 mmol) was added. The mixture was allowed to warm to room temperature and the reaction was then quenched by addition of water. The layers were separated and the aqueous layer was extracted with ethyl acetate. The combined organic extracts were dried (MgSO$_4$), filtered and concentrated under vacuum. The residue was purified by flash chromatography on silica gel using hexane/ethyl acetate (2:1) as eluent to provide the desired product. $^1$H NMR (500 MHz, DMSO-d$_6$): δ 3.76 (s, 2H), 7.63 (m, 1H), 7.90 (m, 2H), 8.05 (m, 1H), 10.0 (s, 1H).

EXAMPLE 317

1,4-dihydroindeno[1,2-c]pyrazole-7-carbaldehyde

The procedure for Example 316 was used, substituting Example 315 for Example 314 to provide the desired product. MS (DCI-NH$_3$): m/z 185 (M+H)$^+$.

EXAMPLE 318

3-iodo-1,4-dihydroindeno[1,2-c]pyrazole-6-carbaldehyde

A solution of Example 316 (2.13 g, 11.6 mmol) and N-iodosuccinimide (3.13 g, 13.9 mmol) in N,N-dimethylformamide (45 mL) was heated to about 80° C. for about 5 hours. The reaction mixture was cooled to room temperature and was concentrated in high vacuum. The residue was partitioned between water and ethyl acetate, the layers were separated and the aqueous layer was extracted with ethyl acetate. The combined organic extracts were dried (MgSO$_4$), filtered and concentrated under vacuum. The residue was purified by flash chromatography on silica gel using hexane/ethyl acetate (2:1) as eluent to provide the desired product. MS (ESI): m/z 309 (M−H)$^−$.

EXAMPLE 319

3-iodo-1,4-dihydroindeno[1,2-c]pyrazole-7-carbaldehyde

The procedure for Example 318 was used, substituting Example 317 for Example 316 to provide the desired product. MS (ESI): m/z 309 (M−H)$^−$.

EXAMPLE 320

3-(3-thienyl)-1,4-dihydroindeno[1,2-c]pyrazole-7-carbaldehyde

A mixture of Example 319 (930 mg, 3.0 mmol), 3-thienylboronic acid (384 mg, 3.0 mmol), tetrakis(triphenylphosphine)palladium(0) (240 mg, 0.21 mmol) and sodium bicarbonate (630 mg, 7.5 mmol) in 1,2-dimethoxyethane (18 mL) and water (6 mL) was stirred under nitrogen in a heavy walled process vial in a microwave synthesizer at about 160° C. for about 10 minutes. The mixture was concentrated under vacuum and the residue was purified by flash chromatography on silica gel using hexane/ethyl acetate (3:1) as eluent to provide 240 mg (30%) of the desired product. MS (ESI): m/z 267 (M+H)$^+$.

EXAMPLE 321

4-{[3-(3-thienyl)-1,4-dihydroindeno[1,2-c]pyrazol-7-yl]methyl}-1-piperazinecarbaldehyde A mixture of Example 320 (67 mg, 0.25 mmol), 1-piperazinecarboxaldehyde (114 mg, 1.0 mmol) and acetic acid (60 mg, 1.0 mmol) in dichloromethane (1.5 mL) was stirred at room temperature for about 5 hours. Then sodium triacetoxyborohydride (210 mg, 1.0 mmol) was added, followed by methanol (1 mL) and the mixture was stirred at room temperature overnight. The mixture was concentrated under vacuum and the residue was purified by preparative HPLC on a Waters Symmetry C8 column (25 mm×100 mm, 7 μm particle size) using a gradient of 10% to 100% acetonitrile: 0.1% aqueous TFA over 8 minutes (10 minutes run time) at a flow rate of 40 mL/minute to provide 54 mg (37%) of the desired product as the trifluoroacetate salt. $^1$H NMR (500 MHz, DMSO-$d_6$) δ 3.00-3.50 (m, 8H), 3.87 (s, 2H), 4.45 (s, 2H), 7.40 (d, J=8 Hz, 1H), 7.58 (d, J=5 Hz, 1H), 7.68 (d, J=8 Hz, 1H), 7.73 (dd, J=5, 3 Hz, 1H), 7.84 (s, 1H), 8.87 (br s, 1H), 8.06 (s, 1H). MS (ESI): m/z 365 (M+H)$^+$.

EXAMPLE 322

N,N-dimethyl-1-{[3-(3-thienyl)-1,4-dihydroindeno[1,2-c]pyrazol-7-yl]methyl}-3-pyrrolidinamine The procedure for Example 321 was used, substituting 3-(dimethylamino)pyrrolidine for 1-piperazinecarboxaldehyde. The crude product was purified by flash chromatography on silica gel using dichloromethane/methanol (10:1)+1% ammonium hydroxide as eluent to provide 64 mg (70%) of the desired product. $^1$H NMR (500 MHz, CDCl$_3$) δ 1.77 (m, 1H), 2.02 (m, 1H), 2.22 (s, 6H), 2.40 (m, 1H), 2.57 (m, 1H), 2.77-2.83 (m, 3H), 3.64 (d, J=10 Hz, 1H), 3.71 (d, J=10 Hz, 1H), 3.78 (s, 2H), 7.26 (d, J=8 Hz, 1H), 7.44 (m, 3H), 7.54 (dd, J=5, 3 Hz, 1H), 7.74 (s, 1H). MS (ESI): m/z 365 (M+H)$^+$.

EXAMPLE 326

5-{6-[(4-methyl-1-piperazinyl)methyl]-1,4-dihydroindeno[1,2-c]pyrazol-3-yl}-2-thiophenecarbaldehyde To a solution of Example 146 (10.4 g, 29.6 mmol) in tetrahydrofuran (200 mL) was slowly added a 2.5M solution of n-butyllithium in hexanes (83.0 mL, 207.1 mmol) at −78° C. The mixture was stirred for about 1 hour before a solution of N,N-dimethylformamide (16.0 mL, 207.1 mmol) in tetrahydrofuran (50 mL) was added dropwise. After stirring for about 1 hour, the reaction was quenched by addition of 10% hydrochloric acid (244 mL) and was gradually warmed to ambient temperature. The reaction mixture was diluted with water and was washed with ethyl acetate. The aqueous layer was basified with potassium carbonate and the product was extracted with ethyl acetate. The combined organic extracts were dried (MgSO$_4$), filtered and evaporated to dryness. The residue was purified by flash chromatography on silica gel using dichloromethane/methanol (5:1) as eluent to provide the desired product. MS (APCI): m/z 378 (M)$^+$.

EXAMPLE 327

5-{7-[(4-methyl-1-piperazinyl)methyl]-1,4-dihydroindeno[1,2-c]pyrazol-3-yl}-2-thiophenecarbaldehyde The procedure for Example 326 was used, substituting Example 138 for Example 146 to provide the desired product. MS (ESI): m/z 379 (M+H)$^+$.

EXAMPLE 328

4-{6-[(4-methyl-1-piperazinyl)methyl]-1,4-dihydroindeno[1,2-c]pyrazol-3-yl}-2-thiophenecarbaldehyde A solution of Example 148 (6.25 g, 14.6 mmol) in tetrahydrofuran (100 mL) was cooled to about 0° C. and sodium hydride (870 mg, 21.8 mmol) was added. After about 5 minutes stirring, the mixture was cooled to about −78° C. and a

| Example Number | R | $^1$H NMR(500 MHz, DMSO-$d_6$) | MS (ESI): | Reference Procedure |
|---|---|---|---|---|
| 323 | 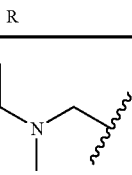 | δ2.40(m, 2H), 2.63(s, 3H), 2.90(s, 3H), 3.10-3.85(m, 5H), 3.88(s, 2H), 4.36(br s, 2H), 7.41(d, J=8Hz, 1H), 7.58(d, J=5Hz, 1H), 7.68(d, J=8Hz, 1H), 7.74(dd, J=5, 3Hz, 1H), 7.87(m, 2H). | m/z 365 (M + H)$^+$. | Example 321 |
| 324 | 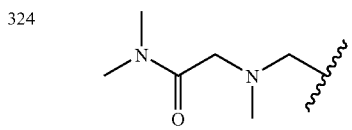 | δ2.79(s, 3H), 3.91(s, 3H), 2.93(s, 3H), 3.87(s, 2H), 4.27(m, 2H), 4.49(m, 2H), 7.46(d, J=8Hz, 1H), 7.58(d, J=5Hz, 1H), 7.67(d, J=8Hz, 1H), 7.73(dd, J=5, 3Hz, 1H), 7.87(d, J=3Hz, 1H), 7.90(s, 1H). | m/z 367 (M + H)$^+$. | Example 321 |
| 325 | 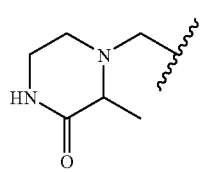 | δ1.62(m, 3H), 3.40(m, 4H), 3.87(s, 2H), 4.32(br s, 2H), 4.80(m, 1H), 7.43(d, J=8Hz, 1H), 7.58(d, J=5Hz, 1H), 7.68(d, J=8Hz, 1H), 7.74(dd, J=5, 3Hz, 1H), 7.86(s, 2H), 8.40(br s, 1H). | m/z 365 (M + H)$^+$. | Example 321 |

2.5M solution of n-butyllithium in hexanes (8.7 mL, 21.8 mmol) was slowly added. The mixture was stirred for about 1 hour before a solution of N,N-dimethylformamide (11.3 mL, 145.6 mmol) in tetrahydrofuran (20 mL) was added dropwise. After stirring for about 1 hour, the reaction was quenched by addition of 10% hydrochloric acid (244 mL) and was gradually warmed to ambient temperature. The reaction mixture was diluted with water and was washed with ethyl acetate. The aqueous layer was basified with potassium carbonate and the product was extracted with ethyl acetate. The combined organic extracts were dried (MgSO$_4$), filtered and evaporated to dryness. The residue was purified by flash chromatography on silica gel using dichloromethane/methanol (5:1) as eluent to provide the desired product. MS (ESI): m/z 379 (M+H)$^+$.

EXAMPLE 329

4-{7-[(4-methyl-1-piperazinyl methyl]-1,4-dihydroindeno[1,2-c]pyrazol-3-yl}-2-thiophenecarbaldehyde The procedure for Example 328 was used, substituting Example 149 for Example 148 to provide the desired product. MS (ESI): m/z 379 (M+H)$^+$.

EXAMPLE 330

N-methyl-5-{6-[(4-methyl-1-piperazinyl)methyl]-1,4-dihydroindeno[1,2-c]pyrazol-3-yl}-2-thiophenecarboxamide To Example 147 (50 mg, 0.116 mmol) in methylamine (12 mL) was added [1,1'bis(diphenylphosphino)ferrocene]-dichloropalladium(II) complex with dichloromethane (1:1) (5.2 mg, 0.006 mmol) and the mixture was carbonylated at 500 psi and about 120° C. for about 16 hours. The mixture was concentrated under vacuum and the residue was purified by preparative HPLC on a Waters Symmetry C8 column (25 mm×100 mm, 7 μm particle size) using a gradient of 10% to 100% acetonitrile:0.1% aqueous TFA over 8 minutes (10 minutes run time) at a flow rate of 40 mL/minute to provide 44 mg (51%) of the desired product as the trifluoroacetate salt. $^1$H NMR (400 MHz, DMSO-d$_6$): δ 2.79 (d, J=4.6 Hz, 3H), 2.82 (s, 3H), 3.00-3.50 (m, 8H), 3.81 (s, 2H), 4.03 (br s, 2H), 7.42 (d, J=7.7 Hz, 1H), 7.45 (d, J=3.9 Hz, 1H), 7.63 (s, 1H), 7.67 (d, J=77 Hz, 1H), 7.73 (d, J=3.9 Hz, 1H), 8.50 (q, J=4.6 Hz, 1H). MS (ESI): m/z 408 (M+H)$^+$.

EXAMPLE 331

5-{1-[bis(4-methoxyphenyl)methyl]-6-[(4-methyl-1-piperazinyl)methyl]-1,4-dihydroindeno[1,2-c]pyrazol-3-yl}-2-thiophenecarbaldehyde To 4,4'-dimethoxybenzhydrol (5.62 g, 23.0 mmol) was carefully added thionyl chloride (20.1 mL, 276 mmol) and the mixture was heated to reflux for about 1 hour. The solution was cooled, evaporated to dryness and the residue was dissolved in tetrahydrofuran (50 mL). This solution was then added to a solution of Example 326 (5.3 g, 14.0 mmol) and triethylamine (5.9 mL, 42.0 mmol) in tetrahydrofuran (100 mL). The reaction mixture was heated to about 50° C. for about 2.5 hours, cooled, diluted with water and extracted with ethyl acetate. The combined organic extracts were dried (Na$_2$SO$_4$), filtered and concentrated under vacuum, and the residue was purified by flash chromatography on silica gel using dichloromethane/methanol (10:1) as eluent to provide the desired product. MS (ESI): m/z 605 (M+H)$^+$.

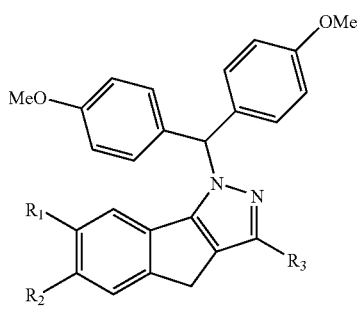

| Example Number | R$_1$ | R$_2$ | R$_3$ | MS (ESI): | Reference Procedure |
|---|---|---|---|---|---|
| 332 | 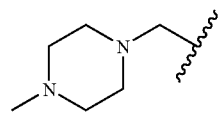 | H | 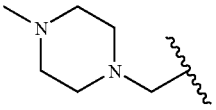 | m/z 605 (M + H)$^+$. | Example 331 |
| 333 | H | 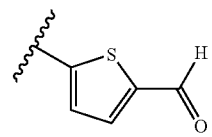 | 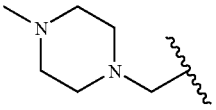 | m/z 605 (M + H)$^+$. | Example 331 |

-continued

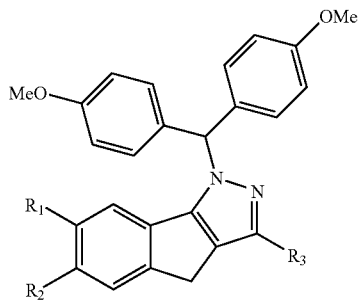

| Example Number | R₁ | R₂ | R₃ | MS (ESI): | Reference Procedure |
|---|---|---|---|---|---|
| 334 | N-methylpiperazinyl-CH₂- | H | thiophene-2-carbaldehyde-4-yl | m/z 605 (M + H)⁺ | Example 331 |

EXAMPLE 335

5-[1-[bis(4-methoxyphenyl methyl]-6-(1H-imidazol-1-ylmethyl)-1,4-dihydroindeno[1,2-c]pyrazol-3-yl]-2-thiophenecarbaldehyde The procedure for Example 57 was used, substituting Example 331 for Example 54 to provide Example 335. MS (ESI): m/z 573 (M+H)⁺.

EXAMPLE 336

N-[(5-{1-[bis(4-methoxyphenyl)methyl]-6-[(4-methyl-1-piperazinyl)methyl]-1,4-dihydroindeno[1,2-c]pyrazol-3-yl}-2-thienyl methyl]-N-methylamine To a solution of Example 331 (1.2 g, 2.0 mmol) in methanol (10 mL) and tetrahydrofuran (5 mL) added a 2M solution of methylamine in tetrahydrofuran (5 mL) and acetic acid (0.6 mL, 10 mmol). Then sodium triacetoxyborohydride (1.25 g, 6 mmol) was added and the mixture was stirred at room temperature for about 5 hours. The mixture was diluted with ethyl acetate, washed with saturated aqueous sodium carbonate and the aqueous phase was extracted with ethyl acetate. The combined organic layers were dried (Na₂SO₄), filtered and concentrated under vacuum. The residue was purified by flash chromatography on silica gel using dichloromethane/methanol (10:1)+1% ammonium hydroxide as eluent to provide the desired product. MS (ESI): m/z 620 (M+H)⁺.

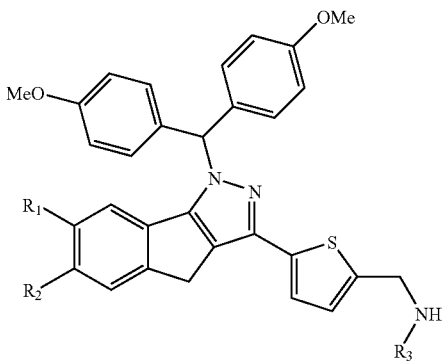

| Example Number | R₁ | R₂ | R₃ | MS (ESI): | Reference Procedure |
|---|---|---|---|---|---|
| 337 | H | 4-methylpiperazinyl-CH₂CH₂- | Et | m/z 634 (M + H)⁺ | Example 336 |

-continued

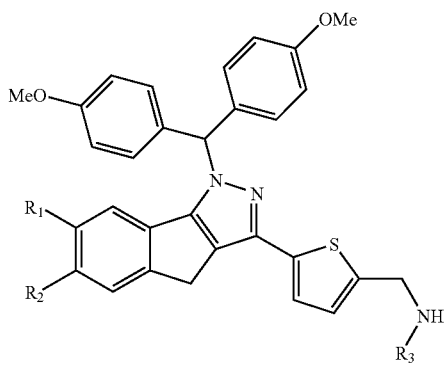

| Example Number | R₁ | R₂ | R₃ | MS (ESI): | Reference Procedure |
|---|---|---|---|---|---|
| 338 | H | 4-methylpiperazinylmethyl | n-butyl | m/z 648 (M + H)⁺ | Example 336 |
| 339 | H | 4-methylpiperazinylmethyl | isopropyl | m/z 648 (M + H)⁺ | Example 336 |
| 340 | H | 4-methylpiperazinylmethyl | cyclopropyl | m/z 646 (M + H)⁺ | Example 336 |
| 341 | H | 4-methylpiperazinylmethyl | isobutyl | m/z 662 (M + H)⁺ | Example 336 |
| 342 | H | 4-methylpiperazinylmethyl | isopentyl | m/z 676 (M + H)⁺ | Example 336 |
| 343 | H | 4-methylpiperazinylmethyl | 2-methoxyethyl (branched) | m/z 664 (M + H)⁺ | Example 336 |

-continued

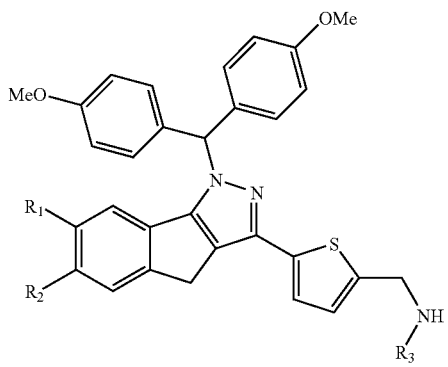

| Example Number | R₁ | R₂ | R₃ | MS (ESI): | Reference Procedure |
|---|---|---|---|---|---|
| 344 | H | (imidazolylethyl) | Me | m/z 588 (M + H)⁺ | Example 336 |
| 345 | (4-methylpiperazinyl-ethyl) | H | Me | m/z 620 (M + H)⁺ | Example 336 |

EXAMPLE 346

3-{5-[(methoxyamino)methyl]-2-thienyl}-6-[(4-methyl-1-piperazinyl methyl]-1,4-dihydroindeno[1,2-c]pyrazole To Example 331 (1.2 g, 2.0 mmol) in methanol (5 mL) was added O-methyl-hydroxylamine hydrochloride (0.42 g, 5.0 mmol) and pyridine (0.43 mL, 5.4 mmol) and the mixture was stirred at about 70° C. overnight. The mixture was cooled to about 0° C., borane-pyridine complex (0.8 mL, 7.0 mmol) was added, followed by concentrated hydrochloric acid (2.5 mL). The mixture was stirred at room temperature overnight and was then concentrated under vacuum. The residue was purified by flash chromatography on silica gel using dichloromethane/methanol (5:1)+2% ammonium hydroxide as eluent to provide the desired product. MS (ESI): m/z 410 (M+H)⁺.

EXAMPLE 347

5-{6-[(4-methyl-1-piperazinyl)methyl]-1,4-dihydroindeno[1,2-c]pyrazol-3-yl}-2-thiophenecarbaldehyde N-phenylsemicarbazone To a solution of Example 331 (60 mg, 0.1 mmol) in 1,4-dioxane (2 mL) was added 4-phenylsemicarbazide (19 mg, 0.12 mmol) and potassium acetate (1 mg, 0.12 mmol) and the mixture was agitated at room temperature for about 6 hours. The solvent was concentrated under vacuum and to the residue was added a 4M solution of hydrochloric acid in 1,4-dioxane (2 mL). The mixture was stirred at room temperature overnight, concentrated under vacuum and the residue was purified by preparative HPLC on a Waters Symmetry C8 column (25 mm×100 mm, 7 μm particle size) using a gradient of 10% to 100% acetonitrile:0.1% aqueous TFA over 8 minutes (10 minutes nm time) at a flow rate of 40 mL/minute to provide 10 mg (12%) of the desired product as the trifluoroacetate salt. ¹H NMR (500 MHz, DMSO-d₆): δ 2.78 (s, 3H), 3.00-3.50 (m, 8H), 3.68 (br s, 2H), 3.80 (s, 2H), 7.02 (m, 1H), 7.32 (m, 3H), 7.45 (m, 2H), 7.55 (s, 1H), 7.61 (m, 2H), 8.17 (s, 1H), 8.67 (s, 1H), 10.78 (s, 1H). MS (ESI): m/z 512 (M+H)⁺.

EXAMPLE 348

5-{6-[(4-methyl-1-piperazinyl)methyl]-1,4-dihydroindeno[1,2-c]pyrazol-3-yl}-2-thiophenecarbaldehyde O-benzyloxime The procedure for Example 347 was used, substituting O-benzylhydroxylamine for 4-phenylsemicarbazide to provide 17 mg (21%) of the desired product as the trifluoroacetate salt. ¹H NMR (500 MHz, DMSO-d₆): δ 2.76 (s, 3H), 3.00-3.50 (m, 8H), 3.71 (br s, 2H), 3.75 (s, 2H), 5.32 (s, 2H), 7.35 (m, 1H), 7.42 (m, 2H), 7.47 (m, 2H), 7.55 (s, 1H), 7.57 (d, J=4 Hz, 1H), 7.99 (s, 1H). MS (ESI): m/z 484 (M+H)⁺.

EXAMPLE 349

({[(1E)-(5-{1-[bis(4-methoxyphenyl)methyl]-6-[(4-methyl-1-piperazinyl methyl]-1,4-dihydroindeno[1,2-c]pyrazol-3-yl}-2-thienyl)methylene]amino}oxy)acetic acid A mixture of Example 331 (175 mg, 0.23 mmol), (aminooxy)acetic acid hemihydrochloride (52 mg, 0.23 mmol), and potassium acetate (22 mg, 0.23 mmol) in a 1:1:1 mixture of water/methanol/1,4-dioxane (6 mL) was stirred at room temperature for about 16 hours. The mixture was diluted with water and was extracted with dichloromethane. The combined organic extracts were dried (MgSO$_4$), filtered and evaporated to dryness to provide the desired product. MS (ESI): m/z 678 (M+H)$^+$.

EXAMPLE 350

N-(3-methylphenyl)-2-({[(1E)-(5-{6-[(4-methyl-1-piperazinyl)methyl]-1,4-dihydroindeno[1,2-c]pyrazol-3-yl}-2-thienyl)methylene]amino}oxy)acetamide To a solution of Example 349 (70 mg, 0.1 mmol) in dichloromethane (3 mL) and N,N-dimethylacetamide (0.5 mL) was added 1-hydroxybenzotriazole hydrate (20 mg, 0.15 mmol), m-toluidine (22 μL, 0.2 mmol) and N-cyclohexylcarbodiimide-N'-methyl polystyrene (1.0 g, 1.3 mmol) and the mixture was agitated at room temperature for about 20 hours. The mixture was filtered and the filtrate was concentrated under vacuum. The residue was suspended in a 4M solution of hydrochloric acid in 1,4-dioxane (1 mL, 4.0 mmol) and the mixture was agitated at room temperature overnight. The mixture was evaporated to dryness and the residue was purified by preparative HPLC on a Waters Symmetry C8 column (25 mm×100 mm, 7 μm particle size) using a gradient of 10% to 100% acetonitrile:0.1% aqueous TFA over 8 minutes (10 minutes run time) at a flow rate of 40 mL/minute to provide 12 mg (15%) of the desired product as the trifluoroacetate salt. $^1$H NMR (500 MHz, DMSO-d$_6$): δ 2.28 (s, 3H), 2.78 (s, 3H), 3.00-3.50 (m, 8H), 3.77 (s, 2H), 3.78 (s, 2H), 4.83 (s, 2H), 6.90 (d, J=7 Hz, 1H), 7.18 (m, 1H), 7.37 (m, 1H), 7.42 (m, 1H), 7.49 (m, 1H), 7.55 (m, 1H), 7.63 (m, 1H), 8.02 (s, 1H), 8.62 (s, 1H), 9.90 (s, 1H). MS (ESI): m/z 541 (M+H)$^+$.

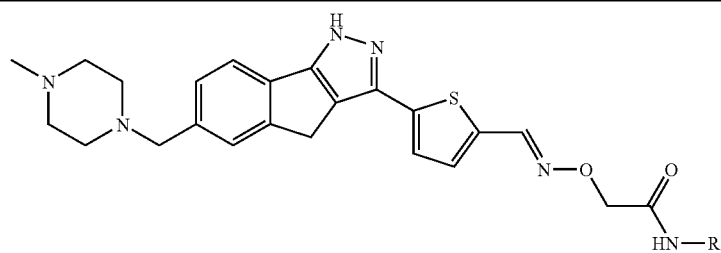

| Example Number | R | $^1$H NMR | MS (ESI): | Reference Procedure |
|---|---|---|---|---|
| 351 | (3-methylphenyl) | (500 MHz, DMSO-d$_6$) δ 2.18(s, 3H), 2.81(s, 3H), 3.00-3.50(m, 8H), 3.80(s, 2H), 4.02(br s, 2H), 4.85(s, 2H), 7.12(m, 1H), 7.20(m, 2H), 7.42(m, 1H), 7.50(m, 2H), 7.64(m, 1H), 8.08(s, 1H), 8.63(s, 1H), 9.28(s, 1H). | m/z 541 (M + H)$^+$. | Example 350 |
| 352 | (4-methylphenyl) | (500 MHz, CDCl$_3$) δ 2.10-2.60(m, 8H), 2.29(s, 3H), 2.85(s, 3H), 3.49(s, 2H), 3.57(br s, 2H), 4.14(s, 2H), 7.12(m, 2H), 7.32(d, J=5Hz, 1H), 7.43(m, 3H), 7.54(s, 1H), 7.67(m, 1H), 7.82(s, 1H), 7.92(s, 1H), 8.44(s, 1H). | m/z 541 (M + H)$^+$. | Example 350 |

EXAMPLE 353 diethyl 2-[(2-methylphenyl)amino]-2-oxoethylphosphonate

A solution of diethylphosphonoacetic acid (250 mg, 1.27 mmol), o-toluidine (136 μL, 1.27 mmol), 2-(1H-benzotriazol-1-yl)-1,1,3,3-tetramethyluronium tetrafluoroborate (610 mg, 1.9 mmol) and N,N-diisopropylethylamine (0.66 mL, 3.81 mmol) in dichloromethane (5 mL) was stirred at ambient temperature for about 17 hour. The reaction was quenched with water, the layers were separated, and the aqueous layer was extracted with dichloromethane. The combined organic extracts were dried (MgSO$_4$), filtered, concentrated under vacuum and the residue was purified by preparative HPLC on a Waters Symmetry C8 column (25 mm×100 mm, 7 μm particle size) using a gradient of 10% to 100% acetonitrile: 0.1% aqueous TFA over 8 minutes (10 minutes run time) at a flow rate of 40 mL/minute to provide the desired product. $^1$H NMR (500 MHz, CDCl$_3$): δ 1.37 (t, J=6.0 Hz, 6H), 2.31 (s, 3H), 3.08 (d, J=20.0 Hz, 2H), 4.16-4.26 (m, 4H), 7.09 (m, 1H), 7.18 (m, 2H), 7.81 (d, J=9.0 Hz, 1H), 8.51 (br s, 1H).

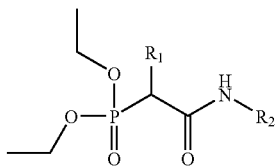

| Example Number | R₁ | R₂ | ¹H NMR(500 MHz, DMSO-d₆) | Reference Procedure |
|---|---|---|---|---|
| 354 | H | 3-methylphenyl | δ1.36(t, J=6.0Hz, 6H), 2.33(s, 3H), 3.02(d, J=20.0Hz, 2H), 4.14-4.24(m, 4H), 6.93(d, J=9.0Hz, 1H), 7.20(t, J=9.0Hz, 1H), 7.33(m, 2H), 8.66(br s, 1H). | Example 353 |
| 355 | H | 4-methylphenyl | δ1.36(t, J=6.0Hz, 6H), 2.31(s, 3H), 3.02(d, J=21.0Hz, 2H), 4.14-4.23(m, 4H), 7.11(d, J=9.0Hz, 2H), 7.39(d, J=9.0Hz, 2H), 8.62(br s, 1H). | Example 353 |
| 356 | Me | 2-methylphenyl | δ1.32-1.38(m, 6H), 1.49-1.54(m, 3H), 2.32(s, 3H), 3.01-3.10(m, 1H), 4.13-4.20(m, 4H), 7.06(m, 1H), 7.19(m, 2H), 7.88(d, J=4H), 7.06(m, 1H), 7.19(m, 2H), 7.88(d, J=10.0Hz, 1H), 8.61(br s, 1H). | Example 353 |
| 357 | Me | 2-CF₃-phenyl | δ1.36-1.40(m, 6H), 1.46-1.51(m, 3H), 3.09-3.18(m, 1H), 4.15-4.24(m, 4H), 7.23-7.31(m, 2H), 7.68(d, J=10.0Hz, 1H), 7.81(s, 1H), 9.49(br s, 1H). | Example 353 |
| 358 | Me | 3-methylphenyl | δ1.31-1.37(m, 6H), 1.46-1.51(m, 3H), 2.31(s, 3H), 2.99-3.08(m, 1H), 4.13-4.21(m, 4H), 6.90(d, J=5.0Hz, 1H), 7.18(t, J=5.0Hz, 1H), 7.32-7.37(m, 2H), 8.78(br s, 1H). | Example 353 |
| 359 | Me | 3-Cl-phenyl | δ1.33-1.38(m, 6H), 1.45-1.50(m, 3H), 3.03-3.12(m, 1H), 4.15-4.22(m, 4H), 7.03(d, J=10.0Hz, 1H), 7.16(t, J=10.0Hz, 1H), 7.33(d, J=10.0Hz, 1H), 7.66(m, 1H), 9.11(br s, 1H). | Example 353 |
| 360 | Me | 3-Br-phenyl | δ1.33-1.38(m, 6H), 1.44-1.49(m, 3H), 3.03-3.12(m, 1H), 4.16-4.21(m, 4H), 7.08(t, J=10.0Hz, 1H), 7.15(d, J=10.0Hz, 1H), 7.40(d, J=10.0Hz, 1H), 7.78(m, 1H), 9.28(br s, 1H). | Example 353 |
| 361 | Me | 4-CF₃-phenyl | δ1.32-1.39(m, 6H), 1.46-1.51(m, 3H), 3.01-3.10(m, 1H), 4.13-4.22(m, 4H), 7.52(d, J=10.0Hz, 2H), 7.64(d, J=10.0Hz, 2H), 9.30(br s, 1H). | Example 353 |

-continued

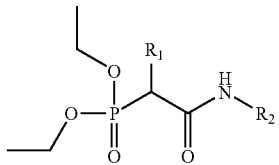

| Example Number | R₁ | R₂ | ¹H NMR(500 MHz, DMSO-d₆) | Reference Procedure |
|---|---|---|---|---|
| 362 | Me | 2-methyl-3-methylphenyl (attached) | δ1.32-1.38(m, 6H), 1.49-1.54(m, 3H), 2.19(s, 3H), 2.29(s, 3H), 3.02-3.11(m, 1H), 4.15-4.23(m, 4H), 6.99(d, J=10.0Hz, 1H), 7.08(t, J=5.0Hz, 1H), 7.54(d, J=10.0Hz, 1H), 8.49(br s, 1H). | Example 353 |
| 363 | Me | 2,5-dimethylphenyl (attached) | δ1.32-1.38(m, 6H), 1.49-1.54(m, 3H), 2.27(s, 3H), 2.31(s, 3H), 3.01-3.10(m, 1H), 4.15-4.22(m, 4H), 6.87(d, J=5.0Hz, 1H), 7.05(d, J=5.0Hz, 1H), 7.72(s, 1H), 8.52(br s, 1H). | Example 353 |

EXAMPLE 364

(2E)-N-(2-methylphenyl)-3-(5-{6-[(4-methyl-1-piperazinyl)methyl]-1,4-dihydroindeno[1,2-c]pyrazol-3-yl}-2-thienyl)acrylamide To a solution of Example 353 (235 mg, 0.825 mmol) in tetrahydrofuran (10 mL) was added a 2M solution of lithium diisopropylamide in heptane/tetrahydro furan/ethylbenzene (0.83 mL, 1.65 mmol) dropwise at room temperature. The mixture was stirred for about 20 minutes and then a solution of Example 331 (100 mg, 0.165 mmol) in tetrahydro furan (5 mL) was added. The reaction was stirred at room temperature overnight and was quenched by addition of saturated aqueous ammonium chloride. The layers were separated and the aqueous layer was extracted with dichloromethane. The combined organic extracts were dried (MgSO₄), filtered, and concentrated under vacuum. The residue was treated with a 4M solution of hydrochloric acid in 1,4-dioxane (5 mL) for about 2 hours, then the mixture was concentrated under vacuum and the residue was purified by preparative HPLC on a Waters Symmetry C8 column (25 mm×100 mm, 7 μm particle size) using a gradient of 10% to 100% acetonitrile:0.1% aqueous TFA over 8 minutes (10 minutes run time) at a flow rate of 40 mL/minute to provide 16 mg (16%) of the desired product as the trifluoroacetate salt. ¹H NMR (500 MHz, DMSO-d₆): δ 2.27 (s, 3H), 2.81 (s, 3H), 3.00-3.50 (m, 8H), 3.82 (s, 2H), 3.94 (br s, 2H), 6.77 (d, J=15.0 Hz, 1H), 7.09 (m, 1H), 7.19 (m, 1H), 7.24 (d, J=7.5 Hz, 1H), 7.41 (d, J=7.8 Hz, 1H), 7.48 (m, 2H), 7.62 (m, 2H), 7.67 (d, J=7.8 Hz, 1H), 7.75 (d, J=15.6 Hz, 1H), 9.46 (s, 1H). MS (ESI): m/z 510 (M+H)⁺.

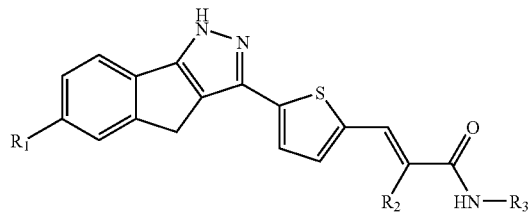

| R₁ | R₂ | R₃ | ¹H NMR | MS (ESI): | Example Number (Reference Procedure) |
|---|---|---|---|---|---|
| 4-methyl-1-piperazinyl-methyl | H | 3-methylphenyl | (500 MHz, DMSO-d₆)δ 2.31(s, 3H), 2.85(s, 3H), 3.00-3.50(m, 8H), 3.83(s, 2H), 4.16(br s, 2H), 6.62(d, J=15.0Hz, 1H), 6.89(d, J=5.0Hz, 1H), 7.21(t, J=5.0Hz, 1H), 7.50(m, 5H), 7.69(m, 2H), 7.75(d, J=15.0Hz, 1H), 10.14(s, 1H). | m/z 510 (M + H)⁺ | Example 365 (Example 364) |

-continued

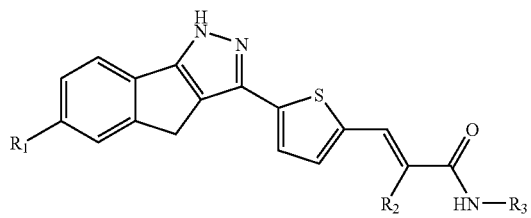

| R₁ | R₂ | R₃ | ¹H NMR | MS (ESI): | Example Number (Reference Procedure) |
|---|---|---|---|---|---|
| 4-methylpiperazinylmethyl | H | 4-methylphenyl | (400 MHz, DMSO-d$_6$)δ 2.27(s, 3H), 2.81(s, 3H), 3.00-3.50(m, 8H), 3.82(s, 2H), 3.98(br s, 2H), 6.60(d, J=15.0Hz, 1H), 7.14(m, 2H), 7.42(d, J=7.1Hz, 1H), 7.48(m, 2H), 7.58(m, 2H), 7.63(s, 1H), 7.67(d, J=7.7Hz, 1H), 7.74(d, J=15.3Hz, 1H), 10.12(s, 1H). | m/z 510 (M + H)⁺ | Example 366 (Example 364) |
| imidazolylmethyl | H | 4-methylphenyl | (400 MHz, DMSO-d$_6$)δ 2.27(s, 3H), 3.79(s, 2H), 5.26(s, 2H), 6.59(d, J=16.0Hz, 1H), 6.92(s, 1H), 7.14(m, 2H), 7.22(s, 1H), 7.29(m, 1H), 7.40-7.52(m, 3H), 7.58(m, 2H), 7.62(m, 1H), 7.73(d, J=16.0Hz, 1H), 7.79(s, 1H), 10.11(s, 1H). | m/z 478 (M + H)⁺ | Example 367 (Example 364) |
| 4-methylpiperazinylmethyl | Me | 2-methylphenyl | (500 MHz, DMSO-d$_6$)δ 2.23(s, 3H), 2.29(s, 3H), 2.79(s, 3H), 3.00-3.50(m, 8H), 3.83(s, 2H), 3.85(br s, 2H), 7.14(m, 1H), 7.20(m, 1H), 7.25(d, J=7.5Hz, 1H), 7.31(d, J=7.2Hz, 1H), 7.38(d, J=5.0Hz, 1H), 7.44(d, J=3.7Hz, 1H), 7.52(d, J=3.7Hz, 1H), 7.60(s, 1H), 7.64(m, 2H), 9.47(s, 1H). | m/z 524 (M + H)⁺ | Example 368 (Example 364) |
| 4-methylpiperazinylmethyl | Me | 2-(trifluoromethyl)phenyl | (500 MHz, DMSO-d$_6$)δ 2.28(s, 3H), 2.82(s, 3H), 3.00-3.50(m, 8H), 3.84(s, 2H), 4.02(br s, 2H), 7.43(m, 2H), 7.48(d, J=3.7Hz, 1H), 7.55(d, J=3.7Hz, 1H), 7.58(t, J=7.8Hz, 1H), 7.64(m, 2H), 7.68(d, J=7.8Hz, 1H), 8.01(d, J=8.7Hz, 1H), 8.19(s, 1H), 10.27(s, 1H). | m/z 578 (M + H)⁺ | Example 369 (Example 364) |
| 4-methylpiperazinylmethyl | Me | 3-methylphenyl | (500 MHz, DMSO-d$_6$)δ 2.26(s, 3H), 2.30(s, 3H), 2.81(s, 3H), 3.00-3.50(m, 8H), 3.83(s, 2H), 3.94(br s, 2H), 6.90(d, J=10.0Hz, 1H), 7.21(t, J=10.0Hz, 1H), 7.41(d, J=7.8Hz, 1H), 7.44(d, J=3.7Hz, 1H), 7.53(m, 4H), 7.62(s, 1H), 7.66(d, J=7.8Hz, 1H), 9.84(s, 1H) | m/z 524 (M + H)⁺ | Example 370 (Example 364) |

-continued

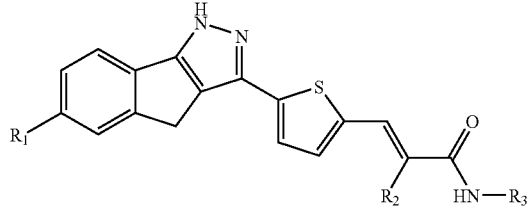

| R₁ | R₂ | R₃ | ¹H NMR | MS (ESI): | Example Number (Reference Procedure) |
|---|---|---|---|---|---|
| 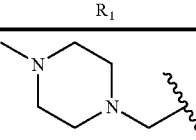 | Me | 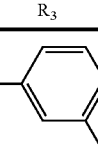 | (300 MHz, DMSO-$d_6$)δ 2.26(s, 3H), 2.80(s, 3H), 3.00-3.50(m, 8H), 3.83(s, 2H), 3.89(br s, 2H), 7.14(m, 1H), 7.39(m, 2H), 7.47(d, J=3.7Hz, 1H), 7.53(d, J=3.7Hz, 1H), 7.60(m, 2H), 7.65(m, 2H), 7.90(t, J=2.0Hz, 1H), 10.12(s, 1H). | m/z 544 (M)⁺ | Example 371 (Example 364) |
| 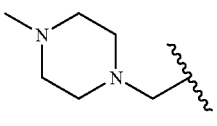 | Me | 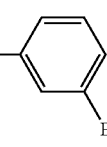 | (300 MHz, DMSO-$d_6$)δ 2.26(s, 3H), 2.78(s, 3H), 3.00-3.50(m, 8H), 3.82(s, 2H), 4.05(br s, 2H), 7.25-7.72(m, 9H), 8.03(t, J=2.0Hz, 1H), 10.09(s, 1H). | m/z 588, 590 (M + H)⁺ | Example 372 (Example 364) |
| 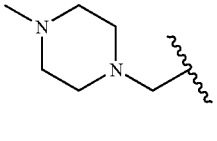 | Me | 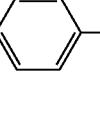 | (500 MHz, DMSO-$d_6$)δ 2.09(s, 3H), 2.80(s, 3H), 3.00-3.50(m, 8H), 3.62(br s, 2H), 3.85(s, 2H), 7.08(m, 4H), 7.44(d, J=3.7Hz, 1H), 7.55(d, J=3.7Hz, 1H), 7.65(br s, 2H), 7.72(d, J=7.8Hz, 1H), 7.87(br s, 1H), 9.56(s, 1H). | m/z 578 (M + H)⁺ | Example 373 (Example 364) |
| 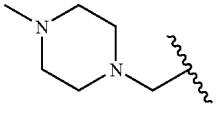 | Me | 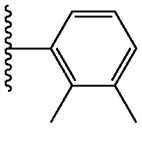 | (500 MHz, DMSO-$d_6$)δ 2.28(s, 6H), 2.81(s, 3H), 3.00-3.50(m, 8H), 3.17(s, 3H), 3.82(s, 2H), 4.94(br s, 2H), 7.41(d, J=7.5Hz, 1H), 7.48(d, J=3.8Hz, 1H), 7.54(d, J=3.7Hz, 1H), 7.62(m, 2H), 7.66(d, J=7.5Hz, 1H), 7.70(m, 1H), 7.95(m, 2H), 10.29(s, 1H). | m/z 538 (M + H)⁺ | Example 374 (Example 364) |
| 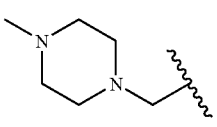 | Me | 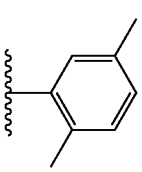 | (500 MHz, DMSO-$d_6$)δ 2.17(s, 3H), 2.28(s, 3H), 2.79(s, 3H), 3.00-3.50(m, 8H), 3.17(s, 3H), 3.82(br s, 4H), 6.96(d, J=7.8Hz, 1H), 7.13(m, 2H), 7.38(d, J=7.5Hz, 1H), 7.44(d, J=4.1Hz, 1H), 7.52(d, J=3.8Hz, 1H), 7.63(m, 3H), 9.41(s, 1H). | m/z 538 (M + H)⁺ | Example 375 (Example 364) |

EXAMPLE 376

N-(2-methylphenyl)-3-(5-{6-[(4-methyl-1-piperazinyl)methyl]-1,4-dihydroindeno[1,2-c]pyrazol-3-yl}-2-thienyl)propanamide To a solution of Example 364 (10 mg, 0.02 mmol) in tetrahydrofuran (1 mL) and methanol (1 mL) was added 10 wt. % palladium on activated carbon (30 mg) and ammonium formate (120 mg, 1.9 mmol) and the mixture was heated to about 60° C. for about 5 hours. The mixture was cooled, filtered through Celite, concentrated under vacuum and the residue was purified by preparative HPLC on a Waters Symmetry C8 column (25 mm×100 mm, 7 μm particle size) using a gradient of 10% to 100% acetonitrile:0.1% aqueous TFA over 8 minutes (10 minutes run time) at a flow rate of 40 mL/minute to provide 3 mg (4%) of the desired product as the trifluoroacetate salt. ¹H NMR (500 MHz, DMSO-d₆): δ 2.16 (s, 3H), 2.75 (t, J=10.0 Hz, 2H), 2.78 (s, 3H), 3.17 (t, J=10.0 Hz, 2H), 3.00-3.50 (m, 8H), 3.72 (s, 2H), 3.80 (br s, 2H), 6.95 (d, J=5.0 Hz, 1H), 7.07 (t, J=5.0 Hz, 1H), 7.17 (m, 2H), 7.28 (m, 1H), 7.37 (m, 2H), 7.56 (s, 1H), 7.62 (d, J=5.0 Hz, 1H), 9.89 (s, 1H). MS (ESI): m/z 512 (M+H)⁺.

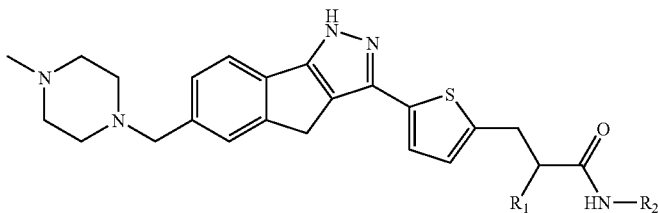

| Example Number | R₁ | R₂ | ¹H NMR(500 MHz, DMSO-d₆) | MS (ESI): | Reference Procedure |
|---|---|---|---|---|---|
| 377 | H | ![3-methylphenyl] | δ2.27(s, 3H), 2.71(t, J=10.0Hz, 2H), 2.78(s, 3H), 3.15(t, J=10.0Hz, 2H), 3.00-3.50(m, 8H), 3.71(s, 2H), 3.84(br s, 2H), 6.85(d, J=5.0Hz, 1H), 6.93(d, J=5.0Hz, 1H), 7.17(m, 1H), 7.26(d, J=5.0Hz, 1H), 7.36(s, 1H), 7.38(s, 1H), 7.44(s, 1H), 7.57(s, 1H), 7.62(d, J=5.0Hz, 1H),0 9.89(s, 1H). | m/z 512 (M + H)⁺ | Example 376 |
| 378 | Me | ![2-CF₃-phenyl] | δ1.20(d, J=5.0Hz, 3H), 2.77(s, 3H), 2.85-2.96(m, 2H), 3.19(m, 1H), 3.00-3.50(m, 8H), 3.66(s, 2H), 3.77(br s, 2H), 6.91(d, J=5.0Hz, 1H), 7.25(d, J=5.0Hz, 1H), 7.34(d, d, J=8.1Hz, 1H), 7.53(s, 1H), 7.60(d, J=7.8Hz, 1H), 7.66(m, 2H), 7.82(m, 2H), 10.33(s, 1H). | m/z 580 (M + H)⁺ | Example 376 |
| 379 | Me | ![3-methylphenyl] | δ1.18(d, J=5.0Hz, 3H), 2.26(s, 3H), 2.78(s, 3H), 2.80-2.91(m, 2H), 3.17(m, 1H), 3.00-3.50(m, 8H), 3.68(s, 2H), 3.81(br s, 2H), 6.85(d, J=10.0Hz, 1H), 6.90(d, J=5.0Hz, 1H), 7.16(t, J=10.0Hz, 1H), 7.25(d, J=5.0Hz, 1H), 7.36(m, 2H), 7.44(s, 1H), 7.54(s, 1H), 7.61(d, J=5.0Hz, 1H), 9.86(s, 1H). | m/z 526 (M + H)⁺ | Example 376 |
| 380 | Me | ![3-Cl-phenyl] | δ1.18(d, J=5.0Hz, 3H), 2.77(s, 3H), 2.83-2.92(m, 2H), 3.18(m, 1H), 3.00-3.50(m, 8H), 3.68(s, 2H), 3.81(br s, 2H), 6.90(d, J=5.0Hz, 1H), 7.03(t, J=10.0Hz, 1H), 7.28(m, 3H), 7.35(d, J=7.8Hz, 1H), 7.54(s, 1H), 7.60(m, 2H), 9.94(s, 1H). | m/z 546 (M)⁺ | Example 376 |

-continued

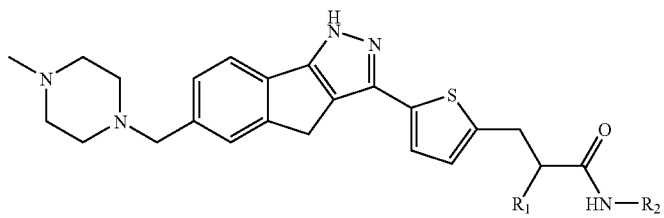

| Example Number | $R_1$ | $R_2$ | $^1H$ NMR(500 MHz, DMSO-$d_6$) | MS (ESI): | Reference Procedure |
|---|---|---|---|---|---|
| 381 | Me | (2,3-dimethylphenyl) | δ1.21(d, J=5.0Hz, 3H), 1.98(s, 3H), 2.21(s, 3H), 2.78(s, 3H), 2.88-2.93(m, 2H), 3.17(m, 1H), 3.00-3.50(m, 8H), 3.72(s, 2H), 3.81(br s, 2H), 6.92(d, J=5.0Hz, 1H), 7.03(m, 3H), 7.28(d, J=5.0Hz, 1H), 7.36(d, J=7.2Hz, 1H), 7.56(s, 1H), 7.62(d, J=7.2Hz, 1H), 9.36(s, 1H). | m/z 540 (M + H)$^+$ | Example 376 |

EXAMPLE 382

(5-{1-[bis(4-methoxyphenyl)methyl]-6-[(4-methyl-1-piperazinyl)methyl]-1,4-dihydroindeno[1,2-c]pyrazol-3-yl}-2-thienyl)methanol To a solution of Example 331 (8.5 g, 14.1 mmol) in methanol (150 mL) and tetrahydrofuran (80 mL) was added sodium borohydride (530 mg, 14.1 mmol) at about 0° C. The mixture was stirred for about 3 hours while being allowed to warm to room temperature and was then concentrated under vacuum. The residue was diluted with water, extracted with ethyl acetate and the combined organic extracts were dried (MgSO$_4$), filtered, and concentrated. The residue was purified by flash chromatography on silica gel using dichloromethane/methanol (10:1) as eluent to provide the desired product. MS (ESI): m/z 607 (M+H)$^+$.

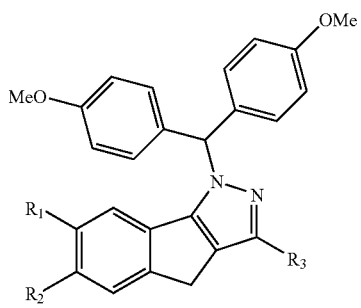

| $R_1$ | $R_2$ | $R_3$ | MS (ESI): | Example Number (Reference Procedure) |
|---|---|---|---|---|
| (4-methylpiperazin-1-yl)methyl | H | 5-(hydroxymethyl)thien-2-yl | m/z 607 (M + H)$^+$ | Example 383 (Example 382) |
| H | (4-methylpiperazin-1-yl)methyl | 5-(hydroxymethyl)thien-3-yl | m/z 607 (M + H)$^+$ | Example 384 (Example 382) |

-continued

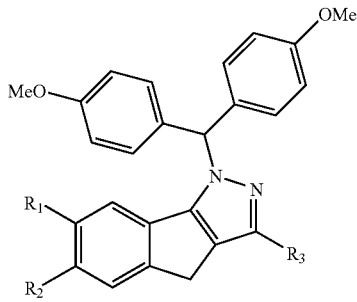

| R₁ | R₂ | R₃ | MS (ESI): | Example Number (Reference Procedure) |
|---|---|---|---|---|
| 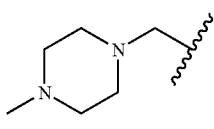 | H | 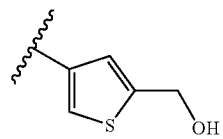 | m/z 607 (M + H)⁺ | Example 385 (Example 382) |

EXAMPLE 386

(5-{7-[(4-methyl-1-piperazinyl)methyl]-1,4-dihydroindeno[1,2-c]pyrazol-3-yl}-2-thienyl)methanol A suspension of Example 382 (61 mg, 0.10 mmol) in a 4M solution of hydrochloric acid in 1,4-dioxane (10 mL, 40.0 mmol) was agitated at room temperature for about 4 hours. The mixture was evaporated to dryness and the residue was purified by preparative HPLC on a Waters Symmetry C8 column (25 mm×100 mm, 7 μm particle size) using a gradient of 10% to 100% acetonitrile:0.1% aqueous TFA over 8 minutes (10 minutes run time) at a flow rate of 40 mL/minute to provide 32 mg (44%) of the desired product as the trifluoroacetate salt. $^1$H NMR (300 MHz, DMSO-d$_6$): δ 2.80 (s, 3H), 3.00-3.50 (m, 8H), 3.76 (s, 2H), 3.96 (br s, 2H), 4.66 (s, 2H), 7.00 (d, J=3.7 Hz, 1H), 7.30 (d, J=3.7 Hz, 1H), 7.32 (s, 1H), 7.58 (s, 1H), 7.69 (s, 1H). MS (ESI): m/z 381 (M+H)⁺.

EXAMPLE 387

(4-{6-[(4-methyl-1-piperazinyl)methyl]-1,4-dihydroindeno[1,2-c]pyrazol-3-yl}-2-thienyl)methanol The procedure for Example 386 was used, substituting Example 384 for Example 382 to provide 14 mg (23%) of the desired product as the trifluoroacetate salt. $^1$H NMR (300 MHz, DMSO-d$_6$) δ 2.15 (s, 3H), 2.15-2.50 (m, 8H), 3.50 (s, 2H), 3.77 (s, 2H), 4.69 (s, 2H), 5.56 (m, 1H), 7.27 (d, J=7.8 Hz, 1H), 7.38 (s, 1H), 7.47 (s, 1H), 7.58 (d, J=7.8 Hz, 1H), 7.69 (s, 1H). MS (ESI): m/z 381 (M+H)⁺.

EXAMPLE 388

(5-{6-[(4-methyl-1-piperazinyl)methyl]-1,4-dihydroindeno[1,2-c]pyrazol-3-yl}-2-thienyl)methyl 2-methylphenylcarbamate To a solution of Example 382 (120 mg, 0.2 mmol) in dichloromethane (0.8 mL) was added o-tolyl isocyanate (30 mg, 0.22 mmol) in dichloromethane (1.0 mL) and the mixture was shaken at room temperature for about 16 hours. The mixture was concentrated under vacuum and the residue was purified by preparative HPLC on a Waters Symmetry C8 column (25 mm×100 mm, 7 μm particle size) using a gradient of 10% to 100% acetonitrile:0.1% aqueous TFA over 8 minutes (10 minutes run time) at a flow rate of 40 mL/minute to provide 11 mg (7%) of the desired product as the trifluoroacetate salt $^1$H NMR (500 MHz, DMSO-d$_6$): δ 2.20 (s, 3H), 2.80 (s, 3H), 3.00-3.50 (m, 8H), 3.76 (s, 2H), 3.90 (br s, 2H), 5.35 (s, 2H,) 7.08 (t, J=7 Hz, 1H), 7.18 (m, 2H), 7.23 (d, J=3 Hz, 1H), 7.35 (m, 2H), 7.39 (d, J=8 Hz, 1H), 7.60 (s, 1H), 7.65 (d, J=7 Hz, 1H), 9.00 (s, 1H). MS (ESI): m/z 514 (M+H)⁺.

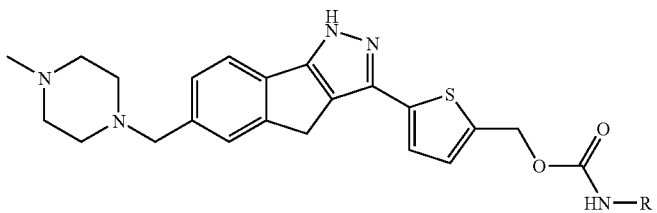

| Example Number | R | ¹H NMR | MS (ESI): | Reference Procedure |
|---|---|---|---|---|
| 389 | *m-tolyl* | (400 MHz, DMSO-d₆) δ 2.26(s, 3H), 2.78(s, 3H), 3.00-3.50(m, 8H), 3.76(s, 2H), 3.84(br s, 2H), 5.34(s, 2H), 6.82(d, J=6Hz, 1H), 7.18(t, J=7Hz, 1H), 7.25-7.38(m, 5H), 7.58(s, 1H), 7.62(d, J=7Hz, 1H), 9.66(s, 1H). | m/z 514 (M + H)⁺ | Example 388 |
| 390 | *p-tolyl* | (500 MHz, DMSO-d₆) δ 2.24(s, 3H), 2.79(s, 3H), 3.00-3.50(m, 8H), 3.76(s, 2H), 3.90(br s, 2H), 5.33(s, 2H), 7.08(m, 2H), 7.20(d, J=5Hz, 1H), 7.25(m, 2H), 7.35(m, 3H), 7.60(s, 1H), 7.62(d, J=5Hz, 1H), 9.65(s, 1H). | m/z 514 (M + H)⁺ | Example 388 |

EXAMPLE 391

3-[5-(azidomethyl)-2-thienyl]-1-[bis(4-methoxyphenyl)methyl]-6-[(4-methyl-1-piperazinyl)methyl]-1,4-dihydroindeno[1,2-c]pyrazole A solution of Example 382 (8.0 g, 13.2 mmol) in tetrahydrofuran (100 mL) was cooled to about 0° C. and diphenylphosphoryl azide (7.1 mL, 33.0 mmol) followed by 1,8-diazabicyclo[5.4.0]undec-7ene (4.9 mL, 33.0 mmol) were added slowly in the dark. After the addition was complete, the mixture was stirred for about 2 hours at ambient temperature in the dark. The mixture was basified by addition of potassium carbonate and concentrated under vacuum. The residue was diluted with water, extracted with ethyl acetate and the combined organic extracts were dried (MgSO₄), filtered, and concentrate. The residue was purified by flash chromatography on silica gel using dichloromethane/methanol (10:1) as eluent to provide the desired product. MS (ESI): m/z 632 (M+H)⁺.

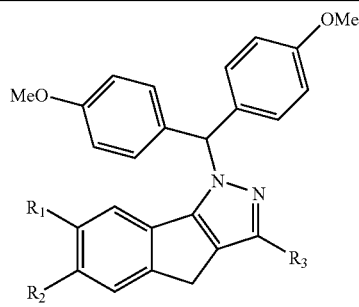

| R₁ | R₂ | R₃ | MS (ESI): | Example Number (Reference Procedure) |
|---|---|---|---|---|
| 4-methyl-piperazinyl-methyl | H | 5-(azidomethyl)-2-thienyl | m/z 632 (M + H)⁺ | Example 392 (Example 391) |
| H | 4-methyl-piperazinyl-methyl | 5-(azidomethyl)-3-thienyl | m/z 632 (M + H)⁺ | Example 393 (Example 391) |

-continued

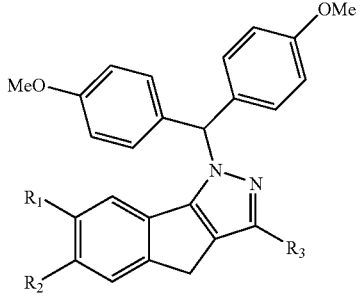

| $R_1$ | $R_2$ | $R_3$ | MS (ESI): | Example Number (Reference Procedure) |
|---|---|---|---|---|
| 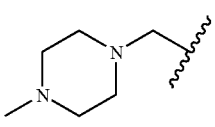 | H | 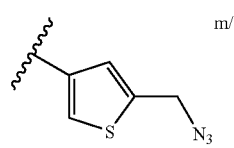 | m/z 632 (M + H)$^+$ | Example 394 (Example 391) |

EXAMPLE 395

(5-{1-[bis(4-methoxyphenyl)methyl]-6-[(4-methyl-1-piperazinyl)methyl]-1,4-dihydroindeno[1,2-c]pyrazol-3-yl}-2-thienyl)methylamine To a solution of Example 391 (7.1 g, 11.2 mmol) in tetrahydrofuran (150 mL) was added triphenylphosine (4.4 g, 16.9 mmol) and the mixture was heated to about 40° C. overnight. Water (15.2 mL) was added and heating to about 40° C. was continued for about 6 hours. The mixture was concentrated under vacuum, diluted with water, basified by addition of potassium carbonate and extracted with ethyl acetate. The combined organic extracts were washed with water and brine, dried (MgSO$_4$), filtered, and concentrated under vacuum. The residue was purified by flash chromatography on silica gel using dichloromethane/methanol (10:1)+ 1% ammonium hydroxide as eluent to provide the desired product. MS (ESI): m/z 606 (M+H)$^+$.

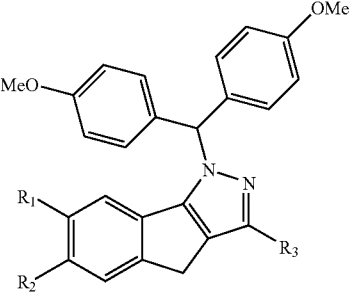

| $R_1$ | $R_2$ | $R_3$ | MS (ESI): | Example Number (Reference Procedure) |
|---|---|---|---|---|
| 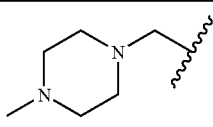 | H | 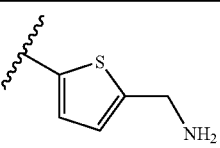 | m/z 606 (M + H)$^+$ | Example 396 (Example 395) |
| H | 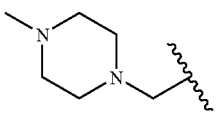 | 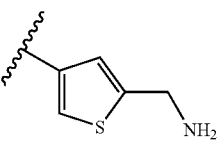 | m/z 606 (M + H)$^+$ | Example 397 (Example 395) |

-continued

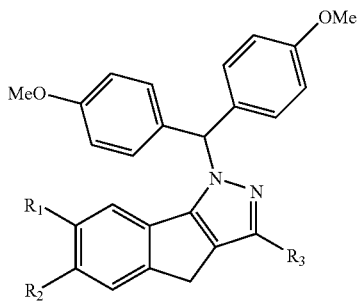

| $R_1$ | $R_2$ | $R_3$ | MS (ESI): | Example Number (Reference Procedure) |
|---|---|---|---|---|
| ![piperazinyl] | H | ![thienyl] | m/z 606 (M + H)⁺ | Example 398 (Example 395) |

EXAMPLE 399

(4-{6-[(4-methyl-1-piperazinyl)methyl]-1,4-dihydroindeno[1,2-c]pyrazol-3-yl}-2-thienyl)methylamine The procedure for Example 386 was used, substituting Example 397 for Example 382 to provide 27 mg (3%) of the desired product as the trifluoroacetate salt. $^1$H NMR (500 MHz, DMSO-$d_6$) δ 2.81 (s, 3H), 3.00-3.50 (m, 8H), 3.79 (s, 2H), 4.00 (br s, 2H), 4.32 (d, J=5.3 Hz, 2H), 7.41 (d, J=7.8 Hz, 1H), 7.60 (s, 1H), 7.67 (m, 2H), 7.87 (d, J=1.5 Hz, 1H), 8.38 (br s, 2H). MS (ESI): m/z 380 (M+H)⁺.

EXAMPLE 400

N-(2-methylphenyl)-N'-[(5-{6-[(4-methyl-1-piperazinyl)methyl]-1,4-dihydroindeno[1,2-c]pyrazol-3-yl}-2-thienyl)methyl]urea To o-tolyl isocyanate (20 mg, 0.11 mmol) was added a solution of Example 395 (60.5 mg, 0.10 mmol) in dichloromethane (1 mL) and the mixture was agitated at room temperature for about 5 hours. The mixture was concentrated under vacuum, the residue was dissolved in ethyl acetate (0.6 mL) and 37% hydrochloric acid in ethanol (0.7 mL) and the mixture was agitated at room temperature overnight. The mixture was concentrated under vacuum and the residue was purified by preparative HPLC on a Waters Symmetry C8 column (25 mm×100 mm, 7 μm particle size) using a gradient of 10% to 100% acetonitrile:0.1% aqueous TFA over 8 minutes (10 minutes run time) at a flow rate of 40 mL/minute to provide 17 mg (20%) of the desired product as the trifluoroacetate salt. $^1$H NMR (500 MHz, DMSO-$d_6$) δ 2.19 (s, 3H), 2.79 (s, 3H), 3.00-3.50 (m, 8H), 3.76 (s, 2H), 3.85 (br s, 2H), 4.50 (d, J=5 Hz, 2H), 6.92 (t, J=5 Hz, 1H), 7.03 (d, J=5 Hz, 1H), 7.11 (m, 3H), 7.32 (d, J=5 Hz, 1H), 7.38 (d, J=8 Hz, 1H), 7.58 (s, 1H), 7.62 (d, J=8 Hz, 1H), 7.79 (s, 1H), 7.82 (d, J=8 Hz, 1H). MS (ESI): m/z 513 (M+H)⁺.

EXAMPLE 401

N-methoxy-N'-(2-methylphenyl)-N-[(5-{6-[(4-methyl-1-piperazinyl)methyl]-1,4-dihydroindeno[1,2-c]pyrazol-3-yl}-2-thienyl)methyl]urea To o-tolyl isocyanate (20 mg, 0.1 mmol) was added a solution of Example 346 (41 mg, 0.1 mmol) in dichloromethane (1 mL) and the mixture was shaken at room temperature for about 4 hours. The mixture was concentrated under vacuum and the residue was purified by preparative HPLC on a Waters Symmetry C8 column (25 mm×100 mm, 7 μm particle size) using a gradient of 10% to 100% acetonitrile:0.1% aqueous TFA over 8 minutes (10 minutes run time) at a flow rate of 40 mL/minute to provide 6 mg (8%) of the desired product as the trifluoroacetate salt. $^1$H NMR (500 MHz, DMSO-$d_6$) δ 2.18 (s, 3H), 2.77 (s, 3H), 3.00-3.50 (m, 8H), 3.73 (s, 2H), 3.76 (s, 3H), 3.79 (br s, 2H), 4.85 (s, 2H), 7.10 (m, 2H), 7.20 (m, 2H), 7.33 (m, 3H), 7.58 (s, 1H), 7.62 (d, J=8 Hz, 1H), 8.68 (s, 1H). MS (ESI): m/z 543 (M+H)⁺.

EXAMPLE 402

N-[(5-{7-[(4-methyl-1-piperazinyl methyl]-1,4-dihydroindeno[1,2-c]pyrazol-3-yl}-2-thienyl)methyl]-N'-phenylurea To phenyl isocyanate (13.1 mg, 0.11 mmol) was added a solution of Example 396 (60.5 mg, 0.10 mmol) in tetrahydrofuran (1 mL) and the mixture was agitated at room temperature overnight. The mixture was concentrated under vacuum, the residue was suspended in 4M hydrochloric acid in 1,4-dioxane (2 mL) and the mixture was agitated at room temperature overnight. The mixture was concentrated under vacuum and the residue was purified by preparative HPLC on a Waters Symmetry C8 column (25 mm×100 mm, 7 μm particle size) using a gradient of 10% to 100% acetonitrile:0.1% aqueous TFA over 8 minutes (10 minutes run time) at a flow rate of 40 mL/minute to provide 30 mg (36%) of the desired product as the trifluoroacetate salt. $^1$H NMR (300 MHz, DMSO-$d_6$) δ 2.79 (s, 3H), 3.00-3.50 (m, 8H), 3.74 (s, 2H), 3.96 (s, 2H), 4.49 (d, J=5.8 Hz, 2H), 6.79 (m, 1H), 6.91

(m, 1H), 7.03 (d, J=3.7 Hz, 1H), 7.24 (m, 2H), 7.30 (m, 2H), 7.43 (m, 2H), 7.59 (d, J=7.8 Hz, 1H), 7.67 (s, 1H), 8.64 (s, 1H). MS (ESI): m/z 499 (M+H)⁺.

EXAMPLE 403

N-methyl-N-(3-methylphenyl)-N'-[(5-{6-[(4-methyl-1-piperazinyl)methyl]-1,4-dihydroindeno[1,2-c]pyrazol-3-yl}-2-thienyl)methyl]urea To a solution of N-methyl-m-toluidine (15 mg, 0.12 mmol) and pyridine (9.5 mg, 0.12 mmol) in dichloromethane (1.5 mL) was added triphosgene (12 mg, 0.04 mmol) in dichloromethane (0.5 mL) at about −30° C. The mixture was stirred at about −30° C. to about −10° C. for about 50 minutes before pyridine (12 mg, 0.15 mmol) was added, followed by a solution of Example 395 (61 mg, 0.1 mmol) in dichloromethane (0.5 mL). The mixture was stirred at room temperature overnight and was then concentrated under vacuum. The residue was dissolved in ethyl acetate (0.6 mL) and hydrochloric acid (0.7 mL, 37% in ethanol) and the mixture was shaken at room temperature overnight. The mixture was concentrated under vacuum and the residue was purified by preparative HPLC on a Waters Symmetry C8 column (25 mm×100 mm, 7 μm particle size) using a gradient of 10% to 100% acetonitrile: 0.1% aqueous TFA over 8 minutes (10 minutes run time) at a flow rate of 40 mL/minute to provide 29 mg (40%) of the desired product as the trifluoroacetate salt. ¹H NMR (500 MHz, DMSO-d₆) δ 2.31 (s, 3H), 2.80 (s, 3H), 3.05-3.45 (m, 8H), 3.15 (s, 3H), 3.77 (s, 2H), 3.95 (br s, 2H), 4.42 (d, J=5 Hz, 2H), 6.62 (t, J=5 Hz, 1H), 6.94 (d, J=5 Hz, 1H), 7.06 (m, 2H), 7.10 (s, 1H), 7.28 (m, 2H), 7.40 (d, J=8 Hz, 1H), 7.58 (s, 1H), 7.62 (d, J=5 Hz, 1H). MS (ESI): m/z 527 (M+H)⁺.

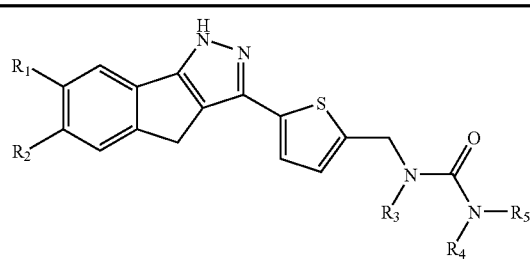

| R₁ | R₂ | R₃ | R₄ | R₅ | MS (ESI): | Example Number (Reference Procedure) |
|---|---|---|---|---|---|---|
| H | 4-methylpiperazinylmethyl | H | H | 2-fluorophenyl | m/z 517 (M + H)⁺ | Example 404 (Example 400) |
| H | 4-methylpiperazinylmethyl | H | H | 2-chlorophenyl | m/z 533 (M)⁺ | Example 405 (Example 400) |
| H | 4-methylpiperazinylmethyl | H | H | 2-bromophenyl | m/z 577, 579 (M + H)⁺ | Example 406 (Example 400) |
| H | 4-methylpiperazinylmethyl | H | H | 2-(trifluoromethyl)phenyl | m/z 567 (M + H)⁺ | Example 407 (Example 400) |
| H | 4-methylpiperazinylmethyl | H | H | 2-biphenyl | m/z 575 (M + H)⁺ | Example 408 (Example 400) |

-continued

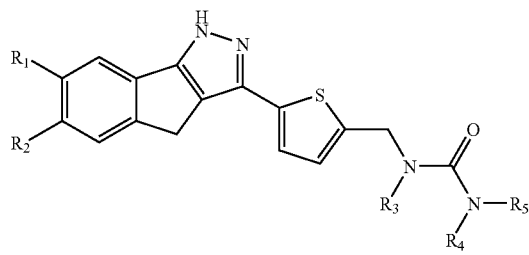

| R₁ | R₂ | R₃ | R₄ | R₅ | MS (ESI): | Example Number (Reference Procedure) |
|---|---|---|---|---|---|---|
| H | N-methylpiperazinyl-CH₂- | H | H | 3-fluorophenyl | m/z 517 (M + H)⁺ | Example 409 (Example 400) |
| H | N-methylpiperazinyl-CH₂- | H | H | 3-chlorophenyl | m/z 533 (M)⁺ | Example 410 (Example 400) |
| H | N-methylpiperazinyl-CH₂- | H | H | 3-bromophenyl | m/z 577, 579 (M + H)⁺ | Example 411 (Example 400) |
| H | N-methylpiperazinyl-CH₂- | H | H | 3-(trifluoromethyl)phenyl | m/z 567 (M + H)⁺ | Example 412 (Example 400) |
| H | N-methylpiperazinyl-CH₂- | H | H | 3-acetylphenyl | m/z 541 (M + H)⁺ | Example 413 (Example 400) |
| H | N-methylpiperazinyl-CH₂- | H | H | 3-ethylphenyl | m/z 527 (M + H)⁺ | Example 414 (Example 400) |
| H | N-methylpiperazinyl-CH₂- | H | H | 3-phenoxyphenyl | m/z 591 (M + H)⁺ | Example 415 (Example 400) |
| H | N-methylpiperazinyl-CH₂- | H | H | 3-(trifluoromethoxy)phenyl | m/z 583 (M + H)⁺ | Example 416 (Example 403) |

-continued

| R₁ | R₂ | R₃ | R₄ | R₅ | MS (ESI): | Example Number (Reference Procedure) |
|---|---|---|---|---|---|---|
| H | 4-methylpiperazin-1-ylmethyl | H | H | 3-(SCF₃)phenyl | m/z 599 (M + H)⁺ | Example 417 (Example 400) |
| H | 4-methylpiperazin-1-ylmethyl | H | H | 4-methylphenyl | m/z 513 (M + H)⁺ | Example 418 (Example 400) |
| H | 4-methylpiperazin-1-ylmethyl | H | H | 4-fluorophenyl | m/z 517 (M + H)⁺ | Example 419 (Example 400) |
| H | 4-methylpiperazin-1-ylmethyl | H | H | 4-(CF₃)phenyl | m/z 567 (M + H)⁺ | Example 420 (Example 400) |
| H | 4-methylpiperazin-1-ylmethyl | H | H | 4-biphenyl | m/z 575 (M + H)⁺ | Example 421 (Example 400) |
| H | 4-methylpiperazin-1-ylmethyl | H | H | 2,3-dimethylphenyl | m/z 527 (M + H)⁺ | Example 422 (Example 400) |
| H | 4-methylpiperazin-1-ylmethyl | H | H | 2,4-dimethylphenyl | m/z 527 (M + H)⁺ | Example 423 (Example 400) |
| H | 4-methylpiperazin-1-ylmethyl | H | H | 3,5-dimethylphenyl | m/z 527 (M + H)⁺ | Example 424 (Example 400) |

-continued

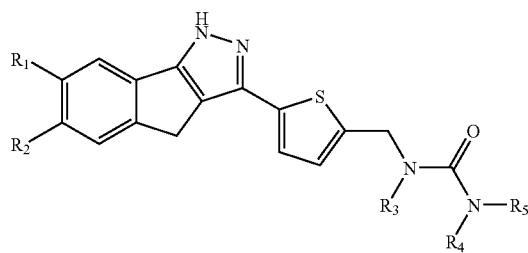

| R₁ | R₂ | R₃ | R₄ | R₅ | MS (ESI): | Example Number (Reference Procedure) |
|---|---|---|---|---|---|---|
| H | 4-methylpiperazin-1-ylmethyl | H | H | 3,5-dichlorophenyl | m/z 567 (M)⁺ | Example 425 (Example 400) |
| H | 4-methylpiperazin-1-ylmethyl | H | H | naphthalen-1-yl | m/z 549 (M + H)⁺ | Example 426 (Example 400) |
| H | 4-methylpiperazin-1-ylmethyl | H | H | 4-fluoro-3-(trifluoromethyl)phenyl | m/z 585 (M + H)⁺ | Example 427 (Example 400) |
| H | 4-methylpiperazin-1-ylmethyl | H | H | 2-fluoro-5-(trifluoromethyl)phenyl | m/z 585 (M + H)⁺ | Example 428 (Example 400) |
| H | 4-methylpiperazin-1-ylmethyl | H | H | 2-chloro-5-(trifluoromethyl)phenyl | m/z 601 (M)⁺ | Example 429 (Example 403) |
| H | 4-methylpiperazin-1-ylmethyl | H | H | 5,6,7,8-tetrahydronaphthalen-1-yl | m/z 553 (M + H)⁺ | Example 430 (Example 403) |

-continued

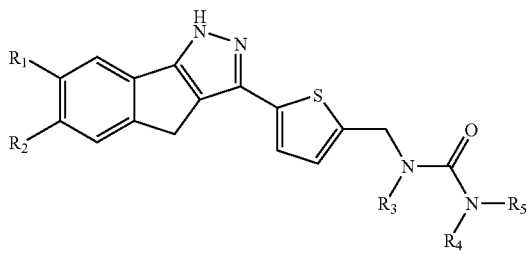

| R₁ | R₂ | R₃ | R₄ | R₅ | MS (ESI): | Example Number (Reference Procedure) |
|---|---|---|---|---|---|---|
| H | N-methylpiperazinylmethyl | H | H | 2,2-difluoro-1,3-benzodioxol-4-yl | m/z 579 (M + H)⁺ | Example 431 (Example 403) |
| H | N-methylpiperazinylmethyl | H | H | 3-(methoxycarbonyl)thiophen-2-yl | m/z 563 (M + H)⁺ | Example 432 (Example 403) |
| H | N-methylpiperazinylmethyl | Me | H | 2-methylphenyl | m/z 527 (M + H)⁺ | Example 433 (Example 400) |
| H | N-methylpiperazinylmethyl | Me | H | 2-isopropylphenyl | m/z 555 (M + H)⁺ | Example 434 (Example 400) |
| H | N-methylpiperazinylmethyl | Me | H | 2-methoxyphenyl | m/z 543 (M + H)⁺ | Example 435 (Example 400) |
| H | N-methylpiperazinylmethyl | Me | H | 2-chlorophenyl | m/z 547 (M)⁺ | Example 436 (Example 403) |
| H | N-methylpiperazinylmethyl | Me | H | 2-cyanophenyl | m/z 538 (M + H)⁺ | Example 437 (Example 400) |

-continued

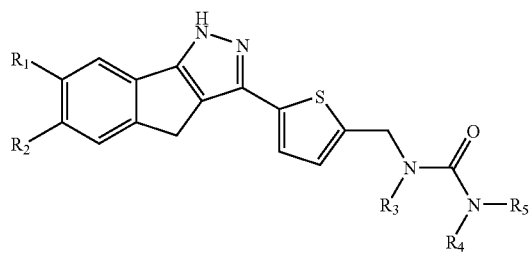

| R₁ | R₂ | R₃ | R₄ | R₅ | MS (ESI): | Example Number (Reference Procedure) |
|---|---|---|---|---|---|---|
| H | 4-methylpiperazin-1-ylmethyl | Me | H | 3-methylphenyl | m/z 527 (M + H)⁺ | Example 438 (Example 400) |
| H | 4-methylpiperazin-1-ylmethyl | Me | H | 3-methoxyphenyl | m/z 543 (M + H)⁺ | Example 439 (Example 400) |
| H | 4-methylpiperazin-1-ylmethyl | Me | H | 3-bromophenyl | m/z 591, 593 (M + H)⁺ | Example 440 (Example 400) |
| H | 4-methylpiperazin-1-ylmethyl | Me | H | 3-CF₃-phenyl | m/z 581 (M + H)⁺ | Example 441 (Example 400) |
| H | 4-methylpiperazin-1-ylmethyl | Me | H | 3-OCF₃-phenyl | m/z 597 (M + H)⁺ | Example 442 (Example 403) |
| H | 4-methylpiperazin-1-ylmethyl | Me | H | 3-SCF₃-phenyl | m/z 613 (M + H)⁺ | Example 443 (Example 400) |
| H | 4-methylpiperazin-1-ylmethyl | Me | H | 4-methylphenyl | m/z 527 (M + H)⁺ | Example 444 (Example 400) |
| H | 4-methylpiperazin-1-ylmethyl | Me | H | 2,4-dimethylphenyl | m/z 541 (M + H)⁺ | Example 445 (Example 400) |

-continued

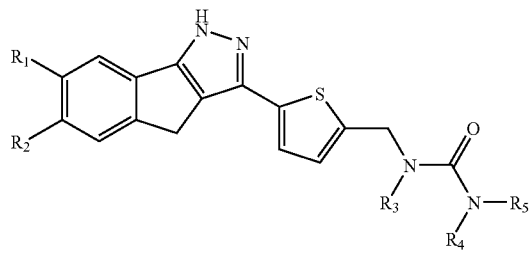

| R₁ | R₂ | R₃ | R₄ | R₅ | MS (ESI): | Example Number (Reference Procedure) |
|---|---|---|---|---|---|---|
| H | 4-methylpiperazin-1-ylmethyl | Me | H | 2,5-difluorophenyl | m/z 549 (M + H)⁺ | Example 446 (Example 400) |
| H | 4-methylpiperazin-1-ylmethyl | Me | H | 2,6-difluorophenyl | m/z 549 (M + H)⁺ | Example 447 (Example 400) |
| H | 4-methylpiperazin-1-ylmethyl | Me | H | 2-chloro-5-(trifluoromethyl)phenyl | m/z 615 (M)⁺ | Example 448 (Example 400) |
| H | 4-methylpiperazin-1-ylmethyl | Me | H | 2-methyl-5-chlorophenyl | m/z 561 (M + H)⁺ | Example 449 (Example 400) |
| H | 4-methylpiperazin-1-ylmethyl | Me | H | 2-fluoro-5-(trifluoromethyl)phenyl | m/z 599 (M + H)⁺ | Example 450 (Example 400) |
| H | 4-methylpiperazin-1-ylmethyl | Me | H | 2-methyl-5-fluorophenyl | m/z 545 (M + H)⁺ | Example 451 (Example 400) |

-continued

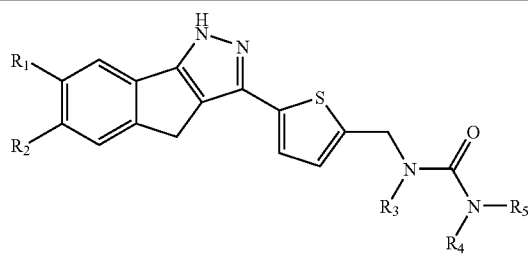

| R₁ | R₂ | R₃ | R₄ | R₅ | MS (ESI): | Example Number (Reference Procedure) |
|---|---|---|---|---|---|---|
| H | 4-methylpiperazin-1-ylmethyl | Me | H | 2-chloro-5-methylphenyl | m/z 562 (M + H)⁺ | Example 452 (Example 400) |
| H | 4-methylpiperazin-1-ylmethyl | Me | H | 2-fluoro-5-methylphenyl | m/z 545 (M + H)⁺ | Example 453 (Example 400) |
| H | 4-methylpiperazin-1-ylmethyl | Me | H | 2-methyl-6-chlorophenyl | m/z 562 (M + H)⁺ | Example 454 (Example 400) |
| H | 4-methylpiperazin-1-ylmethyl | Me | H | 3-fluoro-5-trifluoromethylphenyl | m/z 599 (M + H)⁺ | Example 455 (Example 400) |
| H | 4-methylpiperazin-1-ylmethyl | Me | H | 2,2-difluorobenzo[1,3]dioxol-4-yl | m/z 593 (M + H)⁺ | Example 456 (Example 400) |
| H | 4-methylpiperazin-1-ylmethyl | Et | H | 2,3-dimethylphenyl | m/z 541 (M + H)⁺ | Example 457 (Example 400) |
| H | 4-methylpiperazin-1-ylmethyl | Et | H | 2-methoxyphenyl | m/z 557 (M + H)⁺ | Example 458 (Example 400) |

-continued

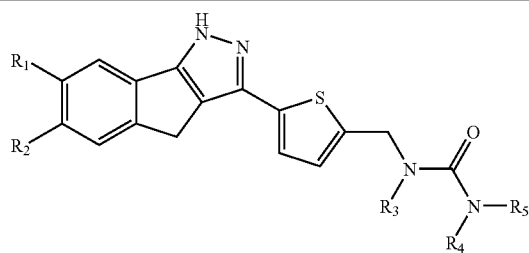

| R₁ | R₂ | R₃ | R₄ | R₅ | MS (ESI): | Example Number (Reference Procedure) |
|---|---|---|---|---|---|---|
| H | N-methylpiperazinyl-CH₂- | Et | H | 2-chlorophenyl | m/z 562 (M + H)⁺ | Example 459 (Example 400) |
| H | N-methylpiperazinyl-CH₂- | Et | H | 3-methylphenyl | m/z 541 (M + H)⁺ | Example 460 (Example 400) |
| H | N-methylpiperazinyl-CH₂- | Et | H | 3-methoxyphenyl | m/z 557 (M + H)⁺ | Example 461 (Example 400) |
| H | N-methylpiperazinyl-CH₂- | Et | H | 3-chlorophenyl | m/z 562 (M + H)⁺ | Example 462 (Example 400) |
| H | N-methylpiperazinyl-CH₂- | Et | H | 3-bromophenyl | m/z 605, 607 (M + H)⁺ | Example 463 (Example 400) |
| H | N-methylpiperazinyl-CH₂- | Et | H | 3-ethylphenyl | m/z 555 (M + H)⁺ | Example 464 (Example 400) |
| H | N-methylpiperazinyl-CH₂- | Et | H | 3-(trifluoromethyl)phenyl | m/z 595 (M + H)⁺ | Example 465 (Example 400) |
| H | N-methylpiperazinyl-CH₂- | Et | H | 2-fluoro-4-methylphenyl | m/z 559 (M + H)⁺ | Example 466 (Example 400) |

-continued

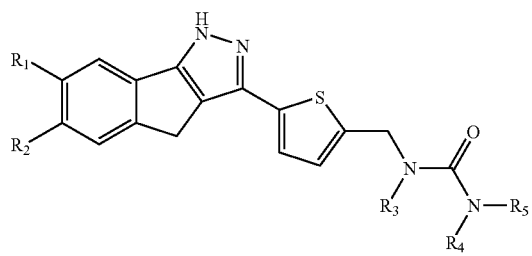

| R₁ | R₂ | R₃ | R₄ | R₅ | MS (ESI): | Example Number (Reference Procedure) |
|---|---|---|---|---|---|---|
| H | N-methylpiperazinyl-CH₂- | Et | H | 3-F, 5-CF₃-phenyl | m/z 613 (M + H)⁺ | Example 467 (Example 400) |
| H | N-methylpiperazinyl-CH₂- | n-Bu | H | 2-methylphenyl | m/z 555 (M + H)⁺ | Example 468 (Example 400) |
| H | N-methylpiperazinyl-CH₂- | n-Bu | H | 2-MeO-phenyl | m/z 571 (M + H)⁺ | Example 469 (Example 400) |
| H | N-methylpiperazinyl-CH₂- | n-Bu | H | 2-F-phenyl | m/z 559 (M + H)⁺ | Example 470 (Example 400) |
| H | N-methylpiperazinyl-CH₂- | n-Bu | H | 3-methylphenyl | m/z 555 (M + H)⁺ | Example 471 (Example 400) |
| H | N-methylpiperazinyl-CH₂- | n-Bu | H | 3-OMe-phenyl | m/z 571 (M + H)⁺ | Example 472 (Example 400) |
| H | N-methylpiperazinyl-CH₂- | i-Pr | H | 2-methylphenyl | m/z 555 (M + H)⁺ | Example 473 (Example 400) |

-continued

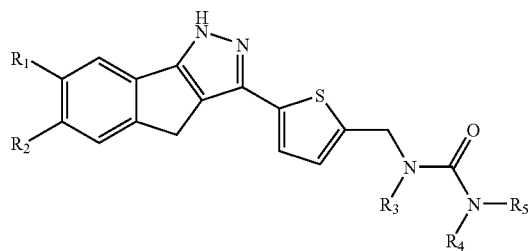

| R₁ | R₂ | R₃ | R₄ | R₅ | MS (ESI): | Example Number (Reference Procedure) |
|---|---|---|---|---|---|---|
| H | 4-methylpiperazin-1-yl-methyl | isopropyl | H | 2-methoxyphenyl | m/z 571 (M + H)⁺ | Example 474 (Example 400) |
| H | 4-methylpiperazin-1-yl-methyl | isopropyl | H | 3-methylphenyl | m/z 555 (M + H)⁺ | Example 475 (Example 400) |
| H | 4-methylpiperazin-1-yl-methyl | cyclopropyl | H | 2-methylphenyl | m/z 553 (M + H)⁺ | Example 476 (Example 400) |
| H | 4-methylpiperazin-1-yl-methyl | cyclopropyl | H | 2-methoxyphenyl | m/z 569 (M + H)⁺ | Example 477 (Example 400) |
| H | 4-methylpiperazin-1-yl-methyl | cyclopropyl | H | 2-fluorophenyl | m/z 557 (M + H)⁺ | Example 478 (Example 400) |
| H | 4-methylpiperazin-1-yl-methyl | cyclopropyl | H | 3-methylphenyl | m/z 553 (M + H)⁺ | Example 479 (Example 400) |
| H | 4-methylpiperazin-1-yl-methyl | isopropyl | H | 3-methylphenyl | m/z 569 (M + H)⁺ | Example 480 (Example 400) |
| H | 4-methylpiperazin-1-yl-methyl | isopentyl | H | 3-methylphenyl | m/z 583 (M + H)⁺ | Example 481 (Example 400) |

-continued

| R₁ | R₂ | R₃ | R₄ | R₅ | MS (ESI): | Example Number (Reference Procedure) |
|---|---|---|---|---|---|---|
| H | 4-methylpiperazin-1-ylmethyl | MeO-CH₂- | H | 2-chlorophenyl | m/z 563 (M)⁺ | Example 482 (Example 401) |
| H | 4-methylpiperazin-1-ylmethyl | MeO-CH₂- | H | 3-methylphenyl | m/z 543 (M + H)⁺ | Example 483 (Example 401) |
| H | 4-methylpiperazin-1-ylmethyl | 3-methoxypropyl | H | 3-methylphenyl | m/z 571 (M + H)⁺ | Example 484 (Example 400) |
| H | 4-methylpiperazin-1-ylmethyl | Me | Me | 3-methylphenyl | m/z 541 (M + H)⁺ | Example 485 (Example 403) |
| H | imidazol-1-ylmethyl | Me | H | 3-methylphenyl | m/z 495 (M + H)⁺ | Example 486 (Example 400) |
| H | imidazol-1-ylmethyl | Me | H | 3-bromophenyl | m/z 559, 561 (M + H)⁺ | Example 487 (Example 400) |
| 4-methylpiperazin-1-ylmethyl | H | H | H | 2-methylphenyl | m/z 513 (M + H)⁺ | Example 488 (Example 402) |
| 4-methylpiperazin-1-ylmethyl | H | H | H | 3-methylphenyl | m/z 513 (M + H)⁺ | Example 489 (Example 402) |

-continued

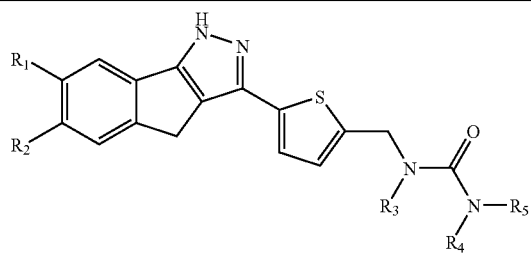

| $R_1$ | $R_2$ | $R_3$ | $R_4$ | $R_5$ | MS (ESI): | Example Number (Reference Procedure) |
|---|---|---|---|---|---|---|
| 4-methylpiperazinylmethyl | H | H | H | 4-methylphenyl | m/z 513 (M + H)$^+$ | Example 490 (Example 402) |
| 4-methylpiperazinylmethyl | H | Me | H | phenyl | m/z 513 (M + H)$^+$ | Example 491 (Example 402) |
| 4-methylpiperazinylmethyl | H | Me | H | 2-methylphenyl | m/z 527 (M + H)$^+$ | Example 492 (Example 402) |
| 4-methylpiperazinylmethyl | H | Me | H | 2-methoxyphenyl | m/z 543 (M + H)$^+$ | Example 493 (Example 402) |
| 4-methylpiperazinylmethyl | H | Me | H | 2-fluorophenyl | m/z 531 (M + H)$^+$ | Example 494 (Example 402) |
| 4-methylpiperazinylmethyl | H | Me | H | 2-chlorophenyl | m/z 547 (M)$^+$ | Example 495 (Example 402) |
| 4-methylpiperazinylmethyl | H | Me | H | 2-bromophenyl | m/z 591, 593 (M + H)$^+$ | Example 496 (Example 402) |
| 4-methylpiperazinylmethyl | H | Me | H | 3-methylphenyl | m/z 527 (M + H)$^+$ | Example 497 (Example 402) |
| 4-methylpiperazinylmethyl | H | Me | H | 3-methoxyphenyl | m/z 543 (M + H)$^+$ | Example 498 (Example 402) |

-continued

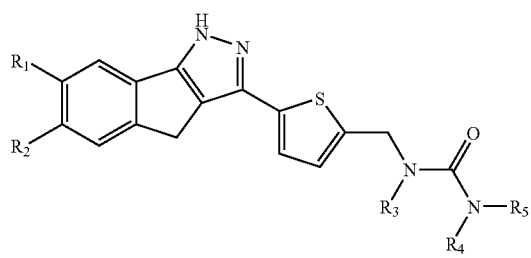

| R₁ | R₂ | R₃ | R₄ | R₅ | MS (ESI): | Example Number (Reference Procedure) |
|---|---|---|---|---|---|---|
| 4-methylpiperazin-1-ylmethyl | H | Me | H | 3-fluorophenyl | m/z 531 (M + H)⁺ | Example 499 (Example 402) |
| 4-methylpiperazin-1-ylmethyl | H | Me | H | 3-chlorophenyl | m/z 547 (M)⁺ | Example 500 (Example 402) |
| 4-methylpiperazin-1-ylmethyl | H | Me | H | 3-bromophenyl | m/z 591, 593 (M + H)⁺ | Example 501 (Example 402) |
| 4-methylpiperazin-1-ylmethyl | H | Me | H | 3-(trifluoromethyl)phenyl | m/z 581 (M + H)⁺ | Example 502 (Example 402) |
| 4-methylpiperazin-1-ylmethyl | H | Me | H | 3-cyanophenyl | m/z 538 (M + H)⁺ | Example 503 (Example 402) |
| 4-methylpiperazin-1-ylmethyl | H | Me | H | 3-(trifluoromethylthio)phenyl | m/z 613 (M + H)⁺ | Example 504 (Example 402) |
| 4-methylpiperazin-1-ylmethyl | H | Me | H | 4-methylphenyl | m/z 527 (M + H)⁺ | Example 505 (Example 402) |
| 4-methylpiperazin-1-ylmethyl | H | Me | H | 4-methoxyphenyl | m/z 543 (M + H)⁺ | Example 506 (Example 402) |

-continued

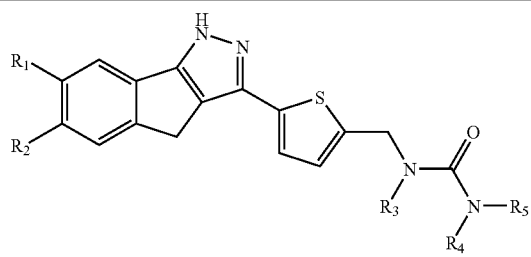

| R₁ | R₂ | R₃ | R₄ | R₅ | MS (ESI): | Example Number (Reference Procedure) |
|---|---|---|---|---|---|---|
| 4-methylpiperazin-1-yl-methyl | H | Me | H | 4-F-phenyl | m/z 531 (M + H)⁺ | Example 507 (Example 402) |
| 4-methylpiperazin-1-yl-methyl | H | Me | H | 4-Cl-phenyl | m/z 547 (M)⁺ | Example 508 (Example 402) |
| 4-methylpiperazin-1-yl-methyl | H | Me | H | 4-Br-phenyl | m/z 591, 593 (M + H)⁺ | Example 509 (Example 402) |
| 4-methylpiperazin-1-yl-methyl | H | Me | H | 4-CF₃-phenyl | m/z 581 (M + H)⁺ | Example 510 (Example 402) |
| 4-methylpiperazin-1-yl-methyl | H | Me | H | 4-OCF₃-phenyl | m/z 597 (M + H)⁺ | Example 511 (Example 402) |
| 4-methylpiperazin-1-yl-methyl | H | Me | H | 4-CN-phenyl | m/z 538 (M + H)⁺ | Example 512 (Example 402) |
| 4-methylpiperazin-1-yl-methyl | H | Me | H | 4-phenyl-phenyl | m/z 589 (M + H)⁺ | Example 513 (Example 402) |
| 4-methylpiperazin-1-yl-methyl | H | Me | H | 4-phenoxy-phenyl | m/z 605 (M + H)⁺ | Example 514 (Example 402) |
| 4-methylpiperazin-1-yl-methyl | H | Me | H | 2,3-dimethyl-phenyl | m/z 541 (M + H)⁺ | Example 515 (Example 402) |

-continued
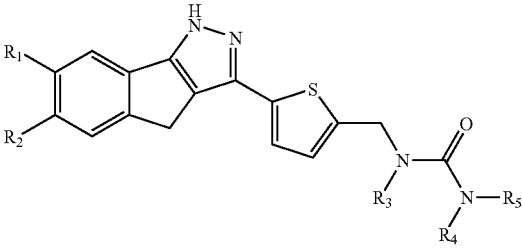
| R₁ | R₂ | R₃ | R₄ | R₅ | MS (ESI): | Example Number (Reference Procedure) |
|---|---|---|---|---|---|---|
| 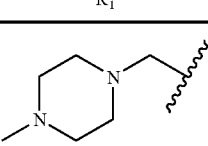 | H | Me | H | 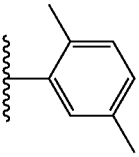 | m/z 541 (M + H)⁺ | Example 516 (Example 402) |
| 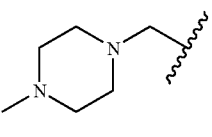 | H | Me | H | 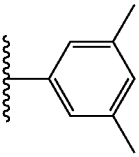 | m/z 541 (M + H)⁺ | Example 517 (Example 402) |
| 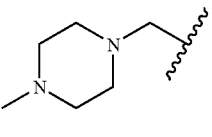 | H | Me | H | 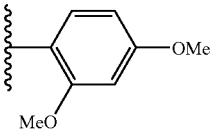 | m/z 573 (M + H)⁺ | Example 518 (Example 402) |
| 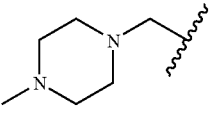 | H | Me | H | 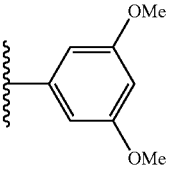 | m/z 573 (M + H)⁺ | Example 519 (Example 402) |
| 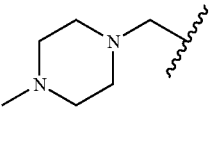 | H | Me | H | 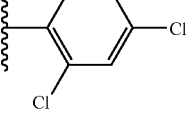 | m/z 581 (M)⁺ | Example 520 (Example 402) |
| 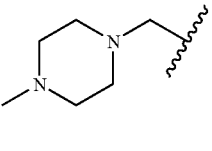 | H | Me | H | 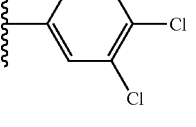 | m/z 581 (M)⁺ | Example 521 (Example 402) |
| 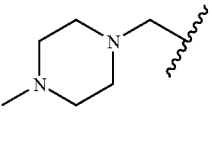 | H | Me | H | 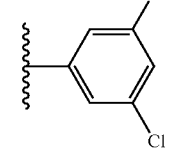 | m/z 581 (M)⁺ | Example 522 (Example 402) |

-continued

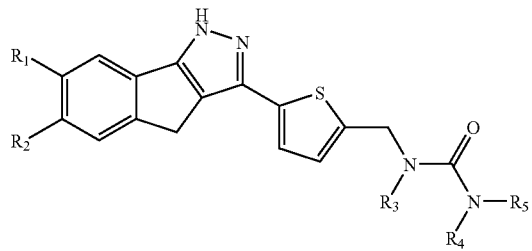

| R₁ | R₂ | R₃ | R₄ | R₅ | MS (ESI): | Example Number (Reference Procedure) |
|---|---|---|---|---|---|---|
| 4-methylpiperazin-1-yl-methyl | H | Me | H | benzo[1,3]dioxol-5-yl | m/z 557 (M + H)⁺ | Example 523 (Example 402) |

-continued

| Example Number | ¹H NMR |
|---|---|
| Example 404 | (500 MHz, DMSO-d₆)δ 2.79(s, 3H), 3.00-3.50(m, 8H), 3.76(s, 2H), 3.84(br s, 2H), 4.51(d, J=5Hz, 2H), 6.94(m, 1H), 7.03(d, J=5Hz, 1H), 7.08(t, J=8Hz, 1H), 7.18(m, 2H), 7.30(d, J=5Hz, 1H), 7.38(d, J=8Hz, 1H), 7.58(s, 1H), 7.62(d, J=8Hz, 1H), 8.13(t, J=8Hz, 1H), 8.42(s, 1H). |
| Example 405 | (500 MHz, DMSO-d₆)δ 2.78(s, 3H), 3.00-3.50(m, 2H), 3.75(s, 2H), 3.84(br s, 2H), 4.52(d, J=5Hz, 2H), 6.96(t, J=5Hz, 1H), 7.03(d, J=5Hz, 1H), 7.26(d, J=5Hz, 1H), 7.32(d, J=5Hz, 1H), 7.38(d, J=8Hz, 1H), 7.42(d, J=8Hz, 1H), 7.59(s, 1H), 7.62(m, 2H), 8.16(s, 1H), 8.19(d, J=8Hz, 1H). |
| Example 406 | (500 MHz, DMSO-d₆)δ 2.79(s, 3H), 3.00-3.50(m, 8H), 3.75(s, 2H), 3.82(br s, 2H), 4.52(d, J=5Hz, 2H), 6.94(t, J=8Hz, 1H), 7.03(d, J=5Hz, 1H), 7.32(m, 2H), 7.38(d, J=8Hz, 1H), 7.60(m, 4H), 7.97(s, 1H), 8.09(d, J=8Hz, 1H). |
| Example 407 | (500 MHz, DMSO-d₆)δ 2.79(s, 3H), 3.00-3.50(m, 8H), 3.76(s, 2H), 3.87(br s, 2H), 4.52(d, J=5Hz, 2H), 7.03(d, J=5Hz, 1H), 7.22(t, J=8Hz, 1H), 7.30(d, J=5Hz, 1H), 7.38(d, J=8Hz, 1H), 7.60(m, 5H), 7.92(s, 1H), 7.99(d, J=8Hz, 1H). |
| Example 408 | (500 MHz, DMSO-d₆)δ 2.79(s, 3H), 3.00-3.50(m, 8H), 3.76(s, 2H), 3.88(br s, 2H), 4.45(d, J=5Hz, 2H), 6.98(d, J=5Hz, 1H), 7.12(t, J=8Hz, 1H), 7.19(m, 2H), 7.30(m, 2H), 7.39(m, 3H), 7.44(m, 3H), 7.58(s, 1H), 7.62(d, J=8Hz, 1H), 7.90(d, J=8Hz, 1H), 8.29(m, 1H). |
| Example 409 | (500 MHz, DMSO-d₆)δ 2.79(s, 3H), 3.00-3.50(m, 8H), 3.76(s, 2H), 3.85(br s, 2H), 4.49(d, J=5Hz, 2H), 6.77(m, 1H), 6.90(t, J=5Hz, 1H), 7.03(d, J=5Hz, 1H), 7.08(d, J=8Hz, 1H), 7.24(m, 2H), 7.38(d, J=8Hz, 1H), 7.44(d, J=8Hz, 1H), 7.58(s, 1H), 7.62(d, J=8Hz, 1H), 8.92(s, 1H). |
| Example 410 | (500 MHz, DMSO-d₆)δ 2.78(s, 3H), 3.00-3.50(m, 8H), 3.75(s, 2H), 3.85(br s, 2H), 4.48(d, J=5Hz, 2H), 6.97(m, 2H), 7.02(d, J=5Hz, 1H), 7.22(m, 2H), 7.30(d, J=5Hz, 1H), 7.38(d, J=8Hz, 1H), 7.58(d, J=8Hz, 1H), 7.62(d, J=8Hz, 1H), 7.72(s, 1H), 8.95(s, 1H). |
| Example 411 | (500 MHz, DMSO-d₆)δ 2.79(s, 3H), 3.00-3.50(m, 8H), 3.75(s, 2H), 3.83(br s, 2H), 4.50(d, J=5Hz, 2H), 6.96(t, J=5Hz, 1H), 7.03(d, J=5Hz, 1H), 7.09(d, J=8Hz, 1H), 7.20(t, J=8Hz, 1H), 7.27(m, 2H), 7.38(d, J=8Hz, 1H), 7.58(s, 1H), 7.62(d, J=8Hz, 1H), 7.83(s, 1H), 8.92(s, 1H). |
| Example 412 | (500 MHz, DMSO-d₆)δ 2.79(s, 3H), 3.00-3.50(m, 8H), 3.78(s, 2H), 3.83(br s, 2H), 4.54(d, J=5Hz, 2H), 6.98(t, J=5Hz, 1H), 7.03(d, J=5Hz, 1H), 7.25(d, J=8Hz, 1H), 7.30(d, J=5Hz, 1H), 7.37(d, J=8Hz, 1H), 7.47(t, J=8Hz, 1H), 7.55(m, 2H), 7.62(d, J=8Hz, 1H), 8.00(s, 1H), 9.07(s, 1H). |
| Example 413 | (500 MHz, DMSO-d₆)δ 2.55(s, 3H), 2.77(s, 3H), 3.00-3.50(m, 8H), 3.73(s, 2H), 3.80(br s, 2H), 4.50(d, J=6Hz, 2H), 6.85(t, J=5Hz, 1H), 7.03(d, J=5Hz, 1H), 7.28(d, J=5Hz, 1H), 7.35(d, J=7Hz, 1H), 7.39(t, J=7Hz, 1H), 7.53(d, J=8Hz, 1H), 7.55(s, 1H), 7.62(d, J=7Hz, 1H), 7.66(d, J=8Hz, 1H), 8.04(s, 1H), 8.88(s, 1H). |
| Example 414 | (500 MHz, DMSO-d₆)δ 1.15(t, J=5Hz, 3H), 2.78(m, 3H), 3.00-3.50(m, 8H), 3.55(q, J=5Hz, 2H), 3.70(s, 2H), 3.72(s, 2H), 4.48(d, J=5Hz, 2H), 5.58(s, 1H), 6.70(t, J=5Hz, 1H), 6.78(d, J=5Hz, 1H), 7.04(d, J=5Hz, 1H), 7.13(t, J=7Hz, 1H), 7.22(d, J=7Hz, 1H), 7.29(m, 2H), 7.50(s, 1H), 7.61(d, J=7Hz, 1H), 8.51(s, 1H). |
| Example 415 | (500 MHz, DMSO-d₆)δ 2.75(s, 3H), 3.00-3.50(m, 8H), 3.72(s, 2H), 3.77(br s, 2H), 4.47(d, J=5Hz, 2H), 6.55(d, J=5Hz, 1H), 6.74(t, J=5Hz, 1H), 7.01(m, 3H), 7.08(d, J=7Hz, 1H), 7.12(t, J=7Hz, 1H), 7.21(m, 2H), 7.26(d, J=5Hz, 1H), 7.34(d, J=7Hz, 1H), 7.38(m, 2H), 7.54(s, 1H), 7.61(d, J=7Hz, 1H), 8.74(s, 1H). |
| Example 416 | (500 MHz, DMSO-d₆)δ 2.77(s, 3H), 3.00-3.50(m, 8H), 3.73(s, 2H), 3.75(br s, 2H), 4.50(d, J=5Hz, 2H), 6.85(d, J=7Hz, 1H), 6.95(t, J=5Hz, 1H), 7.02(d, J=5Hz, 1H), 7.32(m, 4H), 7.57(s, 1H), 7.61(d, J=7Hz, 1H), 7.65(s, 1H), 9.02(s, 1H). |
| Example 417 | (500 MHz, DMSO-d₆)δ 2.77(s, 3H), 3.00-3.50(m, 8H), 3.74(s, 2H), 3.88(br s, 2H), 4.49(d, J=5Hz, 2H), 6.95(t, J=5Hz, 1H), 7.03(d, J=5Hz, 1H), 7.24(t, J=7Hz, 1H), 7.30(d, J=5Hz, 1H), 7.37(d, J=7Hz, 1H), 7.40(t, J=7Hz, 1H), 7.52(d, J=7Hz, 1H), 7.57(s, 1H), 7.64(d, J=7Hz, 1H), 7.97(s, 1H), 9.02(s, 1H). |
| Example 418 | (500 MHz, DMSO-d₆)δ 2.22(s, 3H), 2.79(s, 3H), 3.00-3.50(m, 8H), 3.75(s, 2H), 3.87(br s, 2H), 4.48(d, J=5Hz, 2H), 6.77(t, J=5Hz, 1H), |

-continued

| Example Number | ¹H NMR |
|---|---|
| Example 419 | 7.03(m, 3H), 7.33(m, 3H), 7.38(d, J=8Hz, 1H), 7.57(s, 1H), 7.62(d, J=8Hz, 1H), 8.55(s, 1H). (500 MHz, DMSO-$d_6$)δ 2.79(s, 3H), 3.00-3.50(m, 8H), 3.76(s, 2H), 3.86(br s, 2H), 4.48(d, J=5Hz, 2H), 6.80(t, J=5Hz, 1H), 7.03(d, J=5Hz, 1H), 7.08(t, J=8Hz, 2H), 7.32(d, J=5Hz, 1H), 7.38(d, J=8Hz, 1H), 7.42(m, 2H), 7.58(s, 1H), 7.62(d, J=8Hz, 1H), 8.72(s, 1H). |
| Example 420 | (500 MHz, DMSO-$d_6$)δ 2.79(s, 3H), 3.00-3.50(m, 8H), 3.75(s, 2H), 3.85(br s, 2H), 4.53(d, J=5Hz, 2H), 7.03(m, 2H), 7.30(d, J=5Hz, 1H), 7.38(d, J=8Hz, 1H), 7.57(d, J=5Hz, 1H), 7.59(s, 1H), 7.63(m, 4H), 9.18(s, 1H). |
| Example 421 | (500 MHz, DMSO-$d_6$)δ 2.79(s, 3H), 3.00-3.50(m, 8H), 3.74(s, 2H), 3.77(br s, 2H), 4.50(d, J=5Hz, 2H), 6.82(t, J=5Hz, 1H), 7.02(d, J=5Hz, 1H), 7.29(m, 2H), 7.36(d, J=8Hz, 1H), 7.42(t, J=8Hz, 2H), 7.58(m, 8H), 8.78(s, 1H). |
| Example 422 | (500 MHz, DMSO-$d_6$)δ 2.07(s, 3H), 2.22(s, 3H), 2.78(s, 3H), 3.00-3.50(m, 8H), 3.75(s, 2H), 3.81(br s, 2H), 4.48(d, J=5Hz, 2H), 6.83(d, J=5Hz, 1H), 7.00(m, 3H), 7.32(d, J=5Hz, 1H), 7.38(d, J=8Hz, 1H), 7.52(d, J=8Hz, 1H), 7.58(s, 1H), 7.62(d, J=8Hz, 1H), 7.79(s, 1H). |
| Example 423 | (500 MHz, DMSO-$d_6$)δ 2.15(s, 3H), 2.22(s, 3H), 2.79(s, 3H), 3.00-3.50(m, 8H), 3.76(s, 2H), 3.82(br s, 2H), 4.47(d, J=5Hz, 2H), 6.75(d, J=5Hz, 1H), 7.02(t, J=8Hz, 1H), 7.04(d, J=5Hz, 1H), 7.10(t, J=5Hz, 1H), 7.32(d, J=5Hz, 1H), 7.38(d, J=8Hz, 1H), 7.58(s, 1H), 7.63(m, 2H), 7.67(s, 1H). |
| Example 424 | (500 MHz, DMSO-$d_6$)δ 2.20(s, 6H), 2.79(s, 3H), 3.00-3.50(m, 8H), 3.75(s, 2H), 3.80(br s, 2H), 4.48(d, J=5Hz, 2H), 6.58(s, 1H), 6.77(t, J=5Hz, 1H), 7.02(d, J=5Hz, 1H), 7.03(s, 2H), 7.30(d, J=5Hz, 1H), 7.38(d, J=8Hz, 1H), 7.58(s, 1H), 7.62(d, J=8Hz, 1H), 8.43(s, 1H). |
| Example 425 | (500 MHz, DMSO-$d_6$)δ 2.78(s, 3H), 3.00-3.50(m, 8H), 3.75(s, 2H), 3.83(s, 2H), 4.47(d, J=5Hz, 2H), 7.02(s, 2H), 7.08(d, J=5Hz, 1H), 7.13(t, J=5Hz, 1H), 7.28(d, J=5Hz, 1H), 7.38(d, J=8Hz, 1H), 7.54(s, 2H), 7.58(s, 1H), 7.62(d, J=8Hz, 1H), 9.18(s, 1H). |
| Example 426 | (400 MHz, DMSO-$d_6$)δ 2.75(s, 3H), 3.00-3.50(m, 8H), 3.74(s, 2H), 3.77(br s, 2H), 4.56(d, J=5Hz, 2H), 7.08(d, J=5Hz, 1H), 7.15(t, J=5Hz, 1H), 7.31(d, J=5Hz, 1H), 7.35(d, J=7Hz, 1H), 7.45(t, J=7Hz, 1H), 7.58(m, 4H), 7.91(d, J=7Hz, 1H), 8.00(d, J=7Hz, 1H), 8.10(d, J=7Hz, 1H), 8.65(s, 1H). |
| Example 427 | (400 MHz, DMSO-$d_6$)δ 2.78(s, 3H), 3.00-3.50(m, 8H), 3.73(s, 2H), 3.82(br s, 2H), 4.48(d, J=5Hz, 2H), 6.99(t, J=5Hz, 1H), 7.03(d, J=5Hz, 1H), 7.30(d, J=5Hz, 1H), 7.38(m, 2H), 7.57(s, 1H), 7.62(m, 2H), 8.00(dd, J=6.3Hz, 1H), 9.08(s, 1H). |
| Example 428 | (400 MHz, DMSO-$d_6$)δ 2.80(s, 3H), 3.00-3.50(m, 8H), 3.75(s, 2H), 3.95(br s, 2H), 4.53(d, J=5Hz, 2H), 7.06(d, J=5Hz, 1H), 7.41(m, 5H), 7.60(s, 1H), 7.65(d, J=7Hz, 1H), 8.62(d, J=7Hz, 1H), 8.82(s, 1H). |
| Example 429 | (400 MHz, DMSO-$d_6$)δ 2.75(s, 3H), 3.00-3.50(m, 8H), 3.75(s, 2H), 3.76(br s, 2H), 4.54(d, J=5Hz, 2H), 7.05(d, J=5Hz, 1H), 7.32(m, 2H), 7.52(s, 1H), 7.60(m, 1H), 7.68(d, J=7Hz, 1H), 7.78(m, 1H), 7.98(s, 1H), 8.45(s, 1H), 8.65(s, 1H). |
| Example 430 | (400 MHz, DMSO-$d_6$)δ 1.68(m, 2H), 1.75(m, 2H), 2.52(m, 2H), 2.70(m, 2H), 2.78(s, 3H), 3.00-3.50(m, 8H), 3.75(s, 2H), 3.80(br s, 2H), 4.48(d, J=5Hz, 2H), 6.73(d, J=7Hz, 1H), 7.00(t, J=7Hz, 1H), 7.04(d, J=5Hz, 1H), 7.10(t, J=5Hz, 1H), 7.30(d, J=5Hz, 1H), 7.36(d, J=7Hz, 1H), 7.56(m, 1H), 7.62(m, 3H). |
| Example 431 | (500 MHz, DMSO-$d_6$)δ 2.75(s, 3H), 3.00-3.50(m, 8H), 3.69(br s, 2H), 3.75(s, 2H), 4.52(d, J=5Hz, 2H), 7.01(d, J=5Hz, 1H), 7.04(d, J=5Hz, 1H), 7.07(m, 1H), 7.11(t, J=7Hz, 1H), 7.29(m, 1H), 7.35(d, J=7Hz, 1H), 7.52(s, 1H), 7.60(d, J=7Hz, 1H), 7.76(d, J=7Hz, 1H), 8.79(s, 1H). |
| Example 432 | (500 MHz, DMSO-$d_6$)δ 2.60(s, 3H), 3.00-3.50(m, 8H), 3.61(br s, 2H), 3.72(s, 2H), 3.81(s, 3H), 4.50(d, J=5Hz, 2H), 7.03(s, 1H), 7.30(d, J=5Hz, 2H), 7.50(s, 1H), 7.58(br s, 1H), 7.80(d, J=5Hz, 1H), 7.97(d, J=5Hz, 1H), 8.32(br s, 1H), 9.32(s, 1H). |
| Example 433 | (500 MHz, DMSO-$d_6$)δ 2.20(s, 3H), 2.79(s, 3H), 3.00(s, 3H), 3.00-3.50(m, 8H), 3.77(s, 2H), 3.91(br s, 2H), 4.70(s, 2H), 7.10(m, 2H), 7.17(t, J=8Hz, 1H), 7.20(d, J=8Hz, 1H), 7.24(d, J=8Hz, 1H), 7.33(d, J=5Hz, 1H), 7.39(d, J=8Hz, 1H), 7.59(s, 1H), 7.62(d, J=8Hz, 1H), 7.99(br s, 1H). |
| Example 434 | (500 MHz, DMSO-$d_6$)δ 1.15(d, J=8Hz, 6H), 2.78(s, 3H), 3.98(s, 3H), 3.00-3.50(m, 8H), 3.16(m, 1H), 3.73(s, 2H), 3.87(br s, 2H), 4.70(s, 2H), 7.10(d, J=5Hz, 1H), 7.20(m, 3H), 7.31(d, J=8Hz, 1H), 7.35(d, J=5Hz, 1H), 7.40(d, J=8Hz, 1H), 7.58(s, 1H), 7.62(d, J=8Hz, 1H), 8.03(s, 1H). |
| Example 435 | (500 MHz, DMSO-$d_6$)δ 2.78(s, 3H), 3.00(s, 3H), 3.00-3.50(m, 8H), 3.77(s, 2H), 3.81(s, 3H), 3.88(br s, 2H), 4.72(s, 2H), 6.90(m, 1H), 7.00(m, 2H), 7.13(d, J=5Hz, 1H), 7.33(d, J=5Hz, 1H), 7.39(d, J=8Hz, 1H), 7.55(s, 1H), 7.59(br s, 1H), 7.63(d, J=8Hz, 1H), 7.81(d, J=8Hz, 1H). |
| Example 436 | (500 MHz, DMSO-$d_6$)δ 2.80(s, 3H), 3.00(s, 3H), 3.00-3.50(m, 8H), 3.77(s, 2H), 3.84(br s, 2H), 4.73(s, 2H), 7.13(d, J=5Hz, 1H), 7.18(t, J=8Hz, 1H), 7.34(m, 2H), 7.40(d, J=8Hz, 1H), 7.48(d, J=8Hz, 1H), 7.59(s, 1H), 7.65(m, 2H), 8.09(br s, 1H). |
| Example 437 | (500 MHz, DMSO-$d_6$)δ 2.78(s, 3H), 3.00(s, 3H), 3.00-3.50(m, 8H), 3.74(s, 2H), 3.86(br s, 2H), 4.72(s, 2H), 7.12(d, J=5Hz, 1H), 7.32(d, J=5Hz, 1H), 7.36(d, J=8Hz, 1H), 7.42(d, J=8Hz, 1H), 7.48(t, J=8Hz, 1H), 7.56(s, 1H), 7.63(d, J=8Hz, 1H), 7.81(d, J=8Hz, 1H), 8.01(s, 1H), 8.83(s, 1H). |
| Example 438 | (500 MHz, DMSO-$d_6$)δ 2.27(s, 3H), 2.79(s, 3H), 2.98(s, 3H), 3.00-3.50(m, 8H), 3.73(s, 2H), 3.81(br s, 2H), 4.70(s, 2H), 6.80(d, J=8Hz, 1H), 7.09(d, J=5Hz, 1H), 7.14(t, J=8Hz, 1H), 7.31(m, 2H), 7.35(m, 2H), 7.55(s, 1H), 7.62(d, J=5Hz, 1H), 8.35(s, 1H). |
| Example 439 | (500 MHz, DMSO-$d_6$)δ 2.79(s, 3H), 3.00(s, 3H), 3.00-3.50(m, 8H), 3.75(s, 3H), 3.78(br s, 2H), 4.75(s, 2H), 6.56(d, J=8Hz, 1H), 7.10(m, 2H), 7.15(t, J=8Hz, 1H), 7.21(m, 1H), 7.31(d, J=5Hz, 1H), 7.36(d, J=8Hz, 1H), 7.57(s, 1H), 7.62(d, J=5Hz, 1H), 8.41(s, 1H). |
| Example 440 | (500 MHz, DMSO-$d_6$)δ 2.77(s, 3H), 3.00(s, 3H), 3.00-3.50(m, 8H), 3.73(s, 2H), 3.78(br s, 2H), 4.70(s, 2H), 7.10(d, J=5Hz, 1H), 7.14(d, J=8Hz, 1H), 7.22(t, J=8Hz, 1H), 7.31(d, J=5Hz, 1H), 7.35(d, J=8Hz, 1H), 7.52(bd, J=8Hz, 1H), 7.54(s, 1H), 7.62(d, J=5Hz, 1H), 7.85(s, 1H), 8.62(s, 1H). |
| Example 441 | (500 MHz, DMSO-$d_6$)δ 2.77(s, 3H), 3.00(s, 3H), 3.00-3.50(m, 8H), 3.73(s, 2H), 3.78(br s, 2H), 4.73(s, 2H), 7.10(d, J=5Hz, 1H), 7.31(m, 2H), 7.38(d, J=8Hz, 1H), 7.50(t, J=8Hz, 1H), 7.57(s, 1H), 7.62(d, J=5Hz, 1H), 7.80(d, J=5Hz, 1H), 8.00(s, 1H), 8.80(s, 1H). |
| Example 442 | (400 MHz, DMSO-$d_6$)δ 2.78(s, 3H), 2.99(s, 3H), 3.00-3.50(m, 8H), 3.73(s, 2H), 3.85(br s, 2H), 4.72(s, 2H), 6.95(d, J=7Hz, 1H), 7.10(d, J=5Hz, 1H), 7.32(d, J=5Hz, 1H), 7.38(t, J=7Hz, 2H), 7.55(m, 2H), 7.62(d, J=7Hz, 1H), 7.68(s, 1H), 8.75(s, 1H). |
| Example 443 | (500 MHz, DMSO-$d_6$)δ 2.77(s, 3H), 2.98(s, 3H), 3.00-3.50(m, 8H), 3.78(s, 2H), 3.90(br s, 2H), 4.75(s, 2H), 7.08(d, J=5Hz, 1H), 7.28(m, |

| Example Number | ¹H NMR |
|---|---|
| | 2H), 7.35(d, J=7Hz, 1H), 7.42(t, J=7Hz, 1H), 7.57(s, 1H), 7.61(d, J=7Hz, 1H), 7.75(d, J=7Hz, 1H), 8.00(s, 1H), 8.78(s, 1H). |
| Example 444 | (500 MHz, DMSO-d$_6$)δ 2.22(s, 3H), 2.79(s, 3H), 2.99(s, 3H), 3.00-3.50(m, 8H), 3.73(s, 2H), 3.79(br s, 2H), 4.69(s, 2H), 7.06(m, 2H), 7.09(d, J=5Hz, 1H), 7.30(d, J=5Hz, 1H), 7.34(d, J=8Hz, 1H), 7.39(m, 2H), 7.54(s, 1H), 7.61(d, J=8Hz, 1H), 8.33(br s, 1H). |
| Example 445 | (500 MHz, DMSO-d$_6$)δ 2.15(s, 3H), 2.26(s, 3H), 2.78(s, 3H), 3.00(s, 3H), 3.00-3.50(m, 8H), 3.74(s, 2H), 3.83(br s, 2H), 4.68(s, 2H), 6.89(d, J=5Hz, 1H), 7.08(m, 3H), 7.35(d, J=5Hz, 1H), 7.38(d, J=8Hz, 1H), 7.57(s, 1H), 7.63(d, J=8Hz, 1H), 7.92(s, 1H). |
| Example 446 | (500 MHz, DMSO-d$_6$)δ 2.78(s, 3H), 2.98(s, 3H), 3.00-3.50(m, 8H), 3.78(s, 4H), 4.74(s, 2H), 6.95(m, 1H), 7.08(d, J=3Hz, 1H), 7.26(m, 1H), 7.31(s, 1H), 7.35(d, J=8Hz, 1H), 7.50(m, 1H), 7.55(s, 1H), 7.63(d, J=5Hz, 1H), 8.34(s, 1H). |
| Example 447 | (500 MHz, DMSO-d$_6$)δ 2.78(s, 3H), 2.99(s, 3H), 3.00-3.50(m, 8H), 3.74(s, 2H), 3.78(s, 2H), 4.70(s, 2H), 7.10(d, J=5Hz, 1H), 7.15(t, J=7Hz, 2H), 7.32(m, 3H), 7.55(s, 1H), 7.61(d, J=7Hz, 1H), 8.25(s, 1H). |
| Example 448 | (500 MHz, DMSO-d$_6$)δ 2.78(s, 3H), 3.00(s, 3H), 3.00-3.50(m, 8H), 3.77(s, 2H), 3.83(br s, 2H), 4.76(s, 2H), 7.15(d, J=5Hz, 1H), 7.35(d, J=5Hz, 1H), 7.38(d, J=8Hz, 1H), 7.52(d, J=8Hz, 1H), 7.58(s, 1H), 7.62(d, J=8Hz, 1H), 7.74(d, J=8Hz, 1H), 8.05(q, J=7Hz, 1H), 8.32(s, 1H). |
| Example 449 | (500 MHz, DMSO-d$_6$)δ 2.20(s, 3H), 2.80(s, 3H), 3.00(s, 3H), 3.00-3.50(m, 8H), 3.77(s, 2H), 3.87(br s, 2H), 4.72(s, 2H), 7.12(m, 2H), 7.21(d, J=8Hz, 1H), 7.35(d, J=5Hz, 1H), 7.39(m, 2H), 7.59(s, 1H), 7.63(d, J=8Hz, 1H), 8.04(br s, 1H). |
| Example 450 | (400 MHz, DMSO-d$_6$) 2.78(s, 3H), 3.00(s, 3H), 3.00-3.50(m, 8H), 3.74(s, 2H), 3.89(br s, 2H), 4.72(s, 2H), 7.12(d, J=4Hz, 1H), 7.32(d, J=4Hz, 1H), 7.40(d, J=8Hz, 1H), 7.50(m, 2H), 7.58(s, 1H), 7.65(d, J=8Hz, 1H), 7.98(d, J=8Hz, 1H), 8.50(s, 1H). |
| Example 451 | (500 MHz, DMSO-d$_6$)δ 2.18(s, 3H), 2.77(s, 3H), 2.98(s, 3H), 3.00-3.50(m, 8H), 3.73(s, 2H), 3.82(br s, 2H), 4.70(s, 2H), 6.90(t, J=7Hz, 1H), 7.10(d, J=5Hz, 1H), 7.21(m, 2H), 7.32(m, 2H), 7.55(m, 1H), 7.61(d, J=7Hz, 1H), 8.00(s, 1H). |
| Example 452 | (500 MHz, DMSO-d$_6$)δ 2.30(s, 3H), 2.77(s, 3H), 2.98(s, 3H), 3.00-3.50(m, 8H), 3.73(s, 4H), 4.70(s, 2H), 6.95(d, J=7Hz, 1H), 7.10(d, J=5Hz, 1H), 7.35(m, 2H), 7.45(s, 1H), 7.55(m, 2H), 7.61(m, 1H), 8.02(s, 1H). |
| Example 453 | (500 MHz, DMSO-d$_6$)δ 2.28(s, 3H), 2.78(s, 3H), 2.98(s, 3H), 3.00-3.50(m, 8H), 3.74(s, 4H), 4.69(s, 2H), 6.95(m, 1H), 7.08(m, 2H), 7.32(m, 3H), 7.55(s, 1H), 7.61(d, J=7Hz, 1H), 8.18(s, 1H). |
| Example 454 | (500 MHz, DMSO-d$_6$)δ 2.25(s, 3H), 2.77(s, 3H), 2.98(s, 3H), 3.00-3.50(m, 8H), 3.72(s, 2H), 3.75(br s, 2H), 4.68(s, 2H), 7.08(d, J=5Hz, 1H), 7.19(t, J=7Hz, 1H), 7.25(d, J=7Hz, 1H), 7.35(m, 2H), 7.55(s, 1H), 7.65(m, 1H), 8.12(s, 1H). |
| Example 455 | (500 MHz, DMSO-d$_6$)δ 2.78(s, 3H), 2.99(s, 3H), 3.00-3.50(m, 8H), 3.73(s, 4H), 4.75(s, 2H), 7.11(d, J=4Hz, 1H), 7.21(d, J=7Hz, 1H), 7.32(m, 2H), 7.52(s, 1H), 7.61(d, J=7Hz, 1H), 7.80(m, 2H), 9.00(s, 1H). |
| Example 456 | (500 MHz, DMSO-d$_6$)δ 2.78(s, 3H), 3.00(s, 3H), 3.00-3.50(m, 8H), 3.73(s, 4H), 4.70(s, 2H), 7.16(m, 4H), 7.32(d, J=5Hz, 1H), 7.38(d, J=7Hz, 1H), 7.55(s, 1H), 7.62(d, J=7Hz, 1H), 8.75(s, 1H). |
| Example 457 | (500 MHz, DMSO-d$_6$)δ 1.18(t, J=7Hz, 3H), 2.10(s, 3H), 2.79(s, 3H), 3.00-3.50(m, 8H), 3.42(q, J=7Hz, 2H), 3.73(s, 2H), 3.86(br s, 2H), 4.71(s, 2H), 7.08(t, J=7Hz, 1H), 7.10(d, J=7Hz, 1H), 7.15(t, J=7Hz, 1H), 7.20(d, J=5Hz, 1H), 7.23(d, J=5Hz, 1H), 7.30(d, J=5Hz, 1H), 7.38(d, J=7Hz, 1H), 7.58(s, 1H), 7.65(d, J=7Hz, 1H), 7.95(s, 1H). |
| Example 458 | (500 MHz, DMSO-d$_6$)δ 1.19(t, J=7Hz, 3H), 2.79(s, 3H), 3.00-3.50(m, 8H), 3.42(q, J=7Hz, 2H), 3.74(s, 2H), 3.80(s, 3H), 3.82(br s, 2H), 4.72(s, 2H), 6.89(m, 1H), 7.00(m, 2H), 7.18(d, J=5Hz, 1H), 7.30(d, J=5Hz, 1H), 7.35(d, J=7Hz, 1H), 7.48(s, 1H), 7.58(s, 1H), 7.63(d, J=7Hz, 1H), 7.82(d, J=7Hz, 1H). |
| Example 459 | (500 MHz, DMSO-d$_6$)δ 1.19(t, J=7Hz, 3H), 2.78(s, 3H), 3.00-3.50(m, 8H), 3.42(q, J=7Hz, 2H), 3.73(s, 2H), 3.79(br s, 2H), 4.72(s, 2H), 7.15(m, 2H), 7.35(m, 3H), 7.45(d, J=7Hz, 1H), 7.55(s, 1H), 7.65(d, J=7Hz, 2H), 8.00(s, 1H). |
| Example 460 | (500 MHz, DMSO-d$_6$)δ 1.10(t, J=8Hz, 3H), 2.28(s, 3H), 2.78(s, 3H), 3.00-3.50(m, 8H), 3.42(q, J=8Hz, 2H), 3.73(s, 2H), 3.87(br s, 2H), 4.73(s, 2H), 6.80(d, J=8Hz, 1H), 7.13(m, 2H), 7.35(m, 4H), 7.58(s, 1H), 7.62(d, J=8Hz, 1H), 8.33(s, 1H). |
| Example 461 | (500 MHz, DMSO-d$_6$)δ 1.19(t, J=7Hz, 3H), 2.80(s, 3H), 3.00-3.50(m, 8H), 3.42(q, J=7Hz, 2H), 3.73(s, 5H), 3.88(br s, 2H), 4.72(s, 2H), 6.55(d, J=7Hz, 1H), 7.15(m, 3H), 7.25(s, 1H), 7.31(d, J=5Hz, 1H), 7.38(d, J=7Hz, 1H), 7.58(s, 1H), 7.63(d, J=7Hz, 1H), 8.38(s, 1H). |
| Example 462 | (500 MHz, DMSO-d$_6$)δ 1.11(t, J=7Hz, 3H), 2.79(s, 3H), 3.00-3.50(m, 8H), 3.42(q, J=7Hz, 2H), 3.73(s, 2H), 3.87(br s, 2H), 4.73(s, 2H), 7.02(d, J=7Hz, 1H), 7.12(d, J=5Hz, 1H), 7.29(m, 2H), 7.35(d, J=7Hz, 1H), 7.48(d, J=7Hz, 1H), 7.55(s, 1H), 7.62(d, J=7Hz, 1H), 7.73(s, 1H), 8.60(s, 1H). |
| Example 463 | (500 MHz, DMSO-d$_6$)δ 1.11(t, J=7Hz, 3H), 2.79(s, 3H), 3.00-3.50(m, 8H), 3.42(q, J=7Hz, 2H), 3.73(s, 2H), 3.89(br s, 2H), 4.73(s, 2H), 7.12(m, 2H), 7.25(t, J=7Hz, 1H), 7.30(d, J=5Hz, 1H), 7.38(d, J=7Hz, 1H), 7.55(d, J=7Hz, 1H), 7.59(s, 1H), 7.62(d, J=7Hz, 1H), 8.85(s, 1H), 8.59(s, 1H). |
| Example 464 | (500 MHz, DMSO-d$_6$)δ 1.10(t, J=7Hz, 3H), 1.19(t, J=7Hz, 3H), 2.58(q, J=7Hz, 2H), 2.78(s, 3H), 3.00-3.50(m, 8H), 3.42(q, J=7Hz, 2H), 3.73(s, 2H), 3.85(br s, 2H), 4.76(s, 2H), 6.82(d, J=7Hz, 1H), 7.11(d, J=5Hz, 1H), 7.18(t, J=7Hz, 1H), 7.31(d, J=5Hz, 1H), 7.38(m, 3H), 7.58(s, 1H), 7.63(d, J=7Hz, 1H), 8.35(s, 1H). |
| Example 465 | (500 MHz, DMSO-d$_6$)δ 1.11(t, J=7Hz, 3H), 2.79(s, 3H), 3.00-3.50(m, 8H), 3.42(q, J=7Hz, 2H), 3.72(s, 2H), 3.77(br s, 2H), 4.76(s, 2H), 7.12(d, J=5Hz, 1H), 7.31(m, 2H), 7.35(d, J=7Hz, 1H), 7.52(t, J=7Hz, 1H), 7.55(s, 1H), 7.61(d, J=7Hz, 1H), 7.83(d, J=7Hz, 1H), 8.00(s, 1H), 8.75(s, 1H). |
| Example 466 | (500 MHz, DMSO-d$_6$)δ 1.12(t, J=7Hz, 3H), 2.31(s, 3H), 2.79(s, 3H), 3.00-3.50(m, 8H), 3.42(q, J=7Hz, 2H), 3.75(s, 2H), 3.83(br s, 2H), 4.72(s, 2H), 6.95(m, 1H), 7.08(t, J=7Hz, 1H), 7.12(d, J=5Hz, 1H), 7.35(m, 2H), 7.38(d, J=7Hz, 1H), 7.58(s, 1H), 7.62(d, J=7Hz, 1H), 8.08(s, 1H). |
| Example 467 | (500 MHz, DMSO-d$_6$)δ 1.13(t, J=7Hz, 3H), 2.79(s, 3H), 3.00-3.50(m, 8H), 3.42(q, J=7Hz, 2H), 3.75(s, 2H), 3.92(br s, 2H), 4.75(s, 2H), 7.12(d, J=5Hz, 1H), 7.20(d, J=7Hz, 1H), 7.30(d, J=5Hz, 1H), 7.38(d, J=7Hz, 1H), 7.58(s, 1H), 7.62(d, J=7Hz, 1H), 8.82(m, 2H), 8.95(s, 1H). |
| Example 468 | (500 MHz, DMSO-d$_6$)δ 0.86(t, J=8Hz, 3H), 1.60(m, 2H), 2.18(s, 3H), 2.79(s, 3H), 3.00-3.50(m, 8H), 3.35(t, J=8Hz, 2H), 3.75(s, 2H), 3.87(br s, 2H), 4.70(s, 2H), 7.07(t, J=8Hz, 1H), 7.10(d, J=5Hz, 1H), 7.16(t, J=8Hz, 1H), |

| Example Number | ¹H NMR |
|---|---|
| | 7.19(d, J=8Hz, 1H), 7.22(d, J=8Hz, 1H), 7.30(d, J=5Hz, 1H), 7.39(d, J=8Hz, 1H), 7.58(s, 1H), 7.62(d, J=8Hz, 1H), 7.95(s, 1H). |
| Example 469 | (500 MHz, DMSO-d₆)δ 0.91(t, J=8Hz, 3H), 1.60(m, 2H), 2.79(s, 3H), 3.00-3.50(m, 8H), 3.37(t, J=8Hz, 2H), 3.75(s, 2H), 3.80(s, 3H), 3.88(br s, 2H), 4.75(s, 2H), 6.90(m, 1H), 7.00(m, 2H), 7.16(d, J=5Hz, 1H), 7.36(d, J=5Hz, 1H), 7.40(d, J=8Hz, 1H), 7.48(s, 1H), 7.58(s, 1H), 7.62(d, J=8Hz, 1H), 7.82(d, J=8Hz, 1H). |
| Example 470 | (500 MHz, DMSO-d₆)δ 0.86(t, J=8Hz, 3H), 1.60(m, 2H), 2.80(s, 3H), 3.00-3.50(m, 8H), 3.36(t, J=8Hz, 2H), 3.75(s, 2H), 3.92(br s, 2H), 4.75(s, 2H), 7.18(m, 4H), 7.28(d, J=5Hz, 1H), 7.40(d, J=8Hz, 1H), 7.48(m, 1H), 7.58(s, 1H), 7.62(d, J=8Hz, 1H), 8.18(s, 1H). |
| Example 471 | (500 MHz, DMSO-d₆)δ 0.86(t, J=8Hz, 3H), 1.57(m, 2H), 2.28(s, 3H), 2.79(s, 3H), 3.00-3.50(m, 8H), 3.35(t, J=8Hz, 2H), 3.75(s, 2H), 3.89(br s, 2H), 4.72(s, 2H), 6.80(d, J=8Hz, 1H), 7.10(d, J=5Hz, 1H), 7.13(t, J=8Hz, 1H), 7.31(m, 2H), 7.40(d, J=8Hz, 1H), 7.58(s, 1H), 7.62(d, J=8Hz, 1H), 8.30(s, 1H). |
| Example 472 | (500 MHz, DMSO-d₆)δ 0.86(t, J=8Hz, 3H), 1.57(m, 2H), 2.79(s, 3H), 3.00-3.50(m, 8H), 3.35(t, J=8Hz, 2H), 3.75(s, 5H), 3.87(br s, 2H), 4.76(s, 2H), 6.57(d, J=8Hz, 1H), 7.10(m, 2H), 7.13(t, J=8Hz, 1H), 7.20(m, 1H), 7.30(d, J=5Hz, 1H), 7.40(d, J=8Hz, 1H), 7.58(s, 1H), 7.62(d, J=8Hz, 1H), 8.36(s, 1H). |
| Example 473 | (500 MHz, DMSO-d₆)δ 1.20(d, J=8Hz, 6H), 2.18(s, 3H), 2.79(s, 3H), 3.00-3.50(m, 8H), 3.75(s, 2H), 3.88(br s, 2H), 4.43(m, 1H), 4.70(s, 2H), 7.04(t, J=8Hz, 1H), 7.15(m, 3H), 7.28(m, 2H), 7.40(d, J=8Hz, 1H), 7.58(s, 1H), 7.62(d, J=8Hz, 1H), 7.82(s, 1H). |
| Example 474 | (500 MHz, DMSO-d₆)δ 1.22(d, J=8Hz, 6H), 2.79(s, 3H), 3.00-3.50(m, 8H), 3.75(s, 2H), 3.78(s, 3H), 3.82(br s, 2H), 4.43(m, 1H), 4.70(s, 2H), 6.85(m, 1H), 6.92(m, 2H), 7.20(d, J=5Hz, 1H), 7.36(m, 2H), 7.41(s, 1H), 7.58(s, 1H), 7.62(d, J=8Hz, 1H), 7.92(d, J=8Hz, 1H). |
| Example 475 | (500 MHz, DMSO-d₆)δ 1.18(d, J=8Hz, 6H), 2.26(s, 3H), 2.79(s, 3H), 3.00-3.50(m, 8H), 3.74(s, 2H), 3.84(br s, 2H), 4.43(m, 1H), 4.70(s, 2H), 6.79(d, J=8Hz, 1H), 7.08(d, J=5Hz, 1H), 7.12(t, J=8Hz, 1H), 7.26(m, 2H), 7.33(s, 1H), 7.36(d, J=5Hz, 1H), 7.57(s, 1H), 7.62(d, J=8Hz, 1H), 8.32(s, 1H). |
| Example 476 | (500 MHz, DMSO-d₆)δ 0.81(m, 2H), 0.95(m, 2H), 2.28(s, 3H), 2.63(m, 1H), 2.77(s, 3H), 3.00-3.50(m, 8H), 3.73(s, 2H), 3.77(br s, 2H), 4.67(s, 2H), 6.81(d, J=8Hz, 1H), 7.05(m, J=5Hz, 1H), 7.15(t, J=8Hz, 1H), 7.29(d, J=5Hz, 1H), 7.35(m, 3H), 7.54(s, 1H), 7.61(d, J=8Hz, 1H), 8.20(s, 1H). |
| Example 477 | (500 MHz, DMSO-d₆)δ 0.90(m, 2H), 1.02(m, 2H), 2.63(m, 1H), 2.79(s, 3H), 3.00-3.50(m, 8H), 3.73(s, 2H), 3.78(br s, 2H), 3.85(s, 3H), 4.68(s, 2H), 6.92(t, J=8Hz, 1H), 6.98(t, J=8Hz, 1H), 7.04(d, J=8Hz, 1H), 7.07(d, J=5Hz, 1H), 7.31(d, J=5Hz, 1H), 7.38(d, J=8Hz, 1H), 7.57(s, 1H), 7.62(d, J=8Hz, 1H), 8.16(d, J=8Hz, 1H), 8.21(s, 1H). |
| Example 478 | (500 MHz, DMSO-d₆)δ 0.90(m, 2H), 0.98(m, 2H), 2.63(m, 1H), 2.79(s, 3H), 3.00-3.50(m, 8H), 3.74(s, 2H), 3.79(br s, 2H), 4.68(s, 2H), 7.08(d, J=5Hz, 1H), 7.12(m, 1H), 7.17(t, J=8Hz, 1H), 7.24(m, 1H), 7.32(m, 1H), 7.35(d, J=8Hz, 1H), 7.54(s, 1H), 7.62(d, J=8Hz, 1H), 7.82(t, J=8Hz, 1H), 8.08(s, 1H). |
| Example 479 | (500 MHz, DMSO-d₆)δ 0.88(m, 2H), 0.96(m, 2H), 2.26(s, 3H), 2.63(m, 1H), 2.79(s, 3H), 3.00-3.50(m, 8H), 3.74(s, 2H), 3.78(br s, 2H), 4.68(s, 2H), 7.05(d, J=8Hz, 1H), 7.06(d, J=5Hz, 1H), 7.17(t, J=8Hz, 1H), 7.20(d, J=8Hz, 1H), 7.31(d, J=5Hz, 1H), 7.35(d, J=8Hz, 1H), 7.55(s, 1H), 7.62(m, 2H), 7.85(s, 1H). |
| Example 480 | (500 MHz, DMSO-d₆)δ 0.92(d, J=8Hz, 6H), 2.00(m, 1H), 2.25(s, 3H), 2.78(s, 3H), 3.00-3.50(m, 8H), 3.21(d, J=8Hz, 2H), 3.76(s, 2H), 3.80(br s, 2H), 4.74(s, 2H), 6.80(d, J=8Hz, 1H), 7.09(d, J=5Hz, 1H), 7.13(t, J=8Hz, 1H), 7.30(m, 3H), 7.37(d, J=8Hz, 1H), 7.58(s, 1H), 7.61(d, J=8Hz, 1H), 8.28(s, 1H). |
| Example 481 | (500 MHz, DMSO-d₆)δ 0.90(d, J=8Hz, 6H), 1.43(m, 2H), 1.58(m, 1H), 2.26(s, 3H), 2.78(s, 3H), 3.00-3.50(m, 8H), 3.37(t, J=8Hz, 2H), 3.72(s, 2H), 3.79(br s, 2H), 4.74(s, 2H), 6.80(d, J=8Hz, 1H), 7.09(d, J=5Hz, 1H), 7.13(t, J=8Hz, 1H), 7.30(m, 3H), 7.36(d, J=8Hz, 1H), 7.58(s, 1H), 7.62(d, J=8Hz, 1H), 8.32(s, 1H). |
| Example 482 | (500 MHz, DMSO-d₆)δ 2.80(s, 3H), 3.00-3.50(m, 8H), 3.75(s, 2H), 3.78(br s, 2H), 3.80(s, 3H), 4.88(s, 2H), 7.13(d, J=5Hz, 1H), 7.19(t, J=8Hz, 1H), 7.31(d, J=5Hz, 1H), 7.37(m, 2H), 7.52(d, J=8Hz, 1H), 7.58(s, 1H), 7.62(d, J=8Hz, 1H), 7.82(d, J=8Hz, 1H), 8.72(s, 1H). |
| Example 483 | (500 MHz, DMSO-d₆)δ 2.23(s, 3H), 2.80(s, 3H), 3.00-3.50(m, 8H), 3.75(s, 3H), 3.78(s, 2H), 3.84(br s, 2H), 4.85(s, 2H), 6.82(d, J=8Hz, 1H), 7.12(d, J=5Hz, 1H), 7.17(t, J=8Hz, 1H), 7.30(m, 1H), 7.38(m, 2H), 7.43(s, 1H), 7.58(s, 1H), 7.62(d, J=8Hz, 1H), 9.02(s, 1H). |
| Example 484 | (500 MHz, DMSO-d₆)δ 2.26(s, 3H), 2.80(s, 3H), 3.00-3.50(m, 8H), 3.32(s, 3H), 3.53(s, 4H), 3.73(s, 2H), 3.78(br s, 2H), 4.76(s, 2H), 6.80(d, J=8Hz, 1H), 7.10(d, J=5Hz, 1H), 7.14(t, J=8Hz, 1H), 7.25(d, J=8Hz, 1H), 7.29(m, 2H), 7.38(d, J=8Hz, 1H), 7.58(s, 1H), 7.62(d, J=8Hz, 1H), 8.41(s, 1H). |
| Example 485 | (500 MHz, DMSO-d₆)δ 2.24(s, 3H), 2.79(s, 3H), 3.00-3.50(m, 11H), 3.11(s, 3H), 3.73(br s, 2H), 3.75(s, 2H), 4.52(s, 2H), 6.83(t, J=8Hz, 1H), 6.94(m, 2H), 7.03(d, J=5Hz, 1H), 7.22-7.32(m, 2H), 7.38(d, J=8Hz, 1H), 7.58(s, 1H), 7.62(d, J=8Hz, 1H). |
| Example 486 | (500 MHz, DMSO-d₆)δ 2.27(s, 3H), 2.98(s, 3H), 3.75(s, 2H), 4.70(s, 2H), 5.49(s, 2H), 6.78(d, J=3.7Hz, 1H), 7.08(d, J=5.0Hz, 1H), 7.13(t, J=7.8Hz, 1H), 7.31(m, 2H), 7.35(s, 1H), 7.42(d, J=8.1Hz, 1H), 7.63(s, 1H), 7.66(d, J=7.8Hz, 1H), 7.70(s, 1H), 7.82(s, 1H), 8.36(s, 1H), 9.27(s, 1H). |
| Example 487 | (400 MHz, DMSO-d₆)δ 2.99(s, 3H), 3.74(s, 2H), 4.71(s, 2H), 5.49(s, 2H), 7.09(d, J=4.0Hz, 1H), 7.14(m, 1H), 7.22(t, J=8.0Hz, 1H), 7.31(d, J=3.4Hz, 1H), 7.43(d, J=7.7Hz, 1H), 7.51(m, 1H), 7.62(s, 1H), 7.66(d, J=7.7Hz, 1H), 7.70(d, J=1.5Hz, 1H), 7.81(t, J=1.5Hz, 1H), 7.85(t, J=1.5Hz, 1H), 8.63(s, 1H), 9.26(s, 1H). |
| Example 488 | (300 MHz, DMSO-d₆)δ 2.19(s, 3H), 2.78(s, 3H), 3.00-3.50(m, 8H), 3.74(s, 2H), 3.96(s, 2H), 4.50(t, J=5.8Hz, 2H), 6.90(t, J=7.5Hz, 1H), 7.04(d, J=3.4Hz, 1H), 7.12(m, 3H), 7.30(m, 2H), 7.58(d, J=7.8Hz, 1H), 7.66(s, 1H), 7.77(s, 1H), 7.82(d, J=8.1Hz, 1H). |
| Example 489 | (300 MHz, DMSO-d₆)δ 2.25(s, 3H), 2.79(s, 3H), 3.00-3.50(m, 8H), 3.74(s, 2H), 3.96(s, 2H), 4.48(d, J=5.8Hz, 2H), 6.74(m, 2H), 7.02(d, J=3.4Hz, 1H), 7.11(t, J=7.5Hz, 1H), 7.19(d, J=8.8Hz, 1H), 7.29(m, 3H), 7.58(d, J=7.8Hz, 1H), 7.66(s, 1H), 8.55(s, 1H). |
| Example 490 | (300 MHz, DMSO-d₆)δ 2.22(s, 3H), 2.78(s, 3H), 3.00-3.50(m, 8H), 3.73(2, 2H), 3.88(br s, 2H), 4.47(t, J=5.9Hz, 2H), 6.72(t, J=5.9Hz, 1H), 7.03(m, 3H), 7.29(m, 4H), 7.57(d, J=7.8Hz, 1H), 7.65(s, 1H), 8.52(s, 1H). |

| Example Number | ¹H NMR |
|---|---|
| Example 491 | (500 MHz, DMSO-d$_6$)δ 2.78(s, 3H), 2.99(s, 3H), 3.00-3.50(m, 8H), 3.73(s, 2H), 3.89(br s, 2H), 4.71(s, 2H), 6.96(m, 1H), 7.10(d, J=3.7Hz, 1H), 7.24-7.32(m, 4H), 7.52(m, 2H), 7.57(d, J=7.8Hz, 1H), 7.65(s, 1H), 8.44(s, 1H). |
| Example 492 | (500 MHz, DMSO-d$_6$)δ 2.21(s, 3H), 2.79(s, 3H), 2.99(s, 3H), 3.00-3.50(m, 8H), 3.74(s, 2H), 3.92(br s, 2H), 4.69(s, 2H), 7.07(t, J=7.4Hz, 1H), 7.10(d, 3.4Hz, 1H), 7.15(t, J=7.1Hz, 1H), 7.20(d, J=7.5Hz, 1H), 7.26(d, J=6.8Hz), 7.32(m, 2H), 7.59(d, J=7.8Hz, 1H), 7.67(s, 1H), 7.98(s, 1H). |
| Example 493 | (500 MHz, DMSO-d$_6$)δ 2.79(s, 3H), 3.00(s, 3H), 3.00-3.70(m, 8H), 3.74(s, 2H), 3.82(s, 3H), 3.91(br s, 2H), 4.71(s, 2H), 6.90(m, 1H), 7.01(m, 2H), 7.13(d, J=3.4Hz, 1H), 7.30(d, J=10.3Hz, 1H), 7.33(d, J=3.7Hz, 1H), 7.53, 1H), 7.58(d, J=7.8Hz, 1H), 7.66(s, 1H), 7.81(d, J=7.8Hz, 1H). |
| Example 494 | (500 MHz, DMSO-d$_6$)δ 2.79(s, 3H), 2.99(s, 3H), 3.00-3.50(m, 8H), 3.74(s, 2H), 3.92(br s, 2H), 4.70(s, 2H), 7.10(d, J=3.4Hz, 1H), 7.14(m, 2H), 7.21(m, 1H), 7.32(m, 2H), 7.50(m, 1H), 7.59(d, J=7.8Hz, 1H), 7.67(s, 1H), 8.21(s, 1H). |
| Example 495 | (500 MHz, DMSO-d$_6$)δ 2.79(s, 3H), 3.00(s, 3H), 3.00-3.50(m, 8H), 3.74(s, 2H), 3.89(br s, 2H), 4.71(s, 2H), 7.12(d, J=3.7Hz, 1H), 7.15(t, J=7.6Hz, 1H), 7.29-7.33(m, 3H), 7.47(d, J=8.1Hz, 1H), 7.58(d, J=7.5Hz, 1H), 7.63(d, J=8.1Hz, 1H), 7.66(s, 1H), 8.06(s, 1H). |
| Example 496 | (500 MHz, DMSO-d$_6$)δ 2.78(s, 3H), 3.00(s, 3H), 3.00-3.50(m, 8H), 3.74(s, 2H), 3.88(br s, 2H), 4.71(s, 2H), 7.09(t, J=7.6Hz, 1H), 7.12(d, J=3.7Hz, 1H), 7.25-7.38(m, 3H), 7.53-7.66(m, 3H), 7.79(s, 1H), 8.02(s, 1H). |
| Example 497 | (300 MHz, DMSO-d$_6$)δ 2.27(s, 3H), 2.79(s, 3H), 2.98(s, 3H), 3.00-3.50(m, 8H), 3.73(s, 2H), 3.88(br s, 2H), 4.70(s, 2H), 6.79(d, J=7.4Hz, 1H), 7.11(m, 2H), 7.29-7.40(m, 4H), 7.57(d, J=7.8Hz, 1H), 7.66(s, 1H), 8.35(s, 1H). |
| Example 498 | (500 MHz, DMSO-d$_6$)δ 2.78(s, 3H), 2.99(s, 3H), 3.00-3.50(m, 8H), 3.73(s, 5H), 3.89(br s, 2H), 4.70(s, 2H), 6.55(d, J=9.1Hz, 1H), 7.10(d, J=3.7Hz, 1H), 7.12(dt, J=8.4, 1.5Hz, 1H), 7.15(t, J=7.6Hz, 1H), 7.21(t, J=1.5Hz, 1H), 7.29(d, J=7.8Hz, 1H), 7.32(d, J=3.7Hz, 1H), 7.57(d, J=7.8Hz, 1H), 7.65(s, 1H), 8.41(s, 1H). |
| Example 499 | (500 MHz, DMSO-d$_6$)δ 2.79(s, 3H), 3.00(s, 3H), 3.00-3.50(m, 8H), 3.73(s, 2H), 3.90(br s, 2H), 4.71(s, 2H), 6.77(t, J=9.7Hz, 1H), 7.11(d, J=3.4Hz, 1H), 7.31(m, 4H), 7.51(d, J=12.2Hz, 1H), 7.57(d, J=7.8Hz, 1H), 7.66(s, 1H), 8.65(s, 1H). |
| Example 500 | (500 MHz, DMSO-d$_6$)δ 2.78(s, 3H), 2.99(s, 3H), 3.00-3.50(m, 8H), 3.73(s, 2H), 3.89(br s, 2H), 4.71(s, 2H), 7.01(d, J=9.0Hz, 1H), 7.11(d, J=3.7Hz, 1H), 7.25(m, 4H), 7.46(d, J=7.5Hz, 1H), 7.57(d, J=7.5Hz, 1H), 7.66(s, 1H), 7.72(s, 1H), 8.64(s, 1H). |
| Example 501 | (500 MHz, DMSO-d$_6$)δ 2.78(s, 3H), 2.99(s, 3H), 3.00-3.50(m, 8H), 3.73(s, 2H), 3.87(br s, 2H), 4.71(s, 2H), 7.10(d, J=3.4Hz, 1H), 7.15(m, 1H), 7.23(t, J=7.6Hz, 1H), 7.29(d, J=7.8Hz, 1H), 7.32(d, J=3.4Hz, 1H), 7.51(d, J=8.2Hz, 1H), 7.57(d, J=7.8Hz, 1H), 7.65(s, 1H), 7.85(s, 1H), 8.63(s, 1H). |
| Example 502 | (500 MHz, DMSO-d$_6$)δ 2.78(s, 3H), 3.00(s, 3H), 3.00-3.50(m, 8H), 3.73(s, 2H), 3.88(br s, 2H), 4.73(s, 2H), 7.11(d, J=3.4Hz, 1H), 7.30(m, 3H), 7.50(t, J=7.9Hz, 1H), 7.57(d, J=7.5Hz, 1H), 7.65(s, 1H), 7.82(d, J=8.1Hz, 1H), 7.99(s, 1H), 8.80(s, 1H). |
| Example 503 | (500 MHz, DMSO-d$_6$)δ 2.79(s, 3H), 3.00(s, 3H), 3.00-3.50(m, 8H), 3.73(s, 2H), 3.90(br s, 2H), 4.72(s, 2H), 7.11(d, J=3.4Hz, 1H), 7.30(m, 2H), 7.41(d, J=9.1, 1H), 7.48(t, J=7.8Hz, 1H), 7.58(d, J=7.8Hz, 1H), 7.66(s, 1H), 7.82(d, J=8.1Hz, 1H), 8.01(s, 1H), 8.82(s, 1H). |
| Example 504 | (500 MHz, DMSO-d$_6$)δ 2.78(s, 3H), 3.00(s, 3H), 3.00-3.50(m, 8H), 3.73(s, 2H), 3.87(br s, 2H), 4.72(s, 2H), 7.11(d, J=3.7Hz, 1H), 7.30(m, 3H), 7.43(t, J=8.0Hz, 1H), 7.56(d, 7.8Hz, 1H), 7.65(s, 1H), 7.76(d, J=7.5Hz, 1H), 7.99(s, 1H), 8.75(s, 1H). |
| Example 505 | (500 MHz, DMSO-d$_6$)δ 2.24(s, 3H), 2.79(s, 3H), 2.98(s, 3H), 3.00-3.50(m, 8H), 3.73(s, 2H), 3.91(br s, 2H), 4.69(s, 2H), 7.06(m, 2H), 7.09(d, J=3.4Hz, 1H), 7.31(m, 2H), 7.39(m, 2H), 7.58(d, J=7.8Hz, 1H), 7.66(s, 1H), 8.34(s, 1H). |
| Example 506 | (500 MHz, DMSO-d$_6$)δ 2.79(s, 3H), 2.97(s, 3H), 3.00-3.50(m, 8H), 3.72(s, 3H), 3.74(s, 2H), 3.91(br s, 2H), 4.69(s, 2H), 6.85(m, 2H), 7.09(d, J=3.4Hz, 1H), 7.29(m, 2H), 7.39(m, 2H), 7.58(d, J=7.8Hz, 1H), 7.66(s, 1H), 8.29(s, 1H). |
| Example 507 | (500 MHz, DMSO-d$_6$)δ 2.78(s, 3H), 2.98(s, 3H), 3.00-3.50(m, 8H), 3.73(s, 2H), 3.89(br s, 2H), 4.70(s, 2H), 7.11(m, 3H), 7.30(m, 2H), 7.51(m, 2H), 7.57(d, J=8.1Hz, 1H), 7.65(s, 1H), 8.49(s, 1H). |
| Example 508 | (500 MHz, DMSO-d$_6$)δ 2.79(s, 3H), 2.99(s, 3H), 3.00-3.50(m, 8H), 3.73(s, 2H), 3.91(br s, 2H), 4.70(s, 2H), 7.10(d, J=3.4Hz, 1H), 7.24(m, 2H), 7.31(m, 2H), 7.42(m, 2H), 7.56(m, 1H), 7.66(s, 1H), 8.59(s, 1H). |
| Example 509 | (500 MHz, DMSO-d$_6$)δ 2.79(s, 3H), 2.99(s, 3H), 3.00-3.50(m, 8H), 3.73(s, 2H), 3.90(br s, 2H), 4.70(s, 2H), 7.10(d, J=3.7Hz, 1H), 7.30(m, 2H), 7.43(m, 2H), 7.51(m, 2H), 7.58(d, J=7.8Hz, 1H), 7.65(s, 1H), 8.59(s, 1H). |
| Example 510 | (500 MHz, DMSO-d$_6$)δ 2.79(s, 3H), 3.00(s, 3H), 3.00-3.50(m, 8H), 3.73(s, 2H), 3.91(br s, 2H), 4.73(s, 2H), 7.11(d, J=3.7Hz, 1H), 7.31(m, 2H), 7.57(d, J=7.8Hz, 1H), 7.62(m, 2H), 7.66(s, 1H), 7.76(m, 2H), 8.85(s, 1H). |
| Example 511 | (500 MHz, DMSO-d$_6$)δ 2.78(s, 3H), 3.00(s, 3H), 3.00-3.70(m, 8H), 3.73(s, 2H), 3.88(br s, 2H), 4.71(s, 2H), 7.10(d, J=3.7Hz, 1H), 7.30(m, 4H), 7.57(d, J=7.8Hz, 1H), 7.63(m, 3H), 8.66(s, 1H). |
| Example 512 | (500 MHz, DMSO-d$_6$)δ 2.78(s, 3H), 3.00(s, 3H), 3.00-3.50(m, 8H), 3.72(s, 2H), 3.88(br s, 2H), 4.73(s, 2H), 7.11(d, J=3.8Hz, 1H), 7.29(d, J=8.4Hz, 1H), 7.31(d, J=3.7Hz, 1H), 7.57(d, J=8.7Hz, 1H), 7.65(s, 1H), 7.71(m, 2H), 7.74(m, 2H), 8.95(s, 1H). |
| Example 513 | (500 MHz, DMSO-d$_6$)δ 2.78(s, 3H), 3.00(s, 3H), 3.00-3.50(m, 8H), 3.74(s, 2H), 3.89(br s, 2H), 4.73(s, 2H), 7.11(d, J=3.4Hz, 1H), 7.29(d, J=7.8Hz, 1H), 7.32(m, 2H), 7.44(m, 2H), 7.56(d, J=8.1Hz, 1H), 7.59(m, 2H), 7.63(m, 5H), 8.56(s, 1H). |
| Example 514 | (500 MHz, DMSO-d$_6$)δ 2.78(s, 3H), 2.99(s, 3H), 3.00-3.50(m, 8H), 3.74(s, 2H), 3.88(br s, 2H), 4.71(s, 2H), 6.96(m, 4H), 7.09(m, 2H), 7.29(d, J=7.8Hz, 1H), 7.32(d, J=3.5Hz, 1H), 7.36(m, 2H), 7.53(m, 2H), 7.56(d, J=7.8Hz, 1H), 7.65(s, 1H), 8.48(s, 1H). |
| Example 515 | (500 MHz, DMSO-d$_6$)δ 2.07(s, 3H), 2.26(s, 3H), 2.79(s, 3H), 2.99(s, 3H), 3.00-3.50(m, 8H), 3.74(s, 2H), 3.89(br s, 2H), 4.68(s, 2H), 6.99(m, 1H), 7.04(m, 2H), 7.09(d, J=3.4Hz, 1H), 7.31(m, 2H), 7.59(d, J=7.8, 1H), 7.66(s, 1H), 8.03(s, 1H). |
| Example 516 | (500 MHz, DMSO-d$_6$)δ 2.15(s, 3H), 2.26(s, 3H), 2.79(s, 3H), 2.98(s, 3H), 3.00-3.50(m, 8H), 3.74(s, 2H), 3.89(m, 2H), 4.68(s, 2H), 6.88(d, J=7.5Hz, 1H), 7.08(m, 3H), 7.30(d, J=8.2Hz, 1H), 7.32(d, J=3.5Hz, 1H), 7.58(d, J=7.7Hz, 1H), 7.66(s, 1H), 7.91(s, 1H). |

-continued

| Example Number | ¹H NMR |
|---|---|
| Example 517 | (500 MHz, DMSO-$d_6$)δ 2.23(s, 6H), 2.78(s, 3H), 2.97(s, 3H), 3.00-3.50(m, 8H), 3.73(s, 2H), 3.90(br s, 2H), 4.69(s, 2H), 6.61(s, 1H), 7.09(d, J=3.8Hz, 1H), 7.15(s, 2H), 7.30(m, 2H), 7.57(d, J=7.8Hz, 1H), 7.66(s, 1H), 8.27(s, 1H). |
| Example 518 | (500 MHz, DMSO-$d_6$)δ 2.79(s, 3H), 2.97(s, 3H), 3.00-3.50(m, 8H), 3.74(s, 6H), 3.79(s, 2H), 3.89(m, 2H), 4.68(s, 2H), 6.48(dd, J=2.8, 8.7Hz, 1H), 6.60(d, J=2.5Hz, 1H), 7.10(d, J=3.5Hz, 1H), 7.29(d, J=8.1Hz, 1H), 7.32(d, J=3.7Hz, 1H), 7.45(s, 1H), 7.48(d, J=8.8Hz, 1H), 7.58(d, J=7.8Hz, 1H), 7.66(s, 1H). |
| Example 519 | (500 MHz, DMSO-$d_6$)δ 2.79(s, 3H), 2.98(s, 3H), 3.00-3.50(m, 8H), 3.71(s, 6H), 3.73(s, 2H), 3.89(br s, 2H), 4.70(s, 2H), 6.13(t, J=2.2Hz, 1H), 6.84(m, 2H), 7.09(d, J=3.8Hz, 1H), 7.29(d, J=8.5Hz, 1H), 7.31(d, J=3.7Hz, 1H), 7.57(d, J=7.8Hz, 1H), 7.66(s, 1H), 8.37(s, 1H). |
| Example 520 | (500 MHz, DMSO-$d_6$)δ 2.79(s, 3H), 3.00(s, 3H), 3.00-3.50(m, 8H), 3.74(s, 2H), 3.89(br s, 2H), 4.71(s, 2H), 7.11(d, J=3.4Hz, 1H), 7.30(d, J=9.8Hz, 1H), 7.32(d, J=3.5Hz, 1H), 7.40(dd, J=2.5, 8.8Hz, 1H), 7.58(d, J=7.7Hz, 1H), 7.63(m, 2H), 7.66(s, 1H), 8.16(s, 1H). |
| Example 521 | (500 MHz, DMSO-$d_6$)δ 2.78(s, 3H), 2.99(s, 3H), 3.00-3.50(m, 8H), 3.73(s, 2H), 3.88(br s, 2H), 4.71(s, 2H), 7.11(d, J=3.4Hz, 1H), 7.30(d, J=9.8Hz, 1H), 7.32(d, J=3.5Hz, 1H), 7.51(m, 2H), 7.57(d, J=7.8Hz, 1H), 7.65(s, 1H), 7.91(s, 1H), 8.75(s, 1H). |
| Example 522 | (500 MHz, DMSO-$d_6$)δ 2.78(s, 3H), 3.00(s, 3H), 3.00-3.50(m, 8H), 3.73(s, 2H), 3.87(br s, 2H), 4.71(s, 2H), 7.11(d, J=3.4Hz, 1H), 7.15(t, J=1.9Hz, 1H), 7.29(d, J=7.5Hz, 1H), 7.32(d, J=3.5Hz, 1H), 7.57(d, J=7.8Hz, 1H), 7.65(s, 1H), 7.67(s, 2H), 8.81(s, 1H). |
| Example 523 | (500 MHz, DMSO-$d_6$)δ 2.79(s, 3H), 2.96(s, 3H), 3.00-3.50(m, 8H), 3.74(s, 2H), 3.89(br s, 2H), 4.68(s, 2H), 5.96(s, 2H), 6.81(d, J=8.1Hz, 1H), 6.89(dd, J=8.4, 1.9Hz, 1H), 7.09(d, J=3.4Hz, 1H), 7.18(d, J=1.9Hz, 1H), 7.30(m, 2H), 7.57(d, J=7.8Hz, 1H), 7.66(s, 1H), 8.33(s, 1H). |

EXAMPLE 524

N-[(4-{6-[(4-methyl-1-piperazinyl)methyl]-1,4-dihydroindeno[1,2-c]pyrazol-3-yl}-2-thienyl)methyl]-N'-phenylurea To phenyl isocyanate (13.1 mg, 0.11 mmol) was added a solution of Example 397 (60.5 mg, 0.10 mmol) in tetrahydrofuran (1 mL) and the mixture was agitated at room temperature overnight. The mixture was concentrated under vacuum, the residue was suspended in ethanol (1 mL) and 50% aqueous hydrochloric acid (1 mL), and was agitated at room temperature overnight. The mixture was concentrated under vacuum and the residue was purified by preparative HPLC on a Waters Symmetry C8 column (25 mm×100 mm, 7 μm particle size) using a gradient of 10% to 100% acetonitrile: 0.1% aqueous TFA over 8 minutes (10 minutes run time) at a flow rate of 40 mL/minute to provide 30 mg (36%) of the desired product as the trifluoroacetate salt. ¹H NMR (400 MHz, DMSO-$d_6$) δ 2.77 (s, 3H), 3.00-3.50 (m, 8H), 3.78 (s, 2H), 3.81 (br s, 2H), 4.51 (d, J=5.8 Hz, 2H), 6.77 (t, J=6.1 Hz, 1H), 6.91 (m, 1H), 7.23 (m, 2H), 7.34 (d, J=8.3 Hz, 1H), 7.42 (m, 3H), 7.54 (s, 1H), 7.64 (d, J=7.7 Hz, 1H), 7.67 (d, J=1.5 Hz, 1H), 8.62 (s, 1H). MS (ES): m/z 499 (M+H)⁺.

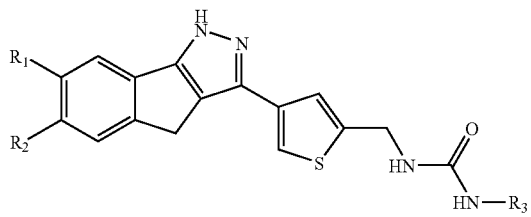

| $R_1$ | $R_2$ | $R_3$ | ¹H NMR(500 MHz, DMSO-$d_6$) | MS (ESI): | Example # (synthesis protocol) |
|---|---|---|---|---|---|
| H | 4-methyl-piperazinyl-ethyl | 2-fluorophenyl | δ2.77(s, 3H), 3.00-3.50(m, 8H), 3.71(s, 2H), 3.79(s, 2H), 4.54(d, J=5.6Hz, 2H), 6.95(m, 1H), 7.09(m, 1H), 7.18(m, 2H), 7.34(m, 1H), 7.43(d, J=1.2Hz, 1H), 7.54(s, 1H), 7.64(d, J=7.8Hz, 1H), 7.69(s, 1H), 8.13(m, 1H), 8.42(d, J=2.5Hz, 1H). | m/z 517 (M + H)⁺ | Example 525 (Example 524) |

-continued

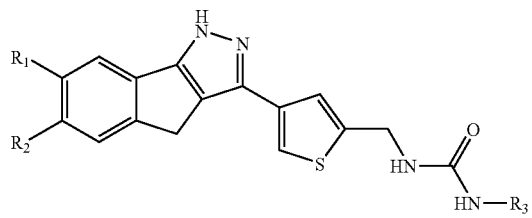

| R₁ | R₂ | R₃ | ¹H NMR(500 MHz, DMSO-d₆) | MS (ESI): | Example # (synthesis protocol) |
|---|---|---|---|---|---|
| H | 4-methylpiperazin-1-yl-ethyl | 2-chlorophenyl | δ2.77(s, 3H), 3.00-3.50(m, 8H), 3.71(s, 2H), 3.79(s, 2H), 4.54(d, J=5.9Hz, 2H), 6.98(m, 1H), 7.26(m, 1H), 7.34(m, 1H), 7.41(dd, J=8.0, 1.4Hz, 1H), 7.45(s, 1H), 7.53(s, 1H), 7.61(m, 2H), 7.69(s, 1H), 8.13(s, 1H), 8.16(dd, J=8.4, 1.6Hz, 1H). | m/z 533 (M)⁺ | Example 526 (Example 524) |
| H | 4-methylpiperazin-1-yl-ethyl | 3-methylphenyl | 2.25(s, 3H), 2.77(s, 3H), 3.00-3.50(m, 8H), 3.78(s, 2H), 3.84(s, 2H), 4.50(d, J=5.9Hz, 2H), 6.74(m, 2H), 7.11(t, J=7.8Hz, 1H), 7.20(d, J=8.3Hz, 1H), 7.26(s, 1H), 7.34(d, J=7.8Hz, 1H), 7.42(s, 1H), 7.54(s, 1H), 7.64(d, J=7.8Hz, 1H), 7.67(s, 1H), 8.53(s, 1H). | m/z 513 (M + H)⁺. | Example 527 (Example 524) |
| H | 4-methylpiperazin-1-yl-ethyl | 3-methoxyphenyl | 2.80(s, 3H), 3.00-3.50(m, 8H), 3.71(d, 3H), 3.79(s, 2H), 3.94(s, 2H), 4.51(d, J=5.6Hz, 2H), 6.49(dd, J=8.1, 1.9Hz, 1H), 6.81(t, J=5.9Hz, 1H), 6.91(d, J=8.1Hz, 1H), 7.13(t, J=8.1Hz, 1H), 7.17(t, J=2.2Hz, 1H), 7.38(d, J=7.8Hz, 1H), 7.43(s, 1H), 7.58(s, 1H), 7.66(d, J=7.8Hz, 1H), 7.68(d, J=1.3Hz, 1H), 8.68(s, 1H). | m/z 529 (M + H)⁺. | Example 528 (Example 524) |
| H | 4-methylpiperazin-1-yl-ethyl | 3-fluorophenyl | 2.78(s, 3H), 3.00-3.50(m, 8H), 3.78(s, 2H), 3.81(s, 2H), 4.51(d, J=5.6Hz, 2H), 6.71(td, J=8.3, 2.2Hz, 1H), 6.90(t, J=6.1Hz, 1H), 7.07(dd, J=8.1, 1.25Hz, 1H), 7.25(m, 1H), 7.35(d, J=6.9Hz, 1H), 7.42(s, 1H), 7.48(m, 1H), 7.55(s, 1H), 7.64(d, J=7.5Hz, 1H), 7.68(d, J=1.3Hz, 1H), 8.91(s, 1H). | m/z 517 (M + H)⁺. | Example 529 (Example 524) |

-continued

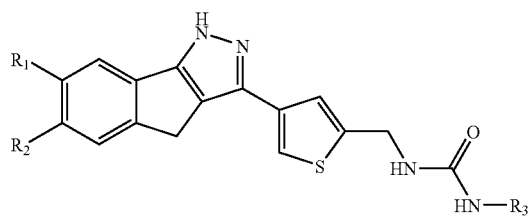

| R1 | R2 | R3 | 1H NMR(500 MHz, DMSO-d6) | MS (ESI): | Example # (synthesis protocol) |
|---|---|---|---|---|---|
| H | 4-methylpiperazin-1-yl-methyl | 3-chlorophenyl | □2.78(s, 3H), 3.00-3.50(m, 8H), 3.71(s, 2H), 3.78(s, 2H), 4.51(d, J=5.9Hz, 2H), 6.91(t, J=6.1Hz, 1H), 6.95(dt, J=7.3, 2.0Hz, 1H), 7.24(m, 2H), 7.35(d, J=7.2Hz, 1H), 7.42(d, J=1.2Hz, 1H), 7.55(s, 1H), 7.64(d, J=7.5Hz, 1H), 7.68(d, J=1.2Hz, 1H), 7.70(t, J=1.9Hz, 1H), 8.89(s, 1H). | m/z 533 (M)+. | Example 530 (Example 524) |
| H | 4-methylpiperazin-1-yl-methyl | 3-SMe-phenyl | □2.43(s, 3H), 2.78(s, 3H), 3.00-3.50(m, 8H), 3.79(s, 2H), 3.96(s, 2H), 4.51(d, J=5.9Hz, 2H), 6.81(m, 2H), 7.12(m, 1H), 7.17(t, J=7.8Hz, 1H), 7.36(d, J=7.5Hz, 1H), 7.42(d, J=1.2Hz, 1H), 7.46(t, J=2.0Hz, 1H), 7.55(s, 1H), 7.65(d, J=7.8Hz, 1H), 7.68(d, J=1.6Hz, 1H), 8.70(s, 1H). | m/z 545 (M + H)+. | Example 531 (Example 524) |
| H | 4-methylpiperazin-1-yl-methyl | 4-methylphenyl | □2.22(s, 3H), 2.79(s, 3H), 3.00-3.50(m, 8H), 3.79(s, 2H), 3.97(s, 2H), 4.50(d, J=5.3Hz, 2H), 6.70(t, J=5.8Hz, 1H), 7.04(m, 2H), 7.30(m, 2H), 7.34(m, 1H), 7.42(s, 1H), 7.52(s, 1H), 7.63(d, J=7.8Hz, 1H), 7.66(d, J=1.6Hz, 1H), 8.48(s, 1H). | m/z 513 (M + H)+. | Example 532 (Example 524) |
| H | 4-methylpiperazin-1-yl-methyl | 4-OMe-phenyl | □2.78(s, 3H), 3.00-3.50(m, 8H), 3.70(m, 3H), 3.78(s, 2H), 3.84(s, 2H), 4.50(d, J=5.6Hz, 2H), 6.67(t, J=6.1Hz, 1H), 6.82(m, 2H), 7.32(m, 2H), 7.35(d, J=7.2Hz, 1H), 7.41(d, J=1.2Hz, 1H), 7.55(s, 1H), 7.64(d, J=7.8Hz, 1H), 7.67(s, 1H), 8.42(s, 1H). | m/z 529 (M + H)+. | Example 533 (Example 524) |
| H | 4-methylpiperazin-1-yl-methyl | 4-fluorophenyl | □2.77(s, 3H), 3.00-3.50(m, 8H), 3.72(s, 2H), 3.78(s, 2H), 4.51(d, J=5.6Hz, 2H), 6.77(t, J=5.9Hz, 1H), 7.07(m, 2H), 7.34(d, J=7.8Hz, 1H), 7.43(m, 3H), 7.54(s, 1H), 7.63(d, J=7.2Hz, 1H), 7.67(s, 1H), 8.66(s, 1H). | m/z 517 (M + H)+. | Example 534 (Example 524) |

-continued

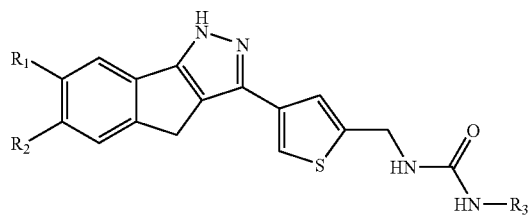

| R1 | R2 | R3 | 1H NMR(500 MHz, DMSO-d6) | MS (ESI): | Example # (synthesis protocol) |
|---|---|---|---|---|---|
| H | 4-methylpiperazin-1-yl-methyl | 4-Cl-phenyl | ☐2.77(s, 3H), 3.00-3.50(m, 8H), 3.69(s, 2H), 3.78(s, 2H), 4.51(d, J=5.9Hz, 2H), 6.83(m, 1H), 7.27(m, 2H), 7.34(d, J=7.5Hz, 1H), 7.42(s, 1H), 7.45(m, 2H), 7.54(s, 1H), 7.64(d, J=8.1Hz, 1H), 7.67(d, J=1.2Hz, 1H), 8.79(s, 1H). | m/z 533 (M)+. | Example 535 (Example 524) |
| H | 4-methylpiperazin-1-yl-methyl | 4-SMe-phenyl | ☐2.42(s, 3H), 2.77(s, 3H), 3.00-3.50(m, 8H), 3.69(s, 2H), 3.78(s, 2H), 4.51(d, J=5.6Hz, 2H), 6.77(t, J=5.9Hz, 1H), 7.18(m, 2H), 7.33(d, J=6.6Hz, 1H), 7.39(m, 2H), 7.42(s, 1H), 7.54(s, 1H), 7.64(d, J=7.8Hz, 1H), 7.67(s, 1H), 8.65(s, 1H). | m/z 545 (M + H)+. | Example 536 (Example 524) |
| H | 4-methylpiperazin-1-yl-methyl | 4-CN-phenyl | ☐2.78(s, 3H), 3.00-3.50(m, 8H), 3.78(s, 2H), 3.83(br s, 2H), 4.53(d, J=5.9Hz, 2H), 7.08(t, J=6.1Hz, 1H), 7.36(d, J=8.1Hz, 1H), 7.43(s, 1H), 7.56(s, 1H), 7.65(m, 6H), 9.26(s, 1H). | m/z 524 (M + H)+. | Example 537 (Example 524) |
| H | 4-methylpiperazin-1-yl-methyl | 2,3-dimethyl-phenyl | ☐2.09(s, 3H), 2.23(s, 3H), 2.79(s, 3H), 3.00-3.50(m, 8H), 3.79(s, 2H), 3.88(s, 2H), 4.51(d, J=5.6Hz, 2H), 6.86(d, J=7.2Hz, 1H), 6.99(m, 2H), 7.37(d, J=7.5Hz, 1H), 7.42(s, 1H), 7.48(d, J=7.8Hz, 1H), 7.57(s, 1H), 7.66(d, J=7.8Hz, 1H), 7.69(d, J=1.2Hz, 1H), 7.82(s, 1H). | m/z 527 (M + H)+. | Example 538 (Example 524) |
| H | 4-methylpiperazin-1-yl-methyl | 2,4-dimethyl-phenyl | ☐2.14(s, 3H), 2.23(s, 3H), 2.78(s, 3H), 3.00-3.50(m, 8H), 3.79(s, 2H), 3.86(br s, 2H), 4.52(d, J=5.6Hz, 2H), 6.72(d, J=7.5Hz, 1H), 7.00(d, J=7.5Hz, 1H), 7.11(t, J=5.9Hz, 1H), 7.37(d, J=7.5Hz, 1H), 7.43(d, J=1.2Hz, 1H), 7.56(s, 1H), 7.63(s, 1H), 7.65(d, J=7.8Hz, 1H), 7.69(d, J=1.2Hz, 1H), 7.71(s, 1H). | m/z 527 (M + H)+. | Example 539 (Example 524) |

-continued

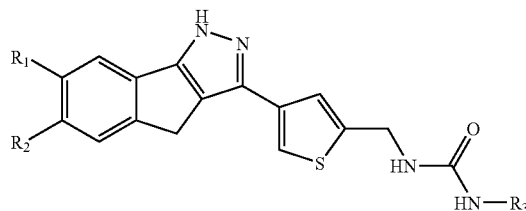

| R₁ | R₂ | R₃ | ¹H NMR(500 MHz, DMSO-d₆) | MS (ESI): | Example # (synthesis protocol) |
|---|---|---|---|---|---|
| H | 4-methylpiperazin-1-yl-methyl | 3,5-dimethylphenyl | 2.20(s, 6H), 2.77(m, 3H), 3.00-3.50(m, 8H), 3.70(br s, 2H), 3.78(s, 2H), 4.50(d, J=5.9Hz, 2H), 6.56(s, 1H), 6.71(t, J=5.9Hz, 1H), 7.04(s, 2H), 7.33(d, J=6.2Hz, 1H), 7.41(d, J=1.2Hz, 1H), 7.53(d, J=1.2Hz, 1H), 7.63(d, J=7.5Hz, 1H), 7.67(s, 1H), 8.43(s, 1H). | m/z 527 (M + H)⁺. | Example 540 (Example 524) |
| H | 4-methylpiperazin-1-yl-methyl | 2,4-dimethoxyphenyl | 2.77(s, 3H), 3.00-3.50(m, 8H), 3.72(s, 3H), 3.78(s, 2H), 3.81(s, 5H), 4.49(d, J=5.6Hz, 2H), 6.44(dd, J=8.9, 2.6Hz, 1H), 6.58(d, J=2.5Hz, 1H), 7.24(t, J=5.8Hz, 1H), 7.34(d, J=8.4Hz, 1H), 7.42(s, 1H), 7.54(s, 1H), 7.64(d, J=7.8Hz, 1H), 7.68(s, 1H), 7.78(s, 1H), 7.88(d, J=8.7Hz, 1H). | m/z 559 (M + H)⁺. | Example 541 (Example 524) |
| H | 4-methylpiperazin-1-yl-methyl | 3,5-dimethoxyphenyl | 2.78(s, 3H), 3.00-3.50(m, 8H), 3.69(s, 6H), 3.79(s, 2H), 3.83(br s, 2H), 4.50(d, J=5.6Hz, 2H), 6.09(t, J=2.0Hz, 1H), 6.65(m, 2H), 6.76(t, J=6.2Hz, 1H), 7.36(d, J=7.2Hz, 1H), 7.42(s, 1H), 7.56(s, 1H), 7.65(d, J=7.5Hz, 1H), 7.67(s, 1H), 8.65(s, 1H). | m/z 559 (M + H)⁺. | Example 542 (Example 524) |
| H | 4-methylpiperazin-1-yl-methyl | 3,4-dichlorophenyl | 2.77(m, 3H), 3.00-3.50(m, 8H), 3.69(s, 2H), 3.77(s, 2H), 4.51(d, J=5.9Hz, 2H), 6.96(t, J=5.8Hz, 1H), 7.29(dd, J=8.7, 2.5Hz, 1H), 7.33(d, J=7.8Hz, 1H), 7.42(s, 1H), 7.47(d, J=9.0Hz, 1H), 7.52(s, 1H), 7.63(d, J=7.5Hz, 1H), 7.67(s, 1H), 7.87(d, J=2.5Hz, 1H), 9.00(s, 1H). | m/z 567 (M)⁺. | Example 543 (Example 524) |
| H | 4-methylpiperazin-1-yl-methyl | 2,4-dichlorophenyl | 2.77(s, 3H), 3.00-3.50(m, 8H), 3.70(s, 2H), 3.79(s, 2H), 4.54(d, J=5.6Hz, 2H), 7.35(m, 2H), 7.45(d, J=1.2Hz, 1H), 7.54(s, 1H), 7.57(d, J=2.5Hz, 1H), 7.64(m, 2H), 7.70(d, J=1.2Hz, 1H), 8.20(d, J=9.0Hz, 1H), 8.23(s, 1H). | m/z 567 (M)⁺. | Example 544 (Example 524) |

-continued

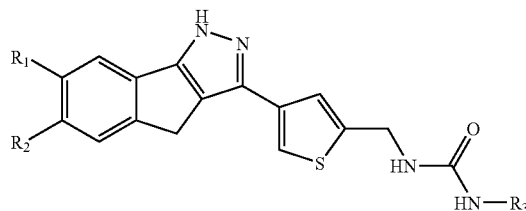

| $R_1$ | $R_2$ | $R_3$ | $^1$H NMR(500 MHz, DMSO-$d_6$) | MS (ESI): | Example # (synthesis protocol) |
|---|---|---|---|---|---|
| H | 4-methylpiperazin-1-ylmethyl | 3,5-dichlorophenyl | 2.79(s, 3H), 3.00-3.50(m, 8H), 3.79(s, 2H), 3.84(br s, 2H), 4.51(d, J=5.9Hz, 2H), 6.86(m, 1H), 7.03(d, J=8.7Hz, 1H), 7.10(m, 1H), 7.36(m, 1H), 7.42(s, 1H), 7.52(d, J=1.9Hz, 1H), 7.56(s, 1H), 7.65(d, J=7.5Hz, 1H), 7.68(d, J=1.2Hz, 1H), 9.12(s, 1H). | m/z 567 (M)$^+$. | Example 545 (Example 524) |
| H | 4-methylpiperazin-1-ylmethyl | ethyl | 1.01(t, J=7.0Hz, 3H), 2.80(s, 3H), 3.04(q, J=7.2Hz, 2H), 3.00-3.50(m, 8H), 3.79(s, 2H), 3.97(s, 2H), 4.40(s, 2H), 5.97(br s, 1H), 6.44(br s, 1H), 7.36(s, 1H), 7.39(d, J=8.1Hz, 1H), 7.59(s, 1H), 7.65(d, J=1.2Hz, 1H), 7.67(d, J=7.8Hz, 1H). | m/z 451 (M + H)$^+$. | Example 546 (Example 524) |
| H | 4-methylpiperazin-1-ylmethyl | n-propyl | 0.85(t, J=7.3Hz, 3H), 1.40(m, 2H), 2.81(s, 3H), 2.98(t, J=6.9Hz, 2H), 3.00-3.50(m, 8H), 3.79(s, 2H), 4.00(s, 2H), 4.41(s, 2H), 6.00(br s, 1H), 6.43(br s, 1H), 7.36(d, J=1.6Hz, 1H), 7.40(d, J=7.8Hz, 1H), 7.59(s, 1H), 7.66(d, J=1.6Hz, 1H), 7.67(d, J=7.8Hz, 1H). | m/z 465 (M + H)$^+$. | Example 547 (Example 524) |
| H | 4-methylpiperazin-1-ylmethyl | isopropyl | 1.05(d, J=6.5Hz, 6H), 2.81(s, 3H), 3.00-3.50(m, 8H), 3.69(m, 1H), 3.79(s, 2H), 3.97(s, 2H), 4.40(s, 2H), 5.84(s, 1H), 6.32(s, 1H), 7.35(s, 1H), 7.39(d, J=7.8Hz, 1H), 7.59(s, 1H), 7.66(d, J=1.6Hz, 1H), 7.67(d, J=7.8Hz, 1H). | m/z 465 (M + H)$^+$. | Example 548 (Example 524) |
| H | 4-methylpiperazin-1-ylmethyl | cyclopentyl | 1.31(m, 2H), 1.50(m, 2H), 1.61(m, 2H), 1.80(m, 2H), 2.80(s, 3H), 3.00-3.50(m, 8H), 3.79(s, 2H), 3.89(m, 1H), 3.97(s, 2H), 4.40(s, 2H), 6.01(br s, 1H), 6.31(s, 1H), 7.36(d, J=1.2Hz, 1H), 7.39(d, J=7.5Hz, 1H), 7.59(s, 1H), 7.66(d, J=1.6Hz, 2H), 7.67(d, J=7.5Hz, 1H). | m/z 491 (M + H)$^+$. | Example 549 (Example 524) |

-continued

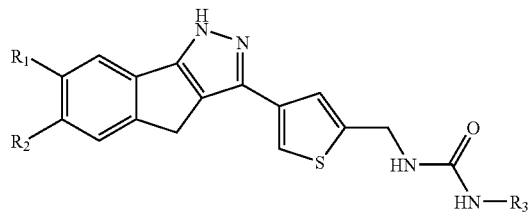

| R₁ | R₂ | R₃ | ¹H NMR(500 MHz, DMSO-d₆) | MS (ESI): | Example # (synthesis protocol) |
|---|---|---|---|---|---|
| H | 4-methylpiperazinyl-CH₂- | cyclohexyl | 1.14(m, 4H), 1.27(m, 2H), 1.51(m, 1H), 1.64(m, 2H), 1.76(m, 2H), 2.77(s, 3H), 3.00-3.50(m, 8H), 3.71(s, 2H), 3.77(s, 2H), 4.40(d, J=5.3Hz, 2H), 5.88(m, 1H), 6.31(s, 1H), 7.34(m, 2H), 7.53(s, 1H), 7.64(m, 2H). | m/z 505 (M + H)⁺. | Example 550 (Example 524) |
| H | 4-methylpiperazinyl-CH₂- | benzyl | 2.78(s, 3H), 3.00-3.50(m, 8H), 3.77(s, 2H), 3.87(br s, 2H), 4.25(d, J=4.4Hz, 2H), 4.45(d, J=4.4Hz, 2H), 6.52(m, 1H), 6.60(m, 1H), 7.22(m, 1H), 7.27(m, 2H), 7.30(m, 2H), 7.37(m, 2H), 7.56(s, 1H), 7.65(m, 2H). | m/z 513 (M + H)⁺. | Example 551 (Example 524) |
| 4-methylpiperazinyl-CH₂- | H | 3-methylphenyl | 2.25(s, 3H), 2.79(s, 3H), 3.00-3.50(m, 8H), 3.79(s, 2H), 3.97(s, 2H), 4.50(d, J=5.6Hz, 2H), 6.73(d, J=7.5Hz, 1H), 6.79(t, J=5.6Hz, 1H), 7.11(dd, J=7.5, 7.5Hz, 1H), 7.18(m, 1H), 7.26(s, 1H), 7.30(d, J=7.8Hz, 1H), 7.33(m, 1H), 7.42(s, 1H), 7.57(d, J=7.8Hz, 1H), 7.68(s, 1H), 8.57(s, 1H). | m/z 513 (M + H). | Example 552 (Example 402) |
| 4-methylpiperazinyl-CH₂- | H | 3-chlorophenyl | 2.80(s, 3H), 3.00-3.50(m, 8H), 3.81(s, 2H), 3.93(br s, 2H), 4.51(d, J=5.9Hz, 2H), 6.95(m, 2H), 7.23(m, 3H), 7.30(d, J=7.5Hz, 1H), 7.34(m, 1H), 7.42(s, 1H), 7.58(d, J=7.5Hz, 1H), 7.69(s, 1H), 8.91(s, 1H). | m/z 533 (M)⁺. | Example 553 (Example 402) |
| 4-methylpiperazinyl-CH₂- | H | 3-bromophenyl | 2.80(s, 3H), 3.00-3.50(m, 8H), 3.80(s, 2H), 3.97(s, 2H), 4.50(d, J=5.6Hz, 2H), 6.96(t, J=5.6Hz, 1H), 7.08(d, J=7.8Hz, 1H), 7.18(m, 2H), 7.26(m, 1H), 7.33(m, 2H), 7.42(s, 1H), 7.58(d, J=7.5Hz, 1H), 7.68(s, 1H), 8.92(s, 1H). | m/z 577, 579(M + H)⁺ | Example 554 (Example 402) |

-continued

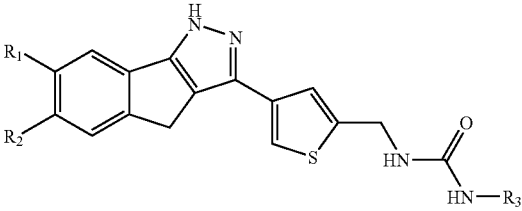

| $R_1$ | $R_2$ | $R_3$ | | $^1$H NMR(500 MHz, DMSO-$d_6$) | MS (ESI): | Example # (synthesis protocol) |
|---|---|---|---|---|---|---|
| 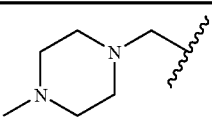 | H | 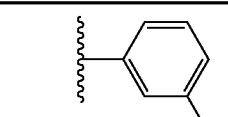 | | 2.80(s, 3H), 3.00-3.50(m, 8H), 3.81(s, 2H), 3.97(s, 2H), 4.52(d, J=5.9Hz, 2H), 7.02(t, J=5.9Hz, 1H), 7.18(d, J=8.7Hz, 1H), 7.25(d, J=7.5Hz, 1H), 7.31(d, J=8.1Hz, 1H), 7.35(m, 1H), 7.43(s, 1H), 7.46(m, 1H), 7.54(m, 1H), 7.58(d, J=7.5Hz, 1H), 7.68(s, 1H), 8.00(s, 1H). | m/z 567 (M + H)$^+$. | Example 555 (Example 402) |
| 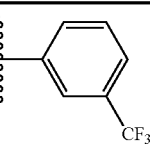 | H | 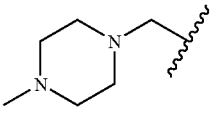 | | 2.79(s, 3H), 3.00-3.50(m, 8H), 3.79(s, 2H), 3.95(bs 2H), 4.53(d, J=5.9Hz, 2H), 7.06(t, J=5.9Hz, 1H), 7.30(d, J=6.6Hz, 2H), 7.36(d, J=7.6Hz, 1H), 7.45(m, 2H), 7.58(d, J=7.6Hz, 1H), 7.63(m, 1H), 7.69(m, 1H), 7.97(s, 1H). | m/z 524 (M + H)$^+$. | Example 556 (Example 402) |
| 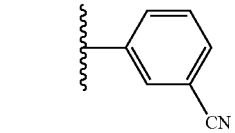 | H | 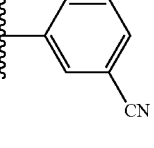 | | 2.80(s, 3H), 3.00-3.50(m, 8H), 3.80(s, 2H), 3.97(s, 2H), 4.51(d, J=5.9Hz, 2H), 7.15(m, 1H), 7.31(d, J=7.8Hz, 1H), 7.34(s, 1H), 7.42(s, 1H), 7.49(m, 1H), 7.52(m, 2H), 7.58(d, J=7.8Hz, 1H), 7.68(s, 1H), 9.17(s, 1H). | m/z 567 (M + H)$^+$. | Example 557 (Example 402) |

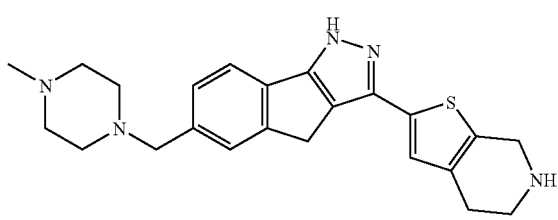

EXAMPLE 558

6-[(4-methylpiperazin-1-yl)methyl]-3-(4,5,6,7-tetrahydrothieno[2,3-c]pyridin-2-yl)-1,4-dihydroindeno[1,2-c]pyrazole To a solution of Example 176 (100 mg, 0.2 mmol) in dichloromethane (1 mL) was added trifluoroacetic acid (760 μl, 9.9 mmol) and the mixture was stirred at ambient temperature for about 90 min. The mixture was concentrated under vacuum and the residue was purified by flash column chromatography on silica gel using dichloromethane/methanol (10:1)+1% ammonium hydroxide as the mobile phase to provide Example 558. MS (ESI): m/z 406 (M+H)$^+$.

EXAMPLE 559

N-(2-methoxyphenyl)-2-{6-[(4-methyl-1-piperazinyl)methyl]-1,4-dihydroindeno[1,2-c]pyrazol-3-yl}-4,7-dihydrothieno[2,3-c]pyridine-6(5H)-carboxamide The procedure for Example 402 was used, substituting Example 558 for Example 396 and 2-methoxyphenyl isocyanate for phenyl isocyanate. The crude product was purified by flash column chromatography on silica gel using dichloromethane/methanol (10:1)+1% ammonium hydroxide as the mobile phase to provide 32 mg (36%) of Example 559.

$^1$H NMR (400 MHz, DMSO-$d_6$) 2.17 (s, 3H), 2.25-3.45 (m, 8H), 2.76 (m, 2H), 3.51 (s,2H) 3.72 (s, 2H), 3.76 (m, 2H), 3.82 (s, 3H), 4.72 (br s, 2H), 6.88 (m, 1H), 7.02 (m, 2H), 7.29 (m, 1H), 7.49 (s, 1H), 7.59 (m, 2H), 7.85 (m, 1H), 8.21 (s, 1H). MS (ESI): m/z 555 (M+H)$^+$.

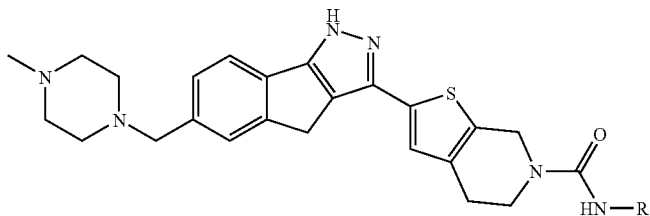

| R | ¹H NMR (500 MHz, DMSO-d₆) | MS (ESI): | Example # (synthesis protocol) | Obtained amt (yield) |
|---|---|---|---|---|
| phenyl | □ 2.76(m, 2H), 2.80(s, 3H), 3.00-3.50 (m, 8H), 3.75(s, 2H), 3.79(m, 2H), 3.94 (br s, 2H), 4.73(s, 2H), 6.95 (m, 1H), 7.21 (s, 1H), 7.25 (m, 2H), 7.39 (d, J=7.8Hz, 1H), 7.48 (m, 2H), 7.59 (s, 1H), 7.64 (d, J= 7.8Hz, 1H), 8.68(s, 1H). | m/z 525 (M + H)⁺. | Example 560 (Example 402) | 27 mg (20%) |
| 2-methylphenyl | □ 2.17(s, 3H), 2.77(m, 2H), 2.81(s, 3H), 3.00-3.50(m, 8H), 3.75(s, 2H), 3.78(m, 2H), 3.97(br s, 2H), 4.72(s, 2H), 7.05(m, 1H), 7.13 (m, 1H), 7.19 (m, 3H), 7.40 (d, J=7.7Hz, 1H), 7.60 (s, 1H), 7.65 (d, J = 7.7Hz, 1H), 8.23(s, 1H). | m/z 539 (M + H)⁺. | Example 561 (Example 402) | 60 mg (43%) |
| 3-methylphenyl | □ 2.26(s, 3H), 2.75(m, 2H), 2.80(s, 3H), 3.00-3.50(m, 8H), 3.75(s, 2H), 3.78(m, 2H), 3.95(br s, 2H), 4.72(s, 2H), 6.77(d, J=7.5Hz, 1H), 7.12 (t, J=7.5Hz, 1H), 7.21 (s, 1H), 7.28 (d, J=8.1Hz, 1H), 7.31 (s, 1H), 7.39 (d, J=7.8Hz, 1H), 7.60(s, 1H), 7.64(d, J=7.8Hz, 1H), 8.61(s, 1H). | m/z 539 (M + H)⁺. | Example 562 (Example 402) | 55 mg (31%) |
| 3-methoxyphenyl | □ 2.76(m, 2H), 2.79(s, 3H), 3.00-3.50 (m, 8H), 3.71(s, 3H), 3.75(s, 2H), 3.78 (m, 2H), 3.88(br s, 2H), 4.72(s, 2H), 6.53 (dd, J=7.8, 1.6Hz, 1H), 7.08 (d, J=8.1 Hz, 1H), 7.14 (t, J=8.4Hz, 1H), 7.17 (t, J= 2.2Hz, 1H), 7.20(s, 1H), 7.38(d, J = 7.8Hz, 1H), 7.58(s, 1H), 7.63(d, J=7.8 Hz, 1H), 8.66 (s, 1H). | m/z 555 (M + H)⁺. | Example 563 (Example 402) | 46 mg (32%) |
| 3-CF₃-phenyl | □ 2.78(m, 2H), 2.80(s, 3H), 3.00-3.50 (m, 8H), 3.75(s, 2H), 3.81(m, 2H), 3.91 (br s, 2H), 4.76(s, 2H), 7.21(s, 1H), 7.29 (d, J=7.8Hz, 1H), 7.39 (d, J=7.8Hz, 1H), 7.49 (t, J=8.1Hz, 1H), 7.59 (s, 1H), 7.64 (d, J=7.8Hz, 1H), 7.78(d, J=8.1 Hz, 1H), 7.94(s, 1H), 9.03(s, 1H). | m/z 593 (M + H)⁺. | Example 564 (Example 402) | 117 mg (78%) |
| 4-methylphenyl | □ 2.23(s, 3H), 2.75(m, 2H), 2.79(s, 3H), 3.00-3.50(m, 8H), 3.75(s, 2H), 3.77(m, 2H), 3.89(br s, 2H), 4.71(s, 2H), 7.05(m, 2H), 7.20 (s, 1H), 7.35 (m, 2H), 7.38 (d, J= 7.7Hz, 1H), 7.58 (s, 1H), 7.64 (d, J = 7.7Hz, 1H), 8.58(s, 1H). | m/z 539 (M + H)⁺. | Example 565 (Example 402) | 58 mg (41%) |
| 4-methoxyphenyl | □ 2.75(m, 2H), 2.80(s, 3H), 3.00-3.50 (m, 8H), 3.71(s, 3H), 3.75(s, 2H), 3.77 (m, 2H), 3.97(br s, 2H), 4.71(s, 2H), 6.84 (m, 2H), 7.20 (s, 1H), 7.36 (m, 2H), 7.40 (d, J=7.7Hz, 1H), 7.60 (s, 1H), 7.65 (d, J= 7.7Hz, 1H), 8.52 (s, 1H). | m/z 555 (M + H)⁺. | Example 566 (Example 402) | 54 mg (38%) |
| 2,3-dimethylphenyl | □ 2.03(s, 3H), 2.16(s, 3H), 2.24(s, 3H), 2.25-2.45(m, 8H), 2.76(m, 2H), 3.51(s, 2H), 3.72(s, 2H), 3.77(m, 2H), 4.71(br s, 2H), 6.96-7.13 (m, 4H), 7.28 (d, J=7.8 Hz, 1H), 7.49 (s, 1H), 7.58 (d, J=7.8Hz, 1H), 8.25 (s, 1H). | m/z 553 (M + H)⁺. | Example 567 (Example 559) | 47 mg (53%) |

| R | ¹H NMR (500 MHz, DMSO-d₆) | MS (ESI): | Example # (synthesis protocol) | Obtained amt (yield) |
|---|---|---|---|---|
| 3,5-dimethylphenyl | 2.21(s, 6H), 2.75(m, 2H), 2.80(s, 3H), 3.00-3.50(m, 8H), 3.75(s, 2H), 3.77(m, 2H), 3.94(br s, 2H), 4.71(s, 2H), 6.60(s, 1H), 7.11 (s, 2H), 7.20 (s, 1H), 7.39 (d, J=7.8Hz, 1H), 7.59 (s, 1H), 7.64 (d, J=7.8Hz, 1H), 8.53(s, 1H). | m/z 553 (M + H)⁺. | Example 568 (Example 402) | 72 mg (50%) |

EXAMPLE 569

N-(2-methoxyphenyl)-2-{6-[(4-methyl-1-piperazinyl)methyl]-1,4-dihydroindeno[1,2-c]pyrazol-3-yl}-4,7-dihydrothieno[2,3-c]pyridine-6(5H)-carboxamide A mixture of o-toluic acid (15 mg, 0.11 mmol), 1-hydroxybenzotriazole hydrate (15 mg, 0.11 mmol) and N-cyclohexylcarbodiimide-N'-methyl polystyrene (240 mg, 0.35 mmol) in N,N-dimethylacetamide/dichloromethane (1:1) (1.5 mL) was shaken at room temperature for about 20 min. Example 395 (58 mg, 0.095 mmol) in dichloromethane (0.7 mL) was added and the mixture was shaken at room temperature overnight. The mixture was filtered and concentrated under vacuum. The residue was dissolved in ethyl acetate (0.6 mL), a 37% solution of hydrochloric acid in ethanol (0.7 mL) was added and the mixture was shaken at room temperature overnight. The mixture was concentrated under vacuum and the residue was purified by preparative HPLC on a Waters Symmetry C8 column (25 mm×100 mm, 7 μm particle size) using a gradient of 10% to 100% acetonitrile:0.1% aqueous TFA over 8 minutes (10 minutes run time) at a flow rate of 40 mL/minute to provide 34 mg (49%) of Example 569 as the trifluoroacetate salt.

¹H NMR (500 MHz, DMSO-d₆) δ 2.38 (s, 3H), 2.80 (s, 3H), 3.00-3.50 (m, 8H), 3.75 (s, 2H), 3.88 (m, 2H), 4.62 (d, J=5 Hz, 2H), 7.04 (d, J=5 Hz, 1H), 7.22-7.38 (m, 6H), 7.58 (s, 1H), 7.62 (d, J=8 Hz, 1H), 8.96 (t, J=5 Hz, 1H). MS (ESI): m/z 498 (M+H)⁺.

| R | ¹H NMR (500 MHz, DMSO-d₆) | MS (ESI): | Example # (synthesis protocol) | Obtained amount (yield) |
|---|---|---|---|---|
| 3-methylphenyl | δ 2.38(s, 3H), 2.79(s, 3H), 3.00-3.50(m, 8H), 3.75(s, 2H), 3.88(br s, 2H), 4.62(d, J=5Hz, 2H), 7.04(d, J=5Hz, 1H), 7.26 (d, J=5Hz, 1H), 7.38 (m, 3H), 7.58 (s, 1H), 7.62(d, J=8Hz, 1H), 7.67(m, 1H), 7.70 (s, 1H), 9.12(t, J=5Hz, 1H) | m/z 498 (M + H)⁺. | Example 570 (Example 569) | 41 mg (60%) |

-continued

| R | ¹H NMR (500 MHz, DMSO-d₆) | MS (ESI): | Example # (synthesis protocol) | Obtained amount (yield) |
|---|---|---|---|---|
| 4-methylbenzyl | δ 2.38(s, 3H), 2.79(s, 3H), 3.00-3.50(m, 8H), 3.75(s, 2H), 3.88(m, 2H), 4.62(d, J=5Hz, 2H), 7.04(d, J=5Hz, 1H), 7.27 (m, 3H), 7.37(d, J=8Hz, 1H), 7.58(br s, 1H), 7.62(d, J=8Hz, 1H), 7.80(m, 2H), 9.09(t, J=5Hz, 1H). | m/z 498 (M + H)⁺. | Example 571 (Example 569) | 49 mg (71%) |
| 2-methylbenzyl | δ 2.26(s, 3H), 2.79(s, 3H), 3.00-3.50(m, 8H), 3.50(s, 2H), 3.74(s, 2H), 3.87(m, 2H), 4.44(d, J=5Hz, 2H), 6.98(d, J=5 Hz, 1H), 7.14(m, 3H), 7.20(m, 1H), 7.28 (d, J=5Hz, 1H), 7.39(d, J=8Hz, 1H), 7.58(s, 1H), 7.62(d, J=8Hz, 1H), 8.61 (t, J=5Hz, 1H). | m/z 512 (M + H)⁺. | Example 572 (Example 569) | 52 mg (74%) |
| 3-methylbenzyl | δ 2.26(s, 3H), 2.79(s, 3H), 3.00-3.50(m, 8H), 3.48(s, 2H), 3.74(s, 2H), 3.82(br s, 2H), 4.44(d, J=5Hz, 2H), 6.97(d, J=5 Hz, 1H), 7.07(m, 3H), 7.20(t, J=8Hz, 1H), 7.26(d, J=5Hz, 1H), 7.39(d, J=8 Hz, 1H), 7.58(s, 1H), 7.62(d, J=8Hz, 1H), 8.64(t, J=5Hz, 1H). | m/z 512 (M + H)⁺. | Example 573 (Example 569) | 54 mg (77%) |
| 4-methylbenzyl | δ 2.26(s, 3H), 2.79(s, 3H), 3.00-3.50(m, 8H), 3.44(s, 2H), 3.74(s, 2H), 3.85(m, 2H), 4.44(d, J=5Hz, 2H), 6.97(d, J=5 Hz, 1H), 7.14(m, 2H), 7.19(m, 2H), 7.26 (d, J=5Hz, 1H), 7.38(d, J=8Hz, 1H), 7.58(s, 1H), 7.62(d, J=8Hz, 1H), 8.64 (t, J=5Hz, 1H). | m/z 512 (M + H)⁺. | Example 574 (Example 569) | 52 mg (74%) |

EXAMPLE 575 tert-butyl 2-{[(5-{1-[bis(4-methoxyphenyl)methyl]-7-[(4-methylpiperazin-1-yl)methyl]-1,4-dihydroindeno[1,2-c]pyrazol-3-yl}thien-2-yl)methyl]amino}-2-oxoethyl(methyl)carbamate To a solution of Example 396 (320 mg, 0.53 mmol) in dichloromethane (10 mL) was added successively N-(t-butoxycarbonyl)sarcosine (125 mg, 0.66 mmol), 1-(3-dimethylaminopropyl)-3-ethylcarbodiimide hydrochloride (253 mg, 1.32 mmol) and 4-(dimethylamino)pyridine (32 mg, 0.26 mmol) and the mixture was stirred at ambient temperature overnight. The mixture was concentrated under vacuum and the residue was purified by flash chromatography on silica gel using dichloromethane/methanol+1% ammonium hydroxide (10:1) as eluent to provide Example 575. MS (DCI-NH₃): m/z 777 (M+H)⁺.

EXAMPLE 576

N²-methyl-N¹-[(5-{7-[(4-methyl-1-piperazinyl)methyl]-1,4-dihydroindeno[1,2-c]pyrazol-3-yl}-2-thienyl)methyl]glycinamide To a solution of Example 575 (310 mg, 0.40 mmol) in dichloromethane was added dropwise trifluoroacetic acid (0.31 mL, 4.0 mmol) and the mixture was stirred at room temperature for about 3 hours. Triethylamine (1.0 mL, 7.2 mmol) was added dropwise and the mixture was evaporated to dryness. The residue was purified by preparative HPLC on a Waters Symmetry C8 column (25 mm×100 mm, 7 μm particle size) using a gradient of 10% to 100% acetonitrile: 0.1% aqueous TFA over 8 minutes (10 minutes run time) at a flow rate of 40 mL/minute to provide 219 mg (60%) of Example 576 as the trifluoroacetate salt. ¹H NMR (300 MHz, DMSO-d₆): δ 2.59 (m, 3H), 2.80 (s, 3H), 3.00-3.50 (m, 8H), 3.73 (s, 2H), 3.76 (m, 2H), 3.95 (br s, 2H), 4.55 (d, J=5.4 Hz, 2H), 7.06 (d, J=3.4 Hz, 1H), 7.31 (m, 2H), 7.59 (d, J=7.5 Hz, 1H), 7.67 (s, 1H), 8.77 (br s, 1H), 9.08 (t, J=8.1 Hz, 1H). MS (ESI): m/z 451 (M+H)⁺.

EXAMPLE 577

1-methyl-3-[(5-{7-[(4-methyl-1-piperazinyl)methyl]-1,4-dihydroindeno[1,2-c]pyrazol-3-yl}-2-thienyl)methyl]-2,4-imidazolidinedione To a solution of Example 576 (60 mg, 0.066 mmol) in tetrahydrofuran (4 mL) was added triethylamine (46 μl, 0.331 mmol) and 1,1'-carbonyldiimidazole (13.4 mg, 0.083 mmol) and the solution was stirred at ambient temperature overnight. The mixture was evaporated to dryness and the residue was purified by preparative HPLC on a Waters Symmetry C8 column (25 mm×100 mm, 7 μm particle size) using a gradient of 10% to 100% acetonitrile:0.1% aqueous TFA over 8 minutes (10 minutes run time) at a flow rate of 40 mL/minute to provide 18 mg (33%) of Example 577 as the trifluoroacetate salt.

$^1$H NMR (500 MHz, DMSO-$d_6$): δ 2.79 (s, 3H), 2.87 (s, 3H), 3.00-3.50 (m, 8H), 3.74 (s, 2H), 3.97 (s, 2H), 4.02 (s, 2H), 4.73 (s, 2H), 7.08 (d, J=3.4 Hz, 1H), 7.28 (d, J=3.4Hz, 1H), 7.30 (d, J=7.8 Hz, 1H), 7.58 (d, J=7.8 Hz, 1H), 7.66 (s, 1H). MS (ESI): m/z 477 (M+H)$^+$.

EXAMPLE 578

2-methyl-N-[(4-{6-[(4-methyl-1-piperazinyl)methyl]-1,4-dihydroindeno[1,2-c]pyrazol-3-yl}-2-thienyl)methyl]benzamide To 1-hydroxybenzotriazole-6-sulfonamidomethyl polystyrene (78 mg, 0.094 mmol) in dichloromethane (1 mL) was added 4-(dimethylamino)pyridine (6.9 mg, 0.056 mmol), followed by a solution of o-toluic acid (19 mg, 0.141 mmol) in N,N-dimethylacetamide. The mixture was agitated at room temperature for about 5 minutes and then a solution of 1,3-diisopropylcarbodiimide (53 mg, 0.423 mmol) in dichloromethane (1 mL) was added. The mixture was agitated for about 2 hour, the solvents were collected by filtration and the resin was washed with N,N-dimethylacetamide and dichloromethane. To the resin was then added a solution of Example 397 (34 mg, 0.056 mmol) and triethylamine (13 μl, 0.094 mmol) in dichloromethane (2 mL) and the mixture was heated to about 55° C. overnight. The resin was collected by filtration and to the filtrate was added polystyrene methylisocyanate (117.5 mg, 0.188 mmol) and methanol (1 mL). The mixture was agitated for about 5 min, then the resin was collected by filtration and the filtrate was evaporated to dryness. The residue was suspended in a 4M solution of hydrochloric acid in 1,4-dioxane (2 mL, 8.0 mmol) and the mixture was agitated at room temperature for about 4 hours. The mixture was evaporated to dryness and the residue was purified by preparative HPLC on a Waters Symmetry C8 column (25 mm×100 mm, 7 μm particle size) using a gradient of 10% to 100% acetonitrile:0.1% aqueous TFA over 8 minutes (10 minutes run time) at a flow rate of 40 mL/minute to provide 21 mg (45%) of Example 578 as the trifluoroacetate salt.

$^1$H NMR (500 MHz, DMSO-$d_6$) δ 2.37 (s, 3H), 2.77 (s, 3H), 3.00-3.50 (m, 8H), 3.74 (br s, 2H), 3.79 (s, 2H), 4.65 (d, J=5.9 Hz, 2H), 7.25 (m, 2H), 7.35 (m, 3H), 7.45 (s, 1H), 7.54 (s, 1H), 7.63 (d, J=7.5 Hz, 1H), 7.69 (s, 1H), 8.96 (t, J=5.9 Hz, 1H). MS (ESI): m/z 498 (M+H)$^+$.

| R | $^1$H NMR (500 MHz, DMSO-$d_6$) | MS (ESI): | Example # (synthesis protocol) | Obtained amt (yield) |
|---|---|---|---|---|
| 3-methylphenyl | 2.37(s, 3H), 2.77(s, 3H), 3.00-3.50 (m, 8H), 3,74(br s, 2H), 3.78(s, 2H), 4.66(d, J=5.9Hz, 2H), 7.33(m, 3H), 7.45(s, 1H), 7.54(s, 1H), 7.63(d, J=7.5 Hz, 1H), 7.68(m, 2H), 7.72(s, 1H), 9.14 (t, J=5.9Hz, 1H). | m/z 498 (M + H)$^+$. | Example 579 (Example 578) | 23 mg (86%) |
| 4-methylphenyl | 2.36(s, 3H), 2.77(s, 3H), 3.00-3.50 (m, 8H), 3,74(br s, 2H), 3.78(s, 2H), 4.66(d, J=5.9Hz, 2H), 7.29(m, 2H), 7.33(d, J=7.5Hz, 1H), 7.45(s, 1H), 7.54(s, 1H), 7.63(d, J=7.5Hz, 1H), 7.66(s, 1H), 7.80(m, 2H), 9.12 (t, J = 5.9Hz, 1H). | m/z 498 (M + H)$^+$. | Example 580 (Example 578) | 19 mg (74%) |
| 4-phenoxyphenyl | 2.77(s, 3H), 3.00-3.50(m, 8H), 3.78 (s, 2H), 3.80(br s, 2H), 4.67(d, J=5.9 Hz, 2H), 7.06(m, 4H), 7.22(t, J=7.5 Hz, 1H), 7.34(d, J=7.5Hz, 1H), 7.44 (m, 3H), 7.54(s, 1H), 7.64 (d, J=7.5Hz, 1H), 7.67(s, 1H), 7.93(m, 2H), 9.15(t, J= 5.9Hz, 1H). | m/z 574 (M + H)$^+$. | Example 581 (Example 578) | 24 mg (77%) |

| R | ¹H NMR (500 MHz, DMSO-d₆) | MS (ESI): | Example # (synthesis protocol) | Obtained amt (yield) |
|---|---|---|---|---|
| ~~~~ OMe, OMe (2,3-dimethoxyphenyl) | 2.77(s, 3H), 3.00-3.50(m, 8H), 3.78 (s, 5H), 3.83(s, 5H), 4.68 (d, J=5.9Hz, 2H), 7.16(m, 3H), 7.34(d, J=7.5Hz, 1H), 7.46(s, 1H), 7.54(s, 1H), 7.64(d, J=7.8Hz, 1H), 7.69(s, 1H), 8.87(t, J = 5.9Hz, 1H). | m/z 544 (M + H)⁺. | Example 582 (Example 578) | 22 mg (76%) |
| ~~~~ 2,4-dichlorophenyl | 2.77(s, 3H), 3.00-3.50(m, 8H), 3.71 (br s, 2H), 3.78(s, 2H), 4.66(d, J=5.9 Hz, 2H), 7.33(d, J=6.9Hz, 1H), 7.50 (m, 4H), 7.63(d, J=7.2Hz, 1H), 7.71 (s, 2H), 9.20(t, J=6.1Hz, 1H). | m/z 552 (M)⁺. | Example 583 (Example 578) | 16 mg (56%) |
| ~~~~ 3,4-dichlorophenyl | 2.77(s, 3H), 3.00-3.50(m, 8H), 3.68 (br s, 2H), 3.78(s, 2H), 4.68(d, J=5.6 Hz, 2H), 7.32(d, J=7.5Hz, 1H), 7.47(s, 1H), 7.52(s, 1H), 7.62(d, J=6.9Hz, 1H), 7.68(s, 1H), 7.79(d, J=8.4Hz, 1H), 7.88(dd, J=8.4, 2.2Hz, 1H), 8.13 (d, J=1.9Hz, 1H), 9.40 (t, J=5.8Hz, 1H). | m/z 552 (M)⁺. | Example 584 (Example 578) | 11 mg (39%) |

EXAMPLE 585

3-methyl-N-[(5-{6-[(4-methyl-1-piperazinyl)methyl]-1,4-dihydroindeno[1,2-c]pyrazol-3yl}-2-thienyl)methyl]benzenesulfonamide To m-toluenesulfonyl chloride (16 μl, 0.11 mmol) was added a solution of Example 395 (58 mg, 0.095 mmol) and triethylamine (50 μl) in dichloromethane (0.7 mL) and the mixture was shaken at room temperature overnight. The mixture was concentrated under vacuum and the residue was dissolved in ethyl acetate (0.6 mL). A 37% solution of hydrochloric acid in ethanol (0.7 mL) was added and the mixture was shaken at room temperature overnight. The mixture was concentrated under vacuum and the residue was purified by preparative HPLC on a Waters Symmetry C8 column (25 mm×100 mm, 7 μm particle size) using a gradient of 10% to 100% acetonitrile:0.1% aqueous TFA over 8 minutes (10 minutes run time) at a flow rate of 40 mL/minute to provide 25 mg (30%) of Example 585 as the trifluoroacetate salt.

¹H NMR (500 MHz, DMSO-d₆) δ 2.39 (s, 3H), 2.79 (s, 3H), 3.00-3.50 (m, 8H), 3.73 (s, 2H), 3.90 (br s, 2H), 4.20 (d, J=5 Hz, 2H), 6.96 (d, J=5 Hz, 1H), 7.23 (d, J=5Hz, 1H), 7.40 (m, 3H), 7.58 (br s, 1H), 7.62 (d, J=8 Hz, 1H), 7.72 (m, 2H), 8.24 (t, J=5 Hz, 1H). MS (ESI): m/z 534 (M+H)⁺.

EXAMPLE 586

4-methyl-N-[(5-{6-[(4-methyl-1-piperazinyl)methyl]-1,4-dihydroindeno[1,2-c]pyrazol-3yl}-2-thienyl)methyl]benzenesulfonamide The procedure for Example 585 was used, substituting p-toluenesulfonyl chloride for m-toluenesulfonyl chloride to provide 22 mg (26%) of Example 586 as the trifluoroacetate salt ¹H NMR (500 MHz, DMSO-d₆) δ 2.39 (s, 3H), 2.79 (s, 3H), 3.00-3.50 (m, 8H), 3.70 (s, 2H), 3.80 (br s, 2H), 4.22 (d, J=5 Hz, 2H), 6.96 (d, J=5 Hz, 1H), 7.23 (d, J=5 Hz, 1H), 7.39 (d, J=5 Hz, 1H), 7.42 (m, 2H), 7.58 (br s, 1H), 7.62 (m, 3H), 8.29 (d, J=5 Hz, 1H). MS (ESI): m/z 534 (M+H)⁺.

EXAMPLE 587

N-[(4-{6-[(4-methyl-1-piperazinyl)methyl]-1,4-dihydroindeno[1,2-c]pyrazol-3-yl}-2-thienyl)methyl]methanesulfonamide To methanesulfonyl chloride (8 μl, 0.1 mmol) was added a solution of Example 397 (60.6 mg, 0.1 mmol) in pyridine (1 mL) and the mixture was agitated at room temperature for about 1 hour. The mixture was concentrated under vacuum, the residue was suspended in ethanol (1 mL) and 50% aqueous hydrochloric acid (1 mL), and was agitated at room temperature overnight. The mixture was concentrated under vacuum and the residue was purified by preparative HPLC on a Waters Symmetry C8 column (25 mm×100 mm, 7 μm particle size) using a gradient of 10% to 100% acetonitrile: 0.1% aqueous TFA over 8 minutes (10 minutes run time) at a flow rate of 40 mL/minute to provide 30 mg (38%) of Example 587 as the trifluoroacetate salt.

$^1$H NMR (500 MHz, DMSO-d$_6$) δ 2.79 (s, 3H), 2.93 (s, 3H), 3.00-3.50 (m, 8H), 3.80 (s, 2H), 3.97 (s, 2H), 4.40 (d, J=6.2 Hz, 2H), 7.38 (d, J=7.8 Hz, 1H), 7.47 (d, J=1.2 Hz, 1H), 7.58 (s, 1H), 7.66 (d, J=7.8 Hz, 1H), 7.74 (d, J=1.6 Hz, 1H), 7.77 (m, 1H). MS (ESI): m/z 458 (M+H)$^+$.

EXAMPLE 593

N,N-dimethyl-N'-[(4-{6-[(4-methyl-1-piperazinyl)methyl]-1,4-dihydroindeno[1,2-c]pyrazol-3yl}-2-thienyl)methyl]sulfamide To dimethylsulfamoyl chloride (11 μl, 0.1 mmol) was added a solution of Example 397 (60.6 mg, 0.1 mmol) in pyridine (1 mL) and the mixture was agitated at room temperature for about 1 hour. The mixture was concentrated under vacuum, the residue was suspended in ethanol (1 mL) and 50% aqueous hydrochloric acid (1 mL), and was agitated at room temperature overnight. The mixture was concentrated under vacuum and the residue was purified by preparative HPLC on a Waters Symmetry C8 column (25 mm×100

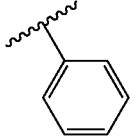

| R | $^1$H NMR (500 MHz, DMSO-d$_6$) | MS (ESI): | Example # (synthesis protocol) | Obtained amt (yield) |
|---|---|---|---|---|
| 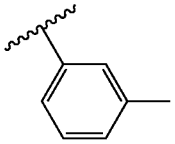 | ☐ 2.80(s, 3H), 3.00-3.50(m, 8H), 3.76(s, 2H), 3.94(br s, 2H), 4.24(d, J=5.9Hz, 2H), 7.35(s, 1H), 7.39(d, J=7.5Hz, 1H), 7.58-7.67(m, 5H), 7.69(s, 1H), 7.84(m, 2H), 8.36 (t, J=5.9Hz, 1H). | m/z 520 (M + H)$^+$. | Example 588 (Example 587) | 24 mg (47%) |
| 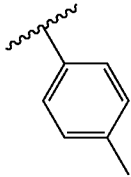 | ☐ 2.36(s, 3H), 2.78(s, 3H), 3.00-3.50(m, 8H), 3.75(s, 2H), 3.84(br s, 2H), 4.24(d, J=5.9Hz, 2H), 7.35(s, 1H), 7.37(d, J=7.5Hz, 1H), 7.43 (m, 1H), 7.47(m, 1H), 7.56(s, 1H), 7.64(m, 3H), 7.67(s, 1H), 8.30(t, J=5.9Hz, 1H). | m/z 534 (M + H)$^+$. | Example 589 (Example 587) | 12 mg (12%) |
| 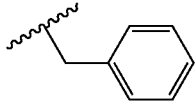 | ☐ 2.35(s, 3H), 2.82(s, 3H), 3.00-3.50(m, 8H), 3.76(s, 2H), 4.08(br s, 2H), 4.20(d, J=5.9Hz, 2H), 7.32(s, 1H), 7.38(m, 2H), 7.42 (d, J=7.5Hz, 1H), 7.62(s, 1H), 7.68(d, J=7.5Hz, 1H), 7.70(s, 1H), 7.71(m, 2H), 8.27 (t, J=5.9Hz, 1H). | m/z 534 (M + H)$^+$. | Example 590 (Example 587) | 24 mg (24%) |
| 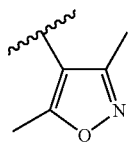 | ☐ 2.79(s, 3H), 3.00-3.50(m, 8H), 3.79(s, 2H), 3.88(br s, 2H), 4.30(d, J=5.9Hz, 2H), 4.37(s, 2H), 7.38(m, 6H), 7.43(s, 1H), 7.57 (s, 1H), 7.65(d, J=7.5Hz, 1H), 7.73(s, 1H), 7.87(t, J=5.9Hz, 1H). | m/z 534 (M + H)$^+$. | Example 591 (Example 587) | 9 mg (9%) |
|  | ☐ 2.33(s, 3H), 2.56(s, 3H), 2.80(s, 3H), 3.00-3.50(m, 8H), 3.77(s, 2H), 3.97(br s, 2H), 4.35(d, J=6.2Hz, 2H), 7.37(s, 1H), 7.39(d, J=7.8Hz, 1H), 7.59(s, 1H), 7.66(d, J=7.8Hz, 1H), 7.70(s, 1H), 8.65(t, J=6.2 Hz, 1H). | m/z 539 (M + H)$^+$. | Example 592 (Example 587) | 28 mg (28%) | mm, 7 μm particle size) using a gradient of 10% to 100% acetonitrile:0.1% aqueous TFA over 8 minutes (10 minutes run time) at a flow rate of 40 mL/minute to provide 6 mg (6%) of Example 593 as the trifluoroacetate salt.

$^1$H NMR (500 MHz, DMSO-d$_6$) δ 2.68 (s, 6H), 2.77 (s, 3H), 3.00-3.50 (m, 8H), 3.76 (br s, 2H), 3.78 (s, 2H), 4.34 (d, J=5.9 Hz, 2H), 7.34 (d, J=7.2 Hz, 1H), 7.45 (s, 1H), 7.54 (s, 1H), 7.63 (d, J=7.2 Hz, 1H), 7.73 (s, 1H), 7.86 (t, J=5.9 Hz, 1H). MS (ESI): m/z 467 (M+H)$^+$.

EXAMPLE 594 phenyl (5-{6-[(4-methyl-1-piperazinyl methyl]-1,4-dihydroindeno[1,2-c]pyrazol-3-yl}-2-thienyl)methylcarbamate To phenyl chloroformate (14 μl, 0.11 mmol) was added a solution of Example 395 (58 mg, 0.095 mmol) and triethylamine (50 μl) in dichloromethane (0.7 mL) and the mixture was shaken at room temperature overnight. The mixture was concentrated under vacuum and the residue was dissolved in ethyl acetate (0.6 mL). A 37% solution of hydrochloric acid in ethanol (0.7 mL) was added and the mixture was shaken at room temperature overnight. The mixture was concentrated under vacuum and the residue was purified by preparative HPLC on a Waters Symmetry C8 column (25 mm×100 mm, 7 μm particle size) using a gradient of 10% to 100% acetonitrile:0.1% aqueous TFA over 8 minutes (10 minutes run time) at a flow rate of 40 mL/minute to provide 33 mg (48%) of Example 594 as the trifluoroacetate salt.

$^1$H NMR (500 MHz, DMSO-d$_6$) δ 2.79 (s, 3H), 3.00-3.50 (m, 8H), 3.78 (s, 2H), 3.97 (s, 2H), 4.44 (d, J=5 Hz, 2H), 7.06 (d, J=5 Hz, 1H), 7.16 (m, 2H), 7.22 (t, J=8Hz, 1H), 7.31 (d, J=5 Hz, 1H), 7.38 (m, 3H), 7.58 (s, 1H), 7.62 (d, J=8 Hz, 1H), 8.42 (t, J=5Hz, 1H). MS (ESI): m/z 500 (M+H)$^+$.

EXAMPLE 595

4-methylphenyl (5-{6-[(4-methyl-1-piperazinyl)methyl]-1,4-dihydroindeno[1,2-c]pyrazol-3yl}-2-thienyl)methylcarbamate The procedure for Example 594 was used, substituting p-tolyl chloroformate for phenyl chloroformate to provide 36 mg (51%) of Example 595 as the trifluoroacetate salt.

$^1$H NMR (500 MHz, DMSO-d$_6$) δ 2.27 (s, 3H), 2.79 (s, 3H), 3.00-3.50 (m, 8H), 3.78 (s, 2H), 3.82 (br s, 2H), 4.50 (d, J=5 Hz, 2H), 7.00 (m, 2H), 7.06 (d, J=5 Hz, 1H), 7.20 (m, 2H), 7.33 (d, J=5 Hz, 1H), 7.38 (d, J=8 Hz, 1H), 7.58 (s, 1H), 7.62 (d, J=8 Hz, 1H), 8.40 (t, J=5Hz, 1H). MS (ESI): m/z 514 (M+H)$^+$.

EXAMPLE 596

N$^1$-(2-methylphenyl)-N$^2$-[(5-{6-[(4-methyl-1-piperazinyl)methyl]-1,4-dihydroindeno[1,2-c]pyrazol-3-yl}-2-thienyl)methyl]glycinamide To phenyl 2-chloro-N-o-tolyl-acetamide (17.5 mg, 0.095 mmol) was added a solution of Example 395 (58 mg, 0.095 mmol) in dichloromethane (0.7 mL) and N,N-dimethylformamide (0.7 mL), followed by sodium carbonate (60 mg, 0.57 mmol) and the mixture was shaken at room temperature overnight. The mixture was concentrated under vacuum and the residue was suspended in ethyl acetate (0.6 mL). A 37% solution of hydrochloric acid in ethanol (1.0 mL) was added and the mixture was shaken at room temperature overnight. The mixture was concentrated under vacuum and the residue was purified by preparative HPLC on a Waters Symmetry C8 column (25 mm×100 mm, 7 μm particle size) using a gradient of 10% to 100% acetonitrile:0.1% aqueous TFA over 8 minutes (10 minutes run time) at a flow rate of 40 mL/minute to provide 25 mg (30%) of Example 596 as the trifluoroacetate salt.

$^1$H NMR (500 MHz, DMSO-d$_6$) δ 2.21 (s, 3H), 2.79 (s, 3H), 3.00-3.50 (m, 8H), 3.73 br s, 2H), 3.78 (s, 2H), 3.99 (s, 2H), 4.50 (s, 2H), 7.15 (t, J=8 Hz, 1H), 7.21 (t, J=8Hz, 1H), 7.24 (d, J=8 Hz, 1H), 7.37 (m, 4H), 7.59 (s, 1H), 7.62 (d, J=8 Hz, 1H), 9.47 (br s, 2H), 9.83 (s, 1H). MS (ESI): m/z 527 (M+H)$^+$.

EXAMPLE 597

2-bromo-N-(3-methylphenyl)acetamide

To a slurry of m-toluidine (15.5 mL, 140 mmol) in a 2N aqueous solution of sodium hydroxide (75 mL) was added dropwise a solution of bromoacetyl chloride (11.6 mL, 140 mmol) in dichloromethane (50 mL) and the reaction mixture was stirred at room temperature for about 30 min. The layers were separated and the organic layer was washed with 1N aqueous hydrochloric acid, dried (MgSO$_4$), filtered and concentrated under vacuum. The residue was triturated twice from dichloromethane/hexane (1:4) to provide 2-bromo-N-m-tolyl-acetamide. MS (DCI-NH$_3$): m/z 245, 247 (M+NH$_3$)$^+$.

EXAMPLE 598

N$^1$-(3-methylphenyl)-N$^2$-[(5-{6-[(4-methyl-1-piperazinyl)methyl]-1,4-dihydroindeno[1,2-c]pyrazol-3-yl}-2-thienyl)methyl]glycinamide The procedure for Example 596 was used, substituting 2-bromo-N-m-tolyl-acetamide for 2-chloro-N-o-tolyl-acetamide to provide 29 mg (35%) of Example 598 as the trifluoroacetate salt.

$^1$H NMR (500 MHz, DMSO-d$_6$) δ 2.28 (s, 3H), 2.79 (s, 3H), 3.00-3.50 (m, 8H), 3.78 (s, 2H), 3.85 (br s, 2H), 3.96 (s, 2H), 4.50 (s, 2H), 6.94 (d, J=5 Hz, 1H), 7.22 (t, J=8Hz, 1H), 7.33 (d, J=5 Hz, 1H), 7.39 (m, 3H), 7.60 (s, 1H), 7.63 (d, J=8 Hz, 1H), 9.47 (br s, 2H), 10.20 (s, 1H). MS (ESI): m/z 527 (M+H)$^+$.

EXAMPLE 599

N-cyano-N'-(3-methylphenyl)-N"-[(5-{6-[(4-methyl-1-piperazinyl)methyl]-1,4-dihydroindeno[1,2-c]pyrazol-3-yl}-2-thienyl)methyl]guanidine A mixture of o-toluidine (14 mg, 0.13 mmol) and diphenyl cyanocarbonimidate (29 mg, 0.12 mmol) in isopropanol (0.5 mL) was shaken for about 3 days. The solvent was removed and the remaining solid was washed with isopropanol and was dried under vacuum. To the solid was added a solution of Example 395 (55 mg, 0.09 mmol) in tetrahydrofuran (0.8 mL) and the mixture was stirred under nitrogen in a heavy walled process vial at about 160 C for about 15 minutes in a microwave synthesizer. The mixture was concentrated under vacuum, the residue was suspended in a 4M solution of hydrochloric acid in 1,4-dioxane (1 mL) and the mixture was shaken at room temperature for about 3.5 hours. The mixture was concentrated under vacuum and the residue was purified by preparative HPLC on a Waters Symmetry C8 column (25 mm×100 mm, 7 μm particle size) using a gradient of 10% to 100% acetonitrile:0.1% aqueous TFA over 8 minutes (10 minutes run time) at a flow rate of 40 mL/minute to provide 25 mg (32%) of Example 599 as the trifluoroacetate salt. ¹H NMR (500 MHz, DMSO-d₆) δ 2.38 (s, 3H), 2.80 (s, 3H), 3.00-3.50 (m, 8H), 3.79 (s, 2H), 3.90 (br s, 2H), 4.60 (d, J=5 Hz, 2H), 7.02 (m, 1H), 7.16 (m, 2H), 7.24 (d, J=8 Hz, 1H), 7.29 (d, J=5 Hz, 1H), 7.33-7.42 (m, 3H), 7.58 (s, 1H), 7.62 (d, J=5Hz, 1H), 10.42 (s, 1H). MS (ESI): m/z 537 (M+H)⁺.

dropwise. The reaction mixture was stirred for about 2.5 hours while being allowed to warm to room temperature, then 3,4-diaminotoluene (25 mg, 0.2 mmol) was added and the solution was stirred at about 35 C for about 2 days. The mixture was evaporated to dryness and the residue was purified by flash column chromatography on silica gel using dichloromethane/methanol (10:1) as eluent to provide Example 605. MS (ESI): m/z 771 (M+H)⁺.

| R₁ | R₂ | ¹H NMR (500 MHz, DMSO-d₆) | MS (ESI): | Example # (synthesis protocol) | Obtained amount (yield) |
|---|---|---|---|---|---|
| H | 2-methylphenyl | δ 2.20(s, 3H), 2.80(s, 3H), 3.00-3.50 (m, 8H), 3.79(s, 2H), 3.82(s, 2H), 4.52 (d, J=5Hz, 2H), 6.99(d, J=5Hz, 1H), 7.14(m, 1H), 7.24(m, 1H), 7.29(d, J=5 Hz, 1H), 7.33-7.42(m, 3H), 7.58(m, 1H), 7.62(m, 1H), 8.92(s, 1H). | m/z 537 (M + H)⁺. | Example 600 (Example 599) | 40 mg (51%) |
| H | 4-methylphenyl | δ 2.38(s, 3H), 2.80(s, 3H), 3.00-3.50 (m, 8H), 3.79(s, 2H), 3.86(br s, 2H), 4.58(d, J=5Hz, 2H), 7.02(d, J=5Hz, 1H), 7.12(d, J=8Hz, 1H), 7.22(d, J=8 Hz, 1H), 7.29(d, J=8Hz, 2H), 7.35-7.40(m, 3H), 7.58(s, 1H), 7.62(d, J=5 Hz, 1H), 10.42(s, 1H). | m/z 537 (M + H)⁺. | Example 601 (Example 599) | 20 mg (25%) |
| Me | 2-methylphenyl | δ 2.22(s, 3H), 2.79(s, 3H), 3.00-3.50 (m, 8H), 3.02(s, 3H), 3.78(s, 2H), 3.82 (br s, 2H), 4.80(s, 2H), 7.09(d, J=5Hz, 1H), 7.17(m, 3H), 7.24(d, J=8Hz, 1H), 7.34(d, J=5Hz, 1H), 7.39(d, J=8 Hz, 1H), 7.59(s, 1H), 7.62(d, J=5Hz, 1H), 8.91(s, 1H). | m/z 551 (M + H)⁺. | Example 602 (Example 599) | 21 mg (30%) |
| Me | 3-methylphenyl | δ 2.28(s, 3H), 2.79(s, 3H), 3.00-3.50 (m, 8H), 3.07(s, 3H), 3.76(s, 2H), 3.82 (br s, 2H), 4.98(s, 2H), 6.97(m, 2H), 7.08(d, J=8Hz, 1H), 7.24(d, J=5Hz, 1H), 7.29(t, J=8Hz, 1H), 7.39(m, 2H), 7.58(s, 1H), 7.62(d, J=5Hz, 1H), 10.04(s, 1H). | m/z 551 (M + H)⁺. | Example 603 (Example 599) | 24 mg (34%) |
| Me | 4-methylphenyl | δ 2.25(s, 3H), 2.80(s, 3H), 2.98(s, 3H), 3.00-3.50(m, 8H), 3.79(s, 2H), 3.83(br s, 2H), 4.80(s, 2H), 6.99(m, 2H), 7.16 (m, 3H), 7.37(d, J=5Hz, 1H), 7.39(d, J= 8Hz, 1H), 7.58(s, 1H), 7.62(d, J=5 Hz, 1H), 9.22(s, 1H). | m/z 551 (M + H)⁺. | Example 604 (Example 599) | 20 mg (29%) |

EXAMPLE 605

N-(2-amino-5-methylphenyl)-N'-[(5-{1-[bis(4-methoxyphenyl)methyl]-6-[(4-methylpiperazin-1-yl)methyl]-1,4-dihydroindeno[1,2-c]pyrazol-3-yl}thien-2-yl)methyl]thiourea A solution of 1,1'-thiocarbonyldiimidazole (26 mg, 0.13 mmol) in acetonitrile (1 mL) and pyridine (1 mL) was cooled to about −20 C and a solution of Example 395 (60 mg, 0.09 mmol) in acetonitrile (1 mL) and pyridine (1 mL) was added

EXAMPLE 606

5-methyl-N-[(5-{6-[(4-methyl-1-piperazinyl)methyl]-1,4-dihydroindeno[1,2-c]pyrazol-3-yl}-2-thienyl)methyl]-1H-benzimidazol-2-amine To a solution of Example 605 (60 mg, 0.08 mmol) in dichloromethane (0.2 mL) and ethanol (4 mL) was added sulfur (5 mg, 0.16 mmol) and mercury(II)oxide (40 mg, 0.18 mmol) and the mixture was heated to reflux for about 2.5 hours. The mixture was cooled to room temperature, filtered

EXAMPLE 608

N-(2-methylphenyl)-N'-(3-{6-[(4-methyl-1-piperazinyl)methyl]-1,4-dihydroindeno[1,2-c]pyrazol-3yl}-2-propynyl)urea To o-tolyl isocyanate (30 mg, 0.15 mmol) was added propargylamine (7.7 mg, 0.14 mmol) in N,N-dimethylformamide (1 mL) and the mixture was stirred at room temperature for about 4 hours. To this solution was added Example 607 (40 mg, 0.1 mmol) followed by dichlorobis(triphenylphosphine)palladium(II) (7 mg, 0.01 mmol), copper iodide (1 mg, 0.005 mmol), triphenylphosphine (8 mg, 0.03 mmol) and triethylamine (0.18 mL, 1.29 mmol) and the mixture was stirred under nitrogen in a heavy walled process vial in a microwave synthesizer at about 120 C for about 25 min. The reaction mixture was filtered through Celite, the filtrate was concentrated under vacuum and the residue was purified by preparative HPLC on a Waters Symmetry C8 column (25 mm×100 mm, 7 µm particle size) using a gradient of 10% to 100% acetonitrile:0.1% aqueous TFA over 8 minutes (10 minutes run time) at a flow rate of 40 mL/minute to provide 27 mg (34%) of Example 608 as the trifluoroacetate salt.

$^1$H NMR (500 MHz, DMSO-$d_6$) δ 2.20 (s, 3H), 2.80 (s, 3H), 3.00-3.50 (m, 8H), 3.67 (s, 2H), 3.81 (br s, 2H), 4.23 (d, J=5 Hz, 2H), 6.90 (t, J=8 Hz, 1H), 7.00 (t, J=6Hz, 1H), 7.11 (t, J=8 Hz, 1H), 7.14 (d, J=7 Hz, 1H), 7.38 (d, J=8 Hz, 1H), 7.57 (s, 1H), 7.62 (d, J=8Hz, 1H), 7.82 (m, 2H). MS (ESI): m/z 455 (M+H)$^+$.

EXAMPLE 607

3-iodo-6-[(4-methylpiperazin-1-yl)methyl]-1,4-dihydroindeno[1,2-c]pyrazole

To a solution of Example 318 (980 mg, 3.16 mmol) in dichloromethane was added 1-methylpiperazine (0.83 mL, 7.5 mmol) and acetic acid (0.43 mL, 7.5 mmol) and the mixture was stirred at room temperature overnight. To this mixture was added sodium triacetoxyborohydride (1.0 g, 4.7 mmol) followed by methanol (5 mL) and stirring at room temperature was continued for about 2 days. The mixture was evaporated to dryness and the residue was purified by flash chromatography on silica gel using dichloromethane/methanol (9:1)+1% ammonium hydroxide as eluent to provide Example 607. MS (ESI): m/z 395 (M+H)$^+$.

(Preceding paragraph, continuation from previous page:)
through Celite and was concentrated under vacuum. To the residue was added a 4M solution of hydrochloric acid in 1,4-dioxane (2 mL) and the mixture was agitated at room temperature overnight. The solution was concentrated under vacuum and the residue was purified by preparative HPLC on a Waters Symmetry C8 column (25 mm×100 mm, 7 µm particle size) using a gradient of 10% to 100% acetonitrile:0.1% aqueous TFA over 8 minutes (10 minutes run time) at a flow rate of 40 mL/minute to provide 5 mg (13%) of Example 606 as the trifluoroacetate salt.

$^1$H NMR (500 MHz, DMSO-$d_6$): ☐ 2.39 (s, 3H), 2.79 (s, 3H), 3.00-3.50 (m, 8H), 3.61 (s, 2H), 3.72 (s, 2H), 4.81 (s, 2H), 7.05 (m, 3H), 7.22 (m, 2H), 7.32 (m, 3H), 7.98 (s, 1H). MS (ESI): m/z 510 (M+H)$^+$.

| $R_1$ | $R_2$ | $^1$H NMR (500 MHz, DMSO-$d_6$) | MS (ESI): | Example # (synthesis protocol) | Obtained amt (yield) |
|---|---|---|---|---|---|
| H | 3-methylphenyl | δ 2.22(s, 3H), 2.80(s, 3H), 3.00-3.50(m, 8H), 3.65(s, 2H), 3.88(br s, 2H), 4.23(d, J=5Hz, 2H), 6.63(t, J=8Hz, 1H), 6.78(d, J=8Hz, 1H), 7.11(t, J=8Hz, 1H), 7.20 (d, J=8Hz, 1H), 7.23(s, 1H), 7.38(d, J=8 Hz, 1H), 7.57(s, 1H), 7.63(d, J=8Hz, 1H), 8.62(s, 1H). | m/z 455 (M + H)$^+$. | Example 609 (Example 608) | 26 mg (33%) |
| H | 4-methylphenyl | δ 2.22(s, 3H), 2.80(s, 3H), 3.00-3.50(m, 8H), 3.65(s, 2H), 3.83(br s, 2H), 4.23(d, J=5Hz, 2H), 6.60(t, J=8Hz, 1H), 7.03(m, 2H), 7.33(m, 2H), 7.38(d, J=8Hz, 1H), 7.57(s, 1H), 7.63(d, J=8Hz, 1H), 8.58(s, 1H). | m/z 455 (M + H)$^+$. | Example 610 (Example 608) | 30 mg (38%) |
| Me | 2-methylphenyl | δ 2.22(s, 3H), 2.80(s, 3H), 3.00-3.50(m, 8H), 3.08(s, 3H), 3.64(s, 2H), 3.83(br s, 2H), 4.75(s, 2H), 6.26(t, J=8Hz, 1H). 7.02(t, J=8Hz, 1H), 7.16(t, J=8Hz, 1H), 7.20(d, J=8Hz, 1H), 7.33(d, J=8Hz, 1H), 7.52(s, 1H), 7.61(d, J=8Hz, 1H), 8.07(s, 1H). | m/z 469 (M + H)$^+$. | Example 611 (Example 608) | 5 mg (7%) |

-continued

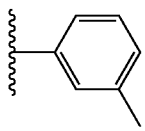

| $R_1$ | $R_2$ | $^1$H NMR (500 MHz, DMSO-$d_6$) | MS (ESI): | Example # (synthesis protocol) | Obtained amt (yield) |
|---|---|---|---|---|---|
| Me | (3-methylphenyl) | δ 2.24(s, 3H), 2.79(s, 3H), 3.00-3.50(m, 8H), 3.08(s, 3H), 3.64(s, 2H), 3.75(br s, 2H), 4.46(s, 2H), 6.79(d, J=8Hz, 1H), 7.15(t, J=8Hz, 1H), 7.30(d, J=8Hz, 1H), 7.34(m, 2H), 7.54(s, 1H), 7.61(d, J=8Hz, 1H), 8.42(s, 1H). | m/z 469 (M + H)$^+$. | Example 612 (Example 608) | 15 mg (22%) |

EXAMPLE 613

3-(2-isopropoxyethoxy)prop-1-yne

To a 60% suspension of sodium hydride in mineral oil (2.3 g, 57.6 mmol) in tetrahydrofuran (65 mL) was added 2-isopropoxyethanol (3.0 g, 28.8 mmol) dropwise at about 0 C. The mixture was stirred for about 30 min, then propargyl bromide (3.2 mL, 28.8 mmol) was added dropwise and the mixture was stirred overnight while being allowed to warm to room temperature. The reaction was quenched by addition of water and the product was extracted with diethyl ether. The combined organic extracts were dried (MgSO$_4$), filtered and the organic solvents were carefully distilled off at atmospheric pressure. The residue was purified by flash chromatography on silica gel using diethyl ether/n-pentane (1:6) as eluent to provide Example 613. $^1$H NMR (500 MHz, CDCl$_3$): δ 1.17 (d, J=6.0 Hz, 6H), 2.42 (t, J=3.0 Hz, 1H), 3.57-3.76 (m, 5H), 4.21 (d, J=3.0 Hz, 2H).

EXAMPLE 614

1-methyl-3-(prop-2-ynyloxy)benzene

A mixture of propargyl benzenesulfonate (1.0 g, 5.1 mmol), m-cresol (0.55 mL, 5.1 mmol) and potassium carbonate (1.1 g, 7.65 mmol) in acetone (40 mL) was stirred at about 56 C for about 2 days. The mixture was cooled, filtered and the solvent was carefully distilled off at atmospheric pressure. The residue was purified by flash chromatography on silica gel using diethyl ether/n-pentane (1:9) as eluent to provide Example 614. $^1$H NMR (500 MHz, CDCl$_3$): □ 2.33 (s, 3H), 2.50 (t, J=3.0 Hz, 1H), 4.66 (d, J=3.0 Hz, 2H), 6.77-6.82 (m, 3H), 7.15-7.21 (m, 1H).

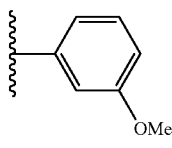

| R | $^1$H NMR (500 MHz, DMSO-$d_6$) | Example # (synthesis protocol) |
|---|---|---|
| 3-methoxyphenyl (OMe) | δ 2.52(t, J=3.0Hz, 1H), 3.79(s, 3H), 4.67(d, J=3.0 Hz, 2H), 6.54-6.59(m, 3H), 7.17-7.23(m, 1H). | Example 615 (Example 614) |
| 3-chlorophenyl (Cl) | δ 2.54(t, J=3.0Hz, 1H), 4.68(d, J=3.0Hz, 2H), 6.85-6.99(m, 3H), 7.19-7.26(m, 1H). | Example 616 (Example 614) |
| 4-chlorophenyl (Cl) | δ 2.52(t, J=3.0Hz, 1H), 4.66(d, J=3.0Hz, 2H), 6.90(d, J=9.0Hz, 2H), 7.25(d, J=9.0Hz, 2H). | Example 617 (Example 614) |

-continued

| R | ¹H NMR (500 MHz, DMSO-d₆) | Example # (synthesis protocol) |
|---|---|---|
| 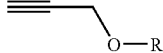 3-CF₃-phenyl | δ 2.55(t, J=3.0Hz, 1H), 4.73(d, J=3.0Hz, 2H), 7.14-7.27(m, 3H), 7.42(m, 1H). | Example 618 (Example 614) |
| 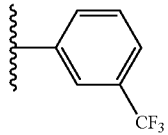 2-methylphenyl | δ 2.24(s, 3H), 2.47(t, J=3.0Hz, 1H), 4.68(d, J=3.0 Hz, 2H), 6.88-6.94(m, 2H), 7.13-7.17(m, 2H). | Example 619 (Example 614) |
| 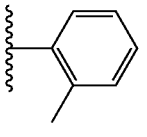 4-F-phenyl | δ 2.51(t, J=3.0Hz, 1H), 4.63(d, J=3.0Hz, 2H), 6.90-7.00(m, 4H). | Example 620 (Example 614) |
| 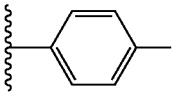 2-Cl-phenyl | δ 2.53(t, J=3.0Hz, 1H), 4.76(d, J=3.0Hz, 2H), 6.92-6.96(m, 1H), 7.07(dd, J=4.0, 12.0Hz, 1H), 7.20-7.24(m, 1H), 7.36(dd, J=4.0, 12.0Hz, 1H). | Example 621 (Example 614) |
| 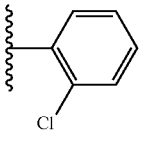 3-OCF₃-phenyl | δ 2.54(t, J=3.0Hz, 1H), 4.69(d, J=3.0Hz, 2H), 6.85-6.92(m, 3H), 7.28-7.32(m, 1H). | Example 622 (Example 614) |
| 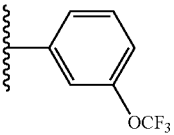 3-isopropoxyphenyl | δ 1.35(d, J=3.0Hz, 6H), 2.47(t, J=3.0Hz, 1H), 4.50(m, 1H), 4.74(d, J=3.0Hz, 2H), 6.81-6.96(m, 3H), 7.06(m, 1H). | Example 623 (Example 614) |
| 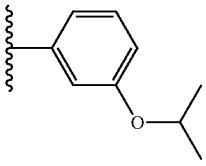 tetrahydrofuranylmethyl | δ 1.58-1.69(m, 1H), 1.84-2.03(m, 3H), 2.43(t, J=3.0Hz, 1H), 3.48-3.61(m, 2H), 3.73-3.92(m, 2H), 4.08(m, 1H), 4.21(d, J=3.0Hz, 2H). | Example 624 (Example 613) |
| 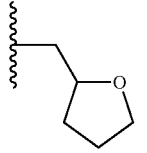 ethoxyethyl | δ 1.22(t, J=6.0Hz, 3H), 2.43(t, J=3.0Hz, 1H), 3.50-3.70(m, 6H), 4.21(d, J=3.0Hz, 2H). | Example 625 (Example 613) |
| 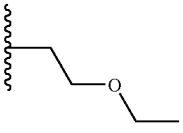 isobutoxyethyl | δ 0.90(d, J=6.0Hz, 6H), 1.88(m, 1H), 2.42(t, J=3.0Hz, 1H), 3.23(d, J=6.0Hz, 2H), 3.62(m, 2H), 3.68(m, 2H), 4.21(d, J=3.0Hz, 2H). | Example 626 (Example 613) |

-continued

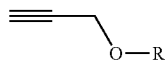

| R | ¹H NMR (500 MHz, DMSO-d₆) | Example # (synthesis protocol) |
|---|---|---|
| ⸺CH₂CH(CH₃)CH₂OCH₃ (isobutyl methyl ether group) | δ 1.18(d, J=6.0Hz, 3H), 2.41(t, J=3.0Hz, 1H), 3.34-3.45(m, 2H), 3.37(s, 3H), 3.85(m, 1H), 4.25(d, J=3.0Hz, 2H). | Example 627 (Example 613) |
| furan-2-ylmethyl | δ 2.46(t, J=3.0Hz, 1H), 4.15(d, J=3.0Hz, 2H), 4.56(s, 2H), 6.34-6.39(m, 2H), 7.42(m, 1H). | Example 628 (Example 613) |
| (tetrahydrofuran-3-yl)methyl | δ 1.57-1.68(m, 1H), 1.97-2.08(m, 1H), 2.44(t, J=3.0Hz, 1H), 2.54(m, 1H), 3.41-3.61(m, 3H), 3.69-3.77(m, 1H), 3.81-3.88(m, 2H), 4.14(d, J=3.0Hz, 2H). | Example 629 (Example 613) |
| (tetrahydro-2H-pyran-2-yl)methyl | δ 1.22-1.67(m, 7H), 2.42(t, J=3.0Hz, 1H), 3.41-3.56(m, 4H), 4.21(d, J=3.0Hz, 2H). | Example 630 (Example 613) |
| tetrahydrofuran-3-yl | δ 1.98-2.05(m, 2H), 2.43(t, J=3.0Hz, 1H), 3.78-3.94(m, 4H), 4.15(d, J=3.0Hz, 2H), 4.36(m, 1H). | Example 631 (Example 613) |
| tetrahydro-2H-pyran-4-yl | δ 1.60(m, 2H), 1.92(m, 2H), 2.41(t, J=3.0Hz, 1H), 3.44(dt, J=4.0, 7.6Hz, 2H), 3.77(m, 1H), 3.96(m, 2H), 4.21(d, J=3.0Hz, 2H). | Example 632 (Example 613) |

EXAMPLE 633

(but-3-ynyloxy)benzene

The procedure for Example 614 was used, substituting 3-butynyl p-toluenesulfonate for propargyl benzenesulfonate and phenol for m-cresol to provide Example 633. ¹H NMR (500 MHz, CDCl₃) δ 2.02 (t, J=2 Hz, 1H), 2.68 (dt, J=8, 2 Hz, 2H), 4.08 (t, J=8 Hz, 2H), 6.96 (m, 3H), 7.30 (m, 2H).

EXAMPLE 634

2-methylpent-4-yn-2-ol

To a slurry of aluminum powder (2.5 g, 93 mmol) and mercury(II) chloride (250 mg, 0.92 mmol) in tetrahydrofuran (45 mL) was added a solution of propargyl bromide (11.1 mL, 100 mmol) in tetrahydrofuran (15 mL) and the mixture was heated to about 45 C for about 30 min. The mixture was cooled to about 0 C, a solution of acetone (8.6 mL, 120 mmol) in tetrahydrofuran (15 mL) was added and the mixture was heated to about 45 C for about 30 min. The reaction mixture was poured into a mixture of ice-water and aqueous saturated ammonium chloride and was extracted with diethyl ether. The combined organic extracts were dried (Na₂SO₄), filtered and concentrated under vacuum to provide Example 634. MS (DCI-NH₃): m/z 99 (M+H)⁺.

EXAMPLE 635

4-[4-(prop-2-ynyloxy)benzyl]morpholine

To a solution of 4-hydroxybenzaldehyde (500 mg, 4.09 mmol) and morpholine (356 mg, 4.09 mmol) in methanol (10 mL) was added macroporous triethylammonium methylpolystyrene borohydride (2.0 g, 6.0 mmol) and the mixture was stirred at ambient temperature for about 2 days. The mixture was filtered and concentrated under vacuum. The residue was dissolved in tetrahydrofuran (20 mL) and to this solution was added propargyl alcohol (229 mg, 4.09 mmol), diphenylphosphino-polystyrene (5.1 g, 8.18 mmol) and diethyl azodicarboxylate (1.06 g, 6.13 mmol). After stirring overnight at room temperature, the mixture was filtered and the filtrate was concentrated under vacuum. The residue was purified by flash chromatography on silica gel using diethyl ether/n-pentane (1:3) as eluent to provide Example 635. MS (DCI-NH$_3$): m/z 232 (M+H)$^+$.

EXAMPLE 636

4-(prop-2-ynyloxy)pyridinium N-oxide

To propargyl alcohol (14.0 mL, 240.5 mmol) was added sodium (386 mg, 16.8 mmol) in small pieces at about 0 C. When all the sodium had dissolved, 4-nitropyridine N-oxide (2.0 g, 14.28 mmol) was added in one portion and the mixture was heated to reflux for about 3 hours. The excess propargyl alcohol was evaporated in high vacuum, the residue was dissolved in water and was neutralized by addition of concentrated hydrochloric acid. The mixture was evaporated to dryness and the residue was digested with chloroform. The combined organic layers were dried (MgSO$_4$) and concentrated under vacuum to provide Example 636. MS (DCI-NH$_3$): m/z 150 (M+H)$^+$.

EXAMPLE 637

4-(prop-2-ynyloxy)pyridine

To a mixture of Example 636 (2.0 g, 13.61 mmol) in chloroform (25 mL) at about 0 C was added dropwise phosphorus trichloride (4 mL, 45.9 mmol). After the addition was complete, the mixture was allowed to warm to room temperature and was then refluxed for about 1 hour. The mixture was cooled, poured onto ice and was basified by addition of concentrated ammonium hydroxide. The mixture was extracted with chloroform and the combined organic extracts were dried (K$_2$CO$_3$) and filtered. The organic solvent was concentrated under vacuum and the residue was purified by flash chromatography on silica gel using dichloromethane/methanol (15:1) as eluent to provide Example 637. MS (DCI-NH$_3$): m/z 134 (M+H)$^+$.

EXAMPLE 638

3-(prop-2-ynyloxy)pyridine

To a mixture of 3-hydroxypyridine (5.0 g, 52 mmol) and potassium hydroxide (8.8 g, 158 mmol) in N,N-dimethylformamide (30 mL) was added propargyl bromide (7.5 g, 63 mmol) dropwise at about 5-10 C and the mixture was stirred at room temperature for about 15 min. The reaction was quenched by addition of water and the product was extracted with dichloromethane. The combined organic extracts were washed with water and then stirred with activated charcoal for 30 min. The mixture was filtered through Celite and the filtrate was concentrated under vacuum to provide Example 638. $^1$H NMR (300 MHz, CDCl$_3$): δ 2.57 (t, J=3.0 Hz, 1H), 4.77 (d, J=3.0 Hz, 2H), 7.30 (m, 2H), 8.27 (dd, J=3.0, 7.6 Hz, 1H), 8.40 (d, J=3.0 Hz, 1H).

EXAMPLE 639

4-prop-2-ynylmorpholine

To a mixture of morpholine (0.78 mL, 8.98 mmol) and potassium carbonate (3.7 g, 26.9 mmol) in acetonitrile (10 mL) was added propargyl bromide (1.0 mL, 8.98 mmol) and the mixture was heated to about 80 C overnight. The reaction was quenched by addition of water and the mixture was extracted with diethyl ether. The combined organic extracts were washed with water, dried (Na$_2$SO$_4$), filtered and concentrated under vacuum to provide Example 639. $^1$H NMR (300 MHz, CD$_3$OD) δ 2.57 (m, 4H) 2.68 (t, J=2.4 Hz, 1H) 3.29 (s, 2H) 3.70 (m, 4H).

EXAMPLE 640

N-prop-2-ynylaniline

A solution of propargyl bromide (0.11 mL, 1 mmol) and aniline (0.46 mL, 5 mmol) in ethanol (2 mL) was stirred at room temperature for about 5 days. The solvent was concentrated under vacuum and the residue was purified by flash chromatography on silica gel using hexane/ethyl acetate (20:1) as eluent to provide Example 640. MS (ESI): m/z 132 (M+H)$^+$.

EXAMPLE 641

1-prop-2-ynylindoline

The procedure for Example 640 was used, substituting indoline for aniline to provide Example 641. MS (ESI): m/z 158 (M+H)$^+$.

EXAMPLE 642

N-prop-2-ynylpyrimidin-2-amine

A mixture of 2-aminopyrimidine (2 g, 20.67 mmol) and propargyl bromide (23 mL, 20.67 mmol) in ethanol (30 mL) was heated to reflux for about 23 hours. The formed precipitate was collected by filtration, washed with ethanol and was recrystallized from ethanol. To the vacuum dried crystals was added water (10 mL) and 10% aqueous sodium hydroxide (5 mL) and the mixture was stirred at room temperature for about 30 min. The solid was collected by filtration, washed with water and was re-crystalized from water to provide Example 642. MS (ESI): m/z 134 (M+H)$^+$.

EXAMPLE 643

N-prop-2-ynylbenzamide

To a solution of propargylamine (6 g, 109 mmol) and triethylamine (15 mL, 109 mmol) in dichloromethane (125 mL) was added dropwise benzoyl chloride (10.5 mL, 90 mmol) at about 0° C. The ice-bath was removed and stirring was continued for about 30 min. Then the reaction mixture was concentrated under vacuum, the residue was diluted with water and was extracted with ethyl acetate. The combined organic extracts were dried (MgSO$_4$), filtered and concentrated under vacuum to provide Example 643. MS (APCI): m/z 160 (M+H)$^+$.

EXAMPLE 644

3-fluoro-N-prop-2-ynylbenzamide

The procedure for Example 643 was used, substituting 3-fluorobenzoyl chloride for benzoyl chloride to provide Example 644. MS (APCI): m/z 178 (M+H)$^+$.

EXAMPLE 645

N-phenylpent-4-ynamide

The procedure for Example 41 was used, substituting 4-pentynoic acid for 6-bromo-4-carboxy-1-indanone and aniline for t-butyl glycinate to provide Example 645. MS (ESI): m/z 174 (M+H)$^+$.

EXAMPLE 646

N-(2-morpholin-4-ylethyl)pent-4-ynamide

To 4-pentynoic acid (981 mg, 10 mmol) was added anhydrous 1-hydroxybenzotriazole (8.11 g, 60 mmol), followed by addition of N,N-dimethylformamide (55 mL) and the mixture was stirred at room temperature until a yellow solution resulted. A solution of 4-(2-aminoethyl)-morpholine (1.31 g, 10.1 mmol) in N,N-dimethylformamide (10 mL) was added, followed by addition of triethylamine (8.35 mL, 60 mmol). After stirring for about 10 min, 1-(3-dimethylaminopropyl)-3-ethylcarbodiimide hydrochloride (6.73 g, 35 mmol) was added and stirring at room temperature was continued overnight. The reaction mixture was diluted with water and was extracted successively with diethyl ether, ethyl acetate, dichloromethane and chloroform/i-propanol (9:1). The combined organic extracts were dried ($Na_2SO_4$), filtered and concentrated under vacuum. The solid residue was purified by silica gel flash chromatography using dichloromethane/methanol (9:1) as eluent to provide Example 646. MS (DCI-$NH_3$): m/z 211 (M+H)$^+$.

EXAMPLE 647

1-[4-(prop-2-ynyloxy)phenyl]-1H-1,2,4-triazole

To 4'-1-(1H-1,2,4-triazol-1-yl) phenol (500 mg, 3.1 mmol) was added N,N-dimethylformamide (5 mL) followed by cesium carbonate (1.27 g, 3.9 mmol) and the brown suspension was stirred at room temperature under nitrogen atmosphere for about 30 min. An 80 wt. % solution of propargyl bromide (0.39 mL, 3.5 mmol) in toluene was added dropwise. After stirring for about 3 hours, the reaction mixture was concentrated to dryness and the residue was partitioned between ethyl acetate and water. The organic layer was separated, dried ($MgSO_4$), filtered and concentrated under vacuum to provide Example 647. MS (DCI-$NH_3$): m/z 200 (M+H)$^+$, 217 (M+$NH_4$)$^+$.

EXAMPLE 648

1-prop-2-ynyl-1H-benzimidazole

To a solution of 1H-benzimidazole (1.0 g, 8.46 mmol) in N,N-dimethylformamide (12 mL) was added a 1M solution of potassium tert-butoxide in tetrahydrofuran (8.04 mL, 8.04 mmol). The solution was stirred at room temperature for about 10 min, before propargyl bromide (0.940 mL, 8.46 mmol) was added dropwise. The solution was stirred at room temperature for about 30 min, poured into a cooled saturated aqueous solution of sodium bicarbonate and was extracted with dichloromethane. The combined organic extracts were washed with water and brine, dried ($Na_2SO_4$), filtered and concentrated under vacuum to provide Example 648. MS (DCI-$NH_3$): m/z 157 (M+H)$^+$.

EXAMPLE 649

1-prop-2-ynyl-1H-benzimidazole

The procedure for Example 648 was used, substituting pyrrolidin-2-one for 1H-benzimidazole and sodium hydride for potassium tert-butoxide to provide Example 649. MS (ESI): m/z 124 (M+H)$^+$.

EXAMPLE 650

3-prop-2-ynyl-1H-indole

To a solution of indole (0.50 g, 4.67 mmol), zinc trifluoromethanesulfonate (1.02 g, 2.8 mmol) and tetrabutylammonium iodide (0.86 g, 2.34 mmol) in toluene (14 mL) was added N,N-diisopropylethylamine (0.89 mL, 5.14 mmol) and the mixture was stirred at room temperature for about 15 min. Propargyl bromide (0.26 mL, 2.34 mmol) was added and the solution was stirred at room temperature for about 4 hours. The solution was quenched by addition of aqueous ammonium chloride and the mixture was extracted with diethyl ether. The combined organic extracts were dried ($MgSO_4$), filtered and concentrated under vacuum, the residue was purified by flash column chromatography on silica gel using hexanes/ethyl acetate (8:1) as the mobile phase to provide Example 650. $^1$H NMR (300 MHz, $CDCl_3$) δ 2.13 (t, J=2.7 Hz, 1H), 3.70 (d, J=2.7 Hz, 2H), 6.55 (s, 1H), 7.37 (m, 2H), 7.64 (m, 2H), 7.98 (br s, 1H).

EXAMPLE 651

2-iodo-1-benzofuran

To a solution of benzofuran (3.0 g, 25.4 mmol) in tetrahydrofuran (36 mL) at about −78° C. was added a 2.5M solution of n-butyllithium in hexanes (10.2 mL, 25.4 mmol). The solution was allowed to warm to about −10° C. and was stirred for about 2 hours. Iodine (6.41 g, 25.4 mmol) was added gradually and the mixture was stirred at about −10° C. for about 30 min. The solution was allowed to warm to room temperature, was quenched by the addition of aqueous ammonium chloride, and was extracted with diethyl ether. The combined organic extracts were washed with aqueous sodium bisulfite and brine, dried ($MgSO_4$), filtered and concentrated under vacuum. The resulting oil was distilled (b.p. 90° C./1.05 mm Hg) to provide Example 651. $^1$H NMR (300 MHz, $CDCl_3$): δ 6.93 (s, 1H), 7.20 (m, 2H), 7.48 (m, 2H).

EXAMPLE 652

(1-benzofuran-2-ylethynyl)(trimethyl)silane

A solution of Example 651 (1.00 g, 4.10 mmol), (trimethylsilyl)acetylene (0.80 mL, 5.68 mmol), dichlorobis(triph enylphosphine)palladium(II) (49 mg, 0.13 mmol), diisopropylamine (1.08 mL, 7.74 mmol) and copper iodide (3 mg, 0.258 mmol) in tetrahydrofuran (5 mL) was stirred at room temperature for about 16 h. The solution was poured into water and was extracted with dichloromethane. The combined organic extracts were washed with brine, dried (MgSO$_4$), filtered and concentrated under vacuum. The residue was purified by flash column chromatography on silica gel using hexane/ethyl acetate (9:1) as eluent to provide Example 652. 1H NMR (300 MHz, CDCl$_3$) δ 0.29 (m, 9H), 6.94 (s, 1H), 7.23 (m, 1H), 7.33 (m, 1H), 7.43 (m, 1H), 7.54 (d, J=7.8 Hz, 1H).

EXAMPLE 653

2-ethynyl-1-benzofuran

A solution of Example 652 (0.74 g, 3.47 mmol) and potassium carbonate (1.45 g, 10.41 mmol) in methanol (3 mL) was stirred at room temperature for about 2 hours. The solution was poured into water and was extracted with diethyl ether. The combined organic extracts were dried (MgSO$_4$), filtered and concentrated under vacuum to provide Example 653. 1H NMR (300 MHz, CDCl$_3$) δ 3.49 (s, 1H), 7.01 (s, 1H), 7.25 (m, 1H), 7.35 (m, 1H), 7.46 (m, 1H), 7.56 (m, 1H).

EXAMPLE 654

3-(5-bromothien-3-yl)-6-[(4-methylpiperazin-1-yl)methyl]indeno[1,2-c]pyrazol-4(1H)-one To a solution of Example 148 (800 mg, 1.87 mmol) in N,N-dimethylformamide (180 mL) was added cesium carbonate (2 g) and the mixture was heated to about 90° C. Air was bubbled through the vigorously stirred mixture and heating was continued overnight. The reaction mixture was cooled, filtered and the filtrate was concentrated under vacuum. The residue was purified by flash chromatography on silica gel using ethyl acetate/methanol (9:1)+1% ammonium hydroxide as eluent to provide Example 654. MS (ESI): m/z 443, 445 (M+H).

EXAMPLE 655

6-[(4-methyl-1-piperazinyl)methyl]-3-[5-(3-phenoxy-1-propynyl)-3-thienyl]-1,4-dihydroindeno[1,2-c]pyrazole The procedure for Example 126 was used, substituting Example 148 for phenyl 2-bromothiophene-4-carboxylate. The crude product was filtered through Celite, the filtrate was concentrated under vacuum and the residue was purified by preparative HPLC on a Waters Symmetry C8 column (25 mm×100 mm, 7 μm particle size) using a gradient of 10% to 100% acetonitrile:0.1% aqueous TFA over 8 minutes (10 minutes run time) at a flow rate of 40 mL/minute to provide 239 mg (62%) of Example 655 as the trifluoroacetate salt. $^1$H NMR (500 MHz, DMSO-d$_6$): δ 2.79 (s, 3H), 3.00-3.50 (m, 8H), 3.82 (s, 2H), 3.89 (br s, 2H), 5.11 (s,2H), 7.01 (m, 1H), 7.05 (m, 2H), 7.35 (m, 3H), 7.57 (s, 1H), 7.66 (d, J=7.8 Hz, 1H),7.74(s,1H), 7.89 (s, 1H). MS (ESI): m/z 481 (M+H)$^+$.

EXAMPLE 656

7-(1H-imidazol-1-ylmethyl)-3-[5-(3-phenoxy-1-propynyl)-3-thienyl]-1,4-dihydroindeno[1,2-c]pyrazole The procedure for Example 126 was used, substituting Example 257 for phenyl 2-bromothiophene-4-carboxylate and tris(dibenzylideneacetone)dipalladium(0) for dichlorobis(triphenylphosphine)palladium(II). The crude product was filtered through Celite, the filtrate was concentrated under vacuum and the residue was purified by preparative HPLC on a Waters Symmetry C8 column (25 mm×100 mm, 7 μm particle size) using a gradient of 10% to 100% acetonitrile:0.1% aqueous TFA over 8 minutes (10 minutes run time) at a flow rate of 40 mL/minute to provide 35 mg (17%) of Example 656 as the trifluoroacetate salt. $^1$H NMR (500 MHz, DMSO-d$_6$): δ 3.83 (s, 2H), 5.11 (s, 2H), 5.51 (s, 2H), 7.00 (m, 1H), 7.05 (m, 2H), 7.35 (m, 3H), 7.60 (d, J=7.8 Hz, 1H), 7.70 (s, 1H), 7.73 (m, 2H), 7.84 (s, 1H), 7.89 (s, 1H), 9.28(s, 1H). MS (ESI): m/z 449 (M+H)$^+$.

EXAMPLE 657

3-{5-[3-(phenylsulfanyl)-1-propynyl]-3-thienyl}-6-(1H-1,2,4-triazol-1-ylmethyl)-1,4-dihydroindeno[1,2-c]pyrazole To a mixture of Example 260 (220 mg, 0.55 mmol) in N,N-dimethylformamide (3.5 mL) was added triphenylphosphine (29 mg, 0.11 mmol), triethylamine (1.16 mL, 8.3 mmol), copper iodide (2.0 mg, 0.12 mmol), phenyl propargyl sulfide (157 μl, 1.10 mmol) and dichlorobis(triphenylphosphine)palladium(II) (39 mg, 0.055 mmol). The mixture was stirred at about 80° C. under an argon atmosphere for about 2 hours, was diluted with water and was extracted with ethyl acetate/diethyl ether. The combined organic extracts were dried (MgSO$_4$), filtered and evaporated in high vacuum. The residue was purified by flash chromatography on silica gel using methanol/ethyl acetate/hexane (1:4:5) as eluent to provide 13 mg (5%) of Example 657. $^1$H NMR (300 MHz, DMSO-d$_6$): δ 3.80 (s, 2H), 4.19 (s, 2H), 5.47 (s, 2H), 7.24-7.83 (m, 10H), 8.00 (s, 1H), 8.71 (s, 1H), 13.18 (s, 1H). MS (ESI): m/z 466 (M+H)$^+$.

| R1 | R2 | R3 | R4 | 1H NMR | MS(ESI): | Example # (synthesis protocol) | Obtained amt (yield) |
|---|---|---|---|---|---|---|---|
| H | (1-methylpiperazin-4-yl)ethyl | H | phenyl | (500MHz, DMSO-d6) δ 2.81(s, 3H), 3.00-3.50(m, 8H), 3.87(s, 2H), 4.00(br s, 2H), 7.41(d, J=7.6Hz, 2H), 7.6Hz, 1H), 7.74(m, 3H), 7.60(m, 3H), 7.69(d, J=7.6Hz, 1H), 7.82(s, 1H), 7.95(s, 1H). | m/z 451 (M+H)+. | Example 658 (Example 655) | 96 mg (52%) |
| H | (1-methylpiperazin-4-yl)ethyl | H | 1-hydroxycyclopentyl | (500MHz, DMSO-d6) δ 1.68(m, 2H), 1.75(m, 4H), 1.90 (m 4H), 2.77(s, 3H), 3.00-3.50(m, 8H), 3.81(s, 2H), 3.91(br s, 2H), 7.335(d, J=7.8Hz, 1H), 7.54(s, 1H), 7.62(d, J=2.3 Hz, 1H), 7.64(d, J=7.8Hz, 1H), 7.81(d, J=1.3Hz, 1H). | m/z 459 (M+2H-OH)+. | Example 659 (Example 655) | 40 mg (43%) |

-continued

| R1 | R2 | R3 | R4 | ¹H NMR | MS(ESI): | Example # (synthesis protocol) | Obtained amt (yield) |
|---|---|---|---|---|---|---|---|
| H | [4-methylpiperazin-1-yl-ethyl] | H | [N-benzyl-N-methyl-aminoethyl] | (500MHz, DMSO-d₆) δ 2.80(s, 3H), 2.81(s, 3H), 3.00-3.50(m, 8H), 3.83(s, 2H), 3.92(br s, 2H), 4.17(m, 2H), 4.38(m, 2H), 7.39(d, J=7.8Hz, 1H), 7.46(m, 2H), 7.50(m, 2H), 7.55(m, 1H), 7.58(s, 1H), 7.66(d, J=7.8 Hz, 1H), 7.85(d, J=1.3Hz, 1H), 7.97(d, J=1.3Hz, 1H). | m/z 508 (M+H)⁺. | Example 660 (Example 655) | 66 mg (67%) |
| H | [4-methylpiperazin-1-yl-ethyl] | H | cyclopentyl | (500MHz, DMSO-d₆) δ 1.60(m, 4H), 1.72(m, 2H), 1.99 (m, 2H), 2.78(s, 3H), 2.93(m, 1H), 3.00-3.50(m, 8H), 3.82(s, 2H), 3.86(br s, 2H), 7.36(d, J=7.5Hz, 1H), 7.56(s, 1H), 7.58(d, J=1.2Hz, 1H), 7.65(d, J=7.5 Hz, 1H), 7.77(d, J=1.2Hz, 1H). | m/z 443 (M+H)⁺. | Example 661 (Example 655) | 26 mg (28%) |

-continued

| R₁ | R₂ | R₃ | R₄ | ¹H NMR | MS(ESI) | Example # (synthesis protocol) | Obtained amt (yield) |
|---|---|---|---|---|---|---|---|
| H | 4-methylpiperazin-1-yl-ethyl | H | CH₂CH₂N(CH₂CH₃)₂ | (500MHz, DMSO-d₆) δ 1.28(t, J=7.2 Hz, 6H), 2.78(s, 3H), 3.00-3.50(m, 8H), 3.27(m, 4H), 3.82(s, 2H), 3.86(br s, 2H), 4.47(s, 2H), 7.37(d, J=7.5Hz, 1H), 7.56 (s, 1H), 7.65(d, J=7.5Hz, 1H), 7.83(d, J=1.2Hz, 1H), 7.96 (d, J=1.2Hz, 1H). | m/z 460 (M+H)⁺ | Example 662 (Example 655) | 38 mg (40%) |
| H | 4-methylpiperazin-1-yl-ethyl | H | CH₂CH₂CN | (500MHz, DMSO-d₆) δ 2.80(s, 3H), 2.85(m, 4H), 3.00-3.50(m, 8H), 3.83(s, 2H), 3.92(br s, 2H), 7.38(d, J=7.5Hz, 1H), 7.58(s, 1H), 7.67(m, 2H), 7.83 (d, J=1.2Hz, 1H). | m/z 428 (M+H)⁺ | Example 663 (Example 655) | 41 mg (46%) |
| H | 4-methylpiperazin-1-yl-ethyl | H | CH(OH)C₅H₁₁ | (500MHz, DMSO-d₆) δ 0.89(t, J=6.9 Hz, 3H), 1.31(m, 4H), 1.44(m, 2H), 1.66(m, 2H), 2.79(s, 3H), 3.00-3.50(m, 8H), 3.83(s, 2H), 3.93(br s, 2H), 4.48 (t, J=6.6Hz, 1H), 7.38(d, J=7.5Hz, 1H), 7.57(s, 1H), 7.65(s, 1H), 7.66(d, J=7.5Hz, 1H), 7.83 (s, 1H). | m/z 475 (M+H)⁺ | Example 664 (Example 655) | 40 mg (43%) |

| R₁ | R₂ | R₃ | R₄ | ¹H NMR | MS(ESI): | Example # (synthesis protocol) | Obtained amt (yield) |
|---|---|---|---|---|---|---|---|
| H | [N-methylpiperazinyl-ethyl] | H | [2-amino-2-methylpropyl] | (500MHz, DMSO-d₆) δ 1.66(s, 6H), 2.80(s, 3H), 3.00-3.50(m, 8H), 3.82(s, 2H), 3.90(br s, 2H), 7.39(d, J=7.8Hz, 1H), 7.57(d, J=7.5Hz, 1H), 7.66(d, J=7.5Hz, 1H), 7.74(d, J=1.3 Hz, 1H), 7.94(d, J= 1.3Hz, 1H), 8.66(br s, 2H). | m/z 432 (M+H)⁺ | Example 665 (Example 655) | 48 mg (53%) |
| H | [N-methylpiperazinyl-ethyl] | H | [p-tolyl] | (500MHz, DMSO-d₆) δ 2.36(s, 3H), 2.77(s, 3H), 3.00-3.50(m, 8H), 3.84(s, 2H), 3.93(br s, 2H), 7.27(m, 2H), 7.35 (d, J=7.8Hz, 1H), 7.47(m, 2H), 7.55(s, 1H), 7.65(d, J=7.8 Hz, 1H), 7.78(d, J= 1.3Hz, 1H), 7.90(d, J=1.3Hz, 1H). | m/z 465 (M+H)⁺ | Example 666 (Example 655) | 13 mg (14%) |
| H | [N-methylpiperazinyl-ethyl] | H | [dimethylaminomethyl] | (500MHz, DMSO-d₆) δ 2.77(s, 3H), 2.89(s, 6H), 3.00-3.50(m, 8H), 3.81(s, 4H), 4.40(s, 2H), 7.34(d, J=7.8Hz, 1H), 7.55(s, 1H), 7.64(d, J=7.8Hz, 1H), 7.83(d, J=1.3 Hz, 1H), 7.95(d, J= 1.3Hz, 1H). | m/z 432 (M+H)⁺ | Example 667 (Example 655) | 45 mg (50%) |

| R1 | R2 | R3 | R4 | ¹H NMR | MS(ESI): | Example # (synthesis protocol) | Obtained amt (yield) |
|---|---|---|---|---|---|---|---|
| H | N-methylpiperazinyl-ethyl | H | 2-pyridyl | (500MHz, DMSO-d₆) δ 2.79(s, 3H), 3.00-3.50(m, 8H), 3.86(s, 2H), 3.91(br s, 2H), 7.38(d, J=7.5Hz, 2H), 7.45(m, 1H), 7.59(s, 1H), 7.68(m, 2H), 7.90(m, 2H), 8.00(d, J=1.2Hz, 1H), 8.64(m, 1H). | m/z 452 (M+H)⁺ | Example 668 (Example 655) | 28 mg (30%) |
| H | N-methylpiperazinyl-ethyl | H | phenethyl | (500MHz, DMSO-d₆) δ 2.79(m, 5H), 2.88(m, 2H), 3.00-3.50(m, 8H), 3.81(s, 2H), 3.89(br s, 2H), 7.23(m, 1H), 7.32(m, 4H), 7.38(d, J=7.7Hz, 1H), 7.57(m, 2H), 7.67(d, J=7.7Hz, 1H), 7.77(s, 1H). | m/z 479 (M+H)⁺ | Example 669 (Example 655) | 38 mg (40%) |
| H | N-methylpiperazinyl-ethyl | H | phthalimidoethyl | (500MHz, DMSO-d₆) δ 2.77(s, 3H), 3.00-3.50(m, 8H), 3.80(s, 2H), 3.88(br s, 2H), 4.70(s, 2H), 7.33(d, J=7.5Hz, 1H), 7.52(s, 1H), 7.63(d, J=7.5Hz, 1H), 7.70(s, 1H), 7.85(s, 1H), 7.89(m, 2H), 7.94(m, 2H). | m/z 534 (M+H)⁺ | Example 670 (Example 655) | 10 mg (10%) |

-continued

| R₁ | R₂ | R₃ | R₄ | ¹H NMR | MS(ESI): | Example # (synthesis protocol) | Obtained amt (yield) |
|---|---|---|---|---|---|---|---|
| H | [1-methylpiperazin-4-yl-ethyl] | H | [thiomorpholine-1,1-dioxide-4-yl-methyl] | (500MHz, DMSO-d₆) δ 2.81(s, 3H), 3.00-3.50(m, 8H), 3.05(m, 4H), 3.18 (m, 4H), 3.81(s, 2H), 3.84(s, 2H), 3.99(br s, 2H), 7.40(d, J=7.8Hz, 2H), 7.60(s, 1H), 7.68(d, J=7.8 Hz, 1H), 7.71(d, J=1.3Hz, 1H), 7.86(d, J=1.3Hz, 1H). | m/z 522 (M+H)⁺ | Example 671 (Example 655) | 62 mg (62%) |
| H | [1-methylpiperazin-4-yl-ethyl] | H | [4-methoxyphenyl-methyl] | (500MHz, DMSO-d₆) δ 2.79(s, 3H), 3.00-3.50(m, 8H), 3.81(s, 3H), 3.86(s, 2H), 3.91(br s, 2H), 7.01(m, 2H), 7.38 (d, J=7.8Hz, 1H), 7.53(m, 2H), 7.58(s, 1H), 7.67(d, J=7.8 Hz, 1H), 7.75(s, 1H), 7.89(s, 1H). | m/z 481 (M+H)⁺ | Example 672 (Example 655) | 36 mg (37%) |
| H | [1-methylpiperazin-4-yl-ethyl] | H | [4-chlorophenyl-methyl] | (500MHz, DMSO-d₆) δ 2.77(s, 3H), 3.00-3.50(m, 8H), 3.84(s, 2H), 3.98(br s, 2H), 7.35(d, J=7.8Hz, 1H), 7.53(m, 2H), 7.55(s, 1H), 7.62(m, 2H), 7.65 (d, J=7.8Hz, 1H), 7.82(d, J=1.3Hz, 1H), 7.94(d, J=1.3 Hz, 1H). | m/z 485 (M)⁺ | Example 673 (Example 655) | 16 mg (17%) |

| R₁ | R₂ | R₃ | R₄ | ¹H NMR | MS(ESI) | Example # (synthesis protocol) | Obtained amt (yield) |
|---|---|---|---|---|---|---|---|
| H | (N-methylpiperazinyl-ethyl) | H | 1-aminocyclohexyl | (500MHz, DMSO-d₆) δ 1.18(m, 2H), 1.56(m, 2H), 1.68(m, 2H), 1.79(m, 2H), 2.09(m, 2H), 2.79(s, 3H), 3.00-3.50(m, 8H), 3.83(s, 2H), 3.88(br s, 2H), 7.38(d, J=7.8Hz, 1H), 7.57(s, 1H), 7.66(d, J=7.8Hz, 1H), 7.78(s, 1H), 7.94(s, 1H), 8.69(br s, 2H). | m/z 472 (M+H)⁺ | Example 674 (Example 655) | 57 mg (60%) |
| H | (N-methylpiperazinyl-ethyl) | H | 3-hydroxypropyl | (500MHz, DMSO-d₆) δ 2.62(t, J=6.5 Hz, 2H), 2.79(s, 3H), 3.00-3.50(m, 8H), 3.60(t, J=6.5Hz, 2H), 3.82(s, 2H), 3.91(br s, 2H), 7.37 (d, J=7.8Hz, 1H), 7.56(s, 1H), 7.61(s, 1H), 7.66(d, J=7.8 Hz, 1H), 7.78(s, 1H). | m/z 419 (M+H)⁺ | Example 675 (Example 655) | 25 mg (28%) |

| R₁ | R₂ | R₃ | R₄ | ¹H NMR | MS(ESI): | Example # (synthesis protocol) | Obtained amt (yield) |
|---|---|---|---|---|---|---|---|
| H | 4-methylpiperazinyl-ethyl | H | 1-hydroxycyclohexyl | (500MHz, DMSO-d₆) δ 1.26(m, 2H), 1.47(m, 2H), 1.58 (m, 2H), 1.66(m, 2H), 1.84(m, 2H), 2.79(s, 3H), 3.00-3.50(m, 8H), 3.83(s, 2H), 3.87(br s, 2H), 7.37(d, J=7.8Hz, 1H), 7.56(s, 1H), 7.64(s, 1H), 7.66(d, J=7.8Hz, 1H), 7.82 (s, 1H). | m/z 473 (M+H)⁺ | Example 676 (Example 655) | 39 mg (41%) |
| H | 4-methylpiperazinyl-ethyl | H | 2-hydroxy-2-methylpropyl | (500MHz, DMSO-d₆) δ 1.49(s, 6H), 2.80(s, 3H), 3.00-3.50(m, 8H), 3.83(s, 2H), 3.93(br s, 2H), 7.38(d, J=7.6Hz, 1H), 7.58(s, 1H), 7.63(d, J=1.3Hz, 1H), 7.67(d, J=7.6 Hz, 1H), 7.83(d, J= 1.3Hz, 1H). | m/z 433 (M+H)⁺ | Example 677 (Example 655) | 46 mg (51%) |
| H | 4-methylpiperazinyl-ethyl | H | 1-hydroxypropyl (sec-butanol) | (500MHz, DMSO-d₆) δ 0.98(t, J=7.5 Hz, 3H), 1.68(m, 2H), 2.79(s, 3H), 3.00-3.50(m, 8H), 3.83(d, J=6.9Hz, 2H), 3.90(br s, 2H), 4.44(t, J=6.2Hz, 1H), 7.37(d, J=7.8 Hz, 1H), 7.57(s, 1H), 7.66(m, 2H), 7.84(s, 1H). | m/z 433 (M+H)⁺ | Example 678 (Example 655) | 35 mg (39%) |

| R1 | R2 | R3 | R4 | 1H NMR | MS(ESI): | Example # (synthesis protocol) | Obtained amt (yield) |
|---|---|---|---|---|---|---|---|
| H | 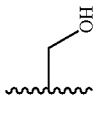 | H |  | (400MHz, DMSO-d6) □ 2.87(s, 3H), 3.00-3.50(m, 8H), 3.86(s, 2H), 4.31(s, 2H), 4.36(s, 2H), 7.48(d, J=7.7Hz, 1H), 7.69(s, 1H), 7.70(s, 1H), 7.73(d, J=7.7Hz, 1H), 7.88 (s, 1H). | m/z 405 (M+H)+ | Example 679 (Example 655) | 71 mg (97%) |
| H |  | H |  | (400MHz, DMSO-d6) □ 1.40(d, J=10.0 Hz, 3H), 2.84(s, 3H), 3.00-3.50(m, 8H), 3.85(s, 2H), 4.14(br s, 2H), 4.65(q, J=10.0Hz, 1H), 7.44 (d, J=7.7Hz, 1H), 7.64(s, 1H), 7.66(s, 1H), 7.71(d, J=7.7 Hz, 1H), 7.86(s, 1H). | m/z 419 (M+H)+ | Example 680 (Example 655) | 18 mg (25%) |
| H |  | H |  | (400MHz, DMSO-d6) δ 2.83(s, 3H), 3.26(s, 3H), 3.00-3.50(m, 8H), 3.49 (m, 2H), 3.62(m, 2H), 3.83(s, 2H), 4.19(s, 2H), 4.44(s, 2H), 7.44(d, J=8.0 Hz, 1H), 7.64(s, 1H), 7.69(d, J=8.0Hz, 1H), 7.73(m, 1H), 7.88(m, 1H). | m/z 463 (M+H)+ | Example 681 (Example 655) | 60 mg (75%) |

-continued

| R₁ | R₂ | R₃ | R₄ | ¹H NMR | MS(ESI): | Example # (synthesis protocol) | Obtained amt (yield) |
|---|---|---|---|---|---|---|---|
| H | ![piperazine-ethyl] | H | 3-methylphenoxymethyl | (500MHz, DMSO-d₆) δ 2.31(s, 3H), 2.80(s, 3H), 3.00-3.50(m, 8H), 3.83(s, 2H), 3.96(s, 2H), 5.08(s, 2H), 6.84(m, 3H), 7.22(t, J=7.8 Hz, 1H), 7.39(d, J=7.8 Hz, 1H), 7.59(s, 1H), 7.67(d, J=7.8 Hz, 1H), 7.74(s, 1H), 7.90(s, 1H). | m/z 495 (M+H)⁺ | Example 682 (Example 655) | 82 mg (49%) |
| H | ![piperazine-ethyl] | H | 3-methoxyphenyl | (500MHz, DMSO-d₆) δ 2.79(s, 3H), 3.00-3.50(m, 8H), 3.76(s, 3H), 3.82(s, 2H), 3.90(s, 2H), 5.09(s, 2H), 6.62(m, 3H), 7.24(t, J=7.8 Hz, 1H), 7.37(d, J=5.0Hz, 1H), 7.57(s, 1H), 7.66(d, J=7.8 Hz, 1H), 7.74(s, 1H), 7.89(s, 1H). | m/z 511 (M+H)⁺ | Example 683 (Example 655) | 95 mg (55%) |
| H | ![piperazine-ethyl] | H | 3-chlorophenyl | (500MHz, DMSO-d₆) δ 2.81(s, 3H), 3.00-3.50(m, 8H), 3.83(s, 2H), 3.98(s, 2H), 5.17(s, 2H), 7.05(m, 2H), 7.16 (m, 1H), 7.38(m, 2H), 7.59(s, 1H), 7.67(d, J=5.0Hz, 1H), 7.75(s, 1H), 7.91(s, 1H). | m/z 515 (M)⁺ | Example 684 (Example 655) | 78 mg (45%) |

-continued
| R1 | R2 | R3 | R4 | 1H NMR | MS(ESI): | Example # (synthesis protocol) | Obtained amt (yield) |
|---|---|---|---|---|---|---|---|
| H | 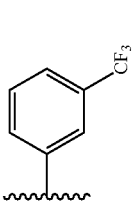 | H | 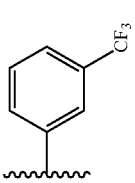 | (500MHz, DMSO-d6) δ 2.80(s, 3H), 3.00-3.50(m, 8H), 3.83(s, 2H), 3.97(br s, 2H), 5.13(s, 2H), 7.09(m, 2H), 7.39 (m, 3H), 7.59(s, 1H), 7.67(d, J=7.8Hz, 1H), 7.74(s, 1H), 7.91(s, 1H). | m/z 515 (M)+. | Example 685 (Example 655) | 54 mg (31%) |
| H | 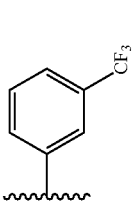 | H | 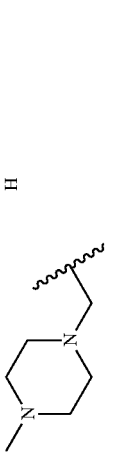 | (500MHz, DMSO-d6) δ 2.80(s, 3H), 3.00-3.50(m, 8H), 3.82(s, 2H), 3.92(br s, 2H), 5.24(s, 2H), 7.38(m, 4H), 7.59 (m, 2H), 7.66(d, J= 7.8Hz, 1H), 7.73(s, 1H), 7.91(s, 1H). | m/z 549 (M+H)+. | Example 686 (Example 655) | 81 mg (45%) |
| H | 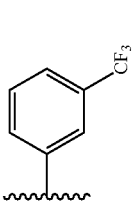 | H | 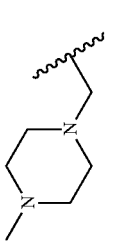 | (400MHz, DMSO-d6) δ 2.84(s, 3H), 3.00-3.70(m, 14H), 3.84(s, 2H), 3.95(m, 2H), 4.15(br s, 2H), 4.31(s, 2H), 5.16(s, 2H), 7.15(m, 2H), 7.44(d, J=8.0Hz, 1H), 7.49(m, 2H), 7.64(s, 1H), 7.70(d, J=8.0Hz, 1H), 7.76 (m, 1H), 7.92(m, 1H). | m/z 580 (M+H)+. | Example 687 (Example 655) | 80 mg (75%) |

-continued

| R₁ | R₂ | R₃ | R₄ | ¹H NMR | MS(ESI): | Example # (synthesis protocol) | Obtained amt (yield) |
|---|---|---|---|---|---|---|---|
| H | *N-methylpiperazinyl-CH₂-* | H | *4-pyridyloxyethyl-* | (500MHz, DMSO-d₆) δ 2.80(s, 3H), 3.00-3.50(m, 8H), 3.82(s, 2H), 4.11(s, 2H), 5.53(s, 2H), 7.39(m, 2H), 7.58(m, 2H), 7.67(m, 2H), 7.72(m, 1H), 7.85(m, 1H), 8.82(m, 1H). | m/z 482 (M+H)⁺ | Example 688 (Example 655) | 47 mg (22%) |
| H | *N-methylpiperazinyl-CH₂-* | H | *ureido-ethyl-* | (500MHz, DMSO-d₆) δ 2.80(s, 3H), 3.00-3.50(m, 8H), 3.82(s, 2H), 3.87(br s, 2H), 4.07(s, 2H), 6.41(br s, 1H), 7.37 (d, J=7.8Hz, 1H), 7.57(s, 1H), 7.66(m, 2H), 7.83(d, J=1.3 Hz, 1H). | m/z 447 (M+H)⁺ | Example 689 (Example 655) | 31 mg (34%) |
| H | *morpholinoethoxy-* | H | *phenoxyethyl-* | (500MHz, DMSO-d₆) δ 3.24(m, 2H), 3.52(m, 2H), 3.60 (m, 2H), 3.72(m, 2H), 3.78(s, 2H), 3.98(m, 2H), 4.41(t, J=5Hz, 2H), 5.10 (s, 2H), 7.01(m, 2H), 7.05(m, 2H), 7.25(s, 1H), 7.35(m, 2H), 7.60(d, J=7Hz, 1H), 7.72(s, 1H), 7.87(s, 1H). | m/z 498 (M+H)⁺ | Example 690 (Example 655) | 50 mg (37%) |

| R1 | R2 | R3 | R4 | 1H NMR | MS(ESI) | Example # (synthesis protocol) | Obtained amt (yield) |
|---|---|---|---|---|---|---|---|
| H | 4-methylpiperazinyl-ethyl | H | isopropoxyethoxyethyl | (400MHz, DMSO-d$_6$) δ 1.08(d, J=4.0 Hz, 6H), 2.83(s, 3H), 3.00-3.50(m, 8H), 3.53(m, 2H), 3.56 (m, 1H), 3.60(m, 2H), 3.84(s, 2H), 4.17(s, 2H), 4.45(s, 2H), 7.44(d, J=8.0 Hz, 1H), 7.63(s, 1H), 7.70(d, J=8.0 Hz, 1H), 7.72(d, J=1.3 Hz, 1H), 7.88(d, J=1.3Hz, 1H). | m/z 491 (M+H)$^+$ | Example 691 (Example 655) | 78 mg (94%) |
| H | H | H | phenoxyethyl | (500MHz, DMSO-d$_6$) δ 2.79(s, 3H), 3.00-3.50(m, 8H), 3.82(s, 2H), 3.90(br s, 2H), 5.11(s, 2H), 7.00(m 1H), 7.06 (m, 2H), 7.29(d, J=7.7Hz, 1H), 7.35(m, 2H), 7.56(d, J=7.7 Hz, 1H), 7.69(s, 1H), 7.73(s, 1H), 7.89(s, 1H). | m/z 481 (M+H)$^+$ | Example 692 (Example 655) | 75 mg (34%) |
| H | H | methoxyacetamido | phenoxyethyl | (500MHz, CD$_3$OD) δ 3.57(s, 3H), 3.78 (s, 2H), 4.14(s, 2H), 5.00(s, 2H), 6.99(m, 1H), 7.04(m, 2H), 7.31(m, 2H), 7.40(t, J=7.8Hz, 1H), 7.55 (d, J=7.5Hz, 1H), 7.59(m, 1H), 7.63(s, 1H), 7.72(s, 1H). | m/z 456 (M+H)$^+$ | Example 693 (Example 655) | 111 mg (52%) |

-continued

| R₁ | R₂ | R₃ | R₄ | ¹H NMR | MS(ESI): | Example # (synthesis protocol) | Obtained amt (yield) |
|---|---|---|---|---|---|---|---|
| H | methylpiperazinyl-ethyl | H | 3-phenoxypropyl | (500MHz, DMSO-d₆) δ 2.79(s, 3H), 2.99(t, J=8Hz, 2H), 3.00-3.50(m, 8H), 3.82(s, 4H), 4.20(t, J=8Hz, 2H), 6.98 (m, 1H), 7.01(m, 2H), 7.35(m, 2H), 7.38(d, J=8Hz, 1H), 7.58(s, 1H), 7.62(m, 2H), 7.80(s, 1H). | m/z 495 (M+H)⁺ | Example 694 (Example 655) | 106 mg (55%) |
| H | methylpiperazinyl-ethyl | H | 2-(o-tolyloxy)ethyl | (500MHz, DMSO-d₆) δ 2.21(s, 3H), 2.87(s, 3H), 3.00-3.50(m, 8H), 3.85(s, 2H), 4.30(s, 2H), 5.13(s, 2H), 6.91(t, J=5.0Hz, 1H), 7.10 (d, J=8.1Hz, 1H), 7.20(m, 2H), 7.48 (d, J=5.0Hz, 1H), 7.68(s, 1H), 7.72(d, J=8.1Hz, 1H), 7.77 (s, 1H), 7.92(s, 1H), 9.50(s, 1H). | m/z 495 (M+H)⁺ | Example 695 (Example 655) | 62 mg (37%) |

| R1 | R2 | R3 | R4 | ¹H NMR | MS(ESI): | Example # (synthesis protocol) | Obtained amt (yield) |
|---|---|---|---|---|---|---|---|
| H | *N-methylpiperazinyl-ethyl* | H | *4-fluorophenoxyethyl* | (500MHz, DMSO-d₆) δ 2.81(s, 3H), 3.00-3.50(m, 8H), 3.83(s, 2H), 4.03(s, 2H), 5.10(s, 2H), 7.09(m, 2H), 7.18 (m, 2H), 7.41(d, J=8.1Hz, 1H), 7.61(s, 1H), 7.68(d, J=8.1 Hz, 1H), 7.75(s, 1H), 7.91(s, 1H), 9.08(s, 1H). | m/z 499 (M+H)⁺ | Example 696 (Example 655) | 67 mg (40%) |
| H | *N-methylpiperazinyl-ethyl* | H | *2-chlorophenoxyethyl* | (500MHz, DMSO-d₆) δ 2.76(s, 3H), 3.00-3.50(m, 8H), 3.35(s, 2H), 3.81(s, 2H), 5.24(s, 2H), 7.03(m, 1H), 7.34 (m, 2H), 7.47(d, J= 8.1Hz, 1H), 7.53(s, 1H), 7.63(d, J=8.1 Hz, 1H), 7.68(s, 1H), 7.75(m, 1H), 7.90 (m, 1H), 9.07(s, 1H). | m/z 515 (M)⁺ | Example 697 (Example 655) | 28 mg (16%) |

-continued

| R1 | R2 | R3 | R4 | ¹H NMR | MS(ESI): | Example # (synthesis protocol) | Obtained amt (yield) |
|---|---|---|---|---|---|---|---|
| H | [N-methylpiperazinyl-ethyl] | H | [3-(OCF3)phenoxyethyl] | (500MHz, DMSO-d6) δ 2.76(s, 3H), 3.00-3.50(m, 8H), 3.34(s, 2H), 3.80(s, 2H), 5.19(s, 2H), 7.01(d, J=5.0Hz, 1H), 7.11(d, J=5.0Hz, 1H), 7.33(d, J=7.5Hz, 1H), 7.48(t, J=8.4Hz, 1H), 7.53(s, 1H), 7.63(d, J=7.5Hz, 1H), 7.69(s, 1H), 7.73(s, 1H), 7.90(s, 1H), 9.08(s, 1H). | m/z 565 (M+H)+ | Example 698 (Example 655) | 45 mg (25%) |
| H | [N-methylpiperazinyl-ethyl] | H | [3-isopropoxyphenoxyethyl] | (400MHz, DMSO-d6) δ 1.28(d, J=4.0Hz, 6H), 2.82(s, 3H), 3.00-3.50(m, 8H), 3.83(s, 2H), 4.04(br s, 2H), 4.56(m, 1H), 5.08(s, 2H), 6.95(m, 2H), 7.02(m, 1H), 7.12(m, 1H), 7.41(d, J=8.0Hz, 1H), 7.61(s, 1H), 7.68(d, J=8.0Hz, 1H), 7.71(d, J=1.5Hz, 1H), 7.88(d, J=1.5Hz, 1H). | m/z 539 (M+H)+ | Example 699 (Example 655) | 20 mg (11%) |

| R<sub>1</sub> | R<sub>2</sub> | R<sub>3</sub> | R<sub>4</sub> | ¹H NMR | MS(ESI): | Example # (synthesis protocol) | Obtained amt (yield) |
|---|---|---|---|---|---|---|---|
| H | [2-(4-methylpiperazin-1-yl)ethyl] | H | [(tetrahydrofuran-2-yl)methyl] | (400MHz, DMSO-d₆) δ 1.55(m, 1H), 1.79(m, 2H), 1.89 (m, 1H), 2.86(s, 3H), 3.00-3.50(m, 8H), 3.36(m, 1H), 3.46 (m, 1H), 3.48(m, 2H), 3.63(m, 1H), 3.72(m, 1H), 3.84(s, 2H), 3.96(m, 1H), 4.37(s, 2H), 4.45(s, 2H), 7.49(d, J=8.0 Hz, 1H), 7.69(s, 1H), 7.73(m, 2H), 7.89 (m, 1H). | m/z 489 (M+H)⁺. | Example 700 (Example 655) | 50 mg (69%) |
| H | [2-(4-methylpiperazin-1-yl)ethyl] | H | [2-(2-ethoxyethoxy)ethyl] | (400MHz, DMSO-d₆) δ 1.11(t, J=4.0 Hz, 3H), 2.86(s, 3H), 3.00-3.50(m, 8H), 3.44(q, J=8.0Hz, 2H), 3.53(m, 2H), 3.63(m, 2H), 3.84(s, 2H), 4.35(s, 2H), 4.44(s, 2H), 7.48(d, J=8.0Hz, 1H), 7.68 (s, 1H), 7.72(m, 2H), 7.89(s, 1H). | m/z 477 (M+H)⁺. | Example 701 (Example 655) | 71 mg (87%) |

| R₁ | R₂ | R₃ | R₄ | ¹H NMR | MS(ESI) | Example # (synthesis protocol) | Obtained amt (yield) |
|---|---|---|---|---|---|---|---|
| H | [4-methylpiperazin-1-yl-ethyl] | H | [CH₂-O-CH₂CH₂-O-CH₂CH(CH₃)₂ (isobutoxyethoxymethyl)] | (400MHz, DMSO-d₆) δ 0.86(d, J=4.0 Hz, 6H), 1.80(m, 1H), 2.85(s, 3H), 3.00-3.50(m, 8H), 3.19(d, J=8.0Hz, 2H), 3.55(m, 2H), 3.65(m, 2H), 3.85(s, 2H), 4.23(s, 2H), 4.47(s, 2H), 7.46(d, J=8.0Hz, 1H), 7.66(s, 1H), 7.72(d, J=8.0Hz, 1H), 7.74(s, 1H), 7.90(s, 1H). | m/z 505 (M+H)⁺ | Example 702 (Example 655) | 74 mg (87%) |
| H | [4-methylpiperazin-1-yl-ethyl] | H | [CH₂-O-CH(CH₃)-CH₂-O-CH₃] | (400MHz, DMSO-d₆) δ 1.12(d, J=8.0 Hz, 3H), 2.85(s, 3H), 3.00-3.50(m, 10H), 3.29(s, 3H), 3.79(m, 1H), 3.85(s, 2H), 4.23(s, 2H), 4.49(s, 2H), 7.46(d, J=8.0 Hz, 1H), 7.66(s, 1H), 7.73(m, 2H), 7.89(s, 1H). | m/z 477 (M+H)⁺ | Example 703 (Example 655) | 72 mg (88%) |
| H | [4-methylpiperazin-1-yl-ethyl] | H | [CH₂-O-CH₂-furan-2-yl] | (400MHz, DMSO-d₆) δ 2.84(s, 3H), 3.00-3.50(m, 8H), 3.85(s, 2H), 4.15(s, 2H), 4.45(s, 2H), 4.55(s, 2H), 6.47(m, 1H), 6.51(m, 1H), 7.44(d, J=8.0Hz, 1H), 7.64(s, 1H), 7.69(m, 2H), 7.76(s, 1H), 7.90(s, 1H). | m/z 485 (M+H)⁺ | Example 704 (Example 655) | 20 mg (20%) |

-continued

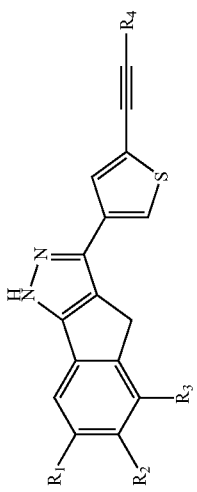

| R<sub>1</sub> | R<sub>2</sub> | R<sub>3</sub> | R<sub>4</sub> | <sup>1</sup>H NMR | MS(ESI): | Example # (synthesis protocol) | Obtained amt (yield) |
|---|---|---|---|---|---|---|---|
| H | *piperazinyl-ethyl* | H | *tetrahydrofuran-3-ylmethoxyethyl* | (400MHz, DMSO-d<sub>6</sub>) δ 1.56(m, 1H), 1.95(m, 1H), 2.50 (m, 1H), 2.85(s, 3H), 3.00-3.50(m, 12H), 3.63(m, 1H), 3.72 (m, 1H), 3.85(s, 2H), 4.19(s, 2H), 4.45(s, 2H), 7.46(d, J=8.0 Hz, 1H), 7.65(s, 1H), 7.71(d, J=8.0Hz, 1H), 7.75(s, 1H), 7.90(s, 1H). | m/z 489 (M+H)<sup>+</sup>. | Example 705 (Example 655) | 25 mg (21%) |
| H | *piperazinyl-ethyl* | H | *tetrahydropyran-2-ylmethoxyethyl* | (400MHz, DMSO-d<sub>6</sub>) δ 1.23(m, 1H), 1.46(m, 2H), 1.56 (m, 1H), 1.78(m, 1H), 2.84(s, 3H), 3.00-3.50(m, 11H), 3.85(s, 2H), 3.87(m, 1H), 4.17(s, 2H), 4.45(s, 2H), 7.45(d, J=8.0Hz, 1H), 7.65 (s, 1H), 7.70(d, J= 8.0Hz, 1H), 7.74(s, 1H), 7.90(m, 1H). | m/z 503 (M+H)<sup>+</sup>. | Example 706 (Example 655) | 23 mg (22%) |

-continued
| R₁ | R₂ | R₃ | R₄ | ¹H NMR | MS(ESI): | Example # (synthesis protocol) | Obtained amt (yield) |
|---|---|---|---|---|---|---|---|
| H | 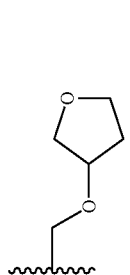 | H | 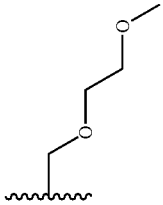 | (400MHz, DMSO-d₆) δ 1.98(m, 2H), 2.84(s, 3H), 3.00-3.50(m, 8H), 3.72 (m, 4H), 3.85(s, 2H), 4.15(s, 2H), 4.34(m, 1H), 4.46(s, 2H), 7.44(d, J=8.0Hz, 1H), 7.64(s, 1H), 7.70(d, J=8.0Hz, 1H), 7.75(s, 1H), 7.90(s, 1H). | m/z 475 (M+H)⁺ | Example 707 (Example 655) | 24 mg (23%) |
| H | H | H | 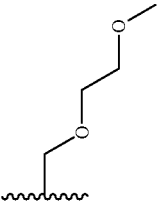 | (400MHz, DMSO-d₆) δ 2.84(s, 3H), 3.00-3.50(m, 8H), 3.27(s, 3H), 3.51(m, 2H), 3.64(m, 2H), 3.86(s, 2H), 4.21(s, 2H), 4.46(s, 2H), 7.37(d, J=8.0Hz, 1H), 7.62(d, J=8.0 Hz, 1H), 7.74(s, 1H), 7.78(s, 1H), 7.89(s, 1H). | m/z 475 (M+H)⁺ | Example 708 (Example 655) | 24 mg (23%) |
| H | H | H | | (400MHz, DMSO-d₆) δ 3.27(s, 3H), 3.51(m, 2H), 3.64 (m, 2H), 3.82(s, 2H), 4.45(s, 2H), 5.52(s, 2H), 7.38(d, J=8.0 Hz, 1H), 7.61(d, J= 8.0Hz, 1H), 7.72(m, 3H), 7.85(s, 1H), 7.88(s, 1H), 8.79(s, 1H). | m/z 431 (M+H)⁺ | Example 709 (Example 655) | 33 mg (50%) |

-continued
| R₁ | R₂ | R₃ | R₄ | ¹H NMR | MS(ESI) | Example # (synthesis protocol) | Obtained amt (yield) |
|---|---|---|---|---|---|---|---|
| H | 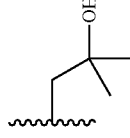 | H | 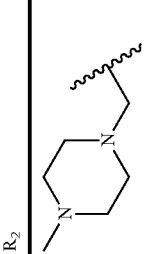 | (500MHz, CD₃OD) δ 1.36(s, 6H), 2.63 (s, 2H), 2.90(s, 3H), 3.08(m, 4H), 3.38(s, 4H), 3.82(s, 2H), 4.00(s, 2H), 7.43(d, J=7.5Hz, 1H), 7.54 (s, 1H), 7.63(s, 2H), 7.73(d, J=7.8Hz, 1H). | m/z 447 (M+H)⁺ | Example 710 (Example 655) | 190 mg (60%) |
| H | H | 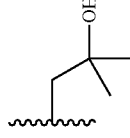 | 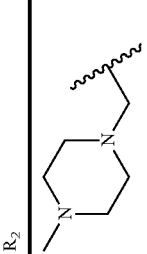 | (500MHz, CD₃OD) δ 2.23(s, 3H), 3.35-4.20(m, 8H), 3.77(s, 2H), 4.42(s, 2H), 7.39(t, J=7.8Hz, 1H), 7.45(d, J=7.8 Hz, 1H), 7.56(d, J=7.2Hz, 1H), 7.77(d, J=1.2Hz, 1H), 7.82 (d, J=1.2Hz, 1H). | m/z 419 (M+H). | Example 711 (Example 655) | 67 mg (13%) |
| H | (same piperazine as row 1) | H | (phenyl-NH-CH₂-CH₂-) | (500MHz, CD₃OD) δ 2.33(2, 3H), 2.45-2.65(m, 8H), 3.61(s, 2H), 3.77(s, 2H), 4.17(s, 2H), 6.71(m, 1H), 6.77(m, 2H), 7.17(m, 2H), 7.33 (d, J=7.5Hz, 1H), 7.53(m, 2H), 7.63 (m, 2H). | m/z 480 (M+H)⁺ | Example 712 (Example 655) | 24 mg (22%) |

-continued

| R₁ | R₂ | R₃ | R₄ | ¹H NMR | MS(ESI) | Example # (synthesis protocol) | Obtained amt (yield) |
|---|---|---|---|---|---|---|---|
| H | *N-methylpiperazinyl-ethyl* | H | *indolinyl-ethyl* | (500MHz, CD₃OD) δ 2.28(s, 3H), 2.45-2.65(m, 8H), 2.97(t, J=8.4Hz, 2H), 3.46 (t, J=8.1Hz, 2H), 3.60(s, 2H), 3.77(s, 2H), 4.24(s, 2H), 6.72(m, 2H), 7.09 (m, 2H), 7.33(d, J=8.4Hz, 1H), 7.52(s, 1H), 7.55(s, 1H), 7.63(m, 2H). | m/z 506 (M+H)⁺ | Example 713 (Example 655) | 4 mg (4%) |
| H | *N-methylpiperazinyl-ethyl* | H | *4-(phenylamino)-4-oxobutyl* | (500MHz, CD₃OD) δ 2.42(s, 3H), 2.45-2.65(m, 8H), 2.69(t, J=7.2Hz, 2H), 2.85 (t, J=7.2Hz, 2H), 3.64(s, 2H), 3.75(m, 2H), 7.10(m, 1H), 7.31(m, 2H), 7.34 (d, J=8.4Hz, 1H), 7.48(m, 1H), 7.55(s, 1H), 7.57(m, 2H), 7.60(s, 1H), 7.68(m, 1H). | m/z 522 (M+H)⁺ | Example 714 (Example 655) | 31 mg (26%) |

-continued

| R₁ | R₂ | R₃ | R₄ | ¹H NMR | MS(ESI): | Example # (synthesis protocol) | Obtained amt (yield) |
|---|---|---|---|---|---|---|---|
| H | [1-methylpiperazin-4-yl-ethyl] | H | [2-(pyrimidin-2-ylamino)ethyl] | (500MHz, CD₃OD) δ 2.28(s, 3H), 2.45-2.65(m, 8H), 3.60(s, 2H), 3.77(s, 2H), 4.65(s, 2H), 7.07 (dd, J=6.9, 4.1Hz, 1H), 7.33(d, J=7.8 Hz, 1H), 7.38(s, 1H), 7.54(s, 1H), 7.60(s, 1H), 7.64(d, J=7.8 Hz, 1H), 7.71(s, 1H), 8.58(dd, J=4.1, 1.9 Hz, 1H), 8.66(dd, J=6.9, 1.9Hz, 1H). | m/z 482 (M+H)⁺ | Example 715 (Example 655) | 12 mg (11%) |
| H | [diethylaminoethylcarbamoyl] | H | [2-phenoxyethyl] | (300MHz, DMSO-d₆) δ 0.98(t, J=7.1 Hz, 6H) 2.56(m, 4H) 3.34(m, 4H) 3.88(s, 2H) 5.11(s, 2H) 7.00 (t, J=7.5Hz, 1H) 7.05(dd, J=8.8, 1.0-Hz, 2H) 7.35(dd, J= 7.5, 1.4Hz, 2H) 7.63 (d, J=8.1Hz, 1H) 7.75(s, 1H) 7.79(d, J=8.8Hz, 1H) 7.91 (s, 1H) 8.16(s, 1H) 8.48(t, J=6.1Hz, 1H) 13.25(s, 1H). | m/z 511 (M+H)⁺ | Example 716 (Example 655) | 62 mg (55%) |

-continued
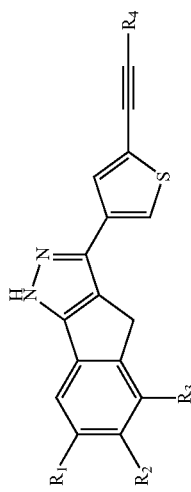
| R$_1$ | R$_2$ | R$_3$ | R$_4$ | $^1$H NMR | MS(ESI): | Example # (synthesis protocol) | Obtained amt (yield) |
|---|---|---|---|---|---|---|---|
| 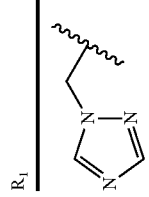 | H | H | 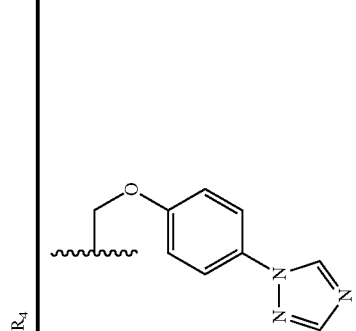 | (400MHz, DMSO-d$_6$): δ 3.72-3.83(m, 2H), 5.18(s, 2H), 5.49(s, 2H), 7.20-7.27(m, 3H), 7.49-7.58(m, 2H), 7.73(s, 1H), 7.78-7.86(m, 2H), 7.88(s, 1H), 7.99(s, 1H), 8.18(s, 1H), 8.69(s, 1H), 9.17(s, 1H), 13.17(s, 1H). | m/z 517 (M+H)$^+$. | Example 717 (Example 655) | 83 mg (32%) |
| 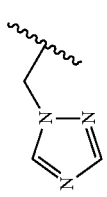 | H | H | 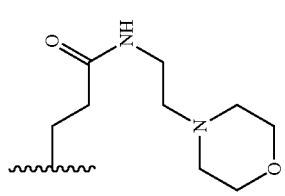 | (500MHz, DMSO-d$_6$): δ 2.29-2.43(m, 8H), 2.69(t, 2H, J=7.5Hz), 3.20(dd, 2H, J=15, 10Hz), 3.25-3.35(m, 3H), 3.53(d, 1H, J=10 Hz), 3.73-3.83(m, 2H), 5.50(s, 2H), 7.24(d, 1H, J=10 Hz), 7.51-7.60(m, 3H), 7.87(t, 1H, J=5Hz), 7.99(s, 1H), 8.70(s, 1H), 13.16(s, 1H). | m/z 528 (M+H)$^+$. | Example 718 (Example 655) | 74 mg (28%) |
| 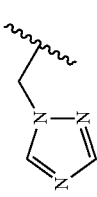 | H | H | 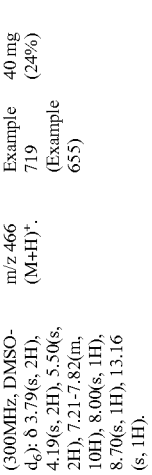 | (300MHz, DMSO-d$_6$): δ 3.79(s, 2H), 4.19(s, 2H), 5.50(s, 2H), 7.21-7.82(m, 10H), 8.00(s, 1H), 8.70(s, 1H), 13.16(s, 1H). | m/z 466 (M+H)$^+$. | Example 719 (Example 655) | 40 mg (24%) |

-continued

| R₁ | R₂ | R₃ | R₄ | ¹H NMR | MS(ESI): | Example # (synthesis protocol) | Obtained amt (yield) |
|---|---|---|---|---|---|---|---|
| ![imidazole-CH2]  (1-imidazolyl-methyl) | H | H | ![benzimidazole-CH2] (1-benzimidazolyl-methyl) | (400MHz, DMSO-d₆) δ 3.77(s, 2H), 4.96(s, 1H), 5.49(s, 2H), 5.70(s, 2H), 7.23(d, J=8.0Hz, 1H), 7.52(m, 4H), 7.73(s, 1H), 7.83(d, J=8.0Hz, 1H), 7.88 (s, 1H), 7.94(d, J=8.0Hz, 1H), 7.99(s, 1H), 8.70(s, 1H), 9.15(s, 1H). | m/z 474 (M+H)⁺ | Example 720 (Example 655) | 60 mg (20%) |
| H | ![pyrazole-CH2] (1-pyrazolyl-methyl) | H | ![benzimidazole-CH2] (1-benzimidazolyl-methyl) | (300MHz, DMSO-d₆) δ 3.79(s, 2H), 4.59(s, 1H), 5.49(s, 2H), 5.82(s, 2H), 7.31(d, J=7.8Hz, 1H), 7.48(s, 1H), 7.67(m, 3H), 7.78(s, 1H), 7.92(m, 2H), 8.04(s, 1H), 8.09(d, J=8.1Hz, 1H), 8.76 (s, 1H), 9.68(s, 1H). | m/z 474 (M+H)⁺ | Example 721 (Example 655) | 30 mg (10%) |

-continued

| R1 | R2 | R3 | R4 | ¹H NMR | MS(ESI): | Example # (synthesis protocol) | Obtained amt (yield) |
|---|---|---|---|---|---|---|---|
| imidazolylmethyl | H | H | pyrrolidinonylmethyl | (500MHz, DMSO-d₆) δ 1.98(m, 2H), 2.26(t, J=8.1Hz, 2H), 3.45(t, J=7.0 Hz, 2H), 3.81(s, 2H), 4.32(s, 2H), 5.13(s, 1H), 5.55(s, 2H), 7.27(d, J=6.8Hz, 1H), 7.55(d, J=7.8 Hz, 1H), 7.58(s, 1H), 7.72(d, J=1.2Hz, 1H), 7.89(d, J=1.2 Hz, 1H), 8.27(s, 1H), 9.09(s, 1H). | m/z 441 (M+H)⁺ | Example 722 (Example 655) | 148 mg (54%) |
| imidazolylmethyl | H | H | indolylmethyl | (300MHz, DMSO-d₆) δ 3.79(s, 2H), 3.85(s, 2H), 3.99(s, 2H), 5.50(s, 2H), 7.04(m, 1H), 7.12 (m, 1H), 7.23(dd, J=7.6, 1.9Hz, 1H), 7.30 (d, J=2.4Hz, 1H), 7.38(d, J=8.1Hz, 1H), 7.54(m, 2H), 7.63(m, 2H), 7.79 (m, 1H), 8.01(s, 1H), 8.72(s, 1H). | m/z 473 (M+H)⁺ | Example 723 (Example 655) | 53 mg (18%) |

-continued
| R₁ | R₂ | R₃ | R₄ | ¹H NMR | MS(ESI) | Example # (synthesis protocol) | Obtained amt (yield) |
|---|---|---|---|---|---|---|---|
| 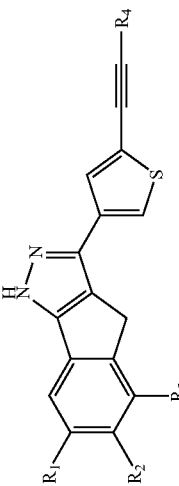 | H | H | 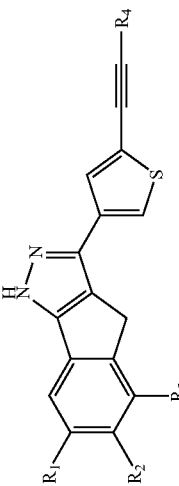 | (300MHz, DMSO-d₆) δ 2.53(m, 2H), 5.61(s, 2H), 7.34(m, 2H), 7.44(m, 2H), 7.61(t, J=7.5Hz, 2H), 7.67(s, 1H), 7.72(d, J=7.8Hz, 1H) 7.96(d, J=1.4Hz, 1H) 8.06(d, J=1.4Hz, 1H) 8.49(m, 1H) 9.33(m, 1H). | m/z 460 (M+H)⁺ | Example 724 (Example 655) | 12 mg (4%) |
| H | 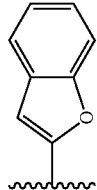 | H | 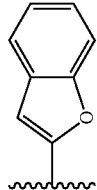 | (300MHz, DMSO-d₆) δ 3.82(s, H), 3.85 (s, 2H), 5.49(s, 2H), 7.32(m, 2H), 7.43 (dd, J=8.5, 1.4Hz, 1H), 7.47(d, J=1.0 Hz, 1H), 7.50(s, 1H), 7.63(dd, J=8.5, 4.4 Hz, 2H), 7.71(m, 1H), 7.93(d, J=1.4 Hz, 1H), 8.01(s, 1H), 8.03(d, J=1.4Hz, 1H), 8.71(s, 1H). | m/z 460 (M+H)⁺ | Example 725 (Example 655) | 64 mg (22%) |
| 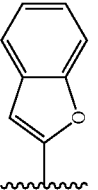 | H | H | 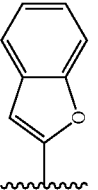 | (500MHz, DMSO-d₆) δ 3.80(s, 2H), 5.08(s, 2H), 5.50(s, 2H), 7.08(m, 2H), 7.18(m, 2H), 7.22 (d, J=7.6Hz, 1H), 7.55(m, 2H), 7.72(s, 1H), 7.85(s, 1H), 8.01(s, 1H), 8.73(s, 1H). | m/z 466 (M-H)⁻ | Example 726 (Example 655) | 50 mg (48%) |
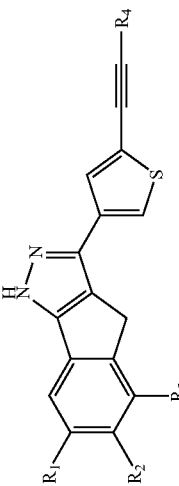

-continued

| R₁ | R₂ | R₃ | R₄ | ¹H NMR | MS(ESI): | Example # (synthesis protocol) | Obtained amt (yield) |
|---|---|---|---|---|---|---|---|
| ![imidazole-CH2] | H | H | ![3-OCF3 phenoxyethyl] | (500MHz, DMSO-d₆) δ 3.80(s, 2H), 5.20(s, 2H), 5.50(s, 2H), 7.02(d, J=7.6 Hz, 1H), 7.08(m, 2H), 7.22(d, J=7.6 Hz, 1H), 7.50(m, 3H), 7.73(s, 1H), 7.88(s, 1H), 8.01(s, 1H), 8.74(s, 1H). | m/z 532 (M-H)⁻ | Example 727 (Example 655) | 40 mg (35%) |
| ![imidazole-CH2] | H | H | ![3-CF3 phenoxyethyl] | (500MHz, DMSO-d₆) δ 3.80(s, 2H), 5.22(s, 2H), 5.52(s, 2H), 7.22(d, J=7.6 Hz, 1H), 7.38(m, 3H), 7.55(m, 3H), 7.73(s, 1H), 7.89(s, 1H), 8.00(s, 1H), 8.72(s, 1H). | m/z 516 (M-H)⁻ | Example 728 (Example 655) | 45 mg (40%) |
| ![imidazole-CH2] | H | H | ![2-Cl phenoxyethyl] | (500MHz, DMSO-d₆) δ 3.80(s, 2H), 5.21(s, 2H), 5.50(s, 2H), 7.02(t, J=7.6 Hz, 1H), 7.22(d, J=7.6 Hz, 1H), 7.32(d, J=7.6 Hz, 1H), 7.38 (t, J=7.6 Hz, 1H), 7.48(d, J=7.6 Hz, 1H), 7.56(m, 2H), 7.74(s, 1H), 7.90(s, 1H), 8.01(s, 1H), 8.73(s, 1H). | m/z 484 (M+H)⁺ | Example 729 (Example 655) | 20 mg (19%) |

-continued

| R₁ | R₂ | R₃ | R₄ | ¹H NMR | MS(ESI): | Example # (synthesis protocol) | Obtained amt (yield) |
|---|---|---|---|---|---|---|---|
| ![imidazole-CH2] | H | H | ![3-chlorophenoxyethyl-thiophene] | (500MHz, DMSO-d₆) δ 3.82(s, 2H), 5.18(s, 2H), 5.52(s, 2H), 7.06(m, 2H), 7.18(d, J=1.6Hz, 1H), 7.23(d, J=7.6 Hz, 1H), 7.38(t, J=7.6Hz, 1H), 7.57(m, 2H), 7.75(s, 1H), 7.91(s, 1H), 8.02(s, 1H), 8.75(s, 1H). | m/z 482 (M-H)⁻. | Example 730 (Example 655) | 45 mg (42%) |
| ![imidazole-CH2] | H | H | ![4-chlorophenoxyethyl-thiophene] | (500MHz, DMSO-d₆) δ 3.79(s, 2H), 5.07(s, 2H), 5.52(s, 2H), 7.08(d, J=7.6 Hz, 2H), 7.22(d, J=7.6Hz, 1H), 7.40(d, J=7.6Hz, 2H), 7.55(m, 2H), 7.73(s, 1H), 7.86(s, 1H), 8.00(s, 1H), 8.73(s, 1H). | m/z 482 (M-H)⁻. | Example 731 (Example 655) | 35 mg (33%) |
| ![imidazole-CH2] | H | H | ![2-methylphenoxyethyl-thiophene] | (500MHz, DMSO-d₆) δ 2.20(s, 3H), 3.80(s, 2H), 5.11(s, 2H), 5.52(t, J=7.6Hz, 2H), 6.92(t, J=7.6Hz, 1H), 7.09(d, J=7.6 Hz, 1H), 7.30(m, 3H), 7.56(m, 2H), 7.75(s, 1H), 7.88(s, 1H), 8.01(s, 1H), 8.74(s, 1H). | m/z 462 (M-H)⁻. | Example 732 (Example 655) | 25 mg (24%) |

-continued

| R₁ | R₂ | R₃ | R₄ | ¹H NMR | MS(ESI) | Example # (synthesis protocol) | Obtained amt (yield) |
|---|---|---|---|---|---|---|---|
| (imidazolylethyl) | H | H | 3-ethoxy-OMe-phenyl | (500MHz, DMSO-d₆) δ 3.78(s, 3H), 3.81(s, 2H), 5.08(s, 2H), 5.52(s, 2H), 6.58(d, J=7.6Hz, 1H), 6.62(m, 2H), 7.23(m, 2H), 7.57(m, 2H), 7.76(s, 1H), 7.89(s, 1H), 8.00(s, 1H), 8.71(s, 1H). | m/z 480 (M+H)⁺ | Example 733 (Example 655) | 30 mg (28%) |
| (imidazolylethyl) | H | H | furan-2-ylmethoxymethyl | (500MHz, DMSO-d₆) δ 3.81(s, 2H), 4.823(s, 2H), 4.55(s, 2H), 5.52(s, 2H), 6.65(d, J=3.6Hz, 1H), 6.72(d, J=3.6Hz, 1H), 7.23(d, J=7.6Hz, 1H), 7.57(m, 2H), 7.68(s, 1H), 7.72(s, 1H), 7.88(s, 1H), 8.02(s, 1H), 8.76(s, 1H). | m/z 454 (M+H)⁺ | Example 734 (Example 655) | 28 mg (27%) |
| (imidazolylethyl) | H | H | tetrahydrofuran-3-ylmethoxymethyl | (500MHz, DMSO-d₆) δ 1.56(m, 1H), 1.95(m, 1H), 2.50(m, 1H), 3.50(m, 2H), 3.60(m, 2H), 3.72(m, 2H), 3.81(s, 2H), 4.44(s, 2H), 5.53(s, 2H), 7.23(d, J=7.6Hz, 2H), 7.57(m, 2H), 7.73(s, 1H), 7.87(s, 1H), 8.03(br s, 1H), 8.77(br s, 1H). | m/z 458 (M+H)⁺ | Example 735 (Example 655) | 21 mg (20%) |

-continued

| R₁ | R₂ | R₃ | R₄ | ¹H NMR | MS(ESI): | Example # (synthesis protocol) | Obtained amt (yield) |
|---|---|---|---|---|---|---|---|
| ![imidazolylethyl] | H | H | ![tetrahydrofuran-2-ylmethoxymethyl] | (500MHz, DMSO-d₆) δ 1.57(m, 1H), 1.80(m, 2H), 1.90 (m, 1H), 3.50(m, 2H), 3.70(m, 2H), 3.81(s, 2H), 3.98(m, 1H), 4.44(s, 2H), 5.54(s, 2H), 7.23(d, J=7.6Hz, 1H), 7.57 (m, 2H), 7.72(s, 1H), 7.86(s, 1H), 8.04(br s, 1H), 8.78(br s, 1H). | m/z 458 (M+H)⁺ | Example 736 (Example 655) | 45 mg (44%) |
| ![imidazolylethyl] | H | H | ![tetrahydrofuran-3-yloxymethyl] | (500MHz, DMSO-d₆) δ 1.97(m, 2H), 3.72(m, 4H), 3.81(s, 2H), 4.37(m, 1H), 4.44(s, 2H), 5.52(s, 2H), 7.23(d, J=7.6 Hz, 1H), 7.58(m, 2H), 7.73(s, 1H), 7.87(s, 1H), 8.04(br s, 1H), 8.76(br s, 1H). | m/z 444 (M+H)⁺ | Example 737 (Example 655) | 38 mg (38%) |
| ![imidazolylethyl] | H | H | ![tetrahydropyran-2-ylmethoxymethyl] | (500MHz, DMSO-d₆) δ 1.22(m, 1H), 1.44(m, 3H), 1.57 (m, 1H), 1.80(m, 1H), 3.60(m, 4H), 3.80(s, 2H), 3.84(m, 1H), 4.43(s, 2H), 5.52(s, 2H), 7.23(d, J=7.6Hz, 1H), 7.57 (m, 2H), 7.73(s, 1H), 7.87(s, 1H), 8.01(s, 1H), 8.76(s, 1H). | m/z 472 (M+H)⁺ | Example 738 (Example 655) | 45 mg (43%) |

-continued

| R$_1$ | R$_2$ | R$_3$ | R$_4$ | $^1$H NMR | MS(ESI): | Example # (synthesis protocol) | Obtained amt (yield) |
|---|---|---|---|---|---|---|---|
| (1H-pyrazol-1-ylmethyl) | H | H | (3-pyridyloxyethyl) | (500MHz, DMSO-d$_6$) δ 3.80(s, 2H), 5.22(s, 2H), 5.52(s, 2H), 7.22(d, J=7.6 Hz, 1H), 7.56(m, 3H), 7.71(m, 1H), 7.75(s, 1H), 7.88(s, 1H), 7.99(s, 1H), 8.34(s, 1H), 8.51(s, 1H), 8.72(s, 1H). | m/z 451 (M+H)$^+$ | Example 739 (Example 655) | 62 mg (39%) |
| (1H-pyrazol-1-ylmethyl) | H | H | (2-ethoxyethoxymethyl) | (500MHz, DMSO-d$_6$) δ 1.12(t, J=7.6 Hz, 3H), 3.53(q, J=7.6Hz, 2H), 3.58(t, J=7.6Hz, 2H), 3.62(t, J=7.6Hz, 2H), 3.79(s, 2H), 4.46(s, 2H), 5.50(s, 2H), 7.23(d, J=7.6Hz, 1H), 7.57(m, 2H), 7.73(s, 1H), 7.86(s, 1H), 8.01(s, 1H), 8.75(s, 1H). | m/z 444 (M−H)$^-$ | Example 740 (Example 655) | 44 mg (33%) |
| (1H-pyrazol-1-ylmethyl) | H | H | (2-isopropoxyethoxymethyl) | (500MHz, DMSO-d$_6$) δ 1.09(d, J=7.6 Hz, 6H), 3.57(t, J=7.6Hz, 2H), 3.59(m, 1H), 3.62(t, J=7.6 Hz, 2H), 3.80(s, 2H), 4.44(s, 2H), 5.49(s, 2H), 7.23(d, J=7.6 Hz, 1H), 7.57(m, 2H), 7.72(s, 1H), 7.85(s, 1H), 8.00(s, 1H), 8.74(s, 1H). | m/z 460 (M+H)$^+$ | Example 741 (Example 655) | 66 mg (48%) |

-continued

| R₁ | R₂ | R₃ | R₄ | ¹H NMR | MS(ESI): | Example # (synthesis protocol) | Obtained amt (yield) |
|---|---|---|---|---|---|---|---|
| ![methylpiperazine carbonyl] | ![methylpiperazine ethyl] | H | ![pyridin-3-yloxyethyl] | (500MHz, DMSO-d₆) δ 2.78(s, 3H), 3.00-3.50(m, 8H), 3.80(s, 2H), 4.02(s, 2H), 5.22(s, 2H), 7.38(d, J=7.6Hz, 1H), 7.50(m, 1H), 7.58(s, 1H), 7.62(m, 2H), 7.77(s, 1H), 7.92(s, 1H), 8.30(d, J=1.6Hz, 1H), 8.47 (s, 1H). | m/z 482 (M+H)⁺ | Example 742 (Example 655) | 85 mg (52%) |
| ![methylpiperazine carbonyl] | H | H | ![4-fluorophenoxyethyl] | (500MHz, DMSO-d₆) δ 2.82(s, 3H), 3.10-3.50(m, 8H), 3.89(s, 2H), 5.08(s, 2H), 7.08(m, 2H), 7.19(t, J=7.6Hz, 2H), 7.39(d, J=7.6Hz, 1H), 7.64(d, J=7.6Hz, 1H), 7.77(d, J=7.6Hz, 2H), 7.92 (s, 1H), 9.85(br s, 1H). | m/z 511 (M−H)⁻ | Example 743 (Example 655) | 85 mg (57%) |
| ![methylpiperazine carbonyl] | H | H | ![3-trifluoromethylphenoxyethyl] | (500MHz, DMSO-d₆) δ 2.82(s, 3H), 3.10-3.50(m, 8H), 3.90(s, 2H), 5.22(s, 2H), 7.38(m, 4H), 7.59(t, J=7.6Hz, 1H), 7.64(d, J=7.6Hz, 1H), 7.77(d, J=7.6Hz, 2H), 7.92(s, 1H), 9.92(br s, 1H). | m/z 563 (M+H)⁺ | Example 744 (Example 655) | 75 mg (48%) |

-continued
| R1 | R2 | R3 | R4 | ¹H NMR | MS(ESI): | Example # (synthesis protocol) | Obtained amt (yield) |
|---|---|---|---|---|---|---|---|
| 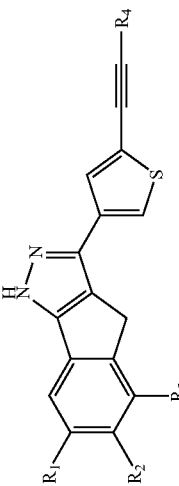 | H | H | 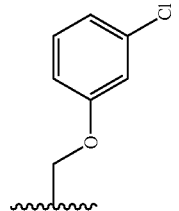 | (500MHz, DMSO-d₆) δ 2.82(s, 3H), 3.10-3.50(m, 8H), 3.88(s, 2H), 5.18(s, 2H), 7.04(m, 2H), 7.18(br s, 1H), 7.38(m, 2H), 7.63(d, J=7.6Hz, 1H), 7.75(s, 1H), 7.77(s, 1H), 7.93(s, 1H), 9.94(br s, 1H). | m/z 529 (M+H)⁺ | Example 745 (Example 655) | 89 mg (59%) |
| 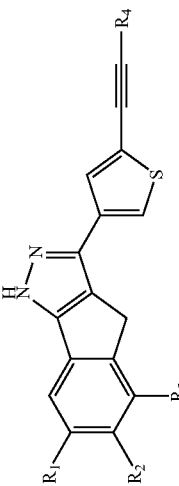 | H | H | 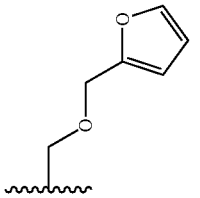 | (500MHz, DMSO-d₆) δ 2.83(s, 3H), 3.10-3.50(m, 8H), 3.92(s, 2H), 4.43(s, 2H), 4.57(d, J=3.6Hz, 2H), 6.47(d, J=3.6Hz, 1H), 6.52(d, J=3.6Hz, 1H), 7.39(d, J=7.6Hz, 1H), 7.65(m, 2H), 7.73(s, 1H), 7.77(s, 1H), 7.91(s, 1H), 9.92(br s, 1H). | m/z 499 (M+H)⁺ | Example 746 (Example 655) | 81 mg (56%) |
| 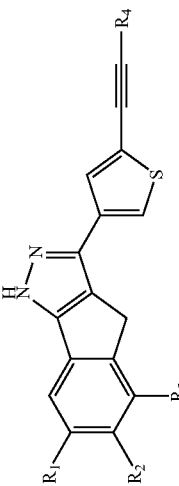 | H | H | 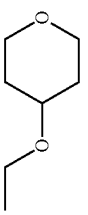 | (500MHz, DMSO-d₆) δ 1.44(m, 2H), 1.92(m, 2H), 2.83(s, 3H), 3.10-3.50(m, 8H), 3.40(t, J=7.6 Hz, 2H), 3.72(m, 1H), 3.82(m, 2H), 3.92(s, 2H), 4.47(s, 2H), 7.38(d, J=7.6 Hz, 1H), 7.62(d, J=7.6 Hz, 1H), 7.77(br s, 2H), 7.88(s, 1H), 9.92(br s, 1H). | m/z 503 (M+H)⁺ | Example 747 (Example 655) | 96 mg (65%) |

-continued
| R$_1$ | R$_2$ | R$_3$ | R$_4$ | $^1$H NMR | MS(ESI): | Example # (synthesis protocol) | Obtained amt (yield) |
|---|---|---|---|---|---|---|---|
| 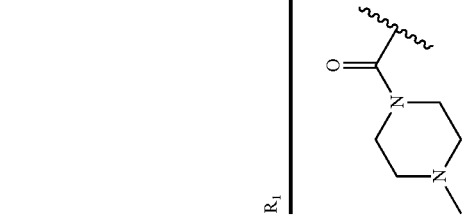 | H | H | 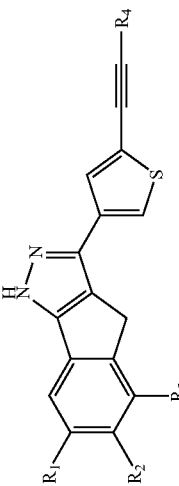 | (500MHz, DMSO-d$_6$) δ 1.12(t, J=7.6 Hz, 3H), 2.82(s, 3H), 3.10-3.45(m, 8H), 3.48(q, J=7.6Hz, 2H), 3.58(t, J=7.6 Hz, 2H), 3.62(t, J=7.6Hz, 2H), 3.92(s, 2H), 4.46(s, 2H), 7.39(d, J=7.6Hz, 1H), 7.63(d, J=7.6 Hz, 1H), 7.77(m, 2H), 7.89(s, 1H), 9.94(s, 1H). | m/z 491 (M+H)$^+$. | Example 748 (Example 655) | 75 mg (52%) |
| 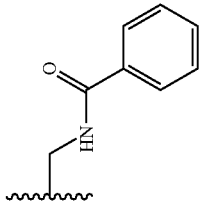 | H | H | 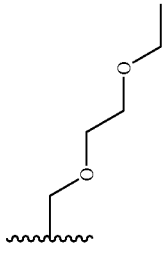 | (500MHz, DMSO-d$_6$) δ 3.80(s, 2H), 4.39(d, J=3.6Hz, 2H), 5.50(s, 2H), 7.22(d, J=7.6Hz, 1H), 7.50(m, 5H), 7.66(s, 1H), 7.80(s, 1H), 7.89(d, J=7.6 Hz, 2H), 7.99(s, 1H), 8.73(s, 1H), 9.03(t, J=3.6Hz, 1H). | m/z 477 (M+H)$^+$. | Example 749 (Example 655) | 64 mg (39%) |

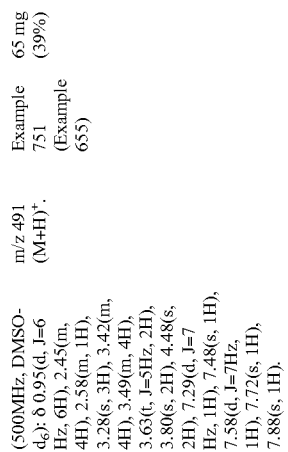
| R₁ | R₂ | R₃ | R₄ | ¹H NMR | MS(ESI): | Example # (synthesis protocol) | Obtained amt (yield) |
|---|---|---|---|---|---|---|---|
| H | 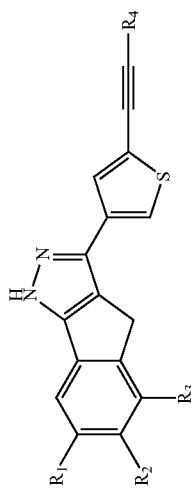 | H | 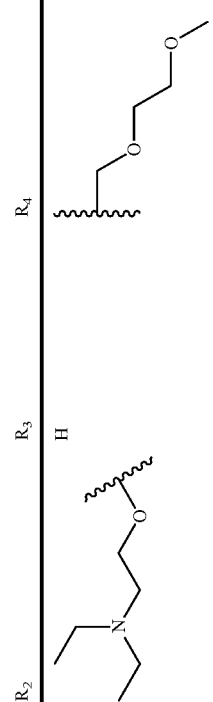 | (500MHz, DMSO-d₆): δ 0.98(t, J=7 Hz, 6H), 2.55(dd, J=7Hz, 4H), 2.78(t, J=7Hz, 2H), 3.25(s, 3H), 3.48(t, J=6Hz, 2H), 3.62(t, J=6Hz, 2H), 3.78(s, 2H), 4.08(t, J=6Hz, 2H), 4.45(s, 2H), 7.15 (s, 1H), 7.52(d, J=7 Hz, 1H), 7.72(s, 1H), 7.83(s, 1H). | m/z 466 (M+H)⁺. | Example 750 (Example 655) | 120 mg (49%) |
| H | 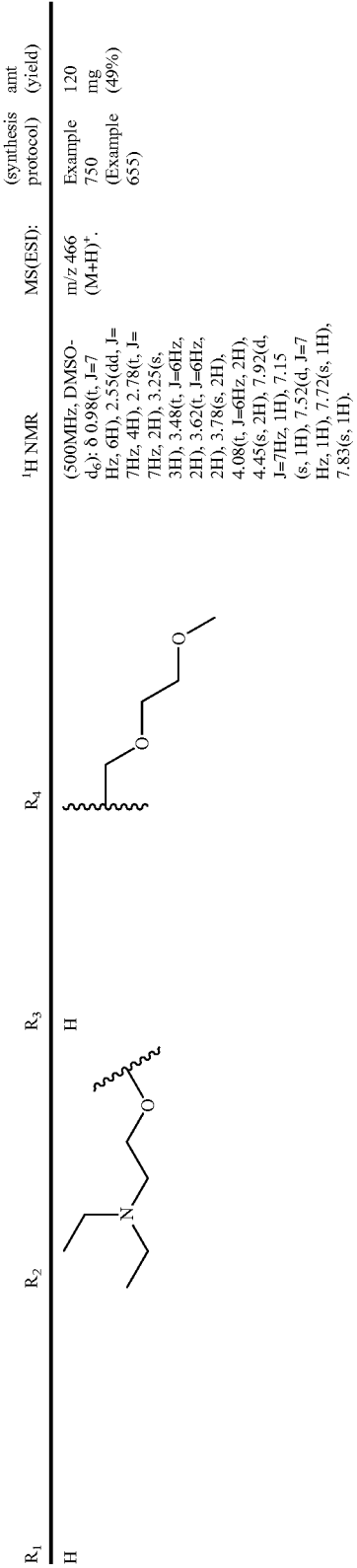 | H |  | (500MHz, DMSO-d₆): δ 0.95(d, J=6 Hz, 6H), 2.45(m, 4H), 2.58(m, 1H), 3.28(s, 3H), 3.42(m, 4H), 3.49(m, 4H), 3.63(t, J=5Hz, 2H), 3.80(s, 2H), 4.48(s, 2H), 7.29(d, J=7 Hz, 1H), 7.48(s, 1H), 7.58(d, J=7Hz, 1H), 7.72(s, 1H), 7.88(s, 1H). | m/z 491 (M+H)⁺. | Example 751 (Example 655) | 65 mg (39%) |

-continued

| R1 | R2 | R3 | R4 | ¹H NMR | MS(ESI): | Example # (synthesis protocol) | Obtained amt (yield) |
|---|---|---|---|---|---|---|---|
| H | ethyl-piperazinyl-ethyl | H | phenoxymethyl | (500MHz, DMSO-d₆): δ 0.98(t, J=6 Hz, 3H), 2.39(m, 6H), 3.35(m, 4H), 3.52(s, 2H), 3.82(s, 2H), 3.89(m, 2H), 5.12(s, 2H), 7.39(d, J=7Hz, 2H), 7.58 (s, 1H), 7.63(d, J=7 Hz, 1H), 7.72(s, 1H), 7.88(s, 1H). | m/z 495 (M+H)⁺ | Example 752 (Example 655) | 50 mg (30%) |
| H | ethyl-piperazinyl-ethyl | H | (2-methoxyethoxy)methyl | (500MHz, DMSO-d₆): δ 1.19(t, J=6 Hz, 3H), 2.98-3.16 (m, 8H), 3.25(s, 3H), 3.28(s, 2H), 3.45(t, J=5Hz, 2H), 3.65(t, J=5Hz, 2H), 3.82 (s, 2H), 3.89(m, 2H), 4.48(s, 2H), 7.39(d, J=7Hz, 1H), 7.58 (s, 1H), 7.63(d, J=7 Hz, 1H), 7.72(s, 1H), 7.88(s, 1H). | m/z 477 (M+H)⁺ | Example 753 (Example 655) | 65 mg (30%) |
| H | imidazolyl | H | (2-methoxyethoxy)methyl | (500MHz, DMSO-d₆): δ 3.28(s, 3H), 3.55(t, J=5Hz, 2H), 3.65(t, J=5Hz, 2H), 3.93(s, 2H), 4.48(s, 2H), 7.78(m, 3H), 7.90(d, J=7Hz, 1H), 7.95(s, 1H), 8.00(s, 1H), 8.25(s, 1H), 9.48(s, 1H). | m/z 417 (M+H)⁺ | Example 754 (Example 655) | 20 mg (32%) |

-continued
| R₁ | R₂ | R₃ | R₄ | ¹H NMR | MS(ESI) | Example # (synthesis protocol) | Obtained amt (yield) |
|---|---|---|---|---|---|---|---|
| H | 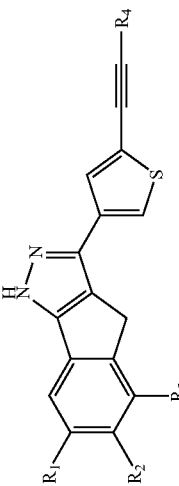 | H | 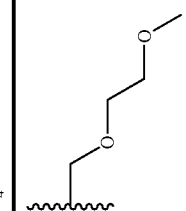 | (500MHz, DMSO-d₆): δ 3.28(s, 3H), 3.55(t, J=5Hz, 2H), 3.65(t, J=5Hz, 2H), 3.90(s, 2H), 4.45(s, 2H), 5.48(s, 2H), 7.41(d, J=7Hz, 1H), 7.58(s, 1H), 7.62(s, 1H), 7.71(m, 3H), 7.88(s, 1H), 9.02(s, 1H), 13.25 (br s, 1H). | m/z 431 (M+H)⁺ | Example 755 (Example 655) | 8 mg (8%) |
| H | H | H | 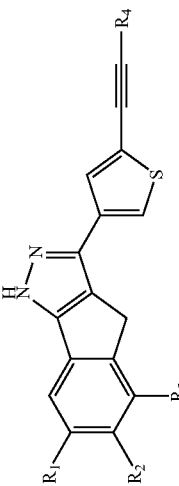 | (500MHz, DMSO-d₆): δ 3.28(s, 3H), 3.52(t, J=5Hz, 2H), 3.62(t, J=5Hz, 2H), 3.90(s, 2H), 4.45(s, 2H), 5.48(s, 2H), 7.25(d, J=7Hz, 1H), 7.58(m, 2H), 7.70(s, 1H), 7.85(s, 1H), 8.00(s, 1H), 8.70(s, 1H), 13.20 (s, 1H). | m/z 432 (M+H)⁺ | Example 756 (Example 655) | 46 mg (22%) |
| H | 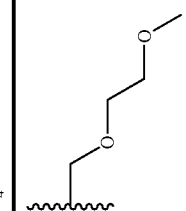 | H | 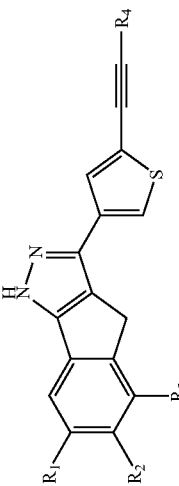 | (500Hz, DMSO-d₆): δ 3.28(s, 3H), 3.52(t, J=5Hz, 2H), 3.62(t, J=5Hz, 2H), 3.90(s, 2H), 4.45(s, 2H), 5.48(s, 2H), 7.26(d, J=7Hz, 1H), 7.45(s, 1H), 7.62(m, 1H), 7.70(s, 1H), 7.82(s, 1H), 8.00(s, 1H), 8.68(s, 1H), 13.15(br s, 1H). | m/z 432 (M+H)⁺ | Example 757 (Example 655) | 90 mg (49%) |
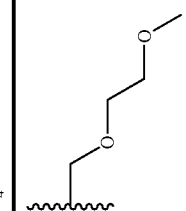

-continued

| R₁ | R₂ | R₃ | R₄ | ¹H NMR | MS(ESI): | Example # (synthesis protocol) | Obtained amt (yield) |
|---|---|---|---|---|---|---|---|
| H | ![piperazine with N-methyl] | H | ![CH₂-O-CH₂CH₂-O-CH₃] | (500MHz, DMSO-d₆): δ 2.85(s, 3H), 3.20(m, 4H), 3.28(s, 3H), 3.55(t, J=5Hz, 2H), 3.65(t, J=5Hz, 2H), 3.73(s, 2H), 3.85(m, 4H), 4.45(s, 2H), 7.02(d, J=7 Hz, 1H), 7.12(s, 1H), 7.55(d, J=7Hz, 1H), 7.70(s, 1H), 7.85(s, 1H), 9.65(br s, 1H). | m/z 449 (M+H)⁺ | Example 758 (Example 655) | 55 mg (27%) |
| H | ![N,N-dimethylaminoethoxy] | H | ![CH₂-O-CH₂CH₂-O-CH₃] | (500MHz, DMSO-d₆): δ 2.85(s, 6H), 3.28(s, 3H), 3.52(t, J=5Hz, 2H), 3.58 (m, 2H), 3.62(t, J=5 Hz, 2H), 3.78(s, 2H), 4.38(m, 2H), 4.45(s, 2H), 7.02(d, J=7 Hz, 1H), 7.22(s, 1H), 7.62(d, J=7Hz, 1H), 7.72(s, 1H), 7.83(s, 1H), 9.65(br s, 1H). | m/z 438 (M+H)⁺ | Example 759 (Example 655) | 140 mg (83%) |

-continued

| R1 | R2 | R3 | R4 | 1H NMR | MS(ESI): | Example # (synthesis protocol) | Obtained amt (yield) |
|---|---|---|---|---|---|---|---|
| H | ~N(CH3)2 with ethylene-O linker | H | methoxyethoxymethyl | (500MHz, DMSO-d6): δ 1.85(t, J=7 Hz, 2H), 2.15(s, 6H), 2.38(t, J=7Hz, 2H), 2.25(s, 3H), 3.52(t, J=5Hz, 2H), 3.62(t, J=5Hz, 2H), 3.78 (s, 2H), 4.02(t, J=7 Hz, 1H), 4.42(s, 2H), 6.92(d, J=7Hz, 1H), 7.15(s, 1H), 7.55(m, 1H), 7.72(s, 1H), 7.83(s, 1H), 12.95(br s, 1H). | m/z 452 (M+H)+ | Example 760 (Example 655) | 50 mg (98%) |
| H | ~O-CH2-C(=O)-N(CH3)2 | H | methoxyethoxymethyl | (500MHz, DMSO-d6): δ 2.85(s, 3H), 3.03(s, 3H), 3.25(s, 3H), 3.55(t, J=5Hz, 2H), 3.65(t, J=5Hz, 2H), 3.78(s, 2H), 4.45(s, 2H), 4.85(s, 2H), 6.92(d, J=7 Hz, 1H), 7.12(s, 1H), 7.52(d, J=7Hz, 1H), 7.72(s, 1H), 7.85(s, 1H). | m/z 452 (M+H)+ | Example 761 (Example 655) | 25 mg (15%) |

-continued

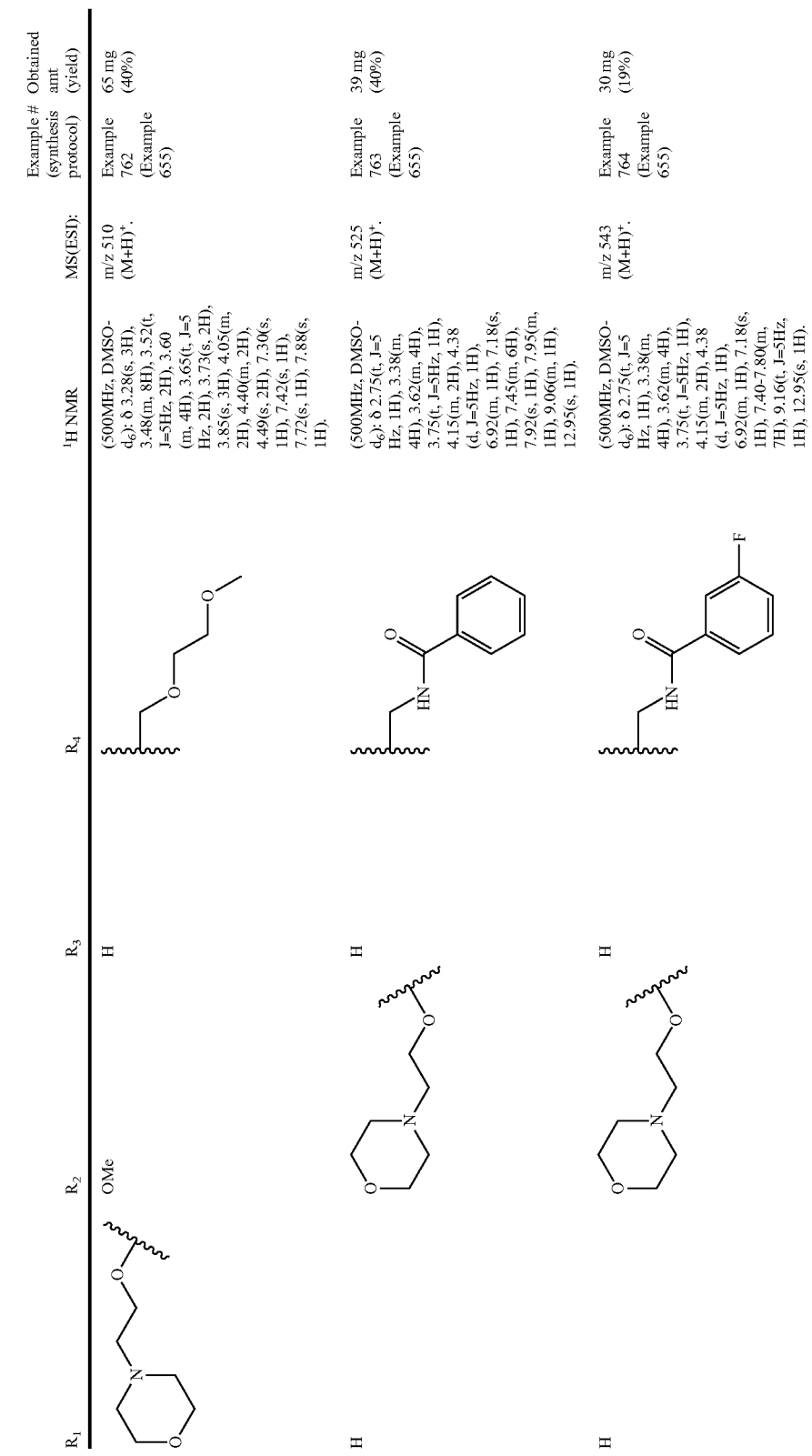

| R₁ | R₂ | R₃ | R₄ | ¹H NMR | MS(ESI): | Example # (synthesis protocol) | Obtained amt (yield) |
|---|---|---|---|---|---|---|---|
| 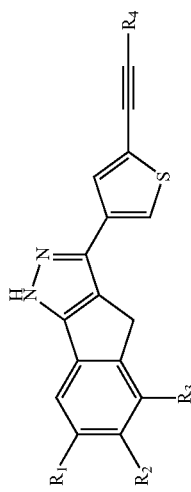 | OMe | H | | (500MHz, DMSO-d₆): δ 3.28(s, 3H), 3.48(m, 8H), 3.52(t, J=5Hz, 2H), 3.60 (m, 4H), 3.65(t, J=5 Hz, 2H), 3.73(s, 2H), 3.85(s, 3H), 4.05(m, 2H), 4.40(m, 2H), 4.49(s, 2H), 7.30(s, 1H), 7.42(s, 1H), 7.72(s, 1H), 7.88(s, 1H). | m/z 510 (M+H)⁺ | Example 762 (Example 655) | 65 mg (40%) |
| H | ⟶O⟶N(morpholine) | H | ⟶NHC(O)Ph | (500MHz, DMSO-d₆): δ 2.75(t, J=5 Hz, 1H), 3.38(m, 4H), 3.62(m, 4H), 3.75(t, J=5Hz, 1H), 4.15(m, 2H), 4.38 (d, J=5Hz, 1H), 6.92(m, 1H), 7.18(s, 1H), 7.45(m, 6H), 7.92(s, 1H), 7.95(m, 1H), 9.06(m, 1H), 12.95(s, 1H). | m/z 525 (M+H)⁺ | Example 763 (Example 655) | 39 mg (40%) |
| H | ⟶O⟶N(morpholine) | H | ⟶NHC(O)(3-F-C₆H₄) | (500MHz, DMSO-d₆): δ 2.75(t, J=5 Hz, 1H), 3.38(m, 4H), 3.62(m, 4H), 3.75(t, J=5Hz, 1H), 4.15(m, 2H), 4.38 (d, J=5Hz, 1H), 6.92(m, 1H), 7.18(s, 1H), 7.40-7.80(m, 7H), 9.16(t, J=5Hz, 1H), 12.95(s, 1H). | m/z 543 (M+H)⁺ | Example 764 (Example 655) | 30 mg (19%) |

-continued

| R1 | R2 | R3 | R4 | ¹H NMR | MS(ESI): | Example # (synthesis protocol) | Obtained amt (yield) |
|---|---|---|---|---|---|---|---|
| H | ~~~O~N(CH3)C(O)CH2O~~~ | H | tetrahydrofuran-2-ylmethoxyethyl | (500MHz, DMSO-d₆): δ 1.85(m, 2H), 2.85(s, 3H), 3.03(s, 3H), 3.50(m, 2H), 3.61(m, 1H), 3.75(m, 2H), 3.78(s, 2H), 3.98(m, 2H), 4.45(s, 2H), 4.85(s, 2H), 6.96(d, J=7Hz, 1H), 7.18(s, 1H), 7.55(d, J=7Hz, 1H), 7.70(s, 1H), 7.85(s, 1H). | m/z 478 (M+H)⁺ | Example 765 (Example 655) | 12 mg (17%) |
| H | ~~~O~N(CH3)C(O)CH2O~~~ | H | phenoxyethyl | (500MHz, DMSO-d₆): δ 2.85(s, 3H), 3.03(s, 3H), 3.78(s, 2H), 4.85(s, 2H), 5.11(s, 2H), 6.93(d, J=7Hz, 2H), 7.08(m, 3H), 7.18(s, 1H), 7.38(t, J=7Hz, 2H), 7.55(d, J=7Hz, 1H), 7.71(s, 1H), 7.88(s, 1H). | m/z 470 (M+H)⁺ | Example 766 (Example 655) | 15 mg (21%) |
| H | ~~~O~N(CH3)C(O)CH2O~~~ | H | methylaminomethyl | (500MHz, DMSO-d₆): δ 2.68(s, 3H), 2.85(s, 3H), 3.03(s, 3H), 3.78(s, 2H), 4.25(s, 2H), 4.82(s, 2H), 6.92(d, J=7 Hz, 1H), 7.15(s, 1H), 7.55(d, J=7Hz, 1H), 7.75(s, 1H), 7.92(s, 1H). | m/z 407 (M+H)⁺ | Example 767 (Example 655) | 30 mg (39%) |

-continued

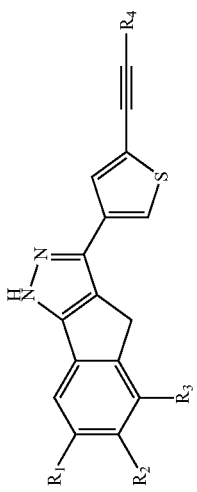

| R$_1$ | R$_2$ | R$_3$ | R$_4$ | $^1$H NMR | MS(ESI): | Example # (synthesis protocol) | Obtained amt (yield) |
|---|---|---|---|---|---|---|---|
| H | [N-methylpiperazinyl-ethyl] | H | [CH$_2$NH-methyl] | (500MHz, DMSO-d$_6$): δ 2.18(s, 3H), 2.38(m, 7H), 3.28 (m, 4H), 3.55(s, 2H), 3.65(s, 2H), 3.80(s, 2H), 7.28(d, J=7 Hz, 1H), 7.49(s, 1H), 7.60(m, 2H), 7.82(s, 1H). | m/z 418 (M+H)$^+$ | Example 768 (Example 655) | 60 mg (65%) |
| H | [N-methylpiperazinyl-ethyl] | H | [CH$_2$-O-methyl] | (500MHz, DMSO-d$_6$): δ 2.80(s, 3H), 3.20(m, 4H), 3.38(s, 3H), 3.45(m, 4H), 3.82(s, 2H), 4.00(s, 2H), 4.42(s, 2H), 7.41(d, J=7Hz, 1H), 7.62(s, 1H), 7.71(d, J=7Hz, 1H), 7.78(s, 1H), 7.82(s, 1H). | m/z 419 (M+H)$^+$ | Example 769 (Example 655) | 88 mg (54%) |
| H | [N-methylpiperazinyl-ethyl] | H | [n-pentyl] | (500MHz, DMSO-d$_6$): δ 0.98(t, J=8 Hz, 3H), 1.45(m, 2H), 1.55(m, 2H), 2.51(t, J=8Hz, 3H), 2.82(s, 3H), 3.82(s, 2H), 4.02(s, 2H), 7.41(d, J=7Hz, 1H), 7.61(s, 2H), 7.68(d, J=7Hz, 1H), 7.79(s, 1H). | m/z 431 (M+H)$^+$ | Example 770 (Example 655) | 88 mg (49%) |

| R₁ | R₂ | ¹H NMR | MS (ESI): | Example # (synthesis protocol) | Obtained amt. (yield) |
|---|---|---|---|---|---|
| OMe | -CH₂-O-Ph | (500 MHz, DMSO-d₆) δ 3.72 (s, 2H), 3.80(s, 3H), 5.10(s, 2H), 6.95(m, 2H), 7.08(m, 2H), 7.22(s, 1H), 7.28-7.60(m, 5H). | m/z 399 (M + H)⁺ | Example 771 (Example 655) | 15.0 mg (13%) |
| N-methylpiperazinyl-CH₂- | -CH₂-O-Ph | (300 MHz, DMSO-d₆) δ 2.79 (s, 3H), 3.00-3.50(m, 8H), 3.78 (s, 2H), 3.84(br s, 2H), 5.10(s, 2H), 6.94(m, 1H), 7.03(m, 2H), 7.11(s, 1H), 7.28(s, 1H), 7.36(m, 3H), 7.58(s, 1H), 7.63 (d, J=7.8Hz, 1H). | m/z 481 (M + H)⁺. | Example 772 (Example 655) | 141 mg (74%) |
| morpholino-CH₂CH₂-O-CH₂- | -CH₂-O-Ph | (400 MHz, DMSO-d₆) δ 3.22 (m, 2H), 3.48(m, 2H), 3.58(m, 2H), 3.68(m, 2H), 3.72(s, 2H), 3.98(m, 2H), 4.41(t, J=5Hz, 2H), 5.11(s, 2H), 7.05(m, 4H), 7.29(s, 1H), 7.39(m, 3H), 7.59 (d, J=7Hz, 1H). | m/z 498 (M + H)⁺. | Example 773 (Example 655) | 52 mg (47%) |
| morpholino- | -CH₂-O-Ph | (500 MHz, DMSO-d₆) δ 3.18 (m, 4H), 3.70(s, 2H), 3.78(m, 4H), 5.10(s, 2H), 6.95(d, J=7 Hz, 1H), 7.01(m, 1H), 7.08(m, 2H), 7.21(s, 1H), 7.36(m, 4H), 7.45(d, J=7Hz, 1H). | m/z 454 (M + H)⁺. | Example 774 (Example 655) | 20 mg (41%) |
| N-methylpiperazinyl- | -CH₂CH₂-CH₂-O-Ph | (500 MHz, DMSO-d₆) δ 2.85 (s, 3H), 3.08(t, J=8Hz, 2H), 3.22(t, J=8Hz, 2H), 3.55(d, J=8Hz, 2H), 3.75(s, 2H), 3.90 (d, J=8Hz, 2H), 5.08(s, 2H), 7.05(m, 4H), 7.26(s, 1H), 7.35 (m, 3H), 7.50(d, J=7Hz, 1H). | m/z 467 (M + H)⁺. | Example 775 (Example 655) | 23 mg (13%) |
| N-methylpiperazinyl-CH₂- | -CH₂CH₂-O-Ph | (500 MHz, DMSO-d₆) δ 2.79 (s, 3H), 2.99(t, J=8Hz, 2H), 3.00-3.50(m, 8H), 3.79 (s, 2H), 3.85(br s, 2H), 4.20(t, J=8 Hz, 2H), 6.98(m, 1H), 7.00(m, 2H), 7.36(m, 4H), 7.39(d, J= 8Hz, 1H), 7.59(s, 1H), 7.62 (J=8Hz, 1H). | m/z 495 (M + H)⁺. | Example 776 (Example 655) | 107 mg (56%) |
| N-methylpiperazinyl-CH₂- | -CH₂-O-(3-pyridyl) | (500 MHz, DMSO-d₆) δ 2.80 (s, 3H), 3.00-3.50(m, 8H), 3.77 (s, 2H), 4.02(s, 2H), 5.23(s, 2H), 7.39(m, 3H), 7.52(m, 1H), 7.60(s, 1H), 7.63(m, 2H), 8.32(br s, 1H), 8.47(s, 1H). | m/z 482 (M + H)⁺. | Example 777 (Example 655) | 88 mg (53%) |
| N-methylpiperazinyl-CH₂- | -CH₂-NH-C(O)-Ph | (500 MHz, DMSO-d₆) δ 2.78 (s, 3H), 3.00-3.50(m, 8H), 3.77 (s, 2H), 3.87(br s, 2H), 4.38(d, J=4.6Hz, 2H), 7.39(m, 3H), 7.50(m, 2H), 7.57(m, 2H), 7.63(d, J=7.6Hz, 1H), 7.88 (d, J=7.6Hz, 2H), 9.02(t, J= 4.6Hz, 1H). | m/z 508 (M + H)⁺. | Example 778 (Example 655) | 65 mg (38%) |
| N-methylpiperazinyl-CH₂- | -CH₂-O-CH₂CH₂-O-CH₂CH₃ | (500 MHz, DMSO-d₆) δ 1.10(t, J=7.6Hz, 3H), 2.80(s, 3H), 3.10-3.40(m, 8H), 3.45(q, J= 7.6Hz, 2H), 3.57(t, J=7.6Hz, 2H), 3.63(t, J=7.6Hz, 2H), 3.77(s, 2H), 3.87(br s, 2H), 4.43(s, 2H), 7.38(m, 3H), 7.58 (s, 1H), 7.62(d, J=7.6Hz, 1H). | m/z 477 (M + H)⁺. | Example 779 (Example 655) | 110 mg (78%) |

| R₁ | R₂ | ¹H NMR | MS (ESI): | Example # (synthesis protocol) | Obtained amt. (yield) |
|---|---|---|---|---|---|
| 4-methylpiperazinyl-ethyl | 2-methoxyethoxy-isopropyl | (500 MHz, DMSO-d₆) δ 1.08 (d, J=7.6Hz, 6H), 2.79(s, 3H), 3.10-3.40(m, 8H), 3.57(t, J=7.6Hz, 2H), 3.59(m, 1H), 3.62(t, J=7.6Hz, 2H), 3.77(s, 2H), 3.85(br s, 2H), 4.42(s, 2H), 7.39(m, 3H), 7.59(s, 1H), 7.62(d, J=7.6Hz, 1H). | m/z 491 (M + H)⁺. | Example 780 (Example 655) | 110 mg (77%) |

EXAMPLE 781

6-[(4-methyl-1-piperazinyl)methyl]-3-[4-(3-phenoxy-1-propynyl)-2-thienyl]-1,4-dihydroindeno[1,2-c]pyrazole The procedure for Example 655 was used, substituting Example 261 for Example 148 to provide 35 mg (31%) of Example 781. ¹H NMR (400 MHz, DMSO-d₆) δ 2.23 (s, 3H), 2.35-2.55 (m, 8H), 3.76 (s, 2H), 4.01 (br s, 2H), 5.05 (s, 2H), 7.00 (m, 1H), 7.05 (m, 2H), 7.29 (d, J=7.7 Hz, 1H), 7.34 (m, 3H), 7.49 (s, 1H), 7.55 (m, 1H), 7.76 (br s, 1H). MS (ESI): m/z 481 (M+H)⁺.

EXAMPLE 782

3-{4-[3-(2-methoxyethoxy)-1-propynyl]-2-thienyl}-6-[(4-methyl-1-piperazinyl)methyl]-1,4-dihydroindeno[1,2-c]pyrazole The procedure for Example 655 was used, substituting Example 261 for Example 148 and Example 127 for phenyl propargyl ether to provide 71 mg (38%) of Example 782 as the trifluoroacetate salt. ¹H NMR (400 MHz, DMSO-d₆) δ 2.79 (s, 3H), 3.27 (s, 3H), 3.00-3.50 (m, 8H), 3.51 (m, 2H), 3.64 (m, 2H), 3.80 (s, 2H), 3.86 (br s, 2H), 4.40 (s, 2H), 7.38 (d, J=7.5 Hz, 1H), 7.46 (s, 1H), 7.58 (s, 1H), 7.63 (d, J=7.5 Hz, 1H), 7.81 (s, 1H). MS (ESI): m/z 463 (M+H)⁺.

EXAMPLE 783

3-{5-[3-(2-methoxyethoxy)-1-propynyl]-3-thienyl}-6-[(4-methyl-1-piperazinyl)methyl]indeno[1,2-c]pyrazol-4(1H)-one The procedure for Example 655 was used, substituting Example 654 for Example 148 and Example 127 for phenyl propargyl ether to provide 59 mg (55%) of Example 783. ¹H NMR (500 MHz, DMSO-d₆): δ 2.78 (s, 3H), 3.05 (m, 4H), 3.28 (s, 3H), 3.45 (m, 4H), 3.55 (t, J=5 Hz, 2H), 3.65 (t, J=5 Hz, 2H), 3.81 (s, 2H), 4.45 (s, 2H), 7.52 (m, 2H), 7.62 (s, 1H), 7.98 (s, 1H), 8.38 (s, 1H), 13.78 (br s, 1H). MS (ESI): m/z 477 (M+H).

| R | ¹H NMR (500 MHz, DMSO-d₆) | MS (ESI): | Example # (synthesis protocol) | Obtained amt (yield) |
|---|---|---|---|---|
| 1-hydroxycyclopentyl | δ 1.75(m, 4H), 1.98(m, 4H), 3.75(s, 2H), 7.19(dd, J=3.4, 5.0Hz, 1H), 7.31(d, J=7.5Hz, 1H), 7.40(t, J=7.5Hz, 1H), 7.49 (d, J=3.4Hz, 1H), 7.59(d, J=5.0Hz, 1H), 7.64(d, J=7.5Hz, 1H). | m/z 347 (M + H)⁺. | Example 784 (Example 655) | 5 mg (2%) |
| 1-hydroxypropyl (sec-butanol) | δ 1.05(t, J=7.5Hz, 3H), 1.74(m, 2H), 3.76(s, 2H), 4.49(t, J=5.0Hz, 1H), 7.19 (dd, J=3.4, 5.0Hz, 1H), 7.34(d, J=7.5 Hz, 1H), 7.41(t, J=7.5Hz, 1H), 7.49(d, J=3.4Hz, 1H), 7.59(d, J=5.0Hz, 1H), 7.64 (d, J=7.5Hz, 1H). | m/z 321 (M + H)⁺. | Example 785 (Example 655) | 13 mg (5%) |
| 1-hydroxybutyl | δ 0.98(t, J=10.0Hz, 3H), 1.55(m, 2H), 1.72(m, 2H), 3.75(s, 2H), 4.55(t, J=10.0 Hz, 1H), 7.19(dd, J=3.4, 5.0Hz, 1H), 7.34 (d, J=7.5Hz, 1H), 7.41(t, J=7.5Hz, 1H), 7.49(d, J=3.4Hz, 1H), 7.59(d, J=5.0 Hz, 1H), 7.64(d, J=7.5Hz, 1H). | m/z 335 (M + H)⁺. | Example 786 (Example 655) | 5 mg (2%) |

-continued

| R | ¹H NMR(500 MHz, DMSO-d₆) | MS (ESI): | Example # (synthesis protocol) | Obtained amt (yield) |
|---|---|---|---|---|
| 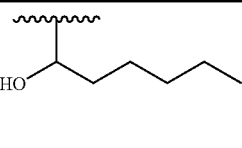 | δ 0.91(t, J=10.0Hz, 3H), 1.35(m, 4H), 1.54(m, 2H), 1.72(m, 2H), 3.75(s, 2H), 4.54(t, J=5.0Hz, 1H), 7.19(dd, J=3.4, 5.0Hz, 1H), 7.34(d, J=7.5Hz, 1H), 7.41 (t, J=7.5Hz, 1H), 7.49(d, J=3.4Hz, 1H), 7.59(d, J=5.0Hz, 1H), 7.64(d, J=7.5Hz, 1H). | m/z 363 (M + H)⁺ | Example 787 (Example 655) | 5 mg (2%) |
| 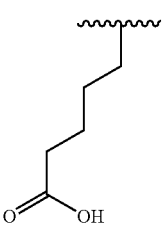 | δ 1.64(m, 2H), 1.75(m, 2H), 2.33(t, J= 10.0Hz, 2H), 2.55(t, J=10.0Hz, 2H), 3.75 (s, 2H), 7.19(dd, J=3.4, 5.0Hz, 1H), 7.34 (d, J=7.5Hz, 1H), 7.41(t, J=7.5Hz, 1H), 7.49(d, J=3.4Hz, 1H), 7.59(d, J=5.0 Hz, 1H), 7.64(d, J=7.5Hz, 1H). | m/z 363 (M + H)⁺. | Example 788 (Example 655) | 6 mg (2%) |
| 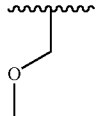 | 3.41(s, 3H), 3.78(s, 2H), 4.43(s, 2H), 7.18 (dd, J=3.4, 5.0Hz, 1H), 7.39(d, J=7.5 Hz, 1H), 7.42(t, J=7.5Hz, 1H), 7.50(d, J= 3.4Hz, 1H), 7.58(d, J=5.0Hz, 1H), 7.67 (d, J=7.5Hz, 1H). | m/z 307 (M + H)⁺. | Example 789 (Example 655) | 10 mg (4%) |
|  | δ 1.55(s, 6H), 3.75(s, 2H), 7.19(dd, J= 3.4, 5.0Hz, 1H), 7.34(d, J=7.5Hz, 1H), 7.41(t, J=7.5Hz, 1H), 7.49(d, J=3.4Hz, 1H), 7.59(d, J=5.0Hz, 1H), 7.64(d, J= 7.5Hz, 1H). | m/z 321 (M + H)⁺. | Example 790 (Example 655) | 13 mg (5%) |
| 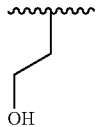 | δ 2.67(t, J=10.0Hz, 2H), 3.67(t, J=10.0 Hz, 2H), 3.75(s, 2H), 7.19(dd, J=3.4, 5.0 Hz, 1H), 7.34(d, J=7.5Hz, 1H), 7.41(t, J= 7.5Hz, 1H), 7.49(d, J=3.4Hz, 1H), 7.59(d, J=5.0Hz, 1H), 7.64(d, J=7.5Hz, 1H). | m/z 307 (M + H)⁺. | Example 791 (Example 655) | 13 mg (5%) |

EXAMPLE 792

2-[3-(4-{1-[bis(4-methoxyphenyl)methyl]-6-[(4-methylpiperazin-1-yl)methyl]-1,4-dihydroindeno[1,2-c]pyrazol-3-yl}thien-2-yl)prop-2-ynyl]-1H-isoindole-1,3(2H)-dione The procedure for Example 331 was used, substituting Example 670 for Example 326 to provide Example 792. MS (ESI): m/z 760 (M+H)⁺.

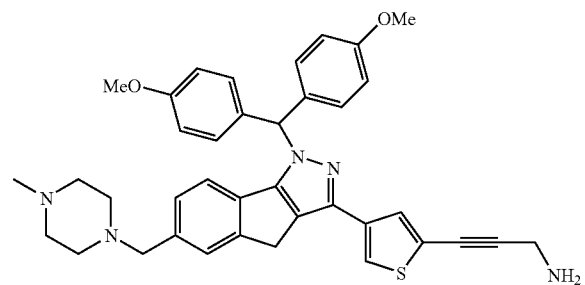

EXAMPLE 793

3-(4-{1-[bis(4-methoxyphenyl)methyl]-6-[(4-methylpiperazin-1-yl)methyl]-1,4-dihydroindeno[1,2-c]pyrazol-3-yl}thien-2-yl)prop-2-yn-1-amine A solution of Example 791 (2.9 g, 3.8 mmol) and anhydrous hydrazine (0.53 mL, 16.9 mmol) in ethanol (30 mL) and tetrahydrofuran (30 mL) was stirred at ambient temperature overnight. Then, tetrahydrofuran (30 mL) was added and the mixture was filtered. The filtrate was concentrated under vacuum and the residue was purified by flash chromatography on silica gel using dichloromethan/methanol (10:1)+1% ammonium hydroxide as eluent to provide Example 793. MS (ESI): m/z 630 (M+H)⁺.

EXAMPLE 794

N-[3-(4-{6-[(4-methyl-1-piperazinyl)methyl]-1,4-dihydroindeno[1,2-c]pyrazol-3-yl}-2-thienyl)-2-propynyl]-N'-phenylurea The procedure for Example 402 was used, substituting Example 793 for Example 396 to provide 32 mg (30%) of Example 794 as the trifluoroacetate salt. $^1$H NMR (500 MHz, DMSO-d$_6$) δ 2.80 (s, 3H), 3.00-3.50 (m, 8H), 3.83 (s, 2H), 3.96 (br s, 2H), 4.20 (d, J=5.5 Hz, 2H), 6.55 (t, J=5.5 Hz, 1H), 6.92 (m, 1H), 7.24 (m, 2H), 7.38 (d, J=7.6 Hz, 1H), 7.41 (m, 2H), 7.58 (s, 1H), 7.67 (m, 2H), 7.84 (s, 1H), 8.70 (s, 1H). MS (ESI): m/z 523 (M+H)$^+$.

EXAMPLE 795

N-(4-fluorophenyl)-N'-[3-(4-{6-[(4-methyl-1-piperazinyl)methyl]-1,4-dihydroindeno[1,2-c]pyrazol-3-yl}-2-thienyl)-2-propynyl]urea The procedure for Example 559 was used, substituting Example 793 for Example 558 and 4-fluorophenyl isocyanate for 2-methoxyphenyl isocyanate to provide 24 mg (49%) of Example 795. $^1$H NMR (500 MHz, DMSO-d$_6$) δ 2.29 (s, 3H), 2.35-2.65 (m, 8H), 3.54 (s, 2H), 3.80 (s, 2H), 4.20 (d, J=5.9 Hz, 2H), 6.63 (t, J=5.9 Hz, 1H), 7.08 (m, 2H), 7.28 (d, J=7.5 Hz, 1H), 7.42 (m, 2H), 7.47 (s, 1H), 7.60 (d, J=7.5 Hz, 1H), 7.67 (s, 1H), 7.83 (s, 1H), 8.73 (s, 1H). MS (ESI): m/z 541 (M+H)$^+$.

EXAMPLE 796

N-(2-methoxyethyl)-N'-[3-(4-{6-[(4-methyl-1-piperazinyl)methyl]-1,4-dihydroindeno[1,2-c]pyrazol-3-yl}-2-thienyl)-2-propynyl]urea The procedure for Example 403 was used, substituting Example 793 for Example 395 and 2-methoxyethylamine for N-methyl-m-toluidine to provide 45 mg (33%) of Example 796 as the trifluoroacetate salt. $^1$H NMR (500 MHz, DMSO-d$_6$) δ 2.80 (s, 3H), 3.00-3.50 (m, 8H), 3.19 (m, 2H), 3.25 (s, 3H), 3.33 (t, J=5.6 Hz, 2H), 3.83 (s, 2H), 3.98 (br s, 2H), 4.11 (s, 2H), 6.10 (br s, 1H), 6.39 (br s, 1H), 7.40 (d, J=7.6 Hz, 1H), 7.60 (s, 1H), 7.65 (d, J=1.2 Hz, 1H), 7.68 (d, J=7.6 Hz, 1H), 7.83 (d, J=1.2 Hz, 1H). MS (ESI): m/z 505 (M+H)$^+$.

| R | $^1$H NMR | MS (ESI): | Example # (synthesis protocol) | Obtained amt (yield) |
| --- | --- | --- | --- | --- |
| HN—(2-methylphenyl) | (500 MHz, DMSO-d$_6$) δ 2.20 (s, 3H), 2.80 (s, 3H), 3.00-3.50 (m, 8H), 3.83 (s, 2H), 3.94 (br s, 2H), 4.22 (d, J=5.5Hz, 2H), 6.46 (t, J=5.5Hz, 1H), 6.89 (m, 2H), 7.13 (m, 2H), 7.39 (d, J=7.6Hz, 1H), 7.59 (s, 1H), 7.68 (m, 2H), 7.81 (s, 1H), 7.86 (s, 1H). | m/z 537 (M + H)$^+$. | Example 797 (Example 794) | 30 mg (28%) |
| HN—(2-methoxyphenyl), MeO | (500 MHz, DMSO-d$_6$) δ 2.81 (s, 3H), 3.00-3.50 (m, 8H), 3.84 (m, 5H), 3.96 (br s, 2H), 4.21 (d, J=5.2Hz, 2H), 6.44 (t, J=5.2Hz, 1H), 6.87 (m, 3H), 6.97 (m, 1H), 7.40 (d, J=7.3Hz, 1H), 7.59 (s, 1H), 7.68 (m, 2H), 7.85 (s, 1H), 8.07 (s, 1H). | m/z 553 (M + H)$^+$. | Example 798 (Example 794) | 26 mg (23%) |
| HN—(2-fluorophenyl), F | (500 MHz, DMSO-d$_6$) δ 2.79 (s, 3H), 3.00-3.50 (m, 8H), 3.83 (s, 2H), 3.91 (br s, 2H), 4.23 (d, J=5.5Hz, 2H), 6.97 (m, 1H), 7.05 (t, J=5.5Hz, 1H), 7.11 (m, 1H), 7.19 (m, 1H), 7.38 (d, J=7.8Hz, 1H), 7.57 (s, 1H), 7.66 (d, J=7.8Hz, 1H), 7.68 (s, 1H), 7.84 (s, 1H), 8.10 (m, 1H), 8.45 (s, 1H). | m/z 541 (M + H)$^+$. | Example 799 (Example 794) | 43 mg (53%) |
| HN—(2-chlorophenyl), Cl | (500 MHz, DMSO-d$_6$) δ 2.79 (s, 3H), 3.00-3.50 (m, 8H), 3.83 (s, 2H), 3.89 (br s, 2H), 4.25 (d, J=5.5Hz, 2H), 6.99 (m, 1H), 7.27 (m, 1H), 7.37 (d, J=7.8Hz, 1H), 7.42 (m, 1H), 7.47 (t, J=5.5Hz, 1H), 7.57 (s, 1H), 7.66 (d, J=7.8Hz, 1H), 7.69 (s, 1H), 7.85 (s, 1H), 8.13 (m, 1H), 8.16 (s, 1H). | m/z 557 (M)$^+$. | Example 800 (Example 794) | 41 mg (51%) |
| HN—(2-bromophenyl), Br | (500 MHz, DMSO-d$_6$) δ 2.79 (s, 3H), 3.00-3.50 (m, 8H), 3.83 (s, 2H), 3.89 (br s, 2H), 4.24 (d, J=5.5Hz, 2H), 6.94 (m, 1H), 7.31 (m, 1H), 7.38 (d, J=7.8Hz, 1H), 7.54 (t, J=5.5Hz, 1H), 7.57 (s, 2H), 7.66 (d, J=7.8Hz, 1H), 7.69 (s, 1H), 7.85 (s, 1H), 7.99 (s, 1H), 8.05 (m, 1H). | 601, 603 (M + H)$^+$. | Example 801 (Example 794) | 41 mg (49%) |

| R | ¹H NMR | MS (ESI): | Example # (synthesis protocol) | Obtained amt (yield) |
|---|---|---|---|---|
| HN-(3-methylphenyl) | (400 MHz, DMSO-d₆) δ 2.25(s, 3H), 2.77(s, 3H), 3.00-3.50(m, 8H), 3.82(s, 2H), 3.98(br s, 2H), 4.19(d, J=5.8Hz, 2H), 6.66(t, J=5.8Hz, 1H), 6.74(d, J=7.4Hz, 1H), 6.99(s, 1H), 7.12(m, 1H), 7.21(d, J=8.0Hz, 1H), 7.25(s, 1H), 7.35(d, J=8.0Hz, 1H), 7.55(s, 1H), 7.64(d, J=7.7Hz, 1H), 7.66(s, 1H), 7.83(s, 1H), 8.61(s, 1H). | m/z 537 (M + H)⁺ | Example 802 (Example 794) | 21 mg (28%) |
| HN-(3-methoxyphenyl) | (400 MHz, DMSO-d₆) δ 2.77(s, 3H), 3.00-3.50(m, 8H), 3.70(s, 3H), 3.81(s, 2H), 3.94(br s, 2H), 4.18(d, J=5.5Hz, 2H), 6.50(dd, J=8.0, 1.8Hz, 1H), 6.63(t, J=5.5Hz, 1H), 6.90(d, J=8.0Hz, 1H), 7.13(m, 2H), 7.35(d, J=7.7Hz, 1H), 7.54(s, 1H), 7.64(m, 2H), 7.82(s, 1H), 8.69(s, 1H). | m/z 553 (M + H)⁺ | Example 803 (Example 794) | 34 mg (30%) |
| HN-(3-fluorophenyl) | (500 MHz, DMSO-d₆) δ 2.79(s, 3H), 3.00-3.50(m, 8H), 3.82(s, 2H), 3.90(br s, 2H), 4.20(d, J=5.6Hz, 2H), 6.72(m, 1H), 6.78(t, J=5.6Hz, 1H), 7.09(m, 1H), 7.26(m, 1H), 7.37(d, J=7.8Hz, 1H), 7.47(m, 1H), 7.57(s, 1H), 7.66(m, 2H), 7.84(s, 1H), 8.97(s, 1H). | m/z 541 (M + H)⁺ | Example 804 (Example 794) | 42 mg (54%) |
| HN-(3-chlorophenyl) | (500 MHz, DMSO-d₆) δ 2.78(s, 3H), 3.00-3.50(m, 8H), 3.82(s, 2H), 3.90(br s, 2H), 4.20(d, J=5.6Hz, 2H), 6.79(t, J=5.6Hz, 1H), 6.96(m, 1H), 7.25(m, 3H), 7.36(d, J=7.8Hz, 1H), 7.56(s, 1H), 7.67(m, 2H), 7.84(s, 1H), 8.95(s, 1H). | m/z 557 (M)⁺ | Example 805 (Example 794) | 52 mg (65%) |
| HN-(3-bromophenyl) | (500 MHz, DMSO-d₆) δ 2.79(s, 3H), 3.00-3.50(m, 8H), 3.82(s, 2H), 3.90(br s, 2H), 4.20(d, J=5.6Hz, 2H), 6.79(t, J=5.6Hz, 1H), 7.10(d, J=8.7Hz, 1H), 7.20(t, J=8.1Hz, 1H), 7.29(d, J=9.0Hz, 1H), 7.37(d, J=7.8Hz, 1H), 7.57(s, 1H), 7.67(m, 2H), 7.84(m, 2H), 8.94(s, 1H). | m/z 601, 603 (M + H)⁺ | Example 806 (Example 794) | 43 mg (51%) |
| HN-(3-trifluoromethylphenyl) | (400 MHz, DMSO-d₆) δ 2.77(s, 3H), 3.00-3.50(m, 8H), 3.81(s, 2H), 3.85(br s, 2H), 4.20(d, J=5.8Hz, 2H), 6.86(t, J=5.8Hz, 1H), 7.25(d, J=7.7Hz, 1H), 7.35(d, J=7.5Hz, 1H), 7.46(t, J=8.3Hz, 1H), 7.54(m, 2H), 7.64(d, J=8.0Hz, 1H), 7.66(d, J=1.5Hz, 1H), 7.82(d, J=1.5Hz, 1H), 7.98(s, 1H), 9.13(s, 1H). | m/z 591 (M + H)⁺ | Example 807 (Example 794) | 41 mg (35%) |
| HN-(4-methylphenyl) | (400 MHz, DMSO-d₆) δ 2.17(s, 3H), 2.73(s, 3H), 2.90-3.45(m, 8H), 3.77(s, 2H), 4.05(br s, 2H), 4.14(d, J=5.5Hz, 2H), 6.55(t, J=5.5Hz, 1H), 6.99(m, 2H), 7.23(m, 2H), 7.31(d, J=7.7Hz, 1H), 7.50(s, 1H), 7.60(m, 2H), 7.78(s, 1H), 8.51(s, 1H). | m/z 537 (M + H)⁺ | Example 808 (Example 794) | 34 mg (31%) |
| HN-(4-methoxyphenyl) | (400 MHz, DMSO-d₆) δ 2.80(s, 3H), 3.00-3.50(m, 8H), 3.70(s, 3H), 3.83(s, 2H), 3.96(br s, 2H), 4,18(d, J=5.5Hz, 2H), 6.55(t, J=5.5Hz, 1H), 6.83(m, 2H), 7.32(m, 2H), 7.38(d, J=7.6Hz, 1H), 7.57(s, 1H), 7.67(m, 2H), 7.84(s, 1H), 8.50(s, 1H). | m/z 553 (M + H)⁺ | Example 809 (Example 794) | 30 mg (27%) |

-continued

| R | $^1$H NMR | MS (ESI): | Example # (synthesis protocol) | Obtained amt (yield) |
|---|---|---|---|---|
| HN–C₆H₄–Cl (4-Cl) | (500 MHz, DMSO-d$_6$)δ 2.26(s, 3H), 2.35-2.65(m, 8H), 3.53(s, 2H), 3.80(s, 2H), 4.20(d, J=5.9Hz, 2H), 6.69(t, J=5.9Hz, 1H), 7.29(m, 3H), 7.44(m, 3H), 7.60(d, J=7.5Hz, 1H), 1H), 7.67(s, 1H), 7.83(s, 1H), 8.85(s, 1H). | m/z 557 (M)$^+$. | Example 810 (Example 794) | 20 mg (40%) |
| HN–C₆H₄–CF₃ (4-CF₃) | (500 MHz, DMSO-d$_6$)δ 2.78(s, 3H), 3.00-3.50(m, 8H), 3.82(s, 2H), 3.90(br s, 2H), 4.22(d, J=5.6Hz, 2H), 6.88(t, J=5.6Hz, 1H), 7.38(d, J=6.8Hz, 1H), 7.59(m, 3H), 7.65(m, 4H), 7.84(s, 1H), 9.20(s, 1H). | m/z 591 (M + H)$^+$. | Example 811 (Example 794) | 37 mg (45%) |
| HN–C₆H₄–N(CH₃)₂ (4-NMe₂) | (500 MHz, DMSO-d$_6$)δ 2.78(s, 3H), 3.00(s, 6H), 3.00-3.50(m, 8H), 3.82(s, 2H), 3.89(br s, 2H), 4.20(d, J=5.6Hz, 2H), 6.67(m, 1H), 7.17(m, 1H), 7.39(m, 3H), 7.58(s, 1H), 7.66(m, 3H), 7.84(s, 1H), 8.71(br s, 1H). | m/z 566 (M + H)$^+$. | Example 812 (Example 794) | 42 mg (46%) |
| HN–C₆H₄–SCF₃ (4-SCF₃) | (500 MHz, DMSO-d$_6$)δ 2.79(s, 3H), 3.00-3.50(m, 8H), 3.82(s, 2H), 3.88(br s, 2H), 4.21(d, J=5.6Hz, 2H), 6.82(t, J=5.6Hz, 1H), 7.24(d, J=7.8Hz, 1H), 7.40(m, 2H), 7.55(m, 2H), 7.66(m, 2H), 7.84(s, 1H), 7.96(s, 1H), 9.07(s, 1H). | m/z 623 (M + H)$^+$. | Example 813 (Example 794) | 27 mg (32%) |
| HN–C₆H₄–CN (4-CN) | (500 MHz, DMSO-d$_6$)δ 2.79(s, 3H), 3.00-3.50(m, 8H), 3.82(s, 2H), 3.90(br s, 2H), 4.22(d, J=5.6Hz, 2H), 6.96(t, J=5.6Hz, 1H), 7.39(d, J=7.5Hz, 1H), 7.60(m, 3H), 7.68(m, 4H), 7.84(s, 1H), 9.32(s, 1H). | m/z 548 (M + H)$^+$. | Example 814 (Example 794) | 36 mg (45%) |
| HN–(2,3-dimethylphenyl) | (500 MHz, DMSO-d$_6$)δ 2.09(s, 3H), 2.24(s, 3H), 2.81(s, 3H), 3.00-3.50(m, 8H), 3.84(s, 2H), 3.96(br s, 2H), 4.20(d, J=5.2Hz, 2H), 6.86(m, 2H), 7.00(t, J=7.8Hz, 1H), 7.40(d, J=7.8Hz, 1H), 7.49(d, J=7.8Hz, 1H), 7.59(s, 1H), 7.68(m, 2H), 7.86(m, 2H). | m/z 551 (M + H)$^+$. | Example 815 (Example 794) | 27 mg (24%) |
| HN–(2,4-dimethylphenyl) | (500 MHz, DMSO-d$_6$)δ 2.16(s, 3H), 2.21(s, 3H), 2.79(s, 3H), 3.00-3.50(m, 8H), 3.83(s, 2H), 3.91(br s, 2H), 4.20(d, J=5.6Hz, 2H), 6.88(t, J=5.6Hz, 1H), 6.91(d, J=7.8Hz, 1H), 6.96(s, 1H), 7.38(d, J=7.8Hz, 1H), 7.55(m, 2H), 7.68(m, 2H), 7.74(s, 1H), 7.84(s, 1H). | m/z 551 (M + H)$^+$. | Example 816 (Example 794) | 42 mg (53%) |
| HN–(2,5-dimethylphenyl) | (500 MHz, DMSO-d$_6$)δ 2.15(s, 3H), 2.23(s, 3H), 2.79(s, 3H), 3.00-3.50(m, 8H), 3.83(s, 2H), 3.92(br s, 2H), 4.21(d, J=5.6Hz, 2H), 6.73(d, J=7.3Hz, 1H), 6.97(t, J=5.6Hz, 1H), 7.01(d, J=7.3Hz, 1H), 7.39(d, J=7.8Hz, 1H), 7.59(s, 1H), 7.63(s, 1H), 7.67(m, 2H), 7.75(s, 1H), 7.84(s, 1H). | m/z 551 (M + H)$^+$. | Example 817 (Example 794) | 25 mg (32%) |
| HN–(3,4-dimethylphenyl) | (500 MHz, DMSO-d$_6$)δ 2.14(s, 3H), 2.17(s, 3H), 2.79(s, 3H), 3.00-3.50(m, 8H), 3.82(s, 2H), 3.91(br s, 2H), 4.18(d, J=5.6Hz, 2H), 6.57(t, J=5.6Hz, 1H), 6.98(d, J=8.1Hz, 1H), 7.14(dd, J=8.1, 2.2Hz, 1H), 7.18(d, J=2.2Hz, 1H), 7.38(d, J=7.5Hz, 1H), 7.57(s, 1H), 7.66(m, 2H), 7.83(s, 1H), 8.47(s, 1H). | m/z 551 (M + H)$^+$. | Example 818 (Example 794) | 41 mg (51%) |

-continued

| R | ¹H NMR | MS (ESI): | Example # (synthesis protocol) | Obtained amt (yield) |
|---|---|---|---|---|
| 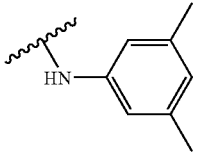 | (500 MHz, DMSO-d₆)δ 2.21(s, 6H), 2.80(s, 3H), 3.00-3.55(m, 8H), 3.83(s, 2H), 3.94(br s, 2H), 4.18(d, J=5.5Hz, 2H), 6.57(s, 1H), 6.62(t, J=5.5Hz, 1H), 7.04(s, 2H), 7.38(d, J=7.9Hz, 1H), 7.58(s, 1H), 7.67(m, 2H), 7.84(s, 1H), 8.53(s, 1H). | m/z 551 (M + H)⁺. | Example 819 (Example 794) | 30 mg (27%) |
| 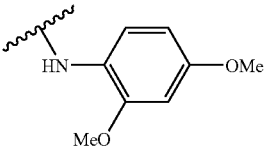 | (500 MHz, DMSO-d₆)δ 2.79(s, 3H), 3.00-3.50(m, 8H), 3.72(s, 3H), 3.82(s, 5H), 3.90(br s, 2H), 4.20(d, J=5.6Hz, 2H), 6.45(dd, J=8.7, 2.6Hz, 1H), 6.58 (d, J=2.6Hz, 1H), 7.09(t, J=5.6Hz, 1H), 7.38(d, J=7.5Hz, 1H), 7.57(s, 1H), 7.66(m, 2H), 7.81(s, 1H), 7.84(d, J =1.2Hz, 1H), 7.86(d, J=8.7Hz, 1H). | m/z 583 (M + H)⁺. | Example 820 (Example 794) | 26 mg (32%) |
| 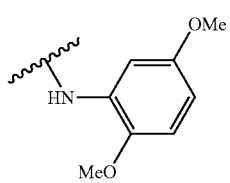 | (500 MHz, DMSO-d₆)δ 2.78(s, 3H), 3.00-3.50(m, 8H), 3.68(s, 3H), 3.79(s, 3H), 3.82(s, 2H), 3.90(br s, 2H), 4.21(d, J=5.6Hz, 2H), 6.45(dd, J=8.8, 3.1Hz, 1H), 6.88(d, J=8.8Hz, 1H), 7.36(m, 2H), 7.57(s, 1H), 7.67(m, 2H), 7.81(d, J=3.1Hz, 1H), 7.84(s, 1H), 8.08(s, 1H). | m/z 583 (M + H)⁺. | Example 821 (Example 794) | 8 mg (10%) |
| 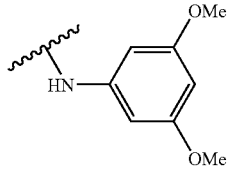 | (500 MHz, DMSO-d₆)δ 2.79(s, 3H), 3.00-3.50(m, 8H), 3.70(s, 6H), 3.82(s, 2H), 3.88(br s, 2H), 4.19(d, J=5.6Hz, 2H), 6.10(t, J=2.4Hz, 1H), 6.63(t, J=5.6Hz, 1H), 6.66(s, 1H), 6.67(s, 1H), 7.37(d, J=7.5Hz, 1H), 7.57(s, 1H), 7.66(m, 2H), 7.83(d, J=1.2Hz, 1H), 8.70(s, 1H). | m/z 583 (M + H)⁺. | Example 822 (Example 794) | 23 mg (27%) |
| 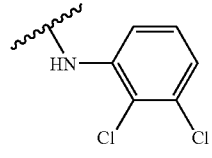 | (500 MHz, DMSO-d₆)δ 2.29(s, 3H), 2.35-2.65(m, 8H), 3.54(s, 2H), 3.80(s, 2H), 4.25(d, J=5.6Hz, 2H), 7.24(dd, J= 7.8, 1.3Hz, 1H), 7.29(m, 2H), 7.48(s, 1H), 7.57(t, J=5.6Hz, 1H), 7.61(d, J= 7.5Hz, 1H), 7.69(s, 1H), 7.85(s, 1H), 8.14(dd, J=8.1, 1.6Hz, 1H), 8.35(s, 1H). | m/z 591 (M)⁺. | Example 823 (Example 794) | 17 mg (32%) |
| 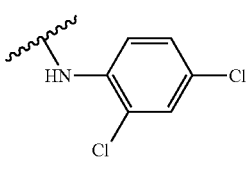 | (500 MHz, DMSO-d₆)δ 2.79(s, 3H), 3.00-3.50(m, 8H), 3.83(s, 2H), 3.91(br s, 2H), 4.24(d, J=5.3Hz, 2H), 7.35(dd, J=8.9, 2.5Hz, 1H), 7.38(d, J=7.8Hz, 1H), 7.51(t, J=5.3Hz, 1H), 7.57(m, 2H), 7.66(d, J=7.8Hz, 1H), 7.69(d, J= 1.2Hz, 1H), 7.85(d, J=1.2Hz, 1H), 8.17 (d, J=8.9Hz, 1H), 8.27(s, 1H). | m/z 591 (M)⁺. | Example 824 (Example 794) | 37 mg (45%) |
| 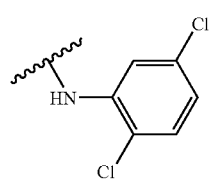 | (500 MHz, DMSO-d₆)δ 2.79(s, 3H), 3.00-3.50(m, 8H), 3.83(s, 2H), 3.91(br s, 2H), 4.25(d, J=5.3Hz, 2H), 7.05(dd, J=8.5, 2.8Hz, 1H), 7.38(d, J=7.6Hz, 1H), 7.46(d, J=8.5Hz, 1H), 7.58(s, 1H), 7.62(t, J=5.3Hz, 1H), 7.66(d, J= 7.6Hz, 1H), 7.69(d, J=1.2Hz, 1H), 7.86 (d, J=1.2Hz, 1H), 8.30(d, J=2.8Hz, 1H), 8.34(s, 1H). | m/z 591 (M)⁺. | Example 825 (Example 794) | 36 mg (43%) |
| 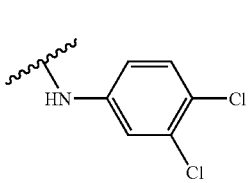 | (500 MHz, DMSO-d₆)δ 2.78(s, 3H), 3.00-3.50(m, 8H), 3.82(s, 2H), 3.88(br s, 2H), 4.20(d, J=5.3Hz, 2H), 7.86(t, J= 5.3Hz, 1H), 7.30(dd, J=8.7, 2.5Hz, 1H), 7.37(d, J=7.2Hz, 1H), 7.48(d, J= 8.7Hz, 1H), 7.56(s, 1H), 7.66(m, 2H), 7.84(d, J=1.2Hz, 1H), 7.87(d, J=2.5Hz, 1H), 9.08(s, 1H). | m/z 591 (M)⁺. | Example 826 (Example 794) | 54 mg (65%) |

| R | ¹H NMR | MS (ESI): | Example # (synthesis protocol) | Obtained amt (yield) |
|---|---|---|---|---|
| HN— (3-F, 5-CF₃ phenyl) | (500 MHz, DMSO-d₆) δ 2.78(s, 3H), 3.00-3.50(m, 8H), 3.82(s, 2H), 3.88(br s, 2H), 4.21(d, J=5.3Hz, 2H), 7.00(t, J=5.3Hz, 1H), 7.16(d, J=8.4Hz, 1H), 7.37(d, J=7.8Hz, 1H), 7.56(s, 1H), 7.61(d, J=8.4Hz, 1H), 7.66(m, 3H), 7.84(d, J=1.2Hz, 1H), 9.37(s, 1H). | m/z 609 (M + H)⁺. | Example 827 (Example 794) | 57 mg (67%) |
| HN— (3,4,5-triOMe phenyl) | (500 MHz, DMSO-d₆) δ 2.79(s, 3H), 3.00-3.50(m, 8H), 3.60(s, 3H), 3.73(s, 6H), 3.82(s, 2H), 3.90(br s, 2H), 4.19(d, J=5.6Hz, 2H), 6.60(t, J=5.6Hz, 1H), 6.79(s, 2H), 7.38(d, J=7.5Hz, 1H), 7.57(s, 1H), 7.66(m, 2H), 7.84(s, 1H), 8.65(s, 1H). | m/z 613 (M + H)⁺. | Example 828 (Example 794) | 38 mg (45%) |
| —N(Me)CH₂CH₂OMe | (500 MHz, DMSO-d₆) δ 2.81(s, 3H), 2.84(s, 3H), 3.00-3.50(m, 8H), 3.26(s, 3H), 3.37(m, 2H), 3.41(m, 2H), 3.83(s, 2H), 3.98(br s, 2H), 4.11(d, J=5.0Hz, 2H), 6.79(t, J=5.0Hz, 1H), 7.40(d, J=7.6Hz, 1H), 7.60(s, 1H), 7.65(d, J=1.2 Hz, 1H), 7.68(d, J=7.6Hz, 1H), 7.83(d, J=1.2Hz, 1H). | m/z 519 (M + H)⁺. | Example 829 (Example 796) | 31 mg (23%) |
| —N(CH₂CH₂OMe)₂ | (500 MHz, DMSO-d₆) δ 2.80(s, 3H), 3.00-3.50(m, 8H), 3.26(s, 6H), 3.41(m, 8H), 3.83(s, 2H), 3.98(br s, 2H), 4.11(d, J=5.0Hz, 2H), 6.76(t, J=5.0Hz, 1H), 7.40(d, J=7.6Hz, 1H), 7.59(s, 1H), 7.65(d, J=1.2Hz, 1H), 7.68(d, J=7.6 Hz, 1H), 7.83(d, J=1.2Hz, 1H). | m/z 563 (M + H)⁺. | Example 830 (Example 796) | 13 mg (9%) |
| pyrrolidinyl | (500 MHz, DMSO-d₆) δ 1.81(m, 4H), 2.81(s, 3H), 3.00-3.50(m, 12H), 3.83(s, 2H), 4.01(br s, 2H), 4.11(br s, 2H), 6.65(m, 1H), 7.40(d, J=7.5Hz, 1H), 7.60(s, 1H), 7.65(d, J=1.2Hz, 1H), 7.68(d, J=7.5Hz, 1H), 7.83(d, J=1.2Hz, 1H). | m/z 501 (M + H)⁺. | Example 831 (Example 796) | 18 mg (13%) |
| piperidinyl | (500 MHz, DMSO-d₆) δ 1.43(m, 4H), 1.54(m, 2H), 2.79(s, 3H), 3.00-3.50(m, 12H), 3.83(s, 2H), 3.90(br s, 2H), 4.10 (d, J=5.3Hz, 2H), 6.95(t, J=5.3Hz, 1H), 7.38(d, J=7.7Hz, 1H), 7.58(s, 1H), 7.65(d, J=1.2Hz, 1H), 7.66(d, J=7.7Hz, 1H), 7.82(d, J=1.2Hz, 1H). | m/z 515 (M + H)⁺. | Example 832 (Example 796) | 30 mg (35%) |
| morpholinyl | (500 MHz, DMSO-d₆) δ 2.81(s, 3H), 3.00-3.50(m, 12H), 3.56(m, 4H), 3.83(s, 2H), 3.99(br s, 2H), 4.13(d, J=5.3Hz, 2H), 6.37(t, J=5.3Hz, 1H), 7.40(d, J=7.6Hz, 1H), 7.60(s, 1H), 7.66(d, J=1.2 Hz, 1H), 7.68(d, J=7.6Hz, 1H), 7.78(d, J=1.2Hz, 1H). | m/z 517 (M + H)⁺. | Example 833 (Example 796) | 85 mg (62%) |

EXAMPLE 834

N-[3-(4-{6-[(4-methyl-1-piperazinyl)methyl]-1,4-dihydroindeno[1,2-c]pyrazol-3-yl}-2-thienyl)-2-propynyl]methanesulfonamide To methanesulfonyl chloride (7 μl, 0.087 mmol) was added a solution of Example 793 (50 mg, 0.079 mmol) in pyridine (1 mL) and the mixture was agitated at room temperature for about 2.5 hours. The mixture was concentrated under vacuum, to the residue was added a 4M solution of hydrochloric acid in 1,4-dioxane and the mixture was agitated at room temperature for about 6 hours. The mixture was concentrated under vacuum and the residue was purified by preparative HPLC on a Waters Symmetry C8 column (25 mm×100 mm, 7 μm particle size) using a gradient of 10% to 100% acetonitrile:0.1% aqueous TFA over 8 minutes (10 minutes run time) at a flow rate of 40 mL/minute to provide 11 mg (32%) of Example 834 as the trifluoroacetate salt. ¹H NMR (500 MHz, CD₃OD) δ 2.28 (s, 3H), 2.40-2.65 (m, 8H), 3.08 (s, 3H), 3.61 (s, 2H), 3.80 (s, 2H), 4.18 (s, 2H), 7.34 (d, J=7.5 Hz, 1H), 7.55 (s, 1H), 7.64 (m, 2H), 7.71 (s, 1H). MS (ESI): m/z 482 (M+H)⁺.

EXAMPLE 835

N-[3-(4-{6-[(4-methyl-1-piperazinyl)methyl]-1,4-dihydroindeno[1,2-c]pyrazol-3-yl}-2-propynyl]benzenesulfonamide The procedure for Example 834 was used, substituting benzenesulfonyl chloride for methanesulfonyl chloride to provide 18 mg (47%) of Example 835 as the trifluoroacetate salt. ¹H NMR (500 MHz, CD₃OD) δ 2.28 (s, 3H), 2.40-2.65 (m, 8H), 3.61 (s, 2H), 3.78 (s, 2H), 4.09 (s, 2H), 7.34 (d, J=7.8 Hz, 1H), 7.38 (s, 1H), 7.59 (m, 6H), 7.93 (m, 2H). MS (ESI): m/z 544 (M+H)⁺.

EXAMPLE 836

N-[3-(4-{6-[(4-methyl-1-piperazinyl)methyl]-1,4-dihydroindeno[1,2-c]pyrazol-3-yl}-2-thineyl)-2-propynyl]acetamide To acetyl chloride (6.8 mg, 0.086 mmol) was added a solution of Example 793 (50 mg, 0.079 mmol) in pyridine (1 mL) and the mixture was agitated for about 2.5 hours. The mixture was concentrated under vacuum, to the residue was added a 4M solution of hydrochloric acid in 1,4-dioxane and the mixture was agitated at room temperature for about 6 hours. The mixture was concentrated under vacuum and the residue was purified by preparative HPLC on a Waters Symmetry C8 column (25 mm×100 mm, 7 μm particle size) using a gradient of 10% to 100% acetonitrile:0.1% aqueous TFA over 8 minutes (10 minutes run time) at a flow rate of 40 mL/minute to provide 2 mg (8%) of Example 836 as the trifluoroacetate salt. ¹H NMR (500 MHz, CD₃OD) δ 1.99 (s, 3H), 2.28 (s, 3H), 2.40-2.65 (m, 8H), 3.61 (s, 2H), 3.80 (s, 2H), 4.22 (s, 2H), 7.34 (d, J=7.5 Hz, 1H), 7.56 (s, 1H), 7.60 (s, 1H), 7.66 (m, 1H), 7.68 (m, 1H). MS (ESI): m/z 446 (M+H)⁺.

EXAMPLE 837

N-[3-(4-{6-[(4-methyl-1-piperazinyl)methyl]-1,4-dihydroindeno[1,2-c]pyrazol-3-yl}-2-propynyl]benzamide The procedure for Example 836 was used, substituting benzoyl chloride for acetyl chloride to provide 14 mg (39%) of Example 837 as the trifluoroacetate salt. ¹H NMR (500 MHz, CD₃OD) δ 2.28 (s, 3H), 2.40-2.65 (m, 8H), 3.60 (s, 2H), 3.79 (s, 2H), 4.45 (s, 2H), 7.33 (d, J=7.8 Hz, 1H), 7.48 (m, 2H), 7.56 (m, 2H), 7.62 (s, 1H), 7.65 (m, 1H), 7.68 (s, 1H), 7.87 (m, 2H). MS (ESI): m/z 508 (M+H)⁺.

EXAMPLE 838 phenyl 3-(4-{6-[(4-methyl-1-piperazinyl methyl]-1,4-dihydroindeno[1,2-c]pyrazol-3-yl}-2-thienyl)-2-propynylcarbamate The procedure for Example 594 was used, substituting Example 793 for Example 395 to provide 4 mg (11%) of Example 838 as the trifluoroacetate salt. ¹H NMR (500 MHz, CD₃OD) δ 2.28 (s, 3H), 2.40-2.65 (m, 8H), 3.61 (s, 2H), 3.80 (s, 2H), 4.25 (s, 2H), 7.14 (m, 2H), 7.22 (m, 1H), 7.36 (m, 3H), 7.55 (s, 1H), 7.65 (m, 2H), 7.69 (s, 1H). MS (ESI): m/z 524 (M+H)³⁰.

EXAMPLE 839

6-[(4-methyl-1-piperazinyl)methyl]-3-{5-[(E)-2-(4-pyridinyl)vinyl]-3-thienyl}-1,4-dihydroindeno[1,2-c]pyrazole To a solution of Example 148 (100 mg, 0.23 mmol) in N,N-dimethylformamide (5 mL) was added 4-vinylpyridine (38 μl, 0.35 mmol), dichlorobis(triphenylphosphine)palladium(II) (8 mg, 0.01 mmol) and triethylamine (0.23 mL, 1.63 mmol) and the mixture was heated to reflux for about 4 hours. The reaction mixture was filtered through Celite, the filtrate was concentrated under vacuum and the residue was purified by preparative HPLC on a Waters Symmetry C8 column (25 mm×100 mm, 7 μm particle size) using a gradient of 10% to 100% acetonitrile:0.1% aqueous TFA over 8 minutes (10 minutes run time) at a flow rate of 40 mL/minute to provide 42 mg (40%) of Example 839 as the trifluoroacetate salt. ¹H NMR (500 MHz, DMSO-d₆): δ 2.80 (s, 3H), 3.00-3.50 (m, 8H), 3.85 (s, 2H), 3.92 (s, 2H), 7.23 (d, J=15.9 Hz, 1H), 7.40 (d, J=7.8 Hz, 1H), 7.60 (s, 1H), 7.67 (d, J=7.8 Hz, 1H), 7.88 (s, 1H), 8.01 (s, 1H), 8.11 (m, 2H), 8.17 (d, J=15.9 Hz, 1H), 8.79 (m, 2H). MS (ESI): m/z 454 (M+H).

EXAMPLE 840

3-(2,2'-bithien-5-yl)-6-[(4-methyl-1-piperazinyl)methyl]-1,4-dihydroindeno[1,2-c]pyrazole To a solution of Example 147 (50 mg, 0.116 mmol) in 1,2-dimethoxyethane (1 mL) and ethanol (0.3 mL) was added 2-thiopheneboronic acid (22 mg, 0.175 mmol), tetrakis(triphenylphosphine)palladium(0) (7 mg, 0.006 mmol) and a 2M aqueous solution of sodium carbonate and the mixture was heated to about 80 C overnight. The reaction mixture was filtered through Celite, the filtrate was concentrated under vacuum and the residue was purified by preparative HPLC on a Waters Symmetry C8 column (25 mm×100 mm, 7 μm particle size) using a gradient of 10% to 100% acetonitrile: 0.1% aqueous TFA over 8 minutes (10 minutes run time) at a flow rate of 40 mL/minute to provide 12 mg (13%) of Example 840 as the trifluoroacetate salt.

¹H NMR (500 MHz, DMSO-d₆): δ 2.79 (s, 3H), 3.00-3.50 (m, 8H), 3.80 (s, 2H), 3.87 (br s, 2H), 7.13 (dd, J=5.3, 3.7 Hz, 1H), 7.37 (m 3H), 7.41 (d, J=4.0 Hz, 1H), 7.54 (dd, J=5.3, 1.3 Hz, 1H), 7.58 (m, 1H), 7.64 (m, 1H). MS (ESI): m/z 433 (M+H).

EXAMPLE 841

3-(2,3'-bithien-5-yl)-6-[(4-methyl-1-piperazinyl)methyl]-1,4-dihydroindeno[1,2-c ]pyrazole The procedure for Example 840 was used, substituting 3-thiopheneboronic acid for 2-thiopheneboronic acid to provide 32 mg (36%) of Example 841 as the trifluoroacetate salt. ¹H NMR (500 MHz, DMSO-d₆): δ 2.80 (s, 3H), 3.00-3.50 (m, 8H), 3.80 (s, 2H), 3.92 (br s, 2H), 7.41 (m, 2H), 7.44 (d, J=3.4 Hz, 1H), 7.48 (dd, J=5.0, 1.3 Hz, 1H), 7.59 (m, 1H), 7.64 (m, 1H), 7.67 (dd, J=5.0, 2.8 Hz, 1H), 7.77 (dd, J=2.8, 1.3 Hz, 1H). MS (ESI): m/z 433 (M+H).

EXAMPLE 842

6-(4-morpholinylmethyl)-3-(2-thienyl-1,4-dihydroindeno[1,2-c]pyrazole

EXAMPLE 842A 3-chloro-1-(4-methylphenyl)propan-1-one

To a solution of aluminum chloride (55.0 g, 0.41 mol) in toluene (220 ml) was added 3-chloropropionyl chloride (50.0 g, 0.39 mol) at 0° C., and the mixture was stirred at ambient temperature for 3 h. The reaction mixture was poured into iced water and extracted with AcOEt. The extract was neutralized with 10% NaHCO3, washed with water and brine, dried over Na2SO4, and concentrated in vacuo. The residue was washed with n-heptane to give Example 842A (63.0 g, 88%) as a pale yellow solid.

EXAMPLE 842B

1-[4-(bromomethyl)phenyl]-3-chloropropan-1-one

A mixture of Example 842A (30.6 g, 0.17 mol) and N-bromosuccinimide (31.3 g, 0.17 mol) in CCl4 (150 ml) was refluxed for 2.5 h. The reaction mixture was filtered and the filtrate was concentrated in vacuo. The residue was diluted with H2O and extracted with AcOEt. The extract was washed with brine, dried over Na2SO4, and concentrated in vacuo. The residue was washed with n-heptane and recrystallized from AcOEt to give Example 842B (22.5 g, 51%) as colorless crystals.

EXAMPLE 842C 5-(bromomethyl)indan-1-one

A mixture of Example 842B (22.5 g, 0.086 mol) and conc. H2SO4 (225 ml) was stirred at 100° C. for 30 min. The reaction mixture was poured into a mixture of iced water and AcOEt, and then activated carbon powder was added. The activated carbon was filtrated off, and the layers were separated. The organic layer was washed with water, 10% NaHCO3 and brine, dried over Na2SO4, and concentrated in vacuo. The residue was purified by column chromatography [SiO2, eluent: AcOEt] to give Example 842C (14.7 g, 76%) as a brown crystalline solid.

EXAMPLE 842D 5-(morpholin-4-ylmethyl)indan-1-one

The desired product was prepared by substituting morpholine for N-methyl piperazine and Example 842C for Example 54 in Example 56.

EXAMPLE 842E 6-(4-morpholinylmethyl)-3-(2-thienyl)-1,4-dihydroindeno[1,2-c]pyrazole The desired product was prepared by substituting Example 842D for Example 56 in Example 138. m.p. 178-179° C.

EXAMPLE 843

N,N-dimethyl-N-{[3-(2-thienyl)-1,4-dihydroindeno[1,2-c]pyrazol-6-yl]methyl}amine

EXAMPLE 843A

5-[(dimethylamino)methyl]indan-1-one

The desired product was prepared by substituting dimethylamine for N-methyl piperazine and Example 842C for Example 54 in Example 56.

EXAMPLE 843B

N,N-dimethyl-N-{[3-(2-thienyl)-1,4-dihydroindeno[1,2-c]pyrazol-6-yl]methyl}amine The desired product was prepared by substituting Example 843A for Example 56 in Example 138. m.p. 204-206° C.

EXAMPLE 844

N,N-dimethyl-1-{[3-(2-thienyl)-1,4-dihydroindeno[1,2-c]pyrazol-6-yl]methyl}-4-piperidinamine

EXAMPLE 844A

5-{[4-(dimethylamino)piperidin-1-yl]methyl}indan-1-one

The desired product was prepared by substituting 4-dimethylaminopiperidine for N-methyl piperazine and Example 842C for Example 54 in Example 56.

EXAMPLE 844B

N,N-dimethyl-1-{[3-(2-thienyl)-1,4-dihydroindeno[1,2-c]pyrazol-6-yl]methyl}-4-piperidinamine The desired product was prepared by substituting Example 844A for Example 56 in Example 138. m.p. 96-98° C.

EXAMPLE 845

6-[(4-methyl-1-piperazinyl)methyl]-3-(3-thienyl)-1,4-dihydroindeno[1,2-c]pyrazole

EXAMPLE 845A

5-[(4-methylpiperazin-1-yl)methyl]indan-1-one

The desired product was prepared by substituting Example 842C for Example 54 in Example 56.

EXAMPLE 845B

6-[(4-methyl-1-piperazinyl)methyl]-3-(3-thienyl)-1,4-dihydroindeno[1,2-c]pyrazole The desired product was prepared by substituting phenyl thiophene-3-carboxylate for phenyl thiophene 2-carboxylate and Example 845 for Example 56 in Example 138. m.p. 115-117° C.

EXAMPLE 846

6-(4-morpholinylmethyl)-3-(3-thienyl)-1,4-dihydroindeno[1,2-c]pyrazole

The desired product was prepared by substituting phenyl thiophene-3-carboxylate for phenyl thiophene 2-carboxylate and Example 842D for Example 56 in Example 138. m.p. 196-198° C.

EXAMPLE 847

6-[(4-ethyl-1-piperazinyl)methyl]-3-(3-thienyl)-1,4-dihydroindeno[1,2-c]pyrazole

EXAMPLE 847A

5-[(4-ethylpiperazin-1-yl)methyl]indan-1-one

The desired product was prepared by substituting N-ethyl piperazine for N-methyl piperazine and Example 842C for Example 54 in Example 56.

EXAMPLE 847

6-[(4-ethyl-1-piperazinyl methyl]-3-(3-thienyl)-1,4-dihydroindeno[1,2-c]pyrazole The desired product was prepared by substituting phenyl thiophene-3-carboxylate for phenyl thiophene 2-carboxylate and Example 847A for Example 56 in Example 138. m.p. 111-112° C.

EXAMPLE 848

6-[(4-ethyl-1-piperazinyl)methyl]-3-(2-thienyl)-1,4-dihydroindeno[1,2-c]pyrazole The desired product was prepared by substituting Example 847A for Example 56 in Example 138. m.p. 169.5-170° C.

EXAMPLE 849

N,N-dimethyl-N-[2-oxo-2-(4-{[3-(3-thienyl)-1,4-dihydroindeno[1,2-c]pyrazol-6-yl]methyl}-1-piperazinyl)ethyl]amine

EXAMPLE 849A 5-({4-[(dimethylamino)acetyl]piperazin-1-yl}methyl)indan-1-one

The desired product was prepared by substituting 2-Dimethylamino-1-piperazin-1-yl-ethanone for N-methyl piperazine and Example 842C for Example 54 in Example 56.

EXAMPLE 849B

N,N-dimethyl-N-[2-oxo-2-(4-{[3-(3-thienyl)-1,4-dihydroindeno[1,2-c]pyrazol-6-yl]methyl}-1-piperazinyl)ethyl]amine The desired product was prepared by substituting phenyl thiophene-3-carboxylate for phenyl thiophene 2-carboxylate and Example 849A for Example 56 in Example 138. m.p. 190-191.5° C.

EXAMPLE 850

N,N-dimethyl-N-[2-oxo-2-(4-{[3-(2-thienyl)-1,4-dihydroindeno[1,2-c]pyrazol-6-yl]methyl}-1--piperazinyl)ethyl]amine The desired product was prepared by substituting Example 849A for Example 56 in Example 138. m.p. 193-197° C.

EXAMPLE 851

6-[(4-pyrimidin-2-ylpiperazin-1-yl)methyl]-3-thien-3-yl-1,4-dihydroindeno[1,2-c]pyrazole

EXAMPLE 851A

5-[(4-pyrimidin-2-ylpiperazin-1-yl)methyl]indan-1-one

The desired product was prepared by substituting 2-piperazin-1-yl-pyrimidine for N-methyl piperazine and Example 842C for Example 54 in Example 56.

EXAMPLE 851B

6-[(4-pyrimidin-2-ylpiperazin-1-yl)methyl]-3-thien-3-yl-1,4-dihydroindeno[1,2-c]pyrazole The desired product was prepared by substituting phenyl thiophene-3-carboxylate for phenyl thiophene 2-carboxylate and Example 851A for Example 56 in Example 138. m.p. 245-247° C.

EXAMPLE 852

N,N-diethyl-N-[(3-thien-3-yl-1,4-dihydroindeno[1,2-c]pyrazol-7-yl)methyl]amine

EXAMPLE 852A

6-[(diethylamino)methyl]indan-1-one

The desired product was prepared by substituting diethylamine for N-methyl piperazine in Example 56.

EXAMPLE 852B

N,N-diethyl-N-[(3-thien-3-yl-1,4-dihydroindeno[1,2-c]pyrazol-7-yl)methyl]amine

The desired product was prepared by substituting phenyl thiophene-3-carboxylate for phenyl thiophene 2-carboxylate and Example 852A for Example 56 in Example 138. m.p. 157-158° C.

EXAMPLE 853

7-[(4-ethylpiperazin-1-yl)methyl]-3-thien-3-yl-1,4-dihydroindeno[1,2-c]pyrazole

EXAMPLE 853A

6-[(4-ethylpiperazin-1-yl methyl]indan-1-one

The desired product was prepared by substituting N-ethylpiperazine for N-methyl piperazine in Example 56.

EXAMPLE 853B

7-[(4-ethylpiperazin-1-yl)methyl]-3-thien-3-yl-1,4-dihydroindeno[1,2-c]pyrazole

The desired product was prepared by substituting phenyl thiophene-3-carboxylate for phenyl thiophene 2-carboxylate and Example 853A for Example 56 in Example 138. m.p. 221-223° C.

EXAMPLE 854

7-[(4-isopropylpiperazin-1-yl)methyl]-3-thien-3-yl-1,4-dihydroindeno[1,2-c]pyrazole

EXAMPLE 854A

6-[(4-isopropylpiperazin-1-yl)methyl]indan-1-one

The desired product was prepared by substituting N-isopropylpiperazine for N-methyl piperazine in Example 56.

EXAMPLE 854B

7-[(4-isopropylpiperazin-1-yl)methyl]-3-thien-3-yl-1,4-dihydroindeno[1,2-c]pyrazole The desired product was prepared by substituting phenyl thiophene-3-carboxylate for phenyl thiophene 2-carboxylate and Example 854A for Example 56 in Example 138. m.p. 182-185° C.

EXAMPLE 855

7-{[4-(2-methoxyethyl)piperazin-1-yl]methyl}-3-thien-3-yl-1,4-dihydroindeno[1,2-c]pyrazole

EXAMPLE 855A

6-{[4-(2-methoxyethyl)piperazin-1-yl]methyl}indan-1-one

The desired product was prepared by substituting 1-(2-methoxy-ethyl)-piperazine for N-methyl piperazine in Example 56.

EXAMPLE 855B

7-{[4-(2-methoxyethyl)piperazin-1-yl]methyl}-3-thien-3-yl-1,4-dihydroindeno[1,2-c]pyrazole The desired product was prepared by substituting phenyl thiophene-3-carboxylate for phenyl thiophene 2-carboxylate and Example 855A for Example 56 in Example 138. m.p. 140.5-141.5° C.

EXAMPLE 856

6-[(4-isonicotinoylpiperazin-1-yl)methyl]-3-thien-3-yl-1,4-dihydroindeno[1,2-c]pyrazole

EXAMPLE 856A

5-[(4-isonicotinoylpiperazin-1-yl)methyl]indan-1-one

The desired product was prepared by substituting 1-isonicotinoylpiperazine for N-methyl piperazine and Example 842C for Example 54 in Example 56.

EXAMPLE 856B

6-[(4-isonicotinoylpiperazin-1-yl)methyl]-3-thien-3-yl-1,4-dihydroindeno[1,2-c]pyrazole The desired product was prepared by substituting phenyl thiophene-3-carboxylate for phenyl thiophene 2-carboxylate and Example 856A for Example 56 in Example 138. m.p. 218-220° C.

EXAMPLE 857

6-{[4-(pyrazin-2-ylcarbonyl)piperazin-1-yl]methyl}-3-thien-3-yl-1,4-dihydroindeno[1,2-c]pyrazole

EXAMPLE 857A

5-{[4-(pyrazin-2-ylcarbonyl)piperazin-1-yl]methyl}indan-1-one

The desired product was prepared by substituting piperazin-1-yl-pyrazin-2-yl-methanone for N-methyl piperazine and Example 842C for Example 54 in Example 56.

EXAMPLE 857B

6-{[4-(pyrazin-2-ylcarbonyl)piperazin-1-yl]methyl}-3-thien-3-yl-1,4-dihydroindeno[1,2-c]pyrazole The desired product was prepared by substituting phenyl thiophene-3-carboxylate for phenyl thiophene 2-carboxylate and Example 857A for Example 56 in Example 138. m.p. 202-204° C.

EXAMPLE 858

7-[(4-isonicotinoylpiperazin-1-yl)methyl]-3-thien-3-yl-1,4-dihydroindeno[1,2-c]pyrazole

EXAMPLE 858A

6-[(4-isonicotinoylpiperazin-1-yl)methyl]indan-1-one

The desired product was prepared by substituting 1-isonicotinoylpiperazine for N-methyl piperazine in Example 56.

EXAMPLE 858B

7-[(4-isonicotinoylpiperazin-1-yl)methyl]-3-thien-3-yl-1,4-dihydroindeno[1,2-c]pyrazole The desired product was prepared by substituting phenyl thiophene-3-carboxylate for phenyl thiophene 2-carboxylate and Example 858A for Example 56 in Example 138. m.p. 168-170° C.

EXAMPLE 859

7-{[4-(pyrazin-2-ylcarbonyl)piperazin-1-yl]methyl}-3-thien-3-yl-1,4-dihydroindeno[1,2-c]pyrazole

EXAMPLE 859A

6-{[4-(pyrazin-2-ylcarbonyl)piperazin-1-yl]methyl}indan-1-one

The desired product was prepared by substituting piperazin-1-yl-pyrazin-2-yl-methanone for N-methyl piperazine in Example 56.

EXAMPLE 859B

7-{[4-(pyrazin-2-ylcarbonyl)piperazin-1-yl]methyl}-3-thien-3-yl-1,4-dihydroindeno[1,2-c]pyrazole The desired product was prepared by substituting phenyl thiophene-3-carboxylate for phenyl thiophene 2-carboxylate and Example 859A for Example 56 in Example 138. m.p. 254-259° C. ° C. (2 HCl salt).

EXAMPLE 860

7-{[4-(morpholin-4-ylacetyl)piperazin-1-yl]methyl}-3-thien-3-yl-1,4-dihydroindeno[1,2-c]pyrazole

EXAMPLE 860A

6-{[4-(morpholin-4-ylacetyl)piperazin-1-yl]methyl}indan-1-one

The desired product was prepared by substituting 2-(4-morpholino)-1-piperazin-1-yl-ethanone for N-methyl piperazine in Example 56.

EXAMPLE 860B

7-{[4-(morpholin-4-ylacetyl)piperazin-1-yl]methyl}-3-thien-3-yl-1,4-dihydroindeno[1,2-c]pyrazole The desired product was prepared by substituting phenyl thiophene-3-carboxylate for phenyl thiophene 2-carboxylate and Example 860A for Example 56 in Example 138. m.p. 240-242° C.

EXAMPLE 861

3-thien-3-yl-7-(thiomorpholin-4-ylmethyl)-1,4-dihydroindeno[1,2-c]pyrazole

EXAMPLE 861A 6-(thiomorpholin-4-ylmethyl)indan-1-one

The desired product was prepared by substituting thiomorpholine for N-methyl piperazine in Example 56.

EXAMPLE 861B 3-thien-3-yl-7-(thiomorpholin-4-ylmethyl)-1,4-dihydroindeno[1,2-c]pyrazole The desired product was prepared by substituting phenyl thiophene-3-carboxylate for phenyl thiophene 2-carboxylate and Example 861A for Example 56 in Example 138. m.p. 193-195° C.

EXAMPLE 862

7-(1H-imidazol-1-ylmethyl)-3-thien-3-yl-1,4-dihydroindeno[1,2-c]pyrazole

The desired product was prepared by substituting phenyl thiophene-3-carboxylate for phenyl thiophene 2-carboxylate and Example 57 for Example 56 in Example 138. m.p. 200-204° C.

EXAMPLE 863

7-(pyrrolidin-1-ylmethyl)-3-thien-3-yl-1,4-dihydroindeno[1,2-c]pyrazole

EXAMPLE 863A 6-(pyrrolidin-1-ylmethyl)indan-1-one

The desired product was prepared by substituting pyrrolidine for N-methyl piperazine in Example 56.

EXAMPLE 863B 7-(pyrrolidin-1-ylmethyl)-3-thien-3-yl-1,4-dihydroindeno[1,2-c]pyrazole The desired product was prepared by substituting phenyl thiophene-3-carboxylate for phenyl thiophene 2-carboxylate and Example 863A for Example 56 in Example 138. m.p. 133-134° C.

EXAMPLE 864

N,N-dimethyl-4-[(3-thien-3-yl-1,4-dihydroindeno[1,2-c]pyrazol-7-yl)methyl]piperazine-1-carboxamide

EXAMPLE 864A

N,N-dimethyl-4-[(3-oxo-2,3-dihydro-1H-inden-5-yl)methyl]piperazine-1-carboxamide The desired product was prepared by substituting piperazine-1-carboxylic acid dimethylamide for N-methyl piperazine in Example 56.

EXAMPLE 864B

N,N-dimethyl-4-[(3-thien-3-yl-1,4-dihydroindeno[1,2-c]pyrazol-7-yl)methyl]piperazine-1-carboxamide The desired product was prepared by substituting phenyl thiophene-3-carboxylate for phenyl thiophene 2-carboxylate and Example 864A for Example 56 in Example 138. m.p. 214-216° C. (2 HCl salt).

EXAMPLE 865

7-{[4-(pyrrolidin-1-ylcarbonyl)piperazin-1-yl]methyl}-3-thien-3-yl-1,4-dihydroindeno[1,2-c]pyrazole

EXAMPLE 865A

6-{[4-(pyrrolidin-1-ylcarbonyl)piperazin-1-yl]methyl}indan-1-one

The desired product was prepared by substituting piperazin-1-yl-pyrrolidin-1-yl-methanone for N-methyl piperazine in Example 56.

EXAMPLE 865B

7-{[4-(pyrrolidin-1-ylcarbonyl)piperazin-1-yl]methyl}-3-thien-3-yl-1,4-dihydroindeno[1,2-c]pyrazole The desired product was prepared by substituting phenyl thiophene-3-carboxylate for phenyl thiophene 2-carboxylate and Example 865A for Example 56 in Example 138. m.p. 214-216° C.

EXAMPLE 866

3-{4-[(3-thien-3-yl-1,4-dihydroindeno[1,2-c]pyrazol-7-yl)methyl]piperazin-1-yl}propanenitrile

EXAMPLE 866A

3-{4-[(3-oxo-2,3-dihydro-1H-inden-5-yl)methyl]piperazin-1-yl}propanenitrile

The desired product was prepared by substituting 3-piperazin-1-yl-propionitrile for N-methyl piperazine in Example 56.

EXAMPLE 866B

3-{4-[(3-thien-3-yl-1,4-dihydroindeno[1,2-c]pyrazol-7-yl)methyl]piperazin-1-yl }propanenitrile The desired product was prepared by substituting phenyl thiophene-3-carboxylate for phenyl thiophene 2-carboxylate and Example 866A for Example 56 in Example 138. m.p. 156-157° C.

EXAMPLE 867

3-thien-3-yl-7-{[4-(3,3,3-trifluoropropyl)piperazin-1-yl]methyl}-1,4-dihydroindeno[1,2-c]pyrazole

EXAMPLE 867A

6-{[4-(3,3,3-trifluoropropyl)piperazin-1-yl]methyl}indan-1-one

The desired product was prepared by substituting 1-(3,3,3-trifluoropropyl)-piperazine for N-methyl piperazine in Example 56.

EXAMPLE 867B 3-thien-3-yl-7-{[4-(3,3,3-trifluoropropyl)piperazin-1-yl]methyl}-1,4-dihydroindeno[1,2-c]pyrazole The desired product was prepared by substituting phenyl thiophene-3-carboxylate for phenyl thiophene 2-carboxylate and Example 867A for Example 56 in Example 138. m.p. 195-200° C. (3 HCl salt).

EXAMPLE 868

7-{[4-(morpholin-4-ylcarbonyl)piperazin-1-yl]methyl}-3-thien-3-yl-1,4-dihydroindeno[1,2-c]pyrazole

EXAMPLE 868A

6-{[4-(morpholin-4-ylcarbonyl piperazin-1-yl]methyl}indan-1-one

The desired product was prepared by substituting morpholin-4-yl-piperazin-1-yl-methanone for N-methyl piperazine in Example 56.

EXAMPLE 868B

7-{[4-(morpholin-4-ylcarbonyl)piperazin-1-yl]methyl}-3-thien-3-yl-1,4-dihydroindeno[1,2-c]pyrazole The desired product was prepared by substituting phenyl thiophene-3-carboxylate for phenyl thiophene 2-carboxylate and Example 868A for Example 56 in Example 138. m.p. 187.5-190° C.

EXAMPLE 869

3-thien-3-yl-7-{[4-(thiomorpholin-4-ylacetyl)piperazin-1-yl]methyl}-1,4-dihydroindeno[1,2-c]pyrazole

EXAMPLE 869A

6-{[4-(thiomorpholin-4-ylacetyl)piperazin-1-yl]methyl}indan-1-one

The desired product was prepared by substituting 1-piperazin-1-yl-2-thiomorpholin-4-yl-ethanone for N-methyl piperazine in Example 56.

EXAMPLE 869B 3-thien-3-yl-7-{[4-(thiomorpholin-4-ylacetyl)piperazin-1-yl]methyl}-1,4-dihydroindeno[1,2-c]pyrazole The desired product was prepared by substituting phenyl thiophene-3-carboxylate for phenyl thiophene 2-carboxylate and Example 869A for Example 56 in Example 138. m.p. 226-228° C.

EXAMPLE 870

7-[(4-propylpiperazin-1-yl)methyl]-3-thien-3-yl-1,4-dihydroindeno[1,2-c]pyrazole

EXAMPLE 870A

6-[(4-propylpiperazin-1-yl)methyl]indan-1-one

The desired product was prepared by substituting 1-propyl piperazine for N-methyl piperazine in Example 56.

EXAMPLE 870B

7-[(4-propylpiperazin-1-yl)methyl]-3-thien-3-yl-1,4-dihydroindeno[1,2-c]pyrazole The desired product was prepared by substituting phenyl thiophene-3-carboxylate for phenyl thiophene 2-carboxylate and Example 870A for Example 56 in Example 138. m.p. 185-187° C.

EXAMPLE 871 tert-butyl 4-[(3-thien-3-yl-1,4-dihydroindeno[1,2-c]pyrazol-7-yl)methyl]piperazine-1-carboxylate

EXAMPLE 871A tert-butyl 4-[(3-oxo-2,3-dihydro-1H-inden-5-yl)methyl]piperazine-1-carboxylate The desired product was prepared by substituting 1-(t-butoxycarbonyl) piperazine for N-methyl piperazine in Example 56.

EXAMPLE 871B tert-butyl 4-[(3-thien-3-yl-1,4-dihydroindeno[1,2-c]pyrazol-7-yl)methyl]piperazine-1-carboxylate The desired product was prepared by substituting phenyl thiophene-3-carboxylate for phenyl thiophene 2-carboxylate and Example 871A for Example 56 in Example 138. m.p. 218-220° C.

EXAMPLE 872

3-{4-[(3-thien-3-yl-1,4-dihydroindeno[1,2-c]pyrazol-7-yl methyl]piperazin-1-yl}propanoic acid A mixture of Example 866 (0.22 g, 0.565 mmol) in 28% HCl/EtOH (7 ml) was refluxed for 15 hours, and then concentrated in vacuo. The residue was dissolved in water, basified with potassium bicarbonate and extracted with ethyl acetate. The extract was washed with brine, dried over sodium sulfate, and then concentrated in vacuo. A mixture of this residue and 5% NaOH (1 ml) in tetrahydrofuran (2 ml) and methanol (1 ml) was refluxed for 1 hour, and then concentrated in vacuo. The residue was poured into water and washed with ethyl acetate. The aqueous layer was acidified with 10% HCl and washed with ethyl acetate. The aqueous layer was concentrated in vacuo. The residue was crystallized by adding ethanol and concentrated in vacuo. The residue was washed with water and ethanol to give Example 872 as a pale brown crystalline solid (0.18 g, 66%). m.p. 189-191° C. (2 HCl salt).

EXAMPLE 873

3-thien-3-yl-7-(1H-1,2,4-triazol-1-ylmethyl)-1,4-dihydroindeno[1,2-c]pyrazole

EXAMPLE 873A 6-(1H-1,2,4-triazol-1-ylmethyl)indan-1-one

The desired product was prepared by substituting 1,2,4-triazole for N-methyl piperazine and DMF for EtOH in Example 56.

EXAMPLE 873B 3-thien-3-yl-7-(1H-1,2,4-triazol-1-ylmethyl)-1,4-dihydroindeno[1,2-c]pyrazole The desired product was prepared by substituting phenyl thiophene-3-carboxylate for phenyl thiophene 2-carboxylate and Example 873A for Example 56 in Example 138. m.p. 243-245° C.

EXAMPLE 874

7-[(2-methyl-1H-imidazol-1-yl)methyl]-3-thien-3-yl-1,4-dihydroindeno[1,2-c]pyrazole

EXAMPLE 874A

6-[(2-methyl-1H-imidazol-1-yl)methyl]indan-1-one

The desired product was prepared by substituting 2-methylimidazole for N-methyl piperazine and DMF for EtOH in Example 56.

EXAMPLE 874B

7-[(2-methyl-1H-imidazol-1-yl)methyl]-3-thien-3-yl-1,4-dihydroindeno[1,2-c]pyrazole The desired product was prepared by substituting phenyl thiophene-3-carboxylate for phenyl thiophene 2-carboxylate and Example 874A for Example 56 in Example 138. m.p. 230-234° C. (decomp.).

EXAMPLE 875

7-[(4-methyl-1H-imidazol-1-yl)methyl]-3-thien-3-yl-1,4-dihydroindeno[1,2-c]pyrazole

EXAMPLE 875A

6-[(4-methyl-1H-imidazol-1-yl)methyl]indan-1-one

The desired product was prepared by substituting 4-methylimidazole for N-methyl piperazine and DMF for EtOH in Example 56.

EXAMPLE 875B

7-[(4-methyl-1H-imidazol-1-yl)methyl]-3-thien-3-yl-1,4-dihydroindeno[1,2-c]pyrazole The desired product was prepared by substituting phenyl thiophene-3-carboxylate for phenyl thiophene 2-carboxylate and Example 875A for Example 56 in Example 138. m.p. 122-125° C.

EXAMPLE 876

7-(1H-pyrazol-1-ylmethyl)-3-thien-3-yl-1,4-dihydroindeno[1,2-c]pyrazole

EXAMPLE 876A 6-(1H-pyrazol-1-ylmethyl)indan-1-one

The desired product was prepared by substituting pyrazole for N-methyl piperazine and DMF for EtOH in Example 56.

EXAMPLE 876B 7-(1H-pyrazol-1-ylmethyl)-3-thien-3-yl-1,4-dihydroindeno[1,2-c]pyrazole The desired product was prepared by substituting phenyl thiophene-3-carboxylate for phenyl thiophene 2-carboxylate and Example 876A for Example 56 in Example 138. m.p. 245-247° C.

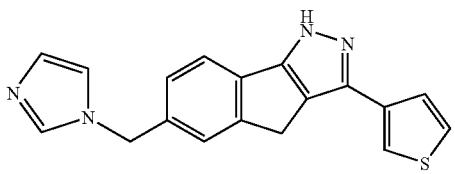

EXAMPLE 877

6-(1H-imidazol-1-ylmethyl)-3-thien-3-yl-1,4-dihydroindeno[1,2-c]pyrazole

EXAMPLE 877A 5-(1H-imidazol-1-ylmethyl)indan-1-one

The desired product was prepared by substituting imidazole for N-methyl piperazine, Example 842C for Example 54 and DMF for EtOH in Example 56.

EXAMPLE 877B 6-(1H-imidazol-1-ylmethyl)-3-thien-3-yl-1,4-dihydroindeno[1,2-c]pyrazole The desired product was prepared by substituting phenyl thiophene-3-carboxylate for phenyl thiophene 2-carboxylate, Example 877A for Example 56 and DMF for EtOH in Example 138. m.p. 255-260° C.

EXAMPLE 878

3-thien-3-yl-6-(1H-1,2,4-triazol-1-ylmethyl)-1,4-dihydroindeno[1,2-c]pyrazole

EXAMPLE 878A 5-(1H-1,2,4-triazol-1-ylmethyl)indan-1-one

The desired product was prepared by substituting 1,2,4-triazole for N-methyl piperazine, Example 842C for Example 54 and DMF for EtOH in Example 56.

EXAMPLE 878B 3-thien-3-yl-6-(1H-1,2,4-triazol-1-ylmethyl)-1,4-dihydroindeno[1,2-c]pyrazole The desired product was prepared by substituting phenyl thiophene-3-carboxylate for phenyl thiophene 2-carboxylate and Example 878A for Example 56 in Example 138. m.p. 252-257° C.

EXAMPLE 879

6-(1H-pyrazol-1-ylmethyl)-3-thien-3-yl-1,4-dihydroindeno[1,2-c]pyrazole

EXAMPLE 879A 5-(1H-pyrazol-1-ylmethyl)indan-1-one

The desired product was prepared by substituting pyrazole for N-methyl piperazine, Example 842C for Example 54 and DMF for EtOH in Example 56.

EXAMPLE 879B 6-(1H-pyrazol-1-ylmethyl)-3-thien-3-yl-1,4-dihydroindeno[1,2-c]pyrazole The desired product was prepared by substituting phenyl thiophene-3-carboxylate for phenyl thiophene 2-carboxylate and Example 879A for Example 56 in Example 138. m.p. 262-270° C.

EXAMPLE 880

6-[(3,5-dimethyl-1H-pyrazol-1-yl)methyl]-3-thien-3-yl-1,4-dihydroindeno[1,2-c]pyrazole

EXAMPLE 880A

5-[(3,5-dimethyl-1H-pyrazol-1-yl)methyl]indan-1-one

The desired product was prepared by substituting 3,5-dimethyl pyrazole for N-methyl piperazine, Example 842C for Example 54 and DMF for EtOH in Example 56.

EXAMPLE 880B

6-[(3,5-dimethyl-1H-pyrazol-1-yl)methyl]-3-thien-3-yl-1,4-dihydroindeno[1,2-c]pyrazole The desired product was prepared by substituting phenyl thiophene-3-carboxylate for phenyl thiophene 2-carboxylate and Example 880A for Example 56 in Example 138. m.p. 257-260° C.

EXAMPLE 881

3-thien-3-yl-7-(1H-1,2,3-triazol-1-ylmethyl)-1,4-dihydroindeno[1,2-c]pyrazole

EXAMPLE 881A 6-(1H-1,2,3-triazol-1-ylmethyl)indan-1-one

EXAMPLE 881B 6-(2H-1,2,3-triazol-2-ylmethyl)indan-1-one 1,2,3-Triazole was substituted for N-methyl piperazine and DMF was substituted for EtOH in Example 56, resulting in a mixture of isomers that were separated by flash chromatography to give Example 881A (34%) and Example 881B (36%).

EXAMPLE 881C 3-thien-3-yl-7-(1H-1,2,3-triazol-1-ylmethyl)-1,4-dihydroindeno[1,2-c]pyrazole The desired product was prepared by substituting phenyl thiophene-3-carboxylate for phenyl thiophene 2-carboxylate and Example 881A for Example 56 in Example 138. m.p. 249-252° C.

EXAMPLE 882

3-thien-3-yl-7-(2H-1,2,3-triazol-2-ylmethyl)-1,4-dihydroindeno[1,2-c]pyrazole

The desired product was prepared by substituting phenyl thiophene-3-carboxylate for phenyl thiophene 2-carboxylate and Example 881B for Example 56 in Example 138. m.p. 217-219° C.

EXAMPLE 883

7-[(2-isopropyl-1H-imidazol-1-yl)methyl]-3-thien-3-yl-1,4-dihydroindeno[1,2-c]pyrazole

EXAMPLE 883A

6-[(2-isopropyl-1H-imidazol-1-yl)methyl]indan-1-one

The desired product was prepared by substituting 2-isopropylimidazole for N-methyl piperazine and DMF for EtOH in Example 56.

EXAMPLE 883B

7-[(2-isopropyl-1H-imidazol-1-yl)methyl]-3-thien-3-yl-1,4-dihydroindeno[1,2-c]pyrazole The desired product was prepared by substituting phenyl thiophene-3-carboxylate for phenyl thiophene 2-carboxylate and Example 883A for Example 56 in Example 138. m.p. 128-129° C.

EXAMPLE 884

7-[(2-ethyl-1H-imidazol-1-yl)methyl]-3-thien-3-yl-1,4-dihydroindeno[1,2-c]pyrazole

EXAMPLE 884A

6-[(2-ethyl-1H-imidazol-1-yl)methyl]indan-1-one

The desired product was prepared by substituting 2-ethylimidazole for N-methyl piperazine and DMF for EtOH in Example 56.

EXAMPLE 884B

7-[(2-ethyl-1H-imidazol-1-yl)methyl]-3-thien-3-yl-1,4-dihydroindeno[1,2-c]pyrazole The desired product was prepared by substituting phenyl thiophene-3-carboxylate for phenyl thiophene 2-carboxylate and Example 884A for Example 56 in Example 138. m.p. 238-239° C.

EXAMPLE 885

6-[(2-propyl-1H-imidazol-1-yl)methyl]-3-thien-3-yl-1,4-dihydroindeno[1,2-c]pyrazole

EXAMPLE 885A

5-[(2-propyl-1H-imidazol-1-yl)methyl]indan-1-one

The desired product was prepared by substituting 2-(n-propyl)imidazole for N-methyl piperazine, Example 842C for Example 54, and DMF for EtOH in Example 56.

EXAMPLE 885B

6-[(2-propyl-1H-imidazol-1-yl)methyl]-3-thien-3-yl-1,4-dihydroindeno[1,2-c]pyrazole The desired product was prepared by substituting phenyl thiophene-3-carboxylate for phenyl thiophene 2-carboxylate and Example 885A for Example 56 in Example 138. m.p. 113-117° C.

EXAMPLE 886

7-[(4-methyl-1H-pyrazol-1-yl)methyl]-3-thien-3-yl-1,4-dihydroindeno[1,2-c]pyrazole

EXAMPLE 886A

6-[(4-methyl-1H-pyrazol-1-yl)methyl]indan-1-one

The desired product was prepared by substituting 4-methylpyrazole for N-methyl piperazine and DMF for EtOH in Example 56.

EXAMPLE 886B

7-[(4-methyl-1H-pyrazol-1-yl)methyl]-3-thien-3-yl-1,4-dihydroindeno[1,2-c]pyrazole The desired product was prepared by substituting phenyl thiophene-3-carboxylate for phenyl thiophene 2-carboxylate and Example 886A for Example 56 in Example 138. m.p. 261.5-263° C.

EXAMPLE 887

6-[(2-isopropyl-1H-imidazol-1-yl)methyl]-3-thien-3-yl-1,4-dihydroindeno[1,2-c]pyrazole

EXAMPLE 887A

5-[(2-isopropyl-1H-imidazol-1-yl)methyl]indan-1-one

The desired product was prepared by substituting 2-isopropylimidazole for N-methyl piperazine, Example 842C for Example 54, and DMF for EtOH in Example 56.

EXAMPLE 887B

6-[(2-isopropyl-1H-imidazol-1-yl)methyl]-3-thien-3-yl-1,4-dihydroindeno[1,2-c]pyrazole The desired product was prepared by substituting phenyl thiophene-3-carboxylate for phenyl thiophene 2-carboxylate and Example 887A for Example 56 in Example 138. m.p. 259.5-262° C.

EXAMPLE 888

6-[(2-ethyl-1H-imidazol-1-yl)methyl]-3-thien-3-yl-1,4-dihydroindeno[1,2-c]pyrazole

EXAMPLE 888A

5-[(2-ethyl-1H-imidazol-1-yl)methyl]indan-1-one

The desired product was prepared by substituting 2-ethylimidazole for N-methyl piperazine, Example 842C for Example 54, and DMF for EtOH in Example 56.

EXAMPLE 888B

6-[(2-ethyl-1H-imidazol-1-yl)methyl]-3-thien-3-yl-1,4-dihydroindeno[1,2-c]pyrazole The desired product was prepared by substituting phenyl thiophene-3-carboxylate for phenyl thiophene 2-carboxylate and Example 888A for Example 56 in Example 138. m.p. 129-132° C.

EXAMPLE 889

3-thien-3-yl-6-(2H-1,2,3-triazol-2-ylmethyl)-1,4-dihydroindeno[1,2-c]pyrazole

EXAMPLE 889A 5-(2H-1,2,3-triazol-2-ylmethyl)indan-1-one 1,2,3-Triazole was substituted for N-methyl piperazine, Example 842C was substituted for Example 54 and DMF was substituted for EtOH in Example 56, resulting in a mixture of isomers that were separated by flash chromatography to give Example 889A (32%) and Example 890A (57%).

EXAMPLE 889B 3-thien-3-yl-6-(2H-1,2,3-triazol-2-ylmethyl)-1,4-dihydroindeno[1,2-c]pyrazole The desired product was prepared by substituting phenyl thiophene-3-carboxylate for phenyl thiophene 2-carboxylate and Example 889A for Example 56 in Example 138. m.p. 238.5-241° C.

EXAMPLE 890

3-thien-3-yl-6-(1H-1,2,3-triazol-1-ylmethyl)-1,4-dihydroindeno[1,2-c]pyrazole

EXAMPLE 890A 5-(1H-1,2,3-triazol-1-ylmethyl)indan-1-one 1,2,3-Triazole was substituted for N-methyl piperazine, Example 842C was substituted for Example 54 and DMF was substituted for EtOH in Example 56, resulting in a mixture of isomers that were separated by flash chromatography to give Example 889A (32%) and Example 890A (57%).

EXAMPLE 890B 3-thien-3-yl-6-(1H-1,2,3-triazol-1-ylmethyl)-1,4-dihydroindeno[1,2-c]pyrazole The desired product was prepared by substituting phenyl thiophene-3-carboxylate for phenyl thiophene 2-carboxylate and Example 890A for Example 56 in Example 138. m.p. 250-254° C.

EXAMPLE 891

3-morpholin-4-yl-N-[(3-thien-3-yl-1,4-dihydroindeno[1,2-c]pyrazol-6-yl)methyl]propanamide

EXAMPLE 891A 5-(azidomethyl)indan-1-one

A mixture of Example 842C (8.56 g, 38.0 mmol) and sodium azide (4.94 g, 76.1 mmol) in N,N-dimethylformamide (43 ml) was stirred at ambient temperature for 2 h. The mixture was diluted with water and extracted with ethyl acetate. The extract was washed with water and brine, dried over sodium sulfate, and concentrated in vacuo. The residue was purified by flash chromatography (1:1 ethyl acetate/heptane) to give Example 891A as a pale yellow oil (3.68 g).

EXAMPLE 891B 6-(azidomethyl)-3-thien-3-yl-1,4-dihydroindeno[1,2-c]pyrazole

The desired product was prepared by substituting phenyl thiophene-3-carboxylate for phenyl thiophene 2-carboxylate and Example 891A for Example 56 in Example 138.

EXAMPLE 891C 6-(azidomethyl)-1-[bis(4-methoxyphenyl)methyl]-3-thien-3-yl-1,4-dihydroindeno[1,2-c]pyrazole The desired product was prepared by substituting Example 891B for Example 326 in Example 331.

EXAMPLE 891D

{1-[bis(4-methoxyphenyl)methyl]-3-thien-3-yl-1,4-dihydroindeno[1,2-c]pyrazol-6-yl}methylamine The desired product was prepared by substituting Example 891C for Example 391 in Example 395.

EXAMPLE 891E

N-({1-[bis(4-methoxyphenyl)methyl]-3-thien-3-yl-1,4-dihydroindeno[1,2-c]pyrazol-6-yl}methyl)-3-chloropropanamide A mixture of Example 891D (2.55 g, 5.17 mmol) and triethylamine (0.86 mL, 6.20 mmol) in THF (25 mL) at 5° C. was treated dropwise with 3-chloropropionyl chloride (0.54 mL, 5.69 mmol). The mixture was stirred at 5° C. for 2 h, then diluted with H2O and extracted with EtOAc. The extract was washed with H2O and brine, dried (Na2SO4), and concentrated in vacuo. The residue was triturated with toluene to give Example 891E as a pale yellow crystalline solid (2.57 g).

EXAMPLE 891F

N-({1-[bis(4-methoxyphenyl)methyl]-3-thien-3-yl-1,4-dihydroindeno[1,2-c]pyrazol-6-yl}methyl)-3-morpholin-4-ylpropanamide A mixture of Example 891E (607 mg, 1.04 mmol), morpholine (232 mg, 2.29 mmol), NaHCO3 (640 mg, 7.62 mmol) and NaI (311 mg, 2.07 mmol) in CH3CN (13 mL) was heated to reflux for 2 d, then concentrated in vacuo. The mixture was diluted with H2O and extracted with EtOAc. The combined organic layers were washed with H2O and brine, dried (Na2SO4) and concentrated in vacuo to give Example 891F as a crude solid (437 mg).

EXAMPLE 891G 3-morpholin-4-yl-N-[(3-thien-3-yl-1,4-dihydroindeno[1,2-c]pyrazol-6-yl)methyl]propanamide The desired compound was prepared by substituting Example 891F for Example 382 in Example 386. m.p. 205-207° C.

EXAMPLE 892

2-morpholin-4-yl-N-[(3-thien-3-yl-1,4-dihydroindeno[1,2-c]pyrazol-6-yl)methyl]acetamide

EXAMPLE 892A

N-({1-[bis(4-methoxyphenyl)methyl]-3-thien-3-yl-1,4-dihydroindeno[1,2-c]pyrazol-6-yl}methyl)-2-chloroacetamide The desired compound was prepared by substituting chloroacetyl chloride for chloropropionyl chloride in Example 891E.

EXAMPLE 892B

N-({1-[bis(4-methoxyphenyl)methyl]-3-thien-3-yl-1,4-dihydroindeno[1,2-c]pyrazol-6-yl}methyl)-2-morpholin-4-ylacetamide The desired compound was prepared by substituting Example 892A for Example 891E in Example 891F.

EXAMPLE 892C 2-morpholin-4-yl-N-[(3-thien-3-yl-1,4-dihydroindeno[1,2-c]pyrazol-6-yl)methyl]acetamide The desired compound was prepared by substituting Example 892B for Example 382 in Example 386. m.p. 176-179° C.

EXAMPLE 893

2-morpholin-4-yl-N-[(3-thien-3-yl-1,4-dihydroindeno[1,2-c]pyrazol-7-yl)methyl]acetamide

EXAMPLE 893A 6-(azidomethyl)indan-1-one

The desired compound was prepared by substituting Example 54 for Example 842C in Example 891A.

EXAMPLE 893B 7-(azidomethyl)-3-thien-3-yl-1,4-dihydroindeno[1,2-c]pyrazole

The desired product was prepared by substituting phenyl thiophene-3-carboxylate for phenyl thiophene 2-carboxylate and Example 893A for Example 56 in Example 138.

EXAMPLE 893C 7-(azidomethyl)-1-[bis(4-methoxyphenyl)methyl]-3-thien-3-yl-1,4-dihydroindeno[1,2-c]pyrazole The desired product was prepared by substituting Example 893B for Example 326 in Example 331.

EXAMPLE 893D

{1-[bis(4-methoxyphenyl)methyl]-3-thien-3-yl-1,4-dihydroindeno[1,2-c]pyrazol-7-yl}methylamine The desired product was prepared by substituting Example 893C for Example 391 in Example 395.

EXAMPLE 893E

N-({1-[bis(4-methoxyphenyl)methyl]-3-thien-3-yl-1,4-dihydroindeno[1,2-c]pyrazol-7-yl}methyl)-2-chloroacetamide The desired product was prepared by substituting Example 893D for Example 891D and chloroacetyl chloride for 3-chloropropionyl chloride in Example 891E.

EXAMPLE 893F

N-({1-[bis(4-methoxyphenyl)methyl]-3-thien-3-yl-1,4-dihydroindeno[1,2-c]pyrazol-7-yl}methyl-2-morpholin-4-ylacetamide The desired product was prepared by substituting Example 893E for Example 891E in Example 891F.

EXAMPLE 893G 2-morpholin-4-yl-N-[(3-thien-3-yl-1,4-dihydroindeno[1,2-c]pyrazol-7-yl)methyl]acetamide The desired compound was prepared by substituting Example 893F for Example 382 in Example 386. m.p. 185-186.5° C.

EXAMPLE 894

3-morpholin-4-yl-N-[(3-thien-3-yl-1,4-dihydroindeno[1,2-c]pyrazol-7-yl)methyl]propanamide

EXAMPLE 894A

N-({1-[bis(4-methoxyphenyl)methyl]-3-thien-3-yl-1,4-dihydroindeno[1,2-c]pyrazol-7-yl}methyl)-3-chloropropanamide The desired compound was prepared by substituting Example 893D for Example 891D in Example 891E.

EXAMPLE 894B

N-({1-[bis(4-methoxyphenyl)methyl]-3-thien-3-yl-1,4-dihydroindeno[1,2-c]pyrazol-7-yl}methyl)-3-morpholin-4-ylpropanamide The desired compound was prepared by substituting Example 894A for Example 891E in Example 891F.

EXAMPLE 894C 3-morpholin-4-yl-N-[(3-thien-3-yl-1,4-dihydroindeno[1,2-c]pyrazol-7-yl)methyl]propanamide The desired compound was prepared by substituting Example 894B for Example 382 in Example 386. m.p. 228-230° C.

EXAMPLE 895

N-(2-morpholin-4-ylethyl)-N'-[(3-thien-3-yl-1,4-dihydroindeno[1,2-c]pyrazol-6-yl)methyl]urea

EXAMPLE 895A

N-({1-[bis(4-methoxyphenyl)methyl]-3-thien-3-yl-1,4-dihydroindeno[1,2-c]pyrazol-6-yl}methyl)-N'-(2-morpholin-4-ylethyl)urea To a solution of Example 891D (800 mg, 1.62 mmol) in THF (15 mL) was added 1,1'-carbonyldiimidazole (320 mg, 1.94 mmol). The mixture was stirred at rt for 2 h, then a solution of 4-(2-aminoethyl)morpholine (253 mg, 1.94 mmol) in THF (3 mL) was added. The resulting mixture was stirred at rt for 6 h, then concentrated in vacuo. The residue was purified by flash chromatography eluting with EtOAc to give a crude oil. (326 mg).

EXAMPLE 895B

N-(2-morpholin-4-ylethyl)-N'-[(3-thien-3-yl-1,4-dihydroindeno[1,2-c]pyrazol-6-yl)methyl]urea The desired compound was prepared by substituting Example 895A for Example 382 in Example 386. m.p. 168-170° C.

EXAMPLE 896

N-[(3-thien-3-yl-1,4-dihydroindeno[1,2-c]pyrazol-7-yl)methyl]nicotinamide

EXAMPLE 896A

N-({1-[bis(4-methoxyphenyl)methyl]-3-thien-3-yl-1,4-dihydroindeno[1,2-c]pyrazol-7-yl}methyl)nicotinamide The desired product was prepared by substituting Example 893D for propargylamine, nicotinoyl chloride for benzoyl chloride and THF for CH2Cl2 in Example 643.

EXAMPLE 896B

N-[(3-thien-3-yl-1,4-dihydroindeno[1,2-c]pyrazol-7-yl)methyl]nicotinamide

The desired compound was prepared by substituting Example 896A for Example 382 in Example 386. m.p. 286-286.5° C.

EXAMPLE 897

N-[(3-thien-3-yl-1,4-dihydroindeno[1,2-c]pyrazol-7-yl)methyl]isonicotinamide

EXAMPLE 897A

N-({1-[bis(4-methoxyphenyl)methyl]-3-thien-3-yl-1,4-dihydroindeno[1,2-c]pyrazol-7-yl}methyl)isonicotinamide The desired product was prepared by substituting Example 893D for propargylamine, isonicotinoyl chloride for benzoyl chloride and THF for CH2Cl2 in Example 643.

EXAMPLE 897B

N-[(3-thien-3-yl-1,4-dihydroindeno[1,2-c]pyrazol-7-yl)methyl]isonicotinamide

The desired compound was prepared by substituting Example 897A for Example 382 in Example 386. m.p. 278-281° C.

EXAMPLE 898

N-[(3-thien-3-yl-1,4-dihydroindeno[1,2-c]pyrazol-7-yl)methyl]-2-thiomorpholin-4-ylacetamide

EXAMPLE 898A

N-({1-[bis(4-methoxyphenyl)methyl]-3-thien-3-yl-1,4-dihydroindeno[1,2-c]pyrazol-7-yl}methyl)-2-thiomorpholin-4-ylacetamide The desired product was prepared by substituting Example 893E for Example 891E and thiomorpholine for morpholine in Example 891F.

EXAMPLE 898B

N-[(3-thien-3-yl-1,4-dihydroindeno[1,2-c]pyrazol-7-yl)methyl]-2-thiomorpholin-4-ylacetamide The desired compound was prepared by substituting Example 898A for Example 382 in Example 386. m.p. 221-224° C.

EXAMPLE 899

2-pyrrolidin-1-yl-N-[(3-thien-3-yl-1,4-dihydroindeno[1,2-c]pyrazol-7-yl)methyl]acetamide

EXAMPLE 899A

N-({1-[bis(4-methoxyphenyl)methyl]-3-thien-3-yl-1,4-dihydroindeno[1,2-c]pyrazol-7-yl}methyl)-2-pyrrolidin-1-ylacetamide The desired product was prepared by substituting Example 893E for Example 891E and pyrrolidine for morpholine in Example 891F.

EXAMPLE 899B 2-pyrrolidin-1-yl-N-[(3-thien-3-yl-1,4-dihydroindeno[1,2-c]pyrazol-7-yl)methyl]acetamide The desired compound was prepared by substituting Example 899A for Example 382 in Example 386. m.p. 201-204° C.

EXAMPLE 900

N-[(3-thien-3-yl-1,4-dihydroindeno[1,2-c]pyrazol-7-yl)methyl]guanidine

EXAMPLE 900A

N-({1-[bis(4-methoxyphenyl)methyl]-3-thien-3-yl-1,4-dihydroindeno[1,2-c]pyrazol-7-yl}methyl)guanidine A mixture of Example 893D (500 mg, 1.01 mmol), 1H-pyrazole-1-carboxamidine hydrochloride (155 mg, 1.06 mmol) and diisopropylethylamine (0.18 mL, 1.06 mmol) in DMF (2.5 mL) was stirred at rt for 16 h, then diluted with H2O and EtOAc and made basic with K2CO3. The resulting precipitate was collected by filtration, then washed with H2O and EtOAc to give Example 900A as a colorless crystalline solid (480 mg).

EXAMPLE 900B

N-[(3-thien-3-yl-1,4-dihydroindeno[1,2-c]pyrazol-7-yl)methyl]guanidine

The desired compound was prepared by substituting Example 900A for Example 382 in Example 386. m.p. 173-176° C.

EXAMPLE 901

4-oxo-4-{[(3-thien-3-yl-1,4-dihydroindeno[1,2-c]pyrazol-7-yl)methyl]amino}butanoic acid

EXAMPLE 901A

4-[({1-[bis(4-methoxyphenyl)methyl]-3-thien-3-yl-1,4-dihydroindeno[1,2-c]pyrazol-7-yl}methyl)amino]4-oxobutanoic acid A mixture of Example 893D (450 mg, 0.912 mmol) and succinic anhydride (100 mg, 1.00 mmol) in toluene (4 mL) was stirred at 80° C. for 2 h. The resulting precipitate was collected by filtration and washed with toluene, giving Example 901A as a pale yellow crystalline solid (510 mg).

EXAMPLE 901B 4-oxo-4-{[(3-thien-3-yl-1,4-dihydroindeno[1,2-c]pyrazol-7-yl)methyl]amino}butanoic acid The desired compound was prepared by substituting Example 901A for Example 382 in Example 386. m.p. 235-236° C.

EXAMPLE 902

N-{5-(1,4-dihydroindeno[1,2-c]pyrazol-3-yl)thien-2-yl]methyl}-N'-(3-methylphenyl)urea

EXAMPLE 902A 3-thien-2-yl-1,4-dihydroindeno[1,2-c]pyrazole

The desired product was prepared by substituting 1-indanone for Example 56 in Example 138.

EXAMPLE 902B 5-(1,4-dihydroindeno[1,2-c]pyrazol-3-yl)thiophene-2-carbaldehyde The desired product was prepared by substituting Example 902A for Example 146 in Example 326.

EXAMPLE 902C

5-{1-[bis(4-methoxyphenyl)methyl]-1,4-dihydroindeno[1,2-c]pyrazol-3-yl}thiophene-2-carbaldehyde The desired product was prepared by substituting Example 902B for Example 326 in Example 331.

EXAMPLE 902D (5-{1-[bis(4-methoxyphenyl)methyl]-1,4-dihydroindeno[1,2-c]pyrazol-3-yl}thien-2-yl)methanol The desired product was prepared by substituting Example 902C for Example 331 in Example 382.

EXAMPLE 902E

3-[5-(azidomethyl)thien-2-yl]-1-[bis(4-methoxyphenyl)methyl]-1,4-dihydroindeno[1,2-c]pyrazole The desired product was prepared by substituting Example 902D for Example 382 in Example 391.

EXAMPLE 902F (5-{1-[bis(4-methoxyphenyl)methyl]-1,4-dihydroindeno[1,2-c]pyrazol-3-yl}thien-2-yl)methylamine The desired product was prepared by substituting Example 902E for Example 391 in Example 395.

EXAMPLE 902G

N-[(5-{1-[bis(4-methoxyphenyl)methyl]-1,4-dihydroindeno[1,2-c]pyrazol-3-yl}thien-2-yl)methyl]-N'-(3-methylphenyl)urea The desired product was prepared by substituting Example 902F for Example 396 and m-tolyl isocyanate for phenyl isocyanate in Example 402.

EXAMPLE 902H

N-{[5-(1,4-dihydroindeno[1,2-c]pyrazol-3-yl)thien-2-yl]methyl}-N'-(3-methylphenyl)urea The desired compound was prepared by substituting Example 902G for Example 382 in Example 386. m.p. 184-187° C.

EXAMPLE 903

N-{[5-(1,4-dihydroindeno[1,2-c]pyrazol-3-yl)thien-2-yl]methyl}-4-methylpiperazine-1-carboxamide

EXAMPLE 903A

N-[(5-{1-[bis(4-methoxyphenyl)methyl]-1,4-dihydroindeno[1,2-c]pyrazol-3-yl}thien-2-yl)methyl]4-methylpiperazine-1-carboxamide The desired product was obtained by substituting Example 902F for Example 891D and N-methylpiperazine for 4-(2-aminoethyl)morpholine in Example 895A.

EXAMPLE 903B

N-{[5-(1,4-dihydroindeno[1,2-c]pyrazol-3-yl)thien-2-yl]methyl)}-4-methylpiperazine-1-carboxamide The desired compound was prepared by substituting Example 903A for Example 382 in Example 386. m.p. 143-145° C.

EXAMPLE 904

N-{[5-(1,4-dihydroindeno[1,2-c]pyrazol-3-yl)-2-thienyl]methyl}-4-morpholinecarboxamide

EXAMPLE 904A

N-[(5-{1-[bis(4-methoxyphenyl)methyl]-1,4-dihydroindeno[1,2-c]pyrazol-3-yl}thien-2-yl)methyl]morpholine-4-carboxamide The desired product was obtained by substituting Example 902F for Example 891D and morpholine for 4-(2-aminoethyl)morpholine in Example 895A.

EXAMPLE 904B

N-{[5-(1,4-dihydroindeno[1,2-c]pyrazol-3-yl)-2-thienyl]methyl}-4-morpholinecarboxamide The desired compound was prepared by substituting Example 904A for Example 382 in Example 386. m.p. 240-247° C.

EXAMPLE 905

N-{[5-(1,4-dihydroindeno[1,2-c]pyrazol-3-yl)-2-thienyl]methyl}-N'-(2-methoxyethyl)urea

EXAMPLE 905A

N-[(5-{1-[bis(4-methoxyphenyl)methyl]-1,4-dihydroindeno[1,2-c]pyrazol-3-yl}thien-2-yl)methyl]-N'-(2-methoxyethyl)urea The desired product was obtained by substituting Example 902F for Example 891D and 2-methoxyethylamine for 4-(2-aminoethyl)morpholine in Example 895A.

EXAMPLE 905B

N-{[5-(1,4-dihydroindeno[1,2-c]pyrazol-3-yl)-2-thienyl]methyl}-N'-(2-methoxyethyl)urea The desired compound was prepared by substituting Example 905A for Example 382 in Example 386. m.p. 164-166° C.

EXAMPLE 906

N-{[5-(1,4-dihydroindeno[1,2-c]pyrazol-3-yl)-2-thienyl]methyl}-N'-[2-(4-morpholinyl)ethyl]urea

EXAMPLE 906A

N-[(5-{1-[bis(4-methoxyphenyl)methyl]-1,4-dihydroindeno[1,2-c]pyrazol-3-yl}thien-2-yl)methyl]-N'-(2-morpholin-4-ylethyl)urea The desired product was obtained by substituting Example 902F for Example 891D in Example 895A.

EXAMPLE 906B

N-{[5-(1,4-dihydroindeno[1,2-c]pyrazol-3-yl)-2-thienyl]methyl}-N'-[2-(4-morpholinyl)ethyl]urea The desired compound was prepared by substituting Example 906A for Example 382 in Example 386. m.p. 170-172.5° C.

EXAMPLE 907

3-methylphenyl[5-(1,4-dihydroindeno[1,2-c]pyrazol-3-yl)thien-2-yl]methylcarbamate

EXAMPLE 907A 3-methylphenyl (5-{1-[bis(4-methoxyphenyl)methyl]-1,4-dihydroindeno[1,2-c]pyrazol-3-yl}thien-2-yl)methylcarbamate To a solution of triphosgene (133 mg, 0.450 mmol) in THF (3 mL) was added dropwise a mixture of Example 902F (600 mg, 1.22 mmol) and diisopropylethylamine (189 mg, 1.46 mmol) in THF (6 mL). The mixture was stirred at rt for 10 min, and a solution of m-cresol (13 0 mg, 1.22 mmol) and diisopropylethylamine (189 mg, 1.46 mmol) in THF (3 mL) was added in one portion. The reaction was stirred at rt for 20 h, then diluted with H2O and extracted with EtOAc. The extract was washed with H2O and brine, dried (Na2SO4) and concentrated in vacuo. The residue was purified by flash chromatography (1:1 EtOAc/heptane) to give Example 907A as a yellow crystalline solid (500 mg).

EXAMPLE 907B 3-methylphenyl[5-(1,4-dihydroindeno[1,2-c]pyrazol-3-yl)thien-2-yl]methylcarbamate The desired compound was prepared by substituting Example 907A for Example 382 in Example 386. m.p. 158-160° C.

EXAMPLE 908

N-[2-(dimethylamino)ethyl]-N'-[(3-thien-3-yl-1,4-dihydroindeno[1,2-c]pyrazol-7-yl)methyl]urea

EXAMPLE 908A

N-({1-[bis(4-methoxyphenyl)methyl]-3-thien-3-yl-1,4-dihydroindeno[1,2-c]pyrazol-7-yl}methyl)-N'-[2-(dimethylamino)ethyl]urea The desired product was obtained by substituting 1,1-dimethyl ethylenediamine for 4-(2-aminoethyl)morpholine in Example 895A.

EXAMPLE 908B

N-[2-(dimethylamino)ethyl]-N'-[(3-thien-3-yl-1,4-dihydroindeno[1,2-c]pyrazol-7-yl)methyl]urea The desired compound was prepared by substituting Example 908A for Example 382 in Example 386. m.p. 247-249° C.

EXAMPLE 909

N-{[5-(1,4-dihydroindeno[1,2-c]pyrazol-3-yl)thien-2-yl]methyl}pyrimidin-2-amine

EXAMPLE 909A

N-[(5-{1-[bis(4-methoxyphenyl)methyl]-1,4-dihydroindeno[1,2-c]pyrazol-3-yl}thien-2-yl)methyl]pyrimidin-2-amine A mixture of Example 902F (700 mg, 1.42 mmol), triethylamine (0.40 mL, 2.84 mmol), and 2-chloropyrimidine (190 mg, 1.70 mmol) in n-BuOH (15 mL) was heated to reflux for 7 h, then concentrated in vacuo. The residue was diluted with H2O and extracted with a mixture of EtOAc and THF. The organic phase was washed with H2O and brine, then dried (Na2SO4) and concentrated in vacuo. The residue was purified by flash chromatography, eluting with 1:1 EtOAc/heptane to give Example 909A as a pale yellow oil (430 mg).

EXAMPLE 909B

N-{[5-(1,4-dihydroindeno[1,2-c]pyrazol-3-yl)thien-2-yl]methyl}pyrimidin-2-amine

The desired compound was prepared by substituting Example 909A for Example 382 in Example 386. m.p. 232-233° C.

EXAMPLE 910

N-[(3-thien-3-yl-1,4-dihydroindeno[1,2-c]pyrazol-7-yl)methyl]pyrimidin-2-amine

EXAMPLE 910A

N-({1-[bis(4-methoxyphenyl)methyl]-3-thien-3-yl-1,4-dihydroindeno[1,2-c]pyrazol-7-yl}methyl)pyrimidin-2-amine The desired product was obtained by substituting Example 893D for Example 902F in Example 909A.

EXAMPLE 910B

N-[(3-thien-3-yl-1,4-dihydroindeno[1,2-c]pyrazol-7-yl)methyl]pyrimidin-2-amine

The desired compound was prepared by substituting Example 910A for Example 382 in Example 386. m.p. 259-260° C.

EXAMPLE 911

N-(3-methylphenyl)-N'-({5-[6-(4-morpholinylmethyl)-1,4-dihydroindeno[1,2-c]pyrazol-3-yl]-2-thienyl}methyl)urea

EXAMPLE 911A

5-[6-(morpholin-4-ylmethyl)-1,4-dihydroindeno[1,2-c]pyrazol-3-yl]thiophene-2-carbaldehyde The desired product was prepared by substituting Example 842 for Example 146 in Example 326.

EXAMPLE 911B

5-[1-[bis(4-methoxyphenyl)methyl]-6-(morpholin-4-ylmethyl)-1,4-dihydroindeno[1,2-c]pyrazol-3-yl]thiophene-2-carbaldehyde The desired product was prepared by substituting Example 911A for Example 326 in Example 331.

EXAMPLE 911C

{5-[1-[bis(4-methoxyphenyl)methyl]-6-(morpholin-4-ylmethyl)-1,4-dihydroindeno[1,2-c]pyrazol-3-yl]thien-2-yl}methanol The desired product was prepared by substituting Example 911B for Example 331 in Example 382.

EXAMPLE 911D

3-[5-(azidomethyl)thien-2-yl]-1-[bis(4-methoxyphenyl)methyl]-6-(morpholin-4-ylmethyl)-1,4-dihydroindeno[1,2-c]pyrazole The desired product was prepared by substituting Example 911C for Example 382 in Example 391.

EXAMPLE 911E

{5-[1-[bis(4-methoxyphenyl)methyl]-6-(morpholin-4-ylmethyl)-1,4-dihydroindeno[1,2-c]pyrazol-3-yl]thien-2-yl}methylamine The desired product was prepared by substituting Example 911D for Example 391 in Example 395.

EXAMPLE 911F

N-({5-[1-[bis(4-methoxyphenyl)methyl]-6-(morpholin-4-ylmethyl)-1,4-dihydroindeno[1,2-c]pyrazol-3-yl]thien-2-yl}methyl)-N'-(3-methylphenyl)urea The desired product was prepared by substituting Example 911E for Example 396 and m-tolyl isocyanate for phenyl isocyanate in Example 402.

EXAMPLE 911G

N-(3-methylphenyl)-N'-({5-[6-(4-morpholinylmethyl)-1,4-dihydroindeno[1,2-c]pyrazol-3-yl]-2-thienyl}methyl)urea The desired compound was prepared by substituting Example 911F for Example 382 in Example 386. m.p. 158.5-161° C.

EXAMPLE 912

6-methyl-7-[(4-methylpiperazin-1-yl)methyl]-3-thien-3-yl-1,4-dihydroindeno[1,2-c]pyrazole

EXAMPLE 912A 4-bromo-3-methylbenzyl methanesulfonate

The desired product was obtained by substituting (4-bromo-3-methyl-phenyl)-methanol for Example 51 in Example 54.

EXAMPLE 912B 3-(4-bromo-3-methylphenyl)propanoic acid

The desired product was obtained by substituting Example 912A for 4-bromobenzyl bromide in Example 1.

EXAMPLE 912C 6-bromo-5-methylindan-1-one

A mixture of Examples 912C and 912D was obtained by substituting Example 912B for 3-(4-bromophenyl)-propionic acid in Example 3. The two isomers were separated by flash chromatography.

EXAMPLE 912D 6-bromo-7-methylindan-1-one

A mixture of Examples 912C and 912D was obtained by substituting Example 912B for 3-(4-bromophenyl)-propionic acid in Example 3. The two isomers were separated by flash chromatography.

EXAMPLE 912E

6'-bromo-5'-methyl-2',3'-dihydrospiro[1,3-dioxolane-2,1'-indene]

The desired product was obtained by substituting Example 912C for 6-bromo-1-indanone in Example 20.

EXAMPLE 912F (5'-methyl-2',3'-dihydrospiro[1,3-dioxolane-2,1'-inden]-6'-yl)methanol The desired product was obtained by substituting Example 912E for Example 20 in Example 28.

EXAMPLE 912G 6-(hydroxymethyl)-5-methylindan-1-one

The desired product was obtained by substituting Example 912F for Example 28 in Example 51.

EXAMPLE 912H (6-methyl-3-oxo-2,3-dihydro-1H-inden-5-yl)methyl methanesulfonate The desired product was obtained by substituting Example 912G for Example 51 in Example 54.

EXAMPLE 912I 5-methyl-6-[(4-methylpiperazin-1-yl)methyl]indan-1-one

The desired product was obtained by substituting Example 912H for Example 54 in Example 56.

EXAMPLE 912J 6-methyl-7-[(4-methylpiperazin-1-yl)methyl]-3-thien-3-yl-1,4-dihydroindeno[1,2-c]pyrazole The desired product was obtained by substituting Example 912I for Example 56 and phenyl thiophene-3-carboxylate for thiophene 2-carboxylate in Example 138. m.p. 210-212° C.

EXAMPLE 913

6-methyl-7-(morpholin-4-ylmethyl)-3-thien-3-yl-1,4-dihydroindeno[1,2-c]pyrazole

EXAMPLE 913A 5-methyl-6-(morpholin-4-ylmethyl)indan-1-one

The desired product was obtained by substituting Example 912H for Example 54 and morpholine for N-methylpiperazine in Example 56.

EXAMPLE 913B 6-methyl-7-(morpholin-4-ylmethyl)-3-thien-3-yl-1,4-dihydroindeno[1,2-c]pyrazole The desired product was obtained by substituting Example 913B for Example 56 and phenyl thiophene-3-carboxylate for thiophene 2-carboxylate in Example 138. m p. 209-210° C.

EXAMPLE 914

8-methyl-7-(morpholin-4-ylmethyl)-3-thien-3-yl-1,4-dihydroindeno[1,2-c]pyrazole

EXAMPLE 914A

6'-bromo-7'-methyl-2',3'-dihydrospiro[1,3-dioxolane-2,1'-indene]

The desired product was obtained by substituting Example 912D for 6-bromo-1-indanone in Example 20.

EXAMPLE 914B (7'-methyl-2',3'-dihydrospiro[1,3-dioxolane-2,1-inden]-6'-yl)methanol The desired product was obtained by substituting Example 914A for Example 20 in Example 28.

EXAMPLE 914C 6-(hydroxymethyl)-7-methylindan-1-one

The desired product was obtained by substituting Example 914B for Example 28 in Example 51.

EXAMPLE 914D (4-methyl-3-oxo-2,3-dihydro-1H-inden-5-yl)methyl methanesulfonate The desired product was obtained by substituting Example 914C for Example 51 in Example 54.

EXAMPLE 914E 7-methyl-6-(morpholin-4-ylmethyl)indan-1-one

The desired product was obtained by substituting Example 914D for Example 54 and morpholine for N-methylpiperazine in Example 56.

EXAMPLE 914F 8-methyl-7-(morpholin-4-ylmethyl)-3-thien-3-yl-1,4-dihydroindeno[1,2-c]pyrazole The desired product was obtained by substituting Example 914E for Example 56 and phenyl thiophene-3-carboxylate for thiophene 2-carboxylate in Example 138. m.p. 272-274° C.

EXAMPLE 915

7-fluoro-6-(morpholin-4-ylmethyl)-3-thien-3-yl-1,4-dihydroindeno[1,2-c]pyrazole

EXAMPLE 915A 3-bromo-4-fluorobenzyl methanesulfonate

The desired product was obtained by substituting (3-bromo-4-fluoro-phenyl)-methanol for Example 51 in Example 54.

EXAMPLE 915B 3-(3-bromo-4-fluorophenyl)propanoic acid

The desired product was obtained by substituting Example 915A for 4-bromobenzyl bromide in Example 1.

EXAMPLE 915C 5-bromo-6-fluoroindan-1-one

The desired product was obtained by substituting Example 915B for 3-(4-bromophenyl)-propionic acid in Example 3.

EXAMPLE 915D

5'-bromo-6'-fluoro-2',3'-dihydrospiro[1,3-dioxolane-2,1'-indene]

The desired product was obtained by substituting Example 915C for 6-bromo-1-indanone in Example 20.

EXAMPLE 915E (6'-fluoro-2',3'-dihydrospiro[1,3-dioxolane-2,1'-inden]-5'-yl)methanol The desired product was obtained by substituting Example 915D for Example 20 in Example 28.

EXAMPLE 915F 6-fluoro-5-(hydroxymethyl)indan-1-one

The desired product was obtained by substituting Example 915E for Example 28 in Example 51.

EXAMPLE 915G (6-fluoro-1-oxo-2,3-dihydro-1H-inden-5-yl)methyl methanesulfonate The desired product was obtained by substituting Example 915F for Example 51 in Example 54.

EXAMPLE 915H 6-fluoro-5-(morpholin-4-ylmethyl)indan-1-one

The desired product was obtained by substituting Example 915G for Example 54 and morpholine for N-methypiperazine in Example 56.

EXAMPLE 915I 7-fluoro-6-(morpholin-4-ylmethyl)-3-thien-3-yl-1,4-dihydroindeno[1,2-c]pyrazole The desired product was obtained by substituting Example 915H for Example 56 and phenyl thiophene-3-carboxylate for phenyl thiophene-2-carboxylate in Example 138. m.p. 221.5-222° C.

EXAMPLE 916

7-fluoro-6-[(4-methylpiperazin-1-yl)methyl]-3-thien-3-yl-1,4-dihydroindeno[1,2-c]pyrazole

EXAMPLE 916A 6-fluoro-5-[(4-methylpiperazin-1-yl)methyl]indan-1-one

The desired product was obtained by substituting Example 915G for Example 54 in Example 56.

EXAMPLE 916B 7-fluoro-6-[(4-methylpiperazin-1-yl)methyl]-3-thien-3-yl-1,4-dihydroindeno[1,2-c]pyrazole The desired product was obtained by substituting Example 916A for Example 56 and phenyl thiophene-3-carboxylate for phenyl thiophene-2-carboxylate in Example 138. m.p. 115-118° C.

EXAMPLE 917

5-methyl-7-[(4-methylpiperazin-1-yl)methyl]-3-thien-3-yl-1,4-dihydroindeno[1,2-c]pyrazole

EXAMPLE 917A 4-bromo-2-methylbenzyl methanesulfonate

The desired product was obtained by substituting (4-bromo-2-methyl-phenyl)-methanol for Example 51 in Example 54.

EXAMPLE 917B 3-(4-bromo-2-methylphenyl)propanoic acid

The desired product was obtained by substituting Example 917A for 4-bromobenzyl bromide in Example 1.

EXAMPLE 917C 6-bromo-4-methylindan-1-one

The desired product was obtained by substituting Example 917B for 3-(4-bromophenyl)-propionic acid in Example 3.

EXAMPLE 917D

6'-bromo-4'-methyl-2',3'-dihydrospiro[1,3-dioxolane-2,1'-indene]

The desired product was obtained by substituting Example 917C for 6-bromo-1-indanone in Example 20.

EXAMPLE 917E (4'-methyl-2',3'-dihydrospiro[1,3-dioxolane-2,1'-inden]-6'-yl)methanol The desired product was obtained by substituting Example 917D for Example 20 in Example 28.

EXAMPLE 917F 6-(hydroxymethyl)-4-methylindan-1-one

The desired product was obtained by substituting Example 917E for Example 28 in Example 51.

EXAMPLE 917G (7-methyl-3-oxo-2,3-dihydro-1H-inden-5-yl)methyl methanesulfonate The desired product was obtained by substituting Example 917F for Example 51 in Example 54.

EXAMPLE 917H 4-methyl-6-[(4-methylpiperazin-1-yl)methyl]indan-1-one

The desired product was obtained by substituting Example 917G for Example 54 in Example 56.

EXAMPLE 917I 5-methyl-7-[(4-methylpiperazin-1-yl)methyl]-3-thien-3-yl-1,4-dihydroindeno[1,2-c]pyrazole The desired product was obtained by substituting Example 917H for Example 56 and phenyl thiophene-3-carboxylate for phenyl thiophene-2-carboxylate in Example 138. m.p. 235-236° C.

EXAMPLE 918

5-methyl-7-(morpholin-4-ylmethyl)-3-thien-3-yl-1,4-dihydroindeno[1,2-c]pyrazole

EXAMPLE 918A 4-methyl-6-(morpholin-4-ylmethyl)indan-1-one

The desired product was obtained by substituting Example 917G for Example 54 and morpholine for N-methypiperazine in Example 56.

EXAMPLE 918B 5-methyl-7-(morpholin-4-ylmethyl)-3-thien-3-yl-1,4-dihydroindeno[1,2-c]pyrazole The desired product was obtained by substituting Example 918A for Example 56 and phenyl thiophene-3-carboxylate for phenyl thiophene-2-carboxylate in Example 138. m.p. 232-233° C.

EXAMPLE 919

7-[(4-ethylpiperazin-1-yl)methyl]-5-methyl-3-thien-3-yl-1,4-dihydroindeno[1,2-c]pyrazole

EXAMPLE 919A

6-[(4-ethylpiperazin-1-yl)methyl]-4-methylindan-1-one

The desired product was obtained by substituting Example 917G for Example 54 and N-ethylpiperazine for N-methypiperazine in Example 56.

EXAMPLE 919B

7-[(4-ethylpiperazin-1-yl)methyl]-5-methyl-3-thien-3-yl-1,4-dihydroindeno[1,2-c]pyrazole The desired product was obtained by substituting Example 919A for Example 56 and phenyl thiophene-3-carboxylate for phenyl thiophene-2-carboxylate in Example 138. m.p. 230-231° C.

EXAMPLE 920

7-[(4-isopropylpiperazin-1-yl)methyl]-5-methyl-3-thien-3-yl-1,4-dihydroindeno[1,2-c]pyrazole

EXAMPLE 920A

6-[(4-isopropylpiperazin-1-yl)methyl]-4-methylindan-1-one

The desired product was obtained by substituting Example 917G for Example 54 and N-isopropylpiperazine for N-methypiperazine in Example 56.

EXAMPLE 920B

7-[(4-isopropylpiperazin-1-yl)methyl]-5-methyl-3-thien-3-yl-1,4-dihydroindeno[1,2-c]pyrazole The desired product was obtained by substituting Example 920A for Example 56 and phenyl thiophene-3-carboxylate for phenyl thiophene-2-carboxylate in Example 138. m.p. 113-114° C.

EXAMPLE 921

5-methyl-7-[(2-methyl-1H-imidazol-1-yl)methyl]-3-thien-3-yl-1,4-dihydroindeno[1,2-c]pyrazole

EXAMPLE 921A 4-methyl-6-[(2-methyl-1H-imidazol-1-yl)methyl]indan-1-one

The desired product was obtained by substituting Example 917G for Example 54, 2-methylimidazole for N-methypiperazine, and DMF for EtOH in Example 56.

EXAMPLE 921B 5-methyl-7-[(2-methyl-1H-imidazol-1-yl)methyl]-3-thien-3-yl-1,4-dihydroindeno[1,2-c]pyrazole The desired product was obtained by substituting Example 921A for Example 56 and phenyl thiophene-3-carboxylate for phenyl thiophene-2-carboxylate in Example 138. m.p. 255-265° C. (decomp.).

EXAMPLE 922

5-methyl-7-[(4-methyl-1H-imidazol-1-yl)methyl]-3-thien-3-yl-1,4-dihydroindeno[1,2-c]pyrazole

EXAMPLE 922A 4-methyl-6-[(4-methyl-1H-imidazol-1-yl)methyl]indan-1-one

A mixture of Example 922A and Example 922B was obtained by substituting Example 917G for Example 54, 4-methylimidazole for N-methypiperazine, and DMF for EtOH in Example 56. The isomers were separated by flash chromatography.

EXAMPLE 922B 4-methyl-6-[(5-methyl-1H-imidazol-1-yl)methyl] indan-1-one

A mixture of Example 922A and Example 922B was obtained by substituting Example 917G for Example 54, 4-methylimidazole for N-methypiperazine, and DMF for EtOH in Example 56. The isomers were separated by flash chromatography.

EXAMPLE 922C 5-methyl-7-[(4-methyl-1H-imidazol-1-yl)methyl]-3-thien-3-yl-1,4-dihydroindeno[1,2-c]pyrazole The desired product was obtained by substituting Example 922A for Example 56 and phenyl thiophene-3-carboxylate for phenyl thiophene-2-carboxylate in Example 138. m.p. 240-242° C.

EXAMPLE 923

5-methyl-7-[(5-methyl-1H-imidazol-1-yl)methyl]-3-thien-3-yl-1,4-dihydroindeno[1,2-c]pyrazole The desired product was obtained by substituting Example 922B for Example 56 and phenyl thiophene-3-carboxylate for phenyl thiophene-2-carboxylate in Example 138. m.p. 290-292° C.

EXAMPLE 924

5-methyl-7-[(5-methyl-1H-imidazol-1-yl)methyl]-3-thien-3-yl-1,4-dihydroindeno[1,2-c]pyrazole

EXAMPLE 924A 6-(1H-imidazol-1-ylmethyl)-4-methylindan-1-one

The desired product was obtained by substituting Example 917G for Example 54, imidazole for N-methypiperazine, and DMF for EtOH in Example 56.

EXAMPLE 924B 5-methyl-7-[(5-methyl-1H-imidazol-1-yl)methyl]-3-thien-3-yl-1,4-dihydroindeno[1,2-c]pyrazole The desired product was obtained by substituting Example 924A for Example 56 and phenyl thiophene-3-carboxylate for phenyl thiophene-2-carboxylate in Example 138. m.p. 260-264° C.

EXAMPLE 925

5-methyl-7-(1H-pyrazol-1-ylmethyl)-3-thien-3-yl-1,4-dihydroindeno[1,2-c]pyrazole

EXAMPLE 925A 4-methyl-6-(1H-pyrazol-1-ylmethyl)indan-1-one

The desired product was obtained by substituting Example 917G for Example 54, pyrazole for N-methypiperazine, and DMF for EtOH in Example 56.

EXAMPLE 925B 5-methyl-7-(1H-pyrazol-1-ylmethyl)-3-thien-3-yl-1,4-dihydroindeno[1,2-c]pyrazole The desired product was obtained by substituting Example 925A for Example 56 and phenyl thiophene-3-carboxylate for phenyl thiophene-2-carboxylate in Example 138. m.p. 271-274° C.

EXAMPLE 926

5-methyl-3-thien-3-yl-7-(1H-1,2,4-triazol-1-ylmethyl)-1,4-dihydroindeno[1,2-c]pyrazole

EXAMPLE 926A 4-methyl-6-(1H-1,2,4-triazol-1-ylmethyl indan-1-one

The desired product was obtained by substituting Example 917G for Example 54, 1,2,4-triazole for N-methypiperazine, and DMF for EtOH in Example 56.

EXAMPLE 926B 5-methyl-3-thien-3-yl-7-(1H-1,2,4-triazol-1-ylmethyl)-1,4-dihydroindeno[1,2-c]pyrazole The desired product was obtained by substituting Example 926A for Example 56 and phenyl thiophene-3-carboxylate for phenyl thiophene-2-carboxylate in Example 138. m.p. 255-257° C.

EXAMPLE 927

5-fluoro-7-(1H-imidazol-1-ylmethyl)-3-thien-3-yl-1,4-dihydroindeno[1,2-c]pyrazole

EXAMPLE 927A 4-bromo-2-fluorobenzyl methanesulfonate

The desired product was obtained by substituting (4-bromo-2-fluoro-phenyl)-methanol for Example 51 in Example 54.

EXAMPLE 927B 3-(4-bromo-2-fluorophenyl)propanoic acid

The desired product was obtained by substituting Example 927A for 4-bromobenzyl bromide in Example 1.

EXAMPLE 927C 6-bromo-4-fluoroindan-1-one

The desired product was obtained by substituting Example 927B for 3-(4-bromophenyl)-propionic acid in Example 3.

EXAMPLE 927D

6'-bromo-4'-fluoro-2',3'-dihydrospiro[1,3-dioxolane-2,1'-indene]

The desired product was obtained by substituting Example 927C for 6-bromo-1-indanone in Example 20.

EXAMPLE 927E (4'-fluoro-2',3'-dihydrospiro[1,3-dioxolane-2,1'-inden]-6'-yl)methanol The desired product was obtained by substituting Example 927D for Example 20 in Example 28.

EXAMPLE 927F 4-fluoro-6-(hydroxymethyl)indan-1-one

The desired product was obtained by substituting Example 927E for Example 28 in Example 51.

EXAMPLE 927G (7-fluoro-3-oxo-2,3-dihydro-1H-inden-5-yl)methyl methanesulfonate The desired product was obtained by substituting Example 927F for Example 51 in Example 54.

EXAMPLE 927H 4-fluoro-6-(1H-imidazol-1-ylmethyl)indan-1-one

The desired product was obtained by substituting Example 927G for Example 54, imidazole for N-methylpiperazine, and DMF for EtOH in Example 56.

EXAMPLE 927I 5-fluoro-7-(1H-imidazol-1-ylmethyl)-3-thien-3-yl-1,4-dihydroindeno[1,2-c]pyrazole The desired product was obtained by substituting Example 927H for Example 56 and phenyl thiophene-3-carboxylate for phenyl thiophene-2-carboxylate in Example 138. m.p. 274-276° C.

EXAMPLE 928

5-fluoro-3-thien-3-yl-7-(1H-1,2,4-triazol-1-ylmethyl)-1,4-dihydroindeno[1,2-c]pyrazole

EXAMPLE 928A 4-fluoro-6-(1H-1,2,4-triazol-1-ylmethyl)indan-1-one

The desired product was obtained by substituting Example 927G for Example 54, 1,2,4-triazole for N-methylpiperazine, and DMF for EtOH in Example 56.

EXAMPLE 928B 5-fluoro-3-thien-3-yl-7-(1H-1,2,4-triazol-1-ylmethyl)-1,4-dihydroindeno[1,2-c]pyrazole The desired product was obtained by substituting Example 928A for Example 56 and phenyl thiophene-3-carboxylate for phenyl thiophene-2-carboxylate in Example 138. m.p. 236-239° C.

EXAMPLE 929

3-thien-3-yl-7-[2-(1H-1,2,4-triazol-1-yl)ethyl]-1,4-dihydroindeno[1,2-c]pyrazole

EXAMPLE 929A (3-oxo-2,3-dihydro-1H-inden-5-yl)acetonitrile

A mixture of Example 54 (10.2 g, 42.5 mmol) and NaCN (4.1 g, 84.9 mmol) in DMF (100 mL) was stirred at 50° C. for 1 h. The mixture was quenched H2O and extracted with EtOAc. The extract was washed with water and brine, dried (Na2SO4) and concentrated in vacuo. The residue was washed with diisopropyl ether, giving Example 929A as brown crystals (5.6 g).

EXAMPLE 929B ethyl (3-oxo-2,3-dihydro-1H-inden-5-yl)acetate

A solution of Example 929A (5.6 g, 32.7 mmol) in 28% HCl/EtOH (56 mL) was stirred at 50° C. for 2.5 h then concentrated in vacuo. The residue was diluted with H2O and adjusted to basic pH using sat. aq. NaHCO3 solution, then extracted with EtOAc. The extract was washed with brine, dried (Na2SO4) and concentrated in vacuo. The residue was purified by flash chromatography (1:1 EtOAc/heptane) to give Example 929B as a pale yellow oil (3.1 g)

EXAMPLE 929C 6-(2-hydroxyethyl)indan-1-ol

A mixture of Example 929B (3.0 g, 13.8 mmol) and NaBH4 (1.56 g, 41.4 mmol) in THF (30 mL) was heated to reflux for 30 min., and then MeOH (3 mL) was added to the mixture. The mixture was then heated to reflux for 2 h then concentrated in vacuo. The residue was diluted with H2O and extracted with EtOAc. The extract was washed with brine, dried (Na2SO4) and concentrated in vacuo to give Example 929C as a colorless oil (2.5 g).

EXAMPLE 929D 6-(2-hydroxyethyl)indan-1-one

A suspension of Example 929C (2.3 g, 13 mmol) and MnO2 (16.5 mmol) in toluene (23 mL) was stirred at 40° C. for 40 h. The reaction mixture was filtered twice. The filtrate was evaporated to give Example 929D as a pale yellow oil (1.9 g).

EXAMPLE 929E 2-(3-oxo-2,3-dihydro-1H-inden-5-yl)ethyl methanesulfonate

The desired compound was prepared by substituting Example 929D for Example 51 in Example 54.

EXAMPLE 929F

6-[2-(1H-1,2,4-triazol-1-yl)ethyl]indan-1-one

The desired product was prepared by substituting Example 929E for Example 54 in Example 57 and 1,2,4-triazole for imidazole, and by heating the reaction to 80° C. instead of stirring at rt.

EXAMPLE 929G 3-thien-3-yl-7-[2-(1H-1,2,4-triazol-1-yl)ethyl]-1,4-dihydroindeno[1,2-c]pyrazole The desired product was prepared by substituting Example 929F for example 56 in Example 138. m.p. 167-168° C.

EXAMPLE 930

7-[2-(1H-imidazol-1-yl)ethyl]-3-thien-3-yl-1,4-dihydroindeno[1,2-c]pyrazole

EXAMPLE 930A

6-[2-(1H-imidazol-1-yl)ethyl]indan-1-one

The desired product was prepared by substituting Example 929E for Example 54 in Example 57 and by heating the reaction to 80° C. instead of stirring at rt.

EXAMPLE 930B

7-[2-(1H-imidazol-1-yl)ethyl]-3-thien-3-yl-1,4-dihydroindeno[1,2-c]pyrazole

The desired product was prepared by substituting Example 930A for example 56 in Example 138. m.p. 212-216° C. (HCl salt).

EXAMPLE 931

6-[2-(1H-imidazol-1-yl)ethyl]-3-thien-3-yl-1,4-dihydroindeno[1,2-c]pyrazole

EXAMPLE 931A (1-oxo-2,3-dihydro-1H-inden-5-yl)acetonitrile

The desired product was prepared by substituting Example 55 for Example 54 in Example 929A.

EXAMPLE 931B ethyl (1-oxo-2,3-dihydro-1H-inden-5-yl)acetate

The desired product was prepared by substituting Example 931A for Example 929A in Example 929B.

EXAMPLE 931C 5-(2-hydroxyethyl indan-1-ol

The desired product was prepared by substituting Example 931B for Example 929B in Example 929C.

EXAMPLE 931D 5-(2-hydroxyethyl)indan-1-one

The desired product was prepared by substituting Example 931C for Example 929C in Example 929D.

EXAMPLE 931E 2-(1-oxo-2,3-dihydro-1H-inden-5-yl)ethyl methanesulfonate

The desired compound was prepared by substituting Example 931D for Example 51 in Example 54.

EXAMPLE 931F

5-[2-(1H-imidazol-1-yl)ethyl]indan-1-one

The desired product was prepared by substituting Example 931E for Example 54 in Example 57 and by heating the reaction to 80° C. instead of stirring at rt.

EXAMPLE 931G

6-[2-(1H-imidazol-1-yl)ethyl]-3-thien-3-yl-1,4-dihydroindeno[1,2-c]pyrazole

The desired product was prepared by substituting Example 931F for Example 56 in Example 138. m.p. 160-165° C. (HCl salt).

EXAMPLE 932 (A-788289.0)

{4-[(3-thien-3-yl-1,4-dihydroindeno[1,2-c]pyrazol-7-yl)methyl]piperazin-1-yl}acetonitrile

EXAMPLE 932A 6-(piperazin-1-ylmethyl)indan-1-one

A solution of Example 871A (0.83 g, 2.50 mmol) in 10% aqueous HCl (4 mL) was stirred at 60° C. for 15 min. The solution was brought to basic pH by the addition of K2CO3, then concentrated in vacuo to give a crude solid.

EXAMPLE 932B

{4-[(3-oxo-2,3-dihydro-1H-inden-5-yl)methyl]piperazin-1-yl}acetonitrile

A mixture of Example 932A (2.50 mmol), chloroacetonitrile (0.16 mL, 2.50 mmol) and K2CO3 (0.69 g, 5.00 mmol) in DMF (4 mL) was stirred at rt for 21 h. The reaction was quenched with H2O and extracted with EtOAc. The extract was washed with H2O and brine, dried (Na2SO4) and concentrated in vacuo to give Example 932B as a pale brown viscous oil (0.70 g).

EXAMPLE 932C

Name

The desired product was prepared by substituting Example 932B for Example 56 in Example 138. m.p. 176-179° C.

EXAMPLE 933

7-(piperazin-1-ylmethyl)-3-thien-3-yl-1,4-dihydroindeno[1,2-c]pyrazole

The desired product was prepared by substituting Example 871B for Example 871A in Example 932A. m.p. 125-130° C.

EXAMPLE 934

4-{4-[(3-thien-3-yl-1,4-dihydroindeno[1,2-c]pyrazol-7-yl)methyl]piperazin-1-yl}butanoic acid

EXAMPLE 934A

4-{4-[(3-oxo-2,3-dihydro-1H-inden-5-yl)methyl]piperazin-1-yl}butanenitrile

The desired product was prepared by substituting 4-piperazin-1-yl-butyronitrile for N-methylpiperazine in Example 56.

EXAMPLE 934B

4-{4-[(3-thien-3-yl-1,4-dihydroindeno[1,2-c]pyrazol-7-yl)methyl]piperazin-1-yl}butanenitrile The desired product was prepared by substituting Example 934A for Example 56 in Example 138.

EXAMPLE 934C

4-{4-[(3-thien-3-yl-1,4-dihydroindeno[1,2-c]pyrazol-7-yl)methyl]piperazin-1-yl}butanoic acid The desired product was prepared by substituting Example 934B for Example 866 in Example 872. m.p. 195-198° C. (2 HCl salt).

EXAMPLE 935

N-[(3-{5-[3-(2-methoxyethoxy)-1-propynyl]-3-thienyl}-1,4-dihydroindeno[1,2-c]purazol-7-yl)methyl]-N,N-dimethylamine

EXAMPLE 935A

6-[(dimethylamino)methyl]indan-1-one

The desired product was prepared by substituting dimethylamine for 1-methylpiperazine in Example 56.

EXAMPLE 935B

N-{[3-(5-bromothien-3-yl)-1,4-dihydroindeno[1,2-c]pyrazol-7-yl]methyl}-N,N-dimethylamine The desired product was prepared by substituting Example 935A for Example 56 and Example 113 for phenyl thiophene-2-carboxylate in Example 138.

EXAMPLE 935C

N-[(3-{5-[3-(2-methoxyethoxy)-1-propynyl]-3-thienyl}-1,4-dihydroindeno[1,2-c]pyrazole-7-yl)methyl]-N,N-dimethylamine The desired product was prepared by substituting Example 935B for 2-bromothiophene-4-carboxylate and Example 127 for phenyl propargyl ether in Example 126. The product was purified by preparative HPLC on a Waters Symmetry C8 column (25 mm×100 mm, 7 □m particle size) using a gradient of 10% to 100% acetonitrile:0.1% aqueous TFA over 8 min (10 min run time) at a flow rate of 40 ml/min to give the desired product as the trifluoroacetic acid salt. 1H NMR (500 MHz, DMSO-D6) δ ppm 2.77 (d, J=4.7 Hz, 6H) 3.27 (s, 3H) 3.51 (dd, J=5.5, 3.9 Hz, 2H) 3.64 (dd, J=5.5, 3.7 Hz, 2H) 3.88 (s, 2H) 4.37 (d, J=4.7 Hz, 2H) 4.45 (s, 2H) 7.40 (dd, J=7.8, 1.6 Hz, 1H) 7.66 (d, J=7.8 Hz, 1H) 7.74 (d, J=1.3 Hz, 1H) 7.83 (s, 1H) 7.89 (d, J=1.6 Hz, 1H) 9.66 (s, 1H) MS (ESI(+)) m/e 408.1 (M+H)+.

EXAMPLE 936

N,N-dimethyl-2-[(3-{5-[3-(tetrahydro-2-furanylmethoxy)-1-propynyl]-3-thienyl}-1,4-dihydroindeno[1,2-c]pyrazol-6-yl)oxy]acetamide The desired product was prepared by substituting Example 265 for 2-bromothiophene-4-carboxylate and Example 624 for phenyl propargyl ether in Example 126. The product was purified by preparative HPLC on a Waters Symmetry C8 column (25 mm×100 mm, 7 □m particle size) using a gradient of 10% to 100% acetonitrile:0.1% aqueous TFA over 8 min (10 min run time) at a flow rate of 40 ml/min to give the desired product as the trifluoroacetic acid salt. 1H NMR (500 MHz, DMSO-D6) δ ppm 1.53-1.60 (m, 1H) 1.74-1.86 (m, 2H) 1.87-1.95 (m, 1 H) 2.86 (s, 3 H) 3.02 (s, 3 H) 3.47-3.52 (m, 2 H) 3.62-3.66 (m, 1H) 3.73-3.77 (m, 1 H) 3.78 (s, 2H) 3.95-4.00 (m, 1H) 4.46 (s, 2H) 4.84 (s, 2H) 6.92 (dd, J=8.3, 2.3 Hz, 1 H) 7.14 (d, J=1.9 Hz, 1 H) 7.52 (d, J=8.1 Hz, 1H) 7.59-7.96 (br s, 1H) 7.71 (d, J=1.3 Hz, 1 H) 7.84 (d, J=1.6 Hz, 1 H) MS (ESI(+)) m/e 478.0 (M+H)+.

EXAMPLE 937

N,N-dimethyl-N-({3-[5-(3-phenoxy-1-propynyl)-3-thienyl]-1,4-dihydroindeno[1,2-c]pyrazole-7-yl}methyl)amine The desired product was prepared by substituting Example 935A for 2-bromothiophene-4-carboxylate in Example 126. The product was purified by preparative HPLC on a Waters Symmetry C8 column (25 mm×100 mm, 7 μm particle size) using a gradient of 10% to 100% acetonitrile:0.1% aqueous TFA over 8 min (10 min run time) at a flow rate of 40 ml/min to give the desired product as the trifluoroacetic acid salt. $^1$H NMR (500 MHz, DMSO-D$_6$) δ ppm 2.78 (s, 6 H) 3.87 (s, 2 H) 4.38 (d, J=4.0 Hz, 2H) 5.11 (s, 2H) 6.99-7.03 (m, 1H) 7.06 (d, J=7.8 Hz, 2 H) 7.34-7.37 (m, 2 H) 7.41 (dd, J=7.8, 1.6 Hz, 1 H) 7.66 (d, J=7.8 Hz, 1H) 7.75 (d, J=1.3 Hz, 1 H) 7.82 (s, 1 H) 7.90 (d, J=1.3 Hz, 1H) 9.85 (s, 1H) MS (ESI(+)) m/e 426.1 (M+H)$^+$.

EXAMPLE 938

3-(5-bromo-3-thienyl)-6-(1H-tetraazol-1-ylmethyl)-1,4-dihydroindeno[1,2-c]pyrazole

EXAMPLE 938A 5-(1H-tetraazol-1-ylmethyl)indan-1-one

To a solution of tetrazole (3 wt. % solution in CH3CN, 77 mL, 26.0 mmol) in CH3CN (140 mL) at room temperature was added Example 55 (5.0 g, 20.8 mmol) eq) and Et3N (3 mL, 21.0 mmol). The solution was stirred at room temperature overnight, then concentrated in vacuo. The residue was taken up in ethyl acetate, washed with saturated NaHCO3 solution and concentrated onto silica gel. The material was purified by flash chromatography on silica gel eluting with 5% MeOH/CH2Cl2. Two isomers co-eluted. The material was rechromatographed eluting with 1% MeOH-methylene chloride. Example 938A was isolated as the major product (1.83 g, 41%). MS (ESI(+)) m/e 215.1 (M+H)$^+$.

EXAMPLE 938B 3-(5-bromo-3-thienyl)-6-(1H-tetraazol-1-ylmethyl)-14-dihydroindeno[1,2-c]pyrazole The desired product was prepared by substituting Example 938A for Example 56 and Example 113 for phenyl thiophene-2-carboxylate in Example 138. 1H NMR (300 MHz, DMSO-D6) δ ppm 3.80 (s, 2H) 5.77 (s, 2H) 7.36 (d, J=8.1 Hz, 1H) 7.55 (s, 1H) 7.61 (d, J=1.4 Hz, 1 H) 7.65 (d, J=7.8 Hz, 1 H) 7.82 (s, 1 H) 9.54 (s, 1 H) 13.19 (s, 1 H).

EXAMPLE 939

5-(4-{7-[(dimethylamino)methyl]-1,4-dihydroindeno[1,2-c]pyrazol-3-yl}-2-thienyl)-4-pentynenitrile The desired product was prepared by substituting Example 935A for 2-bromothiophene-4-carboxylate and pent-4-ynenitrile for phenyl propargyl ether in Example 126. The product was purified by preparative HPLC on a Waters Symmetry C8 column (25 mm×100 mm, 7 μm particle size) using a gradient of 10% to 100% acetonitrile:0.1% aqueous TFA over 8 min (10 min run time) at a flow rate of 40 ml/min to give the desired product as the trifluoroacetic acid salt. 1H NMR (400 MHz, DMSO-D6) δ ppm 2.78 (s, 6 H) 2.81-2.89 (m, 4 H) 3.88 (s, 2 H) 4.38 (s, 2 H) 7.40 (dd, J=7.7, 1.5 Hz, 1 H) 7.65-7.68 (m, 2 H) 7.83 (s, 1H) 7.84 (d, J=1.2 Hz, 1 H) 9.65 (s, 1 H) MS (ESI(+)) m/e 373.0 (M+H)+.

EXAMPLE 940

4-({3-[5-(3-phenoxy-1-propynyl)-3-thienyl]-1,4-dihydroindeno[1,2-c]pyrazol-7-yl}methyl)-2-piperazinone

EXAMPLE 940A

4-[(3-oxo-2,3-dihydro-15H-inden-5-yl)methyl]piperazin-2-one

The desired product was prepared by substituting piperazine-2-one for 1-methylpiperazine in Example 56.

EXAMPLE 940B

4-{[3-(5-bromothien-3-yl)-1,4-dihydroindeno[1,2-c]pyrazol-7-yl]methyl}piperazin-2-one The desired product was prepared by substituting Example 940A for Example 56 and Example 113 for phenyl thiophene-2-carboxylate in Example 138. MS (ESI(+)) m/e 428.9, 430.6 (M+H)+.

EXAMPLE 940C 4-({3-[5-(3-phenoxy-1-propynyl)-3-thienyl]-1,4-dihydroindeno[1,2-c]pyrazol-7yl}methyl)-2-piperazinone The desired product was prepared by substituting Example 940B for 2-bromothiophene-4-carboxylate in Example 126. 1H NMR (400 MHz, DMSO-D6) δ ppm 2.56-2.59 (m, 2H) 2.93 (s, 2H) 3.14-3.17 (m, 2H) 3.61 (s, 2H) 3.78 (s, 2H) 5.09 (s, 2H) 6.99 (t, J=7.4 Hz, 1H) 7.02-7.06 (m, 2H) 7.22 (dd, J=7.7, 1.5 Hz, 1H) 7.34 (dd, J=8.9, 7.2 Hz, 2H) 7.50 (d, J=7.7 Hz, 1H) 7.59 (s, 1H) 7.71 (app s, 2H) 7.86 (s, 1H) 13.15 (s, 1H) MS (ESI(+)) m/e 481.1 (M+H)+.

EXAMPLE 941 ethyl {[3-(4-{6-[(4-methyl-1-piperazinyl)methyl]-1,4-dihydroindeno[1,2-c]pyrazol-3-yl}-2-thienyl)-2-propynyl]oxy}acetate

EXAMPLE 941A ethyl (prop-2-ynyloxy)acetate

The desired product was prepared by substituting ethyl glycolate for 2-isopropoxyethanol in Example 613.

EXAMPLE 941B ethyl {[3-(4-{6-[(4-methyl-1-piperazinyl methyl]-1,4-dihydroindeno[1,2-c]pyrazol-3-yl}-2-thienyl)-2-propynyl]oxy}acetate The desired product was obtained by substituting Example 148 for 2-bromothiophene-4-carboxylate and Example 941A for phenyl propargyl ether in Example 126. The product was purified by preparative HPLC on a Waters Symmetry C8 column (25 mm×100 mm, 7 μm particle size) using a gradient of 10% to 100% acetonitrile:0.1% aqueous TFA over 8 min (10 min run time) at a flow rate of 40 mL/min to give Example 941B as a trifluoroacetic acid salt. 1H NMR (500 MHz, DMSO-D6) δ ppm 1.22 (t, J=7.2 Hz, 3 H) 2.81 (s, 3 H) 2.95-3.58 (m, 8 H) 3.84 (s, 2 H) 4.14 (s, 2H) 4.15 (q, J=7.2 Hz, 2H) 4.23 (s, 2H) 4.54 (d, J=6.9 Hz, 2 H) 7.41 (d, J=7.8 Hz, 1 H) 7.60 (s, 1 H) 7.68 (d, J=7.8 Hz, 1H) 7.75 (s, 1H) 7.90 (s, 1 H) MS (ESI(+)) m/e 491.2 (M+H)+.

EXAMPLE 942

2-{[3-(4-{6-[(4-methyl-1-piperazinyl)methyl]-1,4-dihydroindeno[1,2-c]pyrazole-3-yl}-2-thienyl)-2-propynyl]oxy}acetamide A mixture of Example 941B (120 mg) and 2M NH3/MeOH (2 mL, 4.0 mmol) was stirred at rt for 3 d, then concentrated in vacuo. The residue was purified by preparative HPLC on a Waters Symmetry C8 column (25 mm×100 mm, 7 μm particle size) using a gradient of 10% to 100% acetonitrile:0.1% aqueous TFA over 8 min (10 min run time) at a flow rate of 40 ml/min to give Example 942 as the tris-trifluoroacetic acid salt (130 mg/67%). 1H NMR (500 MHz, DMSO-D6) δ ppm 2.81 (s, 3 H) 2.92-3.59 (m, 8H) 3.84 (s, 2H) 3.95 (s, 2H) 4.00 (s, 2 H) 7.23-7.27 (br. s, 1 H) 7.27-7.31 (br. s, 1H) 7.40 (d, J=7.5 Hz, 1H) 7.60 (s, 1 H) 7.68 (d, J=7.5 Hz, 1 H) 7.75 (d, J=1.3 Hz, 1 H) 7.90 (s, 1 H) MS (ESI(+)) m/e 462.2 (M+H)+.

EXAMPLE 943

3-{5-[3-(phenylsulfonyl)-1-propynyl]-3-thienyl}-7-(1H-1,2,4-triazol-1-ylmethyl)-1,4-dihydroindeno[1,2-c]pyrazole To a solution of Example 719 (110 mg, 0.24 mmol) in THF (3 mL) and MEOH (4 mL) under argon atmosphere at 0° C. was added dropwise a solution of Oxone® (280 mg, 4.5% active 0; 0.78 mmol) in H2O (3 mL). The mixture was stirred for 5 min at 0° C. and at rt for 1.5 h, then extracted with THF-Et2O. The organic phase was washed with H2O while adjusting the aqueous phase to pH 7-8 by the addition of a small amount of NaHCO3, then dried (MgSO4) and concentrated. The residue was purified by preparative HPLC on a Waters Symmetry C8 column (25 mm×100 mm, 7 μm particle size) using a gradient of 10% to 100% acetonitrile:0.1% aqueous TFA over 8 min (10 min run time) at a flow rate of 40 ml/min, and the product was further purified by recrystallization (EtOAc/hexanes) to give Example 943 (19.1 mg, 16%). 1H NMR (300 MHz, DMSO-D6) δ ppm 3.80 (s, 2 H) 4.89 (s, 2 H) 5.51 (s, 2H) 7.25 (d, J=7.1 Hz, 1 H) 7.55-7.57 (m, 2 H) 7.65 (s, 1H) 7.73 (t, J=7.6 Hz, 2H) 7.81-7.87 (m, 2 H) 7.98-8.01 (m, 3H) 8.72 (s, 1 H) 13.24 (s, 1 H) MS (ESI(+)) m/e 498.1 (M+H)$^+$.

EXAMPLE 944

3-[5-(3-methoxy-1-propynyl)-3-thienyl]-7-(1H-1,2,4-triazol-1-ylmethyl)-1,4-dihydroindeno[1,2-c]pyrazole The desired product was obtained by substituting Example 259 for 2-bromothiophene-4-carboxylate and methyl propargyl ether for phenyl propargyl ether in Example 126. The product was purified by preparative HPLC on a Waters Symmetry C8 column (25 mm×100 mm, 7 μm particle size) using a gradient of 10% to 100% acetonitrile:0.1% aqueous TFA over 8 min (10 min run time) at a flow rate of 40 ml/min to give Example 944 as a trifluoroacetic acid salt. 1H NMR (500 MHz, DMSO-D6) δ ppm 3.34 (s, 3 H) 3.81 (s, 2 H) 4.38 (s, 2 H) 5.50 (s, 2 H) 7.24 (dd, J=7.8, 1.6 Hz, 1H) 7.53-7.59 (m, 2H) 7.72 (s, 1H) 7.87 (s, 1H) 8.00 (s, 1 H) 8.70 (s, 1 H)

EXAMPLE 945

3-[5-(1-heptynyl)-3-thienyl]-6-[(4-methyl-1-piperazinyl)methyl]-1,4-dihydroindeno[1,2-c]pyrazole The desired product was obtained by substituting Example 148 for 2-bromothiophene-4-carboxylate and 1-heptyne for phenyl propargyl ether in Example 126. The product was purified by preparative HPLC on a Waters Symmetry C8 column (25 mm×100 mm, 7 μm particle size) using a gradient of 10% to 100% acetonitrile:0.1% aqueous TFA over 8 min (10 min run time) at a flow rate of 40 ml/min to give Example 945 as a trifluoroacetic acid salt. 1H NMR (500 MHz, DMSO-D6) δ ppm 0.90 (t, J=7.17 Hz, 3 H) 1.30-1.43 (m, 4 H) 1.54-1.60 (m, 2H) 2.15 (s, 3 H) 2.23-2.45 (m, 8 H) 2.47-2.54 (m, 2 H) 3.50 (s, 2H) 3.79 (s, 2H) 7.27 (d, J=7.2 Hz, 1 H) 7.47 (s, 1 H) 7.50-7.62 (m, 2 H) 7.76 (s, 1 H) 13.04 (s, 1H) MS (ESI(+)) m/e 445.2 (M+H)$^+$.

EXAMPLE 946

6-[(4-methyl-1-piperazinyl)methyl]-3-[5-(1-pentynyl)-3-thienyl]-1,4-dihydroindeno[1,2-c]pyrazole The desired product was obtained by substituting Example 148 for 2-bromothiophene-4-carboxylate and 1-pentyne for phenyl propargyl ether in Example 126. The product was purified by preparative HPLC on a Waters Symmetry C8 column (25 mm×100 mm, 7 μm particle size) using a gradient of 10% to 100% acetonitrile:0.1% aqueous TFA over 8 min (10 min run time) at a flow rate of 40 ml/min to give Example 946 as a trifluoroacetic acid salt. 1H NMR (500 MHz, DMSO-D6) δ ppm 1.01 (t, J=7.33 Hz, 3 H) 1.55-1.62 (m, 2H) 2.15 (s, 3H) 2.28-2.44 (m, 8 H) 2.47 (t, J=7.0 Hz, 2 H) 3.50 (s, 2 H) 3.79 (s, 2H) 7.27 (d, J=7.8 Hz, 1H) 7.47 (s, 1 H) 7.55-7.60 (m, 2 H) 7.75 (s, 1 H) 13.05 (s, 1 H) MS (ESI(+)) m/e 417.1 (M+H)$^+$.

EXAMPLE 947

6-[(4-methyl-1-piperazinyl)methyl]-3-{5-[3-(tetrahydro-2H-pyran-4-yloxy)-1-proynyl]-3-thienyl}-1,4-dihydroindeno[1,2-c]pyrazole The desired product was obtained by substituting Example 148 for 2-bromothiophene-4-carboxylate and Example 632 for phenyl propargyl ether in Example 126. The product was purified by preparative HPLC on a Waters Symmetry C8 column (25 mm×100 mm, 7 μm particle size) using a gradient of 10% to 100% acetonitrile:0.1% aqueous TFA over 8 min (10 min run time) at a flow rate of 40 ml/min to give Example 947 as the trifluoroacetic acid salt. 1H NMR (500 MHz, DMSO-D6) δ ppm 1.41-1.48 (m, 2 H) 1.87-1.93 (m, 2 H) 2.80 (s, 3H), 3.20-3.61 (m, 10 H) 3.68-3.73 (m, 2H) 3.79-3.81 (m, 1H) 3.83 (s, 2H) 3.99 (s, 2H) 4.47 (s, 2 H) 7.39 (d, J=7.5 Hz, 1 H) 7.59 (s, 1 H) 7.67 (d, J=7.5 Hz, 1H) 7.71 (s, 1H) 7.87 (s, 1 H) MS (ESI(+)) m/e 489.2 (M+H)$^+$.

EXAMPLE 948

3-(5-{3-[2-(difluoromethoxy)ethoxy]-1-propynyl}-3-thienyl)-6-[(4-methyl-1piperazinyl)methyl]-1,4-dihydroindeno[1,2-c]pyrazole

EXAMPLE 948A

3-[2-(difluoromethoxy)ethoxy]prop-1-yne (2-Prop-2-ynyloxy)ethanol (1.3 g, 13 mmol) and Na$_2$SO$_4$ (370 mg, 2.6 mmol) were combined in CH$_3$CN (1.5 mL) and treated with 2,2-difluoro-2-(fluorosulfonyl)acetic acid (2.5 g, 14 mmol). The flask was equipped with a water-cooled condenser and the condenser was equipped with a trap containing NaOH and kept at −78° C. under N$_2$. The reaction mixture was heated at 50° C. for 2 hours, cooled to rt, diluted with saturated Na$_2$CO$_3$ solution (25 mL) and extracted with Et$_2$O (100 mL). The Et$_2$O layer was washed with H$_2$O, dried over Na$_2$SO$_4$, filtered, and the filtrate was concentrated in vacuo. The residue was purified by flash chromatography (4:1 pentane:Et$_2$O) and then further purified by a second flash column (2:1 CH$_2$Cl$_2$:Et$_2$O) to give the title compound (0.125 g, 6.4%).

EXAMPLE 948B 3-(5-{3-[2-(difluoromethoxyethoxy]-1-propynyl}-3-thienyl)-6-[(4-methyl-1-piperazinyl)methyl]-1,4-dihydroindeno[1,2-c]pyrazole The title compound was prepared by using the procedure described in Example 126 except using 3-(5-bromothien-3-yl)-6-[(4-methylpiperazin-1-yl)methyl]-1,4-dihydroindeno[1,2-c]pyrazole and 3-[2-(difluoromethoxy)ethoxy]prop-1-yne instead of phenyl 5-bromothiophene-3-carboxylate and (prop-2-ynyloxy)benzene. The product was purified by preparative HPLC on a Waters Symmetry C8 column (25 mm×100 mm, 7 μm particle size) using a gradient of 10% to 100% acetonitrile:0.1% aqueous trifluoracetic acid (TFA) over 8 minutes (10 minute run time) at a flow rate of 40 ml/min to give the title compound as the trifluoroacetic acid salt. 1H NMR (500 MHz, DMSO-D$_6$) δ ppm 2.82 (s, 3 H 3.02-3.61 (m, 8 H) 3.72-3.73 (m, 2 H) 3.84 (s, 2 H) 3.96-4.05 (m, 5 H) 4.50 (s, 2 H) 7.41 (d, J=7.8 Hz, 1 H) 7.61 (s, 1 H) 7.68 (d, J=7.8 Hz, 1 H) 7.74 (d, J=1.0 Hz, 1 H) 7.89 (d, J=1.0 Hz, 1 H) MS (ESI(+)) m/e 499.1 (M+H)$^+$.

EXAMPLE 949

3-(5-{3-[4-(4-pyridinyl)phenoxy]-1-propynyl}-3-thienyl)-6-(1H-1,2,4-triazol-1-ylmethyl)-1,4-dihydroindeno[1,2-c]pyrazole

EXAMPLE 949A

4-[4-(prop-2-ynyloxy)phenyl]pyridine

The desired product was prepared by substituting 4-(4-pyridinyl)phenol for 4'-1-(1H-1,2,4-triazol-1-yl) phenol in Example 647. MS (ESI(+)) m/e 209.9 (M+H)$^+$.

EXAMPLE 949B 3-(5-{3-[4-(4-pyridinyl)phenoxy]-1-propynyl}-3-thienyl)-6-(1H-1,2,4-triazol-1,4-dihydroindeno[1,2-c]pyrazole The desired product was obtained by substituting Example 260 for 2-bromothiophene-4-carboxylate and Example 949A for phenyl propargyl alcohol in Example 126. The product was purified by preparative HPLC on a C18 column using a gradient of 20% to 100% acetonitrile:0.1% aqueous TFA to give Example 949B as the trifluoroacetic acid salt. 1H NMR (300 MHz, DMSO-D6) δ ppm 8.65-8.98 (m, 3 H), 8.12 (br. s, 2 H), 8.02 (s, 1 H), 7.99 (s, 1 H) 7.89 (s, 1 H), 7.74 (s, 1 H), 7.62 (d, J=9.0 Hz, 1 H), 7.47 (s, 1 H), 7.23-7.34 (m, 3 H), 5.48 (s, 2H), 5.25 (s, 2 H), 3.80 (s, 2 H) MS (ESI(+)) m/e 527.1 (M+H)$^+$.

EXAMPLE 950

3-(5-{3-[4-(4-pyridinyl)phenoxy]-1-propynyl}-3-thienyl-7-(1H-1,2,4-triazol-1-ylmethyl)-1,4-dihydroindeno[1,2-c]pyrazole The desired product was obtained by substituting Example 259 for 2-bromothiophene-4-carboxylate and Example 949A for phenyl propargyl alcohol in Example 126. The product was purified by preparative HPLC on a C18 column using a gradient of 30% to 100% acetonitrile:0.1% aqueous TFA to give Example 950 as the trifluoroacetic acid salt. 1H NMR (300 MHz, DMSO-D6) δ ppm 8.90-9.01 (m, 1 H), 8.73 (br s, 1 H), 8.02 (s, 1 H), 8.00 (s, 1 H), 7.89 (s, 1 H), 7.74 (s, 1 H), 8.50-8.58 (m, 2H), 8.20-8.30 (m, 3H), 5.50 (s, 2 H), 5.25 (s, 2 H), 3.79 (s, 2 H) MS (ESI(+)) m/e 527.1 (M+H)$^+$.

EXAMPLE 951

3-(5-{3-[4-(3-pyridinyl)phenoxy]-1-propynyl}-3-thienyl)-6-(1H-1,2,4-triazol-1-ylmethyl)-1,4-dihydroindeno[1,2-c]pyrazole

EXAMPLE 951A

3-[4-(prop-2-ynyloxy)phenyl]pyridine

The desired product was prepared by substituting 4-(3-pyridinyl)phenol for 4'-1-(1H-1,2,4-triazol-1-yl) phenol in Example 647. MS (ESI(+)) m/e 209.9 (M+H)$^+$.

EXAMPLE 951B 3-(5-{3-[4-(3-pyridinyl)phenoxy]-1-propynyl}-3-thienyl)-6-(1H-1,2,4-triazol-1-ylmethyl)-1,4-dihydroindeno[1,2-c]pyrazole The desired product was obtained by substituting Example 260 for 2-bromothiophene-4-carboxylate and Example 951A for phenyl propargyl alcohol in Example 126. The product was purified by preparative HPLC on a C18 column using a gradient of 30% to 100% acetonitrile:0.1% aqueous TFA to give Example 951B as the trifluoroacetic acid salt. 1H NMR (300 MHz, DMSO-D6) δ ppm 8.91-9.26 (m, 1 H), 8.73 (br s, 2H), 8.27 (d, J=9.0 Hz, 1 H), 7.89 (s, 1 H), 7.80 (s, 1 H), 7.77 (s, 1H), 7.74 (s, 1H), 7.60-7.69 (m, 2H), 7.47 (s, 1 H), 7.29 (d, J=9.0 Hz, 1 H), 7.23 (s, 1 H), 7.20 (s, 1H), 5.48 (s, 2H), 5.20 (s, 2H), 3.80 (s, 2H) MS (ESI(+)) m/e 527.1 (M+H)$^+$.

EXAMPLE 952

3-(5-{3-[4-(3-pyridinyl phenoxy]-1-propynyl}-3-thienyl)-7-(1H-1,2,4-triazol-1-ylmethyl-1,4-dihydroindeno[1,2-c]pyrazole The desired product was obtained by substituting Example 259 for 2-bromothiophene-4-carboxylate and Example 951A for phenyl propargyl alcohol in Example 126. The product was purified by preparative HPLC on a C18 column using a gradient of 30% to 100% acetonitrile:0.1% aqueous TFA to give Example 952 as the trifluoroacetic acid salt. 1H NMR (300 MHz, DMSO-D6) δ ppm 8.87-9.25 (m, 1 H), 8.61-8.87 (m, 2 H), 8.33 (d, J=6.0 Hz, 1 H), 8.04 (br s, 1H), 7.89 (s, 1H), 7.81 (s, 1H), 7.78 (s, 1H), 7.74 (s, 1H), 7.66-7.72 (m, 1 H), 7.51-7.58)m, 2 H), 7.18-7.28 (m, 3H), 5.51 (s, 2H), 5.20 (s, 2H), 3.80 (s, 2 H) MS (ESI(+)) m/e 527.2 (M+H)$^+$.

EXAMPLE 953

3-[4-(3-phenoxy-1-propynyl)-2-thienyl]-7-(1H-1,2,4-triazol-1-ylmethyl)-1,4-dihydroindeno[1,2-c]pyrazole

EXAMPLE 953A 3-(4-bromothien-2-yl)-7-(1H-1,2,4-triazol-1-ylmethyl)-1,4-dihydroindeno[1,2-c]pyrazole The desired product was prepared by substituting Example 873A for Example 56 and Example 125 for phenyl thiophene-2-carboxylate in Example 138. MS (ESI(+)) m/e 397.9, 399.9 (Br pattern) (M+H)$^+$.

EXAMPLE 953B

3-[4-(3-phenoxy-1-propynyl)-2-thienyl]-7-(1H-1,2,4-triazol-1-ylmethyl)-1,4-dihydroindeno[1,2-c]pyrazole The desired product was obtained by substituting Example 953A for 2-bromothiophene-4-carboxylate in Example 126. The product was purified by preparative HPLC on a Waters Symmetry C8 column (25 mm×100 mm, 7 μm particle size) using a gradient of 10% to 100% acetonitrile:0.1% aqueous TFA over 8 min (10 min run time) at a flow rate of 40 ml/min to give Example 953B as a trifluoroacetic acid salt. 1H NMR (500 MHz, DMSO-D6) δ ppm 3.75 (s, 2H) 5.03 (s, 2 H) 5.50 (s, 2 H) 6.98 (t, J=7.3 Hz, 1H) 7.04 (d, J=7.8 Hz, 2H) 7.24 (dd, J=7.8, 1.6 Hz, 1 H) 7.31-7.34 (m, 2 H) 7.42 (s, 1H) 7.49 (s, 1H) 7.55 (d, J=7.8 Hz, 1H) 7.81 (s, 1 H) 7.99 (s, 1 H) 8.69 (s, 1 H) MS (ESI(+)) m/e 450.0 (M+H)$^+$.

EXAMPLE 954

3-{4-[3-(2-methoxyethoxy)-1-propynyl]-2-thienyl}-7-(1H-1,2,4-triazol-1-1-ylmethyl)-1,4-dihydroindeno[1,2-c]pyrazole The desired product was obtained by substituting Example 953A for 2-bromothiophene-4-carboxylate and Example 127 for phenyl propargyl ether in Example 126. The product was purified by preparative HPLC on a Waters Symmetry C8 column (25 mm×100 mm, 7 μm particle size) using a gradient of 10% to 100% acetonitrile:0.1% aqueous TFA over 8 min (10 min run time) at a flow rate of 40 ml/min to give Example 954 as a trifluoroacetic acid salt. 1H NMR (500 MHz, DMSO-D6) δ ppm 3.26 (s, 3 H) 3.49 (dd, J=5.6, 3.7 Hz, 2 H) 3.63 (dd, J=5.5, 3.9 Hz, 2 H) 3.76 (s, 2 H) 4.38 (s, 2 H) 5.50 (s, 2 H) 7.24 (dd, J=8.0, 1.4 Hz, 1 H) 7.43 (s, 1 H) 7.50 (s, 1 H) 7.55 (d, J=7.8 Hz, 1 H) 7.79 (s, 1H) 8.00 (s, 1H) 8.70 (s, 1H) MS (ESI(+)) m/e 432.0 (M+H)$^+$.

EXAMPLE 955

6,7-bis(2-methoxyethoxy)-3-[5-(3-methoxy-1-propynyl]-3-thienyl]-1,4-dihydroindeno[1,2-c]pyrazole

EXAMPLE 955A 5,6-bis(2-methoxyethoxyindan-1-one

A mixture of Example 63 (500 mg, 3.04 mmol), 2-bromoethyl methyl ether (5.0 g, 36.0 mmol) and K2CO3 (5.0 g, 36.2 mmol) in DMF (18 mL) was heated to 100° C. for 3 h. The mixture was concentrated to dryness, taken up in EtOAc (80 mL) and MeOH (10 mL) and filtered. The filtrate was concentrated and purified by flash chromatography (1:1 EtOAc/hexanes) to give Example 955A (554 mg, 65%).

EXAMPLE 955B 3-(5-bromothien-3-yl)-6,7-bis(2-methoxyethoxy)-1,4-dihydroindeno[1,2-c]pyrazole The desired product was prepared by substituting Example 955A for Example 56 and Example 113 for phenyl thiophene-2-carboxylate in Example 138. MS (APCI(+)) m/e 465.5 (M+H)$^+$.

EXAMPLE 955C 6,7-bis(2-methoxyethoxy)-3-[5-(3-methoxy-1-propynyl]-3-thienyl]-1,4-dihydroindeno[1,2-c]pyrazole The desired product was obtained by substituting Example 955B for 2-bromothiophene-4-carboxylate and methyl propargyl ether for phenyl propargyl ether in Example 126. The product was purified by preparative HPLC on a Waters Symmetry C8 column (25 mm×100 mm, 7 μm particle size) using a gradient of 10% to 100% acetonitrile:0.1% aqueous TFA over 8 min (10 ml run time) at a flow rate of 40 ml/min to give Example 955C as a trifluoroacetic acid salt. 1H NMR (500 MHz, DMSO-D6) δ ppm 3.34 (app. s, 9 H) 3.67-3.71 (m, 6 H) 4.14-4.18 (m, 4 H) 4.39 (s, 2 H) 7.22 (s, 1H) 7.25 (s, 1H) 7.70 (d, J=1.2 Hz, 1H) 7.84 (d, J=1.5 Hz, 1H) MS (ESI(+)) m/e 455.1 (M+H)$^+$.

EXAMPLE 956

3-(5-{3-[2-(4-morpholinylethoxy]-1-propynyl}-3-thienyl)-7-(1H-1,2,4-triazol-1-ylmethyl)-1,4-dihydroindeno[1,2-c]pyrazole

EXAMPLE 956A

4-[2-(prop-2-ynyloxy)ethyl]morpholine

The desired product was prepared by substituting 4-(2-hydroxyethyl)-morpholine for 2-isopropoxyethanol in Example 613. MS (APCI) m/e 170.1 (M+H)$^+$.

EXAMPLE 956B 3-(5-{3-[2-(4-morpholinyl)ethoxy]-1-propynyl}-3-thienyl)-7-(1H-1,2,4-triazol-1-ylmethyl)-1,4-dihydroindeno[1,2-c]pyrazole The desired product was obtained by substituting Example 259 for 2-bromothiophene-4-carboxylate and Example 956A for phenyl propargyl alcohol in Example 126. The product was purified by preparative HPLC on a C18 column using a gradient of 30% to 100% acetonitrile:0.1% aqueous TFA to give Example 956B as the trifluoroacetic acid salt. 1H NMR (300 MHz, DMSO-D6) δ ppm 9.81 (br s, 1 H), 8.77 (br s, 1 H), 8.04 (br s, 1 H), 7.89 (s, 1 H), 7.72 (s, 1 H), 7.51-7.59 (m, 2 H), 7.25 (d, J=9.0 Hz, 1 H), 5.51 (s, 2 H), 4.56 (s, 2 H), 3.77-4.03 (m, 8 H), 3.37-3.51 (m, 4 H), 3.07-3.23 (m, 2H) MS (ESI(+)) m/e 487.1 (M+H)$^+$.

EXAMPLE 957

3-(5-{3-[2-(4-morpholinylethoxy]-1-propynyl}-3-thienyl)-6-(1 H-1,2,4-triazol-1-ylmethyl)-1,4-dihydroindeno[1,2-c]pyrazole The desired product was obtained by substituting Example 260 for 2-bromothiophene-4-carboxylate and Example 956A for phenyl propargyl alcohol in Example 126. The product was purified by preparative HPLC on a C18 column using a gradient of 30% to 100% acetonitrile:0.1% aqueous TFA to give Example 957 as the trifluoroacetic acid salt. 1H NMR (300 MHz, DMSO-D6) δ ppm 9.80 (br s, 1 H), 8.74 (br s, 1 H), 8.00-8.07 (m, 1 H), 7.89 (s, 1H), 7.71 (s, 1 H), 7.63 (d, J=9.0 Hz, 1H), 7.48 (s, 1H), 7.30 (d, J=9.0 Hz, 1H), 5.48 (s, 2 H), 4.56 (s, 2 H), 3.65-4.06 (m, 8 H), 3.38-3.62 (m, 4 H), 3.06-3.22 (m, 2 H) MS (ESI(+)) m/e 487.1 (M+H)$^+$.

EXAMPLE 958

3-(5-{3-[4-(2-methoxyethyl)phenoxy]-1-propynyl}-3-thienyl)-6-(1H-1,2,4-triazol-1-ylmethyl)-1,4-dihydroindeno[1,2-c]pyrazole

EXAMPLE 958A 1-(2-methoxyethyl)-4-(prop-2-ynyloxy)benzene

The desired product was prepared by substituting 4-(2-methoxyethyl)phenol for 4'-1-(1H-1,2,4-triazol-1-yl) phenol in Example 647. Rf 0.62 (5% EtOAc/CH2Cl2)

EXAMPLE 958B 3-(5-{3-[4-(2-methoxyethyl)phenoxy]-1-propynyl}-3-thienyl)-6-(1H-1,2,4-triazol-1-ylmethyl)-1,4-dihydroindeno[1,2-c]pyrazole The desired product was obtained by substituting Example 260 for 2-bromothiophene-4-carboxylate and Example 958A for phenyl propargyl alcohol in Example 126. The product was purified by preparative HPLC on a C18 column using a gradient of 30% to 100% acetonitrile:0.1% aqueous TFA to give Example 958B. 1H NMR (300 MHz, DMSO-D6) δ ppm 8.72 (br s, 1 H), 8.02 (br s, 1 H), 7.88 (s, 1H), 7.72 (s, 1H), 7.63 (br d, J=9 Hz, 1 H), 7.47 (s, 1H), 7.29 (d, J=6 Hz, 1 H), 7.20 (s, 1 H), 7.17 (s, 1 H), 6.97 (s, 1H), 6.95 (s, 1 H), 5.48 (s, 2 H), 5.07 (s, 2 H), 3.81 (s, 2 H), 3.50 (t, J=6 Hz, 2H), 3.23 (s, 3H), 2.75 (t, J=6 Hz, 2 H). MS (ESI(+)) m/e 530.0 (M+H)$^+$.

EXAMPLE 959

3-{4-[6-(1H-1,2,4-triazol-1-ylmethyl)-1,4-dihydroindeno[1,2-c]pyrazol-3-yl]-2-thienyl}-2-propynyl 4-morpholinecarboxylate

EXAMPLE 959A prop-2-ynyl morpholine-4-carboxylate

To a solution of morpholine (875 mg, 10 mmol) and triethylamine (2.53 g, 25 mmol) in CH2Cl2 (45 mL) at 0° C. was added dropwise a solution of propargyl chloroformate (1.19 g, 10 mmol) in CH2Cl2 (5 mL) over 20 min. The resulting mixture was stirred for 2 h at 0° C. then at rt overnight. The reaction was poured into H2O and the layers were separated. The organic layer was washed with brine, dried (MgSO4) and concentrated in vacuo. The residue was taken up in Et2O and filtered. The filtrate was concentrated to dryness to give Example 959A (1.14 g, 67%). MS (APCI) m/e 170.0 (M+H)$^+$.

EXAMPLE 959B

3-{4-[6-(1H-1,2,4-triazol-1-ylmethyl)-1,4-dihydroindeno[1,2-c]pyrazol-3-yl]-2-thienyl}-2-propynyl 4-morpholinecarboxylate The desired product was obtained by substituting Example 260 for 2-bromothiophene-4-carboxylate and Example 958A for phenyl propargyl alcohol in Example 126. The product was purified by preparative HPLC on a C18 column using a gradient of 30% to 100% acetonitrile:0.1% aqueous TFA to give Example 959B. 1H NMR (300 MHz, DMSO-D6) δ ppm 8.76 (br s, 1 H), 8.04 (br s, 1 H), 7.89 (s, 1 H), 7.70-7.84 (m, 2 H), 7.61-7.67 (m, 1 H), 7.48 (s, 1H), 7.30 (d, J=9 Hz, 1 H), 5.48 (s, 2 H), 5.01 (s, 2 H), 3.81 (s, 3 H), 3.73-3.79 (m, 1 H), 3.53-3.63 (m, 4 H). MS (CI) m/e 487.1 (M+H)$^+$.

EXAMPLE 960

3-[5-(3-methoxy-1-propynyl)-3-thienyl]-6-[2-(4-morpholinyl)ethoxy]-1,4-dihydroindeno[1,2-c]pyrazole The desired product was obtained by substituting Example 180 for 2-bromothiophene-4-carboxylate and methyl propargyl ether for phenyl propargyl ether in Example 126. 1H NMR (500 MHz, DMSO-D6) δ ppm 2.48-2.51 (m, 4 H) 2.72 (t, J=5.6 Hz, 2 H) 3.34 (s, 3 H) 3.58-3.60 (m, 4 H) 3.78 (s, 2 H) 4.14 (t, J=5.6 Hz, 2H) 4.38 (s, 2H) 6.93 (d, J=8.1 Hz, 1 H) 7.17 (s, 1 H) 7.54 (d, J=7.8 Hz, 1 H) 7.71 (d, J=1.6 Hz, 1 H) 7.86 (s, 1H) 12.95 (s, 1H) MS (ESI(+)) m/e 436.0 (M+H)$^+$.

EXAMPLE 961

3-{5-[3-(3-fluorophenoxy)-1-propynyl]-3-thienyl}-7-(1H-1,2,4-triazol-1-1-ylmethyl)-1,4-dihydroindeno[1,2-c]pyrazole

EXAMPLE 961A 1-fluoro-3-(prop-2-ynyloxy)benzene 3-fluorophenol (4.2 g, 32.5 mmol), propargyl bromide (6.5 g, 55.0 mmol) and K2CO3 (17 g) were combined in acetone (100 mL) and the mixture was heated to reflux overnight. After cooling to rt, the mixture was filtered and the filter cake was washed with Et2O. The filtrate was concentrated and the residue was purified by flash chromatography (10:1 pentane/Et2O) to give Example 961A (5.46 g, 97%).

EXAMPLE 961B

3-{5-[3-(3-fluorophenoxy)-1-propynyl]-3-thienyl}-7-(1H-1,2,4-triazol-1-ylmethyl)-1,4-dihydroindeno[1,2-c]pyrazole The desired product was obtained by substituting Example 259 for 2-bromothiophene-4-carboxylate and Example 961A for phenyl propargyl ether in Example 126. The product was purified by preparative HPLC on a Waters Symmetry C8 column (25 mm×100 mm, 7 μm particle size) using a gradient of 10% to 100% acetonitrile:0.1% aqueous TFA over 8 min (10 min run time) at a flow rate of 40 ml/min to give Example 961B as the trifluoroacetic acid salt. 1H NMR (500 MHz, DMSO-D6) δ ppm 3.80 (s, 2 H) 5.14 (s, 2 H) 5.50 (s, 2H) 6.83 (td, J=8.3, 2.3 Hz, 1 H) 6.90 (dd, J=8.3, 2.0 Hz, 1H) 6.94 (dt, J=11.2, 2.3 Hz, 1H) 7.24 (dd, J=8.1, 1.3 Hz, 1 H) 7.34-7.49 (m, 1 H) 7.53-7.55 (m, 2H) 7.73 (s, 1H) 7.88 (d, J=1.3 Hz, 1 H) 8.00 (s, 1 H) 8.71 (s, 1 H) MS (ESI(+)) m/e 468.0 (M+H)$^+$.

EXAMPLE 962

3-{5-[3-(2-fluorophenoxy)-1-propynyl]-3-thienyl}-7-(1H-1,2,4-triazol -1-ylmethyl)-1,4-dihydroindeno[1,2-c]pyrazole

EXAMPLE 962A 1-fluoro-2-(prop-2-ynyloxy)benzene

The desired product was prepared by substituting 2-fluorophenol for 3-fluorophenol in Example 961A.

EXAMPLE 962B

3-{5-[3-(2-fluorophenoxy)-1-propynyl]-3-thienyl}-7-(1H-1,2,4-triazol -1-ylmethyl)-1,4-dihydroindeno[1,2-c]pyrazole The desired product was obtained by substituting Example 259 for 2-bromothiophene-4-carboxylate and Example 962A for phenyl propargyl ether in Example 126. The product was purified by preparative HPLC on a Waters Symmetry C8 column (25 mm×100 mm, 7 μm particle size) using a gradient of 10% to 100% acetonitrile:0.1% aqueous TFA over 8 min (10 min run time) at a flow rate of 40 ml/min to give Example 962B as the trifluoroacetic acid salt. 1H NMR (500 MHz, DMSO-D6) δ ppm 3.80 (s, 2 H) 5.20 (s, 2 H) 5.50 (s, 2 H) 7.00-7.04 (m, 1H) 7.19 (t, J=7.8 Hz, 1H) 7.24 (dd, J=7.8, 0.9 Hz, 1H) 7.26 (ddd, J=11.7, 8.4, 1.5 Hz, 1 H) 7.32 (td, J=8.4, 1.5 Hz, 1 H) 7.53-7.55 (m, 2 H) 7.73 (s, 1 H) 7.88 (s, 1 H) 8.00 (s, 1 H) 8.70 (s, 1 H) MS (ESI(+)) m/e 468.1 (M+H)$^+$.

EXAMPLE 963

3-{5-[3-(4-fluorophenoxy)-1-propynyl]-3-thienyl}-7-(1H-1,2,3-triazol -1-ylmethyl)-1,4-dihydroindeno[1,2-c]pyrazole

EXAMPLE 963A 1-fluoro-4-(prop-2-ynyloxy)benzene

The desired product was prepared by substituting 4-fluorophenol for 3-fluorophenol in Example 961A.

EXAMPLE 963B 3-(5-bromothien-3-yl)-7-(1H-1,2,3-triazol-1-ylmethyl)-1,4-dihydroindeno[1,2-c]pyrazole The desired product was prepared by substituting Example 881A for Example 56 and Example 113 for phenyl thiophene-2-carboxylate in Example 138. MS (ESI(+)) m/e 397.9, 399.8 (M+H)$^+$.

EXAMPLE 963C

3-{5-[3-(4-fluorophenoxy)-1-propynyl]-3-thienyl}-7-(1H-1,2,3-triazol -1-ylmethyl)-1,4-dihydroindeno[1,2-c]pyrazole The desired product was obtained by substituting Example 963B for 2-bromothiophene-4-carboxylate and Example 963A for phenyl propargyl ether in Example 126. The product was purified by preparative HPLC on a Waters Symmetry C8 column (25 mm×100 mm, 7 µm particle size) using a gradient of 10% to 100% acetonitrile:0.1% aqueous TFA over 8 min (10 min run time) at a flow rate of 40 ml/min to give Example 963C as the trifluoroacetic acid salt. 1H NMR (500 MHz, DMSO-D6) δ ppm 3.80 (s, 2 H) 5.09 (s, 2 H) 5.71 (s, 2H) 7.07 (dd, J=9.0, 4.4 Hz, 2 H) 7.18 (t, J=8.7 Hz, 2 H) 7.25 (dd, J=8.0, 1.0 Hz, 1 H) 7.54-7.56 (m, 2 H) 7.71 (d, J=1.0 Hz, 1 H) 7.76 (s, 1 H) 7.87 (s, 1H) 8.22 (s, 1H) MS (ESI(+)) m/e 468.1 (M+H)$^+$.

EXAMPLE 964

3-{5-[3-(3-fluorophenoxy)-1-propynyl]-3-thienyl}-7-(1H-1,2,3-triazol -1-ylmethyl)-1,4-dihydroindeno[1,2-c]pyrazole The desired product was obtained by substituting Example 963B for 2-bromothiophene-4-carboxylate and Example 961A for phenyl propargyl ether in Example 126. The product was purified by preparative HPLC on a Waters Symmetry C8 column (25 mm×100 mm, 7 µm particle size) using a gradient of 10% to 100% acetonitrile:0.1% aqueous TFA over 8 min (10 min run time) at a flow rate of 40 ml/min to give Example 964. 1H NMR (500 MHz, DMSO-D6) δ ppm 3.80 (s, 2 H) 5.14 (s, 2 H) 5.71 (s, 2 H) 6.83 (td, J=8.3, 2.4 Hz, 1 H) 6.90 (dd, J=8.3, 2.0 Hz, 1 H) 6.94 (dt, J=11.2, 2.4 Hz, 1 H) 7.25 (dd, J=7.8, 1.3 Hz, 1 H) 7.35-7.39 (m, 1 H) 7.54-7.56 (m, 2 H) 7.73 (s, 1 H) 7.76 (s, 1 H) 7.88 (s, 1H) 8.22 (s, 1H) MS (ESI(+)) m/e 468.1 (M+H)$^+$.

EXAMPLE 965

3-{5-[3-(2-fluorophenoxy)-1-propynyl]-3-thienyl}-7-(1H-1,2,3-triazol-1-ylmethyl-1,4-dihydroindeno[1,2-c]pyrazole The desired product was obtained by substituting Example 963B for 2-bromothiophene-4-carboxylate and Example 962A for phenyl propargyl ether in Example 126. The product was purified by preparative HPLC on a Waters Symmetry C8 column (25 mm×100 mm, 7 µm particle size) using a gradient of 10% to 100% acetonitrile:0.1% aqueous TFA over 8 min (10 min run time) at a flow rate of 40 ml/min to give Example 965 as the trifluoroacetic acid salt. 1H NMR (500 MHz, DMSO-D6) δ ppm 3.80 (s, 2 H) 5.20 (s, 2 H) 5.71 (s, 2 H) 7.00-7.04 (m, 1 H) 7.19 (t, J=8.0 Hz, 1 H) 7.24-7.28 (m, 2 H) 7.32 (td, J=8.4, 1.5 Hz, 1 H) 7.54-7.56 (m, 2 H) 7.73 (s, 1 H) 7.76 (s, 1 H) 7.88 (d, J=1.5 Hz, 1 H) 8.22 (s, 1 H) MS (ESI(+)) m/e 468.1 (M+H)$^+$.

EXAMPLE 966

3-{5-[3-(3-fluorophenoxy)-1-propynyl]-3-thienyl}-6-[(4-methyl-1-piperazinyl)methyl]-1,4-dihydroindeno[1,2-c]pyrazole The desired product was obtained by substituting Example 148 for 2-bromothiophene-4-carboxylate and Example 961A for phenyl propargyl ether in Example 126. The product was purified by preparative HPLC on a Waters Symmetry C8 column (25 mm×100 mm, 7 µm particle size) using a gradient of 10% to 100% acetonitrile:0.1% aqueous TFA over 8 min (10 min run time) at a flow rate of 40 ml/min to give Example 966 as the trifluoroacetic acid salt. 1H NMR (500 MHz, DMSO-D6) δ ppm 2.80 (s, 3 H) 2.96-3.52 (m, 8 H) 3.83 (s, 2 H) 3.94 (s, 2 H) 5.15 (s, 2 H) 6.84 (td, J=8.2, 1.7 Hz, 1 H) 6.91 (dd, J=8.1, 1.9 Hz, 1 H) 6.93-6.96 (m, 1 H) 7.35-7.39 (m, 2 H) 7.58 (s, 1 H) 7.67 (d, J=7.8 Hz, 1H) 7.75 (s, 1H) 7.90 (s, 1H) MS (ESI(+)) m/e 499.1 (M+H)$^+$.

EXAMPLE 967

3-{5-[3-(2-fluorophenoxy)-1-propynyl]-3-thienyl}-6-[(4-methyl-1-piperazinyl)methyl]-1,4-dihydroindeno[1,2-c]pyrazole The desired product was obtained by substituting Example 148 for 2-bromothiophene-4-carboxylate and Example 962A for phenyl propargyl ether in Example 126. The product was purified by preparative HPLC on a Waters Symmetry C8 column (25 mm×100 mm, 7 µm particle size) using a gradient of 10% to 100% acetonitrile:0.1% aqueous TFA over 8 min (10 min run time) at a flow rate of 40 ml/min to give Example 967 as the trifluoroacetic acid salt. 1H NMR (500 MHz, DMSO-D6) δ ppm 2.80 (s, 3H) 2.97-3.50 (m, 8H) 3.83 (s, 2H) 3.92 (s, 2H) 5.20 (s, 2H) 7.00-7.04 (m, 1H) 7.20 (t, J=7.8 Hz, 1H) 7.26 (ddd, J=11.7, 8.1, 1.4 Hz, 1H) 7.32 (td, J=8.4, 1.3 Hz, 1H) 7.38 (d, J=7.8 Hz, 1H) 7.58 (s, 1H) 7.66 (d, J=7.8 Hz, 1H) 7.75 (d, J=1.3 Hz, 1H) 7.90 (d, J=1.3 Hz, 1H) MS (ESI(+)) m/e 499.1 (M+H)$^+$.

EXAMPLE 968

6-[(4-methyl-1-piperazinyl)methyl]-3-{5-[(trimethylsilyl)ethynyl]-3-thienyl}-1,4-dihydroindeno[1,2-c]pyrazole The desired product was obtained by substituting Example 148 for 2-bromothiophene-4-carboxylate and trimethylsilylacetylene for phenyl propargyl ether in Example 126. The product was purified by preparative HPLC on a Waters Symmetry C8 column (25 mm×100 mm, 7 µm particle size) using a gradient of 10% to 100% acetonitrile:0.1% aqueous TFA over 8 min (10 min run time) at a flow rate of 40 ml/min to give Example 968 as a trifluoroacetic acid salt. 1H NMR (500 MHz, DMSO-D6) δ ppm 0.00 (s, 9 H) 2.54 (s, 3H) 2.70-3.30 (m, 8H) 3.58 (s, 2 H) 3.68 (s, 2 H) 7.13 (d, J=7.8 Hz, 1 H) 7.32 (s, 1H) 7.41 (d, J=7.8 Hz, 1H) 7.48 (d, J=1.3 Hz, 1H) 7.62 (d, J=1.3 Hz, 1 H) MS (ESI(+)) m/e 447.1 (M+H)$^+$.

EXAMPLE 969

3-(5-ethynyl-3-thienyl)-6-[(4-methyl-1-piperazinyl)methyl]-1,4-dihydroindeno[1,2-c]pyrazole A mixture Example 968 (130 mg, 0.29 mmol) and TBAF (250 mg, 0.96 mmol) in THF (3 mL) was shaken at rt for 0.5 h. The reaction was concentrated in vacuo and the product was purified by flash chromatography (9:1 EtOAc/MeOH) to give the 77 mg (71%) of the desired product. 1H NMR (500 MHz, DMSO-D6) δ ppm 2.00 (s, 1H), 2.18 (m, 4H), 2.38 (m, 4H), 3.48 (s, 2H), 3.79 (s, 2H), 7.26 (d, J=7.0 Hz, 1H), 7.48 (s, 1H), 7.58 (d, J=7.0 Hz, 1H), 7.75 (s, 1H) 7.85 (s, 1H), 13.05 (br s, 1H) MS (ESI(+)) m/e 375.0 (M+H)$^+$.

EXAMPLE 970

3-[5-(3-methoxy-1-propynyl)-3-thienyl]-6-[(4-methyl-1-piperazinyl)methyl]indeno[1,2-c]pyrazol-4(1H)-one

EXAMPLE 970A 3-(5-bromothien-3-yl)-6-[(4-methylpiperazin-1-yl)methyl]indeno[1,2-c]pyrazol-4(1H)-one Example 148 (800 mg, 1.87 mmol) and Cs2CO3 (2 g, 6.14 mmol) were taken up in DMF (180 mL), and a stream of air was bubbled through the mixture as it was heated to 90° C. overnight. After cooling to rt, the mixture was filtered and the filtrate was concentrated to dryness. The residue was purified by flash chromatography (EtOAc/MeOH/NH4OH, 90:9:1) to give Example 970A (503 mg, 60%). MS (ESI(+)) m/e 444 (M+H)$^+$.

EXAMPLE 970B

3-[5-(3-methoxy-1-propynyl)-3-thienyl]-6-[(4-methyl-1-piperazinyl)methyl]indeno[1,2-c]pyrazol-4(1H)-one The desired product was prepared by substituting Example 970A for Example 260 and methyl propargyl ether for phenyl propargyl sulfide in Example 657. The product was purified by preparative HPLC on a Waters Symmetry C8 column (25 mm×100 mm, 7 µm particle size) using a gradient of 10% to 100% acetonitrile:0.1% aqueous TFA over 8 min (10 min run time) at a flow rate of 40 ml/min to give Example 970B as a trifluoroacetic acid salt. 1H NMR (500 MHz, DMSO-D6) δ ppm 2.77 (s, 3H) 2.88-3.14 (m, 8H) 3.33 (s, 3H) 3.68 (s, 2H) 4.38 (s, 2H) 7.49-7.54 (m, 2H) 7.58 (s, 1H) 7.96 (s, 1H) 8.35 (s, 1H) 13.74 (s, 1H) MS (ESI(+)) m/e 433.1 (M+H)$^+$.

EXAMPLE 971

3-(5-bromo-3-thienyl)-6-(2-methoxyethoxy)-1,4-dihydroindeno[1,2-c]pyrazole

EXAMPLE 971A 5-(2-methoxyethoxy)indan-1-one

A mixture of 5-hydroxy-1-indanone (0.87 g, 5.88 mmol), 2-bromoethyl methyl ether (1.8 g, 12.9 mmol) and K2CO3 (2.0 g, 14.5 mmol) in DMF (20 mL) was heated to 100° C. for 2 h. The solution was decanted and concentrated to dryness. The residue was purified by flash chromatography (gradient from 10% to 90% EtOAc in hexanes) to give Example 971A (1.02 g, 84%). MS (ESI(+)) m/e 207.1 (M+H)$^+$.

EXAMPLE 971B 3-(5-bromo-3-thienyl)-6-(2-methoxyethoxy)-1,4-dihydroindeno[1,2-c]pyrazole The desired product was prepared by substituting Example 971A for Example 56 and Example 113 for phenyl thiophene-2-carboxylate in Example 138. 1H NMR (300 MHz, DMSO-D6) δ ppm 3.33 (s, 3 H) 3.67-3.70 (m, 2H) 3.76 (s, 2H) 4.13-4.16 (m, 2H) 6.94 (dd, J=8.5, 2.0 Hz, 1H) 7.17 (d, J=2.0 Hz, 1 H) 7.53 (d, J=8.5 Hz, 1 H) 7.61 (s, 1H) 7.80 (s, 1H) 12.95 (s, 1 H) MS (ESI(+)) m/e 390.9, 392.8 (Br pattern) (M+H)$^+$.

EXAMPLE 972

N-[3-(4-{7-[(4-methyl-1-piperazinyl)methyl]-1,4-dihydroindeno[1,2-c]pyrazol-3-yl}-2-thienyl)-2-propynyl]-2-pyridinecarboxamide

EXAMPLE 972A

N-prop-2-ynylpyridine-2-carboxamide

A solution of propargyl amine (1.00 g, 18.2 mmol), nicotinoyl chloride hydrochloride (1.67 g, 9.08 mmol) and triethylamine (1.3 mL, 9.3 mmol) was stirred at rt for 48 h. The mixture was partitioned between H2O and THF/Et2O. The aqueous phase was treated with NaHCO3 solution and extracted with Et2O, EtOAc and CH2Cl2. The combined EtOAc and CH2Cl2 extracts were dried (MgSO4) and concentrated to give Example 972A as a brown, crystalline solid (0.37 g, 26%). MS (ESI(+)) m/e 161.0 (M+H)$^+$.

EXAMPLE 972B

N-[3-(4-{7-[(4-methyl-1piperazinyl)methyl]-1,4-dihydroindeno[1,2-c]pyrazol-3-yl}-2-thienyl)-2-propynyl]-2-pyridinecarboxamide The desired product was prepared by substituting Example 149 for Example 260 and Example 972A for phenyl propargyl sulfide in Example 657. The product was purified by preparative HPLC on a Waters Symmetry C8 column (25 mm×100 mm, 7 µm particle size) using a gradient of 10% to 100% acetonitrile:0.1% aqueous TFA over 8 min (10 min run time) at a flow rate of 40 ml/min, and the purest fraction was taken up in aqueous NaHCO3 solution and extracted with Et2O/THF and CH2Cl2 to give Example 972B as the free base (30 mg, 17%). 1H NMR (300 MHz, DMSO-D6) δ ppm 2.15 (s, 3H) 2.25-2.48 (m, 8H) 3.52 (s, 2H) 3.78 (s, 2H) 4.42 (d, J=5.4 Hz, 2H) 7.20 (d, J=7.8 Hz, 1H) 7.48 (d, J=7.5 Hz, 1H) 7.54 (dd, J=7.8, 4.8 Hz, 1H) 7.58 (s, 1H) 7.68 (s, 1H) 7.83 (s, 1H) 8.24 (dt, J=8.0, 1.9 Hz, 1H) 8.74 (dd, J=4.9, 1.5 Hz, 1H) 9.05 (d, J=2.0 Hz, 1H) 9.28 (t, J=5.4 Hz, 1H) 13.13 (s, 1H) MS (ESI(+)) m/e 509.1 (M+H)$^+$.

EXAMPLE 973

3-{5-[3-(phenylsulfinyl)-1-propynyl]-3-thienyl}-7-(1H-1,2,4-triazol-1-ylmethyl)-1,4-dihydroindeno[1,2-c]pyrazole A solution of Example 719 (60 mg, 0.13 mmol) in THF (3 mL) and MeOH (3 mL) at 0° C. was treated with a solution of Oxone® (30 mg, 4.5% active O, 0.083 mmol) in H2O (3 mL), warmed to rt and stirred for 3 h. An additional 20 mg of Oxone® (0.056 mmol) in H2O (1 mL) was added dropwise and the reaction was stirred for another 2 h. The mixture was poured into dilute NaHCO3 solution and extracted with THF/Et2O (2:1) and CH2Cl2. The organic layers were dried (MgSO4) and concentrated, and the residue was crystallized from DMSO/MeOH. The crude product was dissolved in CH2Cl2/MeOH, concentrated to dryness, and triturated with Et2O to give Example 973 (12 mg, 16%). 1H NMR (300 MHz, DMSO-D6) δ ppm 3.80 (s, 2H) 4.19 (d, J=16.5 Hz, 1H) 4.35 (d, J=16.5 Hz, 1H) 5.50 (s, 2H) 7.24 (dd, J=7.8, 1.0 Hz, 1H) 7.54-7.67 (m, 6H) 7.72-7.78 (m, 2H) 7.84 (s, 1H) 8.00 (s, 1H) 8.71 (s, 1H) 13.19 (s, 1H) MS (ESI(+)) m/e 482.0 (M+H)$^+$.

EXAMPLE 974

N-(3-chlorophenyl)-N-(3-{4-[6-(1H-1,2,4-triazol-1-ylmethyl)-1,4-dihydroindeno[1,2-c]pyrazol-3-yl]-2-thienyl}-2-propynyl)amine

EXAMPLE 974A

N-(3-chlorophenyl)-N-prop-2-ynylamine

A solution of 3-chloroaniline (1.0 g, 7.8 mmol), propargyl bromide (0.95 mL, 8.6 mmol) and diisopropylethylamine (1.5 mL, 8.6 mmol) in toluene (23 mL) was heated to 90° C. for 14 h. The solution was cooled, diluted with ethyl acetate and washed with water. The organic phase was concentrated onto silica gel and purified by flash chromatography eluting with hexanes/ethyl acetate (20:1) to give Example 974A as an oil (0.71 g, 55%).

EXAMPLE 974B

N-(3-chlorophenyl)-N-(3-{4-[6-(1H-1,2,4-triazol-1-ylmethyl)-1,4-dihydroindeno[1,2-c]pyrazol-3-yl]-2-thienyl}-2-propynyl)amine The desired product was obtained by substituting Example 974A for phenyl propargyl ether and Example 260 for 2-bromothiophene-4-carboxylate in Example 126. The product was purified by preparative HPLC on a Waters Symmetry C8 column (25 mm×100 mm, 7 μm particle size) using a gradient of 10% to 100% acetonitrile:0.1% aqueous TFA over 8 min (10 min run time) at a flow rate of 40 ml/min to give Example 974B as the trifluoroacetic acid salt. 1H NMR (300 MHz, DMSO-D6) δ ppm 3.79 (s, 2H) 4.22 (s, 2H) 5.48 (s, 2H) 6.62-6.67 (m, 2H) 6.72 (t, J=2.2 Hz, 1H) 7.15 (t, J=8.0 Hz, 1H) 7.29 (dd, J=7.8, 0.9 Hz, 1H) 7.48 (s, 1H) 7.62 (d, J=7.8 Hz, 1H) 7.62 (d,J=1.4 Hz, 1H) 7.81 (d, J=1.4 Hz, 1H) 8.01 (s, 1H) 8.71 (s, 1H).

EXAMPLE 975

1-{4-[(3-{4-[6-(1H-1,2,4-triazol-1-ylmethyl)-1,4-dihydroindeno[1,2-c]pyrazol-3yl]-2-thienyl}-2-propynyl)amino]phenyl}ethanone

EXAMPLE 975A

1-[4-(prop-2-ynylamino)phenyl]ethanone

The desired product was prepared by substituting 4'-aminoacetophenone for 3-chloroaniline in Example 974A. MS (ESI(+)) m/e 174.0 (M+H)$^+$.

EXAMPLE 975B

1-{4-[(3-{4-[6-(1H-1,2,4-triazol-1-ylmethyl)-1,4-dihydroindeno[1,2-c]pyrazol-3-yl]-2-thienyl}-2-propynyl)amino]phenyl}ethanone The desired product was obtained by substituting Example 975A for phenyl propargyl ether and Example 260 for 2-bromothiophene-4-carboxylate in Example 126. The product was purified by preparative HPLC on a Waters Symmetry C8 column (25 mm×100 mm, 7 μm particle size) using a gradient of 10% to 100% acetonitrile:0.1% aqueous TFA over 8 min (10 min run time) at a flow rate of 40 ml/min to give Example 975B as the trifluoroacetic acid salt. 1H NMR (300 MHz, DMSO-D6) δ ppm 2.43 (s, 3H) 3.79 (s, 2H) 4.30 (s, 2H) 5.48 (s, 2H) 6.74 (d, J=8.8 Hz, 2H) 7.03 (s, 1H) 7.29 (d, J=7.8 Hz, 1H) 7.47 (s, 1H) 7.61-7.64 (m, 2H) 7.78-7.81 (m, 3H) 8.02 (s, 1H) 8.73 (s, 1H) MS (CI) m/e 491.1 (M+H)$^+$.

EXAMPLE 976

N-(3-methylphenyl)-N-(3-{4-[6-(1H-1,2,4-triazol-1-ylmethyl)-1,4-dihydroindeno[1,2-c]pyrazol-3-yl]-2-thienyl}-2-propynyl)amine

EXAMPLE 976A

N-(3-methylphenyl)-N-prop-2-ynylamine

The desired product was prepared by substituting m-toluidine for 3-chloroaniline in Example 974A. MS (CI) m/e 146.0 (M+H)$^+$.

EXAMPLE 976B

N-(3-methylphenyl)-N-(3-{4-[6-(1H-1,2,4-triazol-1-ylmethyl)-1,4-dihydroindeno[1,2-c]pyrazol-3-yl]-2-thienyl}-2-propynyl)amine The desired product was obtained by substituting Example 976A for phenyl propargyl ether and Example 260 for 2-bromothiophene-4-carboxylate in Example 126. The product was purified by preparative HPLC on a Waters Symmetry C8 column (25 mm×100 mm, 7 μm particle size) using a gradient of 10% to 100% acetonitrile:0.1% aqueous TFA over 8 min (10 min run time) at a flow rate of 40 ml/min to give Example 976B as the trifluoroacetic acid salt. 1H NMR (300 MHz, DMSO-D6) δ ppm 2.22 (s, 3H) 3.79 (s, 2H) 4.17 (s, 2H) 5.48 (s, 2H) 6.44-6.52 (m, 3H) 7.02 (t, J=7.8 Hz, 1H) 7.29 (d, J=7.8 Hz, 1H) 7.47 (s, 1H) 7.61-7.64 (m, 2H) 7.79 (d, J=1.4 Hz, 1H) 8.01 (s, 1H) 8.71 (s, 1H) MS (CI) m/e 463.1 (M+H)$^+$.

EXAMPLE 977 ethyl {4-[(3-{4-[6-(1H-1,2,4-triazol-1-ylmethyl)-1,4-dihydroindeno[1,2-c]pyrazol-3-yl]-2-thienyl}-2-propynyl)amino]phenyl}acetate

EXAMPLE 977A ethyl[4-(prop-2-ynylamino)phenyl]acetate

The desired product was prepared by substituting (4-Amino-phenyl)-acetic acid ethyl ester for 3-chloroaniline in Example 974A. MS (ESI(+)) m/e 218.1 (M+H)$^+$.

EXAMPLE 977B ethyl {4-[(3-{4-[6-(1H-1,2,4-triazol-1-ylmethyl)-1,4-dihydroindeno[1,2-c]pyrazol-3-yl]-2-thienyl}-2-propynyl)amino]phenyl}acetate The desired product was obtained by substituting Example 977A for phenyl propargyl ether and Example 260 for 2-bromothiophene-4-carboxylate in Example 126. The product was purified by preparative HPLC on a Waters Symmetry C8 column (25 mm×100 mm, 7 μm particle size) using a gradient of 10% to 100% acetonitrile:0.1% aqueous TFA over 8 min (10 min run time) at a flow rate of 40 ml/min to give Example 977B as the trifluoroacetic acid salt. 1H NMR (300 MHz, DMSO-D6) δ ppm 1.17 (t, J=7.1 Hz, 3H) 3.48 (s, 2H) 3.79 (s, 2H) 4.05 (q, J=7.1 Hz, 2H) 4.17 (s, 2H) 5.47 (s, 2H) 6.65 (d, J=8.5 Hz, 2H) 7.03 (d, J=8.5 Hz, 2H) 7.29 (d, J=8.1 Hz, 1H) 7.47 (s, 1H) 7.62 (m, 2H) 7.79 (d, J=1.0 Hz, 1H) 8.00 (s, 1H) 8.70 (s, 1H) MS (CI) m/e 535.2 (M+H)$^+$.

EXAMPLE 978

N-(3-{4-[6-(1H-1,2,4-triazol-1-ylmethyl)-1,4-dihydroindeno[1,2-c]pyrazol-3-yl]-2-thienyl}-2-propynyl)-N-[4-(trifluoromethyl)phenyl]amine

EXAMPLE 978A

N-prop-2-ynyl-N-[4-(trifluoromethyl)phenyl]amine

The desired product was prepared by substituting 4-(trifluoromethyl)aniline for 3-chloroaniline in Example 974A. MS (CI) m/e 199.9 (M+H)$^+$.

EXAMPLE 978B

N-(3-{4-[6-(1H-1,2,4-triazol-1-ylmethyl-1,4-dihydroindeno[1,2-c]pyrazol-3-yl]-2-thienyl}-2-propynyl)-N-[4-(trifluoromethyl)phenyl]amine The desired product was prepared by substituting Example 978A for phenyl propargyl ether and Example 260 for 2-bromothiophene-4-carboxylate in Example 126. The product was purified by preparative HPLC on a C18 column using a gradient of 30% to 100% acetonitrile:0.1% aqueous TFA to give Example 978B as the trifluoroacetic acid salt. 1H NMR (300 MHz, DMSO-D6) δ ppm 3.79 (s, 2H) 4.28 (s, 2H) 5.47 (s, 2H) 6.81 (d, J=8.5 Hz, 2H) 6.88 (s, 1H) 7.29 (dd, J=7.6, 1.5 Hz, 1H) 7.45-7.47 (m, 3H) 7.61-7.63 (m, 2H) 7.81 (d, J=1.4 Hz, 1H) 8.00 (s, 1H) 8.70 (s, 1H) MS (CI) m/e 517.0 (M+H)$^+$.

EXAMPLE 979

3-[5-(1-benzothien-2-ylethynyl)-3-thienyl]-7-(1H-1,2,4-triazol-1-ylmethyl)-1,4-dihydroindeno[1,2-c]pyrazole

EXAMPLE 979A 2-iodo-1-benzothiophene

The desired product was prepared by substituting benzothiophene for benzofuran in Example 651. MS (CI) m/e 259.9 (M+H)$^+$.

EXAMPLE 979B (1-benzothien-2-ylethynyl)(trimethyl)silane

The desired product was prepared by substituting Example 979A for Example 651 in Example 652. MS (CI) m/e 230.9 (M+H)$^+$.

EXAMPLE 979C 2-ethynyl-1-benzothiophene

The desired product was prepared by substituting Example 979B for Example 652 in Example 653.

EXAMPLE 979D

3-[5-(1-benzothien-2-ylethynyl)-3-thienyl]-7-(1H-1,2,4-triazol-1-ylmethyl)-1,4-dihydroindeno[1,2-c]pyrazole The desired product was obtained by substituting Example 979C for phenyl propargyl ether and Example 259 for 2-bromothiophene-4-carboxylate in Example 126. The product was purified by preparative HPLC on a Waters Symmetry C8 column (25 mm×100 mm, 7 μm particle size) using a gradient of 10% to 100% acetonitrile:10 mM aq. NH4OAc over 8 min (10 min run time) at a flow rate of 40 ml/min to give Example 979D. 1H NMR (300 MHz, DMSO-D6) δ ppm 3.85 (s, 2H) 5.49 (s, 2H) 7.30 (d, J=6.8 Hz, 1H) 7.43-7.50 (m, 3H) 7.64 (d, J=6.1 Hz, 1H) 7.85 (s, 1H) 7.88-7.92 (m, 2H) 7.99-8.03 (m, 3H) 8.70 (s, 1H) 13.14-13.32 (br s, 1H) MS (CI) m/e 517.0 (M+H)$^+$.

EXAMPLE 980

6-(2-methoxyethoxy)-3-[5-(3-phenoxy-1-propenyl)-3-thienyl]-1,4-dihydroindeno[1,2-c]pyrazole The desired product was obtained by substituting Example 971B for 2-bromothiophene-4-carboxylate in Example 126. 1H NMR (500 MHz, DMSO-D6) δ ppm 3.31 (s, 3H) 3.66-3.68 (m, 2H) 3.75 (s, 2H) 4.13 (dd, J=5.5, 3.9 Hz, 2H) 5.09 (s, 2H) 6.92 (dd, J=8.4, 2.5 Hz, 1H) 6.99 (t, J=7.5 Hz, 1H) 7.04 (d, J=7.8 Hz, 2H) 7.15-7.16 (m, 1H) 7.31-7.35 (m, 2H) 7.52 (d, J=8.1 Hz, 1H) 7.69 (s, 1H) 7.83 (s, 1H) MS (ESI(+)) m/e 443.1 (M+H)$^+$.

EXAMPLE 981

3-[5-(1-heptynyl)-3-thienyl]-6-[(4-methyl-1-piperazinyl)methyl]indeno[1,2-c]pyrazol-4(1H)-one The desired product was prepared by substituting Example 970A for Example 260 and 1-heptyne for phenyl propargyl sulfide in Example 657. 1H NMR (500 MHz, DMSO-D6) δ ppm 0.90 (t, J=7.2 Hz, 3H) 1.30-1.43 (m, 4H) 1.54-1.60 (m, 2H) 2.15 (s, 3H) 2.25-2.45 (m, 8H) 2.48-2.51 (m, 2H) 3.49 (s, 2H) 7.44-7.48 (m, 2H) 7.50 (s, 1H) 7.84 (d, J=1.2 Hz, 1H) 8.26 (d, J=1.2 Hz, 1H) 13.66 (s, 1H) MS (ESI(+)) m/e 459.1 (M+H)$^+$.

EXAMPLE 982

3,4,5-trimethoxy-N-[3-(4-{7-[(4-methyl-1-piperazinyl)methyl]-1,4-dihydroindeno[1,2-c]pyrazol-3-yl}-2-thienyl)-2-propynyl]benzamide

EXAMPLE 982A 3,4,5-trimethoxy-N-prop-2-ynylbenzamide

A solution of propargyl amine (1.00 g, 17.8 mmol) and 3,4,5-trimethoxybenzoyl chloride (2.08 g, 8.9 mmol) in THF (40 mL) was stirred at rt for 19 h. The mixture was partitioned between 1N HCl and THF-Et2O. The extracts were dried (MgSO4) and concentrated to dryness. The residue was recrystallized from THF/Et2O to give Example 982A (1.66 g, 75%). MS (ESI(+)) m/e 250.0 (M+H)$^+$.

EXAMPLE 982B 3,4,5-trimethoxy-N-[3-(4-{7-[(4-methyl-1-piperazinyl)methyl]-1,4-dihydroindeno[1,2-c]pyrazol-3-yl}-2-thienyl)-2-propynyl]benzamide The desired product was prepared by substituting Example 982A for phenyl propargyl ether and Example 149 for 2-bromothiophene-4-carboxylate in Example 126. The product was purified by preparative HPLC on a C18 column using a gradient of 30% to 100% acetonitrile:0.1% aqueous TFA to give the product as the trifluoroacetic acid salt. The salt was partitioned between NaHCO3 solution and THF/Et2O, extracting the aqueous phase further with EtOAc, then dried (MgSO4) and concentrated to give Example 982B as the free base. 1H NMR (300 MHz, DMSO-D6) δ ppm 2.15 (s, 3H) 2.25-2.46 (m, 8H) 3.52 (s, 2H) 3.71 (s, 3H) 3.78 (s, 2H) 3.84 (s, 6H) 4.40 (d, J=5.4 Hz, 2H) 7.20 (d, J=8.5 Hz, 1H) 7.25 (s, 2H) 7.48 (d, J=7.8 Hz, 1H) 7.58 (s, 1H) 7.67 (s, 1H) 7.83 (s, 1H) 9.02 (t, J=5.4 Hz, 1H) 13.11 (s, 1H) MS (ESI(+)) m/e 598.2 (M+H)$^+$.

EXAMPLE 983

2-methoxy-N-[3-(4-{7-[(4-methyl-1-piperazinyl)methyl]-1,4-dihydroindeno[1,2-c]pyrazol-3-yl}-2-thienyl)-2-propynyl]acetamide

EXAMPLE 983A 2-methoxy-N-prop-2-ynylacetamide

The desired product was prepared by substituting methoxyacetyl chloride for 3,4,5-trimethoxybenzoyl chloride in Example 982A. MS (ESI(+)) m/e 128.0 (M+H)$^+$.

EXAMPLE 983B 2-methoxy-N-[3-(4-{7-[(4-methyl-1-piperazinyl)methyl]-1,4-dihydroindeno[1,2-c]pyrazol-3-yl}-2-thienyl)-2-propynyl]acetamide The desired product was prepared by substituting Example 983A for phenyl propargyl ether and Example 149 for 2-bromothiophene-4-carboxylate in Example 126. The product was purified by preparative HPLC on a C18 column using a gradient of 30% to 100% acetonitrile:0.1% aqueous TFA, and the resulting product was further purified by triturating with EtOAc, followed by recrystallization from CH2Cl2/EtOAc/Hexanes to give Example 983B (13.8 mg, 8.2%). 1H NMR (300 MHz, DMSO-D6) δ ppm 2.15 (s, 3H) 2.26-2.45 (m, 8H) 3.32 (s, 3H) 3.52 (s, 2H) 3.78 (s, 2H) 3.87 (s, 2H) 4.19 (d, J=5.8 Hz, 2H) 7.20 (dd, J=7.8, 1.4 Hz, 1H) 7.48 (d, J=7.8 Hz, 1H) 7.58 (s, 1H) 7.65 (s, 1H) 7.82 (s, 1H) 8.39 (t, J=5.8 Hz, 1H) 13.13 (s, 1H) MS (ESI(+)) m/e 476.2 (M+H)$^+$.

EXAMPLE 984

3-(5-ethynyl-3-thienyl)-6-(2-methoxyethoxy)-1,4-dihydroindeno[1,2-c]pyrazole

EXAMPLE 984A 6-(2-methoxyethoxy)-3-{5-[(trimethylsilyl)ethynyl]thien-3-yl}-1,4-dihydroindeno[1,2-c]pyrazole The desired product was obtained by substituting Example 971B for 2-bromothiophene-4-carboxylate and trimethylsilyl acetylene for phenyl propargyl ether in Example 126.

EXAMPLE 984B 3-(5-ethynyl-3-thienyl)-6-(2-methoxyethoxy)-1,4-dihydroindeno[1,2-c]pyrazole The desired product was prepared by substituting Example 984A for Example 968 in Example 969. 1H NMR (500 MHz, DMSO-D6) δ ppm 3.33 (s, 3H) 3.67-3.69 (m, 2H) 3.77 (s, 2H) 4.13-4.15 (m, 2H) 4.64 (s, 1H) 6.94 (dd, J=8.4, 2.2 Hz, 1H) 7.17 (d, J=2.2 Hz, 1H) 7.53 (d, J=8.4 Hz, 1H) 7.73 (d, J=1.3 Hz, 1H) 7.83 (d, J=1.3 Hz, 1H) MS (ESI(+)) m/e 337.0 (M+H)$^+$.

EXAMPLE 985

3-[5-(3-isopropoxy-1-propynyl)-3-thienyl]-7-(1H-1,2,3-triazol-1-ylmethyl)-1,4-dihydroindeno[1,2-c]pyrazole

EXAMPLE 985A 3-isopropoxyprop-1-yne

The desired product was prepared by substituting isopropanol for 2-isopropoxyethanol and Et2O for THF in Example 613.

EXAMPLE 985B

3-[5-(3-isopropoxy-1-propynyl)-3-thienyl]-7-(1H-1,2,3-triazol-1-ylmethyl)-1,4-dihydroindeno[1,2-c]pyrazole The desired product was obtained by substituting Example 985A for phenyl propargyl ether and Example 963B for 2-bromothiophene-4-carboxylate in Example 126. The product was purified by preparative HPLC on a Waters Symmetry C8 column (25 mm×100 mm, 7 μm particle size) using a gradient of 10% to 100% acetonitrile:0.1% aqueous TFA over 8 min (10 min run time) at a flow rate of 40 ml/min to give Example 985B as the trifluoroacetic acid salt. 1H NMR (500 MHz, DMSO-D6) δ ppm 1.14 (d, J=5.9 Hz, 6H) 3.74-3.81 (m, 1H) 3.81 (s, 2H) 4.40 (s, 2H) 5.71 (s, 2H) 7.26 (dd, J=7.8, 1.3 Hz, 1H) 7.55-7.56 (m, 2H) 7.70 (d, J=1.3 Hz, 1H) 7.76 (s, 1H) 7.85 (d, J=1.3 Hz, 1H) 8.23 (s, 1H) MS (ESI(+)) m/e 416.0 (M+H)$^+$.

EXAMPLE 986

3-{5-[3-(3-isopropylphenoxy)-1-propynyl]-3-thienyl}-7-(1H-1,2,3-triazol-1-ylmethyl)-1,4-dihydroindeno[1,2-c]pyrazole

EXAMPLE 986A 1-isopropyl-3-(prop-2-ynyloxy)benzene

The desired product was prepared by substituting 3-isopropylphenol for 3-fluorophenol in Example 961A.

EXAMPLE 986B

3-{5-[3-(3-isopropylphenoxy)-1-propynyl]-3-thienyl}-7-(1H-1,2,3-triazol-1-ylmethyl)-1,4-dihydroindeno[1,2-c]pyrazole The desired product was obtained by substituting Example 986A for phenyl propargyl ether and Example 963B for 2-bromothiophene-4-carboxylate in Example 126. The product was purified by preparative HPLC on a Waters Symmetry C8 column (25 mm×100 mm, 7 μm particle size) using a gradient of 10% to 100% acetonitrile:0.1% aqueous TFA over 8 min (10 min run time) at a flow rate of 40 ml/min to give Example 986B. 1H NMR (500 MHz, DMSO-D6) δ ppm 1.21 (d, J=6.9 Hz, 6H) 2.84-2.92 (m, 1H) 3.79 (s, 2H) 5.09 (s, 2H) 5.71 (s, 2H) 6.85 (dd, J=8.3, 2.7 Hz, 1H) 6.88 (d, J=7.8 Hz, 1H) 6.91-6.92 (m, 1H) 7.23-7.26 (m, 2H) 7.54-7.56 (m, 2H) 7.71 (d, J=1.3 Hz, 1H) 7.76 (d, J=1.0 Hz, 1H) 7.87 (d, J=1.3 Hz, 1H) 8.22 (s, 1H) MS (ESI(+)) m/e 492.1 (M+H)$^+$.

EXAMPLE 987

3-[5-(3-isopropoxy-1-propynyl)-3-thienyl]-7-(1H-1,2,4-triazol-1-ylmethyl)-1,4-dihydroindeno[1,2-c]pyrazole The desired product was obtained by substituting Example 985A for phenyl propargyl ether and Example 259 for 2-bromothiophene-4-carboxylate in Example 126. The product was purified by preparative HPLC on a Waters Symmetry C8 column (25 mm×100 mm, 7 μm particle size) using a gradient of 10% to 100% acetonitrile:0.1% aqueous TFA over 8 min (10 min run time) at a flow rate of 40 ml/min to give Example 987 as the trifluoroacetic acid salt. 1H NMR (500 MHz, DMSO-D6) δ ppm 1.14 (d, J=5.9 Hz, 6H) 3.75-3.81 (m, 1H) 3.80 (s, 2H) 4.40 (s, 2H) 5.50 (s, 2H) 7.24 (dd, J=8.0, 1.3 Hz, 1H) 7.53-7.55 (m, 2H) 7.70 (s, 1H) 7.85 (d, J=1.3 Hz, 1H) 8.01 (s, 1H) 8.71 (s, 1H) MS (ESI(+)) m/e 416.0 (M+H)$^+$.

EXAMPLE 988

6,7-bis(2-methoxyethoxy)-3-[5-(3-phenoxy-1-propynyl)-3-thienyl]-1,4-dihydroindeno[1,2-c]pyrazole The desired product was obtained by substituting Example 955B for 2-bromothiophene-4-carboxylate in Example 126. The product was purified by preparative HPLC on a Waters Symmetry C8 column (25 mm×100 mm, 7 μm particle size) using a gradient of 10% to 100% acetonitrile:0.1% aqueous TFA over 8 min (10 min run time) at a flow rate of 40 ml/min to give Example 988 as a trifluoroacetic acid salt. 1H NMR (500 MHz, DMSO-D6) δ ppm 3.34 (s, 3H) 3.34 (s, 3H) 3.67-3.70 (m, 6H) 4.13-4.17 (m, 4H) 5.10 (s, 2H) 7.00 (t, J=7.3 Hz, 1H) 7.05 (d, J=8.1 Hz, 2H) 7.21 (s, 1H) 7.24 (s, 1H) 7.35 (dd, J=8.7, 7.2 Hz, 2H) 7.70 (d, J=1.3 Hz, 1H) 7.84 (d, J=1.3 Hz, 1H) MS(ESI(+)) m/e 517.1 (M+H)$^+$.

EXAMPLE 989

7-(1H-1,2,3-triazol-1-ylmethyl)-3-(5-{3-[3-(trifluoromethyl phenoxy]-1-propynyl}-3-thienyl)-1,4-dihydroindeno[1,2-c]pyrazole The desired product was prepared by substituting Example 618 and Example 963B for phenyl propargyl ether and 2-bromothiophene-4-carboxylate, respectively, in Example 126. The product was purified by preparative HPLC on a Waters Symmetry C8 column (25 mm×100 mm, 7 μm particle size) using a gradient of 10% to 100% acetonitrile:0.1% aqueous TFA over 8 min (10 min run time) at a flow rate of 40 ml/min. 1H NMR (500 MHz, DMSO-D6) δ ppm 3.79 (s, 2H) 5.23 (s, 2H) 5.71 (s, 2H) 7.25 (dd, J=7.8, 1.6 Hz, 1H) 7.37 (m, 3H) 7.55 (m, 2H) 7.59 (t, J=7.8 Hz, 1H) 7.72 (s, 1H) 7.76 (s, 1H) 7.88 (s, 1H) 8.22 (s, 1H) 12.74-13.65 (br. s., 1H) MS (ESI(+)) m/e 518.0 (M+H)$^+$.

EXAMPLE 990

3-{5-[3-(2-isopropoxyethoxy)-1-propynyl]-3-thienyl}-7-(1H-1,2,3-triazol-1-ylmethyl)-1,4-dihydroindeno[1,2-c]pyrazole The desired product was prepared by substituting Example 613 and Example 963B for phenyl propargyl ether and 2-bromothiophene-4-carboxylate, respectively, in Example 126. The product was purified by preparative HPLC on a Waters Symmetry C8 column (25 mm×100 mm, 7 μm particle size) using a gradient of 10% to 100% acetonitrile:0.1% aqueous TFA over 8 min (10 min run time) at a flow rate of 40 ml/min. 1H NMR (500 MHz, DMSO-D6) δ ppm 1.09 (d, J=5.9 Hz, 6H) 3.53 (dd, J=5.9, 3.7 Hz, 2H) 3.55-3.60 (m, 1H) 3.61 (dd, J=5.3, 4.4 Hz, 2H) 3.81 (s, 2H) 4.45 (s, 2H) 5.71 (s, 2H) 7.26 (dd, J=7.8, 1.6 Hz) 7.55 (d, J=7.8 Hz, 1H) 7.56 (s, 1H) 7.71 (s, 1H) 7.76 (s, 1H) 7.86 (s, 1H) 8.23 (s, 1H) 12.92-13.46 (br. s., 1H) MS (ESI(+)) m/e 460.0 (M+H)$^+$.

EXAMPLE 991

3-{5-[3-(2-isopropoxyethoxy)-1-propynyl]-3-thienyl}-7-(2H-1,2,3-triazol-2-ylmethyl)-1,4-dihydroindeno[1,2-c]pyrazole

EXAMPLE 991A 3-(5-bromothien-3-yl)-7-(2H-1,2,3-triazol-2-ylmethyl)-1,4-dihydroindeno[1,2-c]pyrazole The desired product was prepared by substituting Example 113 and Example 881B for phenyl thiophene-2-carboxylate and Example 56, respectively, in Example 138.

EXAMPLE 991B

3-{5-[3-(2-isopropoxyethoxy)-1-propynyl]-3-thienyl}-7-(2H-1,2,3-triazol-2-ylmethyl)-1,4-dihydroindeno[1,2-c]pyrazole The desired product was prepared by substituting Example 613 and Example 991A for phenyl propargyl ether and 2-bromothiophene-4-carboxylate, respectively, in Example 126. The product was purified by preparative HPLC on a Waters Symmetry C8 column (25 mm×100 mm, 7 μm particle size) using a gradient of 10% to 100% acetonitrile:0.1% aqueous TFA over 8 nin (10 min run time) at a flow rate of 40 ml/min. 1H NMR (500 MHz, DMSO-D6) δ ppm 1.09 (d, J=5.9 Hz, 6H) 3.53 (dd, J=5.8, 3.9 Hz, 2H) 3.55-3.60 (m, 1H) 3.61 (dd, J=6.6, 3.1 Hz, 2H) 3.80 (s, 2H) 4.45 (s, 2H) 5.74 (s, 2H) 7.22 (br. d., J=7.8 Hz, 1H) 7.52 (br. s., 1H) 7.53 (d, J=7.8 Hz, 1H) 7.71 (br. s., 1H) 7.83 (s, 2H) 7.86 (br. s., 1H) 13.09-13.25 (br. s., 1H) MS (ESI(+)) m/e 460.1 (M+H)$^+$.

EXAMPLE 992

3-[5-(3-phenoxy-1-propynyl)-3-thienyl]-7-(2H-1,2,3-triazol-2-ylmethyl)-1,4-dihydroindeno[1,2-c]pyrazole The desired product was prepared by substituting Example 991A for 2-bromothiophene-4-carboxylate in Example 126. The product was purified by preparative HPLC on a Waters Symmetry C8 column (25 mm×100 mm, 7 μm particle size) using a gradient of 10% to 100% acetonitrile:0.1% aqueous TFA over 8 min (10 min run time) at a flow rate of 40 ml/min. 1H NMR (500 MHz, DMSO-D6) δ ppm 3.79 (s, 2H) 5.10 (s, 2H) 5.74 (s, 2H) 7.00 (t, J=7.3 Hz, 1H) 7.05 (dd, J=8.7, 0.9 Hz, 2H) 7.21 (dd, J=7.8, 1.6 Hz, 1H) 7.33-7.36 (m, 2H) 7.51 (s, 1H) 7.53 (d, J=7.8 Hz, 1H) 7.72 (s, 1H) 7.83 (s, 2H) 7.87 (s, 1H) 12.85-13.44 (br. s., 1H) MS (ESI(+)) m/e 450.0 (M+H)$^+$.

EXAMPLE 993

3-chloro-N-[3-(4-{7-[(4-methyl-1-piperazinyl)methyl]-1,4-dihydroindeno[1,2-c]pyrazol-3-yl}-2-thienyl)-2-propynyl]benzamide

EXAMPLE 993A 3-chloro-N-prop-2-ynylbenzamide

The desired product was prepared by substituting 3-chlorobenzoyl chloride for 3,4,5-trimethoxybenzoyl chloride in Example 982A. MS (ESI(+)) m/e 194.0 (M+H)$^+$.

EXAMPLE 993B 3-chloro-N-[3-(4-{7-[(4-methyl-1-piperazinyl)methyl]-1,4-dihydroindeno[1,2-c]pyrazol-3-yl}-2-thienyl)-2-propynyl]benzamide The desired product was prepared by substituting Example 993A for phenyl propargyl ether and Example 149 for 2-bromothiophene-4-carboxylate in Example 126. The product was purified by preparative HPLC on a Waters Symmetry C8 column (25 mm×100 mm, 7 μm particle size) using a gradient of 10% to 100% acetonitrile:0.1% aqueous TFA over 8 min (10 min run time) at a flow rate of 40 ml/min, and the resulting product was partitioned between NaHCO3 solution and THF/EtOAc, extracting the aqueous phase further with EtOAc, then dried (MgSO4) and concentrated to give Example 993B as the free base. 1H NMR (300 MHz, DMSO-D6) δ ppm 2.15 (s, 3H) 2.26-2.46 (m, 8H) 3.52 (s, 2H) 3.78 (s, 2H) 4.39 (d, J=5.4 Hz, 2H) 7.20 (dd, J=7.8, 1.2 Hz, 1H) 7.48 (d, J=7.8 Hz, 1H) 7.54 (t, J=7.8 Hz, 1H) 7.57 (s, 1H) 7.64 (ddd, J=8.1, 2.0, 1.0 Hz, 1H) 7.68 (s, 1H) 7.83 (s, 1H) 7.87 (ddd, J=7.6, 1.4, 1.2 Hz, 1H) 7.95 (t, J=1.9 Hz, 1H) 9.21 (t, J=5.4 Hz, 1H) 13.04-13.22 (br. s., 1H) MS (ESI(+)) m/e 542.1 (M+H)$^+$.

EXAMPLE 994

2-fluoro-N-[3-(4-{7-[(4-methyl-1-piperazinyl)methyl]-1,4-dihydroindeno[1,2-c]pyrazol-3yl}-2-thienyl)-2-propynyl]-5-(trifluoromethyl)benzamide

EXAMPLE 994A 2-fluoro-N-prop-2-ynyl-5-(trifluoromethyl)benzamide

The desired product was prepared by substituting 2-fluoro-5-(trifluoromethyl)-benzoyl chloride for 3,4,5-trimethoxybenzoyl chloride in Example 982A.

EXAMPLE 994B 2-fluoro-N-[3-(4-{7-[(4-methyl-1-piperazinyl)methyl]-1,4-dihydroindeno[1,2-c]pyrazol-3-yl}-2-thienyl)-2-propynyl]-5-(trifluoromethyl)benzamide The desired product was prepared by substituting Example 994A for phenyl propargyl ether and Example 149 for 2-bromothiophene-4-carboxylate in Example 126. The product was purified by preparative HPLC on a Waters Symmetry C8 column (25 mm×100 mm, 7 μm particle size) using a gradient of 10% to 100% acetonitrile:0.1% aqueous TFA over 8 min (10 min run time) at a flow rate of 40 ml/min, and the resulting product was partitioned between NaHCO3 solution and EtOAc, extracting the aqueous phase further with CH2Cl2, then dried (MgSO4), concentrated and triturated with Et2O to give Example 993B as the free base. 1H NMR (300 MHz, DMSO-D6) δ ppm 2.15 (s, 3H) 2.26-2.46 (m, 8H) 3.52 (s, 2H) 3.78 (s, 2H) 4.40 (d, J=5.1 Hz, 2H) 7.20 (d, J=7.5 Hz, 1H) 7.48 (d, J=7.5 Hz, 1H) 7.56-7.62 (m, 2H) 7.69 (s, 1H) 7.84 (s, 1H) 7.95-8.03 (m, 2H) 9.13-9.17 (m, 1H) 13.02-13.24 (br. s., 1H) MS (ESI(+)) m/e 594.1 (M+H)$^+$.

EXAMPLE 995

2-methyl-N-[3-(4-{7-[(4-methyl-1-piperazinyl)methyl]-1,4-dihydroindeno[1,2-c]pyrazol-3-yl}-2-thienyl)-2-propynyl]propanamide

EXAMPLE 995A 2-methyl-N-prop-2-ynylpropanamide

The desired product was prepared by substituting isobutyryl chloride for 3,4,5-trimethoxybenzoyl chloride in Example 982A.

EXAMPLE 995B 2-methyl-N-[3-(4-{7-[(4-methyl-1-piperazinyl)methyl]-1,4-dihydroindeno[1,2-c]pyrazol-3-yl}-2-thienyl)-2-propynyl]propanamide The desired product was prepared by substituting Example 995A for phenyl propargyl ether and Example 149 for 2-bromothiophene-4-carboxylate in Example 126. The product was purified by preparative HPLC on a Waters Symmetry C8 column (25 mm×100 mm, 7 μm particle size) using a gradient of 10% to 100% acetonitrile:0.1% aqueous TFA over 8 min (10 min run time) at a flow rate of 40 ml/min, and the resulting product was partitioned between NaHCO3 solution and THF/EtOAc, extracting the aqueous phase further with CH2Cl2/THF, then dried (MgSO4), concentrated and triturated with Et2O to give Example 993B as the free base. 1H NMR (500 MHz, DMSO-D6) δ ppm 1.03 (d, J=6.6 Hz, 6H) 2.15 (s, 3H) 2.18-2.47 (m, 9H) 3.53 (s, 2H) 3.78 (s, 2H) 4.16 (d, J=5.3 Hz, 2H) 7.20 (d, J=6.2 Hz, 1H) 7.48 (d, J=7.8 Hz, 1H) 7.58 (s, 1H) 7.66 (s, 1H) 7.82 (s, 1H) 8.29 (s, 1H) 12.97-13.23 (br. s., 1H) MS (ESI(+)) m/e 474.2 (M+H)+.

EXAMPLE 996

N-(2-bromophenyl)-N-(3-{4-[6-(1H-1,2,4-triazol-1-ylmethyl)-1,4-dihydroindeno[1,2-c]pyrazol-3-yl]-2-thienyl}-2-propynyl)amine

EXAMPLE 996A

N-(2-bromophenyl)-N-prop-2-ynylamine

The desired product was prepared by substituting 2-bromoaniline for 3-chloroaniline in Example 974A.

EXAMPLE 996B

N-(2-bromophenyl)-N-(3-{4-[6-(1H-1,2,4-triazol-1-ylmethyl)-1,4-dihydroindeno[1,2-c]pyrazol-3-yl]-2-thienyl}-2-propynyl)amine The desired product was prepared by substituting Example 996A for phenyl propargyl ether and Example 260 for 2-bromothiophene-4-carboxylate in Example 126. The product was purified by preparative HPLC on a Waters Symmetry C8 column (25 mm×100 mm, 7 μm particle size) using a gradient of 10% to 100% acetonitrile:10 mM aq. NH4OAc over 8 min (10 min run time) at a flow rate of 40 ml/min to give Example 996B. 1H NMR (300 MHz, DMSO-D6) δ ppm 3.80 (s, 2H) 4.31 (d, J=6.4 Hz, 2H) 5.47 (s, 2H) 5.81 (t, J=6.4 Hz, 1H) 6.62 (td, J=7.6, 1.4 Hz, 1H) 6.88 (dd, J=8.3, 1.5 Hz, 1H) 7.24-7.30 (m, 2H) 7.44-7.47 (m, 2H) 7.63-7.65 (m, 2H) 7.81 (s, 1H) 8.00 (s, 1H) 8.69 (s, 1H) 13.13 (s, 1H) MS (ESI(+)) m/e 527.1, 529.0 (M+H)+.

EXAMPLE 997

N-(5-fluoro-2-methylphenyl)-N-(3-{4-[6-(1H-1,2,4-triazol-1-ylmethyl)-1,4-dihydroindeno[1,2-c]pyrazol-3-yl]-2-thienyl}-2-propynyl)amine

EXAMPLE 997A

N-(5-fluoro-2-methylphenyl)-N-prop-2-ynylamine

The desired product was prepared by substituting 5-fluoro-2-methylaniline for 3-chloroaniline in Example 974A.

EXAMPLE 997B

N-(5-fluoro-2-methylphenyl)-N-(3-{4-[6-(1H-1,2,4-triazol-1-ylmethyl)-1,4-dihydroindeno[1,2-c]pyrazol-3-yl]-2-thienyl}-2-propynl)amine The desired product was prepared by substituting Example 997A for phenyl propargyl ether and Example 260 for 2-bromothiophene-4-carboxylate in Example 126. The product was purified by preparative HPLC on a Waters Symmetry C8 column (25 mm×100 mm, 7 μm particle size) using a gradient of 10% to 100% acetonitrile:10 mM aq. NH4OAc over 8 min (10 min run time) at a flow rate of 40 ml/min. 1H NMR (300 MHz, DMSO-D6) δ ppm 2.07 (s, 3H) 3.80 (s, 2H) 4.25 (d, J=6.1 Hz, 2H) 5.47 (s, 2H) 5.79-5.83 (m, 1H) 6.35 (td, J=8.5, 2.7 Hz, 1H) 6.50 (dd, J=12.2, 2.7 Hz, 1H) 6.99 (t, J=8.0 Hz, 1H) 7.28 (d, J=8.1 Hz, 1H) 7.47 (s, 1H) 7.63-7.65 (m, 2H) 7.81 (s, 1H) 8.00 (s, 1H) 8.70 (s, 1H) 13.14 (s, 1H) MS(ESI (+)) m/e 481.1 (M+H)+.

EXAMPLE 998

3-{5-[3-(2-isopropoxyethoxy)-1-propynyl]-3-thienyl}-6-(2-methoxyethoxy)-1,4-dihydroindeno[1,2-c]pyrazole The desired product was obtained by substituting Example 971B for 2-bromothiophene-4-carboxylate and Example 613 for phenyl propargyl ether in Example 126. 1H NMR (500 MHz, DMSO-D6) δ ppm 1.10 (d, J=6.2 Hz, 6H) 3.33 (s, 3H) 3.54 (dd, J=5.8, 3.9 Hz, 2H) 3.55-3.60 (m, 1H) 3.62 (dd, J=6.6, 4.4 Hz, 2H) 3.67-3.69 (m, 2H) 3.77 (s, 2H) 4.14 (dd, J=5.5, 3.9 Hz, 2H) 4.45 (s, 2H) 6.94 (dd, J=8.4, 2.2 Hz, 1H) 7.17 (d, J=1.9 Hz, 1H) 7.53 (d, J=8.7 Hz, 1H) 7.70 (s, 1H) 7.84 (s, 1H) 12.95 (s, 1H) MS (ESI(+)) m/e 453.1 (M+H)+.

EXAMPLE 999

6-(2-methoxyethoxy)-3-{5-[3-(tetrahydro-2H-pyran-4-yloxy)-1-propynyl]-3-thienyl}-1,4-dihydroindeno[1,2-c]pyrazole The desired product was obtained by substituting Example 971B for 2-bromothiophene-4-carboxylate and Example 632 for phenyl propargyl ether in Example 126. ¹H NMR (500 MHz, DMSO-D6) δ ppm 1.42-1.48 (m, 2H) 1.89-1.92 (m, 2H) 3.33 (s, 3H) 3.35-3.40 (m, 2H) 3.68 (dd, J=5.2, 3.9 Hz, 2H) 3.70-3.74 (m, 1H) 3.77 (s, 2H) 3.82 (td, J=11.5, 4.4 Hz, 2H) 4.14-4.15 (m, 2H) 4.48 (s, 2H) 6.94 (dd, J=8.1, 2.2 Hz, 1H) 7.17 (d, J=1.6 Hz, 1H) 7.53 (d, J=7.8 Hz, 1H) 7.69 (s, 1H) 7.83 (s, 1H) MS (ESI(+)) m/e 451.1 (M+H)+.

EXAMPLE 1000

N-(3-{4-[7-(1H-1,2,4-triazol-1-ylmethyl)-1,4-dihydroindeno[1,2-c]pyrazol-3-yl]-2-thienyl}-2-propynyl)-1,3-benzoxazol-2-amine

EXAMPLE 1000A

N-prop-2-ynyl-1,3-benzoxazol-2-amine

A solution of 2-chlorobenzoxazole (1.53 g, 10 mmol) in CH3CN (5 mL) was added dropwise to a mixture of propargyl amine (550 mg, 9.9 mmol) and Et3N (2.09 mmol, 15 mmol) and CH3CN (10 mL) under N2, and the resulting mixture was heated to reflux for 4 h, then stirred overnight at rt. The mixture was filtered, and the filtrate was partitioned between EtOAc (100 mL) and brine. The aqueous layer was extracted with EtOAc and the combined organic layers were dried (MgSO4) and concentrated to dryness. The crude solid was diluted with heptane (20 mL) and Et2O (50 mL) and the mixture was heated to boiling and filtered hot. The filtrate was concentrated to dryness, then taken up in boiling Et2O (50 mL) and the solution was cooled and filtered. The filtrate was diluted with hexane (125 mL) and cooled to −20° C. for 4 h, and the crystallized product was collected by filtration (1.1 g, 64%). MS (APCI(+)) m/e 173.0 (M+H)+.

EXAMPLE 1000B

N-(3-{4-[7-(1H-1,2,4-triazol-1-ylmethyl)-1,4-dihydroindeno[1,2-c]pyrazol-3-yl]-2-thienyl}-2-propynyl)-1,3-benzoxazol-2-amine The desired product was prepared by substituting Example 259 for 2-bromothiophene-4-carboxylate and Example 1000A for phenyl propargyl ether in Example 126. 1H NMR (300 MHz, DMSO-D6) δ ppm 8.71 (s, 1H) 8.49 (t, J=6 Hz, 1H) 8.01 (s, 1H) 7.50-7.88 (m, 4H) 6.92-7.45 (m, 6H); 5.50 (s, 2H); 4.45 (d, J=6 Hz, 2H); 3.74-3.84 (m, 2H) MS (DCI/NH3) m/e 490.1 (M+H)+.

EXAMPLE 1001

3-{5-[5-oxo-5-(1-pyrrolidinyl)-1-pentynyl]-3-thienyl}-7-(1H-1,2,4-triazol-1-ylmethyl)-1,4-dihydroindeno[1,2-c]pyrazole

EXAMPLE 1001A 1-pent-4-ynoylpyrrolidine

To a solution of 4-pentynoic acid (981 mg, 10 mmol) in THF (40 mL) and DMF (2 drops) was added dropwise oxalyl chloride (0.96 mL, 11 mmol) over 10 min. The solution was stirred for 3 h at rt, then the flask was cooled in an ice bath and a solution of pyrrolidine (1.65 mL, 20 mmol) and Et3N (1.74 mL, 12.5 mmol) in THF (10 mL) was added dropwise over 17 min. The resulting suspension was stirred overnight, then filtered. The filtrate was partitioned between EtOAc (300 mL) and H2O. The layers were separated and the aqueous layer was extracted with EtOAc. The combined organic layers were dried (Na2SO4) and concentrated to dryness, giving the desired product as a brown solid (1.32 g, 87%). MS (APCI (+)) m/e 152.1 (M+H)+.

EXAMPLE 1001B

3-{5-[5-oxo-5-(1-pyrrolidinyl)-1-pentynyl]-3-thienyl}-7-(1H-1,2,4-triazol-1-ylmethyl)-1,4-dihydroindeno[1,2-c]pyrazole The desired product was prepared by substituting Example 259 for 2-bromothiophene-4-carboxylate and Example 1001A for phenyl propargyl ether in Example 126. 1H NMR (300 MHz, DMSO-D6) δ ppm 13.16 (s, 1 H) 8.71 (s, 1H) 8.00 (s, 1H) 7.68-7.88 (m, 1H) 7.50-7.61 (m, 3 H) 7.24 (dd, J=9.0, 1.5 Hz, 1 H) 5.50 (s, 2 H) 3.74-3.85 (m, 2 H) 3.16-3.49 (m, 4 H) 2.65-2.73 (m, 2 H) 2.54-2.72 (m, 2 H) 1.72-1.94 (m, 4H). MS (ESI(+)) m/e 469.1 (M+H)+.

EXAMPLE 1002

3-(5-{5-[(2S)-2-(methoxymethyl)-1-pyrrolidinyl]-5-oxo-1-pentynyl}-3-thienyl)-7-(1H-1,2,4-triazol-1-ylmethyl)-1,4-dihydroindeno[1,2-c]pyrazole

EXAMPLE 1002A (2S)-2-(methoxymethyl)-1-pent-4-ynoylpyrrolidine

The desired product was prepared by substituting 4-pentynoic acid and S-(+)-2-(methoxymethyl)pyrrolidine for 4-carboxy-1-indanone and dimethylamine hydrochloride, respectively, in Example 40. MS (APCI(+)) m/e 196.1 (M+H)+.

EXAMPLE 1002B 3-(5-{5-[(2S)-2-(methoxymethyl)-1-pyrrolidinyl]-5-oxo-1-pentynyl}-3-thienyl)-7-(1H-1,2,4-triazol-1-ylmethyl)-1,4-dihydroindeno[1,2-c]pyrazole The desired product was prepared by substituting Example 259 for 2-bromothiophene-4-carboxylate and Example 1002A for phenyl propargyl ether in Example 126. 1H NMR (300 MHz, DMSO-D6) δ ppm 13.16 (s, 1 H); 8.71 (s, 1H); 8.00 (s, 1H); 7.67-7.87 (m, 1H); 7.50-7.61 (m, 3 H); 7.24 (dd, J=9.0, 1.5 Hz, 1 H); 5.50 (s, 2 H); 4.01-4.20 (m, 1 H); 3.74-3.84 (m, 2H); 3.40-3.53 (m, 2 H); 3.16-3.28 (m, 5 H); 2.65-2.72 (m, 2 H); 2.54-2.62 (m, 2 H); 1.73-1.97 (m, 4 H) MS (DCI/NH3) m/e 513.2 (M+H)+.

EXAMPLE 1003

N-(2-methoxyethyl)-5-{4-[7-(1H-1,2,4-triazol-1-ylmethyl)-1,4-dihydroindeno[1,2-c]pyrazol-3-yl]-2-thienyl}-4-pentynamide

EXAMPLE 1003A

N-(2-methoxyethyl)pent-4-ynamide

The desired product was prepared by substituting 2-methoxyethylamine for pyrrolidine in Example 1001A. MS (APCI (+)) m/e 156.1 (M+H)+.

EXAMPLE 1003B

N-(2-methoxyethyl)-5-{4-[7-(1H-1,2,4-triazol-1-ylmethyl)-1,4-dihydroindeno[1,2-c]pyrazol-3-yl]-2-thienyl}-4-pentynamide The desired product was prepared by substituting Example 259 for 2-bromothiophene-4-carboxylate and Example 1003A for phenyl propargyl ether in Example 126. 1H NMR (300 MHz, DMSO-D6) δ ppm 13.17 (s, 1 H) 8.71 (s, 1H) 7.98-8.09 (m, 2 H) 7.78 (s, 1H) 7.50-7.62 (m, 3 H) 7.24 (d, J=9.0 Hz, 1 H) 5.50 (s, 2 H) 4.73-4.84 (m, 2H) 3.16-3.40 (m, 7 H) 2.63-2.75 (m, 2 H) 2.39 (t, J=9.0 Hz, 2 H) MS (ESI(+)) m/e 473.1 (M+H)+.

EXAMPLE 1004

N-4-pyridinyl-5-{4-[7-(1H-1,2,4-triazol-1-ylmethyl)-1,4-dihydroindeno[1,2-c]pyrazol-3-yl]-2-thienyl}-4-pentynamide

EXAMPLE 1004A

N-pyridin-4-ylpent-4-ynamide

The desired product was prepared by substituting 4-pentynoic acid and 4-aminopyridine for 4-carboxy-1-indanone and dimethylamine hydrochloride, respectively, in Example 40. MS (APCI(+)) m/e 175.1 (M+H)+.

EXAMPLE 1004B

Name

The desired product was prepared by substituting Example 259 for 2-bromothiophene-4-carboxylate and Example 1004A for phenyl propargyl ether in Example 126. 1H NMR (300 MHz, DMSO-D6) δ ppm 10.43 (br. s., 1 H) 8.71 (s, 1 H) 8.38-8.49 (m, 2 H) 8.00 (s, 1 H) 7.76 (s, 1 H) 7.50-7.65 (m, 4

H) 7.34 (s, 2H) 7.23 (d, J=9 Hz, 1H) 5.50 (s, 2H) 3.76 (s, 2 H) 3.63-3.84 (m, 4 H) MS (ESI(+)) m/e 492.0 (M+H)+.

EXAMPLE 1005

3-{5-[5-(4-morpholinyl)-5-oxo-1-pentynyl]-3-thienyl}-7-(1H-1,2,4-triazol-1-ylmethyl)-1,4-dihydroindeno[1,2-c]pyrazole

EXAMPLE 1005A 4-pent-4-ynoylmorpholine

The desired product was prepared by substituting morpholine for pyrrolidine in Example 1001A. MS (APCI(+)) m/e 168.1 (M+H)+.

EXAMPLE 1005B

3-{5-[5-(4-morpholinyl)-5-oxo-1-pentynyl]-3-thienyl}-7-(1H-1,2,4-triazol-1-ylmethyl)-1,4-dihydroindeno[1,2-c]pyrazole The desired product was prepared by substituting Example 259 for 2-bromothiophene-4-carboxylate and Example 1005A for phenyl propargyl ether in Example 126. 1H NMR (300 MHz, DMSO-D6) δ ppm 13.17 (s, 1 H) 8.71 (s, 1H) 8.00 (s, 1H) 7.68-7.89 (m, 1H) 7.51-7.62 (m, 3 H) 7.24 (dd, J=9.0, 1.5 Hz, 1 H) 5.50 (s, 2 H) 3.74-3.84 (m, 2 H) 3.40-3.63 (m, 8 H) 2.41-2.75 (m, 4 H) MS (ESI(+)) m/e 485.2 (M+H)+.

EXAMPLE 1006

N-2-pyridinyl-5-{4-[7-(1H-1,2,4-triazol-1-ylmethyl)-1,4-dihydroindeno[1,2-c]pyrazol-3-yl]-2-thienyl}-4-pentynamide

EXAMPLE 1006A

N-pyridin-2-ylpent-4-ynamide

The desired product was prepared by substituting 4-pentynoic acid and 2-aminopyridine for 4-carboxy-1-indanone and dimethylamine hydrochloride, respectively, in Example 40. MS (APCI(+)) m/e 175.1 (M+H)+.

EXAMPLE 1006B

N-2-pyridinyl-5-{4-[7-(1H-1,2,4-triazol-1-ylmethyl)-1,4-dihydroindeno[1,2-c]pyrazol-3-yl]-2-thienyl}-4-pentynamide The desired product was prepared by substituting Example 259 for 2-bromothiophene-4-carboxylate and Example 1006A for phenyl propargyl ether in Example 126. 1H NMR (300 MHz, DMSO-D6) δ ppm 10.56 (s, 1 H) 8.71 (s, 1H) 8.29-8.35 (m, 1 H) 8.10 (d, J=9.0 Hz, 1 H) 8.00 (s, 1H) 7.84-7.96 (m, 1H) 7.69-7.82 (m, 2H) 7.50-7.61 (m, 3H) 7.23 (dd, J=1.5, 9.0 Hz, 1H) 7.05-7.13 (m, 1H) 5.50 (s, 2H) 3.77 (s, 2H) 2.68-2.83 (m, 4H) MS (ESI(+)) m/e 492.1 (M+H)+.

EXAMPLE 1007

4-methoxy-N-[3-(4-{7-[(4-methyl-1-piperazinyl)methyl]-1,4-dihydroindeno[1,2-c]pyrazol-3-yl}-2-thienyl)-2-propynyl]benzamide

EXAMPLE 1007A 4-methoxy-N-prop-2-ynylbenzamide

The desired product was prepared by substituting p-anisoyl chloride for 3,4,5-trimethoxybenzoyl chloride in Example 982A. MS (ESI(+)) m/e 190.0 (M+H)+.

EXAMPLE 1007B 4-methoxy-N-[3-(4-{7-[(4-methyl-1-piperazinyl)methyl]-1,4-dihydroindeno[1,2-c]pyrazol-3-yl}-2-thienyl)-2-propynyl]benzamide The desired product was prepared by substituting Example 1007A for phenyl propargyl ether and Example 149 for 2-bromothiophene-4-carboxylate in Example 126. The product was purified by preparative HPLC on a Waters Symmetry C8 column (25 mm×100 mm, 7 μm particle size) using a gradient of 10% to 100% acetonitrile:0.1% aqueous TFA over 8 min (10 min run time) at a flow rate of 40 ml/min to give Example 1007B as the trifluoroacetic acid salt. 1H NMR (300 MHz, DMSO-D6) δ ppm 2.24-2.42 (m, 2 H) 2.78 (s, 3 H) 2.89-3.12 (m, 6 H) 3.65 (s, 2 H) 3.80 (s, 2 H) 3.82 (s, 3 H) 4.36 (d, J=5.4 Hz, 2H) 7.02 (d, J=8.8 Hz, 2H) 7.24 (d, J=7.8 Hz, 1 H) 7.53 (d, J=7.8 Hz, 1 H) 7.63 (s, 1 H) 7.67 (d, J=1.4 Hz, 1H) 7.83 (d, J=1.4 Hz, 1H) 7.88 (d, J=8.8 Hz, 2H) 8.91 (t, J=5.6 Hz, 1 H) 9.33-9.50 (br. s., 1 H) MS (ESI(+)) m/e 538.2 (M+H)+.

EXAMPLE 1008

2-methoxy-N-[3-(4-{7-[(4-methyl-1-piperazinyl)methyl]-1,4-dihydroindeno[1,2-c]pyrazol-3-yl}-2-thienyl)-2-propynyl]benzamide

EXAMPLE 1008A 2-methoxy-N-prop-2-ynylbenzamide

The desired product was prepared by substituting o-anisoyl chloride for 3,4,5-trimethoxybenzoyl chloride in Example 982A. MS (ESI(+)) m/e 190.0 (M+H)+.

EXAMPLE 1008B 2-methoxy-N-[3-(4-{7-[(4-methyl-1-piperazinyl)methyl]-1,4-dihydroindeno[1,2-c]pyrazol-3-yl}-2-thienyl)-2-propynyl]benzamide The desired product was prepared by substituting Example 1008A for phenyl propargyl ether and Example 149 for 2-bromothiophene-4-carboxylate in Example 126. The product was purified by preparative HPLC on a Waters Symmetry C8 column (25 mm×100 mm, 7 μm particle size) using a gradient of 10% to 100% acetonitrile:0.1% aqueous TFA over 8 min (10 min run time) at a flow rate of 40 ml/min, and the resulting product was partitioned between NaHCO3 solution and THF/EtOAc, extracting the aqueous phase further with $CH_2Cl_2$, then dried (MgSO4), concentrated and triturated with Et2O to give Example 1008B as the free base. 1H NMR (300 MHz, DMSO-D6) δ ppm 2.15 (s, 3 H) 2.25-2.47 (m, 8 H) 3.52 (s, 2H) 3.78 (s, 2H) 3.92 (s, 3H) 4.38 (d, J=5.6 Hz, 2 H) 7.06 (t, J=7.6 Hz, 1 H) 7.16 (d, J=8.1 Hz, 1 H) 7.20 (d, J=8.8 Hz, 1H) 7.47-7.53 (m, 2 H) 7.57 (s, 1 H) 7.67 (s, 1H) 7.82 (dd, J=7.8, 1.7 Hz, 2H) 8.70 (t, J=5.6 Hz, 1 H) 13.12 (s, 1 H) MS (ESI(+)) m/e 538.1 (M+H)+.

EXAMPLE 1009

N-[3-(4-{7-[(4-methyl-1-piperazinyl)methyl]-1,4-dihydroindeno[1,2-c]pyrazol-3-yl}-2-thienyl)-2-propynyl]acetamide

EXAMPLE 1009A

N-prop-2-ynylacetamide

The desired product was prepared by substituting acetyl chloride for 3,4,5-trimethoxybenzoyl chloride in Example 982A. MS (ESI(+)) m/e 98.1 (M+H)$^+$.

EXAMPLE 1009B

N-[3-(4-{7-[(4-methyl-1-piperazinyl)methyl]-1,4-dihydroindeno[1,2-c]pyrazol-3-yl}-2-thienyl)-2-propynyl]acetamide The desired product was prepared by substituting Example 1009A for phenyl propargyl ether and Example 149 for 2-bromothiophene-4-carboxylate in Example 126. The product was purified by preparative HPLC on a Waters Symmetry C8 column (25 mm×100 mm, 7 μm particle size) using a gradient of 10% to 100% acetonitrile:0.1% aqueous TFA over 8 min (10 min run time) at a flow rate of 40 ml/min, and the resulting product was partitioned between NaHCO3 solution and THF/EtOAc, extracting the aqueous phase further with CH2Cl2, then dried (MgSO4), concentrated and triturated with Et2O to give Example 1009B as the free base. 1H NMR (300 MHz, DMSO-D6) δ ppm 1.86 (s, 3 H) 2.15 (s, 3H) 2.24-2.45 (m, 8 H) 3.52 (s, 2H) 3.78 (s, 2H) 4.16 (d, J=5.1 Hz, 2 H) 7.20 (d, J=7.8 Hz, 1 H) 7.48 (d, J=7.8 Hz, 1 H) 7.58 (s, 1 H) 7.66 (s, 1 H) 7.83 (s, 1 H) 8.37-8.45 (m, 1 H) 13.12 (s, 1H) MS (ESI(+)) m/e 446.1 (M+H)$^+$.

EXAMPLE 1010

N-(3-chlorophenyl)-N-[3-(4-{6-[(4-methyl-1-piperazinyl)methyl]-1,4-dihydroindeno[1,2-c]pyrazol-3-yl}-2-thienyl)-2-propynyl]amine The desired product was prepared by substituting Example 974A for phenyl propargyl ether and Example 148 for 2-bromothiophene-4-carboxylate in Example 126. The product was purified by preparative HPLC on a Waters Symmetry C8 column (25 mm×100 mm, 7 μm particle size) using a gradient of 10% to 100% acetonitrile: 10 mM aq. NH4OAc over 8 min (10 min run time) at a flow rate of 40 ml/min. 1 H NMR (300 MHz, DMSO-D6) δ ppm 2.15 (s, 3H) 2.27-2.47 (m, 8H) 3.50 (s, 2 H) 3.79 (s, 2 H) 4.22 (d, J=6.1 Hz, 2 H) 6.46 (t, J=6.1 Hz, 1H) 6.62-6.67 (m, 2 H) 6.73 (t, J=2.0 Hz, 1 H) 7.15 (t, J=8.0 Hz, 1H) 7.27 (d, J=7.1 Hz, 1H) 7.46 (s, 1 H) 7.59 (d, J=8.1 Hz, 1 H) 7.63 (s, 1 H) 7.82 (s, 1 H) 13.07 (s, 1 H) MS (ESI(+)) m/e 514.0 (M+H)$^+$.

EXAMPLE 1011

(8aS)-octahydropyrrolo[1,2-a]pyrazine

The title compound was prepared according to the procedure described in de Costa, B. R. et al. J. Med. Chem. 36 (1993) 2311.

EXAMPLE 1012

1-Cyclopropylpiperazine

The title compound was prepared according to the procedure described in Gillaspy, M. L. et al. Tetrahedron Lett. 36 (1995) 7399.

EXAMPLE 1013 tert-butyl 4-(methylsulfonyl)piperazine-1-carboxylate

Tert-butyl piperazine-1-carboxylate (5.3 g, 28.5 mmol) and triethylamine (6 mL) were combined in dichloromethane (60 mL) and treated with methanesulfonyl chloride (2.6 mL, 33.6 mmol) at about 0° C. The mixture was stirred at about 0° C. for about 30 min, water (100 mL) was added and the mixture was extracted with dichloromethane. The combined organic layers were dried over MgSO$_4$, filtered and concentrated under vacuum to provide the desired product. $^1$H NMR (300 MHz, CDCL$_3$): δ 1.42 (s, 9H), 2.80 (s, 3H), 3.18 (t, J=7.0 Hz, 4H), 3.56 (t, J=7.0 Hz, 4H).

EXAMPLE 1014

1-(methylsulfonyl)piperazine

To a solution of Example 1013 (8.2 g, 28.5 mmol) in dichloromethane (40 mL) was added trifluoroacetic acid (30 mL) at about 0° C. The mixture was stirred at room temperature for about 4 h and was then concentrated under vacuum. The residue was basified with sodium carbonate and was extracted with dichloromethane. The combined organic extracts were dried over Na$_2$SO$_4$, filtered and concentrated under vacuum to provide the desired product. $^1$H NMR (300 MHz, CDCL$_3$): δ 2.80 (s, 3H), 3.00 (t, J=7.0 Hz, 4H), 3.21 (t, J=7.0 Hz, 4H).

EXAMPLE 1015

4-Methyl-piperidin-4-ol

The title compound was prepared according to the procedure described in van Niel, M. B. et al. J. Med. Chem. 42 (1999) 2087.

EXAMPLE 1016

5,6-difluoroindan-1-one

The title compound was prepared by substituting 3,4-difluorophenylpropionic acid for Example 1 in Example 3. $^1$H NMR (300 MHz, CDCL$_3$): δ 2.72 (t, J=7.0 Hz, 2H), 3.12 (t, J=7.0 Hz, 2H), 7.28 (ddt, J=6.0, 9.0, 1.0 Hz, 1H), 7.52 (ddt, J=6.0, 9.0, 1.0 Hz, 1H).

EXAMPLE 1017

(3-bromo-4-fluorophenyl)methanol

To a solution of 3-bromo-4-fluorobenzaldehyde (35.0 g, 172.4 mmol) in methanol (400 mL) and tetrahydrofuran (200 mL) was added sodium borohydride (6.5 g, 172.4 mmol) in portions at about 0° C. The mixture was stirred for about 3 h while being allowed to warm to ambient temperature. The solvents were removed under vacuum, the residue was diluted with water (600 mL) and was extracted with ethyl acetate. The combined organic extracts were dried (MgSO$_4$), filtered and evaporated under reduced pressure to provide the desired product. MS (DCI-NH$_3$): m/z 204, 206 (M)$^+$.

EXAMPLE 1018

3-bromo-4-fluorobenzal methanesulfonate

The title compound was prepared by substituting Example 1017 for Example 51 in Example 54. MS (DCI-NH$_3$): m/z 300, 302 (M+NH$_4$)$^+$.

EXAMPLE 1019

3-(3-Bromo-4-fluoro-phenyl)-propionic acid

The title compound was prepared by substituting Example 1018 for 4-bromobenzyl bromide in Example 1. MS (DCI-NH$_3$): m/z 264, 266 (M+NH$_4$)$^+$.

EXAMPLE 1020

5-Bromo-6-fluoroindan-1-one

The title compound was prepared by substituting Example 1019 for Example 1 in Example 3. MS (DCI-NH$_3$): m/z 246, 248 (M+NH$_4$)$^+$.

EXAMPLE 1021

5'-Bromo-6'-fluoro-2',3'-dihydrospiro[1,3-dioxolane-2,1'-indene]

The title compound was prepared by substituting Example 1020 for Example 3 in Example 20. MS (DCI-NH$_3$): m/z 273, 275 (M+H)$^+$.

EXAMPLE 1022

6'-fluoro-2',3'-dihydrospiro[1,3-dioxolane-2,1'-inden]-5'-ylmethanol

The title compound was prepared by substituting Example 1021 for Example 20 in Example 28. MS (DCI-NH$_3$): m/z 225 (M+H)$^+$.

EXAMPLE 1023

2',3'-dihydrospiro[1,3-dioxolane-2,1'-inden]-5'-ylethan-2-ol

A solution of Example 21 (470 mg, 1.84 mmol) in tetrahydrofuran (5.5 mL) was cooled to about −78° C. and a 1.6 M solution of n-butyllithium in hexanes (1.44 mL, 2.3 mmol) was added dropwise. To his mixture was added a solution of ethylene oxide (1.21 g, 27.5 mmol) in diethyl ether (2.1 mL) at about −78° C. The mixture was warmed to about 0° C. over about 2 h and stirring at this temperature was continued for about another 2 h. The reaction was quenched by addition of water (10 mL) and the mixture was extracted with ethyl acetate. The combined organic extracts were dried (MgSO$_4$), filtered and evaporated under reduced pressure. The residue was purified by column chromatography on silica gel using hexane/ethyl acetate (1:1) as the mobile phase to provide the desired product. MS (DCI-NH$_3$): m/z 221 (M+H)$^+$.

EXAMPLE 1024

6-Fluoro-5-hydroxymethyl-indan-1-one

The title compound was prepared by substituting Example 1022 for Example 28 in Example 51. MS (DCI-NH$_3$): m/z 181 (M+H)$^+$.

EXAMPLE 1025

5-(2-Hydroxyethyl)indan-1-one

The title compound was prepared by substituting Example 1023 for Example 28 in Example 51. MS (DCI-NH$_3$): m/z 177 (M+H)$^+$.

EXAMPLE 1026

(6-fluoro-1-oxo-2,3-dihydro-1H-inden-5-yl)methyl methanesulfonate

The title compound was prepared by substituting Example 1024 for Example 51 in Example 54. MS (DCI-NH$_3$): m/z 276 (M+NH$_4$)$^+$.

EXAMPLE 1027

2-(1-oxo-2,3-dihydro-1H-inden-5-yl)ethyl methanesulfonate

The title compound was prepared by substituting Example 1025 for Example 51 in Example 54. MS (DCI-NH$_3$): m/z 272 (M+NH$_4$)$^+$.

EXAMPLE 1028

6-Fluoro-5-(4-methylpiperazin-1-ylmethyl)indan-1-one

The title compound was prepared by substituting Example 1026 for Example 54 in Example 56. MS (DCI-NH$_3$): m/z 263 (M+H)$^+$.

EXAMPLE 1029

6-Fluoro-5-(4'-methylpiperazin-1'-yl)indan-1-one

A mixture of 5,6-difluoro-1-indanone (1.5 g, 8.92 mmol), 1-methylpiperazine (1.0 g, 10.0 mmol) and potassium carbonate (2.49 g, 18.0 mmol) in N,N-dimethylformamide (20 mL) was heated to about 110° C. for about 17 h. The reaction mixture was poured into water and was extracted with ethyl acetate. The combined organic extracts were washed with brine, dried (Na$_2$SO$_4$), filtered and evaporated under reduced pressure. The residue was purified by flash column chromatography on silica gel using dichloromethane/methanol/ammonium hydroxide (95:4.5:0.5) as the mobile phase to provide the desired product.

| Example Number | R₁ | R₂ | R₃ | MS | Reference Procedure |
|---|---|---|---|---|---|
| 1030 | 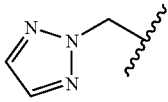 | H | H | (DCI-NH₃): m/z 214 (M + H)⁺. | Example 56 |
| 1031 | 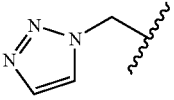 | H | H | (DCI-NH₃): m/z 214 (M + H)⁺. | Example 56 |
| 1032 | H | 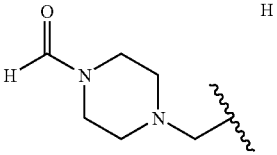 | H | (ESI): m/z 259 (M + H)⁺. | Example 56 |
| 1033 | F | 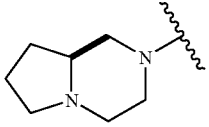 | H | (DCI-NH₃): m/z 275 (M + H)⁺. | Example 1029 |
| 1034 | H | 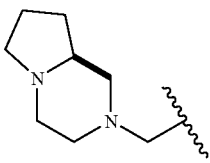 | H | (ESI): m/z 271 (M + H)⁺. | Example 56 |
| 1035 | H | 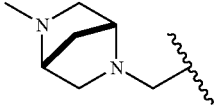 | H | (DCI-NH₃): m/z 257 (M + H)⁺. | Example 56 |
| 1036 | H | 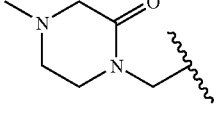 | H | (DCI-NH₃): m/z 259 (M + H)⁺. | Example 56 |
| 1037 | H | 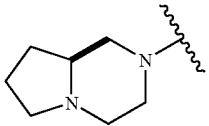 | H | (DCI-NH₃): m/z 257 (M + H)⁺. | Example 1029 |
| 1038 | H | 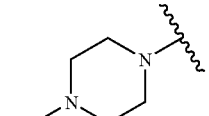 | H | (DCI-NH₃): m/z 257 (M + H)⁺. | Example 1029 |
| | H | 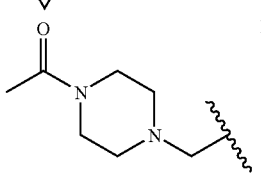 | H | (DCI-NH₃): m/z 273 (M + H)⁺. | Example 56 |

-continued

| Example Number | R₁ | R₂ | R₃ | MS | Reference Procedure |
|---|---|---|---|---|---|
| 1040 | F | ![piperazine with cyclopropyl] | H | (DCI-NH₃): m/z 275 (M + H)⁺. | Example 1029 |
| 1041 | H | ![methylsulfonyl piperazine ethyl] | H | (ESI): m/z 309 (M + H)⁺. | Example 56 |
| 1042 | F | ![methylsulfonyl piperazine] | H | (ESI): m/z 313 (M + H)⁺. | Example 1029 |
| 1043 | H | ![4-hydroxy-4-methylpiperidine] | H | (DCI-NH₃): m/z 246 (M + H)⁺. | Example 1029 |
| 1044 | H | ![cyclopropyl piperazine ethyl] | H | (DCI-NH₃): m/z 271 (M + H)⁺. | Example 56 |
| 1045 | H | ![4-methylpiperazine propyl] | H | (DCI-NH₃): m/z 259 (M + H)⁺. | Example 56 |

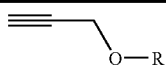

| Example Number | R | ¹H NMR(300 MHz, CDCl₃) | Synthesis protocol |
|---|---|---|---|
| 1046 | ![cyclopentyl] | δ 1.54(m, 2H), 1.66-1.79(m, 6H), 2.39(t, J=3.0Hz, 1H), 4.10(d, J=3.0Hz, 3H). | Example 613 |
| 1047 | ![isopropyl] | δ 1.17(d, J=6.0Hz, 6H), 1.93(s, 1H), 3.80 (m, 1H), 4.19(s, 2H). | Example 613 |

-continued

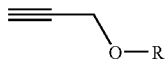

| Example Number | R | ¹H NMR(300 MHz, CDCl₃) | Synthesis protocol |
| --- | --- | --- | --- |
| 1048 | (cyclopropylmethyl) | δ 0.25(m, 2H), 0.57(m, 2H), 1.07(m, 1H), 2.41(t, J=3.0Hz, 1H), 3.37(d, J=6.0Hz, 2H), 4.17(d, J=6.0Hz, 2H) | Example 613 |
| 1049 | (cyclobutyl) | δ 1.54(m, 1H), 1.71(m, 1H), 1.97(m, 2H), 2.22(m, 2H), 2.39(t, J=3.0Hz, 1H), 4.05(d, J=3.0Hz, 2H), 4.11(m, 1H). | Example 613 |
| 1050 | (CH₂CF₃) | δ 2.35(s, 2H), 2.52(m, 1H), 3.87(d, J=3.0Hz, 2H). | Example 613 |
| 1051 | (CH(CH₂F)₂) | δ 2.46(t, J=3.0Hz, 1H), 3.74(m, 1H), 3.84(m, 1H), 4.24(d, J=3.0Hz, 2H), 4.51(m, 1H), 4.67(m, 1H). | Example 613 |
| 1052 | (cyclohexyl) | δ 1.19-1.35(m, 5H), 1.55(m, 1H), 1.74(m, 2H), 1.91(m, 2H), 2.38(t, J=3.0Hz, 1H), 3.47(m, 1H), 4.17(d, J=3.0Hz, 2H). | Example 613 |

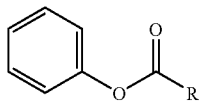

| Example Number | R | MS (DCI-NH₃): | Reference Procedure |
| --- | --- | --- | --- |
| 1053 | (4-thienyl with 2-C≡C-CH₂-O-iPr) | m/z 318 (M + NH₄)⁺. | Example 126 |
| 1054 | (4-thienyl with 2-C≡C-CH₂-O-cyclopropylmethyl) | m/z 330 (M + NH₄)⁺. | Example 126 |
| 1055 | (4-thienyl with 2-C≡C-CH₂-O-cyclobutyl) | m/z 330 (M + NH₄)⁺. | Example 126 |

-continued
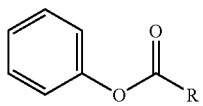
| Example Number | R | MS (DCI-NH₃): | Reference Procedure |
|---|---|---|---|
| 1056 | 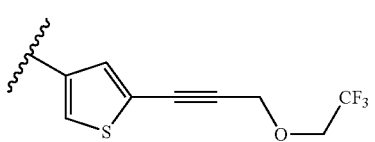 | m/z 358 (M + NH₄)⁺. | Example 126 |
| 1057 | 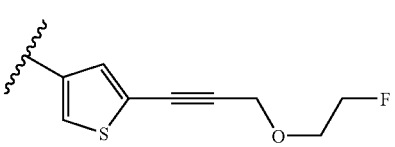 | m/z 322 (M + NH₄)⁺. | Example 126 |
| 1058 | 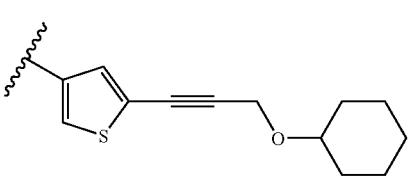 | m/z 358 (M + NH₄)⁺. | Example 126 |
| Example Number | R₁ | R₂ | R₃ | R₄ | MS (ESI): | Reference Procedure |
|---|---|---|---|---|---|---|
| 1059 | 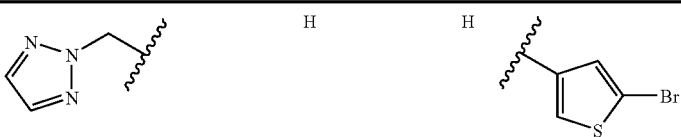 | H | H | (thiophene-Br) | m/z 399 (M + H)⁺. | Example 138 |
| 1060 | 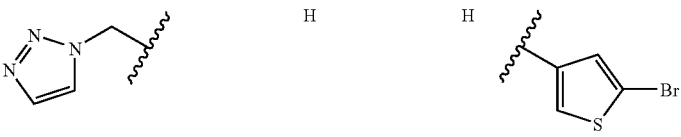 | H | H | (thiophene-Br) | m/z 399 (M + H)⁺. | Example 138 |
| 1061 | H | 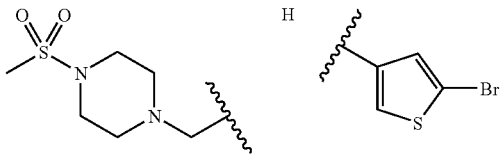 | H | (thiophene-Br) | (ESI): m/z 493 (M + H)⁺. | Example 138 |
| 1062 | F | 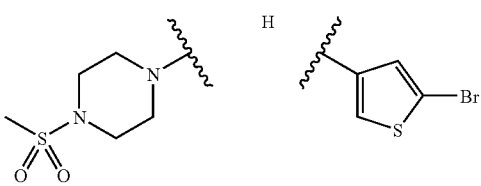 | H | (thiophene-Br) | (ESI): m/z 497 (M + H)⁺. | Example 138 |

EXAMPLE 1063

3-{5-[3-(2-Methoxy-ethoxy)-prop-1-ynyl]-thiophen-3-yl}-7-[1,2,3]triazol-2-ylmethyl-1,4-dihydro-indeno[1,2-c]pyrazole The title compound was prepared by substituting Example 1059 for Example 148 and by substituting Example 127 for (prop-2-ynyloxy)benzene in Example 655. $^1$H NMR (300 MHz, DMSO-$d_6$): δ 3.27 (s, 3H), 3.50 (m, 2H), 3.64 (m, 2H), 3.81 (s, 2H), 4.45 (s, 2H), 5.71 (s, 2H), 7.24-7.27 (m, 1H), 7.52-7.65 (m, 3H), 7.72 (s, 1H), 7.77 (s, 1H), 7.86 (s, 1H), 8.24 (s, 1H). MS (ESI): m/z 432 (M+H)$^+$.

EXAMPLE 1064

3-{5-[3-(2-Methoxy-ethoxy)-prop-1-ynyl]-thiophen-3-yl}-7-[1,2,3]triazol-1-ylmethyl-1,4-dihydro-indeno[1,2-c]pyrazole The title compound was prepared by substituting Example 1060 for Example 148 and by substituting Example 127 for (prop-2-ynyloxy)benzene in Example 655. $^1$H NMR (300 MHz, DMSO-$d_6$): δ 3.27 (s, 3H), 3.50 (m, 2H), 3.64 (m, 2H), 3.81 (s, 2H), 4.45 (s, 2H), 5.75 (s, 2H), 7.19-7.22 (m, 1H), 7.52-7.54 (m, 2H), 7.72 (d, J=3.0 Hz, 1H), 7.84 (s, 2H), 7.88 (d, J=3.0 Hz, 1H). MS (ESI): m/z 432 (M+H)$^+$.

EXAMPLE 1065

4-{3-[5-(3-Phenoxy-prop-1-ynyl)-thiophen-3-yl]-1,4-dihydro-indeno[1,2-c]pyrazol-6-ylmethyl}-piperazine-1-carbaldehyde The title compound was prepared by substituting Example 1032 for Example 56 and by substituting Example 126 for Example 110 in Example 138. $^1$H NMR (300 MHz, DMSO-$d_6$): δ 2.33-2.42 (m, 4H), 3.35-3.41 (m, 4H), 3.56 (s, 2H), 3.81 (s, 2H), 5.11 (s, 2H), 6.98-7.07 (m, 3H), 7.29-7.38 (m, 3H), 7.49 (m, 1H), 7.62 (d, J=9.0 Hz, 1H), 7.74 (s, 1H), 7.89 (m, 1H), 7.99 (s, 1H), 13.1 (s, 1H). MS (ESI): m/z 495 (M+H)$^+$.

EXAMPLE 1066

3-[5-(3-Cyclopentyloxy-prop-1-ynyl)-thiophen-3-yl]-6-(4-methyl-piperazin-1-ylmethyl)-1,4-dihydro-indeno[1,2-c]pyrazole The title compound was prepared by substituting Example 1046 for (prop-2-ynyloxy)benzene in Example 655. $^1$H NMR (300 MHz, DMSO-$d_6$): δ 1.48-1.73 (m, 8H), 2.79 (s, 3H), 3.02-3.25 (m, 5H), 3.30-3.52 (m, 3H), 3.83 (s, 4H), 4.11 (m, 1H), 4.38 (s, 2H), 7.36 (d, J=9.0 Hz, 1H), 7.56 (s, 1H), 7.66 (d, J=6.0 Hz, 1H), 7.72 (m, 1H), 7.87 (m, 1H). MS (ESI): m/z 473 (M+H)$^+$.

EXAMPLE 1067

7-Fluoro-6-(hexahydro-pyrrolo[1,2-a]pyrazin-2-yl)-3-[5-(3-isopropoxy-prop-1-ynyl)-thiophen-3-yl]-1,4-dihydro-indeno[1,2-c]pyrazole The title compound was prepared by substituting Example 1033 for Example 56 and by substituting Example 1053 for Example 110 in Example 138. $^1$H NMR (300 MHz, DMSO-$d_6$): δ 1.15 (d, J=6.0 Hz, 6H), 3.05 (m, 2H), 3.27 (m, 2H), 3.35-3.50 (m, 4H), 3.61-3.65 (m, 2H), 3.79-3.82 (m, 5H), 3.92 (m, 1H), 4.41 (s, 2H), 7.35 (t, J=9.0 Hz, 1H), 7.45 (d, J=12.0 Hz, 1H), 7.70 (s, 1H), 7.86 (s, 1H). MS (ESI): m/z 477 (M+H)$^+$.

EXAMPLE 1068

3-[5-(3-Cyclopropylmethoxy-prop-1-ynyl)-thiophen-3-yl]-7-fluoro-6-(4-methyl-piperazin-1-ylmethyl)-1,4-dihydro-indeno[1,2-c]pyrazole The title compound was prepared by substituting Example 1028 for Example 56 and by substituting Example 1054 for Example 110 in Example 138. $^1$H NMR (300 MHz, CDCl$_3$): δ 0.27 (m, 2H), 0.58 (m, 2H), 1.12 (m, 1H), 2.38 (s, 3H), 2.50-2.80 (m, 8H), 3.43 (d, J=9.0 Hz, 2H), 3.66 (s, 2H), 3.70 (s, 2H), 4.44 (s, 2H), 7.38 (d, J=9.0 Hz, 1H), 7.43 (m, 1H), 7.47 (m, 2H). MS (ESI): m/z 477 (M+H)$^+$.

EXAMPLE 1069

3-[5-(3-Cyclopropylmethoxy-prop-1-ynyl)-thiophen-3-yl]-7-fluoro-6-(4-methyl-piperazin-1yl)-1,4-dihydro-indeno[1,2-c]pyrazole The title compound was prepared by substituting Example 1029 for Example 56 and by substituting Example 1054 for Example 110 in Example 138. $^1$H NMR (300 MHz, DMSO-$d_6$): δ 0.22 (m, 2H), 0.50 (m, 2H), 1.04 (m, 1H), 2.89 (s, 3H), 3.00-3.50 (m, 8H), 3.55 (d, J=9.0 Hz, 2H), 3.78 (s, 2H), 4.43 (s, 2H), 7.33 (d, J=6.0 Hz, 1H), 7.44 (d, J=12.0 Hz, 1H), 7.70 (d, J=3.0 Hz, 1H), 7.86 (d, J=3.0 Hz, 1H), 9.75 (s, 1H). MS (ESI): m/z 463 (M+H)$^+$.

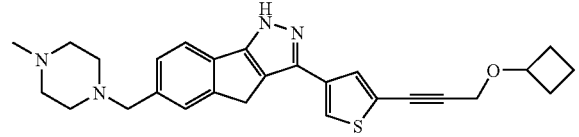

EXAMPLE 1070

3-[5-(3-Cyclobutoxy-prop-1-ynyl)-thiophen-3-y]-6-(4-methyl-piperazin-1-ylmethyl)-1,4-dihydro-indeno[1,2-c]pyrazole The title compound was prepared by substituting Example 80 for Example 56 and by substituting Example 1055 for Example 110 in Example 138. $^1$H NMR (300 MHz, CDCl$_3$): δ 1.57 (m, 1H), 1.73 (m, 1H), 2.04 (m, 2H), 2.29 (m, 2H), 2.35 (s, 3H), 2.50-2.80 (m, 8H), 3.59 (s, 2H), 3.73 (s, 2H), 4.17 (m, 1H), 4.31 (s, 2H), 7.31 (d, J=6.0 Hz, 1H), 7.43 (m, 1H), 7.50 (m, 2H), 7.65 (d, J=6.0 Hz, 1H). MS (ESI): m/z 459 (M+H)$^+$.

EXAMPLE 1071

7-Fluoro-6-(hexahydro-pyrrolo[1,2-a]pyrazin-2-yl)-3-{5-[3-(2,2,2-trifluoro-ethoxy)-prop-1-ynyl]-thiophen-3-yl}-1,4-dihydro-indeno[1,2-c]pyrazole The title compound was prepared by substituting Example 1033 for Example 56 and by substituting Example 1056 for Example 110 in Example 138. $^1$H NMR (300 MHz, DMSO-$d_6$): δ 1.96-2.12 (m, 2H), 2.20 (m, 1H), 3.04 (m, 2H), 3.27 (m, 1H), 3.38-3.48 (m, 4H), 3.61-3.92 (m, 3H), 3.78 (s, 2H), 4.18 (q, J=9.0 Hz, 2H), 4.65 (s, 2H), 7.35 (t, J=9.0 Hz, 1H), 7.43 (d, J=12.0 Hz, 1H), 7.76 (s, 1H), 7.90 (s, 1H). MS (ESI): m/z 517 (M+H)$^+$.

EXAMPLE 1072

3-[5-(3-Cyclopropylmethoxy-prop-1-ynyl)-4-thiophen-3-yl]-6-(hexahydro-pyrrolo[1,2-a]pyrazin-2-ylmethyl)-1,4-dihydro-indeno[1,2-c]pyrazole The title compound was prepared by substituting Example 1034 for Example 56 and by substituting Example 1054 for Example 110 in Example 138. $^1$H NMR (300 MHz, CDCl$_3$): δ 0.28 (m, 2H), 0.60 (m, 2H), 1.12 (m, 1H), 1.71-1.93 (m, 5H), 2.17 (m, 2H), 2.39 (m, 2H), 2.88 (m, 1H), 2.99-3.11 (m, 3H), 3.44 (d, J=6.0 Hz, 2H), 3.64 (d, J=9.0 Hz, 2H), 3.75 (s, 2H), 4.44 (s, 2H), 7.32 (d, J=6.0 Hz, 1H), 7.44 (m, 1H), 7.51 (m, 2H), 7.67 (d, J=9.0 Hz, 1H). MS (ESI): m/z 485 (M+H)$^+$.

EXAMPLE 1073

7-Fluoro-6-(4-methyl-piperazin-1-yl)-3-[5-(3-phenoxy-prop-1-ynyl)-thiophen-3-yl]-1,4-dihydro-indeno[1,2-c]pyrazole The title compound was prepared by substituting Example 1029 for Example 56 and by substituting Example 126 for Example 110 in Example 138. $^1$H NMR (300 MHz, CDCl$_3$): δ 2.44 (s, 3H), 2.73 (m, 4H), 3.23 (m, 4H), 3.64 (s, 2H), 4.95 (s, 2H), 7.02-7.12 (m, 4H), 7.31-7.41 (m, 4H), 7.46 (m, 1H). MS (ESI): m/z 485 (M+H)$^+$.

EXAMPLE 1074

3-[5-(3-Cyclopropylmethoxy-prop-1-ynyl)-thiophen-3-yl]-6-(5-methyl-2,5-diaza-bicyclo[2.2.1]hept-2-ylmethyl)-1,4-dihydro-indeno[1,2-c]pyrazole The title compound was prepared by substituting Example 1035 for Example 56 and by substituting Example 1054 for Example 110 in Example 138. $^1$H NMR (300 MHz, DMSO-ds): δ 0.21 (m, 2H), 0.50 (m, 2H), 1.04 (m, 1H), 2.88 (s, 3H), 3.35 (s, 2H), 3.37 (s, 2H), 3.86 (s, 2H), 3.41-3.82 (m, 8H), 4.44 (s, 2H), 7.52 (m, 1H), 7.71 (s, 1H), 7.74 (s, 2H), 7.90 (m, 1H). MS (ESI): m/z 471 (M+H)$^+$.

EXAMPLE 1075

3-[5-(3-Cyclopropylmethox-prop-1-ynyl)-thiophen-3-yl]-7-fluoro-6-(hexahydro-pyrrolo[1,2-a]pyrazin-2-ylmethyl)-1,4-dihydro-indeno[1,2-c]pyrazole The title compound was prepared by substituting Example 1033 for Example 56 and by substituting Example 1054 for Example 110 in Example 138. $^1$H NMR (300 MHz, CDCl$_3$): δ 0.26 (m, 2H), 0.57 (m, 2H), 1.12 (m, 1H), 1.59 (m, 1H), 1.83-1.97 (m, 4H), 2.34 (m, 2H), 2.58 (m, 1H), 2.72 (m, 1H), 3.04 (m, 1H), 3.17-3.23 (m, 2H), 3.43 (d, J=9.0 Hz, 2H), 3.48-3.56 (m, 1H), 3.60 (s, 2H), 4.43 (s, 2H), 7.12 (d, J=6.0 Hz, 1H), 7.32 (d, J=12.0 Hz, 1H), 7.38 (s, 1H), 7.43 (s, 1H). MS (ESI): m/z 489 (M+H)$^+$.

EXAMPLE 1076

4-{3-[5-(3-Cyclopropylmethoxy-prop-1-ynyl)-thiophen-3-yl]-1,4-dihydro-indeno[1,2-c]pyrazol-6-ylmethyl}-piperazine-1-carbaldehyde The title compound was prepared by substituting Example 1032 for Example 56 and by substituting Example 1054 for Example 110 in Example 138. $^1$H NMR (300 MHz, CDCl$_3$): δ 0.27 (m, 2H), 0.58 (m, 2H), 1.12 (m, 1H), 2.53 (m, 4H), 3.43 (s, 2H), 3.45 (s, 2H), 3.64 (m, 4H), 3.71 (s, 2H), 4.43 (s, 2H), 7.30 (d, J=6.0 Hz, 1H), 7.44 (m, 1H), 7.49 (m, 1H), 7.52 (s, 1H), 7.64 (d, J=9.0 Hz, 1H), 8.04 (s, 1H). MS (ESI): m/z 473 (M+H)$^+$.

EXAMPLE 1077

1-{3-[5-(3-Cyclopropylmethoxy-prop-1-ynyl)-thiophen-3-yl]-1,4-dihydro-indeno[1,2-c]pyrazol-6-ylmethyl}-4-methyl-piperazin-2-one The title compound was prepared by substituting Example 1036 for Example 56 and by substituting Example 1054 for Example 110 in Example 138. $^1$H NMR (300 MHz, DMSO-d$_6$): δ 0.22 (m, 2H), 0.51 (m, 2H), 1.04 (m, 1H), 2.22 (s, 3H), 2.58 (t, J=6.0 Hz, 2H), 3.04 (s, 2H), 3.23 (t, J=6.0 Hz, 2H), 3.36 (d, J=6.0 Hz, 2H), 3.82 (s, 2H), 4.43 (s, 2H), 4.58 (s, 2H), 7.23 (d, J=9.0 Hz, 1H), 7.42 (s, 1H), 7.63 (d, J=9.0 Hz, 1H), 7.72 (s, 1H), 7.87 (s, 1H), 13.1 (s, 1H). MS (ESI): m/z 473 (M+H)$^+$.

EXAMPLE 1078

3-[5-(3-Cyclopropylmethoxy-prop-1-ynyl)-thiophen-3-yl]-6-(hexahydro-pyrrolo[1,2-a]pyrazin-2-yl)-1,4-dihydro-indeno[1,2-c]pyrazole The title compound was prepared by substituting Example 1037 for Example 56 and by substituting Example 1054 for Example 110 in Example 138. $^1$H NMR (300 MHz, CDCl$_3$): δ 0.27 (m, 2H), 0.58 (m, 2H), 1.12 (m, 1H), 1.60 (m, 1H), 1.82-1.98 (m, 4H), 2.32 (m, 2H), 2.50 (m, 1H), 2.70 (t, J=12.0 Hz, 1H), 3.05 (m, 1H), 3.18 (m, 2H), 3.43 (d, J=9.0 Hz, 2H), 3.65 (s, 2H), 3.80 (m, 1H), 4.43 (s, 2H), 6.90 (dd, J=9.0, 3.0 Hz, 1H), 7.10 (m, 1H), 7.41 (m, 1H), 7.47 (m, 1H), 7.53 (d, J=9.0 Hz, 1H). MS (ESI): m/z 471 (M+H)$^+$.

EXAMPLE 1079

6-(4-Cyclopropyl-piperazin-1-yl)-3-{5-[3-(2-fluoro-ethoxy)-prop-1-ynyl]-thiophen-3-yl}-1,4-dihydro-indeno[1,2-c]pyrazole The title compound was prepared by substituting Example 1038 for Example 56 and by substituting Example 1057 for Example 110 in Example 138. $^1$H NMR (300 MHz, CDCl$_3$): δ 0.51-0.59 (m, 4H), 1.77 (m, 1H), 2.87 (t, J=6.0 Hz, 4H), 3.27 (t, J=6.0 Hz, 4H), 3.62 (s, 2H), 3.80 (t, J=3.0 Hz, 1H), 3.90 (t, J=3.0 Hz, 1H), 4.49 (s, 2H), 4.55 (t, J=6.0 Hz, 1H), 4.71 (t, J=6.0 Hz, 1H), 6.86 (dd, J=9.0, 3.0 Hz, 1H), 7.08 (m, 1H), 7.42 (m, 1H), 7.47 (m, 1H), 7.50 (d, J=9.0 Hz, 1H). MS (ESI): m/z 463 (M+H)$^+$.

EXAMPLE 1080

3-[5-(3-Cyclohexyloxy-prop-1-ynyl)-thiophen-3-yl]-6-(4-methyl-piperazin-1-ylmethyl)-1,4-dihydro-indeno[1,2-c]pyrazole The title compound was prepared by substituting Example 80 for Example 56 and by substituting Example 1058 for Example 110 in Example 138. $^1$H NMR (300 MHz, CDCl$_3$): δ 1.22-1.39 (m, 5H), 1.55 (m, 1H), 1.76 (m, 2H), 1.96 (m, 2H), 2.36 (s, 3H), 2.50-2.80 (m, 8H), 3.53 (m, 1H), 3.58 (s, 2H), 3.70 (s, 2H), 4.43 (s, 2H), 7.29 (s, 1H), 7.43 (m, 1H), 7.49 (m, 2H), 7.63 (d, J=9.0 Hz, 1H). MS (ESI): m/z 487 (M+H)$^+$.

EXAMPLE 1081

1-(4-{3-[5-(3-Cyclopropylmethoxy-prop-1-ynyl)-thiophen-3-yl]-1,4-dihydro-indeno[1,2-c]pyrazol-6-ylmethyl}-piperazin-1-yl)-ethanone The title compound was prepared by substituting Example 1039 for Example 56 and by substituting Example 1054 for Example 110 in Example 138. $^1$H NMR (300 MHz, CDCl$_3$): δ 0.27 (m, 2H), 0.60 (m, 2H), 1.12 (m, 1H), 2.10 (s, 3H), 2.50-2.80 (m, 8H), 3.44 (d, J=6.0 Hz, 2H), 3.68 (s, 4H), 4.44 (s, 2H), 7.29 (d, J=6.0 Hz, 1H), 7.45 (m, 1H), 7.50 (m, 1H), 7.53 (m, 1H), 7.63 (d, J=6.0 Hz, 1H). MS (ESI): m/z 487 (M+H)$^+$.

EXAMPLE 1082

1-(4-{3-[5-(3-Isopropoxy-prop-1-ynyl)-thiophen-3-yl]-1,4-dihydro-indeno[1,2-c]pyrazol-6-ylmethyl}-piperazin-1-yl)-ethanone The title compound was prepared by substituting Example 1039 for Example 56 and by substituting Example 1053 for Example 110 in Example 138. $^1$H NMR (300 MHz, CDCl$_3$): δ 1.24 (d, J=6.0 Hz, 6H), 2.10 (s, 3H), 2.55 (m, 4H), 3.51 (m, 4H), 3.67 (s, 4H), 3.85 (m, 1H), 4.40 (s, 2H), 7.29 (d, J=6.0 Hz, 1H), 7.45 (m, 1H), 7.49 (m, 114), 7.53 (m, 1H), 7.63 (d, J=6.0 Hz, 1H). MS (ESI): m/z 475 (M+H)$^+$.

EXAMPLE 1083

6-(4-Cyclopropyl-piperazin-1-yl)-7-fluoro-3-[5-(3-isopropoxy-prop-1-ynyl)-thiophen-3-yl]-1,4-dihydro-indeno[1,2-c]pyrazole The title compound was prepared by substituting Example 1040 for Example 56 and by substituting Example 1053 for Example 110 in Example 138. $^1$H NMR (300 MHz, DMSO-d$_6$): δ 0.34 (m, 2H), 0.46 (m, 2H), 1.14 (d, J=6.0 Hz, 6H), 1.70 (m, 1H), 2.71 (m, 4H), 3.01 (m, 4H), 3.32 (s, 2H), 3.75 (m, 1H), 4.41 (s, 2H), 7.21 (d, J=9.0 Hz, 1H), 7.38 (d, J=12.0 Hz, 1H), 7.70 (s, 1H), 7.85 (d, 1H), 13.0 (s, 1H). MS (ESI): m/z 477 (M+H)$^+$.

EXAMPLE 1084

3-[5-(3-Cyclopropylmethoxy-prop-1-ynyl)-thiophen-3-yl]-6-(4-methanesulfonyl-piperazin-1-ylmethyl-1,4-dihydro-indeno[1,2-c]pyrazole The title compound was prepared by substituting Example 1061 for Example 148 and by substituting Example 1048 for (prop-2-ynyloxy)benzene in Example 655. $^1$H NMR (400 MHz, DMSO-d$_6$): δ 0.20 (m, 2H), 0.46 (m, 2H), 1.00 (m, 1H), 2.50 (m, 4H), 2.83 (s, 3H), 3.17 (m, 4H), 3.36 (d, J=8.0 Hz, 2H), 3.58 (s, 2H), 3.80 (s, 2H), 4.40 (s, 2H), 7.28 (d, J=8.0 Hz, 1H), 7.47 (s, 1H), 7.60 (d, J=8.0 Hz, 1H), 7.68 (s, 1H), 7.82 (s, 1H), 13.10 (s, 1H). MS (ESI): m/z 523 (M+H)$^+$.

EXAMPLE 1085

3-[5-(3-Cyclopropylmethoxy-prop-1-ynyl)-thiophen-3-yl]-7-fluoro-6-(4-methanesulfonyl-piperazin-1-yl)-1,4-dihydro-indeno[1,2-c]pyrazole The title compound was prepared by substituting Example 1062 for Example 148 and by substituting Example 1048 for (prop-2-ynyloxy)benzene in Example 655. $^1$H NMR (500 MHz, DMSO-d$_6$): δ 0.20 (m, 2H), 0.50 (m, 2H), 1.02 (m, 1H), 2.92 (s, 3H), 3.19 (m, 4H), 3.30 (m, 4H), 3.36 (d, J=8.0 Hz, 2H), 3.78 (s, 2H), 4.42 (s, 2H), 7.27 (d, J=8.0 Hz, 1H), 7.42 (d, J=10.0 Hz, 1H), 7.72 (s, 1H), 7.85 (s, 1H), 13.20 (s, 1H). MS (ESI): m/z 527 (M+H)$^+$.

EXAMPLE 1086

7-Fluoro-6-(4-methyl-piperazin-1-ylmethyl)-3-[5-(3-phenoxy-prop-1-ynyl)-thiophen-3-yl]-1,4-dihydro-indeno[1,2-c]pyrazole The title compound was prepared by substituting Example 1028 for Example 56 and by substituting Example 126 for Example 110 in Example 138. $^1$H NMR (500 MHz, DMSO-d$_6$): δ 2.15 (s, 3H), 2.26-2.47 (m, 8H), 3.54 (s, 2H), 3.79 (brs, 2H), 5.11 (s, 2H), 6.99-7.02 (m, 1H), 7.05 (m, 2H), 7.33-7.36 (m, 2H), 7.40 (d, J=6.6 Hz, 1H), 7.53 (d, J=6.6 Hz, 1H), 7.72 (s, 1H), 7.89 (s, 1H), 13.21 (br s, 1H). MS (ESI): m/z 499 (M+H)$^+$.

EXAMPLE 1087

6-[2-(4-Methyl-piperazin-1-yl)-ethyl]-3-[5-(3-phenoxy-prop-1-ynyl)-thiophen-3-yl]1,4-dihydro-indeno[1,2-c]pyrazole The title compound was prepared by substituting Example 1045 for Example 56 and by substituting Example 126 for Example 110 in Example 138. $^1$H NMR (500 MHz, DMSO-d$_6$): δ 2.14 (s, 3H), 2.24-2.50 (m, 8H), 2.52 (dd, J=8.6, 7.2 Hz, 2H), 2.77 (dd, J=8.6, 7.2 Hz, 2H), 3.75 (brs, 2H), 5.09 (s, 2H), 6.98-7.01 (m, 1H), 7.05 (m, 2H), 7.19 (d, J=7.8, 1H), 7.32-7.35 (m, 2H), 7.39 (s, 1H), 7.53 (d, J=7.8 Hz, 1H), 7.71 (s, 1H), 7.86 (s, 1H), 13.05 (br s, 1H). MS (ESI): m/z 495 (M+H)$^+$.

EXAMPLE 1088

3-[5-(3-Isopropoxy-prop-1-ynyl)-thiophen-3-yl]-6-(4-methyl-piperazin-1-yl)-1,4-dihydro-indeno[1,2-c]pyrazole The title compound was prepared by substituting Example 65 for Example 56 and by substituting Example 1053 for Example 110 in Example 138. $^1$H NMR (500 MHz, DMSO-d$_6$): δ 1.16 (d, J=6 Hz, 1H), 2.88 (s, 2H), 3.02 (m, 2H), 3.19 (m, 2H), 3.54 (m, 2H), 3.78 (m, 3H), 4.39 (m, 2H), 4.41 (s, 2H), 7.01 (d, J=10.0 Hz, 1H), 7.24 (s, 1H), 7.53 (d, J=10.0 Hz, 1H), 7.69 (s, 1H), 7.83 (s, 1H), 9.72 (bs, 1H). MS (ESI): m/z 433 (M+H)$^+$.

EXAMPLE 1089

6-(4-Methyl-piperazin-1-yl)-3-[5-(3-phenoxy-prop-1-ynyl)-thiophen-3-yl]-1,4-dihydro-indeno[1,2-c]pyrazole The title compound was prepared by substituting Example 65 for Example 56 and by substituting Example 126 for Example 110 in Example 138. $^1$H NMR (500 MHz, DMSO-d$_6$): δ 2.87 (s, 2H), 3.00 (m, 2H), 3.17 (m, 2H), 3.52 (m, 2H), 3.74 (s, 2H), 3.87 (m, 2H), 5.09 (s, 2H), 6.97-7.08 (m, 3H), 7.22-7.34 (m, 2H), 7.53 (m, 3H), 7.61 (m, 3H). MS (ESI): m/z 467 (M+H)$^+$.

EXAMPLE 1090

3-[5-(3-Cyclopropylmethoxy-prop-1-ynyl)-thiophen-3-yl]-6-(4-methyl-piperazin-1-ylmethyl)-1,4-dihydro-indeno[1,2-c]pyrazole The title compound was prepared by substituting Example 80 for Example 56 and by substituting Example 1054 for Example 110 in Example 138. $^1$H NMR (500 MHz, DMSO-$d_6$): δ 0.22 (m, 2H), 0.50 (m, 2H), 1.05 (m, 1H), 1.18 (m, 4H), 2.67 (m, 2H), 3.08 (m, 4H), 3.35 (d, J=9 Hz, 2H), 3.69 (m, 2H), 3.82 (s, 2H), 4.43 (s, 3H), 7.30 (s, 1H), 7.60 (m, 1H), 7.63 (s, 1H), 7.70 (m, 1H), 7.88 (s, 1H), 13.11 (s, 1H). MS (ESI): m/z 459 (M+H)$^+$.

EXAMPLE 1091

3-[5-(3-Cyclopropylmethoxy-prop-1-ynyl)-thiophen-3-yl]-6-(4-cyclopropyl-piperazin-1-yl)-1,4-dihydro-indeno[1,2-c]pyrazole The title compound was prepared by substituting Example 1038 for Example 56 and by substituting Example 1054 for Example 110 in Example 138. $^1$H NMR (500 MHz, CD$_3$OD): δ 0.26 (m, 2H), 0.50 (m, 2H), 0.55 (m, 4H), 1.09 (m, 1H), 1.77 (m, 1H), 2.85 (t, J=9 Hz, 4H), 3.23 (t, J=9 Hz, 4H), 3.44 (d, J=9.0 Hz, 2H), 3.74 (s, 2H), 4.44 (s, 2H), 6.98 (dd, J=9.0, 3.0 Hz, 1H), 7.21 (s, 1H), 7.54 (dd, J=9.0, 3.0 Hz, 1H), 7.60 (s, 1H), 7.67 (s, 1H). MS (ESI): m/z 445 (M+H)$^+$.

EXAMPLE 1092

1-{3-[5-(3-Cyclopropylmethoxy-prop-1-ynyl)-thiophen-3-yl]-1,4-dihydro-indeno[1,2-c]pyrazol-6-yl}-4-methyl-piperidin-4-ol The title compound was prepared by substituting Example 1043 for Example 56 and by substituting Example 1054 for Example 110 in Example 138. $^1$H NMR (500 MHz, CD$_3$OD): δ 0.27 (m, 2H), 0.58 (m, 2H), 1.09 (m, 1H), 1.39 (s, 3H), 1.68 (m, 1H), 1.96 (m, 2H), 2.06 (m, 2H), 3.44 (t, J=9 Hz, 4H), 3.58 (d, J=14.0 Hz, 2H), 3.87 (d, J=14.0 Hz, 2H), 3.92 (s, 2H), 4.44 (s, 2H), 7.58 (m, 2H), 7.63 (s, 1H), 7.73 (s, 1H), 7.84 (m, 3H). MS (ESI): m/z 460 (M+H)$^+$.

EXAMPLE 1093

3-[5-(3-Cyclopropylmethoxy-prop-1-ynyl)-thiophen-3-yl]-6-(4-cyclopropyl-piperazin-1-ylmethyl)-1,4-dihydro-indeno[1,2-c]pyrazole The title compound was prepared by substituting Example 1044 for Example 56 and by substituting Example 1054 for Example 110 in Example 138. $^1$H NMR (500 MHz, DMSO-$d_6$): δ 0.26 (m, 2H), 0.57 (m, 4H), 0.64 (m, 2H), 1.07 (m, 1H), 2.07 (m, 1H), 3.06 (m, 4H), 3.22 (m, 4H), 3.44 (m, 2H), 3.87 (s, 2H), 4.29 (s, 2H), 4.44 (s, 2H), 7.49 (s, d, J=10 Hz, 1H), 7.63 (s, 1H), 7.69 (s, 1H), 7.73 (s, 1H), 7.79 (d, J=10 Hz, 1H). MS (ESI): m/z 485 (M+H)$^+$.

EXAMPLE 1094

(4-Methyl-piperazin-1-yl)-{1-[5-(3-phenoxy-prop-1-ynyl)-thiophen-3-yl]-3,8-dihydro-2,3,7-triaza-cyclopenta[a]inden-5-yl}-methanone

EXAMPLE 1094A

3-Amino-cyclopent-2-enone

The title compound was prepared according to the procedure given in: Kikani, B. B. et al. Synthesis, 1991, 176

EXAMPLE 1094B

5-Oxo-6,7-dihydro-5H-[1]pyrindine-3-carboxylic acid ethyl ester

Ethyl 2-formyl-3-oxopropanoate (3.2 g, 22 mmol) in diethyl ether (25 mL) was teated with triethylamine (3.5 mL, 25 mmol) at about 0° C. The mixture was stirred at room temperature for about 1 h before the diethyl ether was removed in vacuo. To the residue was added a solution of p-toluenesulfonyl chloride (4.5 g, 23.6 mmol) in N,N-dimethylformamide (60 mL) at about 0° C. The mixture was stirred for about 5 h while being allowed to warm to room temperature. 3-Aminocyclopent-2-en-1-one (1.75 g, 18 mmol) was added and the mixture was heated to about 85-90° C. over night. The mixture was cooled to room temperature and was concentrated in vacuo. The residue was diluted with chloroform (200 mL), washed with sodium carbonate solution, filtered through Celite, and concentrated under vacuum. The residue was purified by flash column chromatography on silica gel using dichloromethane/methanol/ammonium hydroxide (95:4.5:0.5) as the mobile phase to provide the title compound: $^1$H NMR (300 MHz, CDCL$_3$): δ 1.42 (t, J=8.0 Hz, 3H), 2.82 (t, J=8.0 Hz, 2H), 3.38 (t, J=8.0 Hz, 2H), 4.42 (q, J=8.0 Hz, 3H), 8.60 (s, 1H), 9.40 (s, 1H).

EXAMPLE 1094C

1-[5-(3-Phenoxy-prop-1-ynyl)-thiophen-3-yl]-3,8-dihydro-2,3,7-triaza-cyclopenta[a]indene-5-carboxylic acid ethyl ester To a mixture of Example 126 (1.5 g, 4.6 mmol) and a 60% suspension of sodium hydride in mineral oil (470 mg, 11.7 mmol) in tetrahydrofuran (10 mL) was added a solution of Example 1094B (1.0 g, 4.8 mmol) in tetrahydrofuran (15 mL) dropwise over a period of about 30 min. The mixture was stirred at room temperature for about 2 h and then the reaction was quenched by slow addition of a solution of acetic acid (0.9 g, 15 mmol) in methanol (80 mL). The solvents were evaporated to dryness under vacuum. The residue was dissolved in ethanol (100 mL), hydrazine monohydrate (0.5 g, 10 mmol) and acetic acid (0.6 g, 10 mmol) were added and the mixture was heated to reflux for about 1 hour. The mixture was cooled, concentrated under vacuum and the residue was purified by flash chromatography on silica gel using dichloromethane/methanol (10:1)+1% ammonium hydroxide as eluent to provide the title compound. $^1$H NMR (300 MHz, DMSO-$d_6$): δ 1.42 (t, J=8.0 Hz, 3H), 4.01 (s, 2H), 4.40 (q, J=8.0 Hz, 3H), 5.10 (s, 2H), 7.02 (m, 3H), 7.38 (m, 2H), 7.80 (s, 1H), 8.00 (s, 1H), 8.40 (s, 1H), 9.00 (s, 1H), 13.50 (s, 1H).

EXAMPLE 1094D

1-[5-(3-Phenoxy-prop-1-ynyl)-thiophen-3-yl]-3,8-dihydro-2,3,7-triaza-cyclopenta[a]indene-5-carboxylic acid To Example 1094C (88 mg, 0.2 mmol) in (1:1) methanol/tetrahydrofuran (2 mL) was added a 1N aqueous solution of sodium hydroxide (2 mL). The mixture was stirred at room temperature over night and was then acidified by slow addition of a 1N aqueous solution of hydrogen chloride. The mixture was concentrated, the precipitate was filtered, washed with water and dried in vacuum to give the title compound. $^1$H NMR (300 MHz, DMSO-d$_6$): δ 4.01 (s, 2H), 5.12 (s, 2H), 7.02 (m, 3H), 7.38 (m, 2H), 7.80 (s, 1H), 8.00 (s, 1H), 8.39 (s, 1H), 8.98 (s, 1H), 13.45 (s, 1H).

EXAMPLE 1094E (4-Methyl-piperazin-1-yl)-{1-[5-(3-phenoxy-prop-1-ynyl)-thiophen-3-yl]-3,8-dihydro-2,3,7-triaza-cyclopenta[a]inden-5-yl}-methanone A mixture of Example 1094D (68 mg, 0.16 mmol), N-cyclohexylcarbodiimide-N'-methyl polystyrene (1.0 g, 1.28 mmol) and 1-hydroxybenzotriazole hydrate (44 mg, 0.33 mmol) in (2:1) dichloromethane/N,N-dimethylacetamide (10 mL) was agitated for about 15 min. 1-Methylpiperazine (77 mg, 0.77 mmol) was added, the mixture was agitated at room temperature for about 18 h, filtered and concentrated under vacuum. The residue was purified by flash column chromatography on silica gel using dichloromethane/methanol/ammonium hydroxide (100:8:0.1) as the mobile phase to provide the title compound. $^1$H NMR (500 MHz, DMSO-d$_6$): δ 2.23 (s, 3H), 2.39 (m, 4H), 3.40 (m, 2H), 3.63 (m, 2H), 3.97 (s, 2H), 5.09 (s, 2H), 7.03 (m, 3H), 7.38 (m, 2H), 7.80 (s, 1H), 8.01 (m, 2H), 8.41 (s, 1H), 13.41 (s, 1H). MS (ESI): m/z 496 (M+H)$^+$.

EXAMPLE 1095

2-Methyl-N-{3-[4-(6-[1,2,4]triazol-1-ylmethyl-1,4-dihydro-indeno[1,2-c]pyrazol-3-yl)-thiophen-2-yl]-prop-2-ynyl}-benzenesulfonamide The title compound was prepared by substituting 2-methyl-N-prop-2-ynyl-benzenesulfonamide for (prop-2-ynyloxy)benzene and by substituting Example 260 for phenyl 5-bromothiophene-3-carboxylate in Example 126. $^1$H NMR (500 MHz, DMSO-D$_6$), δ ppm 2.63 (s, 3H), 3.81 (s, 2H), 4.04 (d, J=5.61 Hz, 2H), 5.51 (s, 2H), 7.32 (d, J=7.80 Hz, 1H), 7.37-7.42 (m, 2H), 7.45 (d, J=1.25 Hz, 1H), 7.49-7.53 (m, 2H), 7.64 (d, J=7.80 Hz, 1H), 7.82 (d, J=1.56 Hz, 1H), 7.88-7.94 (m, 1H), 8.11-8.18 (m, 1H), 8.26 (t, J=5.93 Hz, 1H), 8.91 (s, 1H); MS ESI(+) m/e 527 (M+H)$^+$.

EXAMPLE 1096

3-Methyl-N-{3-[4-(6-[1,2,4]triazol-1-ylmethyl-1,4-dihydro-indeno[1,2-c]pyrazol-3-yl)-thiophen-2-yl]-prop-2-ynyl}-benzenesulfonamide The title compound was prepared by substituting 3-methyl-N-prop-2-ynyl-benzenesulfonamide for (prop-2-ynyloxy)benzene and by substituting Example 260 for phenyl 5-bromothiophene-3-carboxylate in Example 126. $^1$H NMR (500 MHz, DMSO-D$_6$) δ ppm 2.37 (s, 3H), 3.79 (d, J=4.05 Hz, 2H), 4.02-4.07 (m, 2H), 5.49 (s, 2H), 7.30 (d, J=7.49 Hz, 1H), 7.42-7.51 (m, 3H), 7.53-7.58 (m, 1H), 7.60-7.64 (m, 2H), 7.65-7.69 (m, 1H), 7.78-7.83 (m, 1H), 8.05 (s, 1H), 8.18 (t, J=5.93 Hz, 1H), 8.77 (s, 1H); MS ESI(+) m/e 527 (M+H)$^+$.

EXAMPLE 1097

2-Fluoro-N-{3-[4-(6-[1,2,4]triazol-1-ylmethyl-1,4-dihydro-indeno[1,2-c]pyrazol-3-yl)-thiophen-2-yl]-prop-2-ynyl}-benzenesulfonamide The title compound was prepared by substituting 2-fluoro-N-prop-2-ynyl-benzenesulfonamide for (prop-2-ynyloxy)benzene and by substituting Example 260 for phenyl 5-bromothiophene-3-carboxylate in Example 126. $^1$H NMR (500 MHz, DMSO-D$_6$) δ ppm 3.78 (s, 2H), 4.12 (s, 2H), 5.47 (s, 2H), 7.29 (d, J=7.80 Hz, 1H), 7.36-7.46 (m, 3H), 7.49 (s, 1H), 7.62 (s, 1H), 7.65-7.70 (m, 1H), 7.77 (s, 1H), 7.84-7.88 (m, 1H), 7.98 (s, 1H), 8.46-8.50 (m, J=1.25 Hz, 1H), 8.67 (s, 1H), 13.13 (s, 1H); MS ESI(+) m/e 531 (M+H)$^+$.

EXAMPLE 1098

4-Fluoro-N-{3-[4-(6-[1,2,4]triazol-1-ylmethyl-1,4-dihydro-indeno[1,2-c]pyrazol-3-yl)-thiophen-2-yl]-prop-2-ynyl}-benzenesulfonamide The title compound was prepared by substituting 4-fluoro-N-prop-2-ynyl-benzenesulfonamide for (prop-2-ynyloxy)benzene and by substituting Example 260 for phenyl 5-bromothiophene-3-carboxylate in Example 126. $^1$H NMR (500 MHz, DMSO-D$_6$) δ ppm 3.79 (s, 2H), 4.07 (d, J=6.24 Hz, 2H), 5.48 (s, 2H), 7.28 (d, J=7.49 Hz, 1H), 7.41-7.43 (m, 2H), 7.44 (d, J=1.87 Hz, 1H), 7.47 (s, 1H), 7.64 (m, 1H), 7.80 (s, 1H), 7.90-7.94 (m, 2H), 8.09 (s, 1H), 8.27 (t, J=5.77 Hz, 1H), 8.81 (s, 1H), 13.13 (s, 1H); MS ESI(+) m/e 531 (M+H)$^+$.

EXAMPLE 1099

3-Chloro-N-{3-[4-(6-[1,2,4]triazol-1-ylmethyl-1,4-dihydro-indeno[1,2-c]pyrazol-3-yl)-thiophen-2-yl]-prop-2-ynyl}-benzenesulfonamide The title compound was prepared by substituting 3-chloro-N-prop-2-ynyl-benzenesulfonamide for (prop-2-ynyloxy)benzene and by substituting Example 260 for phenyl 5-bromothiophene-3-carboxylate in Example 126. $^1$H NMR (500 MHz, DMSO-D$_6$) δ ppm 3.78 (s, 2H), 4.11 (s, 2H), 5.47 (s, 2H), 7.29 (d, J=7.80 Hz, 1H), 7.42-7.45 (m, J=2.50 Hz, 1H), 7.49 (s, 1H), 7.63 (s, 1H), 7.64 (s, 1H), 7.68-7.71 (m, 1H), 7.79 (s, 1H), 7.81-7.84 (m, 1H), 7.87 (t, J=1.87 Hz, 1H), 7.98 (s, 1H), 8.40 (s, 1H), 8.67 (s, 1H), 13.13 (s, 1H); MS ESI(+) m/e 547 (M+H)$^+$.

EXAMPLE 1100

4-Chloro-N-{3-[4-(6-[1,2,4]triazol-1-ylmethyl-1,4-dihydro-indeno[1,2-c]pyrazol-3-yl)-thiophen-2-yl]-prop-2-ynyl}-benzenesulfonamide The title compound was prepared by substituting 4-chloro-N-prop-2-ynyl-benzenesulfonamide for (prop-2-ynyloxy)benzene and by substituting Example 260 for phenyl 5-bromothiophene-3-carboxylate in Example 126. $^1$H NMR (500 MHz, DMSO-D$_6$) δ ppm 3.79 (s, 2H), 3.79 (s, 1H), 4.08 (d, J=5.93 Hz, 2H), 5.47 (s, 2H), 7.29 (d, J=7.80 Hz, 1H), 7.43 (d, J=1.56 Hz, 1H), 7.48 (s, 1H), 7.62 (d, J=7.80 Hz, 1H), 7.66 (d, J=8.73 Hz, 2H), 7.79 (d, J=1.25 Hz, 1H), 7.86 (d, J=8.73 Hz, 2H), 7.99 (s, 1H), 8.34 (t, J=6.08 Hz, 1H), 8.69 (s, 1H), 13.11 (s, 1H); MS ESI(+) m/e 547 (M+H)$^+$.

EXAMPLE 1101

3-Fluoro-N-{3-[4-(6-[1,2,4]triazol-1-ylmethyl-1,4-dihydro-indeno[1,2-c]pyrazol-3-yl)-thiophen-2-yl]-prop-2-ynyl}-benzenesulfonamide The title compound was prepared by substituting 3-fluoro-N-prop-2-ynyl-benzenesulfonamide for (prop-2-ynyloxy)benzene and by substituting Example 260 for phenyl 5-bromothiophene-3-carboxylate in Example 126. $^1$H NMR (500 MHz, DMSO-D$_6$) δ ppm 3.78 (s, 2H), 4.10 (s, 2H), 5.47 (s, 2H), 7.29 (d, J=7.80 Hz, 1H), 7.44 (s, 1H), 7.46-7.51 (m, 2H), 7.63-7.65 (m, 2H), 7.66 (t, J=2.18 Hz, 1H), 7.70-7.73 (m, 1H), 7.78 (s, 1H), 7.98 (s, 1H), 8.39 (s, 1H), 8.67 (s, 1H), 13.14 (s, 1H); MS ESI(+) m/e 531 (M+H)$^+$.

EXAMPLE 1102

4-Methyl-N-{3-[4-(6-[1,2,4]triazol-1-ylmethyl-1,4-dihydro-indeno[1,2-c]pyrazol-3-yl)-thiophen-2-yl]-prop-2-ynyl}-benzenesulfonamide The title compound was prepared by substituting 4-methyl-N-prop-2-ynyl-benzenesulfonamide for (prop-2-ynyloxy)benzene and by substituting Example 260 for phenyl 5-bromothiophene-3-carboxylate in Example 126. $^1$H NMR (400 MHz, DMSO-D$_6$) δ ppm 2.33 (s, 3H), 3.79 (s, 2H), 4.03 (s, 2H), 5.48 (s, 2H), 7.30 (d, J=8.59 Hz, 1H), 7.39 (d, J=7.98 Hz, 2H), 7.44 (s, 1H), 7.49 (s, 1H), 7.63 (d, J=5.83 Hz, 1H), 7.74 (d, J=8.29 Hz, 2H), 7.79 (s, 1H), 7.99 (s, 1H), 8.13 (s, 1H), 8.69 (s, 1H), 13.15 (s, 1H); MS ESI(+) m/e 527 (M+H)$^+$.

EXAMPLE 1103

N-{3-[4-(6-[1,2,4]Triazol-1-ylmethyl-1,4-dihydro-indeno[1,2-c]pyrazol-3-yl)-thiophen-2-yl]-prop-2-ynyl}-3-trifluoromethyl-benzenesulfonamide The title compound was prepared by substituting N-prop-2-ynyl-3-trifluoromethylbenzenesulfonamide for (prop-2-ynyloxy)benzene and by substituting Example 260 for phenyl 5-bromothiophene-3-carboxylate in Example 126. $^1$H NMR (500 MHz, DMSO-D$_6$) δ ppm 3.75 (s, 2H), 4.14 (d, J=6.24 Hz, 2H), 5.50 (s, 2H), 7.23 (d, J=7.80 Hz, 1H), 7.39 (s, 1H), 7.51-7.56 (m, 2H), 7.77 (s, 1H), 7.85 (t, J=7.95 Hz, 1H), 7.99 (d, J=8.11 Hz, 1H), 8.04-8.11 (m, 1H), 8.14 (s, 1H), 8.17 (d, J=7.80 Hz, 1H), 8.51 (t, J=6.08 Hz, 1H), 8.81 (s, 1H); MS ESI(+) m/e 581 (M+H)$^+$.

EXAMPLE 1104 (A-842679.0)

N-{3-[4-(6-[1,2,4]Triazol-1-ylmethyl-1,4-dihydro-indeno[1,2-c]pyrazol-3-yl)-thiophen-2-yl]-prop-2-ynyl}-2-trifluoromethoxy-benzenesulfonamide The title compound was prepared by substituting N-prop-2-ynyl-2-trifluoromethylbenzenesulfonamide for (prop-2-ynyloxy)benzene and by substituting Example 260 for phenyl 5-bromothiophene-3-carboxylate in Example 126. $^1$H NMR (500 MHz, DMSO-D$_6$) δ ppm 3.78 (s, 2H), 4.13 (d, J=5.93 Hz, 2H), 5.48 (s, 2H), 7.29 (d, J=7.80 Hz, 1H), 7.41 (d, J=0.94 Hz, 1H), 7.49 (s, 1H), 7.53-7.58 (m, 2H), 7.62 (d, J=7.80 Hz, 1H), 7.72-7.76 (m, 1H), 7.77 (d, J=1.25 Hz, 1H), 8.01 (dd, J=8.11, 1.56 Hz, 1H), 8.07 (s, 1H), 8.39 (t, J=6.08 Hz, 1H), 8.80 (s, 1H); MS ESI(+) m/e 597 (M+H)$^+$.

EXAMPLE 1105

N-(3-{4-[7-(4-Methyl-piperazin-1-ylmethyl)-2,4-dihydro-indeno[1,2-c]pyrazol-3-yl]-thiophen-2-yl}-prop-2-ynyl)-isonicotinamide The title compound was prepared by substituting Example 149 for 2-bromothiophene-4-carboxylate and N-prop-2-ynyl-isonicotinamide for (prop-2-ynyloxy)benzene in Example 126. $^1$H NMR (300 MHz, DMSO-D$_6$) δ ppm 2.15 (s, 3H), 2.20-2.48 (m, 8H), 3.52 (s, 2H), 3.78 (s, 2H), 4.42 (d, J=5.42 Hz, 2H), 7.20 (d, J=7.80 Hz, 1H), 7.48 (d, J=7.80 Hz, 1H), 7.57 (s, 1H), 7.68 (s, 1H), 7.78-7.83 (m, 3H), 8.75 (m, 2H), 9.38 (t, J=5.42 Hz, 1H), 13.12 (s, 1H); MS ESI(+) m/e 509.4 (M+H)$^+$.

EXAMPLE 1106

3-{5-[3-(2,2-Dimethyl-[1,3]dioxolan-4-ylmethoxy)-prop-1-ynyl]-thiophen-3-yl}-7-(4-methyl-piperazin-1-ylmethyl)-2,4-dihydro-indeno[1,2-c]pyrazole

EXAMPLE 1106A 2,2-Dimethyl-4-prop-2-ynyloxymethyl-[1,3]dioxolane

A 0° C. solution of (2,2-dimethyl-1,3-dioxolan-4-yl)methanol (Aldrich, 1 g) in THF (20 mL) was treated with NaH (327 mg, 60% oil dispersion), then refluxed for 60 min. The resulting suspension was cooled in an ice bath, treated with nBu$_4$NI (55 mg) and propargyl bromide (0.9 mL) then stirred at r.t. for 2 h. The reaction was partitioned between water and ether (2×) and the combined ether extacts were dried (MgSO$_4$), concentrated to give 1.3 g of the title compound. MS ESI(+) m/e 170.9 (M+H)$^+$.

EXAMPLE 1106B

3-{5-[3-(2,2-Dimethyl-[1,3]dioxolan-4-ylmethoxy)-prop-1-ynyl]-thiophen-3-yl}-7-(4-methyl-piperazin-1-ylmethyl)-2,4-dihydro-indeno[1,2-c]pyrazole The title compound was prepared by substituting Example 149 for 2-bromothiophene-4-carboxylate and Example 1106A for (prop-2-ynyloxy)benzene in Example 126. $^1$H NMR (300 MHz, DMSO-D$_6$) δ ppm 1.28 (s, 3H), 1.34 (s, 3H), 2.21 (s, 3H), 2.41 (s, 8H), 3.56 (m, 4H), 3.62-3.67 (m, 1H), 3.80 (m, 2H), 3.99-4.04 (m, 1H), 4.20-4.28 (m, 1H), 4.49 (s, 2H), 7.21 (d, J=7.80 Hz, 1H), 7.49 (d, J=7.80 Hz, 1H), 7.50-7.90 (m, 3H), 13.15 (s, 1H); MS ESI(+) m/e 519.2 (M+H)$^+$.

EXAMPLE 1107

5-Fluoro-7-(4-methyl-piperazin-1-ylmethyl)-3-[5-(3-phenoxy-prop-1-ynyl)-thiophen-3-yl]-1,4-dihydro-indeno[1,2-c]pyrazole

EXAMPLE 1107A

4-Fluoro-6-(4-methyl-piperazin-1-ylmethyl)-indan-1-one

The title compound was prepared by substituting 3-[2-fluoro-4-(4-methyl-piperazin-1-ylmethyl)-phenyl]propionic acid (J. Med. Chem. 1991, 2504) for Example 1 in Example 3

EXAMPLE 1107B

5-Fluoro-7-(4-methyl-piperazin-1-ylmethyl)-3-[5-(3-phenoxy-prop-1-ynyl)-thiophen-3-yl]-1,4-dihydro-indeno[1,2-c]pyrazole The title compound was prepared by substituting Example 1107A for Example 56 and 5-(3-phenoxy-prop-1-ynyl)-thiophene-3-carboxylic acid phenyl ester for Example 110 in Example 138. $^1$H NMR (300 MHz, DMSO-D$_6$) δ ppm 2.19 (s, 3 H); 2.28-2.48 (m, 8H); 3.56 (s, 2 H); 3.86 (s, 2 H); 5.11 (s, 2 H); 6.95-7.12 (m, 4H); 7.35 (dd, J=8.48, 7.46 Hz, 2H); 7.45 (s, 1 H); 7.77 (s, 1 H); 7.94 (s, 1H); 13.27 (s, 1H). MS (ESI) m/e 499(M+1)$^+$, 497(M−1)$^−$.

EXAMPLE 1108 A-862356.6

3-[5-(3-Cyclopropylmethoxy-prop-1-ynyl)-thiophen-3-yl]-5-fluoro-7-(4-methyl-piperazin-1-ylmethyl)-1,4-dihydro-indeno[1,2-c]pyrazole The title compound was prepared by substituting Example 1107A for Example 56 and 5-(3-cyclopropylmethoxy-prop-1-ynyl)-thiophene-3-carboxylic acid phenyl ester for Example 110 in Example 138. 1H NMR (300 MHz, DMSO-D$_6$) δ ppm 0.08-0.31 (m, J=6.44 Hz, 2 H); 0.35-0.61 (m, J=10.17 Hz, 2H); 0.89-1.22 (m, 1H); 2.79 (s, 3H); 2.90-3.22 (m, 4H); 3.36 (d, J=6.78 Hz, 2 H); 3.37-3.66 (m, 4 H); 3.73 (s, 2H); 3.89 (s, 2H); 4.40 (s, 2H); 7.12 (d, J=9.83 Hz, 1H); 7.51 (s, 1 H); 7.75 (s, 1 H); 7.92 (d, J=1.36 Hz, 1 H); 9.35 (s, 1 H). MS (ESI) m/e 477(M+1)$^+$, 475(M−1)$^−$

EXAMPLE 1109

3-{5-[3-(cyclopropylmethoxy)prop-1-ynyl]thien-3-yl}-6-(4-methylpiperazin-1-yl)-1H-[1]benzofuro[3,2-c]pyrazole

EXAMPLE 1109A

2-Bromo-1-(4-fluoro-2-hydroxy-phenyl)-ethanone

A solution of 1-(4-fluoro-2-hydroxy-phenyl)-ethanone (15.4 g, Aldrich) in EtOAc (100 mL) was treated with AlCl$_3$ (133 mg), stirred at r.t. for 30 min, treated with montmorillonite K10 (2.5 g) stirred an additional 30 min then treated with a solution of bromine (7.05 mL) in EtOAc (100 mL) (added dropwise via addition funnel over 1.5 h). The reaction was stirred at r.t. for 1 h, cooled in a an ice bath and quenched with water added dropwise. The mixture was diluted with EtOAc, filtered through celite and the filtrate was extracted with EtOAc (2×). The combined organic extracts were dried (Na2SO4), concentrated and teh crude product was purified via silica gel chromatography eluting with 5% EtOAc-hexanes to give 3.31 g of the title compound. MS (ESI) m/e 437(2M+H)$^+$.

EXAMPLE 1109B

6-Fluoro-benzofuran-3-one

CsCO$_3$ (5.36 g) was added in portions over 10 min to an ice cold solution of Example 1109A (3.2 g) in DMF (140 mL). The resulting mixture was stirred for 30 min then diluted with water and extracted with ether (3×). the combined extracts were dried (Na$_2$SO$_4$), and concentrated to give 1.6 g of the title compound. MS ESI(−) m/e 151.1 (M−H)$^−$.

EXAMPLE 1109C 6-(4-Methyl-piperazin-1-yl)-benzofuran-3-one

A mixture of Example 1109B (0.152 g) and 1-methylpiperazine (0.22 g) in DMSO (1 ml) was heated at 150 C for 30 min, allowed to cool to r.t. (room temperature) then partitioned between water and EtOAc. Organics were dried (Na$_2$SO$_4$), concentrated and purified via silica gel chromatography eluting with 5% MeOH-CH$_2$Cl$_2$ to give the title compound. MS ESI(+)m/e 233.0(M+H)$^+$.

EXAMPLE 1109D 3-(5-bromothien-3-yl)-6-(4-methylpiperazin-1-yl)-1H-[1]benzofuro[3,2-c]pyrazole The title compound was prepared by substituting Examples 1109C and 113 for Examples 56 and 110 respectively in Example 138. MS DCI/NH$_3$ m/e 417.0, 419.0 (M+H)$^+$.

EXAMPLE 1109E

3-{5-[3-(cyclopropylmethoxy)prop-1-ynyl]thien-3-yl}-6-(4-methylpiperazin-1-yl)-1H-[1]benzofuro[3,2-c]pyrazole The title compound was prepared by substituting Example 1109D for 2-bromothiophene-4-carboxylate and Example 1048 for (prop-2-ynyloxy)benzene in Example 126. $^1$H NMR (DMSO-d$_6$, 300 MHz): 13.30 (s, 1/2H); 13.02 (s, 1/2H); 7.85 (s, 1H); 8.65-8.74(m, 1H); 8.55-8.62(m, 1H); 7.17-7.25(m, 1H); 6.96-7.07(m, 1H); 4.44(s, 2H); 3.36(d, 2H, J=6); 3.21-3.28(m, 4H); 2.43-2.54(m, 4H); 2.24 (s, 3H); 0.99-1.10 (m, 1H); 0.47-0.55(m, 2H); 0.19-0.26 (m, 2H). MS ESI(+) m/e 447.0(M+H)$^+$.

EXAMPLE 1110

3-{5-[3-(cyclopentyloxy)prop-1-ynyl]thien-3-yl}-6-(4-methylpiperazin-1-yl)-1H-[1]benzofuro[3,2-c]pyrazole The title compound was prepared by substituting Example 1109D for 2-bromothiophene-4-carboxylate and Example 1046 for (prop-2-ynyloxy)benzene in Example 126. $^1$H NMR (300 MHz, DMSO-d$_6$):13.28 (bs, 1/2H); 13.02 (bs, 1/2H); 7.84 (s, 1H); 7.57-7.73 (m, 2H); 7.20 (s, 1H); 6.96-7.05 (m, 1H); 4.38 (s, 2H); 4.08-4.16 (m, 1H); 3.20-3.28 (m, 4H); 2.45-2.54 (m, 4H); 2.24 (s, 3H); 1.59-1.79 (m, 6H); 1.47-1.59 (m,2H). MS ESI(+)m/e 461.2(M+H)$^+$.

EXAMPLE 1111

3-{5-[3-(cyclopropylmethoxy)prop-1-ynyl]thien-3-yl}-6-piperidin-1-yl-1H-[1]benzofuro[3,2-c]pyrazole

EXAMPLE 1111A 3-(5-bromothien-3-yl)-6-piperidin-1-yl-1H-[1]benzofuro[3,2-c]pyrazole The title compound was prepared by substituting piperidine for 1-methylpiperazine in Examples 1109C and 1109D. MS ESI(+) m/e 402.0,404.0(M+H)$^+$.

EXAMPLE 1111B

3-{5-[3-(cyclopropylmethoxy)prop-1-ynyl]thien-3-yl}-6-piperidin-1-yl-1H-[1]benzofuro[3,2c]pyrazole The title compound was prepared by substituting Example 1111A for 2-bromothiophene-4-carboxylate and Example 1048 for (prop-2-ynyloxy)benzene in Example 126. $^1$H NMR (300 MHz, DMSO-$d_6$): 13.25 (bs, 1/2H); 12.99 (bs, 1/2H); 7.84 (s, 1H); 7.66-7.73 (m, 1H); 7.51-7.60 (m, 1H); 7.13-7.21 (m, 1H); 6.93-7.05 (m, 1H); 4.44 (s, 2H); 3.36 (d, 2H, J=6); 3.21-3.28 (m, 4H); 1.51-1.70 (m, 6H); 0.99-1.10 (m, 1H); 0.47-0.55 (m, 2H); 0.19-0.26 (c, 2H). ESI(+): m/e 432.1(M+H)$^+$.

EXAMPLE 1112

3-[5-(3-isopropoxyprop-1-ynyl)thien-3-yl]-6-piperidin-1-yl-1H-[1]benzofuro[3,2-c]pyrazole The title compound was prepared by substituting Example 1111A for 2-bromothiophene-4-carboxylate and Example 1047 for (prop-2-ynyloxy)benzene in Example 126. $^1$H NMR (300 MHz, DMSO-$d_6$): 13.26(s, 1/2H); 12.99(s, 1/2H); 7.81-7.86 (m, 1H); 7.53-7.72 (m, 2H); 7.14-7.21 (m, 1H); 6.93-7.05 (m, 1H); 4.42 (s, 2H); 3.74-3.84 (m,1 H); 3.21-3.28 (m, 4H); 2.51-2.72 (m, 6H); 1.15 (d, 6H, J=6). ESI(+)m/e 420.2 (M+H)$^+$.

EXAMPLE 1113

3-{5-[3-(cyclopentyloxy)prop-1-ynyl]thien-3-yl}-6-piperidin-1-yl-1H-[1]benzofuro[3,2-c]pyrazole The title compound was prepared by substituting Example 1111A for 2-bromothiophene-4-carboxylate and Example 1046 for (prop-2-ynyloxy)benzene in Example 126. $^1$H NMR (300 MHz, DMSO-$d_6$): 13.26(s, 1/2H); 12.99(s, 1/2H); 7.81-7.87 (m, 1H); 7.64-7.72 (m, 2H); 7.13-7.22(m, 1H); 6.94-7.04 (m, 1H); 4.38(s, 2H); 4.08-4.16 (m, 1H); 3.20-3.28 (m, 4H); 1.44-1.79 (m, 14H). ESI(+) m/e 446.1 (M+H)$^+$.

EXAMPLE 1114

N,N-dimethyl-N-(4-{[4-(6-piperidin-1-yl-1H-[1]benzofuro[3,2-c]pyrazol-3-yl)thien-2-yl]ethynyl}phenyl)amine The title compound was prepared by substituting Example 1111A for 2-bromothiophene-4-carboxylate and N-(4-ethynylphenyl)-N,N-dimethylamine for (prop-2-ynyloxy)benzene in Example 126. $^1$H NMR (300 MHz, DMSO-$d_6$): 13.26 (s, 1/2H); 12.99 (s, 1/2H); 7.79-7.83 (m, 1H); 7.64-7.70 (m, 2H); 7.41 (s, 1H); 7.38 (s, 1H); 7.15-7.22(m, 1H); 6.94-7.05 (m, 1H); 6.75 (s, 1H); 6.72 (s, 1H); 3.21-3.29(m,4H); 2.97 (s, 6H); 1.52-1.70 (m, 6H); ESI(+)m/e 467.2 (M+H)$^+$.

EXAMPLE 1115

3-{5-[3-(cyclopentyloxy)prop-1-ynyl]thien-3-yl}-6-morpholin-4-yl-1H-[1]benzofuro[3,2-c]pyrazole

EXAMPLE 1115A 3-(5-bromothien-3-yl)-6-morpholin-4-yl-1H-[1]benzofuro[3,2-c]pyrazole The title compound was prepared by substituting morpholine for 1-methylpiperazine in Examples 1109C and 1109D. ESI(+)m/e 405.9(M+H)$^+$.

EXAMPLE 1115B

3-{5-[3-(cyclopentyloxy)prop-1-ynyl]thien-3-yl}-6-morpholin-4-yl-1H-[1]benzofuro[3,2-c]pyrazole The title compound was prepared by substituting Example 1115A for 2-bromothiophene-4-carboxylate and Example 1046 for (prop-2-ynyloxy)benzene in Example 126. $^1$H NMR (300 MHz, DMSO-$d_6$): 13.31 (s, 1/2H); 13.03 (s, 1/2H); 7.85 (s, 1H); 7.64-7.75 (m, 2H); 7.19-7.27 (m, 1H); 6.96-7.07 (m, 1H); 4.38 (s, 2H); 4.08-4.16 (m, 1H); 3.71-3.82 (m, 4H); 3.07-3.16 (m, 4H); 1.41-1.79 (m, 8H); ESI(+) m/e 448.4 (M+H)$^+$.

EXAMPLE 1116

3-{5-[3-(cyclopropylmethoxy)prop-1-ynyl]thien-3-yl}-6-morpholin-4-yl-1H-[1]benzofuro[3,2-c]pyrazole The title compound was prepared by substituting Example 1115A for 2-bromothiophene-4-carboxylate and Example 1048 for (prop-2-ynyloxy)benzene in Example 126. $^1$H NMR (300 MHz, DMSO-$d_6$): 13.32 (s, 1/2H); 13.03 (s, 1/2H); 7.83-7.88 (m, 1H); 7.66-7.75 (m, 1H); 7.56-7.64 (m, 1H); 7.19-7.27 (m, 1H); 6.96-7.07 (m, 1H); 4.44 (s, 2H); 3.72-3.84 (m, 4H); 3.36 (d, 2H, J=6);3.18-3.26 (m, 4H); 0.99-1.11 (m, 1H); 0.47-0.55 (m, 2H); 0.19-0.25 (m, 2H); ESI(+)m/e 434.1 (M+H)$^+$.

EXAMPLE 1117

6-morpholin-4-yl-3-(5-{[4-(trifluoromethyl)phenyl]ethynyl}thien-3-yl)-1H-[1]benzofuro[3,2-c]pyrazole The title compound was prepared by substituting Example 1115A for 2-bromothiophene-4-carboxylate and 1-ethynyl-4-trifluoromethylbenzene for (prop-2-ynyloxy)benzene in Example 126. $^1$H NMR (300 MHz, DMSO-$d_6$): 13.37 (bs, 1/2H); 13.08 (bs, 1/2H); 7.97 (s, 1H); 7.80-7.88 (m, 5H); 7.58-7.66 (m, 1H); 7.20-7.29 (m, 1H); 6.98-7.09(m,1H); 3.74-3.82 (m, 4H); 3.19-3.27 (m, 4H). ESI(+) m/e 494.1 (M+H)$^+$, 511.3 (M+NH$_4$)$^+$.

EXAMPLE 1118

6-morpholin-4-yl-3-(5-{[3-(trifluoromethyl)phenyl]ethynyl}thien-3-yl)-1H-[1]benzofuro[3,2-c]pyrazole The title compound was prepared by substituting Example 1115A for 2-bromothiophene-4-carboxylate and 1-ethynyl-3-trifluoromethylbenzene for (prop-2-ynyloxy)benzene in Example 126. $^1$H NMR (300 MHz, DMSO-$d_6$): 13.38 (s, 1/2H); 13.08 (s, 1/2H); 7.89-8.01 (m, 3H); 7.78-7.88 (m, 2H); 7.58-7.76 (m,2H); 7.19-7.28 (m, 1H); 6.98-7.09 (m, 1H); 3.74-3.82 (m, 4H); 3.18-3.26 (m, 4H). ESI(+) m/e 494.2 (M+H)$^+$; 511.3 (M+NH$_4$)$^+$.

EXAMPLE 1119

3-{5-[3-(cyclopropylmethoxy)prop-1-ynyl]thien-3-yl}-N-methyl-N-(pyridin-3-ylmethyl)-1H-[1]benzofuro[3,2-c]pyrazol-6-amine The title compound was prepared by substituting N-methyl-N-(pyridin-3-ylmethyl)amine for 1-methylpiperazine in Examples 1109C, D and E. $^1$H NMR (300 MHz, DMSO-$d_6$):

13.19 (s, 1/2H); 12.94 (s, 1/2H); 8.49 (bs, 2H); 7.83 (dd, 1H, J=1.5,6); 7.51-7.72 (m, 3H); 7.30-7.42 (m, 1H); 6.98 (dd, 1H, J=1.5,12); 6.75-6.87 (m, 1H); 4.73 (s, 2H); 4.43 (s, 2H); 3.36 (d, 2H, J=6); 3.13 (s, 3H); 0.99-1.10 (m, 1H); 0.47-0.54 (m, 2H); 0.19-0.25 (m, 2H); ESI(+)m/e 469.2 (M+H)+.

EXAMPLE 1120

3-{5-[3-(cyclopropylmethoxy)prop-1-ynyl]thien-3-yl}-N-(2-methoxyethyl)-N-methyl-1H-[1]benzofuro[3,2-c]pyrazol-6-amine

EXAMPLE 1120A

[1-(5-Bromo-thiophen-3-yl)-3H-8-oxa-2,3-diazacyclopenta[a]inden-6-yl]-(2-methoxy-ethyl)-methylamine The title compound was prepared by substituting (2-methoxy-ethyl)-methyl-amine for 1-methylpiperazine in Examples 1109C and 1109D. MS ESI(+)m/e 406.0, 408.0 (M+H)+.

EXAMPLE 1120B

3-{5-[3-(cyclopropylmethoxy)prop-1-ynyl]thien-3-yl}-N-(2-methoxyethyl)-N-methyl-1H-[1]benzofuro[3,2-c]pyrazol-6-amine The title compound was prepared by substituting Example 1120A for 2-bromothiophene-4-carboxylate and Example 1048 for (prop-2-ynyloxy)benzene in Example 126. 1H NMR (300 MHz, DMSO-d6): 13.17 (s, 1/2H); 12.92 (s, 1/2H); 7.81-7.86 (m, 1H); 7.60-7.73 (m, 2H); 6.91-6.98 (m, 1H); 6.71-6.82 (m, 1H); 4.44 (s, 2H); 3.50-3.63 (m, 4H); 3.34-3.39 (m, 2H); 3.27 (s, 3H); 3.00 (s, 3H); 0.99-1.10 (m, 1H); 0.47-0.55 (m, 2H); 0.19-0.26 (2H); MS ESI(+)m/e 436.1(M+H)+.

EXAMPLE 1121

3-[5-(3-isopropoxyprop-1-ynyl)thien-3-yl]-N-(2-methoxyethyl)-N-methyl-1H-[1]benzofuro[3,2-c]pyrazol-6-amine The title compound was prepared by substituting Example 1120A for 2-bromothiophene-4-carboxylate and Example 1047 for (prop-2-ynyloxy)benzene in Example 126. 1H NMR (300 MHz, DMSO-d6): 13.17 (s, 1/2H); 12.92 (s, 1/2H); 7.81-7.86 (m, 1H); 7.60-7.73 (m, 2H); 6.91-6.98 (m, 1H); 6.71-6.82 (m, 1H); 4.41 (s, 2H); 3.72-3.85 (m, 1H); 3.56-3.62 (m, 2H); 3.49-3.56 (m, 2H); 3.27 (s, 3H); 3.00 (s, 3H); 1.15 (d, 6H, J=6); MS ESI(+)m/e 424.2 (M+H)+.

EXAMPLE 1122

N-(3-{5-[3-(cyclopropylmethoxy)prop-1-ynyl]thien-3-yl}-1H-[1]benzofuro[3,2-c]pyrazol-6-yl)-N,N',N'-trimethylethane-1,2-diamine The title compound was prepared by substituting N,N,N'-trimethylethane-1,2-diamine for 1-methylpiperazine in examples 1109C, D and E. 1H NMR (300 MHz, DMSO-d6): 13.16 (bs, 1/2H); 12.95 (bs, 1/2H); 7.84 (s, 1H); 7.71-7.93 (m, 2H); 6.90 (s, 1H); 6.73 (bd, 1H, J=9); 4.44 (s, 2H); 3.50 (t, 2H, J=6); 3.36 (d, 2H, J=6);2.99 (s, 3H); 2.43 (t, 2H, J=6); 2.21 (s, 6H); 0.99-1.12 (m, 1H); 0.46-0.54 (m, 2H); 0.19-0.25 (m, 2H). MS ESI(+)m/e 449.0 (M+H)+.

EXAMPLE 1123

6-(4-cyclopropylpiperazin-1-yl)-3-[5-(3-isopropoxyprop-1-ynyl)thien-3-yl]-1,4-dihydroindeno[1,2-c]pyrazole The title compound was prepared by substituting Examples 1038 and 1053 for Examples 56 and 110, respectively in Example 138. 1H NMR (300 MHz, CDCL3): δ 0.51-0.59 (m, 4H), 1.24 (d, J=6.0 Hz, 6H), 1.72-1.79 (m, 1H), 2.85-2.88 (m, 4H), 3.25-3.28 (m, 4H), 3.65 (s, 1H), 3.80-3.93 (m, 1H), 4.40 (s, 1H), 6.88 (dd, J=8.1, 2.0 Hz, 1H), 7.10 (d, J=2.1 Hz, 1H), 7.40 (d, J=1.4 Hz, 1H), 7.47 (d, J=1.4 Hz, 1H), 7.53 (d, J=8.1 Hz, 1H). MS (ESI): m/z 459 (M+H)+.

It will be evident to one skilled in the art that the present invention is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of formula (I)

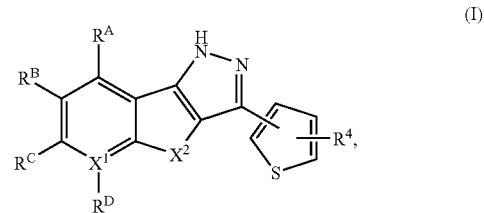

or a therapeutically acceptable salt thereof, wherein
$X^1$ is selected from the group consisting of C and N;
$X^2$ is selected from the group consisting of $CH_2$, C=O, and O;
$R^A$, $R^B$, and $R^C$ are independently selected from the group consisting of hydrogen, alkoxyalkoxy, alkoxyalkoxyalkyl, alkoxyalkyl, alkoxycarbonyl, carboxy, halogen, heteroaryl, heteroarylalkoxy, heteroarylalkyl, heteroarylcarbonyl, heteroaryloxy, heterocycle, heterocyclealkoxy, heterocyclealkyl, heterocyclecarbonyl, heterocycleoxy, $R^aR^bN$—, $(R^aR^bN)$alkoxy, $(R^aR^bN)$alkyl, $(R^aR^bN)$carbonyl, and $(NR^aR^bN)$carbonylalkoxy, and $(R^aR^bN)$carbonylalkyl;
$R^D$ is absent or selected from the group consisting of hydrogen, alkoxyalkoxy, alkoxyalkoxyalkyl, alkoxyalkyl, alkoxycarbonyl, carboxy, halogen, heteroaryl, heteroarylalkoxy, heteroarylalkyl, heteroarylcarbonyl, heteroaryloxy, heterocycle, heterocyclealkoxy, heterocyclealkyl, heterocyclecarbonyl, heterocycleoxy, $R^aR^bN$—, $(R^aR^bN)$alkoxy, $(R^aR^bN)$alkyl, $(R^aR^bN)$carbonyl, and $(NR^aR^bN)$carbonylalkoxy, and $(R^aR^bN)$carbonylalkyl;
$R^a$ and $R^b$ are independently selected from the group consisting of hydrogen, alkoxyalkyl, alkyl, alkylcarbonyl, formyl, heteroarylalkyl, heterocyclealkyl, and $(Z^1Z^2N)$alkyl;
$Z^1$ and $Z^2$ are independently selected from the group consisting of hydrogen, alkyl, formyl, and alkylcarbonyl;

$R^4$ is selected from the group consisting of heteroaryl, C≡$CR^5$, $(CH_2)_nNR^6C(O)NR^7R^8$, $(CH_2)_nNR^6C(O)OR^8$, $(CH_2)_nNR^6C(NCN)NR^7R^8$, $(CH_2)_nOC(O)NR^7R^8$, CH=$NNR^6C(O)NR^7R^8$, CH=$NOR^8$, and CH=$NOCH_2C(O)NR^7R^8$;

n is 1, 2, 3, 4, or 5;

$R^5$ is selected from the group consisting of alkoxyalkoxyalkyl, alkoxyalkyl, alkoxycarbonylalkoxyalkyl, alkyl, aryl, aryloxyalkyl, arylthioalkyl, arylsulfinylalkyl, arylsulfonylalkyl, cycloalkyl, cycloalkylalkoxyalkyl, cycloalkylalkyl, cycloalkyloxyalkyl, haloalkoxyalkyl, haloalkoxyalkoxyalkyl, heteroaryl, heteroarylalkoxyalkyl, heteroarylalkyl, heteroaryloxyalkyl, heterocycle, heterocyclealkoxyalkyl, heterocyclealkyl, heterocyclecarbonylalkyl, heterocyclecarbonyloxyalkyl, heterocycleoxyalkyl, $(NR^aR^b)$carbonylalkoxyalkyl, $(NR^cR^d)$alkyl, $(CH_2)_nNR^6C(O)NR^7R^8$, $(CH_2)_nNR^6C(O)OR^8$, $(CH_2)_nNR^6C(NCN)NR^7R^8$, $(CH_2)_nOC(O)NR^7R^8$, and CH=$NNR^6C(O)NR^7R^8$;

$R^c$ is selected from the group consisting of hydrogen and alkyl;

$R^d$ is selected from the group consisting of alkylsulfonyl, arylsulfonyl, heteroarylcarbonyl, and heteroarylcarbonyl;

$R^6$ and $R^7$ are each independently selected from the group consisting of hydrogen, alkoxy, alkoxyalkyl, alkyl, aryl, arylalkyl, cycloalkyl, and cycloalkylalkyl; and $R^8$ is selected from the group consisting of hydrogen, alkoxyalkoxyalkyl, alkoxyalkyl, alkoxycarbonylalkoxyalkyl, alkoxycarbonylalkyl, alkyl, aryl, arylalkoxyalkyl, arylalkyl, aryloxyalkyl, arylthioalkyl, arylsulfinylalkyl, arylsulfonylalkyl, cyanoalkyl, cycloalkyl, cycloalkylalkyl, haloalkoxyalkoxyalkyl, haloalkoxyalkyl, haloalkyl, heteroaryl, heteroarylalkoxyalkyl, heteroarylalkyl, heteroaryloxyalkyl, heterocycle, heterocyclealkoxyalkyl, heterocyclealkyl, heterocyclecarbonyloxyalkyl, heterocycleoxyalkyl, heterocyclealkyl, hydroxyalkyl, $(R^aR^bN)$alkyl, $(R^aR^bN)$carbonylalkoxyalkyl, and $(R^aR^bN)$carbonylalkyl; or $R^7$ and $R^8$, together with the nitrogen atom to which they are attached, form a heterocycle ring selected from the group consisting of piperazine, piperidine, and morpholine.

2. The compound of claim 1 wherein $R^4$ is $(CH_2)_nNR^6C(O)NR^7R^8$.

3. The compound of claim 1 wherein $R^4$ is $(CH_2)_nNR^6C(O)OR^8$.

4. The compound of claim 1 wherein $R^4$ is $(CH_2)_nNR^6C(NCN)NR^7R^8$.

5. The compound of claim 1 wherein $R^4$ is $(CH_2)_nOC(O)NR^7R^8$.

6. The compound of claim 1 wherein $R^4$ is CH=$NNR^6C(O)NR^7R^8$.

7. The compound of claim 1 wherein $R^4$ is CH=$NOR^8$.

8. The compound of claim 1 wherein $R^4$ is CH=$NOCH_2C(O)NR^7R^8$.

9. The compound of claim 1 wherein $R^4$ is C≡$CR^5$.

10. The compound of claim 1 wherein $X^1$ is selected from the group consisting of C and N;

$X^2$ is selected from the group consisting of $CH_2$ and O;

$R^A$ is hydrogen;

$R^B$ is selected from the group consisting of heteroaryl, heteroarylalkoxy, heteroarylalkyl, heteroarylcarbonyl, heteroaryloxy, heterocycle, heterocyclealkoxy, heterocyclealkyl, heterocyclecarbonyl, heterocycleoxy, $R^aR^bN$—, $(R^aR^bN)$alkoxy, $(R^aR^bN)$alkyl, $(R^aR^bN)$carbonyl, $(NR^aR^b)$carbonylalkoxy, and $(R^aR^bN)$carbonylalkyl;

$R^C$ is selected from the group consisting of hydrogen, alkoxyalkoxy, alkoxyalkoxyalkyl, alkoxyalkyl, alkoxycarbonyl, carboxy, and halogen;

$R^D$ is absent or selected from the group consisting of hydrogen and halogen;

$R^a$ and $R^b$ are independently selected from the group consisting of hydrogen, alkoxyalkyl, alkyl, alkylcarbonyl, formyl, heteroarylalkyl, heterocyclealkyl, and $(Z^1Z^2N)$alkyl;

$Z^1$ and $Z^2$ are independently selected from the group consisting of hydrogen, alkyl, formyl, and alkylcarbonyl;

$R^4$ is C≡$CR^5$;

$R^5$ is selected from the group consisting of alkoxyalkoxyalkyl, alkoxycarbonylalkoxyalkyl, arylthioalkyl, arylsulfinylalkyl, arylsulfonylalkyl, cycloalkyl, cycloalkylalkoxyalkyl, cycloalkylalkyl, cycloalkyloxyalkyl, haloalkoxyalkoxyalkyl, heteroaryl, heteroaryloxyalkyl, heterocycle, heterocyclecarbonylalkyl, heterocyclecarbonyloxyalkyl, heterocycleoxyalkyl, $(NR^aR^b)$carbonylalkoxyalkyl, $(NR^cR^d)$alkyl;

$R^c$ is selected from the group consisting of hydrogen and alkyl; and $R^d$ is selected from the group consisting of alkylsulfonyl, arylsulfonyl, heteroarylcarbonyl, and heteroarylcarbonyl.

11. The compound of claim 1 wherein $X^1$ is selected from the group consisting of C and N;

$X^2$ is selected from the group consisting of $CH_2$ and O;

$R^A$ is hydrogen;

$R^B$ is selected from the group consisting of hydrogen, alkoxyalkoxy, alkoxyalkoxyalkyl, alkoxyalkyl, alkoxycarbonyl, carboxy, and halogen;

$R^C$ is selected from the group consisting of heteroaryl, heteroarylalkoxy, heteroarylalkyl, heteroarylcarbonyl, heteroaryloxy, heterocycle, heterocyclealkoxy, heterocyclealkyl, heterocyclecarbonyl, heterocycleoxy, $R^aR^bN$—, $(R^aR^bN)$alkoxy, $(R^aR^bN)$alkyl, $(R^aR^bN)$carbonyl, $(NR^aR^b)$carbonylalkoxy, and $(R^aR^bN)$carbonylalkyl;

$R^D$ is absent or selected from the group consisting of hydrogen and halogen;

$R^a$ and $R^b$ are independently selected from the group consisting of hydrogen, alkoxyalkyl, alkyl, alkylcarbonyl, formyl, heteroarylalkyl, heterocyclealkyl, and $(Z^1Z^2N)$alkyl;

$Z^1$ and $Z^2$ are independently selected from the group consisting of hydrogen, alkyl, formyl, and alkylcarbonyl;

$R^4$ is C≡$CR^5$;

$R^5$ is selected from the group consisting of alkoxyalkoxyalkyl, alkoxycarbonylalkoxyalkyl, arylthioalkyl, arylsulfinylalkyl, arylsulfonylalkyl, cycloalkyl, cycloalkylalkoxyalkyl, cycloalkylalkyl, cycloalkyloxyalkyl, haloalkoxyalkoxyalkyl, heteroaryl, heteroaryloxyalkyl, heterocycle, heterocyclecarbonylalkyl, heterocyclecarbonyloxyalkyl, heterocycleoxyalkyl, $(NR^aR^b)$carbonylalkoxyalkyl, $(NR^cR^d)$alkyl;

$R^c$ is selected from the group consisting of hydrogen and alkyl; and $R^d$ is selected from the group consisting of alkylsulfonyl, arylsulfonyl, heteroarylcarbonyl, and heteroarylcarbonyl.

12. The compound of claim 1 wherein $R^4$ is C≡$CR^5$; and $R^5$ is selected from the group consisting of alkoxyalkoxyalkyl and haloalkoxyalkoxyalkyl.

13. The compound of claim 1 wherein $R^4$ is C≡$CR^5$; $R^5$ is selected from the group consisting of alkoxyalkoxyalkyl and haloalkoxyalkoxyalkyl; $R^B$ is selected from the group consisting of heteroarylalkyl and heterocyclealkyl; and $R^A$, $R^C$, $R^D$, $R^2$, and $R^3$ are hydrogen.

14. The compound according to claim 13 selected from the group consisting of
- 3-{5-[3-(2-methoxyethoxy)-1-propynyl]-3-thienyl}-7-[(4-methyl-1-piperazinyl)methyl]-1,4-dihydroindeno[1,2-c]pyrazole;
- 7-(1H-imidazol-1-ylmethyl)-3-{5-[3-(2-methoxyethoxy)-1-propynyl]-3-thienyl}-1,4-dihydroindeno[1,2-c]pyrazole;
- 3-{5-[3-(2-ethoxyethoxy)-1-propynyl]-3-thienyl}-7-(1H-1,2,4-triazol-1-ylmethyl)-1,4-dihydroindeno[1,2-c]pyrazole;
- 3-{5-[3-(2-isopropoxyethoxy)-1-propynyl]-3-thienyl}-7-(1H-1,2,4-triazol-1-ylmethyl)-1,4-dihydroindeno[1,2-c]pyrazole;
- -{5-[3-(2-methoxyethoxy)-1-propynyl]-3-thienyl}-7-(1H-1,2,4-triazol-1-ylmethyl)-1,4-dihydroindeno[1,2-c]pyrazole;
- 3-{4-[3-(2-methoxyethoxy)-1-propynyl]-2-thienyl}-7-(1H-1,2,4-triazol-1-ylmethyl)-1,4-dihydroindeno[1,2-c]pyrazole;
- 3-{5-[3-(2-isopropoxyethoxy)-1-propynyl]-3-thienyl}-7-(1H-1,2,3-triazol-1-ylmethyl)-1,4-dihydroindeno[1,2-c]pyrazole; and
- 3-{5-[3-(2-isopropoxyethoxy)-1-propynyl]-3-thienyl}-7-(2H-1,2,3-triazol-2-ylmethyl)-1,4-dihydroindeno[1,2-c]pyrazole.

15. The compound of claim 1 wherein $R^4$ is C≡$CR^5$; $R^5$ is selected from the group consisting of alkoxyalkoxyalkyl and haloalkoxyalkoxyalkyl; $R^C$ is selected from the group consisting of heteroarylalkyl and heterocyclealkyl; and $R^A$, $R^B$, $R^D$, $R^2$, and $R^3$ are hydrogen.

16. The compound according to claim 15 selected from the group consisting of
- 3-{5-[3-(2-methoxyethoxy)-1-propynyl]-3-thienyl}-6-[(4-methyl-1-piperazinyl)methyl]-1,4-dihydroindeno[1,2-c]pyrazole;
- 3-{5-[3-(2-isopropoxyethoxy)-1-propynyl]-3-thienyl}-6-[(4-methyl-1-piperazinyl)methyl]-1,4-dihydroindeno[1,2-c]pyrazole;
- 3-{5-[3-(2-ethoxyethoxy)-1-propynyl]-3-thienyl}-6-[(4-methyl-1-piperazinyy)methyl]-1,4-dihydroindeno[1,2-c]pyrazole;
- 3-{5-[3-(2-isobutoxyethoxy)-1-propynyl]-3-thienyl}-6-[(4-methyl-1-piperazinyl)methyl]-1,4-dihydroindeno[1,2-c]pyrazole;
- 3-{5-[3-(2-methoxy-1-methylethoxy)-1-propynyl]-3-thienyl}-6-[(4-methyl-1-piperazinyl)methyl]-1,4-dihydroindeno[1,2-c]pyrazole;
- 6-[(4-isopropyl-1-piperazinyl)methyl]-3-{5-[3-(2-methoxyethoxy)-1-propynyl]-3-thienyl}-1,4-dihydroindeno[1,2-c]pyrazole;
- 6-[(4-ethyl-1-piperazinyl)methyl]-3-{5-[3-(2-methoxyethoxy)-1-propynyl]-3-thienyl}-1,4-dihydroindeno[1,2-c]pyrazole;
- 6-(1H-imidazol-1-ylmethyl)-3-{5-[3-(2-methoxyethoxy)-1-propynyl]-3-thienyl}-1,4-dihydroindeno[1,2-c]pyrazole;
- 3-{5-[3-(2-methoxyethoxy)-1-propynyl]-3-thienyl}-6-(1H-1,2,4-triazol-1-ylmethyl)-1,4-dihydroindeno[1,2-c]pyrazole;
- 3-{5-[3-(2-ethoxyethoxy)-1-propynyl]-2-thienyl}-6-[(4-methyl-1-piperazinyl)methyl]-1,4-dihydroindeno[1,2-c]pyrazole;
- 3-{5-[3-(2-isopropoxyethoxy)-1-propynyl]-2-thienyl}-6-[(4-methyl-1-piperazinyl)methyl]-1,4-dihydroindeno[1,2-c]pyrazole; and
- 3-{4-[3-(2-methoxyethoxy)-1-propynyl]-2-thienyl}-6-[(4-methyl-1-piperazinyl)methyl]-1,4-dihydroindeno[1,2-c]pyrazole.

17. The compound according to claim 9 which is 3-(5-{3-[2-(difluoromethoxy)ethoxy]-1-propynyl}-3-thienyl)-6-[(4-methyl-1-piperazinyl)methyl]-1,4-dihydroindeno[1,2-c]pyrazole.

18. The compound according to claim 1 selected from the group consisting of
- 3-[5-(3-Cyclopropylmethoxy-prop-1-ynyl)-thiophen-3-yl]-7-fluoro-6-(4-methyl-piperazin-1-yl)-1,4-dihydro-indeno[1,2-c]pyrazole;
- 1-{3-[5-(3-Cyclopropylmethoxy-prop-1-ynyl)-thiophen-3-yl]-1,4-dihydro-indeno[1,2-c]pyrazol-6-ylmethyl}-4-methyl-piperazin-2-one;
- 6-(4-Cyclopropyl-piperazin-1-yl)-3-{5-[3-(2-fluoro-ethoxy)-prop-1-ynyl]-thiophen-3-yl}-1,4-dihydro-indeno[1,2-c]pyrazole;
- 3-[5-(3-Isopropoxy-prop-1-ynyl)-thiophen-3-yl]-6-(4-methyl-piperazin-1-yl)-1,4-dihydro-indeno[1,2-c]pyrazole; and
- 6-(4-cyclopropylpiperazin-1-yl)-3-[5-(3-isopropoxyprop-1-ynyl)thien-3-yl]-1,4-dihydroindeno[1,2-c]pyrazole.

19. A pharmaceutical composition comprising a compound of formula (I) or a therapeutically acceptable salt thereof, in combination with a therapeutically acceptable carrier.

20. A method for inhibiting a protein kinase in a patient in recognized need of such treatment comprising administering to the patient a therapeutically acceptable amount of a compound of formula (I), or a therapeutically acceptable salt thereof.

* * * * *